United States Patent
Adams et al.

(10) Patent No.: US 9,512,236 B2
(45) Date of Patent: Dec. 6, 2016

(54) AMINO ACID SEQUENCES DIRECTED AGAINST GPCRS AND POLYPEPTIDES COMPRISING THE SAME FOR THE TREATMENT OF GPCR-RELATED DISEASES AND DISORDERS

(71) Applicant: Ablynx N.V., Zwijnaarde (BE)

(72) Inventors: Hendrik Adams, Rotterdam (NL); Michael John Scott Saunders, Brussels (BE); Johannes Joseph Wilhelmus De Haard, Oudelande (NL); Christophe Blanchetot, Destelbergen (BE); Martine Smit, Amsterdam (NL); Regorius Leurs, Amsterdam (NL); Sven Jähnichen, Schwarme (DE); Peter Vanlandschoot, Bellem (BE); Francis Descamps, Roeselare (BE); Maria Gonzalez Pajuelo, Porto (PT); Pascal Gerard Merchiers, Tielen (BE); Catelijne Stortelers, Ghent (BE); Philippe Van Rompaey, Melle (BE); David Andre Baptiste Maussang-Detaille, Rotterdam (NL); Maarten Van Roy, Zwijnaarde (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

(21) Appl. No.: 13/650,600

(22) Filed: Oct. 12, 2012

(65) Prior Publication Data

US 2013/0130379 A1 May 23, 2013

Related U.S. Application Data

(63) Continuation-in-part of application No. 12/520,299, filed as application No. PCT/EP2007/064243 on Dec. 19, 2007, now abandoned, application No. 13/650,600, which is a continuation-in-part of application No. 12/992,982, filed as application No. PCT/EP2009/056026 on May 18, 2009, now Pat. No. 9,212,226, application No. 13/650,600, which is a continuation-in-part of application No. PCT/EP2012/055499, filed on Mar. 28, 2012.

(60) Provisional application No. 60/875,860, filed on Dec. 19, 2006, provisional application No. 61/053,847, filed on May 16, 2008, provisional application No. 61/102,142, filed on Oct. 2, 2008, provisional application No. 61/468,250, filed on Mar. 28, 2011, provisional application No. 61/540,272, filed on Sep. 28, 2011, provisional application No. 61/600,263, filed on Feb. 17, 2012.

(51) Int. Cl.
C07K 16/46 (2006.01)
C07K 16/28 (2006.01)

(52) U.S. Cl.
CPC ......... *C07K 16/468* (2013.01); *C07K 16/2866* (2013.01); *C07K 16/2869* (2013.01); C07K 2317/22 (2013.01); C07K 2317/31 (2013.01); C07K 2317/34 (2013.01); C07K 2317/35 (2013.01); C07K 2317/92 (2013.01)

(58) Field of Classification Search
None
See application file for complete search history.

(56) References Cited

U.S. PATENT DOCUMENTS

| | | |
|---|---|---|
| 8,937,164 B2 | 1/2015 | Descamps et al. |
| 9,212,226 B2 | 12/2015 | Blanchetot et al. |
| 2002/0106739 A1 | 8/2002 | Oakley et al. |
| 2004/0170634 A1 | 9/2004 | Burns et al. |
| 2007/0167443 A1 | 7/2007 | Melikian et al. |
| 2010/0062004 A1 | 3/2010 | Adams et al. |
| 2011/0206660 A1 | 8/2011 | Blanchetot et al. |
| 2011/0262438 A1 | 10/2011 | Descamps et al. |
| 2014/0178390 A1 | 6/2014 | Descamps et al. |
| 2014/0227270 A1 | 8/2014 | Descamps et al. |

FOREIGN PATENT DOCUMENTS

| | | |
|---|---|---|
| EP | 0 368 684 A1 | 5/1990 |
| EP | 0 542 810 | 5/1993 |
| EP | 1 316 801 A1 | 9/2002 |
| JP | 2008-539772 A | 11/2008 |
| JP | 2008-539775 A | 11/2008 |

(Continued)

OTHER PUBLICATIONS

[No Author Listed] Nature Reviews Drug Discovery GPCR Questionnaire Participants. The state of GPCR research in 2004. Nat Rev Drug Discov. Jul. 2004;3(7):575, 577-626.

(Continued)

*Primary Examiner* — Ruixiang Li
(74) *Attorney, Agent, or Firm* — Wolf, Greenfield & Sacks, P.C.

(57) ABSTRACT

The present invention relates to amino acid sequences that are directed against G-protein coupled receptors (GPCRs), as well as to compounds or constructs, and in particular proteins and polypeptides, that comprise or essentially consist of one or more such amino acid sequences. The invention also relates to nucleic acids encoding such amino acid sequences and; to methods for preparing such amino acid sequences and polypeptides; to host cells expressing or capable of expressing such amino acid sequences or polypeptides; to compositions, and in particular to pharmaceutical compositions, that comprise such amino acid sequences, polypeptides, nucleic acids and/or host cells; and to uses of such amino acid sequences or polypeptides, nucleic acids, host cells and/or compositions, in particular for prophylactic, therapeutic or diagnostic purposes.

4 Claims, 3 Drawing Sheets

(56) References Cited

FOREIGN PATENT DOCUMENTS

| | | |
|---|---|---|
| JP | 2010-500876 A | 1/2010 |
| JP | 2010-506912 A | 3/2010 |
| WO | WO 91/01743 A1 | 2/1991 |
| WO | WO 99/50461 A1 | 10/1999 |
| WO | WO 01/45746 A2 | 6/2001 |
| WO | WO 02/076489 A1 | 10/2002 |
| WO | WO 03/050531 A2 | 6/2003 |
| WO | WO 03/066830 A2 | 8/2003 |
| WO | WO 2004/041867 A2 | 5/2004 |
| WO | WO 2004/051268 A1 | 6/2004 |
| WO | WO 2004/064595 A2 | 8/2004 |
| WO | WO 2004/106377 A1 | 12/2004 |
| WO | WO 2005/018629 | 3/2005 |
| WO | WO 2005/019824 | 3/2005 |
| WO | WO 2005/044792 A2 | 5/2005 |
| WO | WO 2006/003388 A2 | 1/2006 |
| WO | WO 2006/030220 A1 | 3/2006 |
| WO | WO 2006/038027 A2 | 4/2006 |
| WO | WO 2006/047417 A2 | 5/2006 |
| WO | WO 2006/089141 A2 | 8/2006 |
| WO | WO 2006/116319 A2 | 11/2006 |
| WO | WO 2007/042289 A2 | 4/2007 |
| WO | WO 2007/051063 A2 | 5/2007 |
| WO | WO 2007/118670 A1 | 10/2007 |
| WO | WO 2008/028977 A2 | 3/2008 |
| WO | WO 2008/048519 A2 | 4/2008 |
| WO | WO 2008/068280 A1 | 6/2008 |
| WO | WO 2009/138519 A1 | 11/2009 |
| WO | WO 2010/010119 A1 | 1/2010 |
| WO | WO 2010/043650 A2 | 4/2010 |
| WO | WO 2010/070145 A2 | 6/2010 |
| WO | WO 2010/141986 A1 | 12/2010 |
| WO | WO 2011/117423 A1 | 9/2011 |

OTHER PUBLICATIONS

André et al., Enhancing functional production of G protein-coupled receptors in Pichia pastoris to levels required for structural studies via a single expression screen. Protein Sci. May 2006;15(5):1115-26. Epub Apr. 5, 2006.

Baribaud et al., Antigenically distinct conformations of CXCR4. J Virol. Oct. 2001;75(19):8957- 67.

Bednarek et al., Ligands of the melanocortin receptors, 2002-2003 update. Expert Opin Ther Patents. 2004;14(3):327-336.

Binz et al., Engineering novel binding proteins from nonimmunoglobulin domains. Nat Biotechnol. Oct. 2005;23(10):1257-68.

Carnec et al., Anti-CXCR4 monoclonal antibodies recognizing overlapping epitopes differ significantly in their ability to inhibit entry of human immunodeficiency virus type 1. J Virol. Feb. 2005;79(3):1930-3.

Coutts et al., Localisation of cannabinoid CB(1) receptor immunoreactivity in the guinea pig and rat myenteric plexus. J Comp Neurol. Jul. 8, 2002;448(4):410-22.

Dahmen et al., Expression of olfactory receptors in Xenopus oocytes. J Neurochem. Mar. 1992;58(3):1176-9.

Dimitrov et al., A mechanism of resistance to HIV-1 entry: inefficient interactions of CXCR4 with CD4 and gp120 in macrophages. Virology. Jun. 20, 1999;259(1):1-6.

Dove Pettit et al., Immunohistochemical localization of the neural cannabinoid receptor in rat brain. J Neurosci Res. Feb. 1, 1998;51(3):391-402.

Gensure et al., Parathyroid hormone and parathyroid hormone-related peptide, and their receptors. Biochem Biophys Res Commun. Mar. 18, 2005;328(3):666-78.

George et al., G-protein-coupled receptor oligomerization and its potential for drug discovery. Nat Rev Drug Discov. Oct. 2002;1(10):808-20.

Getting, Targeting melanocortin receptors as potential novel therapeutics. Pharmacol Ther. Jul. 2006;111(1):1-15. Epub Feb. 20, 2006.

Halaby et al., The immunoglobulin fold family: sequence analysis and 3D structure comparisons. Protein Eng. Jul. 1999;12(7):563-71.

Hassaine et al., Semliki Forest virus vectors for overexpression of 101 G protein-coupled receptors in mammalian host cells. Protein Expr Purif. Feb. 2006;45(2):343-51. Epub Jul. 11, 2005.

Hoffman et al., A biosensor assay for studying ligand-membrane receptor interactions: binding of antibodies and HIV-1 Env to chemokine receptors. Proc Natl Acad Sci U S A. Oct. 10, 2000;97(21):11215-20.

Holliger et al., Engineered antibody fragments and the rise of single domains. Nat Biotechnol. Sep. 2005;23(9):1126-36.

Holt et al., Domain antibodies: proteins for therapy. Trends Biotechnol. Nov. 2003;21(11):484-90.

Hoogenboom et al., Selection-dominant and nonaccessible epitopes on cell-surface receptors revealed by cell-panning with a large phage antibody library. Eur J Biochem. Mar. 1999;260(3):774-84.

Hoogenboom, Selecting and screening recombinant antibody libraries. Nat Biotechnol. Sep. 2005;23(9):1105-16.

Houamed et al., Cloning, expression, and gene structure of a G protein-coupled glutamate receptor from rat brain. Science. May 31, 1991;252(5010):1318-21.

Hovius et al., Characterization of a mouse serotonin 5-HT3 receptor purified from mammalian cells. J Neurochem. Feb. 1998;70(2):824-34.

Howard et al., Orphan G-protein-coupled receptors and natural ligand discovery. Trends Pharmacol Sci. Mar. 2001;22(3):132-40.

Hutchings et al., Therapeutic antibodies directed at G protein-coupled receptors. MAbs. Nov.-Dec. 2010;2(6):594-606. Epub Nov. 1, 2010.

Jacoby et al., The 7 TM G-protein-coupled receptor target family. ChemMedChem. Aug. 2006;1(8):761-82.

Jähnichen et al., CXCR4 nanobodies (VHH-based single variable domains) potently inhibit chemotaxis and HIV-1 replication and mobilize stem cells. Proc Natl Acad Sci U S A. Nov. 23, 2010;107(47):20565-70. Epub Nov. 8, 2010.

Kenakin, Efficacy as a vector: the relative prevalence and paucity of inverse agonism. Mol Pharmacol. Jan. 2004;65(1):2-11.

Kenakin, Principles: receptor theory in pharmacology. Trends Pharmacol Sci. Apr. 2004;25(4):186-92.

Kiefer, In vitro folding of alpha-helical membrane proteins. Biochim Biophys Acta. Feb. 17, 2003;1610(1):57-62.

Kim et al., Enhancement of colorectal tumor targeting using a novel biparatopic monoclonal antibody against carcinoembryonic antigen in experimental radioimmunoguided surgery. Int J Cancer. Feb. 1, 2002;97(4):542-7.

Lagane et al., CXCR4 dimerization and beta-arrestin-mediated signaling account for the enhanced chemotaxis to CXCL12 in WHIM syndrome. Blood. Jul. 1, 2008;112(1):34-44. doi: 10.1182/blood-2007-07-102103. Epub Apr. 24, 2008.

Lieby et al., The clonal analysis of anticardiolipin antibodies in a single patient with primary antiphospholipid syndrome reveals an extreme antibody heterogeneity. Blood. Jun. 15, 2001;97(12):3820-8.

Lundstrom et al., Structural genomics on membrane proteins: comparison of more than 100 GPCRs in 3 expression systems. J Struct Funct Genomics. Jun. 2006;7(2):77-91. Epub Nov. 22, 2006.

Marinissen et al., G-protein-coupled receptors and signaling networks: emerging paradigms. Trends Pharmacol Sci. Jul. 2001;22(7):368-76.

McIntosh et al., CB1 cannabinoid receptor: cellular regulation and distribution in N18TG2 neuroblastoma cells. Mol Brain Res. Jan. 1998;53(1-2):163-73.

Milligan, Constitutive activity and inverse agonists of G protein-coupled receptors: a current perspective. Mol Pharmacol. Dec. 2003;64(6):1271-6.

Misumi et al., A novel cyclic peptide immunization strategy for preventing HIV-1/AIDS infection and progression. J Biol Chem. Aug. 22, 2003;278(34):32335-43. Epub May 27, 2003.

Mitrirattanakul et al., Expression of cannabinoid 1 receptors in rat dorsal root ganglia remains unchanged after spinal nerve ligation. 33$^{rd}$ Annual Meeting Soc Neurosci. Nov. 10, 2003;Program No. 483.9. Abstract.

(56) References Cited

OTHER PUBLICATIONS

Nicholson et al., Peripheral administration of a melanocortin 4-receptor inverse agonist prevents loss of lean body mass in tumor-bearing mice. J Pharmacol Exp Ther. May 2006;317(2):771-7. Epub Jan. 25, 2006.

Pacher et al., The endocannabinoid system as an emerging target of pharmacotherapy. Pharmacol Rev. Sep. 2006;58(3):389-462.

Pierce et al., Seven-transmembrane receptors. Nat Rev Mol Cell Biol. Sep. 2002;3(9):639-50.

Raman et al., Role of chemokines in tumor growth. Cancer Lett. Oct. 28, 2007;256(2):137-65. Epub Jul. 12, 2007.

Rios et al., G-protein-coupled receptor dimerization: modulation of receptor function. Pharmacol Ther. Nov.-Dec. 2001;92(2-3):71-87.

Robert et al., Tumor targeting with newly designed biparatopic antibodies directed against two different epitopes of the carcinoembryonic antigen (CEA). Int J Cancer. Apr. 12, 1999;81(2):285-91.

Rosenkilde et al., Virally encoded 7TM receptors. Oncogene. Mar. 26, 2001;20(13):1582-93.

Sadee et al., Genetic variations in human G protein-coupled receptors: implications for drug therapy. AAPS PharmSci. 2001;3(3):E22.

Schlyer et al., I want a new drug: G-protein-coupled receptors in drug development. Drug Discov Today. Jun. 2006;11(11-12):481-93.

Sui et al., Identification of CD4 and transferrin receptor antibodies by CXCR4 antibody-guided Pathfinder selection. Eur J Biochem. Nov. 2003;270(22):4497-506.

Surgand et al., A chemogenomic analysis of the transmembrane binding cavity of human G-protein-coupled receptors. Proteins. Feb. 1, 2006;62(2):509-38.

Ulrich et al., DNA and RNA aptamers: from tools for basic research towards therapeutic applications. Comb Chem High Throughput Screen. Sep. 2006;9(8):619-32.

Vaday et al., CXCR4 and CXCL12 (SDF-1) in prostate cancer: inhibitory effects of human single chain Fv antibodies. Clin Cancer Res. Aug. 15, 2004;10(16):5630-9.

Vilardaga et al., Differential conformational requirements for activation of G proteins and the regulatory proteins arrestin and G protein-coupled receptor kinase in the G protein-coupled receptor for parathyroid hormone (PTH)/PTH-related protein. J Biol Chem. Sep. 7, 2001;276(36):33435-43. Epub May 31, 2001.

Ward et al., Binding activities of a repertoire of single immunoglobulin variable domains secreted from *Escherichia coli*. Nature. Oct. 12, 1989;341(6242):544-6.

[No Author Listed], Monoclonal Antibody Anti-CXCR7/RDC1; K0223-3 9C4 Mouse IgG1 [kappa] 100 [mu]g. Jan. 12, 2009.

Balabanian et al., The chemokine SDF-1/CXCL12 binds to and signals through the orphan receptor RDC1 in T lymphocytes. J Biol Chem. Oct. 21, 2005;280(42):35760-6. Epub Aug. 17, 2005.

Burns et al., A novel chemokine receptor for SDF-1 and I-TAC involved in cell survival, cell adhesion, and tumor development. J Exp Med. Sep. 4, 2006;203(9):2201-13. Epub Aug. 28, 2006.

Caldas et al., Humanization of the anti-CD18 antibody 6.7: an unexpected effect of a framework residue in binding to antigen. Mol Immunol. May 2003;39(15):941-52.

Casset et al., A peptide mimetic of an anti-CD4 monoclonal antibody by rational design. Biochem Biophys Res Commun. Jul. 18, 2003;307(1):198-205.

Chien et al., Significant structural and functional change of an antigen-binding site by a distant amino acid substitution: proposal of a structural mechanism. Proc Natl Acad Sci U S A. Jul. 1989;86(14):5532-6.

De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.

Desmyter et al., Three camelid VHH domains in complex with porcine pancreatic alpha-amylase. Inhibition and versatility of binding topology. J Biol Chem. Jun. 28, 2002;277(26):23645-50. Epub Apr. 17, 2002.

Genbank Submission; NCBI; Accession No. NM_000609.5; Bracci et al.; Mar. 21, 2010. 4 pages.

Giusti et al., Somatic diversification of S107 from an antiphosphocholine to an anti-DNA autoantibody is due to a single base change in its heavy chain variable region. Proc Natl Acad Sci U S A. May 1987;84(9):2926-30.

Güssow et al., Humanization of monoclonal antibodies. Methods Enzymol. 1991;203:99-121.

Hachet-Haas et al, Small Neutralizing Molecules to Inhibit Actions of the Chemokine CXCL12. Journal of Biological Chemistry. 2008; 283(34): 23189-23199.

Hartmann et al., A crosstalk between intracellular CXCR7 and CXCR4 involved in rapid CXCL12-triggered integrin activation but not in chemokine-triggered motility of human T lymphocytes and CD34+ cells. J Leukoc Biol. Oct. 2008;84(4):1130-40. Epub Jul. 24, 2008.

Hoffmann et al., Conformational changes in G-protein-coupled receptors-the quest for functionally selective conformations is open. Br J Pharmacol. Mar. 2008;153 Suppl 1:S358-66. Epub Dec. 3, 2007.

Holm et al., Functional mapping and single chain construction of the anti-cytokeratin 8 monoclonal antibody TS1. Mol Immunol. Feb. 2007;44(6):1075-84. Epub Sep. 20, 2006.

Kim et al., Efficient targeting of gastric cancer cells using radiolabeled anti-carcinoembryonic antigen-specific T84.66 fragments in experimental radioimmunoguided surgery. Anticancer Res. Mar.-Apr. 2004;24(2B):663-70.

Kollmar et al., CXCR4 and CXCR7 regulate angiogenesis and CT26.WT tumor growth independent from SDF-1. Int J Cancer. Mar. 15, 2010;126(6):1302-15.

Luker et al., Imaging chemokine receptor dimerization with firefly luciferase complementation. FASEB J. Mar. 2009;23(3):823-34. Epub Nov. 10, 2008.

MacCallum et al., Antibody-antigen interactions: contact analysis and binding site topography. J Mol Biol. Oct. 11, 1996;262(5):732-45.

Maksym et al., The role of stromal-derived factor-1—CXCR7 axis in development and cancer. Eur J Pharmacol. Dec. 25, 2009;625(1-3):31-40. Epub Oct. 14, 2009.

Mariuzza et al., The structural basis of antigen-antibody recognition. Annu Rev Biophys Biophys Chem. 1987;16:139-59.

Miao et al., CXCR7 (RDC1) promotes breast and lung tumor growth in vivo and is expressed on tumor-associated vasculature. Proc Natl Acad Sci USA. Oct. 2, 2007;104(40):15735-40. Epub Sep. 26, 2007.

Michel et al., How reliable are G-protein-coupled receptor antibodies? Naunyn Schmiedebergs Arch Pharmacol. Apr. 2009;379(4):385-8. Epub Jan. 27, 2009.

Rudikoff et al., Single amino acid substitution altering antigen-binding specificity. Proc Natl Acad Sci U S A. Mar. 1982;79(6):1979-83.

Vajdos et al., Comprehensive functional maps of the antigen-binding site of an anti-ErbB2 antibody obtained with shotgun scanning mutagenesis. J Mol Biol. Jul. 5, 2002;320(2):415-28.

Vassilatis et al., The G protein-coupled receptor repertoires of human and mouse. Proc Natl Acad Sci U S A. Apr. 15, 2003;100(8):4903-8. Epub Apr. 4, 2003.

Wang et al., The role of CXCR7/RDC1 as a chemokine receptor for CXCL12/SDF-1 in prostate cancer. J Biol Chem. Feb. 15, 2008;283(7):4283-94. Epub Dec. 5, 2007.

Winkler et al., Changing the antigen binding specificity by single point mutations of an anti-p24 (HIV-1) antibody. J Immunol. Oct. 15, 2000;165(8):4505-14.

Wu et al., Humanization of a murine monoclonal antibody by simultaneous optimization of framework and CDR residues. J Mol Biol. Nov. 19, 1999;294(1):151-62.

Zabel et al., Elucidation of CXCR7-mediated signaling events and inhibition of CXCR4-mediated tumor cell transendothelial migration by CXCR7 ligands. J Immunol. Sep. 1, 2009;183(5):3204-11.

Chen et al., Selection and analysis of an optimized anti-VEGF antibody: crystal structure of an affinity-matured Fab in complex with antigen. J Mol Biol. Nov. 5, 1999;293(4):865-81.

(56) References Cited

OTHER PUBLICATIONS

Lamminmäki et al., Crystal structure of a recombinant anti-estradiol Fab fragment in complex with 17beta-estradiol. J Biol Chem. Sep. 28, 2001;276(39):36687-94. Epub Jul. 12, 2001.

Muyldermans, Single domain camel antibodies: current status. J Biotechnol. Jun. 2001;74(4):277-302.

Padlan et al., Structure of an antibody-antigen complex: crystal structure of the HyHEL-10 Fab-lysozyme complex. Proc Natl Acad Sci U S A. Aug. 1989;86(15):5938-42.

Brown et al., Tolerance of single, but not multiple, amino acid replacements in antibody VHCDR 2: a means of minimizing B cell wastage from somatic hypermutation? J Immunol. May 1, 1996;156(9):3285-91.

Hattermann et al., The chemokine receptor CXCR7 is highly expressed in human glioma cells and mediates antiapoptotic effects. Cancer Res. Apr. 15, 2010;70(8):3299-308. doi: 10.1158/0008-5472.CAN-09-3642. Epub Apr. 13, 2010.

Maussang et al., Llama-derived single variable domains (nanobodies) directed against chemokine receptor CXCR7 reduce head and neck cancer cell growth in vivo. J Biol Chem. Oct. 11, 2013;288(41):29562-72. doi: 10.1074/jbc.M113.498436. Epub Aug. 26, 2013.

Xia et al., Expressions of CXCR7/ligands may be involved in oral carcinogenesis. J Mol Histol. Apr. 2011;42(2):175-80. doi: 10.1007/s10735-011-9322-x. Epub Mar. 26, 2011.

Zheng et al., Chemokine receptor CXCR7 regulates the invasion, angiogenesis and tumor growth of human hepatocellular carcinoma cells. J Exp Clin Cancer Res. Apr. 11, 2010;29:31. doi:10.1186/1756-9966-29-31.

a Family 1 b Family 2 c Family 3

SEQUENCE LISTING

<160> NUMBER OF SEQ ID NOS: 585

<210> SEQ ID NO 1
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)

```
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Pro Phe Ser Xaa Xaa
            20                  25                  30

Xaa Xaa Xaa Trp Phe Arg Gln Ala Pro Gly Lys Gln Arg Asp Ser Val
        35                  40                  45

Ala Xaa Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
65                  70                  75                  80

Val Tyr Arg Cys Tyr Phe Xaa Xaa Xaa Xaa Xaa Trp Gly Gln Gly Thr
                85                  90                  95

Gln Val Thr Val Ser Ser
            100

<210> SEQ ID NO 2
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 2

Gln Val Lys Leu Glu Glu Ser Gly Gly Gly Leu Val Gln Ala Gly Gly
1               5                   10                  15

Ser Leu Arg Leu Ser Cys Val Gly Ser Gly Arg Thr Phe Ser Xaa Xaa
            20                  25                  30

Xaa Xaa Xaa Trp Phe Arg Leu Ala Pro Gly Lys Glu Arg Glu Phe Val
        35                  40                  45

Ala Xaa Xaa Xaa Xaa Xaa Arg Phe Thr Ile Ser Arg Asp Thr Ala Ser
    50                  55                  60

Asn Arg Gly Tyr Leu His Met Asn Asn Leu Thr Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 3
<211> LENGTH: 102
```

```
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 3

Ala Val Gln Leu Val Asp Ser Gly Gly Gly Leu Val Gln Ala Gly Asp
1               5                   10                  15

Ser Leu Lys Leu Ser Cys Ala Leu Thr Gly Gly Ala Phe Thr Xaa Xaa
                20                  25                  30

Xaa Xaa Xaa Trp Phe Arg Gln Thr Pro Gly Arg Glu Arg Glu Phe Val
            35                  40                  45

Ala Xaa Xaa Xaa Xaa Xaa Arg Phe Thr Ile Ser Arg Asp Asn Ala Lys
        50                  55                  60

Asn Met Val Tyr Leu Arg Met Asn Ser Leu Ile Pro Glu Asp Ala Ala
65                  70                  75                  80

Val Tyr Ser Cys Ala Ala Xaa Xaa Xaa Xaa Xaa Trp Gly Gln Gly Thr
                85                  90                  95

Leu Val Thr Val Ser Ser
            100

<210> SEQ ID NO 4
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 4

Gln Val Gln Leu Val Glu Ser Gly Gly Gly Leu Val Glu Ala Gly Gly
1               5                   10                  15

Ser Leu Arg Leu Ser Cys Thr Ala Ser Glu Ser Pro Phe Arg Xaa Xaa
                20                  25                  30

Xaa Xaa Xaa Trp Phe Arg Gln Thr Ser Gly Gln Glu Arg Glu Phe Val
            35                  40                  45

Ala Xaa Xaa Xaa Xaa Xaa Arg Phe Thr Ile Ser Arg Asp Asp Ala Lys
        50                  55                  60

Asn Thr Val Trp Leu His Gly Ser Thr Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95
```

```
Gln Val Thr Val Ser Ser
            100

<210> SEQ ID NO 5
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 5

Ala Val Gln Leu Val Glu Ser Gly Gly Gly Leu Val Gln Gly Gly Gly
1               5                   10                  15

Ser Leu Arg Leu Ala Cys Ala Ala Ser Glu Arg Ile Phe Asp Xaa Xaa
            20                  25                  30

Xaa Xaa Xaa Trp Tyr Arg Gln Gly Pro Gly Asn Glu Arg Glu Leu Val
        35                  40                  45

Ala Xaa Xaa Xaa Xaa Xaa Arg Phe Thr Ile Ser Met Asp Tyr Thr Lys
    50                  55                  60

Gln Thr Val Tyr Leu His Met Asn Ser Leu Arg Pro Glu Asp Thr Gly
65                  70                  75                  80

Leu Tyr Tyr Cys Lys Ile Xaa Xaa Xaa Xaa Xaa Trp Gly Gln Gly Thr
                85                  90                  95

Gln Val Thr Val Ser Ser
            100

<210> SEQ ID NO 6
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 6

Asp Val Lys Phe Val Glu Ser Gly Gly Gly Leu Val Gln Ala Gly Gly
1               5                   10                  15

Ser Leu Arg Leu Ser Cys Val Ala Ser Gly Phe Asn Phe Asp Xaa Xaa
            20                  25                  30

Xaa Xaa Xaa Trp Phe Arg Gln Ala Pro Gly Lys Glu Arg Glu Glu Val
        35                  40                  45

Ala Xaa Xaa Xaa Xaa Xaa Arg Phe Thr Ile Ser Ser Glu Lys Asp Lys
```

-continued

```
                50                  55                  60
Asn Ser Val Tyr Leu Gln Met Asn Ser Leu Lys Pro Glu Asp Thr Ala
 65                  70                  75                  80

Leu Tyr Ile Cys Ala Gly Xaa Xaa Xaa Xaa Trp Gly Arg Gly Thr
                 85                  90                  95

Gln Val Thr Val Ser Ser
            100

<210> SEQ ID NO 7
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 7

Gln Val Arg Leu Ala Glu Ser Gly Gly Gly Leu Val Gln Ser Gly Gly
  1               5                  10                  15

Ser Leu Arg Leu Ser Cys Val Ala Ser Gly Ser Thr Tyr Thr Xaa Xaa
                 20                  25                  30

Xaa Xaa Xaa Trp Tyr Arg Gln Tyr Pro Gly Lys Gln Arg Ala Leu Val
             35                  40                  45

Ala Xaa Xaa Xaa Xaa Xaa Arg Phe Thr Ile Ala Arg Asp Ser Thr Lys
     50                  55                  60

Asp Thr Phe Cys Leu Gln Met Asn Asn Leu Lys Pro Glu Asp Thr Ala
 65                  70                  75                  80

Val Tyr Tyr Cys Tyr Ala Xaa Xaa Xaa Xaa Xaa Trp Gly Gln Gly Thr
                 85                  90                  95

Gln Val Thr Val Ser Ser
            100

<210> SEQ ID NO 8
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 8

Glu Val Gln Leu Val Glu Ser Gly Gly Gly Leu Val Gln Ala Gly Gly
  1               5                  10                  15
```

```
Ser Leu Arg Leu Ser Cys Ala Ala Ser Gly Phe Thr Ser Asp Xaa Xaa
            20                  25                  30

Xaa Xaa Xaa Trp Phe Arg Gln Ala Pro Gly Lys Pro Arg Glu Gly Val
            35                  40                  45

Ser Xaa Xaa Xaa Xaa Xaa Arg Phe Thr Ile Ser Thr Asp Asn Ala Lys
 50                  55                  60

Asn Thr Val His Leu Leu Met Asn Arg Val Asn Ala Glu Asp Thr Ala
 65                  70                  75                  80

Leu Tyr Tyr Cys Ala Val Xaa Xaa Xaa Xaa Xaa Trp Gly Arg Gly Thr
                 85                  90                  95

Arg Val Thr Val Ser Ser
            100

<210> SEQ ID NO 9
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 9

Gln Val Gln Leu Val Glu Ser Gly Gly Gly Leu Val Gln Pro Gly Gly
 1               5                  10                  15

Ser Leu Arg Leu Ser Cys Gln Ala Ser Gly Asp Ile Ser Thr Xaa Xaa
            20                  25                  30

Xaa Xaa Xaa Trp Tyr Arg Gln Val Pro Gly Lys Leu Arg Glu Phe Val
            35                  40                  45

Ala Xaa Xaa Xaa Xaa Xaa Arg Phe Thr Ile Ser Gly Asp Asn Ala Lys
 50                  55                  60

Arg Ala Ile Tyr Leu Gln Met Asn Asn Leu Lys Pro Asp Asp Thr Ala
 65                  70                  75                  80

Val Tyr Tyr Cys Asn Arg Xaa Xaa Xaa Xaa Xaa Trp Gly Gln Gly Thr
                 85                  90                  95

Gln Val Thr Val Ser Pro
            100

<210> SEQ ID NO 10
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
```

<223> OTHER INFORMATION: Xaa is any amino acid

<400> SEQUENCE: 10

```
Gln Val Pro Val Val Glu Ser Gly Gly Gly Leu Val Gln Ala Gly Asp
1               5                   10                  15

Ser Leu Arg Leu Phe Cys Ala Val Pro Ser Phe Thr Ser Thr Xaa Xaa
            20                  25                  30

Xaa Xaa Xaa Trp Phe Arg Gln Ala Pro Gly Lys Glu Arg Glu Phe Val
        35                  40                  45

Ala Xaa Xaa Xaa Xaa Xaa Arg Phe Thr Ile Ser Arg Asn Ala Thr Lys
    50                  55                  60

Asn Thr Leu Thr Leu Arg Met Asp Ser Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100
```

<210> SEQ ID NO 11
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 11

```
Glu Val Gln Leu Val Glu Ser Gly Gly Gly Leu Val Gln Ala Gly Asp
1               5                   10                  15

Ser Leu Arg Leu Phe Cys Thr Val Ser Gly Gly Thr Ala Ser Xaa Xaa
            20                  25                  30

Xaa Xaa Xaa Trp Phe Arg Gln Ala Pro Gly Glu Lys Arg Glu Phe Val
        35                  40                  45

Ala Xaa Xaa Xaa Xaa Xaa Arg Phe Thr Ile Ala Arg Glu Asn Ala Gly
    50                  55                  60

Asn Met Val Tyr Leu Gln Met Asn Asn Leu Lys Pro Asp Asp Thr Ala
65                  70                  75                  80

Leu Tyr Thr Cys Ala Ala Xaa Xaa Xaa Xaa Xaa Trp Gly Arg Gly Thr
                85                  90                  95

Gln Val Thr Val Ser Ser
            100
```

<210> SEQ ID NO 12
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid

```
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 12

Ala Val Gln Leu Val Glu Ser Gly Gly Asp Ser Val Gln Pro Gly Asp
1               5                   10                  15

Ser Gln Thr Leu Ser Cys Ala Ala Ser Gly Arg Thr Asn Ser Xaa Xaa
            20                  25                  30

Xaa Xaa Xaa Trp Phe Arg Gln Ala Pro Gly Lys Glu Arg Val Phe Leu
        35                  40                  45

Ala Xaa Xaa Xaa Xaa Xaa Arg Phe Thr Ile Ser Arg Asp Ser Ala Lys
    50                  55                  60

Asn Met Met Tyr Leu Gln Met Asn Asn Leu Lys Pro Gln Asp Thr Ala
65                  70                  75                  80

Val Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 13
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 13

Ala Val Gln Leu Val Glu Ser Gly Gly Gly Leu Val Gln Ala Gly Gly
1               5                   10                  15

Ser Leu Arg Leu Ser Cys Val Val Ser Gly Leu Thr Ser Ser Xaa Xaa
            20                  25                  30

Xaa Xaa Xaa Trp Phe Arg Gln Thr Pro Trp Gln Glu Arg Asp Phe Val
        35                  40                  45

Ala Xaa Xaa Xaa Xaa Xaa Arg Phe Thr Ile Ser Arg Asp Asn Tyr Lys
    50                  55                  60

Asp Thr Val Leu Leu Glu Met Asn Phe Leu Lys Pro Glu Asp Thr Ala
65                  70                  75                  80

Ile Tyr Tyr Cys Ala Ala Xaa Xaa Xaa Xaa Xaa Trp Gly Gln Gly Thr
                85                  90                  95

Gln Val Thr Val Ser Ser
            100

<210> SEQ ID NO 14
<211> LENGTH: 102
<212> TYPE: PRT
```

<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 14

Ala Val Gln Leu Val Glu Ser Gly Gly Gly Leu Val Gln Ala Gly Ala
1               5                   10                  15

Ser Leu Arg Leu Ser Cys Ala Thr Ser Thr Arg Thr Leu Asp Xaa Xaa
            20                  25                  30

Xaa Xaa Xaa Trp Phe Arg Gln Ala Pro Gly Arg Asp Arg Glu Phe Val
        35                  40                  45

Ala Xaa Xaa Xaa Xaa Xaa Arg Phe Thr Val Ser Arg Asp Ser Ala Glu
50                  55                  60

Asn Thr Val Ala Leu Gln Met Asn Ser Leu Lys Pro Glu Asp Thr Ala
65                  70                  75                  80

Val Tyr Tyr Cys Ala Ala Xaa Xaa Xaa Xaa Xaa Trp Gly Gln Gly Thr
                85                  90                  95

Arg Val Thr Val Ser Ser
            100

<210> SEQ ID NO 15
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Thr Val Ser Arg Leu Thr Ala His Xaa Xaa
            20                  25                  30

Xaa Xaa Xaa Trp Phe Arg Gln Ala Pro Gly Lys Glu Arg Glu Ala Val
        35                  40                  45

Ser Xaa Xaa Xaa Xaa Xaa Arg Phe Thr Ile Ser Arg Asp Tyr Ala Gly
50                  55                  60

Asn Thr Ala Phe Leu Gln Met Asp Ser Leu Lys Pro Glu Asp Thr Gly
65                  70                  75                  80

Val Tyr Tyr Cys Ala Thr Xaa Xaa Xaa Xaa Xaa Trp Gly Gln Gly Thr
                85                  90                  95

```
Gln Val Thr Val Ser Ser
            100

<210> SEQ ID NO 16
<211> LENGTH: 102
<212> TYPE: PRT
<213> ORGANISM: Artificial
<220> FEATURE:
<223> OTHER INFORMATION: KERE-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 16

Glu Val Gln Leu Val Glu Ser Gly Gly Glu Leu Val Gln Ala Gly Gly
1               5                   10                  15

Ser Leu Lys Leu Ser Cys Thr Ala Ser Gly Arg Asn Phe Val Xaa Xaa
            20                  25                  30

Xaa Xaa Xaa Trp Phe Arg Arg Ala Pro Gly Lys Glu Arg Glu Phe Val
        35                  40                  45

Ala Xaa Xaa Xaa Xaa Xaa Arg Phe Thr Val Ser Arg Asp Asn Gly Lys
    50                  55                  60

Asn Thr Ala Tyr Leu Arg Met Asn Ser Leu Lys Pro Glu Asp Thr Ala
65                  70                  75                  80

Asp Tyr Tyr Cys Ala Val Xaa Xaa Xaa Xaa Xaa Leu Gly Ser Gly Thr
                85                  90                  95

Gln Val Thr Val Ser Ser
            100

<210> SEQ ID NO 17
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 17

Ala Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Xaa Xaa
            20                  25                  30

Xaa Xaa Xaa Trp Val Arg Gln Ala Pro Gly Lys Val Leu Glu Trp Val
        35                  40                  45

Ser Xaa Xaa Xaa Xaa Xaa Arg Phe Thr Ile Ser Arg Asp Asn Ala Lys
    50                  55                  60
```

```
Asn Thr Leu Tyr Leu Gln Met Asn Ser Leu Lys Pro Glu Asp Thr Ala
 65                  70                  75                  80

Val Tyr Tyr Cys Val Lys Xaa Xaa Xaa Xaa Gly Ser Gln Gly Thr
                 85                  90                  95

Gln Val Thr Val Ser Ser
                100

<210> SEQ ID NO 18
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 18

Glu Val Gln Leu Val Glu Ser Gly Gly Gly Leu Val Gln Pro Gly Gly
  1               5                  10                  15

Ser Leu Arg Leu Ser Cys Val Cys Val Ser Ser Gly Cys Thr Xaa Xaa
             20                  25                  30

Xaa Xaa Xaa Trp Val Arg Gln Ala Pro Gly Lys Ala Glu Glu Trp Val
             35                  40                  45

Ser Xaa Xaa Xaa Xaa Xaa Arg Phe Lys Ile Ser Arg Asp Asn Ala Lys
 50                  55                  60

Lys Thr Leu Tyr Leu Gln Met Asn Ser Leu Gly Pro Glu Asp Thr Ala
 65                  70                  75                  80

Met Tyr Tyr Cys Gln Arg Xaa Xaa Xaa Xaa Xaa Arg Gly Gln Gly Thr
                 85                  90                  95

Gln Val Thr Val Ser Ser
                100

<210> SEQ ID NO 19
<211> LENGTH: 102
<212> TYPE: PRT
<213> ORGANISM: Artificial
<220> FEATURE:
<223> OTHER INFORMATION: GLEW-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 19

Glu Val Gln Leu Val Glu Ser Gly Gly Gly Leu Ala Leu Pro Gly Gly
  1               5                  10                  15

Ser Leu Thr Leu Ser Cys Val Phe Ser Gly Ser Thr Phe Ser Xaa Xaa
```

```
                    20                  25                  30
Xaa Xaa Xaa Trp Val Arg His Thr Pro Gly Lys Ala Glu Glu Trp Val
            35                  40                  45

Ser Xaa Xaa Xaa Xaa Arg Phe Thr Ile Ser Arg Asp Asn Ala Lys
    50                  55                  60

Asn Thr Leu Tyr Leu Glu Met Asn Ser Leu Ser Pro Glu Asp Thr Ala
65                  70                  75                  80

Met Tyr Tyr Cys Gly Arg Xaa Xaa Xaa Xaa Arg Ser Lys Gly Ile
                85                  90                  95

Gln Val Thr Val Ser Ser
            100

<210> SEQ ID NO 20
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 20

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Xaa Xaa
            20                  25                  30

Xaa Xaa Xaa Trp Phe Arg Gln Ala Pro Gly Lys Glu Arg Glu Phe Val
            35                  40                  45

Ala Xaa Xaa Xaa Xaa Xaa Arg Phe Thr Ile Ser Arg Asp Asn Ala Lys
    50                  55                  60

Asn Thr Val Tyr Leu Gln Met Asn Ser Leu Lys Pro Glu Asp Thr Ala
65                  70                  75                  80

Val Tyr Tyr Cys Ala Ala Xaa Xaa Xaa Xaa Xaa Arg Gly Gln Gly Thr
                85                  90                  95

Gln Val Thr Val Ser Ser
            100

<210> SEQ ID NO 21
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid
```

<400> SEQUENCE: 21

Asp Val Gln Leu Val Glu Ser Gly Gly Asp Leu Val Gln Pro Gly Gly
1               5                   10                  15

Ser Leu Arg Leu Ser Cys Ala Ala Ser Gly Phe Ser Phe Asp Xaa Xaa
            20                  25                  30

Xaa Xaa Xaa Trp Leu Arg Gln Thr Pro Gly Lys Gly Leu Glu Trp Val
        35                  40                  45

Gly Xaa Xaa Xaa Xaa Arg Phe Thr Ile Ser Arg Asp Asn Ala Lys
    50                  55                  60

Asn Met Leu Tyr Leu His Leu Asn Asn Leu Lys Ser Glu Asp Thr Ala
65                  70                  75                  80

Val Tyr Tyr Cys Arg Arg Xaa Xaa Xaa Xaa Xaa Leu Gly Gln Gly Thr
                85                  90                  95

Gln Val Thr Val Ser Ser
            100

<210> SEQ ID NO 22
<211> LENGTH: 102
<212> TYPE: PRT
<213> ORGANISM: Artificial
<220> FEATURE:
<223> OTHER INFORMATION: P,R,S 103-class Nanobody
<220> FEATURE:
<221> NAME/KEY: misc_feature
<222> LOCATION: (31)..(35)
<223> OTHER INFORMATION: Xaa is any amino acid
<220> FEATURE:
<221> NAME/KEY: misc_feature
<222> LOCATION: (50)..(54)
<223> OTHER INFORMATION: Xaa is any amino acid
<220> FEATURE:
<221> NAME/KEY: misc_feature
<222> LOCATION: (87)..(91)
<223> OTHER INFORMATION: Xaa is any amino acid

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr Xaa Xaa
            20                  25                  30

Xaa Xaa Xaa Trp Val Arg Gln Ala Pro Gly Lys Ala Glu Trp Val
        35                  40                  45

Ser Xaa Xaa Xaa Xaa Xaa Arg Phe Lys Ile Ser Arg Asp Asn Ala Lys
    50                  55                  60

Lys Thr Leu Tyr Leu Gln Met Asn Ser Leu Gly Pro Glu Asp Thr Ala
65                  70                  75                  80

Met Tyr Tyr Cys Gln Arg Xaa Xaa Xaa Xaa Xaa Arg Gly Gln Gly Thr
                85                  90                  95

Gln Val Thr Val Ser Ser
            100

<210> SEQ ID NO 23
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 23

Gln Val Gln Arg Val Glu Ser Gly Gly Gly Leu Val Gln Ala Gly Gly
1               5                   10                  15

```
Ser Leu Arg Leu Ser Cys Ala Ala Ser Gly Arg Thr Ser Ser
            20                  25                  30
```

<210> SEQ ID NO 24
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 24

```
Gln Val Gln Leu Val Glu Ser Gly Gly Gly Leu Val Gln Thr Gly Asp
1               5                   10                  15

Ser Leu Ser Leu Ser Cys Ser Ala Ser Gly Arg Thr Phe Ser
            20                  25                  30
```

<210> SEQ ID NO 25
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 25

```
Gln Val Lys Leu Glu Glu Ser Gly Gly Gly Leu Val Gln Ala Gly Asp
1               5                   10                  15

Ser Leu Arg Leu Ser Cys Ala Ala Thr Gly Arg Ala Phe Gly
            20                  25                  30
```

<210> SEQ ID NO 26
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 26

```
Ala Val Gln Leu Val Glu Ser Gly Gly Gly Leu Val Gln Pro Gly Glu
1               5                   10                  15

Ser Leu Gly Leu Ser Cys Val Ala Ser Gly Arg Asp Phe Val
            20                  25                  30
```

<210> SEQ ID NO 27
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 27

```
Glu Val Gln Leu Val Glu Ser Gly Gly Gly Leu Val Gln Ala Gly Gly
1               5                   10                  15

Ser Leu Arg Leu Ser Cys Glu Val Leu Gly Arg Thr Ala Gly
            20                  25                  30
```

<210> SEQ ID NO 28
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 28

```
Gln Val Gln Leu Val Glu Ser Gly Gly Gly Trp Val Gln Pro Gly Gly
```

```
1               5                   10                  15
Ser Leu Arg Leu Ser Cys Ala Ala Ser Glu Thr Ile Leu Ser
            20                  25                  30

<210> SEQ ID NO 29
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 29

Gln Val Gln Leu Val Glu Ser Gly Gly Gly Thr Val Gln Pro Gly Gly
1               5                   10                  15

Ser Leu Asn Leu Ser Cys Val Ala Ser Gly Asn Thr Phe Asn
            20                  25                  30

<210> SEQ ID NO 30
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 30

Glu Val Gln Leu Val Glu Ser Gly Gly Gly Leu Ala Gln Pro Gly Gly
1               5                   10                  15

Ser Leu Gln Leu Ser Cys Ser Ala Pro Gly Phe Thr Leu Asp
            20                  25                  30

<210> SEQ ID NO 31
<211> LENGTH: 30
<212> TYPE: PRT
<213> ORGANISM: Artificial
<220> FEATURE:
<223> OTHER INFORMATION: KERE-class Nanobody FW1 sequence

<400> SEQUENCE: 31

Ala Gln Glu Leu Glu Glu Ser Gly Gly Gly Leu Val Gln Ala Gly Gly
1               5                   10                  15

Ser Leu Arg Leu Ser Cys Ala Ala Ser Gly Arg Thr Phe Asn
            20                  25                  30

<210> SEQ ID NO 32
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 32

Val Glu Ser Gly Gly Gly Leu Val Gln Pro Gly Gly Ser Leu Arg Leu
1               5                   10                  15

Ser Cys Ala Ala Ser Gly
            20

<210> SEQ ID NO 33
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 33
```

Val Asp Ser Gly Gly Gly Leu Val Gln Ala Gly Asp Ser Leu Lys Leu
1               5                   10                  15

Ser Cys Ala Leu Thr Gly
            20

<210> SEQ ID NO 34
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 34

Val Asp Ser Gly Gly Gly Leu Val Gln Ala Gly Asp Ser Leu Arg Leu
1               5                   10                  15

Ser Cys Ala Ala Ser Gly
            20

<210> SEQ ID NO 35
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 35

Val Asp Ser Gly Gly Gly Leu Val Glu Ala Gly Gly Ser Leu Arg Leu
1               5                   10                  15

Ser Cys Gln Val Ser Glu
            20

<210> SEQ ID NO 36
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 36

Gln Asp Ser Gly Gly Gly Ser Val Gln Ala Gly Gly Ser Leu Lys Leu
1               5                   10                  15

Ser Cys Ala Ala Ser Gly
            20

<210> SEQ ID NO 37
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 37

Val Gln Ser Gly Gly Arg Leu Val Gln Ala Gly Asp Ser Leu Arg Leu
1               5                   10                  15

Ser Cys Ala Ala Ser Glu
            20

<210> SEQ ID NO 38
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 38

```
Val Glu Ser Gly Gly Thr Leu Val Gln Ser Gly Asp Ser Leu Lys Leu
1               5                   10                  15

Ser Cys Ala Ser Ser Thr
            20
```

<210> SEQ ID NO 39
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 39

```
Met Glu Ser Gly Gly Asp Ser Val Gln Ser Gly Gly Ser Leu Thr Leu
1               5                   10                  15

Ser Cys Val Ala Ser Gly
            20
```

<210> SEQ ID NO 40
<211> LENGTH: 22
<212> TYPE: PRT
<213> ORGANISM: Artificial
<220> FEATURE:
<223> OTHER INFORMATION: KERE-class Nanobody FW1 sequence

<400> SEQUENCE: 40

```
Gln Ala Ser Gly Gly Gly Leu Val Gln Ala Gly Gly Ser Leu Arg Leu
1               5                   10                  15

Ser Cys Ser Ala Ser Val
            20
```

<210> SEQ ID NO 41
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 41

```
Trp Phe Arg Gln Ala Pro Gly Lys Glu Arg Glu Phe Val Ala
1               5                   10
```

<210> SEQ ID NO 42
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 42

```
Trp Phe Arg Gln Thr Pro Gly Arg Glu Arg Glu Phe Val Ala
1               5                   10
```

<210> SEQ ID NO 43
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 43

```
Trp Tyr Arg Gln Ala Pro Gly Lys Gln Arg Glu Met Val Ala
1               5                   10
```

<210> SEQ ID NO 44
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 44

Trp Tyr Arg Gln Gly Pro Gly Lys Gln Arg Glu Leu Val Ala
1               5                   10

<210> SEQ ID NO 45
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 45

Trp Ile Arg Gln Ala Pro Gly Lys Glu Arg Glu Gly Val Ser
1               5                   10

<210> SEQ ID NO 46
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 46

Trp Phe Arg Glu Ala Pro Gly Lys Glu Arg Glu Gly Ile Ser
1               5                   10

<210> SEQ ID NO 47
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 47

Trp Tyr Arg Gln Ala Pro Gly Lys Glu Arg Asp Leu Val Ala
1               5                   10

<210> SEQ ID NO 48
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 48

Trp Phe Arg Gln Ala Pro Gly Lys Gln Arg Glu Glu Val Ser
1               5                   10

<210> SEQ ID NO 49
<211> LENGTH: 14
<212> TYPE: PRT
<213> ORGANISM: Artificial
<220> FEATURE:
<223> OTHER INFORMATION: KERE-class Nanobody FW2 sequence

<400> SEQUENCE: 49

Trp Phe Arg Gln Pro Pro Gly Lys Val Arg Glu Phe Val Gly
1               5                   10

<210> SEQ ID NO 50

```
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 50

Arg Phe Thr Ile Ser Arg Asp Asn Ala Lys Asn Thr Val Tyr Leu Gln
1               5                   10                  15
Met Asn Ser Leu Lys Pro Glu Asp Thr Ala Val Tyr Arg Cys Tyr Phe
            20                  25                  30

<210> SEQ ID NO 51
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 51

Arg Phe Ala Ile Ser Arg Asp Asn Asn Lys Asn Thr Gly Tyr Leu Gln
1               5                   10                  15
Met Asn Ser Leu Glu Pro Glu Asp Thr Ala Val Tyr Tyr Cys Ala Ala
            20                  25                  30

<210> SEQ ID NO 52
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 52

Arg Phe Thr Val Ala Arg Asn Asn Ala Lys Asn Thr Val Asn Leu Glu
1               5                   10                  15
Met Asn Ser Leu Lys Pro Glu Asp Thr Ala Val Tyr Tyr Cys Ala Ala
            20                  25                  30

<210> SEQ ID NO 53
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 53

Arg Phe Thr Ile Ser Arg Asp Ile Ala Lys Asn Thr Val Asp Leu Leu
1               5                   10                  15
Met Asn Asn Leu Glu Pro Glu Asp Thr Ala Val Tyr Tyr Cys Ala Ala
            20                  25                  30

<210> SEQ ID NO 54
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 54

Arg Leu Thr Ile Ser Arg Asp Asn Ala Val Asp Thr Met Tyr Leu Gln
1               5                   10                  15
Met Asn Ser Leu Lys Pro Glu Asp Thr Ala Val Tyr Tyr Cys Ala Ala
            20                  25                  30
```

-continued

```
<210> SEQ ID NO 55
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 55

Arg Phe Thr Ile Ser Arg Asp Asn Ala Lys Asn Thr Val Tyr Leu Gln
1               5                   10                  15

Met Asp Asn Val Lys Pro Glu Asp Thr Ala Ile Tyr Tyr Cys Ala Ala
            20                  25                  30

<210> SEQ ID NO 56
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 56

Arg Phe Thr Ile Ser Lys Asp Ser Gly Lys Asn Thr Val Tyr Leu Gln
1               5                   10                  15

Met Thr Ser Leu Lys Pro Glu Asp Thr Ala Val Tyr Tyr Cys Ala Thr
            20                  25                  30

<210> SEQ ID NO 57
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 57

Arg Phe Thr Ile Ser Arg Asp Ser Ala Lys Asn Met Met Tyr Leu Gln
1               5                   10                  15

Met Asn Asn Leu Lys Pro Gln Asp Thr Ala Val Tyr Tyr Cys Ala Ala
            20                  25                  30

<210> SEQ ID NO 58
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 58

Arg Phe Thr Ile Ser Arg Glu Asn Asp Lys Ser Thr Val Tyr Leu Gln
1               5                   10                  15

Leu Asn Ser Leu Lys Pro Glu Asp Thr Ala Val Tyr Tyr Cys Ala Ala
            20                  25                  30

<210> SEQ ID NO 59
<211> LENGTH: 32
<212> TYPE: PRT
<213> ORGANISM: Artificial
<220> FEATURE:
<223> OTHER INFORMATION: KERE-class Nanobody FW3 sequence

<400> SEQUENCE: 59

Arg Phe Thr Ile Ser Arg Asp Tyr Ala Gly Asn Thr Ala Tyr Leu Gln
1               5                   10                  15

Met Asn Ser Leu Lys Pro Glu Asp Thr Gly Val Tyr Tyr Cys Ala Thr
            20                  25                  30
```

<210> SEQ ID NO 60
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 60

Trp Gly Gln Gly Thr Gln Val Thr Val Ser Ser
1               5                   10

<210> SEQ ID NO 61
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 61

Trp Gly Lys Gly Thr Leu Val Thr Val Ser Ser
1               5                   10

<210> SEQ ID NO 62
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 62

Arg Gly Gln Gly Thr Arg Val Thr Val Ser Ser
1               5                   10

<210> SEQ ID NO 63
<211> LENGTH: 11
<212> TYPE: PRT
<213> ORGANISM: Artificial
<220> FEATURE:
<223> OTHER INFORMATION: KERE-class Nanobody FW4 sequence

<400> SEQUENCE: 63

Trp Gly Leu Gly Thr Gln Val Thr Ile Ser Ser
1               5                   10

<210> SEQ ID NO 64
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 64

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 65
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 65

Glu Val His Leu Val Glu Ser Gly Gly Gly Leu Val Arg Pro Gly Gly
1               5                   10                  15

```
                1               5                  10                  15
Ser Leu Arg Leu Ser Cys Ala Ala Phe Gly Phe Ile Phe Lys
                20                  25                  30
```

<210> SEQ ID NO 66
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 66

```
Gln Val Lys Leu Glu Glu Ser Gly Gly Gly Leu Ala Gln Pro Gly Gly
1               5                   10                  15
Ser Leu Arg Leu Ser Cys Val Ala Ser Gly Phe Thr Phe Ser
                20                  25                  30
```

<210> SEQ ID NO 67
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 67

```
Glu Val Gln Leu Val Glu Ser Gly Gly Gly Leu Val Gln Pro Gly Gly
1               5                   10                  15
Ser Leu Arg Leu Ser Cys Val Cys Val Ser Ser Gly Cys Thr
                20                  25                  30
```

<210> SEQ ID NO 68
<211> LENGTH: 30
<212> TYPE: PRT
<213> ORGANISM: Artificial
<220> FEATURE:
<223> OTHER INFORMATION: GLEW-class Nanobody FW1 sequence

<400> SEQUENCE: 68

```
Glu Val Gln Leu Val Glu Ser Gly Gly Gly Leu Ala Leu Pro Gly Gly
1               5                   10                  15
Ser Leu Thr Leu Ser Cys Val Phe Ser Gly Ser Thr Phe Ser
                20                  25                  30
```

<210> SEQ ID NO 69
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 69

```
Val Glu Ser Gly Gly Gly Leu Val Gln Pro Gly Gly Ser Leu Arg Leu
1               5                   10                  15
Ser Cys Ala Ala Ser Gly
                20
```

<210> SEQ ID NO 70
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 70

-continued

```
Glu Glu Ser Gly Gly Gly Leu Ala Gln Pro Gly Gly Ser Leu Arg Leu
1               5                   10                  15

Ser Cys Val Ala Ser Gly
            20

<210> SEQ ID NO 71
<211> LENGTH: 22
<212> TYPE: PRT
<213> ORGANISM: Artificial
<220> FEATURE:
<223> OTHER INFORMATION: GLEW-class Nanobody FW1 sequence

<400> SEQUENCE: 71

Val Glu Ser Gly Gly Gly Leu Ala Leu Pro Gly Gly Ser Leu Thr Leu
1               5                   10                  15

Ser Cys Val Phe Ser Gly
            20

<210> SEQ ID NO 72
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 72

Trp Val Arg Gln Ala Pro Gly Lys Val Leu Glu Trp Val Ser
1               5                   10

<210> SEQ ID NO 73
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 73

Trp Val Arg Arg Pro Pro Gly Lys Gly Leu Glu Trp Val Ser
1               5                   10

<210> SEQ ID NO 74
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 74

Trp Val Arg Gln Ala Pro Gly Met Gly Leu Glu Trp Val Ser
1               5                   10

<210> SEQ ID NO 75
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 75

Trp Val Arg Gln Ala Pro Gly Lys Glu Pro Glu Trp Val Ser
1               5                   10

<210> SEQ ID NO 76
<211> LENGTH: 14
<212> TYPE: PRT
<213> ORGANISM: Artificial
```

```
<220> FEATURE:
<223> OTHER INFORMATION: GLEW-class Nanobody FW2 sequence

<400> SEQUENCE: 76

Trp Val Arg Gln Ala Pro Gly Lys Asp Gln Glu Trp Val Ser
1               5                   10

<210> SEQ ID NO 77
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 77

Trp Val Arg Gln Ala Pro Gly Lys Ala Glu Glu Trp Val Ser
1               5                   10

<210> SEQ ID NO 78
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 78

Trp Val Arg Gln Ala Pro Gly Lys Gly Leu Glu Trp Val Ala
1               5                   10

<210> SEQ ID NO 79
<211> LENGTH: 14
<212> TYPE: PRT
<213> ORGANISM: Artificial
<220> FEATURE:
<223> OTHER INFORMATION: GLEW-class Nanobody FW2 sequence

<400> SEQUENCE: 79

Trp Val Arg Gln Ala Pro Gly Arg Ala Thr Glu Trp Val Ser
1               5                   10

<210> SEQ ID NO 80
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 80

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Tyr Cys Val Lys
                20                  25                  30

<210> SEQ ID NO 81
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 81

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
                20                  25                  30
```

<210> SEQ ID NO 82
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 82

Arg Phe Thr Ser Ser Arg Asp Asn Ala Lys Ser Thr Leu Tyr Leu Gln
1               5                   10                  15

Met Asn Asp Leu Lys Pro Glu Asp Thr Ala Leu Tyr Tyr Cys Ala Arg
            20                  25                  30

<210> SEQ ID NO 83
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 83

Arg Phe Ile Ile Ser Arg Asp Asn Ala Lys Asn Thr Leu Tyr Leu Gln
1               5                   10                  15

Met Asn Ser Leu Gly Pro Glu Asp Thr Ala Met Tyr Tyr Cys Gln Arg
            20                  25                  30

<210> SEQ ID NO 84
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 84

Arg Phe Thr Ala Ser Arg Asp Asn Ala Lys Asn Thr Leu Tyr Leu Gln
1               5                   10                  15

Met Asn Ser Leu Lys Ser Glu Asp Thr Ala Arg Tyr Tyr Cys Ala Arg
            20                  25                  30

<210> SEQ ID NO 85
<211> LENGTH: 32
<212> TYPE: PRT
<213> ORGANISM: Artificial
<220> FEATURE:
<223> OTHER INFORMATION: GLEW-class Nanobody FW3 sequence

<400> SEQUENCE: 85

Arg Phe Thr Ile Ser Arg Asp Asn Ala Lys Asn Thr Leu Tyr Leu Gln
1               5                   10                  15

Met Asp Asp Leu Gln Ser Glu Asp Thr Ala Met Tyr Tyr Cys Gly Arg
            20                  25                  30

<210> SEQ ID NO 86
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 86

Gly Ser Gln Gly Thr Gln Val Thr Val Ser Ser
1               5                   10

<210> SEQ ID NO 87

```
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 87

Leu Arg Gly Gly Thr Gln Val Thr Val Ser Ser
1               5                   10

<210> SEQ ID NO 88
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 88

Arg Gly Gln Gly Thr Leu Val Thr Val Ser Ser
1               5                   10

<210> SEQ ID NO 89
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 89

Arg Ser Arg Gly Ile Gln Val Thr Val Ser Ser
1               5                   10

<210> SEQ ID NO 90
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 90

Trp Gly Lys Gly Thr Gln Val Thr Val Ser Ser
1               5                   10

<210> SEQ ID NO 91
<211> LENGTH: 11
<212> TYPE: PRT
<213> ORGANISM: Artificial
<220> FEATURE:
<223> OTHER INFORMATION: GLEW-class Nanobody FW4 sequence

<400> SEQUENCE: 91

Trp Gly Gln Gly Thr Gln Val Thr Val Ser Ser
1               5                   10

<210> SEQ ID NO 92
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 92

Ala Val Gln Leu Val Glu Ser Gly Gly Gly Leu Val Gln Ala Gly Gly
1               5                   10                  15
Ser Leu Arg Leu Ser Cys Ala Ala Ser Gly Arg Thr Phe Ser
            20                  25                  30
```

<210> SEQ ID NO 93
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 93

Gln Val Gln Leu Gln Glu Ser Gly Gly Gly Met Val Gln Pro Gly Gly
1               5                   10                  15

Ser Leu Arg Leu Ser Cys Ala Ala Ser Gly Phe Asp Phe Gly
            20                  25                  30

<210> SEQ ID NO 94
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 94

Glu Val His Leu Val Glu Ser Gly Gly Gly Leu Val Arg Pro Gly Gly
1               5                   10                  15

Ser Leu Arg Leu Ser Cys Ala Ala Phe Gly Phe Ile Phe Lys
            20                  25                  30

<210> SEQ ID NO 95
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 95

Gln Val Gln Leu Ala Glu Ser Gly Gly Gly Leu Val Gln Pro Gly Gly
1               5                   10                  15

Ser Leu Lys Leu Ser Cys Ala Ala Ser Arg Thr Ile Val Ser
            20                  25                  30

<210> SEQ ID NO 96
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 96

Gln Glu His Leu Val Glu Ser Gly Gly Gly Leu Val Asp Ile Gly Gly
1               5                   10                  15

Ser Leu Arg Leu Ser Cys Ala Ala Ser Glu Arg Ile Phe Ser
            20                  25                  30

<210> SEQ ID NO 97
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 97

Gln Val Lys Leu Glu Glu Ser Gly Gly Gly Leu Ala Gln Pro Gly Gly
1               5                   10                  15

Ser Leu Arg Leu Ser Cys Val Ala Ser Gly Phe Thr Phe Ser
            20                  25                  30

<210> SEQ ID NO 98
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Val Cys Val Ser Ser Gly Cys Thr
            20                  25                  30

<210> SEQ ID NO 99
<211> LENGTH: 30
<212> TYPE: PRT
<213> ORGANISM: Artificial
<220> FEATURE:
<223> OTHER INFORMATION: P,R,S 103-class Nanobody FW1 sequence

<400> SEQUENCE: 99

Glu Val Gln Leu Val Glu Ser Gly Gly Gly Leu Ala Leu Pro Gly Gly
1               5                   10                  15

Ser Leu Thr Leu Ser Cys Val Phe Ser Gly Ser Thr Phe Ser
            20                  25                  30

<210> SEQ ID NO 100
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 100

Val Glu Ser Gly Gly Gly Leu Val Gln Ala Gly Gly Ser Leu Arg Leu
1               5                   10                  15

Ser Cys Ala Ala Ser Gly
            20

<210> SEQ ID NO 101
<211> LENGTH: 22
<212> TYPE: PRT
<213> ORGANISM: Artificial
<220> FEATURE:
<223> OTHER INFORMATION: P,R,S 103-class Nanobody FW1 sequence

<400> SEQUENCE: 101

Ala Glu Ser Gly Gly Gly Leu Val Gln Pro Gly Gly Ser Leu Lys Leu
1               5                   10                  15

Ser Cys Ala Ala Ser Arg
            20

<210> SEQ ID NO 102
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 102

Trp Phe Arg Gln Ala Pro Gly Lys Glu Arg Glu Phe Val Ala
1               5                   10

```
<210> SEQ ID NO 103
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 103

Trp Val Arg Gln Ala Pro Gly Lys Val Leu Glu Trp Val Ser
1               5                   10

<210> SEQ ID NO 104
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 104

Trp Val Arg Arg Pro Pro Gly Lys Gly Leu Glu Trp Val Ser
1               5                   10

<210> SEQ ID NO 105
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 105

Trp Ile Arg Gln Ala Pro Gly Lys Glu Arg Glu Gly Val Ser
1               5                   10

<210> SEQ ID NO 106
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 106

Trp Val Arg Gln Tyr Pro Gly Lys Glu Pro Glu Trp Val Ser
1               5                   10

<210> SEQ ID NO 107
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 107

Trp Phe Arg Gln Pro Pro Gly Lys Glu His Glu Phe Val Ala
1               5                   10

<210> SEQ ID NO 108
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 108

Trp Tyr Arg Gln Ala Pro Gly Lys Arg Thr Glu Leu Val Ala
1               5                   10

<210> SEQ ID NO 109
```

-continued

```
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 109

Trp Leu Arg Gln Ala Pro Gly Gln Gly Leu Glu Trp Val Ser
1               5                   10

<210> SEQ ID NO 110
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 110

Trp Leu Arg Gln Thr Pro Gly Lys Gly Leu Glu Trp Val Gly
1               5                   10

<210> SEQ ID NO 111
<211> LENGTH: 14
<212> TYPE: PRT
<213> ORGANISM: Artificial
<220> FEATURE:
<223> OTHER INFORMATION: P,R,S 103-class Nanobody FW2 sequence

<400> SEQUENCE: 111

Trp Val Arg Gln Ala Pro Gly Lys Ala Glu Glu Phe Val Ser
1               5                   10

<210> SEQ ID NO 112
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 112

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
                20                  25                  30

<210> SEQ ID NO 113
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 113

Arg Phe Thr Ile Ser Arg Asp Asn Ala Arg Asn Thr Leu Tyr Leu Gln
1               5                   10                  15

Met Asp Ser Leu Ile Pro Glu Asp Thr Ala Leu Tyr Tyr Cys Ala Arg
                20                  25                  30

<210> SEQ ID NO 114
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 114
```

Arg Phe Thr Ile Ser Arg Asp Asn Ala Lys Asn Glu Met Tyr Leu Gln
1               5                   10                  15

Met Asn Asn Leu Lys Thr Glu Asp Thr Gly Val Tyr Trp Cys Gly Ala
            20                  25                  30

<210> SEQ ID NO 115
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 115

Arg Phe Thr Ile Ser Ser Asp Ser Asn Arg Asn Met Ile Tyr Leu Gln
1               5                   10                  15

Met Asn Asn Leu Lys Pro Glu Asp Thr Ala Val Tyr Tyr Cys Ala Ala
            20                  25                  30

<210> SEQ ID NO 116
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 116

Arg Phe Thr Ile Ser Arg Asp Asn Ala Lys Asn Met Leu Tyr Leu His
1               5                   10                  15

Leu Asn Asn Leu Lys Ser Glu Asp Thr Ala Val Tyr Tyr Cys Arg Arg
            20                  25                  30

<210> SEQ ID NO 117
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 117

Arg Phe Thr Ile Ser Arg Asp Asn Ala Lys Lys Thr Val Tyr Leu Arg
1               5                   10                  15

Leu Asn Ser Leu Asn Pro Glu Asp Thr Ala Val Tyr Ser Cys Asn Leu
            20                  25                  30

<210> SEQ ID NO 118
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 118

Arg Phe Lys Ile Ser Arg Asp Asn Ala Lys Lys Thr Leu Tyr Leu Gln
1               5                   10                  15

Met Asn Ser Leu Gly Pro Glu Asp Thr Ala Met Tyr Tyr Cys Gln Arg
            20                  25                  30

<210> SEQ ID NO 119
<211> LENGTH: 32
<212> TYPE: PRT
<213> ORGANISM: Artificial
<220> FEATURE:
<223> OTHER INFORMATION: P,R,S 103-class Nanobody FW3 sequence

<400> SEQUENCE: 119

```
Arg Phe Thr Val Ser Arg Asp Asn Gly Lys Asn Thr Ala Tyr Leu Arg
1               5                   10                  15

Met Asn Ser Leu Lys Pro Glu Asp Thr Ala Asp Tyr Tyr Cys Ala Val
                20                  25                  30
```

<210> SEQ ID NO 120
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 120

```
Arg Gly Gln Gly Thr Gln Val Thr Val Ser Ser
1               5                   10
```

<210> SEQ ID NO 121
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 121

```
Leu Arg Gly Gly Thr Gln Val Thr Val Ser Ser
1               5                   10
```

<210> SEQ ID NO 122
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 122

```
Gly Asn Lys Gly Thr Leu Val Thr Val Ser Ser
1               5                   10
```

<210> SEQ ID NO 123
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 123

```
Ser Ser Pro Gly Thr Gln Val Thr Val Ser Ser
1               5                   10
```

<210> SEQ ID NO 124
<211> LENGTH: 11
<212> TYPE: PRT
<213> ORGANISM: Artificial
<220> FEATURE:
<223> OTHER INFORMATION: P,R,S 103-class Nanobody FW4 sequence

<400> SEQUENCE: 124

```
Ser Ser Gln Gly Thr Leu Val Thr Val Ser Ser
1               5                   10
```

<210> SEQ ID NO 125
<211> LENGTH: 11
<212> TYPE: PRT
<213> ORGANISM: Artificial
<220> FEATURE:
<223> OTHER INFORMATION: P,R,S 103-class Nanobody FW4 sequence

```
<400> SEQUENCE: 125

Arg Ser Arg Gly Ile Gln Val Thr Val Ser Ser
1               5                   10

<210> SEQ ID NO 126
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 126

Glu Val Gln Leu Val Glu Ser Gly Gly Gly Leu Val Gln Ala Gly Gly
1               5                   10                  15

Ser Leu Arg Leu Ala Cys Ala Ala Ser Gly Ser Ile Phe Ser
            20                  25                  30

<210> SEQ ID NO 127
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 127

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser
            20                  25                  30

<210> SEQ ID NO 128
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 128

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Thr
            20                  25                  30

<210> SEQ ID NO 129
<211> LENGTH: 30
<212> TYPE: PRT
<213> ORGANISM: Artificial
<220> FEATURE:
<223> OTHER INFORMATION: nanbody or nanobody fragment

<400> SEQUENCE: 129

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Asn
            20                  25                  30

<210> SEQ ID NO 130
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 130
```

Glu Val Gln Leu Val Glu Ser Gly Gly Gly Leu Val Gln Ala Gly Gly
1               5                   10                  15

Ser Leu Arg Leu Ser Cys Ala Ala Ser Arg Arg Thr Phe Ser
            20                  25                  30

<210> SEQ ID NO 131
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 131

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Val
            20                  25                  30

<210> SEQ ID NO 132
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 132

Glu Val Gln Leu Val Lys Ser Gly Gly Gly Leu Val Gln Ala Gly Gly
1               5                   10                  15

Ser Leu Arg Leu Ser Cys Ala Ala Ser Gly Arg Thr Leu Ser
            20                  25                  30

<210> SEQ ID NO 133
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 133

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Arg
            20                  25                  30

<210> SEQ ID NO 134
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 134

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser
            20                  25                  30

<210> SEQ ID NO 135
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 135

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser
            20                  25                  30

<210> SEQ ID NO 136
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 136

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Leu Thr
            20                  25                  30

<210> SEQ ID NO 137
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 137

Glu Val Gln Leu Val Glu Ser Gly Gly Gly Leu Glu Gln Ala Gly Gly
1               5                   10                  15

Ser Leu Arg Leu Ser Cys Ala Val Ser Arg Ser Ile Phe Glu
            20                  25                  30

<210> SEQ ID NO 138
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 138

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser
            20                  25                  30

<210> SEQ ID NO 139
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 139

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Arg
            20                  25                  30

<210> SEQ ID NO 140
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 140

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Thr
            20                  25                  30

<210> SEQ ID NO 141
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 141

Glu Val Gln Leu Val Glu Ser Gly Gly Gly Leu Val Gln Ala Gly Gly
1               5                   10                  15

Ser Leu Arg Leu Ala Cys Ala Ala Ser Gly Ser Ile Phe Ser
            20                  25                  30

<210> SEQ ID NO 142
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 142

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Asn
            20                  25                  30

<210> SEQ ID NO 143
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 143

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser
            20                  25                  30

<210> SEQ ID NO 144
<211> LENGTH: 30
<212> TYPE: PRT
<213> ORGANISM: Artificial
<220> FEATURE:
<223> OTHER INFORMATION: nanbody or nanobody fragment

<400> SEQUENCE: 144

Glu Val Gln Leu Val Glu Ser Gly Gly Gly Leu Val Gln Ala Gly Gly
1               5                   10                  15

Ser Leu Arg Leu Ser Cys Ser Ser Ser Gly Phe Thr Ser Thr
            20                  25                  30

<210> SEQ ID NO 145
<211> LENGTH: 30
<212> TYPE: PRT
<213> ORGANISM: Artificial
<220> FEATURE:

<223> OTHER INFORMATION: Nanobody or Nanobody fragment

<400> SEQUENCE: 145

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe Ala
            20                  25                  30

<210> SEQ ID NO 146
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 147
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 147

Glu Val Gln Leu Val Glu Ser Gly Gly Gly Leu Val Gln Thr Gly Gly
1               5                   10                  15

Ser Leu Arg Leu Ser Cys Ala Ala Ser Gly Met Thr Phe Arg
            20                  25                  30

<210> SEQ ID NO 148
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 148

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Arg Ser Ser
            20                  25                  30

<210> SEQ ID NO 149
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 149

Glu Val Gln Leu Val Glu Ser Gly Gly Gly Leu Val Gln Ala Gly Gly
1               5                   10                  15

Ser Leu Arg Leu Ser Cys Val Ala Ser Gly Asn Ile Phe Ser
            20                  25                  30

<210> SEQ ID NO 150
<211> LENGTH: 30
<212> TYPE: PRT
<213> ORGANISM: Artificial

```
<220> FEATURE:
<223> OTHER INFORMATION: Nanobody or Nanobody fragment

<400> SEQUENCE: 150

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Arg Ser Ser
            20                  25                  30

<210> SEQ ID NO 151
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 151

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser
            20                  25                  30

<210> SEQ ID NO 152
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 152

Lys Val Gln Leu Val Glu Ser Gly Gly Gly Leu Val Gln Ala Gly Gly
1               5                   10                  15

Ser Leu Arg Leu Ser Cys Ala Ala Ser Ala Ser Ile Ile Ser
            20                  25                  30

<210> SEQ ID NO 153
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 153

Glu Val Gln Leu Val Glu Ser Gly Gly Gly Leu Val Gln Ala Gly Gly
1               5                   10                  15

Ser Leu Arg Leu Ser Cys Ala Ala Ser Ala Ser Ile Ile Ser
            20                  25                  30

<210> SEQ ID NO 154
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 154

Lys Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser
            20                  25                  30

<210> SEQ ID NO 155
<211> LENGTH: 30
<212> TYPE: PRT
```

<213> ORGANISM: Artificial
<220> FEATURE:
<223> OTHER INFORMATION: Nanobody or Nanobody fragment

<400> SEQUENCE: 155

```
Glu Val Gln Leu Val Glu Ser Gly Gly Gly Leu Val Gln Ala Gly Gly
1               5                   10                  15

Ser Leu Arg Leu Ser Cys Ala Ala Ser Ala Ser Ile Ile Ser
            20                  25                  30
```

<210> SEQ ID NO 156
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 156

```
Glu Val Gln Leu Val Glu Ser Gly Gly Gly Leu Val Gln Ala Gly Gly
1               5                   10                  15

Ala Leu Arg Leu Ser Cys Thr Ala Ser Gly Ile Thr Phe Lys
            20                  25                  30
```

<210> SEQ ID NO 157
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 157

```
Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Arg Ser Ser
            20                  25                  30
```

<210> SEQ ID NO 158
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 158

```
Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Arg Ser Ser
            20                  25                  30
```

<210> SEQ ID NO 159
<211> LENGTH: 29
<212> TYPE: PRT
<213> ORGANISM: Artificial
<220> FEATURE:
<223> OTHER INFORMATION: Nanobody or Nanobody fragment

<400> SEQUENCE: 159

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe
            20                  25
```

<210> SEQ ID NO 160
<211> LENGTH: 30

```
<212> TYPE: PRT
<213> ORGANISM: Artificial
<220> FEATURE:
<223> OTHER INFORMATION: nanbody or nanobody fragment

<400> SEQUENCE: 160

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe Ser
            20                  25                  30

<210> SEQ ID NO 161
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 161

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Asn
            20                  25                  30

<210> SEQ ID NO 162
<211> LENGTH: 29
<212> TYPE: PRT
<213> ORGANISM: Artificial
<220> FEATURE:
<223> OTHER INFORMATION: Nanobody or Nanobody fragment

<400> SEQUENCE: 162

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe
            20                  25

<210> SEQ ID NO 163
<211> LENGTH: 29
<212> TYPE: PRT
<213> ORGANISM: Artificial
<220> FEATURE:
<223> OTHER INFORMATION: Nanobody or Nanobody fragment

<400> SEQUENCE: 163

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe
            20                  25

<210> SEQ ID NO 164
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 164

Glu Val Gln Leu Val Glu Ser Gly Gly Gly Leu Val Gln Ala Gly Gly
1               5                   10                  15

Ser Leu Arg Leu Ser Cys Val Ala Ser Gly Phe Ser Phe Asp
            20                  25                  30

<210> SEQ ID NO 165
```

```
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 165

Glu Val Gln Leu Val Glu Ser Gly Gly Gly Leu Val Gln Ala Gly Gly
1               5                   10                  15

Ser Leu Arg Leu Ser Cys Ala Ala Ser Glu Ser Ile Ser Ser
            20                  25                  30

<210> SEQ ID NO 166
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 166

Glu Val Gln Leu Val Glu Ser Gly Gly Gly Leu Val Gln Ala Gly Lys
1               5                   10                  15

Ser Leu Ser Leu Ser Cys Ala Ala Ser Asp Ser Arg Phe Ser
            20                  25                  30

<210> SEQ ID NO 167
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 167

Phe Asn Ala Met Gly
1               5

<210> SEQ ID NO 168
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 168

Asn Tyr Asp Met Gly
1               5

<210> SEQ ID NO 169
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 169

Asn Tyr Asp Met Gly
1               5

<210> SEQ ID NO 170
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 170
```

Asn His Asp Met Gly
1               5

<210> SEQ ID NO 171
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 171

Ser Phe Val Met Ala
1               5

<210> SEQ ID NO 172
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 172

Asn Tyr Asp Met Gly
1               5

<210> SEQ ID NO 173
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 173

Asn Tyr Asp Met Gly
1               5

<210> SEQ ID NO 174
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 174

Asn Tyr Asp Met Gly
1               5

<210> SEQ ID NO 175
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 175

Asn Tyr Asp Val Gly
1               5

<210> SEQ ID NO 176
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 176

Asn Tyr Asp Met Gly

```
1               5
```

<210> SEQ ID NO 177
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 177

```
Asn Tyr Asp Met Gly
1               5
```

<210> SEQ ID NO 178
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 178

```
Thr Asn Thr Met Ala
1               5
```

<210> SEQ ID NO 179
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 179

```
Asn His Asp Val Gly
1               5
```

<210> SEQ ID NO 180
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 180

```
Asn Tyr Asp Leu Gly
1               5
```

<210> SEQ ID NO 181
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 181

```
Asn His Asp Met Gly
1               5
```

<210> SEQ ID NO 182
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 182

```
Phe Asn Ala Met Gly
1               5
```

<210> SEQ ID NO 183
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 183

Asp His Asp Val Gly
1               5

<210> SEQ ID NO 184
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 184

Asn Tyr Asp Met Gly
1               5

<210> SEQ ID NO 185
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 185

Asp Tyr Ala Ile Gly
1               5

<210> SEQ ID NO 186
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 186

Asn Asn Ile Met Gly
1               5

<210> SEQ ID NO 187
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 187

Gly Tyr Ala Ile Gly
1               5

<210> SEQ ID NO 188
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 188

Leu Tyr Ala Leu Ser
1               5

```
<210> SEQ ID NO 189
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 189

Phe Asp Asp Met Gly
1               5

<210> SEQ ID NO 190
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 190

Asp Asn Leu Met Gly
1               5

<210> SEQ ID NO 191
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 191

Phe Asn Asp Met Gly
1               5

<210> SEQ ID NO 192
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 192

Asn Tyr Ala Met Gly
1               5

<210> SEQ ID NO 193
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 193

Ser Ala Ala Leu Gly
1               5

<210> SEQ ID NO 194
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 194

Ser Ala Ala Leu Gly
1               5
```

```
<210> SEQ ID NO 195
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 195

Ile Ser Leu Val Gly
1               5

<210> SEQ ID NO 196
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 196

Ser Ala Ala Leu Gly
1               5

<210> SEQ ID NO 197
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 197

Arg Tyr Asp Met Gly
1               5

<210> SEQ ID NO 198
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 198

Phe Asp Asp Met Gly
1               5

<210> SEQ ID NO 199
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 199

Phe Asp Asp Met Gly
1               5

<210> SEQ ID NO 200
<211> LENGTH: 6
<212> TYPE: PRT
<213> ORGANISM: Artificial
<220> FEATURE:
<223> OTHER INFORMATION: Nanobody or Nanobody fragment

<400> SEQUENCE: 200

Ala Asn Asn Ile Met Gly
1               5

<210> SEQ ID NO 201
```

```
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 201

Asp Asn Ile Met Gly
1               5

<210> SEQ ID NO 202
<211> LENGTH: 12
<212> TYPE: PRT
<213> ORGANISM: Artificial
<220> FEATURE:
<223> OTHER INFORMATION: Nanobody or Nanobody fragment

<400> SEQUENCE: 202

Asp Asn Ser Met Gly Trp Tyr Arg Gln Ala Pro Gly
1               5                   10

<210> SEQ ID NO 203
<211> LENGTH: 6
<212> TYPE: PRT
<213> ORGANISM: Artificial
<220> FEATURE:
<223> OTHER INFORMATION: Nanobody or Nanobody fragment

<400> SEQUENCE: 203

Ala Asn Asn Ile Met Gly
1               5

<210> SEQ ID NO 204
<211> LENGTH: 6
<212> TYPE: PRT
<213> ORGANISM: Artificial
<220> FEATURE:
<223> OTHER INFORMATION: Nanobody or Nanobody fragment

<400> SEQUENCE: 204

Ala Asn Asn Ile Met Gly
1               5

<210> SEQ ID NO 205
<211> LENGTH: 5
<212> TYPE: PRT
<213> ORGANISM: Artificial
<220> FEATURE:
<223> OTHER INFORMATION: nanbody or nanobody fragment

<400> SEQUENCE: 205

Asp Tyr Ala Ile Gly
1               5

<210> SEQ ID NO 206
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 206

Phe Asn Ala Met Gly
1               5

<210> SEQ ID NO 207
<211> LENGTH: 9
```

<212> TYPE: PRT
<213> ORGANISM: Artificial
<220> FEATURE:
<223> OTHER INFORMATION: Nanobody or Nanobody fragment

<400> SEQUENCE: 207

Gly Arg Phe Asn Ile Leu Asn Met Gly
1               5

<210> SEQ ID NO 208
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 208

Trp Tyr Arg Gln Ala Pro Gly Lys Gln Arg Glu Leu Leu Ala
1               5                   10

<210> SEQ ID NO 209
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 209

Trp Phe Arg Gln Ala Pro Gly Lys Glu Arg Glu Phe Val Ala
1               5                   10

<210> SEQ ID NO 210
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 210

Trp Phe Arg Gln Ala Pro Gly Lys Glu Arg Glu Phe Val Ala
1               5                   10

<210> SEQ ID NO 211
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 211

Trp Phe Arg Gln Ala Pro Gly Lys Glu Arg Glu Phe Val Ala
1               5                   10

<210> SEQ ID NO 212
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 212

Trp Phe Arg Gln Ala Pro Gly Lys Glu Arg Glu Phe Val Ala
1               5                   10

<210> SEQ ID NO 213
<211> LENGTH: 14
<212> TYPE: PRT

```
<213> ORGANISM: Artificial
<220> FEATURE:
<223> OTHER INFORMATION: Nanobody or Nanobody fragment

<400> SEQUENCE: 213

Trp Phe Arg Gln Ala Pro Gly Lys Glu Arg Glu Phe Val Ala
1               5                   10

<210> SEQ ID NO 214
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 214

Trp Phe Arg Gln Ala Pro Gly Lys Glu Arg Glu Phe Val Ala
1               5                   10

<210> SEQ ID NO 215
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 215

Trp Phe Arg Gln Ala Pro Gly Lys Glu Arg Glu Phe Val Ala
1               5                   10

<210> SEQ ID NO 216
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 216

Trp Phe Arg Gln Ala Pro Gly Lys Glu Arg Glu Phe Val Ala
1               5                   10

<210> SEQ ID NO 217
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 217

Trp Phe Arg Gln Ala Pro Gly Lys Glu Arg Glu Phe Val Ala
1               5                   10

<210> SEQ ID NO 218
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 218

Trp Phe Arg Gln Ala Pro Gly Lys Glu Arg Glu Phe Val Ala
1               5                   10

<210> SEQ ID NO 219
<211> LENGTH: 14
<212> TYPE: PRT
<213> ORGANISM: Artificial
```

```
<220> FEATURE:
<223> OTHER INFORMATION: Nanobody or Nanobody fragment

<400> SEQUENCE: 219

Trp Phe Arg Gln Ala Pro Gly Lys Gln Arg Glu Leu Val Ala
1               5                   10

<210> SEQ ID NO 220
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 220

Trp Phe Arg Gln Ala Pro Gly Lys Glu Arg Glu Phe Val Ala
1               5                   10

<210> SEQ ID NO 221
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 221

Trp Phe Arg Gln Ala Pro Gly Lys Glu Arg Glu Phe Val Ala
1               5                   10

<210> SEQ ID NO 222
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 222

Trp Phe Arg Gln Ala Pro Gly Lys Glu Arg Glu Phe Val Ala
1               5                   10

<210> SEQ ID NO 223
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 223

Trp Tyr Arg Gln Ala Pro Gly Lys Gln Arg Glu Leu Leu Ala
1               5                   10

<210> SEQ ID NO 224
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 224

Trp Phe Arg Gln Ala Pro Gly Lys Glu Arg Glu Phe Val Ala
1               5                   10

<210> SEQ ID NO 225
<211> LENGTH: 14
<212> TYPE: PRT
<213> ORGANISM: Artificial
<220> FEATURE:
```

<223> OTHER INFORMATION: Nanobody or Nanobody fragment

<400> SEQUENCE: 225

Trp Phe Arg Gln Ala Pro Gly Lys Glu Arg Glu Phe Val Ala
1               5                   10

<210> SEQ ID NO 226
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 226

Trp Phe Arg Gln Ala Pro Gly Lys Ala Arg Thr Gly Val Ser
1               5                   10

<210> SEQ ID NO 227
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 227

Trp Tyr Arg Gln Pro Pro Gly Lys Glu Arg Glu Phe Val Ala
1               5                   10

<210> SEQ ID NO 228
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 228

Trp Phe Arg Gln Ala Pro Gly Lys Glu Arg Glu Gly Val Ser
1               5                   10

<210> SEQ ID NO 229
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 229

Trp Tyr Arg Gln Ala Pro Gly Glu Arg Arg Glu Val Val Ala
1               5                   10

<210> SEQ ID NO 230
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 230

Trp Tyr Arg Gln Ala Pro Gly Lys Gln Arg Glu Phe Val Ala
1               5                   10

<210> SEQ ID NO 231
<211> LENGTH: 14
<212> TYPE: PRT
<213> ORGANISM: Artificial
<220> FEATURE:
<223> OTHER INFORMATION: Nanobody or Nanobody fragment

```
<400> SEQUENCE: 231

Trp Tyr Arg Gln Ala Pro Gly Lys Gln Arg Glu Phe Val Ala
1               5                   10

<210> SEQ ID NO 232
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 232

Trp Tyr Arg Gln Ala Pro Gly Lys Gln Arg Glu Phe Val Ala
1               5                   10

<210> SEQ ID NO 233
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 233

Trp Phe Arg Gln Ala Pro Gly Lys Glu Arg Glu Trp Val Ala
1               5                   10

<210> SEQ ID NO 234
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 234

Trp Tyr Arg Gln Ala Pro Gly Lys Arg Arg Glu Phe Val Ala
1               5                   10

<210> SEQ ID NO 235
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 235

Trp Tyr Arg Gln Ala Pro Gly Arg Arg Arg Glu Phe Val Ala
1               5                   10

<210> SEQ ID NO 236
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 236

Trp Tyr Arg Gln Ala Pro Gly Lys Gln Arg Glu Phe Val Ala
1               5                   10

<210> SEQ ID NO 237
<211> LENGTH: 14
<212> TYPE: PRT
<213> ORGANISM: Artificial
<220> FEATURE:
<223> OTHER INFORMATION: Nanobody or Nanobody fragment
```

```
<400> SEQUENCE: 237

Trp Tyr Arg Gln Ala Pro Gly Lys Arg Arg Glu Phe Val Ala
1               5                   10

<210> SEQ ID NO 238
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 238

Trp Tyr Arg Gln Ala Pro Gly Lys Glu Arg Glu Trp Val Thr
1               5                   10

<210> SEQ ID NO 239
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 239

Trp Tyr Arg Gln Ala Pro Gly Lys Gln Arg Glu Phe Val Gly
1               5                   10

<210> SEQ ID NO 240
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 240

Trp Tyr Arg Gln Ala Pro Gly Lys Gln Arg Glu Phe Val Ala
1               5                   10

<210> SEQ ID NO 241
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 241

Trp Tyr Arg Gln Pro Pro Gly Lys Glu Arg Glu Phe Val Ala
1               5                   10

<210> SEQ ID NO 242
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 242

Trp Tyr Arg Gln Ala Pro Gly Lys Gln Arg Glu Phe Val Ala
1               5                   10

<210> SEQ ID NO 243
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 243
```

Trp Gln Arg Glu Leu Val Ala Ile Lys Phe Ser Gly Gly Thr
1               5                   10

<210> SEQ ID NO 244
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 244

Trp Tyr Arg Gln Pro Pro Gly Lys Glu Arg Glu Phe Val Ala
1               5                   10

<210> SEQ ID NO 245
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 245

Trp Tyr Arg Gln Pro Pro Gly Lys Glu Arg Glu Phe Val Ala
1               5                   10

<210> SEQ ID NO 246
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 246

Trp Phe Arg Gln Ala Pro Gly Gln Asp Arg Glu Pro Leu Ala
1               5                   10

<210> SEQ ID NO 247
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 247

Trp Tyr Arg Gln Gly Pro Gly Lys Leu Arg Glu Leu Val Ala
1               5                   10

<210> SEQ ID NO 248
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 248

Trp Tyr Arg Gln Ala Pro Gly Lys Gln Arg Glu Trp Val Thr
1               5                   10

<210> SEQ ID NO 249
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 249

Val Ile Thr Arg Asp Gly Ile Thr Lys Tyr Ala Asp Ser Val Lys Gly
1               5                   10                  15

<210> SEQ ID NO 250
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 250

Thr Ile Arg Trp Ser Thr Ser Ser Thr Tyr Tyr Ala Asp Ser Val Lys
1               5                   10                  15

Gly

<210> SEQ ID NO 251
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 251

Thr Ile Arg Trp Ser Thr Ser Glu Thr Tyr Tyr Ala Asp Ser Val Lys
1               5                   10                  15

Gly

<210> SEQ ID NO 252
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 252

Thr Val Arg Trp Gly Thr Ser Ser Thr Tyr Tyr Ala Asp Ser Val Lys
1               5                   10                  15

Gly

<210> SEQ ID NO 253
<211> LENGTH: 18
<212> TYPE: PRT
<213> ORGANISM: Artificial
<220> FEATURE:
<223> OTHER INFORMATION: Nanobody or Nanobody fragment

<400> SEQUENCE: 253

Ala Ile Tyr Gly Thr Gly Gly Glu Leu Val Tyr Tyr Glu Asn Ser Val
1               5                   10                  15

Lys Gly

<210> SEQ ID NO 254
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 254

Thr Ile Arg Trp Ser Thr Ser Glu Thr Tyr Tyr Ala Asp Ser Val Lys
1               5                   10                  15

Gly

```
<210> SEQ ID NO 255
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 255

Thr Ile Arg Trp Ser Thr Gly Glu Thr Tyr Tyr Thr Asp Ser Val Lys
1               5                   10                  15
Gly

<210> SEQ ID NO 256
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 256

Thr Ile Arg Trp Ser Thr Ser Glu Thr Tyr Tyr Ala Asp Ser Val Lys
1               5                   10                  15
Gly

<210> SEQ ID NO 257
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 257

Thr Ile Arg Trp Ser Thr Ser Ser Thr Tyr Tyr Ala Asp Pro Val Lys
1               5                   10                  15
Gly

<210> SEQ ID NO 258
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 258

Thr Ile Arg Trp Ser Thr Ser Glu Thr Tyr Tyr Ala Asp Ser Val Lys
1               5                   10                  15
Gly

<210> SEQ ID NO 259
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 259

Thr Ile Arg Trp Ser Thr Ser Glu Thr Tyr Tyr Ala Asp Ser Val Lys
1               5                   10                  15
Gly

<210> SEQ ID NO 260
<211> LENGTH: 16
<212> TYPE: PRT
<213> ORGANISM: Artificial
```

```
<220> FEATURE:
<223> OTHER INFORMATION: Nanobody or Nanobody fragment

<400> SEQUENCE: 260

Arg Ile Ser Ser Thr Gly Asp Thr Asn Tyr Ala Asp Ser Val Lys Gly
1               5                   10                  15

<210> SEQ ID NO 261
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 261

Thr Met Arg Trp Ser Thr Gly Ser Thr Tyr Tyr Ala Asp Ser Val Lys
1               5                   10                  15

Gly

<210> SEQ ID NO 262
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 262

Thr Ile Arg Trp Ser Thr Ser Glu Thr Tyr Tyr Ala Asp Ser Val Lys
1               5                   10                  15

Gly

<210> SEQ ID NO 263
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 263

Thr Ile Arg Trp Gly Thr Thr Asp Thr Tyr Tyr Ala Asp Ser Val Lys
1               5                   10                  15

Gly

<210> SEQ ID NO 264
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 264

Val Ile Thr Arg Asp Gly Ile Thr Lys Tyr Ala Asp Ser Val Lys Gly
1               5                   10                  15

<210> SEQ ID NO 265
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 265

Thr Ile Arg Trp Ser Ser Lys Ser Thr Tyr Tyr Ala Asp Ser Val Lys
1               5                   10                  15
```

Gly

```
<210> SEQ ID NO 266
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 266

Thr Ile Arg Trp Ser Thr Arg Glu Thr Tyr Tyr Thr Asp Ser Val Lys
1               5                   10                  15

Gly

<210> SEQ ID NO 267
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 267

Ile Ile Ser Arg Ser Asp Gly Ser Thr Trp Tyr Ala Asp Ser Val Lys
1               5                   10                  15

Gly

<210> SEQ ID NO 268
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 268

His Val Ser His Asp Gly Asp Ser Met Tyr Ala Val Ser Val Lys Gly
1               5                   10                  15

<210> SEQ ID NO 269
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 269

Cys Ser Asn Lys Asp Gly Ser Thr Ala Tyr Ser Asp Ser Val Lys Gly
1               5                   10                  15

<210> SEQ ID NO 270
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 270

Thr Ile Thr Ile Asp Gly Lys Thr Asn Tyr Ala Glu Pro Leu Lys Gly
1               5                   10                  15

<210> SEQ ID NO 271
<211> LENGTH: 16
<212> TYPE: PRT
<213> ORGANISM: Artificial
<220> FEATURE:
<223> OTHER INFORMATION: Nanobody or Nanobody fragment
```

```
<400> SEQUENCE: 271

Gly Ile Thr Leu Gly Gly Ser Thr Ile Tyr Ala Asp Ser Val Lys Gly
1               5                   10                  15

<210> SEQ ID NO 272
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 272

His Met Ser His Asp Gly Thr Thr Asn Tyr Glu Asp Ser Val Lys Gly
1               5                   10                  15

<210> SEQ ID NO 273
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 273

Gly Ile Pro Val Gly Gly Ser Thr Val Tyr Ala Asp Ser Val Lys Gly
1               5                   10                  15

<210> SEQ ID NO 274
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 274

Ser Ile Asn Trp Ser Gly Gly Ser Thr Tyr Tyr Glu Asp Ser Val Glu
1               5                   10                  15
Gly

<210> SEQ ID NO 275
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 275

Gly Ile Leu Ser Asp Gly Arg Glu Leu Tyr Val Asp Ser Val Lys Gly
1               5                   10                  15

<210> SEQ ID NO 276
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 276

Gly Ile Leu Ser Asp Gly Arg Glu Leu Tyr Val Asp Ser Val Lys Gly
1               5                   10                  15

<210> SEQ ID NO 277
<211> LENGTH: 16
<212> TYPE: PRT
<213> ORGANISM: Artificial
<220> FEATURE:
<223> OTHER INFORMATION: Nanobody or Nanobody fragment
```

```
<400> SEQUENCE: 277

His Ile Tyr Ser Asp Gly Ser Ile Asn Tyr Gly Asn Ser Val Lys Gly
1               5                   10                  15

<210> SEQ ID NO 278
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 278

Gly Ile Leu Ser Asp Gly Arg Glu Leu Tyr Val Asp Ser Val Lys Gly
1               5                   10                  15

<210> SEQ ID NO 279
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 279

Thr Ile Thr Ser Glu Gly Thr Ala Asn Ser Ala Asp Ser Val Lys Gly
1               5                   10                  15

<210> SEQ ID NO 280
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 280

Gly Ile Thr Leu Gly Gly Ser Thr Ile Tyr Ala Asp Ser Val Lys Gly
1               5                   10                  15

<210> SEQ ID NO 281
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 281

Gly Ile Thr Leu Gly Gly Ser Thr Ile Tyr Ala Asp Ser Val Lys Gly
1               5                   10                  15

<210> SEQ ID NO 282
<211> LENGTH: 16
<212> TYPE: PRT
<213> ORGANISM: Artificial
<220> FEATURE:
<223> OTHER INFORMATION: nanbody or nanobody fragment

<400> SEQUENCE: 282

His Val Ser His Asp Gly Tyr Ser Met Tyr Ala Val Ser Val Glu Gly
1               5                   10                  15

<210> SEQ ID NO 283
<211> LENGTH: 16
<212> TYPE: PRT
<213> ORGANISM: Artificial
<220> FEATURE:
<223> OTHER INFORMATION: Nanobody or Nanobody fragment
```

```
<400> SEQUENCE: 283

His Met Ser Arg Asp Gly Thr Ser Asn Tyr Glu Asp Ser Val Lys Gly
1               5                   10                  15

<210> SEQ ID NO 284
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 284

Thr Asp Ile Ala Glu Ser Ala Lys Gly
1               5

<210> SEQ ID NO 285
<211> LENGTH: 15
<212> TYPE: PRT
<213> ORGANISM: Artificial
<220> FEATURE:
<223> OTHER INFORMATION: Nanobody or Nanobody fragment

<400> SEQUENCE: 285

His Val Ser His Asp Gly Asp Ser Met Tyr Ala Val Ser Val Lys
1               5                   10                  15

<210> SEQ ID NO 286
<211> LENGTH: 15
<212> TYPE: PRT
<213> ORGANISM: Artificial
<220> FEATURE:
<223> OTHER INFORMATION: Nanobody or Nanobody fragment

<400> SEQUENCE: 286

His Val Ser Asp Asp Gly Asp Ser Met Tyr Ala Val Ser Val Lys
1               5                   10                  15

<210> SEQ ID NO 287
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 287

Cys Ile Thr Ser Gly Gly Thr Arg Asn Tyr Asn Pro Ser Val Met Ala
1               5                   10                  15

<210> SEQ ID NO 288
<211> LENGTH: 15
<212> TYPE: PRT
<213> ORGANISM: Artificial
<220> FEATURE:
<223> OTHER INFORMATION: Nanobody or Nanobody fragment

<400> SEQUENCE: 288

Gln Ile Thr Asp Leu His Lys Asp Tyr Ala Glu Ser Ala Lys Gly
1               5                   10                  15

<210> SEQ ID NO 289
<211> LENGTH: 16
<212> TYPE: PRT
<213> ORGANISM: Artificial
<220> FEATURE:
<223> OTHER INFORMATION: Nanobody or Nanobody fragment

<400> SEQUENCE: 289
```

Thr Leu Leu Ser Thr Gly Ser Pro Ile Tyr Ala Asp Ser Val Lys Gly
1               5                   10                  15

<210> SEQ ID NO 290
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 290

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys His Thr
                20                  25                  30

<210> SEQ ID NO 291
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 291

Arg Phe Thr Ile Ser Ser Asp Asn Thr Lys Asn Thr Val Asp Leu Arg
1               5                   10                  15

Met Asn Ser Leu Thr Pro Glu Asp Thr Ala Val Tyr Tyr Cys Ala Ala
                20                  25                  30

<210> SEQ ID NO 292
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 292

Arg Phe Thr Ile Ser Lys Asp Asn Thr Lys Asn Thr Val Ala Leu Gln
1               5                   10                  15

Met Asn Ser Leu Thr Pro Glu Asp Thr Ala Leu Tyr Tyr Cys Ala Ala
                20                  25                  30

<210> SEQ ID NO 293
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 293

Arg Phe Thr Ile Ser Ser Asp Asn Thr Lys Asn Thr Val Ala Leu Gln
1               5                   10                  15

Met Asn Arg Leu Thr Pro Glu Asp Thr Gly Val Tyr Tyr Cys Ala Ala
                20                  25                  30

<210> SEQ ID NO 294
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 294

Arg Phe Thr Ile Ser Arg Asp Asn Ala Lys Ser Thr Met Tyr Leu Gln

```
                1               5                   10                  15
Met Asn Ser Leu Lys Pro Glu Asp Thr Gly Val Tyr Tyr Cys Ala Val
                20                  25                  30
```

<210> SEQ ID NO 295
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 295

```
Arg Phe Thr Ile Ser Ser Asp Asn Thr Lys Asn Thr Val Asp Leu Gln
1               5                   10                  15
Met Asn Ser Leu Thr Pro Glu Asp Thr Ala Val Tyr Tyr Cys Ala Ala
                20                  25                  30
```

<210> SEQ ID NO 296
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 296

```
Arg Phe Thr Ile Ser Lys Asp Asn Thr Lys Asn Thr Val Asp Leu Gln
1               5                   10                  15
Met Asn Ser Leu Thr Pro Glu Asp Thr Ala Val Tyr Tyr Cys Ala Ser
                20                  25                  30
```

<210> SEQ ID NO 297
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 297

```
Arg Phe Thr Ile Ser Ser Asp Asn Ala Lys Asn Thr Val Asp Leu Gln
1               5                   10                  15
Met Asn Ser Leu Thr Pro Gly Asp Thr Gly Val Tyr Tyr Cys Ala Ala
                20                  25                  30
```

<210> SEQ ID NO 298
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 298

```
Arg Phe Thr Ile Ser Ser Asp Asn Ile Lys Asn Thr Val Asp Leu Gln
1               5                   10                  15
Met Asn Ser Leu Thr Pro Glu Asp Thr Ala Val Tyr Tyr Cys Ala Ala
                20                  25                  30
```

<210> SEQ ID NO 299
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 299

Arg Phe Thr Ile Ser Ser Asn Thr Lys Asn Thr Val Asp Leu Gln
1               5                   10                  15

Met Asn Ser Leu Thr Pro Glu Asp Thr Ala Val Tyr Tyr Cys Ala Ala
            20                  25                  30

<210> SEQ ID NO 300
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 300

Arg Phe Thr Ile Ser Lys Asp Asn Thr Lys Asn Thr Val Ala Leu Gln
1               5                   10                  15

Met Asn Ser Leu Thr Pro Glu Asp Thr Ala Leu Tyr Tyr Cys Ala Ala
            20                  25                  30

<210> SEQ ID NO 301
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 301

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys His Val
            20                  25                  30

<210> SEQ ID NO 302
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 302

Arg Phe Thr Ile Ser Ser Asp Asn Thr Lys Asn Thr Val Asp Leu Gln
1               5                   10                  15

Met Asn Ser Leu Thr Pro Glu Asp Thr Ala Val Tyr Tyr Cys Ala Ala
            20                  25                  30

<210> SEQ ID NO 303
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 303

Arg Phe Thr Ile Ser Ser Asp Asn Ala Lys Asn Thr Val Asp Leu Gln
1               5                   10                  15

Met Asn Ser Leu Thr Pro Glu Asp Thr Gly Val Tyr Tyr Cys Ala Ala
            20                  25                  30

<210> SEQ ID NO 304
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 304

Arg Phe Thr Ile Ser Ser Asp Asn Thr Lys Asn Thr Val His Leu Gln
1               5                   10                  15

Met Asn Ser Leu Thr Pro Glu Asp Thr Gly Val Tyr Tyr Cys Ala Ala
            20                  25                  30

<210> SEQ ID NO 305
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 305

Arg Phe Thr Ile Ser Arg Asp Asn Ala Lys Asn Thr Met Tyr Leu Gln
1               5                   10                  15

Met Asn Ser Leu Lys Pro Glu Asp Thr Ala Val Tyr Tyr Cys His Thr
            20                  25                  30

<210> SEQ ID NO 306
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 306

Arg Phe Thr Ile Ser Ser Asp Asn Thr Lys Asn Thr Val Asp Leu Arg
1               5                   10                  15

Met Asn Ser Leu Thr Pro Glu Asp Thr Ala Val Tyr Tyr Cys Ala Ala
            20                  25                  30

<210> SEQ ID NO 307
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 307

Arg Phe Thr Ile Ser Ser Asp Asn Thr Lys Asn Thr Val His Leu Gln
1               5                   10                  15

Met Asn Ser Leu Thr Pro Glu Asp Thr Ala Val Tyr Tyr Cys Ala Ala
            20                  25                  30

<210> SEQ ID NO 308
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 308

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 309
<211> LENGTH: 30
<212> TYPE: PRT
<213> ORGANISM: Artificial
<220> FEATURE:
<223> OTHER INFORMATION: Nanobody or Nanobody fragment

```
<400> SEQUENCE: 309

Arg Phe Ala Ile Ser Arg Lys Asp Ala Thr Asn Leu Tyr Leu Gln Met
1               5                   10                  15

Asn Ser Leu Lys Pro Glu Asp Thr Ala Ile Tyr Phe Cys Arg
            20                  25                  30

<210> SEQ ID NO 310
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 310

Arg Phe Thr Ile Ser Arg Asp Asn Ala Lys Asn Thr Val Tyr Leu Glu
1               5                   10                  15

Met Asn Gly Leu Lys Pro Glu Asp Ala Ala Ile Tyr Tyr Cys Ala Thr
            20                  25                  30

<210> SEQ ID NO 311
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 311

Arg Phe Thr Ile Ser Arg Asp Asn Ala Lys Asn Thr Ile Tyr Leu Gln
1               5                   10                  15

Met Asn Ser Leu Lys Pro Glu Asp Thr Ala Val Tyr Tyr Cys Asn Ala
            20                  25                  30

<210> SEQ ID NO 312
<211> LENGTH: 32
<212> TYPE: PRT
<213> ORGANISM: Artificial
<220> FEATURE:
<223> OTHER INFORMATION: nanbody or nanobody fragment

<400> SEQUENCE: 312

Arg Phe Thr Ile Ser Met Asp Ser Ala Arg Asn Thr Gly Tyr Leu Gln
1               5                   10                  15

Met Asn Ser Leu Lys Pro Glu Asp Thr Ala Val Tyr Tyr Cys Asn Ala
            20                  25                  30

<210> SEQ ID NO 313
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 313

Arg Phe Thr Ile Ser Arg Glu Asn Ala Lys Asn Thr Leu Tyr Leu His
1               5                   10                  15

Met Asn Ser Leu Lys Pro Glu Asp Thr Ala Ile Tyr Tyr Cys Arg Leu
            20                  25                  30

<210> SEQ ID NO 314
<211> LENGTH: 32
<212> TYPE: PRT
<213> ORGANISM: Artificial
<220> FEATURE:
<223> OTHER INFORMATION: Nanobody or Nanobody fragment
```

<400> SEQUENCE: 314

Arg Phe Thr Ile Ser Met Asp Ser Ala Arg Asn Arg Gly Tyr Leu Gln
1               5                   10                  15

Met Asn Ser Leu Lys Pro Glu Asp Thr Ala Val Tyr Tyr Cys Asn Ala
            20                  25                  30

<210> SEQ ID NO 315
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 315

Arg Phe Thr Ile Ser Arg Asp Asn Ala Lys Asn Thr Val Asn Leu Gln
1               5                   10                  15

Met Asn Ser Leu Lys Pro Glu Asp Thr Ala Val Tyr Tyr Cys Ala Ala
            20                  25                  30

<210> SEQ ID NO 316
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 316

Arg Phe Thr Val Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Leu
            20                  25                  30

<210> SEQ ID NO 317
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 317

Arg Phe Thr Val Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Leu
            20                  25                  30

<210> SEQ ID NO 318
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 318

Arg Phe Thr Ile Ser Arg Asp Asn Ala Lys Asn Thr Val Asp Leu Gln
1               5                   10                  15

Met Asn Asn Leu Lys Pro Glu Asp Thr Ala Val Tyr Tyr Cys Arg Leu
            20                  25                  30

<210> SEQ ID NO 319
<211> LENGTH: 32
<212> TYPE: PRT
<213> ORGANISM: Artificial
<220> FEATURE:

<223> OTHER INFORMATION: Nanobody or Nanobody fragment

<400> SEQUENCE: 319

Arg Phe Thr Val Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Leu
            20                  25                  30

<210> SEQ ID NO 320
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 320

Arg Phe Thr Ile Ser Arg Asp Asn Ala Lys Asn Thr Val Tyr Leu Gln
1               5                   10                  15

Met Asn Ser Leu Lys Ser Glu Asp Thr Ala Val Tyr Tyr Cys Asn Ala
            20                  25                  30

<210> SEQ ID NO 321
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 321

Arg Phe Thr Ile Ser Met Asp Ser Ala Arg Asn Thr Gly Tyr Leu Gln
1               5                   10                  15

Met Asn Ser Leu Lys Pro Glu Asp Thr Ala Val Tyr Tyr Cys Asn Ala
            20                  25                  30

<210> SEQ ID NO 322
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 322

Arg Phe Thr Ile Ser Met Asp Ser Ala Arg Asn Thr Gly Tyr Leu Gln
1               5                   10                  15

Met Ser Ser Leu Lys Pro Glu Asp Thr Ala Val Tyr Tyr Cys Asn Ala
            20                  25                  30

<210> SEQ ID NO 323
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 323

Arg Phe Thr Ile Ser Arg Glu Asn Ala Thr Asn Leu Tyr Leu Gln Met
1               5                   10                  15

Asn Ser Leu Lys Pro Glu Asp Thr Ala Ile Tyr Phe Cys Arg
            20                  25                  30

<210> SEQ ID NO 324
<211> LENGTH: 32
<212> TYPE: PRT
<213> ORGANISM: Artificial

<220> FEATURE:
<223> OTHER INFORMATION: Nanobody or Nanobody fragment

<400> SEQUENCE: 324

Arg Phe Thr Ile Ser Arg Glu Asn Ala Lys Asn Thr Leu Tyr Leu Gln
1               5                   10                  15

Met Asn Ser Leu Lys Pro Glu Asp Thr Ala Ile Tyr Tyr Cys Arg Leu
            20                  25                  30

<210> SEQ ID NO 325
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 325

Arg Phe Thr Ile Ser Arg Asp Asn Ala Lys Asn Thr Val Tyr Leu Gln
1               5                   10                  15

Met Asn Ser Leu Arg Pro Glu Asp Thr Ala Val Tyr Tyr Cys Arg Leu
            20                  25                  30

<210> SEQ ID NO 326
<211> LENGTH: 31
<212> TYPE: PRT
<213> ORGANISM: Artificial
<220> FEATURE:
<223> OTHER INFORMATION: Nanobody or Nanobody fragment

<400> SEQUENCE: 326

Gly Arg Phe Thr Ile Ser Arg Lys Asp Ala Thr Asn Leu Tyr Leu Gln
1               5                   10                  15

Met Asn Ser Leu Lys Pro Glu Asp Thr Ala Ile Tyr Phe Cys Arg
            20                  25                  30

<210> SEQ ID NO 327
<211> LENGTH: 31
<212> TYPE: PRT
<213> ORGANISM: Artificial
<220> FEATURE:
<223> OTHER INFORMATION: Nanobody or Nanobody fragment

<400> SEQUENCE: 327

Gly Arg Phe Thr Ile Ser Arg Lys Asn Ala Thr Asn Leu Tyr Leu Gln
1               5                   10                  15

Met Asn Ser Leu Lys Pro Glu Asp Thr Ala Ile Tyr Phe Cys Arg
            20                  25                  30

<210> SEQ ID NO 328
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 328

Arg Phe Arg Ile Asp Arg Asp Asn Ser Val Lys Thr Val Tyr Leu Gln
1               5                   10                  15

Ile Asn Thr Leu Lys Pro Glu Asp Thr Ala Val Tyr Tyr Cys Ser Thr
            20                  25                  30

<210> SEQ ID NO 329
<211> LENGTH: 32
<212> TYPE: PRT

<213> ORGANISM: Artificial
<220> FEATURE:
<223> OTHER INFORMATION: Nanobody or Nanobody fragment

<400> SEQUENCE: 329

Arg Phe Thr Ile Ser Arg Asp Asn Ala Lys Asn Thr Val Asp Leu Gln
1               5                   10                  15

Met Asn Ser Leu Lys Pro Glu Asp Thr Gly Val Tyr Tyr Cys Ala Ala
            20                  25                  30

<210> SEQ ID NO 330
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 330

Arg Phe Thr Ile Ser Arg Asp His Ala Lys Asn Thr Val Tyr Leu Gln
1               5                   10                  15

Met His Ser Leu Lys Pro Asp Asp Thr Ala Asn Tyr Ile Cys Phe Ala
            20                  25                  30

<210> SEQ ID NO 331
<211> LENGTH: 12
<212> TYPE: PRT
<213> ORGANISM: Artificial
<220> FEATURE:
<223> OTHER INFORMATION: Nanobody or Nanobody fragment

<400> SEQUENCE: 331

Gly Leu Pro Thr Gly Arg Gly Ser His Ser Asp Tyr
1               5                   10

<210> SEQ ID NO 332
<211> LENGTH: 10
<212> TYPE: PRT
<213> ORGANISM: Artificial
<220> FEATURE:
<223> OTHER INFORMATION: nanbody or nanobody fragment

<400> SEQUENCE: 332

Arg Ser Val Tyr Ser Tyr Glu Tyr Asn Tyr
1               5                   10

<210> SEQ ID NO 333
<211> LENGTH: 10
<212> TYPE: PRT
<213> ORGANISM: Artificial
<220> FEATURE:
<223> OTHER INFORMATION: nanbody or nanobody fragment

<400> SEQUENCE: 333

Arg Ser Val Tyr Ser Tyr Glu Tyr Asn Tyr
1               5                   10

<210> SEQ ID NO 334
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 334

Arg Ser Val Tyr Ser Tyr Glu Tyr Thr Tyr
1               5                   10

<210> SEQ ID NO 335
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 335

Glu Leu Thr Val Arg Ser Ile Asp Leu Arg Arg Pro Leu Glu Tyr Asp
1               5                   10                  15

Tyr

<210> SEQ ID NO 336
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 336

Arg Ser Val Tyr Ser Tyr Glu Tyr Asn Tyr
1               5                   10

<210> SEQ ID NO 337
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 337

Arg Ser Val Tyr Ser Tyr Glu Tyr Asn Tyr
1               5                   10

<210> SEQ ID NO 338
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 338

Arg Ser Val Tyr Ser Tyr Asp Tyr Asn Tyr
1               5                   10

<210> SEQ ID NO 339
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 339

Arg Ser Val Tyr Ser Tyr Glu Tyr Asn Tyr
1               5                   10

<210> SEQ ID NO 340
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 340

Arg Ser Val Tyr Ser Tyr Glu Tyr Asn Tyr

```
1               5                    10
```

<210> SEQ ID NO 341
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 341

```
Arg Ser Val Tyr Ser Tyr Glu Tyr Asn Tyr
1               5                    10
```

<210> SEQ ID NO 342
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 342

```
Ala Gly Pro Tyr Gly Ser Lys Phe Ala
1               5
```

<210> SEQ ID NO 343
<211> LENGTH: 10
<212> TYPE: PRT
<213> ORGANISM: Artificial
<220> FEATURE:
<223> OTHER INFORMATION: nanbody or nanobody fragment

<400> SEQUENCE: 343

```
Arg Ser Val Tyr Ser Tyr Glu Tyr Asn Tyr
1               5                    10
```

<210> SEQ ID NO 344
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 344

```
Arg Ser Val Tyr Ser Tyr Asp Tyr Asn Tyr
1               5                    10
```

<210> SEQ ID NO 345
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 345

```
Arg Ser Val Tyr Ser Tyr Glu Tyr Thr Tyr
1               5                    10
```

<210> SEQ ID NO 346
<211> LENGTH: 12
<212> TYPE: PRT
<213> ORGANISM: Artificial
<220> FEATURE:
<223> OTHER INFORMATION: Nanobody or Nanobody fragment

<400> SEQUENCE: 346

```
Gly Leu Pro Thr Gly Arg Gly Ser His Ser Asp Tyr
1               5                    10
```

```
<210> SEQ ID NO 347
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 347

Arg Ser Val Tyr Ser Tyr Glu Tyr Asn Tyr
1               5                   10

<210> SEQ ID NO 348
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 348

Arg Ser Val Tyr Ser Tyr Glu Tyr Asn Tyr
1               5                   10

<210> SEQ ID NO 349
<211> LENGTH: 13
<212> TYPE: PRT
<213> ORGANISM: Artificial
<220> FEATURE:
<223> OTHER INFORMATION: Nanobody or Nanobody fragment

<400> SEQUENCE: 349

Gln Leu Arg His Asn Phe Gly Met Gly Asp Tyr Asp Tyr
1               5                   10

<210> SEQ ID NO 350
<211> LENGTH: 12
<212> TYPE: PRT
<213> ORGANISM: Artificial
<220> FEATURE:
<223> OTHER INFORMATION: Nanobody or Nanobody fragment

<400> SEQUENCE: 350

Leu Leu Asn Ile Pro Thr Gln Gly Arg Met Glu Gly
1               5                   10

<210> SEQ ID NO 351
<211> LENGTH: 12
<212> TYPE: PRT
<213> ORGANISM: Artificial
<220> FEATURE:
<223> OTHER INFORMATION: Nanobody or Nanobody fragment

<400> SEQUENCE: 351

Lys Ser Gly Arg Tyr Cys Leu Ser His Met Asp Tyr
1               5                   10

<210> SEQ ID NO 352
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 352

Val Phe Ser Arg Gly Pro Leu Thr Tyr
1               5
```

```
<210> SEQ ID NO 353
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 353

Ala Leu Asp Gly Tyr Ser Gly Ser Ser
1               5

<210> SEQ ID NO 354
<211> LENGTH: 12
<212> TYPE: PRT
<213> ORGANISM: Artificial
<220> FEATURE:
<223> OTHER INFORMATION: Nanobody or Nanobody fragment

<400> SEQUENCE: 354

Leu Thr Ile Pro Thr Thr Gly Arg Ala Glu Gly Phe
1               5                   10

<210> SEQ ID NO 355
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 355

Tyr Leu Asp Gly Tyr Ser Gly Ser Ser
1               5

<210> SEQ ID NO 356
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 356

Lys Arg Gly His Tyr Ser Arg Glu Tyr Asp Tyr
1               5                   10

<210> SEQ ID NO 357
<211> LENGTH: 7
<212> TYPE: PRT
<213> ORGANISM: Artificial
<220> FEATURE:
<223> OTHER INFORMATION: Nanobody or Nanobody fragment

<400> SEQUENCE: 357

Asp Ile Asp Tyr Arg Asp Tyr
1               5

<210> SEQ ID NO 358
<211> LENGTH: 7
<212> TYPE: PRT
<213> ORGANISM: Artificial
<220> FEATURE:
<223> OTHER INFORMATION: Nanobody or Nanobody fragment

<400> SEQUENCE: 358

Asp Ile Asp Tyr Arg Asp Tyr
1               5
```

```
<210> SEQ ID NO 359
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 359

Leu Asp Thr Ala Arg Gly Val Gly Tyr
1               5

<210> SEQ ID NO 360
<211> LENGTH: 7
<212> TYPE: PRT
<213> ORGANISM: Artificial
<220> FEATURE:
<223> OTHER INFORMATION: Nanobody or Nanobody fragment

<400> SEQUENCE: 360

Asp Ile Asp Tyr Arg Asp Tyr
1               5

<210> SEQ ID NO 361
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 361

Gln Phe Thr Leu Ala Arg His Leu Val Tyr
1               5                   10

<210> SEQ ID NO 362
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 362

Ala Leu Asp Gly Tyr Ser Gly Ser Ser
1               5

<210> SEQ ID NO 363
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 363

Val Leu Asp Gly Tyr Ser Gly Ser Ser
1               5

<210> SEQ ID NO 364
<211> LENGTH: 13
<212> TYPE: PRT
<213> ORGANISM: Artificial
<220> FEATURE:
<223> OTHER INFORMATION: Nanobody or Nanobody fragment

<400> SEQUENCE: 364

Leu Leu Thr Ile Pro Pro Gln Gly Arg Met Glu Gly Phe
1               5                   10

<210> SEQ ID NO 365
```

```
<211> LENGTH: 12
<212> TYPE: PRT
<213> ORGANISM: Artificial
<220> FEATURE:
<223> OTHER INFORMATION: Nanobody or Nanobody fragment

<400> SEQUENCE: 365

Leu Thr Ile Pro Thr Thr Gly Arg Lys Glu Gly Phe
1               5                   10

<210> SEQ ID NO 366
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 366

Phe Leu Pro Ser Leu Ala Met Gly Tyr
1               5

<210> SEQ ID NO 367
<211> LENGTH: 13
<212> TYPE: PRT
<213> ORGANISM: Artificial
<220> FEATURE:
<223> OTHER INFORMATION: Nanobody or Nanobody fragment

<400> SEQUENCE: 367

Leu Leu Asn Ile Pro Thr Gln Gly Arg Met Glu Gly Phe
1               5                   10

<210> SEQ ID NO 368
<211> LENGTH: 13
<212> TYPE: PRT
<213> ORGANISM: Artificial
<220> FEATURE:
<223> OTHER INFORMATION: Nanobody or Nanobody fragment

<400> SEQUENCE: 368

Leu Leu Asn Ile Pro Thr Gln Gly Arg Met Glu Gly Phe
1               5                   10

<210> SEQ ID NO 369
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 369

Glu Leu Asp Arg Gln Gly Gly Ser Ala His Glu Cys Arg Glu Tyr Asp
1               5                   10                  15

Thr

<210> SEQ ID NO 370
<211> LENGTH: 9
<212> TYPE: PRT
<213> ORGANISM: Artificial
<220> FEATURE:
<223> OTHER INFORMATION: Nanobody or Nanobody fragment

<400> SEQUENCE: 370

Phe Arg Gly Ile Met Arg Pro Asp Tyr
1               5
```

```
<210> SEQ ID NO 371
<211> LENGTH: 8
<212> TYPE: PRT
<213> ORGANISM: Artificial
<220> FEATURE:
<223> OTHER INFORMATION: Nanobody or Nanobody fragment

<400> SEQUENCE: 371

Arg Leu Thr Pro Thr Gly Thr Val
1               5

<210> SEQ ID NO 372
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 372

Trp Gly Gln Gly Thr Gln Val Thr Val Ser Ser
1               5                   10

<210> SEQ ID NO 373
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 373

Trp Gly Gln Gly Thr Gln Val Thr Val Ser Ser
1               5                   10

<210> SEQ ID NO 374
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 374

Trp Gly Gln Gly Thr Gln Val Thr Val Ser Ser
1               5                   10

<210> SEQ ID NO 375
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 375

Trp Gly Gln Gly Thr Gln Val Thr Val Ser Ser
1               5                   10

<210> SEQ ID NO 376
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 376

Trp Gly Gln Gly Thr Gln Val Thr Val Ser Ser
1               5                   10

<210> SEQ ID NO 377
```

```
<211> LENGTH: 11
<212> TYPE: PRT
<213> ORGANISM: Artificial
<220> FEATURE:
<223> OTHER INFORMATION: nanbody or nanobody fragment

<400> SEQUENCE: 377

Trp Gly Gln Gly Thr Gln Val Thr Val Ser Ser
1               5                   10

<210> SEQ ID NO 378
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 378

Trp Gly Gln Gly Thr Gln Val Thr Val Ser Ser
1               5                   10

<210> SEQ ID NO 379
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 379

Trp Gly Gln Gly Thr Gln Val Thr Val Ser Ser
1               5                   10

<210> SEQ ID NO 380
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 380

Trp Gly Gln Gly Thr Gln Val Thr Val Ser Ser
1               5                   10

<210> SEQ ID NO 381
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 381

Trp Gly Gln Gly Thr Gln Val Thr Val Ser Ser
1               5                   10

<210> SEQ ID NO 382
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 382

Trp Gly Gln Gly Thr Gln Val Thr Val Ser Ser
1               5                   10

<210> SEQ ID NO 383
<211> LENGTH: 11
```

```
<212> TYPE: PRT
<213> ORGANISM: Artificial
<220> FEATURE:
<223> OTHER INFORMATION: Nanobody or Nanobody fragment

<400> SEQUENCE: 383

Trp Gly Gln Gly Thr Gln Val Thr Val Ser Ser
1               5                   10

<210> SEQ ID NO 384
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 384

Trp Gly Gln Gly Thr Gln Val Thr Val Ser Ser
1               5                   10

<210> SEQ ID NO 385
<211> LENGTH: 11
<212> TYPE: PRT
<213> ORGANISM: Artificial
<220> FEATURE:
<223> OTHER INFORMATION: nanbody or nanobody fragment

<400> SEQUENCE: 385

Trp Gly Gln Gly Thr Gln Val Thr Val Ser Ser
1               5                   10

<210> SEQ ID NO 386
<211> LENGTH: 11
<212> TYPE: PRT
<213> ORGANISM: Artificial
<220> FEATURE:
<223> OTHER INFORMATION: nanbody or nanobody fragment

<400> SEQUENCE: 386

Trp Gly Gln Gly Thr Gln Val Thr Val Ser Ser
1               5                   10

<210> SEQ ID NO 387
<211> LENGTH: 11
<212> TYPE: PRT
<213> ORGANISM: Artificial
<220> FEATURE:
<223> OTHER INFORMATION: nanbody or nanobody fragment

<400> SEQUENCE: 387

Trp Gly Gln Gly Thr Gln Val Thr Val Ser Ser
1               5                   10

<210> SEQ ID NO 388
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 388

Trp Gly Gln Gly Thr Gln Val Thr Val Ser Ser
1               5                   10

<210> SEQ ID NO 389
<211> LENGTH: 11
<212> TYPE: PRT
```

<213> ORGANISM: Artificial
<220> FEATURE:
<223> OTHER INFORMATION: Nanobody or Nanobody fragment

<400> SEQUENCE: 389

Trp Gly Gln Gly Thr Gln Val Thr Val Ser Ser
1               5                   10

<210> SEQ ID NO 390
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 390

Trp Gly Gln Gly Thr Gln Val Thr Val Ser Ser
1               5                   10

<210> SEQ ID NO 391
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 391

Trp Gly Gln Gly Thr Gln Val Thr Val Ser Ser
1               5                   10

<210> SEQ ID NO 392
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 392

Trp Gly Ile Gly Thr Leu Val Thr Val Ser Ser
1               5                   10

<210> SEQ ID NO 393
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 393

Trp Gly Arg Gly Thr Gln Val Thr Val Ser Ser
1               5                   10

<210> SEQ ID NO 394
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 394

Trp Gly Gln Gly Thr Gln Val Thr Val Ser Ser
1               5                   10

<210> SEQ ID NO 395
<211> LENGTH: 11
<212> TYPE: PRT
<213> ORGANISM: Artificial

<220> FEATURE:
<223> OTHER INFORMATION: Nanobody or Nanobody fragment

<400> SEQUENCE: 395

Trp Gly Gln Gly Thr Gln Val Thr Val Ser Ser
1               5                   10

<210> SEQ ID NO 396
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 396

Trp Gly Gln Gly Thr Gln Val Thr Val Ser Ser
1               5                   10

<210> SEQ ID NO 397
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 397

Trp Gly Gln Gly Thr Gln Val Thr Val Ser Ser
1               5                   10

<210> SEQ ID NO 398
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 398

Trp Gly Gln Gly Thr Gln Val Thr Val Ser Ser
1               5                   10

<210> SEQ ID NO 399
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 399

Trp Gly Gln Gly Thr Gln Val Thr Val Ser Ser
1               5                   10

<210> SEQ ID NO 400
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 400

Trp Gly Gln Gly Thr Gln Val Thr Val Ser Ser
1               5                   10

<210> SEQ ID NO 401
<211> LENGTH: 11
<212> TYPE: PRT
<213> ORGANISM: Artificial
<220> FEATURE:

-continued

<223> OTHER INFORMATION: Nanobody or Nanobody fragment

<400> SEQUENCE: 401

Trp Gly Gln Gly Thr Gln Val Thr Val Ser Ser
1               5                   10

<210> SEQ ID NO 402
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 402

Trp Gly Gln Gly Thr Gln Val Thr Val Ser Ser
1               5                   10

<210> SEQ ID NO 403
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 403

Trp Gly Gln Gly Thr Gln Val Thr Val Ser Ser
1               5                   10

<210> SEQ ID NO 404
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 404

Trp Gly Gln Gly Thr Gln Val Thr Val Ser Ser
1               5                   10

<210> SEQ ID NO 405
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 405

Trp Gly Gln Gly Thr Gln Val Thr Val Ser Ser
1               5                   10

<210> SEQ ID NO 406
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 406

Trp Gly Gln Gly Thr Gln Val Thr Val Ser Ser
1               5                   10

<210> SEQ ID NO 407
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 407

Trp Gly Gln Gly Thr Gln Val Thr Val Ser Ser
1               5                   10

<210> SEQ ID NO 408
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 408

Trp Gly Gln Gly Thr Gln Val Thr Val Ser Ser
1               5                   10

<210> SEQ ID NO 409
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 409

Trp Gly Gln Gly Thr Gln Val Thr Val Ser Ser
1               5                   10

<210> SEQ ID NO 410
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 410

Trp Gly Gln Gly Thr Gln Val Thr Val Ser Ser
1               5                   10

<210> SEQ ID NO 411
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 411

Trp Gly Gln Gly Thr Gln Val Thr Val Ser Ser
1               5                   10

<210> SEQ ID NO 412
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 412

Trp Gly Gln Gly Thr Gln Val Thr Val Ser Ser
1               5                   10

<210> SEQ ID NO 413
<211> LENGTH: 120
<212> TYPE: PRT
<213> ORGANISM: Artificial
<220> FEATURE:
<223> OTHER INFORMATION: Nanobody or Nanobody fragment

<400> SEQUENCE: 413

Glu Val Gln Leu Val Glu Ser Gly Gly Gly Leu Val Gln Ala Gly
1               5                   10                  15

Ser Leu Arg Leu Ala Cys Ala Ala Ser Gly Ser Ile Phe Ser Phe Asn
            20                  25                  30

Ala Met Gly Trp Tyr Arg Gln Ala Pro Gly Lys Gln Arg Glu Leu Leu
        35                  40                  45

Ala Val Ile Thr Arg Asp Gly Ile Thr Lys Tyr Ala Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys His
            85                  90                  95

Thr Gly Leu Pro Thr Gly Arg Gly Ser His Ser Asp Tyr Trp Gly Gln
        100                 105                 110

Gly Thr Gln Val Thr Val Ser Ser
115                 120

<210> SEQ ID NO 414
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 414

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Asn Tyr
            20                  25                  30

Asp Met Gly Trp Phe Arg Gln Ala Pro Gly Lys Glu Arg Glu Phe Val
        35                  40                  45

Ala Thr Ile Arg Trp Ser Thr Ser Thr Tyr Tyr Ala Asp Ser Val
    50                  55                  60

Lys Gly Arg Phe Thr Ile Ser Ser Asp Asn Thr Lys Asn Thr Val Asp
65                  70                  75                  80

Leu Arg Met Asn Ser Leu Thr Pro Glu Asp Thr Ala Val Tyr Tyr Cys
            85                  90                  95

Ala Ala Arg Ser Val Tyr Ser Tyr Glu Tyr Asn Tyr Trp Gly Gln Gly
        100                 105                 110

Thr Gln Val Thr Val Ser Ser
115

<210> SEQ ID NO 415
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 415

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Thr Asn Tyr
            20                  25                  30

Asp Met Gly Trp Phe Arg Gln Ala Pro Gly Lys Glu Arg Glu Phe Val
        35                  40                  45

```
Ala Thr Ile Arg Trp Ser Thr Ser Glu Thr Tyr Tyr Ala Asp Ser Val
    50                  55                  60

Lys Gly Arg Phe Thr Ile Ser Lys Asp Asn Thr Lys Asn Thr Val Ala
 65                  70                  75                  80

Leu Gln Met Asn Ser Leu Thr Pro Glu Asp Thr Ala Leu Tyr Tyr Cys
                 85                  90                  95

Ala Ala Arg Ser Val Tyr Ser Tyr Glu Tyr Asn Tyr Trp Gly Gln Gly
            100                 105                 110

Thr Gln Val Thr Val Ser Ser
115

<210> SEQ ID NO 416
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 416

Glu Val Gln Leu Val Glu Ser Gly Gly Gly Leu Val Gln Ala Gly Gly
  1               5                  10                  15

Ser Leu Arg Leu Ser Cys Ala Ala Ser Gly Arg Thr Leu Asn Asn His
             20                  25                  30

Asp Met Gly Trp Phe Arg Gln Ala Pro Gly Lys Glu Arg Glu Phe Val
         35                  40                  45

Ala Thr Val Arg Trp Gly Thr Ser Thr Tyr Tyr Ala Asp Ser Val
    50                  55                  60

Lys Gly Arg Phe Thr Ile Ser Ser Asp Asn Thr Lys Asn Thr Val Ala
 65                  70                  75                  80

Leu Gln Met Asn Arg Leu Thr Pro Glu Asp Thr Gly Val Tyr Tyr Cys
                 85                  90                  95

Ala Ala Arg Ser Val Tyr Ser Tyr Glu Tyr Thr Tyr Trp Gly Gln Gly
            100                 105                 110

Thr Gln Val Thr Val Ser Ser
            115

<210> SEQ ID NO 417
<211> LENGTH: 127
<212> TYPE: PRT
<213> ORGANISM: Artificial
<220> FEATURE:
<223> OTHER INFORMATION: Nanobody or Nanobody fragment

<400> SEQUENCE: 417

Glu Val Gln Leu Val Glu Ser Gly Gly Gly Leu Val Gln Ala Gly Gly
  1               5                  10                  15

Ser Leu Arg Leu Ser Cys Ala Ala Ser Arg Arg Thr Phe Ser Ser Phe
             20                  25                  30

Val Met Ala Trp Phe Arg Gln Ala Pro Gly Lys Glu Arg Glu Phe Val
         35                  40                  45

Ala Ala Ile Tyr Gly Thr Gly Gly Glu Leu Val Tyr Tyr Glu Asn Ser
    50                  55                  60

Val Lys Gly Arg Phe Thr Ile Ser Arg Asp Asn Ala Lys Ser Thr Met
 65                  70                  75                  80

Tyr Leu Gln Met Asn Ser Leu Lys Pro Glu Asp Thr Gly Val Tyr Tyr
                 85                  90                  95

Cys Ala Val Glu Leu Thr Val Arg Ser Ile Asp Leu Arg Arg Pro Leu
            100                 105                 110
```

-continued

Glu Tyr Asp Tyr Trp Gly Gln Gly Thr Gln Val Thr Val Ser Ser
        115                 120                 125

<210> SEQ ID NO 418
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 418

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Val Asn Tyr
            20                  25                  30

Asp Met Gly Trp Phe Arg Gln Ala Pro Gly Lys Glu Arg Glu Phe Val
        35                  40                  45

Ala Thr Ile Arg Trp Ser Thr Ser Glu Thr Tyr Tyr Ala Asp Ser Val
    50                  55                  60

Lys Gly Arg Phe Thr Ile Ser Ser Asp Asn Thr Lys Asn Thr Val Asp
65                  70                  75                  80

Leu Gln Met Asn Ser Leu Thr Pro Glu Asp Thr Ala Val Tyr Tyr Cys
                85                  90                  95

Ala Ala Arg Ser Val Tyr Ser Tyr Glu Tyr Asn Tyr Trp Gly Gln Gly
            100                 105                 110

Thr Gln Val Thr Val Ser Ser
        115

<210> SEQ ID NO 419
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 419

Glu Val Gln Leu Val Lys Ser Gly Gly Gly Leu Val Gln Ala Gly Gly
1               5                   10                  15

Ser Leu Arg Leu Ser Cys Ala Ala Ser Gly Arg Thr Leu Ser Asn Tyr
            20                  25                  30

Asp Met Gly Trp Phe Arg Gln Ala Pro Gly Lys Glu Arg Glu Phe Val
        35                  40                  45

Ala Thr Ile Arg Trp Ser Thr Gly Glu Thr Tyr Tyr Thr Asp Ser Val
    50                  55                  60

Lys Gly Arg Phe Thr Ile Ser Lys Asp Asn Thr Lys Asn Thr Val Asp
65                  70                  75                  80

Leu Gln Met Asn Ser Leu Thr Pro Glu Asp Thr Ala Val Tyr Tyr Cys
                85                  90                  95

Ala Ser Arg Ser Val Tyr Ser Tyr Glu Tyr Asn Tyr Trp Gly Gln Gly
            100                 105                 110

Thr Gln Val Thr Val Ser Ser
        115

<210> SEQ ID NO 420
<211> LENGTH: 119
<212> TYPE: PRT
<213> ORGANISM: Artificial
<220> FEATURE:
<223> OTHER INFORMATION: Nanobody or Nanobody fragment

```
<400> SEQUENCE: 420

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Arg Asn Tyr
            20                  25                  30

Asp Met Gly Trp Phe Arg Gln Ala Pro Gly Lys Glu Arg Glu Phe Val
        35                  40                  45

Ala Thr Ile Arg Trp Ser Thr Ser Glu Thr Tyr Tyr Ala Asp Ser Val
    50                  55                  60

Lys Gly Arg Phe Thr Ile Ser Ser Asp Asn Ala Lys Asn Thr Val Asp
65                  70                  75                  80

Leu Gln Met Asn Ser Leu Thr Pro Gly Asp Thr Gly Val Tyr Tyr Cys
                85                  90                  95

Ala Ala Arg Ser Val Tyr Ser Tyr Asp Tyr Asn Tyr Trp Gly Gln Gly
            100                 105                 110

Thr Gln Val Thr Val Ser Ser
        115

<210> SEQ ID NO 421
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 421

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Asn Tyr
            20                  25                  30

Asp Val Gly Trp Phe Arg Gln Ala Pro Gly Lys Glu Arg Glu Phe Val
        35                  40                  45

Ala Thr Ile Arg Trp Ser Thr Ser Ser Thr Tyr Tyr Ala Asp Pro Val
    50                  55                  60

Lys Gly Arg Phe Thr Ile Ser Ser Asp Asn Ile Lys Asn Thr Val Asp
65                  70                  75                  80

Leu Gln Met Asn Ser Leu Thr Pro Glu Asp Thr Ala Val Tyr Tyr Cys
                85                  90                  95

Ala Ala Arg Ser Val Tyr Ser Tyr Glu Tyr Asn Tyr Trp Gly Gln Gly
            100                 105                 110

Thr Gln Val Thr Val Ser Ser
        115

<210> SEQ ID NO 422
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 422

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Asn Tyr
            20                  25                  30

Asp Met Gly Trp Phe Arg Gln Ala Pro Gly Lys Glu Arg Glu Phe Val
        35                  40                  45
```

Ala Thr Ile Arg Trp Ser Thr Ser Glu Thr Tyr Tyr Ala Asp Ser Val
            50                  55                  60

Lys Gly Arg Phe Thr Ile Ser Ser Ser Asn Thr Lys Asn Thr Val Asp
 65                  70                  75                  80

Leu Gln Met Asn Ser Leu Thr Pro Glu Asp Thr Ala Val Tyr Tyr Cys
                85                  90                  95

Ala Ala Arg Ser Val Tyr Ser Tyr Glu Tyr Asn Tyr Trp Gly Gln Gly
            100                 105                 110

Thr Gln Val Thr Val Ser Ser
        115

<210> SEQ ID NO 423
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 423

Glu Val Gln Leu Met Glu Ser Gly Gly Gly Leu Val Gln Ala Gly Gly
 1               5                   10                  15

Ser Leu Arg Leu Ser Cys Ala Ala Ser Gly Arg Thr Leu Thr Asn Tyr
            20                  25                  30

Asp Met Gly Trp Phe Arg Gln Ala Pro Gly Lys Glu Arg Glu Phe Val
        35                  40                  45

Ala Thr Ile Arg Trp Ser Thr Ser Glu Thr Tyr Tyr Ala Asp Ser Val
            50                  55                  60

Lys Gly Arg Phe Thr Ile Ser Lys Asp Asn Thr Lys Asn Thr Val Ala
 65                  70                  75                  80

Leu Gln Met Asn Ser Leu Thr Pro Glu Asp Thr Ala Leu Tyr Tyr Cys
                85                  90                  95

Ala Ala Arg Ser Val Tyr Ser Tyr Glu Tyr Asn Tyr Trp Gly Gln Gly
            100                 105                 110

Thr Gln Val Thr Val Ser Ser
        115

<210> SEQ ID NO 424
<211> LENGTH: 117
<212> TYPE: PRT
<213> ORGANISM: Artificial
<220> FEATURE:
<223> OTHER INFORMATION: Nanobody or Nanobody fragment

<400> SEQUENCE: 424

Glu Val Gln Leu Val Glu Ser Gly Gly Gly Leu Glu Gln Ala Gly Gly
 1               5                   10                  15

Ser Leu Arg Leu Ser Cys Ala Val Ser Arg Ser Ile Phe Glu Thr Asn
            20                  25                  30

Thr Met Ala Trp Phe Arg Gln Ala Pro Gly Lys Gln Arg Glu Leu Val
        35                  40                  45

Ala Arg Ile Ser Ser Thr Gly Asp Thr Asn Tyr Ala Asp Ser Val Lys
        50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys His
                85                  90                  95

Val Ala Gly Pro Tyr Gly Ser Lys Phe Ala Trp Gly Gln Gly Thr Gln

Val Thr Val Ser Ser
        115

<210> SEQ ID NO 425
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 425

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Asn His
            20                  25                  30

Asp Val Gly Trp Phe Arg Gln Ala Pro Gly Lys Glu Arg Glu Phe Val
        35                  40                  45

Ala Thr Met Arg Trp Ser Thr Gly Ser Thr Tyr Tyr Ala Asp Ser Val
    50                  55                  60

Lys Gly Arg Phe Thr Ile Ser Ser Asp Asn Thr Lys Asn Thr Val Asp
65                  70                  75                  80

Leu Gln Met Asn Ser Leu Thr Pro Glu Asp Thr Ala Val Tyr Tyr Cys
                85                  90                  95

Ala Ala Arg Ser Val Tyr Ser Tyr Glu Tyr Asn Tyr Trp Gly Gln Gly
            100                 105                 110

Thr Gln Val Thr Val Ser Ser
        115

<210> SEQ ID NO 426
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 426

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Arg Asn Tyr
            20                  25                  30

Asp Leu Gly Trp Phe Arg Gln Ala Pro Gly Lys Glu Arg Glu Phe Val
        35                  40                  45

Ala Thr Ile Arg Trp Ser Thr Ser Glu Thr Tyr Tyr Ala Asp Ser Val
    50                  55                  60

Lys Gly Arg Phe Thr Ile Ser Ser Asp Asn Ala Lys Asn Thr Val Asp
65                  70                  75                  80

Leu Gln Met Asn Ser Leu Thr Pro Glu Asp Thr Gly Val Tyr Tyr Cys
                85                  90                  95

Ala Ala Arg Ser Val Tyr Ser Tyr Asp Tyr Asn Tyr Trp Gly Gln Gly
            100                 105                 110

Thr Gln Val Thr Val Ser Ser
        115

<210> SEQ ID NO 427
<211> LENGTH: 119
<212> TYPE: PRT
<213> ORGANISM: Artificial
<220> FEATURE:

<223> OTHER INFORMATION: Nanobody or Nanobody fragment

<400> SEQUENCE: 427

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Thr Asn His
            20                  25                  30

Asp Met Gly Trp Phe Arg Gln Ala Pro Gly Lys Glu Arg Glu Phe Val
        35                  40                  45

Ala Thr Ile Arg Trp Gly Thr Thr Asp Thr Tyr Tyr Ala Asp Ser Val
    50                  55                  60

Lys Gly Arg Phe Thr Ile Ser Ser Asp Asn Thr Lys Asn Thr Val His
65                  70                  75                  80

Leu Gln Met Asn Ser Leu Thr Pro Glu Asp Thr Gly Val Tyr Tyr Cys
                85                  90                  95

Ala Ala Arg Ser Val Tyr Ser Tyr Glu Tyr Thr Tyr Trp Gly Gln Gly
            100                 105                 110

Thr Gln Val Thr Val Ser Ser
        115

<210> SEQ ID NO 428
<211> LENGTH: 120
<212> TYPE: PRT
<213> ORGANISM: Artificial
<220> FEATURE:
<223> OTHER INFORMATION: Nanobody or Nanobody fragment

<400> SEQUENCE: 428

Glu Val Gln Leu Val Glu Ser Gly Gly Gly Leu Val Gln Ala Gly Gly
1               5                   10                  15

Ser Leu Arg Leu Ala Cys Ala Ala Ser Gly Ser Ile Phe Ser Phe Asn
            20                  25                  30

Ala Met Gly Trp Tyr Arg Gln Ala Pro Gly Lys Gln Arg Glu Leu Leu
        35                  40                  45

Ala Val Ile Thr Arg Asp Gly Ile Thr Lys Tyr Ala Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys His
                85                  90                  95

Thr Gly Leu Pro Thr Gly Arg Gly Ser His Ser Asp Tyr Trp Gly Gln
            100                 105                 110

Gly Thr Gln Val Thr Val Ser Ser
        115                 120

<210> SEQ ID NO 429
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 429

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Asn Asp His
            20                  25                  30

Asp Val Gly Trp Phe Arg Gln Ala Pro Gly Lys Glu Arg Glu Phe Val

```
                35                  40                  45
Ala Thr Ile Arg Trp Ser Ser Lys Ser Thr Tyr Tyr Ala Asp Ser Val
 50                  55                  60

Lys Gly Arg Phe Thr Ile Ser Ser Asp Asn Thr Lys Asn Thr Val Asp
 65                  70                  75                  80

Leu Arg Met Asn Ser Leu Thr Pro Glu Asp Thr Ala Val Tyr Tyr Cys
                 85                  90                  95

Ala Ala Arg Ser Val Tyr Ser Tyr Glu Tyr Asn Tyr Trp Gly Gln Gly
                100                 105                 110

Thr Gln Val Thr Val Ser Ser
            115

<210> SEQ ID NO 430
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 430

Glu Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Leu Ser Asn Tyr
                20                  25                  30

Asp Met Gly Trp Phe Arg Gln Ala Pro Gly Lys Glu Arg Glu Phe Val
                35                  40                  45

Ala Thr Ile Arg Trp Ser Thr Arg Glu Thr Tyr Tyr Thr Asp Ser Val
 50                  55                  60

Lys Gly Arg Phe Thr Ile Ser Ser Asp Asn Thr Lys Asn Thr Val His
 65                  70                  75                  80

Leu Gln Met Asn Ser Leu Thr Pro Glu Asp Thr Ala Val Tyr Tyr Cys
                 85                  90                  95

Ala Ala Arg Ser Val Tyr Ser Tyr Glu Tyr Asn Tyr Trp Gly Gln Gly
                100                 105                 110

Thr Gln Val Thr Val Ser Ser
            115

<210> SEQ ID NO 431
<211> LENGTH: 122
<212> TYPE: PRT
<213> ORGANISM: Artificial
<220> FEATURE:
<223> OTHER INFORMATION: Nanobody or Nanobody fragment

<400> SEQUENCE: 431

Glu Val Gln Leu Val Glu Ser Gly Gly Gly Leu Val Gln Ala Gly Gly
 1               5                  10                  15

Ser Leu Arg Leu Ser Cys Ser Ser Ser Gly Phe Thr Ser Thr Asp Tyr
                20                  25                  30

Ala Ile Gly Trp Phe Arg Gln Ala Pro Gly Lys Ala Arg Thr Gly Val
                35                  40                  45

Ser Ile Ile Ser Arg Ser Asp Gly Ser Thr Trp Tyr Ala Asp Ser Val
 50                  55                  60

Lys Gly Arg Phe Thr Ile Ser Ser Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95
```

Ala Ala Gln Leu Arg His Asn Phe Gly Met Gly Asp Tyr Asp Tyr Trp
            100                 105                 110

Gly Gln Gly Thr Gln Val Thr Val Ser Ser
            115                 120

<210> SEQ ID NO 432
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 432

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe Ala Asn Asn
            20                  25                  30

Ile Met Gly Trp Tyr Arg Gln Pro Gly Lys Glu Arg Glu Phe Val
            35                  40                  45

Ala His Val Ser His Asp Gly Asp Ser Met Tyr Ala Val Ser Val Lys
    50                  55                  60

Gly Arg Phe Ala Ile Ser Arg Lys Asp Ala Thr Asn Leu Tyr Leu Gln
65                  70                  75                  80

Met Asn Ser Leu Lys Pro Glu Asp Thr Ala Ile Tyr Phe Cys Arg Leu
                85                  90                  95

Leu Asn Ile Pro Thr Gln Gly Arg Met Glu Gly Phe Trp Gly Gln Gly
            100                 105                 110

Thr Gln Val Thr Val Ser Ser
            115

<210> SEQ ID NO 433
<211> LENGTH: 120
<212> TYPE: PRT
<213> ORGANISM: Artificial
<220> FEATURE:
<223> OTHER INFORMATION: Nanobody or Nanobody fragment

<400> SEQUENCE: 433

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Gly Tyr
            20                  25                  30

Ala Ile Gly Trp Phe Arg Gln Ala Pro Gly Lys Glu Arg Glu Gly Val
            35                  40                  45

Ser Cys Ser Asn Lys Asp Gly Ser Thr Ala Tyr Ser Asp Ser Val Lys
    50                  55                  60

Gly Arg Phe Thr Ile Ser Arg Asp Asn Ala Lys Asn Thr Val Tyr Leu
65                  70                  75                  80

Glu Met Asn Gly Leu Lys Pro Glu Asp Ala Ala Ile Tyr Tyr Cys Ala
                85                  90                  95

Thr Lys Ser Gly Arg Tyr Cys Leu Ser His Met Asp Tyr Trp Gly Ile
            100                 105                 110

Gly Thr Leu Val Thr Val Ser Ser
            115                 120

<210> SEQ ID NO 434
<211> LENGTH: 117
<212> TYPE: PRT
<213> ORGANISM: Artificial

```
<220> FEATURE:
<223> OTHER INFORMATION: Nanobody or Nanobody fragment

<400> SEQUENCE: 434

Glu Val Gln Leu Val Glu Ser Gly Gly Gly Leu Val Gln Thr Gly Gly
1               5                   10                  15

Ser Leu Arg Leu Ser Cys Ala Ala Ser Gly Met Thr Phe Arg Leu Tyr
            20                  25                  30

Ala Leu Ser Trp Tyr Arg Gln Ala Pro Gly Glu Arg Arg Glu Val Val
        35                  40                  45

Ala Thr Ile Thr Ile Asp Gly Lys Thr Asn Tyr Ala Glu Pro Leu Lys
    50                  55                  60

Gly Arg Phe Thr Ile Ser Arg Asp Asn Ala Lys Asn Thr Ile Tyr Leu
65                  70                  75                  80

Gln Met Asn Ser Leu Lys Pro Glu Asp Thr Ala Val Tyr Tyr Cys Asn
                85                  90                  95

Ala Val Phe Ser Arg Gly Pro Leu Thr Tyr Trp Gly Arg Gly Thr Gln
            100                 105                 110

Val Thr Val Ser Ser
        115

<210> SEQ ID NO 435
<211> LENGTH: 117
<212> TYPE: PRT
<213> ORGANISM: Artificial
<220> FEATURE:
<223> OTHER INFORMATION: Nanobody or Nanobody fragment

<400> SEQUENCE: 435

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Arg Ser Ser Phe Asp
            20                  25                  30

Asp Met Gly Trp Tyr Arg Gln Ala Pro Gly Lys Gln Arg Glu Phe Val
        35                  40                  45

Ala Gly Ile Thr Leu Gly Gly Ser Thr Ile Tyr Ala Asp Ser Val Lys
    50                  55                  60

Gly Arg Phe Thr Ile Ser Met Asp Ser Ala Arg Asn Thr Gly Tyr Leu
65                  70                  75                  80

Gln Met Asn Ser Leu Lys Pro Glu Asp Thr Ala Val Tyr Tyr Cys Asn
                85                  90                  95

Ala Ala Leu Asp Gly Tyr Ser Gly Ser Ser Trp Gly Leu Gly Thr Gln
            100                 105                 110

Val Thr Val Ser Ser
        115

<210> SEQ ID NO 436
<211> LENGTH: 120
<212> TYPE: PRT
<213> ORGANISM: Artificial
<220> FEATURE:
<223> OTHER INFORMATION: Nanobody or Nanobody fragment

<400> SEQUENCE: 436

Glu Val Gln Leu Val Glu Ser Gly Gly Gly Leu Val Gln Ala Gly Gly
1               5                   10                  15

Ser Leu Arg Leu Ser Cys Val Ala Ser Gly Asn Ile Phe Ser Asp Asn
            20                  25                  30
```

```
Leu Met Gly Trp Tyr Arg Gln Ala Pro Gly Lys Gln Arg Glu Phe Val
         35                  40                  45

Ala His Met Ser His Asp Gly Thr Thr Asn Tyr Glu Asp Ser Val Lys
 50                  55                  60

Gly Arg Phe Thr Ile Ser Arg Glu Asn Ala Lys Asn Thr Leu Tyr Leu
 65                  70                  75                  80

His Met Asn Ser Leu Lys Pro Glu Asp Thr Ala Ile Tyr Tyr Cys Arg
                 85                  90                  95

Leu Leu Thr Ile Pro Thr Thr Gly Arg Ala Gly Phe Trp Gly Gln
                100                 105                 110

Gly Thr Gln Val Thr Val Ser Ser
        115                 120

<210> SEQ ID NO 437
<211> LENGTH: 117
<212> TYPE: PRT
<213> ORGANISM: Artificial
<220> FEATURE:
<223> OTHER INFORMATION: Nanobody or Nanobody fragment

<400> SEQUENCE: 437

Glu Val Gln Leu Val Glu Ser Gly Gly Gly Leu Val Gln Ala Gly Gly
 1               5                  10                  15

Ser Leu Arg Leu Ser Cys Ala Ala Ser Arg Ser Arg Ser Ser Phe Asn
                 20                  25                  30

Asp Met Gly Trp Tyr Arg Gln Ala Pro Gly Lys Gln Arg Glu Phe Val
         35                  40                  45

Ala Gly Ile Pro Val Gly Gly Ser Thr Val Tyr Ala Asp Ser Val Lys
 50                  55                  60

Gly Arg Phe Thr Ile Ser Met Asp Ser Ala Arg Asn Arg Gly Tyr Leu
 65                  70                  75                  80

Gln Met Asn Ser Leu Lys Pro Glu Asp Thr Ala Val Tyr Tyr Cys Asn
                 85                  90                  95

Ala Tyr Leu Asp Gly Tyr Ser Gly Ser Ser Trp Gly Gln Gly Thr Gln
                100                 105                 110

Val Thr Val Ser Ser
        115

<210> SEQ ID NO 438
<211> LENGTH: 120
<212> TYPE: PRT
<213> ORGANISM: Artificial
<220> FEATURE:
<223> OTHER INFORMATION: Nanobody or Nanobody fragment

<400> SEQUENCE: 438

Glu Val Gln Leu Val Glu Ser Gly Gly Gly Leu Val Gln Ala Gly Gly
 1               5                  10                  15

Ser Leu Arg Leu Ser Cys Ala Ala Ser Gly Leu Thr Phe Ser Asn Tyr
                 20                  25                  30

Ala Met Gly Trp Phe Arg Gln Ala Pro Gly Lys Glu Arg Glu Trp Val
         35                  40                  45

Ala Ser Ile Asn Trp Ser Gly Ser Thr Tyr Tyr Glu Asp Ser Val
 50                  55                  60

Glu Gly Arg Phe Thr Ile Ser Arg Asp Asn Ala Lys Asn Thr Val Asn
 65                  70                  75                  80

Leu Gln Met Asn Ser Leu Lys Pro Glu Asp Thr Ala Val Tyr Tyr Cys
                 85                  90                  95
```

-continued

Ala Ala Lys Arg Gly His Tyr Ser Arg Glu Tyr Asp Tyr Trp Gly Gln
                100                 105                 110

Gly Thr Gln Val Thr Val Ser Ser
            115                 120

<210> SEQ ID NO 439
<211> LENGTH: 115
<212> TYPE: PRT
<213> ORGANISM: Artificial
<220> FEATURE:
<223> OTHER INFORMATION: Nanobody or Nanobody fragment

<400> SEQUENCE: 439

Lys Val Gln Leu Val Glu Ser Gly Gly Gly Leu Val Gln Ala Gly Gly
1               5                   10                  15

Ser Leu Arg Leu Ser Cys Ala Ala Ser Ala Ser Ile Ile Ser Ser Ala
            20                  25                  30

Ala Leu Gly Trp Tyr Arg Gln Ala Pro Gly Lys Arg Arg Glu Phe Val
        35                  40                  45

Ala Gly Ile Leu Ser Asp Gly Arg Glu Leu Tyr Val Asp Ser Val Lys
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Asp Ile Asp Tyr Arg Asp Tyr Trp Gly Gln Gly Thr Gln Val Thr
            100                 105                 110

Val Ser Ser
        115

<210> SEQ ID NO 440
<211> LENGTH: 115
<212> TYPE: PRT
<213> ORGANISM: Artificial
<220> FEATURE:
<223> OTHER INFORMATION: Nanobody or Nanobody fragment

<400> SEQUENCE: 440

Glu Val Gln Leu Val Glu Ser Gly Gly Gly Leu Val Gln Ala Gly Gly
1               5                   10                  15

Ser Leu Arg Leu Ser Cys Ala Ala Ser Ala Ser Ile Ile Ser Ser Ala
            20                  25                  30

Ala Leu Gly Trp Tyr Arg Gln Ala Pro Gly Arg Arg Arg Glu Phe Val
        35                  40                  45

Ala Gly Ile Leu Ser Asp Gly Arg Glu Leu Tyr Val Asp Ser Val Lys
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Asp Ile Asp Tyr Arg Asp Tyr Trp Gly Gln Gly Thr Gln Val Thr
            100                 105                 110

Val Ser Ser
        115

<210> SEQ ID NO 441
<211> LENGTH: 117
<212> TYPE: PRT

<213> ORGANISM: Artificial
<220> FEATURE:
<223> OTHER INFORMATION: Nanobody or Nanobody fragment

<400> SEQUENCE: 441

Lys Val Gln Leu Val Glu Ser Gly Gly Gly Leu Val Gln Ala Gly
1               5                   10                  15

Ser Leu Arg Leu Ser Cys Ala Ala Ser Gly Ser Ile Phe Ser Ile Ser
            20                  25                  30

Leu Val Gly Trp Tyr Arg Gln Ala Pro Gly Lys Gln Arg Glu Phe Val
        35                  40                  45

Ala His Ile Tyr Ser Asp Gly Ser Ile Asn Tyr Gly Asn Ser Val Lys
50                  55                  60

Gly Arg Phe Thr Ile Ser Arg Asp Asn Ala Lys Asn Thr Val Asp Leu
65                  70                  75                  80

Gln Met Asn Asn Leu Lys Pro Glu Asp Thr Ala Val Tyr Tyr Cys Arg
                85                  90                  95

Leu Leu Asp Thr Ala Arg Gly Val Gly Tyr Trp Gly Gln Gly Thr Gln
            100                 105                 110

Val Thr Val Ser Ser
        115

<210> SEQ ID NO 442
<211> LENGTH: 115
<212> TYPE: PRT
<213> ORGANISM: Artificial
<220> FEATURE:
<223> OTHER INFORMATION: Nanobody or Nanobody fragment

<400> SEQUENCE: 442

Glu Val Gln Leu Val Glu Ser Gly Gly Gly Leu Val Gln Ala Gly Gly
1               5                   10                  15

Ser Leu Arg Leu Ser Cys Ala Ala Ser Ala Ser Ile Ile Ser Ser Ala
            20                  25                  30

Ala Leu Gly Trp Tyr Arg Gln Ala Pro Gly Lys Arg Arg Glu Phe Val
        35                  40                  45

Ala Gly Ile Leu Ser Asp Gly Arg Glu Leu Tyr Val Asp Ser Val Lys
50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Asp Ile Asp Tyr Arg Asp Tyr Trp Gly Gln Gly Thr Gln Val Thr
            100                 105                 110

Val Ser Ser
        115

<210> SEQ ID NO 443
<211> LENGTH: 118
<212> TYPE: PRT
<213> ORGANISM: Artificial
<220> FEATURE:
<223> OTHER INFORMATION: Nanobody or Nanobody fragment

<400> SEQUENCE: 443

Glu Val Gln Leu Val Glu Ser Gly Gly Gly Leu Val Gln Ala Gly Gly
1               5                   10                  15

Ala Leu Arg Leu Ser Cys Thr Ala Ser Gly Ile Thr Phe Lys Arg Tyr
            20                  25                  30

```
Asp Met Gly Trp Tyr Arg Gln Ala Pro Gly Lys Glu Arg Glu Trp Val
        35                  40                  45

Thr Thr Ile Thr Ser Glu Gly Thr Ala Asn Ser Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Ser Glu Asp Thr Ala Val Tyr Tyr Cys Asn
                 85                  90                  95

Ala Gln Phe Thr Leu Ala Arg His Leu Val Tyr Trp Gly Gln Gly Thr
                100                 105                 110

Gln Val Thr Val Ser Ser
                115
```

<210> SEQ ID NO 444
<211> LENGTH: 117
<212> TYPE: PRT
<213> ORGANISM: Artificial
<220> FEATURE:
<223> OTHER INFORMATION: Nanobody or Nanobody fragment

<400> SEQUENCE: 444

```
Glu Val Gln Leu Val Glu Ser Gly Gly Gly Leu Val Gln Ala Gly Gly
 1               5                  10                  15

Ser Leu Arg Leu Ser Cys Ala Ala Ser Arg Ser Arg Ser Ser Phe Asp
                 20                  25                  30

Asp Met Gly Trp Tyr Arg Gln Ala Pro Gly Lys Gln Arg Glu Phe Val
        35                  40                  45

Gly Gly Ile Thr Leu Gly Gly Ser Thr Ile Tyr Ala Asp Ser Val Lys
 50                  55                  60

Gly Arg Phe Thr Ile Ser Met Asp Ser Ala Arg Asn Thr Gly Tyr Leu
 65                  70                  75                  80

Gln Met Asn Ser Leu Lys Pro Glu Asp Thr Ala Val Tyr Tyr Cys Asn
                 85                  90                  95

Ala Ala Leu Asp Gly Tyr Ser Gly Ser Ser Trp Gly Gln Gly Thr Gln
                100                 105                 110

Val Thr Val Ser Ser
                115
```

<210> SEQ ID NO 445
<211> LENGTH: 117
<212> TYPE: PRT
<213> ORGANISM: Artificial
<220> FEATURE:
<223> OTHER INFORMATION: Nanobody or Nanobody fragment

<400> SEQUENCE: 445

```
Glu Val Gln Leu Val Glu Ser Gly Gly Gly Leu Val Gln Ala Gly Gly
 1               5                  10                  15

Ser Leu Arg Leu Ser Cys Ala Ala Ser Arg Ser Arg Ser Ser Phe Asp
                 20                  25                  30

Asp Met Gly Trp Tyr Arg Gln Ala Pro Gly Lys Gln Arg Glu Phe Val
        35                  40                  45

Ala Gly Ile Thr Leu Gly Gly Ser Thr Ile Tyr Ala Asp Ser Val Lys
 50                  55                  60

Gly Arg Phe Thr Ile Ser Met Asp Ser Ala Arg Asn Thr Gly Tyr Leu
 65                  70                  75                  80

Gln Met Ser Ser Leu Lys Pro Glu Asp Thr Ala Val Tyr Tyr Cys Asn
```

```
                85                  90                  95
Ala Val Leu Asp Gly Tyr Ser Gly Ser Ser Trp Gly Gln Gly Thr Gln
                100                 105                 110
Val Thr Val Ser Ser
        115

<210> SEQ ID NO 446
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 446

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe Ala Asn Asn
            20                  25                  30

Ile Met Gly Trp Tyr Arg Gln Pro Pro Gly Lys Glu Arg Glu Phe Val
        35                  40                  45

Ala His Val Ser His Asp Gly Tyr Ser Met Tyr Ala Val Ser Val Glu
    50                  55                  60

Gly Arg Phe Thr Ile Ser Arg Glu Asn Ala Thr Asn Leu Tyr Leu Gln
65                  70                  75                  80

Met Asn Ser Leu Lys Pro Glu Asp Thr Ala Ile Tyr Phe Cys Arg Leu
                85                  90                  95

Leu Thr Ile Pro Pro Gln Gly Arg Met Glu Gly Phe Trp Gly Gln Gly
                100                 105                 110

Thr Gln Val Thr Val Ser Ser
        115

<210> SEQ ID NO 447
<211> LENGTH: 120
<212> TYPE: PRT
<213> ORGANISM: Artificial
<220> FEATURE:
<223> OTHER INFORMATION: Nanobody or Nanobody fragment

<400> SEQUENCE: 447

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe Ser Asp Asn
            20                  25                  30

Ile Met Gly Trp Tyr Arg Gln Ala Pro Gly Lys Gln Arg Glu Phe Val
        35                  40                  45

Ala His Met Ser Arg Asp Gly Thr Ser Asn Tyr Glu Asp Ser Val Lys
    50                  55                  60

Gly Arg Phe Thr Ile Ser Arg Glu Asn Ala Lys Asn Thr Leu Tyr Leu
65                  70                  75                  80

Gln Met Asn Ser Leu Lys Pro Glu Asp Thr Ala Ile Tyr Tyr Cys Arg
                85                  90                  95

Leu Leu Thr Ile Pro Thr Thr Gly Arg Lys Glu Gly Phe Trp Gly Gln
                100                 105                 110

Gly Thr Gln Val Thr Val Ser Ser
        115                 120

<210> SEQ ID NO 448
<211> LENGTH: 117
```

<212> TYPE: PRT
<213> ORGANISM: Artificial
<220> FEATURE:
<223> OTHER INFORMATION: Nanobody or Nanobody fragment

<400> SEQUENCE: 448

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Asn Asp Asn
            20                  25                  30

Ser Met Gly Trp Tyr Arg Gln Ala Pro Gly Trp Gln Arg Glu Leu Val
        35                  40                  45

Ala Ile Lys Phe Ser Gly Gly Thr Thr Asp Ile Ala Glu Ser Ala Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Arg
                85                  90                  95

Leu Phe Leu Pro Ser Leu Ala Met Gly Tyr Trp Gly Gln Gly Thr Gln
            100                 105                 110

Val Thr Val Ser Ser
        115

<210> SEQ ID NO 449
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 449

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe Ala Asn Asn
            20                  25                  30

Ile Met Gly Trp Tyr Arg Gln Pro Pro Gly Lys Glu Arg Glu Phe Val
        35                  40                  45

Ala His Val Ser His Asp Gly Asp Ser Met Tyr Ala Val Ser Val Lys
    50                  55                  60

Gly Arg Phe Thr Ile Ser Arg Lys Asp Ala Thr Asn Leu Tyr Leu Gln
65                  70                  75                  80

Met Asn Ser Leu Lys Pro Glu Asp Thr Ala Ile Tyr Phe Cys Arg Leu
                85                  90                  95

Leu Asn Ile Pro Thr Gln Gly Arg Met Glu Gly Phe Trp Gly Gln Gly
            100                 105                 110

Thr Gln Val Thr Val Ser Ser
        115

<210> SEQ ID NO 450
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 450

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Ile Phe Ala Asn Asn

-continued

```
                20                  25                  30
Ile Met Gly Trp Tyr Arg Gln Pro Pro Gly Lys Glu Arg Glu Phe Val
            35                  40                  45

Ala His Val Ser Asp Asp Gly Asp Ser Met Tyr Ala Val Ser Val Lys
 50                  55                  60

Gly Arg Phe Thr Ile Ser Arg Lys Asn Ala Thr Asn Leu Tyr Leu Gln
 65                  70                  75                  80

Met Asn Ser Leu Lys Pro Glu Asp Thr Ala Ile Tyr Phe Cys Arg Leu
                85                  90                  95

Leu Asn Ile Pro Thr Gln Gly Arg Met Glu Gly Phe Trp Gly Gln Gly
            100                 105                 110

Thr Gln Val Thr Val Ser Ser
            115

<210> SEQ ID NO 451
<211> LENGTH: 125
<212> TYPE: PRT
<213> ORGANISM: Artificial
<220> FEATURE:
<223> OTHER INFORMATION: Nanobody or Nanobody fragment

<400> SEQUENCE: 451

Glu Val Gln Leu Val Glu Ser Gly Gly Gly Leu Val Gln Ala Gly Gly
 1               5                  10                  15

Ser Leu Arg Leu Ser Cys Val Ala Ser Gly Phe Ser Phe Asp Asp Tyr
                20                  25                  30

Ala Ile Gly Trp Phe Arg Gln Ala Pro Gly Gln Asp Arg Glu Pro Leu
            35                  40                  45

Ala Cys Ile Thr Ser Gly Gly Thr Arg Asn Tyr Asn Pro Ser Val Met
 50                  55                  60

Ala Arg Phe Arg Ile Asp Arg Asp Asn Ser Val Lys Thr Val Tyr Leu
 65                  70                  75                  80

Gln Ile Asn Thr Leu Lys Pro Glu Asp Thr Ala Val Tyr Tyr Cys Ser
                85                  90                  95

Thr Glu Leu Asp Arg Gln Gly Gly Ser Ala His Glu Cys Arg Glu Tyr
            100                 105                 110

Asp Thr Trp Gly Gln Gly Thr Gln Val Thr Val Ser Ser
            115                 120                 125

<210> SEQ ID NO 452
<211> LENGTH: 116
<212> TYPE: PRT
<213> ORGANISM: Artificial
<220> FEATURE:
<223> OTHER INFORMATION: Nanobody or Nanobody fragment

<400> SEQUENCE: 452

Glu Val Gln Leu Val Glu Ser Gly Gly Gly Leu Val Gln Ala Gly Gly
 1               5                  10                  15

Ser Leu Arg Leu Ser Cys Ala Ala Ser Glu Ser Ile Ser Ser Phe Asn
                20                  25                  30

Ala Met Gly Trp Tyr Arg Gln Gly Pro Gly Lys Leu Arg Glu Leu Val
            35                  40                  45

Ala Gln Ile Thr Asp Leu His Lys Asp Tyr Ala Glu Ser Ala Lys Gly
 50                  55                  60

Arg Phe Thr Ile Ser Arg Asp Asn Ala Lys Asn Thr Val Asp Leu Gln
 65                  70                  75                  80
```

```
Met Asn Ser Leu Lys Pro Glu Asp Thr Gly Val Tyr Tyr Cys Ala Ala
             85                  90                  95

Phe Arg Gly Ile Met Arg Pro Asp Tyr Trp Gly Gln Gly Thr Gln Val
            100                 105                 110

Thr Val Ser Ser
        115

<210> SEQ ID NO 453
<211> LENGTH: 120
<212> TYPE: PRT
<213> ORGANISM: Artificial
<220> FEATURE:
<223> OTHER INFORMATION: Nanobody or Nanobody fragment

<400> SEQUENCE: 453

Glu Val Gln Leu Val Glu Ser Gly Gly Gly Leu Val Gln Ala Gly Lys
1               5                   10                  15

Ser Leu Ser Leu Ser Cys Ala Ala Ser Asp Ser Arg Phe Ser Gly Arg
            20                  25                  30

Phe Asn Ile Leu Asn Met Gly Trp Tyr Arg Gln Ala Pro Gly Lys Gln
            35                  40                  45

Arg Glu Trp Val Thr Thr Leu Leu Ser Thr Gly Ser Pro Ile Tyr Ala
50                  55                  60

Asp Ser Val Lys Gly Arg Phe Thr Ile Ser Arg Asp His Ala Lys Asn
65                  70                  75                  80

Thr Val Tyr Leu Gln Met His Ser Leu Lys Pro Asp Asp Thr Ala Asn
             85                  90                  95

Tyr Ile Cys Phe Ala Arg Leu Thr Pro Thr Gly Thr Val Trp Gly Gln
            100                 105                 110

Gly Thr Gln Val Thr Val Ser Ser
            115                 120

<210> SEQ ID NO 454
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 454

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser
            20                  25                  30

<210> SEQ ID NO 455
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 455

Glu Val Gln Leu Val Glu Ser Gly Gly Gly Leu Val Gln Ala Gly Gly
1               5                   10                  15

Ser Leu Arg Leu Ser Cys Thr Ala Ser Glu Arg Thr Phe Ser
            20                  25                  30

<210> SEQ ID NO 456
<211> LENGTH: 30
<212> TYPE: PRT
```

```
<213> ORGANISM: Artificial
<220> FEATURE:
<223> OTHER INFORMATION: Nanobody or Nanobody fragment

<400> SEQUENCE: 456

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 457
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 457

Glu Val Gln Leu Val Glu Ser Gly Gly Gly Leu Val His Ala Gly Asp
1               5                   10                  15

Ser Leu Arg Leu Ser Cys Ala Ala Ser Gly Phe Thr Leu Asp
            20                  25                  30

<210> SEQ ID NO 458
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 458

Glu Val Gln Leu Val Glu Ser Gly Gly Gly Leu Ala Gln Pro Gly Gly
1               5                   10                  15

Ser Leu Arg Leu Ser Cys Val Ala Ser Gly Phe Ser Leu Ala
            20                  25                  30

<210> SEQ ID NO 459
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 459

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 460
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 460

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp
            20                  25                  30

<210> SEQ ID NO 461
<211> LENGTH: 30
```

<212> TYPE: PRT
<213> ORGANISM: Artificial
<220> FEATURE:
<223> OTHER INFORMATION: Nanobody or Nanobody fragment

<400> SEQUENCE: 461

Glu Val Gln Leu Val Glu Ser Gly Gly Gly Leu Val Gln Pro Gly Gly
1               5                   10                  15

Ser Met Arg Leu Ser Cys Ala Ala Ser Gly Ser Ser Leu Asp
            20                  25                  30

<210> SEQ ID NO 462
<211> LENGTH: 30
<212> TYPE: PRT
<213> ORGANISM: Artificial
<220> FEATURE:
<223> OTHER INFORMATION: Nanobody or Nanobody fragment

<400> SEQUENCE: 462

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp
            20                  25                  30

<210> SEQ ID NO 463
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 463

Asp His Asp Met Gly
1               5

<210> SEQ ID NO 464
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 464

Ser Tyr Asn Met Gly
1               5

<210> SEQ ID NO 465
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 465

Asp Tyr Ala Val Ser
1               5

<210> SEQ ID NO 466
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 466

Asp Tyr Ala Val Ser

```
1               5

<210> SEQ ID NO 467
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 467

Asp Tyr Ala Ile Ser
1               5

<210> SEQ ID NO 468
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 468

Asp Tyr Ala Ile Gly
1               5

<210> SEQ ID NO 469
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 469

Glu Tyr Ala Ile Gly
1               5

<210> SEQ ID NO 470
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 470

Ala Tyr Gly Leu Gly
1               5

<210> SEQ ID NO 471
<211> LENGTH: 5
<212> TYPE: PRT
<213> ORGANISM: Artificial
<220> FEATURE:
<223> OTHER INFORMATION: Nanobody or Nanobody fragment

<400> SEQUENCE: 471

Asp Tyr Ala Ile Gly
1               5

<210> SEQ ID NO 472
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 472

Trp Phe Arg Gln Ala Pro Gly Lys Glu Arg Glu Phe Val Ala
1               5                   10
```

```
<210> SEQ ID NO 473
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 473

Trp Phe Arg Gln Ala Pro Gly Lys Glu Arg Val Phe Val Ala
1               5                   10

<210> SEQ ID NO 474
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 474

Trp Phe Arg Arg Ala Pro Gly Lys Glu Arg Glu Gly Val Ser
1               5                   10

<210> SEQ ID NO 475
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 475

Trp Phe Arg Gln Ala Pro Gly Lys Ala Arg Glu Gly Leu Ser
1               5                   10

<210> SEQ ID NO 476
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 476

Trp Phe Arg Gln Ala Pro Gly Lys Val Arg Glu Gly Val Ser
1               5                   10

<210> SEQ ID NO 477
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 477

Trp Phe Arg Gln Ala Pro Gly Lys Glu Arg Glu Gly Val Ser
1               5                   10

<210> SEQ ID NO 478
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 478

Trp Phe Arg Gln Ala Pro Gly Lys Glu Arg Glu Gly Val Ser
1               5                   10
```

<210> SEQ ID NO 479
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 479

Trp Phe Arg Gln Ala Pro Gly Lys Glu Arg Glu Gly Val Ser
1               5                   10

<210> SEQ ID NO 480
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 480

Trp Phe Arg Gln Ala Pro Gly Lys Glu Arg Glu Gly Val Ser
1               5                   10

<210> SEQ ID NO 481
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 481

Thr Met Arg Trp Gly Thr Ser Ser Thr Tyr Tyr Ala Asp Ser Val Lys
1               5                   10                  15

Gly

<210> SEQ ID NO 482
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 482

Val Ile Asp Trp Ser Gly Gly Leu Ala Tyr Tyr Ala Asp Ser Val Lys
1               5                   10                  15

Gly

<210> SEQ ID NO 483
<211> LENGTH: 18
<212> TYPE: PRT
<213> ORGANISM: Artificial
<220> FEATURE:
<223> OTHER INFORMATION: Nanobody or Nanobody fragment

<400> SEQUENCE: 483

Cys Ile Ser Ser Ser Ser Ser Ser Asp Thr Tyr Tyr Ala Asp Ser Val
1               5                   10                  15

Arg Gly

<210> SEQ ID NO 484
<211> LENGTH: 17
<212> TYPE: PRT
<213> ORGANISM: Artificial
<220> FEATURE:
<223> OTHER INFORMATION: Nanobody or Nanobody fragment

```
<400> SEQUENCE: 484

Cys Ile Ser Ala Glu Asp Gly Ser Thr Tyr Tyr Ala Asp Ser Val Lys
1               5                   10                  15

Gly

<210> SEQ ID NO 485
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 485

Cys Ile Ser Ser Ser Asp Gly Ser Thr Tyr Tyr Ala Asp Ser Val Lys
1               5                   10                  15

Gly

<210> SEQ ID NO 486
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 486

Cys Ile Ser Ser Ser Asp Gly Ser Thr Tyr Tyr Ala Asp Ser Val Lys
1               5                   10                  15

Gly

<210> SEQ ID NO 487
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 487

Cys Ile Ser Arg Ser Asp Gly Ser Thr Tyr Tyr Ala Pro Ser Val Lys
1               5                   10                  15

Gly

<210> SEQ ID NO 488
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 488

Cys Ile Ser Gly Ser Asp Asn Ser Thr Tyr Tyr Ala Asp Ser Val Lys
1               5                   10                  15

Gly

<210> SEQ ID NO 489
<211> LENGTH: 17
<212> TYPE: PRT
<213> ORGANISM: Artificial
<220> FEATURE:
<223> OTHER INFORMATION: Nanobody or Nanobody fragment

<400> SEQUENCE: 489

Cys Ile Thr Ser Ser Asp Gly Ser Thr Tyr Tyr Ala Asp Ser Val Lys
1               5                   10                  15
```

Gly

<210> SEQ ID NO 490
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 490

Arg Phe Thr Ile Ser Ser Asp Asn Thr Lys Asn Thr Val Tyr Leu Gln
1               5                   10                  15
Met Asn Ser Leu Thr Pro Glu Asp Thr Ala Val Tyr Tyr Cys Ala Ala
            20                  25                  30

<210> SEQ ID NO 491
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 491

Arg Phe Thr Ile Ser Arg Asp Asn Ala Lys Lys Thr Val Tyr Leu Gln
1               5                   10                  15
Met Asn Ser Leu Lys Pro Glu Asp Thr Ala Val Tyr Tyr Cys Ala Ala
            20                  25                  30

<210> SEQ ID NO 492
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 492

Arg Phe Ser Ile Ser Arg Asp Ser Ala Lys Asn Thr Val Tyr Leu Gln
1               5                   10                  15
Met Asn Ser Leu Lys Pro Glu Asp Thr Ala Val Tyr Tyr Cys Ala Ala
            20                  25                  30

<210> SEQ ID NO 493
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 493

Arg Phe Ile Ile Ser Arg Asp Asn Ala Lys Asn Thr Val Tyr Leu Gln
1               5                   10                  15
Met Asn Ser Leu Lys Pro Glu Asp Thr Ala Val Tyr Tyr Cys Ala Ala
            20                  25                  30

<210> SEQ ID NO 494
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 494

Arg Phe Thr Ile Ser Arg Asp Asn Ala Lys Asn Ala Val Tyr Leu Gln
1               5                   10                  15

```
Met Ser Thr Leu Lys Pro Glu Asp Thr Ala Val Tyr Tyr Cys Ala Ala
            20                  25                  30

<210> SEQ ID NO 495
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 495

Arg Phe Thr Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Ala Ala
            20                  25                  30

<210> SEQ ID NO 496
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 496

Arg Phe Thr Ile Ser Ser Asp Asn Ala Lys Asn Thr Val Tyr Leu Gln
1               5                   10                  15

Met Asn Ser Leu Lys Pro Glu Asp Thr Ala Val Tyr Tyr Cys Ala Val
            20                  25                  30

<210> SEQ ID NO 497
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 497

Arg Phe Ser Ile Ser Arg Asp Ile Ala Lys Asn Thr Val Tyr Leu Gln
1               5                   10                  15

Met Asn Gly Leu Lys Pro Glu Asp Thr Ala Val Tyr Tyr Cys Ala Ala
            20                  25                  30

<210> SEQ ID NO 498
<211> LENGTH: 32
<212> TYPE: PRT
<213> ORGANISM: Artificial
<220> FEATURE:
<223> OTHER INFORMATION: Nanobody or Nanobody fragment

<400> SEQUENCE: 498

Arg Phe Thr Ile Ser Arg Asp Asn Ala Lys Asn Thr Val Tyr Leu Gln
1               5                   10                  15

Ile Asn Ser Leu Lys Pro Glu Asp Thr Ala Val Tyr Tyr Cys Ala Ala
            20                  25                  30

<210> SEQ ID NO 499
<211> LENGTH: 10
<212> TYPE: PRT
<213> ORGANISM: Artificial
<220> FEATURE:
<223> OTHER INFORMATION: Nanobody or Nanobody fragment

<400> SEQUENCE: 499

Arg Ser Val Tyr Ser Tyr Glu Tyr Thr Tyr
```

```
1               5                   10
```

<210> SEQ ID NO 500
<211> LENGTH: 15
<212> TYPE: PRT
<213> ORGANISM: Artificial
<220> FEATURE:
<223> OTHER INFORMATION: Nanobody or Nanobody fragment

<400> SEQUENCE: 500

```
Arg Ser Val Tyr Arg Gly Ser Thr Lys Pro Tyr Glu Tyr Asp Tyr
1               5                   10                  15
```

<210> SEQ ID NO 501
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 501

```
Asp Arg His Cys Leu Gly Ser Asp Trp Asp Glu Tyr Asp Tyr
1               5                   10
```

<210> SEQ ID NO 502
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 502

```
Glu Asp Ser Cys Leu Ser Ser Asp Tyr Asp Ala Tyr Asp Gly
1               5                   10
```

<210> SEQ ID NO 503
<211> LENGTH: 14
<212> TYPE: PRT
<213> ORGANISM: Artificial
<220> FEATURE:
<223> OTHER INFORMATION: Nanobody or Nanobody fragment

<400> SEQUENCE: 503

```
Glu Arg Ser Cys Leu Ser Ser Asp Tyr Asp Ser Tyr Asp Ala
1               5                   10
```

<210> SEQ ID NO 504
<211> LENGTH: 13
<212> TYPE: PRT
<213> ORGANISM: Artificial
<220> FEATURE:
<223> OTHER INFORMATION: Nanobody or Nanobody fragment

<400> SEQUENCE: 504

```
Asp Leu Gly Tyr Gly Ser Asn Cys Leu Glu Tyr Asp Phe
1               5                   10
```

<210> SEQ ID NO 505
<211> LENGTH: 13
<212> TYPE: PRT
<213> ORGANISM: Artificial
<220> FEATURE:
<223> OTHER INFORMATION: Nanobody or Nanobody fragment

<400> SEQUENCE: 505

```
Asp Leu Glu Tyr Gly Ser Asn Cys Tyr Glu Tyr Asp Ser
1               5                   10
```

<210> SEQ ID NO 506
<211> LENGTH: 25
<212> TYPE: PRT
<213> ORGANISM: Artificial
<220> FEATURE:
<223> OTHER INFORMATION: Nanobody or Nanobody fragment

<400> SEQUENCE: 506

Lys Phe Leu Gly Phe Arg Gln Arg Ser Pro Thr Trp Phe Ser Arg Ser
1               5                   10                  15

Trp Ser Glu Gly Ser Asp Tyr Gln Tyr
            20                  25

<210> SEQ ID NO 507
<211> LENGTH: 13
<212> TYPE: PRT
<213> ORGANISM: Artificial
<220> FEATURE:
<223> OTHER INFORMATION: Nanobody or Nanobody fragment

<400> SEQUENCE: 507

Asp Leu Gly Val Gly Thr Gln Cys Asp Glu Tyr Asp Tyr
1               5                   10

<210> SEQ ID NO 508
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 508

Trp Gly Gln Gly Thr Gln Val Thr Val Ser Ser
1               5                   10

<210> SEQ ID NO 509
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 509

Trp Gly Gln Gly Thr Gln Val Thr Val Ser Ser
1               5                   10

<210> SEQ ID NO 510
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 510

Trp Gly Gln Gly Thr Gln Val Thr Val Ser Ser
1               5                   10

<210> SEQ ID NO 511
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 511

Trp Gly Gln Gly Thr Gln Val Thr Val Ser Ser
1               5                   10

<210> SEQ ID NO 512
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 512

Trp Gly Gln Gly Thr Gln Val Thr Val Ser Ser
1               5                   10

<210> SEQ ID NO 513
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 513

Trp Gly Gln Gly Thr Gln Val Thr Val Ser Ser
1               5                   10

<210> SEQ ID NO 514
<211> LENGTH: 11
<212> TYPE: PRT
<213> ORGANISM: Artificial
<220> FEATURE:
<223> OTHER INFORMATION: nanbody or nanobody fragment

<400> SEQUENCE: 514

Trp Gly Gln Gly Thr Gln Val Thr Val Ser Ser
1               5                   10

<210> SEQ ID NO 515
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 515

Trp Gly Gln Gly Thr Gln Val Thr Val Ser Ser
1               5                   10

<210> SEQ ID NO 516
<211> LENGTH: 11
<212> TYPE: PRT
<213> ORGANISM: Artificial
<220> FEATURE:
<223> OTHER INFORMATION: Nanobody or Nanobody fragment

<400> SEQUENCE: 516

Trp Gly Gln Gly Thr Gln Val Thr Val Ser Ser
1               5                   10

<210> SEQ ID NO 517
<211> LENGTH: 119
<212> TYPE: PRT
<213> ORGANISM: Artificial
<220> FEATURE:
<223> OTHER INFORMATION: Nanobody or Nanobody fragment

<400> SEQUENCE: 517

Glu Val Gln Leu Val Glu Ser Gly Gly Gly Leu Val Gln Ala Gly Gly

```
                1               5                  10                 15
            Ser Leu Arg Leu Ser Cys Ala Ala Ser Gly Arg Thr Leu Ser Asp His
                        20                  25                  30

Asp Met Gly Trp Phe Arg Gln Ala Pro Gly Lys Glu Arg Glu Phe Val
                        35                  40                  45

Ala Thr Met Arg Trp Gly Thr Ser Ser Thr Tyr Tyr Ala Asp Ser Val
                        50                  55                  60

Lys Gly Arg Phe Thr Ile Ser Ser Asp Asn Lys Asn Thr Val Tyr
            65                  70                  75                  80

Leu Gln Met Asn Ser Leu Thr Pro Glu Asp Thr Ala Val Tyr Tyr Cys
                        85                  90                  95

Ala Ala Arg Ser Val Tyr Ser Tyr Glu Tyr Thr Tyr Trp Gly Gln Gly
                        100                 105                 110

Thr Gln Val Thr Val Ser Ser
                        115
```

<210> SEQ ID NO 518
<211> LENGTH: 124
<212> TYPE: PRT
<213> ORGANISM: Artificial
<220> FEATURE:
<223> OTHER INFORMATION: Nanobody or Nanobody fragment

<400> SEQUENCE: 518

```
            Glu Val Gln Leu Val Glu Ser Gly Gly Gly Leu Val Gln Ala Gly Gly
            1               5                  10                 15

Ser Leu Arg Leu Ser Cys Thr Ala Ser Glu Arg Thr Phe Ser Ser Tyr
                        20                  25                  30

Asn Met Gly Trp Phe Arg Gln Ala Pro Gly Lys Glu Arg Val Phe Val
                        35                  40                  45

Ala Val Ile Asp Trp Ser Gly Gly Leu Ala Tyr Tyr Ala Asp Ser Val
                        50                  55                  60

Lys Gly Arg Phe Thr Ile Ser Arg Asp Asn Ala Lys Lys Thr Val Tyr
            65                  70                  75                  80

Leu Gln Met Asn Ser Leu Lys Pro Glu Asp Thr Ala Val Tyr Tyr Cys
                        85                  90                  95

Ala Ala Arg Ser Val Tyr Arg Gly Ser Thr Lys Pro Tyr Glu Tyr Asp
                        100                 105                 110

Tyr Trp Gly Gln Gly Thr Gln Val Thr Val Ser Ser
                        115                 120
```

<210> SEQ ID NO 519
<211> LENGTH: 124
<212> TYPE: PRT
<213> ORGANISM: Artificial
<220> FEATURE:
<223> OTHER INFORMATION: Nanobody or Nanobody fragment

<400> SEQUENCE: 519

```
            Glu Val Gln Leu Val Glu Ser Gly Gly Gly Leu Val Gln Pro Gly Gly
            1               5                  10                 15

Ser Leu Arg Leu Ser Cys Ala Ala Ser Gly Phe Thr Leu Asp Asp Tyr
                        20                  25                  30

Ala Val Ser Trp Phe Arg Arg Ala Pro Gly Lys Glu Arg Glu Gly Val
                        35                  40                  45

Ser Cys Ile Ser Ser Ser Ser Ser Ser Asp Thr Tyr Tyr Ala Asp Ser
                        50                  55                  60
```

Val Arg Gly Arg Phe Ser Ile Ser Arg Asp Ser Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Asp Arg His Cys Leu Gly Ser Asp Trp Asp Glu Tyr Asp
            100                 105                 110

Tyr Trp Gly Gln Gly Thr Gln Val Thr Val Ser Ser
            115                 120

<210> SEQ ID NO 520
<211> LENGTH: 123
<212> TYPE: PRT
<213> ORGANISM: Artificial
<220> FEATURE:
<223> OTHER INFORMATION: Nanobody or Nanobody fragment

<400> SEQUENCE: 520

Glu Val Gln Leu Val Glu Ser Gly Gly Gly Leu Val His Ala Gly Asp
1               5                   10                  15

Ser Leu Arg Leu Ser Cys Ala Ala Ser Gly Phe Thr Leu Asp Asp Tyr
                20                  25                  30

Ala Val Ser Trp Phe Arg Gln Ala Pro Gly Lys Ala Arg Glu Gly Leu
            35                  40                  45

Ser Cys Ile Ser Ala Glu Asp Gly Ser Thr Tyr Tyr Ala Asp Ser Val
        50                  55                  60

Lys Gly Arg Phe Ile Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Asp Ser Cys Leu Ser Ser Asp Tyr Asp Ala Tyr Asp Gly
            100                 105                 110

Trp Gly Gln Gly Thr Gln Val Thr Val Ser Ser
        115                 120

<210> SEQ ID NO 521
<211> LENGTH: 123
<212> TYPE: PRT
<213> ORGANISM: Artificial
<220> FEATURE:
<223> OTHER INFORMATION: Nanobody or Nanobody fragment

<400> SEQUENCE: 521

Glu Val Gln Leu Val Glu Ser Gly Gly Gly Leu Ala Gln Pro Gly Gly
1               5                   10                  15

Ser Leu Arg Leu Ser Cys Val Ala Ser Gly Phe Ser Leu Ala Asp Tyr
                20                  25                  30

Ala Ile Ser Trp Phe Arg Gln Ala Pro Gly Lys Val Arg Glu Gly Val
            35                  40                  45

Ser Cys Ile Ser Ser Ser Asp Gly Ser Thr Tyr Tyr Ala Asp Ser Val
        50                  55                  60

Lys Gly Arg Phe Thr Ile Ser Arg Asp Asn Ala Lys Asn Ala Val Tyr
65                  70                  75                  80

Leu Gln Met Ser Thr Leu Lys Pro Glu Asp Thr Ala Val Tyr Tyr Cys
                85                  90                  95

Ala Ala Glu Arg Ser Cys Leu Ser Ser Asp Tyr Asp Ser Tyr Asp Ala
            100                 105                 110

Trp Gly Gln Gly Thr Gln Val Thr Val Ser Ser
        115                 120

<210> SEQ ID NO 522
<211> LENGTH: 122
<212> TYPE: PRT
<213> ORGANISM: Artificial
<220> FEATURE:
<223> OTHER INFORMATION: Nanobody or Nanobody fragment

<400> SEQUENCE: 522

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Asp Tyr
            20                  25                  30

Ala Ile Gly Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Gly Tyr Gly Ser Asn Cys Leu Glu Tyr Asp Phe Trp
            100                 105                 110

Gly Gln Gly Thr Gln Val Thr Val Ser Ser
        115                 120
```

<210> SEQ ID NO 523
<211> LENGTH: 122
<212> TYPE: PRT
<213> ORGANISM: Artificial
<220> FEATURE:
<223> OTHER INFORMATION: Nanobody or Nanobody fragment

<400> SEQUENCE: 523

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Glu Tyr
            20                  25                  30

Ala Ile Gly Trp Phe Arg Gln Ala Pro Gly Lys Glu Arg Glu Gly Val
        35                  40                  45

Ser Cys Ile Ser Arg Ser Asp Gly Ser Thr Tyr Tyr Ala Pro Ser Val
    50                  55                  60

Lys Gly Arg Phe Thr Ile Ser Ser Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Val Asp Leu Glu Tyr Gly Ser Asn Cys Tyr Glu Tyr Asp Ser Trp
            100                 105                 110

Gly Gln Gly Thr Gln Val Thr Val Ser Ser
        115                 120
```

<210> SEQ ID NO 524
<211> LENGTH: 134
<212> TYPE: PRT
<213> ORGANISM: Artificial
<220> FEATURE:
<223> OTHER INFORMATION: Nanobody or Nanobody fragment

<400> SEQUENCE: 524

```
Glu Val Gln Leu Val Glu Ser Gly Gly Gly Leu Val Gln Pro Gly Gly
1               5                   10                  15

Ser Met Arg Leu Ser Cys Ala Ala Ser Gly Ser Ser Leu Asp Ala Tyr
            20                  25                  30

Gly Leu Gly Trp Phe Arg Gln Ala Pro Gly Lys Glu Arg Glu Gly Val
            35                  40                  45

Ser Cys Ile Ser Gly Ser Asp Asn Ser Thr Tyr Tyr Ala Asp Ser Val
50                      55                  60

Lys Gly Arg Phe Ser Ile Ser Arg Asp Ile Ala Lys Asn Thr Val Tyr
65                      70                  75                  80

Leu Gln Met Asn Gly Leu Lys Pro Glu Asp Thr Ala Val Tyr Tyr Cys
                85                  90                  95

Ala Ala Lys Phe Leu Gly Phe Arg Gln Arg Ser Pro Thr Trp Phe Ser
                100                 105                 110

Arg Ser Trp Ser Glu Gly Ser Asp Tyr Gln Tyr Trp Gly Gln Gly Thr
                115                 120                 125

Gln Val Thr Val Ser Ser
            130

<210> SEQ ID NO 525
<211> LENGTH: 122
<212> TYPE: PRT
<213> ORGANISM: Artificial
<220> FEATURE:
<223> OTHER INFORMATION: Nanobody or Nanobody fragment

<400> SEQUENCE: 525

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Asp Tyr
            20                  25                  30

Ala Ile Gly Trp Phe Arg Gln Ala Pro Gly Lys Glu Arg Glu Gly Val
            35                  40                  45

Ser Cys Ile Thr Ser Ser Asp Gly Ser Thr Tyr Tyr Ala Asp Ser Val
50                      55                  60

Lys Gly Arg Phe Thr Ile Ser Arg Asp Asn Ala Lys Asn Thr Val Tyr
65                      70                  75                  80

Leu Gln Ile Asn Ser Leu Lys Pro Glu Asp Thr Ala Val Tyr Tyr Cys
                85                  90                  95

Ala Ala Asp Leu Gly Val Gly Thr Gln Cys Asp Glu Tyr Asp Tyr Trp
                100                 105                 110

Gly Gln Gly Thr Gln Val Thr Val Ser Ser
                115                 120

<210> SEQ ID NO 526
<211> LENGTH: 122
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 526

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
                35                  40                  45

Ser Gly Ile Lys Ser Ser Gly Asp Ser Thr Arg Tyr Ala Gly Ser Val
        50                  55                  60

Lys Gly Arg Phe Thr Ile Ser Arg Asp Asn Ala Lys Asn Met Leu Tyr
 65                  70                  75                  80

Leu Gln Met Tyr Ser Leu Lys Pro Glu Asp Thr Ala Val Tyr Tyr Cys
                85                  90                  95

Ala Lys Ser Arg Val Ser Arg Thr Gly Leu Tyr Thr Tyr Asp Asn Arg
            100                 105                 110

Gly Gln Gly Thr Gln Val Thr Val Ser Ser
            115                 120

<210> SEQ ID NO 527
<211> LENGTH: 128
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 527

Glu Val Gln Leu Met Glu Ser Gly Gly Gly Leu Val Gln Ala Gly Gly
 1               5                  10                  15

Ser Leu Arg Leu Ser Cys Ala Ala Ser Gly Arg Thr Phe Asn Asn Tyr
                20                  25                  30

Ala Met Gly Trp Phe Arg Arg Ala Pro Gly Lys Glu Arg Glu Phe Val
            35                  40                  45

Ala Ala Ile Thr Arg Ser Gly Val Arg Ser Gly Val Ser Ala Ile Tyr
        50                  55                  60

Gly Asp Ser Val Lys Asp Arg Phe Thr Ile Ser Arg Asp Asn Ala Lys
 65                  70                  75                  80

Asn Thr Leu Tyr Leu Gln Met Asn Ser Leu Lys Pro Glu Asp Thr Ala
                85                  90                  95

Val Tyr Thr Cys Ala Ala Ser Ala Ile Gly Ser Gly Ala Leu Arg Arg
            100                 105                 110

Phe Glu Tyr Asp Tyr Ser Gly Gln Gly Thr Gln Val Thr Val Ser Ser
            115                 120                 125

<210> SEQ ID NO 528
<211> LENGTH: 254
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 528

Glu Val Gln Leu Val Glu Ser Gly Gly Gly Leu Val Gln Thr Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Gly Ile Lys Ser Ser Gly Asp Ser Thr Arg Tyr Ala Gly Ser Val
        50                  55                  60

Lys Gly Arg Phe Thr Ile Ser Arg Asp Asn Ala Lys Asn Met Leu Tyr
 65                  70                  75                  80

Leu Gln Met Tyr Ser Leu Lys Pro Glu Asp Thr Ala Val Tyr Tyr Cys
```

```
                85                  90                  95
Ala Lys Ser Arg Val Ser Arg Thr Gly Leu Tyr Thr Tyr Asp Asn Arg
            100                 105                 110

Gly Gln Gly Thr Gln Val Thr Val Ser Ser Gly Gly Gly Ser Gly
            115                 120                 125

Gly Gly Gly Ser Glu Val Gln Leu Val Glu Ser Gly Gly Gly Leu Val
    130                 135                 140

Gln Thr Gly Gly Ser Leu Arg Leu Ser Cys Ala Ala Ser Gly Phe Thr
145                 150                 155                 160

Phe Ser Ser Tyr Ala Met Ser Trp Val Arg Gln Ala Pro Gly Lys Gly
                165                 170                 175

Leu Glu Trp Val Ser Gly Ile Lys Ser Ser Gly Asp Ser Thr Arg Tyr
            180                 185                 190

Ala Gly Ser Val Lys Gly Arg Phe Thr Ile Ser Arg Asp Asn Ala Lys
        195                 200                 205

Asn Met Leu Tyr Leu Gln Met Tyr Ser Leu Lys Pro Glu Asp Thr Ala
    210                 215                 220

Val Tyr Tyr Cys Ala Lys Ser Arg Val Ser Arg Thr Gly Leu Tyr Thr
225                 230                 235                 240

Tyr Asp Asn Arg Gly Gln Gly Thr Gln Val Thr Val Ser Ser
                245                 250

<210> SEQ ID NO 529
<211> LENGTH: 276
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 529

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Asn Asn Tyr
            20                  25                  30

Ala Met Gly Trp Phe Arg Arg Ala Pro Gly Lys Glu Arg Glu Phe Val
        35                  40                  45

Ala Ala Ile Thr Arg Ser Gly Val Arg Ser Gly Val Ser Ala Ile Tyr
    50                  55                  60

Gly Asp Ser Val Lys Asp Arg Phe Thr Ile Ser Arg Asp Asn Ala Lys
65                  70                  75                  80

Asn Thr Leu Tyr Leu Gln Met Asn Ser Leu Lys Pro Glu Asp Thr Ala
                85                  90                  95

Val Tyr Thr Cys Ala Ala Ser Ala Ile Gly Ser Gly Ala Leu Arg Arg
            100                 105                 110

Phe Glu Tyr Asp Tyr Ser Gly Gln Gly Thr Gln Val Thr Val Ser Ser
        115                 120                 125

Gly Gly Gly Gly Ser Gly Gly Gly Ser Gly Gly Gly Gly Ser Gly
    130                 135                 140

Gly Gly Ser Glu Val Gln Leu Met Glu Ser Gly Gly Gly Leu Val
145                 150                 155                 160

Gln Ala Gly Gly Ser Leu Arg Leu Ser Cys Ala Ala Ser Gly Arg Thr
                165                 170                 175

Phe Asn Asn Tyr Ala Met Gly Trp Phe Arg Arg Ala Pro Gly Lys Glu
            180                 185                 190
```

```
Arg Glu Phe Val Ala Ala Ile Thr Arg Ser Gly Val Arg Ser Gly Val
            195                 200                 205

Ser Ala Ile Tyr Gly Asp Ser Val Lys Asp Arg Phe Thr Ile Ser Arg
            210                 215                 220

Asp Asn Ala Lys Asn Thr Leu Tyr Leu Gln Met Asn Ser Leu Lys Pro
225                 230                 235                 240

Glu Asp Thr Ala Val Tyr Thr Cys Ala Ala Ser Ala Ile Gly Ser Gly
            245                 250                 255

Ala Leu Arg Arg Phe Glu Tyr Asp Tyr Ser Gly Gln Gly Thr Gln Val
            260                 265                 270

Thr Val Ser Ser
            275

<210> SEQ ID NO 530
<211> LENGTH: 265
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 530

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Gly Ile Lys Ser Ser Gly Asp Ser Thr Arg Tyr Ala Gly Ser Val
        50                  55                  60

Lys Gly Arg Phe Thr Ile Ser Arg Asp Asn Ala Lys Asn Met Leu Tyr
65                  70                  75                  80

Leu Gln Met Tyr Ser Leu Lys Pro Glu Asp Thr Ala Val Tyr Tyr Cys
            85                  90                  95

Ala Lys Ser Arg Val Ser Arg Thr Gly Leu Tyr Thr Tyr Asp Asn Arg
            100                 105                 110

Gly Gln Gly Thr Gln Val Thr Val Ser Ser Gly Gly Gly Ser Gly
            115                 120                 125

Gly Gly Gly Ser Gly Gly Gly Ser Glu Val Gln Leu Met Glu Ser
        130                 135                 140

Gly Gly Gly Leu Val Gln Ala Gly Gly Ser Leu Arg Leu Ser Cys Ala
145                 150                 155                 160

Ala Ser Gly Arg Thr Phe Asn Asn Tyr Ala Met Gly Trp Phe Arg Arg
            165                 170                 175

Ala Pro Gly Lys Glu Arg Glu Phe Val Ala Ala Ile Thr Arg Ser Gly
            180                 185                 190

Val Arg Ser Gly Val Ser Ala Ile Tyr Gly Asp Ser Val Lys Asp Arg
            195                 200                 205

Phe Thr Ile Ser Arg Asp Asn Ala Lys Asn Thr Leu Tyr Leu Gln Met
            210                 215                 220

Asn Ser Leu Lys Pro Glu Asp Thr Ala Val Tyr Thr Cys Ala Ala Ser
225                 230                 235                 240

Ala Ile Gly Ser Gly Ala Leu Arg Arg Phe Glu Tyr Asp Tyr Ser Gly
            245                 250                 255

Gln Gly Thr Gln Val Thr Val Ser Ser
            260                 265
```

<210> SEQ ID NO 531
<211> LENGTH: 270
<212> TYPE: PRT
<213> ORGANISM: Artificial Sequence
<220> FEATURE:
<223> OTHER INFORMATION: Nanobody, Nanobody constructs or fragments thereof

<400> SEQUENCE: 531

```
Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Lys Ser Ser Gly Asp Ser Thr Arg Tyr Ala Gly Ser Val
    50                  55                  60

Lys Gly Arg Phe Thr Ile Ser Arg Asp Asn Ala Lys Asn Met Leu Tyr
65                  70                  75                  80

Leu Gln Met Tyr Ser Leu Lys Pro Glu Asp Thr Ala Val Tyr Tyr Cys
                85                  90                  95

Ala Lys Ser Arg Val Ser Arg Thr Gly Leu Tyr Thr Tyr Asp Asn Arg
            100                 105                 110

Gly Gln Gly Thr Gln Val Thr Val Ser Ser Gly Gly Gly Gly Ser Gly
        115                 120                 125

Gly Gly Gly Ser Gly Gly Gly Ser Gly Gly Gly Ser Glu Val
    130                 135                 140

Gln Leu Met Glu Ser Gly Gly Leu Val Gln Ala Gly Gly Ser Leu
145                 150                 155                 160

Arg Leu Ser Cys Ala Ala Ser Gly Arg Thr Phe Asn Asn Tyr Ala Met
                165                 170                 175

Gly Trp Phe Arg Arg Ala Pro Gly Lys Glu Arg Glu Phe Val Ala Ala
            180                 185                 190

Ile Thr Arg Ser Gly Val Arg Ser Gly Val Ser Ala Ile Tyr Gly Asp
        195                 200                 205

Ser Val Lys Asp Arg Phe Thr Ile Ser Arg Asp Asn Ala Lys Asn Thr
    210                 215                 220

Leu Tyr Leu Gln Met Asn Ser Leu Lys Pro Glu Asp Thr Ala Val Tyr
225                 230                 235                 240

Thr Cys Ala Ala Ser Ala Ile Gly Ser Gly Ala Leu Arg Arg Phe Glu
                245                 250                 255

Tyr Asp Tyr Ser Gly Gln Gly Thr Gln Val Thr Val Ser Ser
            260                 265                 270
```

<210> SEQ ID NO 532
<211> LENGTH: 405
<212> TYPE: PRT
<213> ORGANISM: Artificial Sequence
<220> FEATURE:
<223> OTHER INFORMATION: Nanobody, Nanobody constructs or fragments thereof

<400> SEQUENCE: 532

```
Glu Val Gln Leu Val Glu Ser Gly Gly Gly Leu Val Gln Pro Gly Gly
1               5                   10                  15

Ser Leu Arg Ile Ser Cys Ala Ala Ser Gly Ser Ile Tyr Leu Ile Asn
            20                  25                  30
```

Tyr Met Gly Trp Tyr Arg Gln Ala Pro Gly Lys Gln Arg Glu Leu Val
            35                  40                  45

Ala Thr Leu Thr Ser Gly Gly Ser Thr Asn Tyr Ala Gly Ser Val Lys
 50                  55                  60

Gly Arg Phe Ala Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ile Gly Gly Thr Leu Tyr Asp Arg Arg Arg Phe Glu Ser Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Ser Gly Gly Gly Gly
            130                 135                 140

Ser Gly Gly Gly Gly Ser Gly Gly Gly Gly Ser Glu Val Gln Leu Val
145                 150                 155                 160

Glu Ser Gly Gly Gly Leu Val Gln Thr Gly Ala Ser Leu Arg Leu Ser
                165                 170                 175

Cys Ala Ala Ser Gly Arg Thr Phe Ser Asn Tyr Ala Met Gly Trp Phe
            180                 185                 190

Arg Gln Ala Pro Gly Lys Glu Arg Glu Arg Val Ala Ala Ile Thr Pro
            195                 200                 205

Arg Ala Phe Thr Thr Tyr Tyr Ala Asp Ser Val Lys Gly Arg Phe Thr
            210                 215                 220

Ile Ser Arg Asp Asn Ala Lys Asn Thr Ala Tyr Leu Gln Met Val Ser
225                 230                 235                 240

Leu Lys Pro Glu Asp Thr Ala Val Tyr Tyr Cys Ala Ala Gln Leu Val
                245                 250                 255

Gly Ser Gly Ser Asn Leu Gly Arg Gln Glu Ser Tyr Ala Tyr Trp Gly
            260                 265                 270

Gln Gly Thr Leu Val Thr Val Ser Ser Gly Gly Gly Ser Gly Gly
            275                 280                 285

Gly Ser Glu Val Gln Leu Val Glu Ser Gly Gly Gly Leu Val Gln Pro
            290                 295                 300

Gly Asn Ser Leu Arg Leu Ser Cys Ala Ala Ser Gly Phe Thr Phe Ser
305                 310                 315                 320

Ser Phe Gly Met Ser Trp Val Arg Gln Ala Pro Gly Lys Gly Leu Glu
                325                 330                 335

Trp Val Ser Ser Ile Ser Gly Ser Gly Ser Asp Thr Leu Tyr Ala Asp
            340                 345                 350

Ser Val Lys Gly Arg Phe Thr Ile Ser Arg Asp Asn Ala Lys Thr Thr
            355                 360                 365

Leu Tyr Leu Gln Met Asn Ser Leu Arg Pro Glu Asp Thr Ala Val Tyr
370                 375                 380

Tyr Cys Thr Ile Gly Gly Ser Leu Ser Arg Ser Ser Gln Gly Thr Leu
385                 390                 395                 400

Val Thr Val Ser Ser
                405

<210> SEQ ID NO 533
<211> LENGTH: 431
<212> TYPE: PRT
<213> ORGANISM: Artificial Sequence
<220> FEATURE:

<223> OTHER INFORMATION: Nanobody, Nanobody constructs or fragments thereof

<400> SEQUENCE: 533

```
Glu Val Gln Leu Val Glu Ser Gly Gly Gly Leu Val Gln Pro Gly Gly
1               5                   10                  15
Ser Leu Arg Ile Ser Cys Ala Ala Ser Gly Ser Ile Tyr Leu Ile Asn
            20                  25                  30
Tyr Met Gly Trp Tyr Arg Gln Ala Pro Gly Lys Gln Arg Glu Leu Val
        35                  40                  45
Ala Thr Leu Thr Ser Gly Gly Ser Thr Asn Tyr Ala Gly Ser Val Lys
    50                  55                  60
Gly Arg Phe Ala Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Ile Gly Gly Thr Leu Tyr Asp Arg Arg Arg Phe Glu Ser Trp Gly Gln
            100                 105                 110
Gly Thr Leu Val Thr Val Ser Ser Gly Gly Gly Gly Ser Gly Gly Gly
        115                 120                 125
Gly Ser Gly Gly Gly Ser Gly Gly Gly Ser Gly Gly Gly
    130                 135                 140
Ser Gly Gly Gly Ser Gly Gly Gly Ser Glu Val Gln Leu Val
145                 150                 155                 160
Glu Ser Gly Gly Gly Leu Val Gln Thr Gly Ala Ser Leu Arg Leu Ser
                165                 170                 175
Cys Ala Ala Ser Gly Arg Thr Phe Ser Asn Tyr Ala Met Gly Trp Phe
            180                 185                 190
Arg Gln Ala Pro Gly Lys Glu Arg Glu Arg Val Ala Ala Ile Thr Pro
        195                 200                 205
Arg Ala Phe Thr Thr Tyr Tyr Ala Asp Ser Val Lys Gly Arg Phe Thr
    210                 215                 220
Ile Ser Arg Asp Asn Ala Lys Asn Thr Ala Tyr Leu Gln Met Val Ser
225                 230                 235                 240
Leu Lys Pro Glu Asp Thr Ala Val Tyr Tyr Cys Ala Ala Gln Leu Val
                245                 250                 255
Gly Ser Gly Ser Asn Leu Gly Arg Gln Glu Ser Tyr Ala Tyr Trp Gly
            260                 265                 270
Gln Gly Thr Leu Val Thr Val Ser Ser Gly Gly Gly Gly Ser Gly Gly
        275                 280                 285
Gly Gly Ser Gly Gly Gly Ser Gly Gly Gly Ser Gly Gly Gly
    290                 295                 300
Gly Ser Gly Gly Gly Ser Gly Gly Gly Ser Glu Val Gln Leu
305                 310                 315                 320
Val Glu Ser Gly Gly Gly Leu Val Gln Pro Gly Asn Ser Leu Arg Leu
                325                 330                 335
Ser Cys Ala Ala Ser Gly Phe Thr Phe Ser Ser Phe Gly Met Ser Trp
            340                 345                 350
Val Arg Gln Ala Pro Gly Lys Gly Leu Glu Trp Val Ser Ser Ile Ser
        355                 360                 365
Gly Ser Gly Ser Asp Thr Leu Tyr Ala Asp Ser Val Lys Gly Arg Phe
    370                 375                 380
Thr Ile Ser Arg Asp Asn Ala Lys Thr Thr Leu Tyr Leu Gln Met Asn
385                 390                 395                 400
```

```
Ser Leu Arg Pro Glu Asp Thr Ala Val Tyr Tyr Cys Thr Ile Gly Gly
            405                 410                 415

Ser Leu Ser Arg Ser Ser Gln Gly Thr Leu Val Thr Val Ser Ser
            420                 425                 430

<210> SEQ ID NO 534
<211> LENGTH: 405
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 534

Glu Val Gln Leu Val Glu Ser Gly Gly Gly Leu Val Gln Thr Gly Ala
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Arg Val
            35                  40                  45

Ala Ala Ile Thr Pro Arg Ala Phe Thr Thr Tyr Tyr Ala Asp Ser Val
            50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Val Gly Ser Gly Ser Asn Leu Gly Arg Gln Glu Ser
            100                 105                 110

Tyr Ala Tyr Trp Gly Gln Gly Thr Leu Val Thr Val Ser Ser Gly Gly
            115                 120                 125

Gly Ser Gly Gly Gly Gly Ser Gly Gly Gly Ser Gly Gly Gly
            130                 135                 140

Gly Ser Gly Gly Gly Gly Ser Gly Gly Gly Ser Gly Gly Gly Gly
145                 150                 155                 160

Ser Glu Val Gln Leu Val Glu Ser Gly Gly Gly Leu Val Gln Pro Gly
            165                 170                 175

Gly Ser Leu Arg Ile Ser Cys Ala Ala Ser Gly Ser Ile Tyr Leu Ile
            180                 185                 190

Asn Tyr Met Gly Trp Tyr Arg Gln Ala Pro Gly Lys Gln Arg Glu Leu
            195                 200                 205

Val Ala Thr Leu Thr Ser Gly Gly Ser Thr Asn Tyr Ala Gly Ser Val
            210                 215                 220

Lys Gly Arg Phe Ala Ile Ser Arg Asp Asn Ala Lys Asn Thr Val Tyr
225                 230                 235                 240

Leu Gln Met Asn Ser Leu Lys Pro Glu Asp Thr Ala Val Tyr Tyr Cys
                245                 250                 255

Asn Ile Gly Gly Thr Leu Tyr Asp Arg Arg Phe Glu Ser Trp Gly
            260                 265                 270

Gln Gly Thr Leu Val Thr Val Ser Ser Gly Gly Gly Ser Gly Gly
            275                 280                 285

Gly Ser Glu Val Gln Leu Val Glu Ser Gly Gly Gly Leu Val Gln Pro
            290                 295                 300

Gly Asn Ser Leu Arg Leu Ser Cys Ala Ala Ser Gly Phe Thr Phe Ser
305                 310                 315                 320

Ser Phe Gly Met Ser Trp Val Arg Gln Ala Pro Gly Lys Gly Leu Glu
```

```
                          325                 330                 335
Trp Val Ser Ser Ile Ser Gly Ser Gly Ser Asp Thr Leu Tyr Ala Asp
            340                 345                 350

Ser Val Lys Gly Arg Phe Thr Ile Ser Arg Asp Asn Ala Lys Thr Thr
            355                 360                 365

Leu Tyr Leu Gln Met Asn Ser Leu Arg Pro Glu Asp Thr Ala Val Tyr
            370                 375                 380

Tyr Cys Thr Ile Gly Gly Ser Leu Ser Arg Ser Ser Gln Gly Thr Leu
385                 390                 395                 400

Val Thr Val Ser Ser
                405

<210> SEQ ID NO 535
<211> LENGTH: 406
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 535

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Ala
            20                  25                  30

Ala Met Gly Trp Tyr Arg Gln Ala Thr Gly Lys Gln Arg Glu Leu Val
        35                  40                  45

Ala Thr Ile Thr Asp Gly Gly Thr Thr Thr Tyr Ala Asp Ser Val Lys
    50                  55                  60

Gly Arg Val Thr Ile Ser Arg Asp Arg Ser Ala Asn Thr Val Tyr Leu
65                  70                  75                  80

Ala Met Asn Asn Leu Lys Pro Asp Asp Thr Ala Val Tyr Tyr Cys Tyr
                85                  90                  95

Ala Tyr Leu Arg Tyr Thr Ser Arg Val Pro Gly Asp Asn Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Gly Ser Gly Gly Gly Ser Gly Gly Gly
    130                 135                 140

Gly Ser Gly Gly Gly Ser Gly Gly Gly Ser Glu Val Gln Leu
145                 150                 155                 160

Val Glu Ser Gly Gly Leu Val Gln Thr Gly Ala Ser Leu Arg Leu
                165                 170                 175

Ser Cys Ala Ala Ser Gly Arg Thr Phe Ser Asn Tyr Ala Met Gly Trp
            180                 185                 190

Phe Arg Gln Ala Pro Gly Lys Glu Arg Glu Arg Val Ala Ala Ile Thr
        195                 200                 205

Pro Arg Ala Phe Thr Thr Tyr Ala Asp Ser Val Lys Gly Arg Phe
    210                 215                 220

Thr Ile Ser Arg Asp Asn Ala Lys Asn Thr Ala Tyr Leu Gln Met Val
225                 230                 235                 240

Ser Leu Lys Pro Glu Asp Thr Ala Val Tyr Tyr Cys Ala Ala Gln Leu
                245                 250                 255

Val Gly Ser Gly Ser Asn Leu Gly Arg Gln Glu Ser Tyr Ala Tyr Trp
            260                 265                 270
```

Gly Gln Gly Thr Leu Val Thr Val Ser Ser Gly Gly Gly Ser Gly
              275                 280                 285

Gly Gly Ser Glu Val Gln Leu Val Glu Ser Gly Gly Gly Leu Val Gln
         290                 295                 300

Pro Gly Asn Ser Leu Arg Leu Ser Cys Ala Ala Ser Gly Phe Thr Phe
305                 310                 315                 320

Ser Ser Phe Gly Met Ser Trp Val Arg Gln Ala Pro Gly Lys Gly Leu
                325                 330                 335

Glu Trp Val Ser Ser Ile Ser Gly Ser Gly Ser Asp Thr Leu Tyr Ala
            340                 345                 350

Asp Ser Val Lys Gly Arg Phe Thr Ile Ser Arg Asp Asn Ala Lys Thr
        355                 360                 365

Thr Leu Tyr Leu Gln Met Asn Ser Leu Arg Pro Glu Asp Thr Ala Val
    370                 375                 380

Tyr Tyr Cys Thr Ile Gly Gly Ser Leu Ser Arg Ser Ser Gln Gly Thr
385                 390                 395                 400

Leu Val Thr Val Ser Ser
                405

<210> SEQ ID NO 536
<211> LENGTH: 408
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 536

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Asn Tyr
            20                  25                  30

Asp Met Gly Trp Phe Arg Gln Ala Pro Gly Lys Glu Arg Glu Phe Val
        35                  40                  45

Gly Ala Ser Trp Trp Ser Gly Gly Ala Pro Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Ala Asn Ser Leu Arg Pro Glu Asp Thr Ala Val Tyr Tyr Cys
                85                  90                  95

Ala Ala Lys Arg Leu Arg Ser Phe Ala Ser Gly Gly Ser Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Ser Gly Gly Gly Gly Ser Gly Gly Gly Gly Ser Glu Val
145                 150                 155                 160

Gln Leu Val Glu Ser Gly Gly Gly Leu Val Gln Thr Gly Ala Ser Leu
                165                 170                 175

Arg Leu Ser Cys Ala Ala Ser Gly Arg Thr Phe Ser Asn Tyr Ala Met
            180                 185                 190

Gly Trp Phe Arg Gln Ala Pro Gly Lys Glu Arg Glu Arg Val Ala Ala
        195                 200                 205

Ile Thr Pro Arg Ala Phe Thr Thr Tyr Tyr Ala Asp Ser Val Lys Gly
    210                 215                 220

```
Arg Phe Thr Ile Ser Arg Asp Asn Ala Lys Asn Thr Ala Tyr Leu Gln
225                 230                 235                 240

Met Val Ser Leu Lys Pro Glu Asp Thr Ala Val Tyr Tyr Cys Ala Ala
                245                 250                 255

Gln Leu Val Gly Ser Gly Ser Asn Leu Gly Arg Gln Glu Ser Tyr Ala
            260                 265                 270

Tyr Trp Gly Gln Gly Thr Leu Val Thr Val Ser Ser Gly Gly Gly Gly
        275                 280                 285

Ser Gly Gly Gly Ser Glu Val Gln Leu Val Glu Ser Gly Gly Gly Leu
    290                 295                 300

Val Gln Pro Gly Asn Ser Leu Arg Leu Ser Cys Ala Ala Ser Gly Phe
305                 310                 315                 320

Thr Phe Ser Ser Phe Gly Met Ser Trp Val Arg Gln Ala Pro Gly Lys
                325                 330                 335

Gly Leu Glu Trp Val Ser Ser Ile Ser Gly Ser Gly Ser Asp Thr Leu
            340                 345                 350

Tyr Ala Asp Ser Val Lys Gly Arg Phe Thr Ile Ser Arg Asp Asn Ala
        355                 360                 365

Lys Thr Thr Leu Tyr Leu Gln Met Asn Ser Leu Arg Pro Glu Asp Thr
370                 375                 380

Ala Val Tyr Tyr Cys Thr Ile Gly Gly Ser Leu Ser Arg Ser Ser Gln
385                 390                 395                 400

Gly Thr Leu Val Thr Val Ser Ser
                405

<210> SEQ ID NO 537
<211> LENGTH: 408
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 537

Glu Val Gln Leu Val Glu Ser Gly Gly Gly Leu Val Gln Thr Gly Ala
1               5                   10                  15

Ser Leu Arg Leu Ser Cys Ala Ala Ser Gly Arg Thr Phe Ser Asn Tyr
                20                  25                  30

Ala Met Gly Trp Phe Arg Gln Ala Pro Gly Lys Glu Arg Glu Arg Val
            35                  40                  45

Ala Ala Ile Thr Pro Arg Ala Phe Thr Thr Tyr Tyr Ala Asp Ser Val
        50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Val Gly Ser Gly Ser Asn Leu Gly Arg Gln Glu Ser
            100                 105                 110

Tyr Ala Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Ala Gly
```

```
                165                 170                 175
Asp Ser Leu Arg Leu Ser Cys Ala Ala Ser Gly Leu Thr Phe Ser Asn
            180                 185                 190

Tyr Asp Met Gly Trp Phe Arg Gln Ala Pro Gly Lys Glu Arg Glu Phe
        195                 200                 205

Val Gly Ala Ser Trp Trp Ser Gly Gly Ala Pro Tyr Tyr Ser Asp Ser
    210                 215                 220

Val Lys Gly Arg Phe Thr Ile Ser Arg Asp Asn Ala Lys Asn Thr Val
225                 230                 235                 240

Tyr Leu Gln Ala Asn Ser Leu Arg Pro Glu Asp Thr Ala Val Tyr Tyr
            245                 250                 255

Cys Ala Ala Lys Arg Leu Arg Ser Phe Ala Ser Gly Gly Ser Tyr Asp
        260                 265                 270

Tyr Trp Gly Gln Gly Thr Leu Val Thr Val Ser Gly Gly Gly Gly
    275                 280                 285

Ser Gly Gly Gly Ser Glu Val Gln Leu Val Glu Ser Gly Gly Gly Leu
290                 295                 300

Val Gln Pro Gly Asn Ser Leu Arg Leu Ser Cys Ala Ala Ser Gly Phe
305                 310                 315                 320

Thr Phe Ser Ser Phe Gly Met Ser Trp Val Arg Gln Ala Pro Gly Lys
            325                 330                 335

Gly Leu Glu Trp Val Ser Ser Ile Ser Gly Ser Gly Ser Asp Thr Leu
        340                 345                 350

Tyr Ala Asp Ser Val Lys Gly Arg Phe Thr Ile Ser Arg Asp Asn Ala
    355                 360                 365

Lys Thr Thr Leu Tyr Leu Gln Met Asn Ser Leu Arg Pro Glu Asp Thr
370                 375                 380

Ala Val Tyr Tyr Cys Thr Ile Gly Gly Ser Leu Ser Arg Ser Ser Gln
385                 390                 395                 400

Gly Thr Leu Val Thr Val Ser Ser
            405

<210> SEQ ID NO 538
<211> LENGTH: 120
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 538

Glu Val Gln Leu Val Glu Ser Gly Gly Gly Leu Val Gln Pro Gly Gly
1               5                   10                  15

Ser Leu Arg Ile Ser Cys Ala Ala Ser Gly Ser Ile Tyr Leu Ile Asn
            20                  25                  30

Tyr Met Gly Trp Tyr Arg Gln Ala Pro Gly Lys Gln Arg Glu Leu Val
        35                  40                  45

Ala Thr Leu Thr Ser Gly Gly Ser Thr Asn Tyr Ala Gly Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Ile Gly Gly Thr Leu Tyr Asp Arg Arg Phe Glu Ser Trp Gly Gln
        100                 105                 110
```

```
Gly Thr Gln Val Thr Val Ser Ser
        115                 120
```

<210> SEQ ID NO 539
<211> LENGTH: 126
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 539

```
Glu Val Gln Leu Val Glu Ser Gly Gly Gly Leu Val Gln Thr Gly Ala
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Arg Val
        35                  40                  45

Ala Ala Ile Thr Pro Arg Ala Phe Thr Thr Tyr Tyr Ala Asp Ser Val
    50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Val Gly Ser Gly Ser Asn Leu Gly Arg Gln Glu Ser
            100                 105                 110

Tyr Ala Tyr Trp Gly Gln Gly Thr Gln Val Thr Val Ser Ser
        115                 120                 125
```

<210> SEQ ID NO 540
<211> LENGTH: 121
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 540

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Ala
            20                  25                  30

Ala Met Gly Trp Tyr Arg Gln Ala Thr Gly Lys Gln Arg Glu Leu Val
        35                  40                  45

Ala Thr Ile Thr Asp Gly Gly Thr Thr Tyr Ala Asp Ser Val Lys
    50                  55                  60

Gly Arg Val Thr Ile Ser Arg Asp Arg Ser Ala Asn Thr Val Tyr Leu
65                  70                  75                  80

Ala Met Asn Asn Leu Lys Pro Asp Asp Thr Ala Val Tyr Tyr Cys Tyr
                85                  90                  95

Ala Tyr Leu Arg Tyr Thr Ser Arg Val Pro Gly Asp Asn Tyr Trp Gly
            100                 105                 110

Gln Gly Thr Gln Val Thr Val Ser Ser
        115                 120
```

<210> SEQ ID NO 541
<211> LENGTH: 123
<212> TYPE: PRT
<213> ORGANISM: Artificial Sequence
<220> FEATURE:

-continued

<223> OTHER INFORMATION: Nanobody, Nanobody constructs or fragments
      thereof

<400> SEQUENCE: 541

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Asn Tyr
            20                  25                  30

Asp Met Gly Trp Phe Arg Gln Ala Pro Gly Lys Glu Arg Glu Phe Val
        35                  40                  45

Gly Ala Ser Trp Trp Ser Gly Gly Ala Pro Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Ala Asn Ser Leu Arg Pro Glu Asp Thr Ala Val Tyr Tyr Cys
                85                  90                  95

Ala Ala Lys Arg Leu Arg Ser Phe Ala Ser Gly Gly Ser Tyr Asp Tyr
            100                 105                 110

Trp Gly Gln Gly Thr Gln Val Thr Val Ser Ser
        115                 120

<210> SEQ ID NO 542
<211> LENGTH: 30
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 542

Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser
            20                  25                  30

<210> SEQ ID NO 543
<211> LENGTH: 30
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 543

Glu Val Gln Leu Met Glu Ser Gly Gly Gly Leu Val Gln Ala Gly Gly
1               5                   10                  15

Ser Leu Arg Leu Ser Cys Ala Ala Ser Gly Arg Thr Phe Asn
            20                  25                  30

<210> SEQ ID NO 544
<211> LENGTH: 30
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 544

Glu Val Gln Leu Val Glu Ser Gly Gly Gly Leu Val Gln Pro Gly Gly
1               5                   10                  15

Ser Leu Arg Ile Ser Cys Ala Ala Ser Gly Ser Ile Tyr Leu
            20                  25                  30

<210> SEQ ID NO 545
<211> LENGTH: 30
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 545

Glu Val Gln Leu Val Glu Ser Gly Gly Gly Leu Val Gln Thr Gly Ala
1               5                   10                  15

Ser Leu Arg Leu Ser Cys Ala Ala Ser Gly Arg Thr Phe Ser
            20                  25                  30

<210> SEQ ID NO 546
<211> LENGTH: 30
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 546

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser
            20                  25                  30

<210> SEQ ID NO 547
<211> LENGTH: 30
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 547

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser
            20                  25                  30

<210> SEQ ID NO 548
<211> LENGTH: 5
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 548

Ser Tyr Ala Met Ser
1               5

<210> SEQ ID NO 549
<211> LENGTH: 5
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 549

Asn Tyr Ala Met Gly
1               5

<210> SEQ ID NO 550
<211> LENGTH: 5
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 550

Ile Asn Tyr Met Gly
1               5

<210> SEQ ID NO 551
<211> LENGTH: 5
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 551

Asn Tyr Ala Met Gly
1               5

<210> SEQ ID NO 552
<211> LENGTH: 5
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 552

Ile Ala Ala Met Gly
1               5

<210> SEQ ID NO 553
<211> LENGTH: 5
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 553

Asn Tyr Asp Met Gly
1               5

<210> SEQ ID NO 554
<211> LENGTH: 14
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 554

Trp Val Arg Gln Ala Pro Gly Lys Gly Leu Glu Trp Val Ser
1               5                   10

<210> SEQ ID NO 555
<211> LENGTH: 14
<212> TYPE: PRT
<213> ORGANISM: Artificial Sequence
<220> FEATURE:
<223> OTHER INFORMATION: Nanobody, Nanobody constructs or fragments
      thereof

```
<400> SEQUENCE: 555

Trp Phe Arg Arg Ala Pro Gly Lys Glu Arg Glu Phe Val Ala
1               5                   10

<210> SEQ ID NO 556
<211> LENGTH: 14
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 556

Trp Tyr Arg Gln Ala Pro Gly Lys Gln Arg Glu Leu Val Ala
1               5                   10

<210> SEQ ID NO 557
<211> LENGTH: 14
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 557

Trp Phe Arg Gln Ala Pro Gly Lys Glu Arg Glu Arg Val Ala
1               5                   10

<210> SEQ ID NO 558
<211> LENGTH: 14
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 558

Trp Tyr Arg Gln Ala Thr Gly Lys Gln Arg Glu Leu Val Ala
1               5                   10

<210> SEQ ID NO 559
<211> LENGTH: 14
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 559

Trp Phe Arg Gln Ala Pro Gly Lys Glu Arg Glu Phe Val Gly
1               5                   10

<210> SEQ ID NO 560
<211> LENGTH: 17
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 560

Gly Ile Lys Ser Ser Gly Asp Ser Thr Arg Tyr Ala Gly Ser Val Lys
1               5                   10                  15

Gly
```

```
<210> SEQ ID NO 561
<211> LENGTH: 21
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 561

Ala Ile Thr Arg Ser Gly Val Arg Ser Gly Val Ser Ala Ile Tyr Gly
1               5                   10                  15

Asp Ser Val Lys Asp
            20

<210> SEQ ID NO 562
<211> LENGTH: 16
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 562

Thr Leu Thr Ser Gly Gly Ser Thr Asn Tyr Ala Gly Ser Val Lys Gly
1               5                   10                  15

<210> SEQ ID NO 563
<211> LENGTH: 17
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 563

Ala Ile Thr Pro Arg Ala Phe Thr Thr Tyr Tyr Ala Asp Ser Val Lys
1               5                   10                  15

Gly

<210> SEQ ID NO 564
<211> LENGTH: 16
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 564

Thr Ile Thr Asp Gly Gly Thr Thr Thr Tyr Ala Asp Ser Val Lys Gly
1               5                   10                  15

<210> SEQ ID NO 565
<211> LENGTH: 17
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 565

Ala Ser Trp Trp Ser Gly Gly Ala Pro Tyr Tyr Ser Asp Ser Val Lys
1               5                   10                  15

Gly

<210> SEQ ID NO 566
<211> LENGTH: 32
```

```
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 566

Arg Phe Thr Ile Ser Arg Asp Asn Ala Lys Asn Met Leu Tyr Leu Gln
1               5                   10                  15

Met Tyr Ser Leu Lys Pro Glu Asp Thr Ala Val Tyr Tyr Cys Ala Lys
            20                  25                  30

<210> SEQ ID NO 567
<211> LENGTH: 32
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 567

Arg Phe Thr Ile Ser Arg Asp Asn Ala Lys Asn Thr Leu Tyr Leu Gln
1               5                   10                  15

Met Asn Ser Leu Lys Pro Glu Asp Thr Ala Val Tyr Thr Cys Ala Ala
            20                  25                  30

<210> SEQ ID NO 568
<211> LENGTH: 32
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 568

Arg Phe Ala Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Ile
            20                  25                  30

<210> SEQ ID NO 569
<211> LENGTH: 32
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 569

Arg Phe Thr Ile Ser Arg Asp Asn Ala Lys Asn Thr Ala Tyr Leu Gln
1               5                   10                  15

Met Val Ser Leu Lys Pro Glu Asp Thr Ala Val Tyr Tyr Cys Ala Ala
            20                  25                  30

<210> SEQ ID NO 570
<211> LENGTH: 32
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 570

Arg Val Thr Ile Ser Arg Asp Arg Ser Ala Asn Thr Val Tyr Leu Ala
1               5                   10                  15
```

Met Asn Asn Leu Lys Pro Asp Asp Thr Ala Val Tyr Tyr Cys Tyr Ala
            20                  25                  30

<210> SEQ ID NO 571
<211> LENGTH: 32
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 571

Arg Phe Thr Ile Ser Arg Asp Asn Ala Lys Asn Thr Val Tyr Leu Gln
1               5                   10                  15

Ala Asn Ser Leu Arg Pro Glu Asp Thr Ala Val Tyr Tyr Cys Ala Ala
            20                  25                  30

<210> SEQ ID NO 572
<211> LENGTH: 13
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 572

Ser Arg Val Ser Arg Thr Gly Leu Tyr Thr Tyr Asp Asn
1               5                   10

<210> SEQ ID NO 573
<211> LENGTH: 15
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 573

Ser Ala Ile Gly Ser Gly Ala Leu Arg Arg Phe Glu Tyr Asp Tyr
1               5                   10                  15

<210> SEQ ID NO 574
<211> LENGTH: 12
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 574

Gly Gly Thr Leu Tyr Asp Arg Arg Arg Phe Glu Ser
1               5                   10

<210> SEQ ID NO 575
<211> LENGTH: 17
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 575

Gln Leu Val Gly Ser Gly Ser Asn Leu Gly Arg Gln Glu Ser Tyr Ala
1               5                   10                  15

Tyr

```
<210> SEQ ID NO 576
<211> LENGTH: 13
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 576

Tyr Leu Arg Tyr Thr Ser Arg Val Pro Gly Asp Asn Tyr
1               5                   10

<210> SEQ ID NO 577
<211> LENGTH: 14
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 577

Lys Arg Leu Arg Ser Phe Ala Ser Gly Gly Ser Tyr Asp Tyr
1               5                   10

<210> SEQ ID NO 578
<211> LENGTH: 11
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 578

Arg Gly Gln Gly Thr Gln Val Thr Val Ser Ser
1               5                   10

<210> SEQ ID NO 579
<211> LENGTH: 11
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 579

Ser Gly Gln Gly Thr Gln Val Thr Val Ser Ser
1               5                   10

<210> SEQ ID NO 580
<211> LENGTH: 11
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 580

Trp Gly Gln Gly Thr Gln Val Thr Val Ser Ser
1               5                   10

<210> SEQ ID NO 581
<211> LENGTH: 11
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 581
```

Trp Gly Gln Gly Thr Gln Val Thr Val Ser Ser
1               5                   10

<210> SEQ ID NO 582
<211> LENGTH: 11
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 582

Trp Gly Gln Gly Thr Gln Val Thr Val Ser Ser
1               5                   10

<210> SEQ ID NO 583
<211> LENGTH: 11
<212> TYPE: PRT
<213> ORGANISM: Artificial Sequence
<220> FEATURE:
<223> OTHER INFORMATION: Nanobody, Nanobody constructs or fragments
      thereof

<400> SEQUENCE: 583

Trp Gly Gln Gly Thr Gln Val Thr Val Ser Ser
1               5                   10

<210> SEQ ID NO 584
<211> LENGTH: 360
<212> TYPE: PRT
<213> ORGANISM: Homo sapiens

<400> SEQUENCE: 584

Met Glu Gly Ile Ser Ser Ile Pro Leu Pro Leu Leu Gln Ile Tyr Thr
1               5                   10                  15

Ser Asp Asn Tyr Thr Glu Glu Met Gly Ser Gly Asp Tyr Asp Ser Met
                20                  25                  30

Lys Glu Pro Cys Phe Arg Glu Glu Asn Ala Asn Phe Asn Lys Ile Phe
            35                  40                  45

Leu Pro Thr Ile Tyr Ser Ile Ile Phe Leu Thr Gly Ile Val Gly Asn
        50                  55                  60

Gly Leu Val Ile Leu Val Met Gly Tyr Gln Lys Lys Leu Arg Ser Met
65                  70                  75                  80

Thr Asp Lys Tyr Arg Leu His Leu Ser Val Ala Asp Leu Leu Phe Val
                85                  90                  95

Ile Thr Leu Pro Phe Trp Ala Val Asp Ala Val Ala Asn Trp Tyr Phe
            100                 105                 110

Gly Asn Phe Leu Cys Lys Ala Val His Val Ile Tyr Thr Val Asn Leu
        115                 120                 125

Tyr Ser Ser Val Leu Ile Leu Ala Phe Ile Ser Leu Asp Arg Tyr Leu
    130                 135                 140

Ala Ile Val His Ala Thr Asn Ser Gln Arg Pro Arg Lys Leu Leu Ala
145                 150                 155                 160

Glu Lys Val Val Tyr Val Gly Val Trp Ile Pro Ala Leu Leu Leu Thr
                165                 170                 175

Ile Pro Asp Phe Ile Phe Ala Asn Val Ser Glu Ala Asp Asp Arg Tyr
            180                 185                 190

Ile Cys Asp Arg Phe Tyr Pro Asn Asp Leu Trp Val Val Val Phe Gln
        195                 200                 205

```
Phe Gln His Ile Met Val Gly Leu Ile Leu Pro Gly Ile Val Ile Leu
    210                 215                 220
Ser Cys Tyr Cys Ile Ile Ile Ser Lys Leu Ser His Ser Lys Gly His
225                 230                 235                 240
Gln Lys Arg Lys Ala Leu Lys Thr Thr Val Ile Leu Ile Leu Ala Phe
                245                 250                 255
Phe Ala Cys Trp Leu Pro Tyr Tyr Ile Gly Ile Ser Ile Asp Ser Phe
                260                 265                 270
Ile Leu Leu Glu Ile Ile Lys Gln Gly Cys Glu Phe Glu Asn Thr Val
                275                 280                 285
His Lys Trp Ile Ser Ile Thr Glu Ala Leu Ala Phe Phe His Cys Cys
            290                 295                 300
Leu Asn Pro Ile Leu Tyr Ala Phe Leu Gly Ala Lys Phe Lys Thr Ser
305                 310                 315                 320
Ala Gln His Ala Leu Thr Ser Val Ser Arg Gly Ser Ser Leu Lys Ile
                325                 330                 335
Leu Ser Lys Gly Lys Arg Gly Gly His Ser Ser Val Ser Thr Glu Ser
                340                 345                 350
Glu Ser Ser Ser Phe His Ser Ser
                355                 360

<210> SEQ ID NO 585
<211> LENGTH: 362
<212> TYPE: PRT
<213> ORGANISM: Homo sapiens

<400> SEQUENCE: 585

Met Asp Leu His Leu Phe Asp Tyr Ser Glu Pro Gly Asn Phe Ser Asp
1               5                   10                  15
Ile Ser Trp Pro Cys Asn Ser Ser Asp Cys Ile Val Val Asp Thr Val
                20                  25                  30
Met Cys Pro Asn Met Pro Asn Lys Ser Val Leu Leu Tyr Thr Leu Ser
            35                  40                  45
Phe Ile Tyr Ile Phe Ile Phe Val Ile Gly Met Ile Ala Asn Ser Val
    50                  55                  60
Val Val Trp Val Asn Ile Gln Ala Lys Thr Thr Gly Tyr Asp Thr His
65                  70                  75                  80
Cys Tyr Ile Leu Asn Leu Ala Ile Ala Asp Leu Trp Val Val Leu Thr
                85                  90                  95
Ile Pro Val Trp Val Val Ser Leu Val Gln His Asn Gln Trp Pro Met
                100                 105                 110
Gly Glu Leu Thr Cys Lys Val Thr His Leu Ile Phe Ser Ile Asn Leu
            115                 120                 125
Phe Gly Ser Ile Phe Phe Leu Thr Cys Met Ser Val Asp Arg Tyr Leu
    130                 135                 140
Ser Ile Thr Tyr Phe Thr Asn Thr Pro Ser Ser Arg Lys Lys Met Val
145                 150                 155                 160
Arg Arg Val Val Cys Ile Leu Val Trp Leu Leu Ala Phe Cys Val Ser
                165                 170                 175
Leu Pro Asp Thr Tyr Tyr Leu Lys Thr Val Thr Ser Ala Ser Asn Asn
                180                 185                 190
Glu Thr Tyr Cys Arg Ser Phe Tyr Pro Glu His Ser Ile Lys Glu Trp
            195                 200                 205
Leu Ile Gly Met Glu Leu Val Ser Val Val Leu Gly Phe Ala Val Pro
    210                 215                 220
```

-continued

```
Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
                245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
        275                 280                 285

Leu Glu His Ala Leu Phe Thr Ala Leu His Val Thr Gln Cys Leu Ser
    290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
        355                 360
```

AMINO ACID SEQUENCES DIRECTED AGAINST GPCRS AND POLYPEPTIDES COMPRISING THE SAME FOR THE TREATMENT OF GPCR-RELATED DISEASES AND DISORDERS

RELATED APPLICATIONS

This application is a continuation-in-part of: international application PCT/EP2012/055499, filed Mar. 28, 2012, which was published under PCT Article 21(2) in English, and claims the benefit under 35 U.S.C. §119(e) of U.S. provisional application Ser. No. 61/600,263 filed Feb. 17, 2012, U.S. provisional application Ser. No. 61/540,272 filed Sep. 28, 2011, and U.S. provisional application Ser. No. 61/468,250 filed Mar. 28, 2011; and of U.S. application Ser. No. 12/992,982, filed May 18, 2009, which is a national stage filing under 35 U.S.C. §371 of international application PCT/EP2009/056026, filed May 18, 2009, which was published under PCT Article 21(2) in English, and claims the benefit under 35 U.S.C. §119(e) of U.S. provisional application Ser. No. 61/102,142, filed Oct. 2, 2008, and U.S. provisional application Ser. No. 61/053,847, filed May 16, 2008; and of U.S. application Ser. No. 12/520,299, filed Dec. 19, 2007, which is a national stage filing under 35 U.S.C. §371 of international application PCT/EP2007/064243, filed Dec. 19, 2007, which was published under PCT Article 21(2) in English, and claims the benefit under 35 U.S.C. §119(e) of U.S. provisional application Ser. No. 60/875,860, filed Dec. 19, 2006; the disclosures of each of which are incorporated by reference herein in their entireties.

FIELD OF THE INVENTION

The present invention relates to amino acid sequences that are directed against (as defined herein) G-protein coupled receptors (GPCRs), as well as to compounds or constructs, and in particular proteins and polypeptides, that comprise or essentially consist of one or more such amino acid sequences (also referred to herein as "amino acid sequences of the invention", "compounds of the invention", and "polypeptides of the invention", respectively).

The invention also relates to nucleic acids encoding such amino acid sequences and polypeptides (also referred to herein as "nucleic acids of the invention" or "nucleotide sequences of the invention"); to methods for preparing such amino acid sequences and polypeptides; to host cells expressing or capable of expressing such amino acid sequences or polypeptides; to compositions, and in particular to pharmaceutical compositions, that comprise such amino acid sequences, polypeptides, nucleic acids and/or host cells; and to uses of such amino acid sequences or polypeptides, nucleic acids, host cells and/or compositions, in particular for prophylactic, therapeutic or diagnostic purposes, such as the prophylactic, therapeutic or diagnostic purposes mentioned herein.

Other aspects, embodiments, advantages and applications of the invention will become clear from the further description herein.

BACKGROUND

G-protein-coupled receptors (GPCRs) are the largest class of cell-surface receptors (more than 1000 genes are present in the human genome). They can be activated by a diverse array of stimuli, e.g. hormones, peptides, amino acids, photons of light, and these receptors play a large role in the central nervous system and in the periphery. GPCRs are proteins with 7 transmembrane domains with highly conserved domains. It was estimated that in the year 2000 half of all modern drugs and almost one-quarter of the top 200 best-selling drugs are directed against or modulate GPCR targets (approximately 30 in total). However, due to their architecture of 7 membrane-spanning helices and their strong tendency to aggregate, it's a very challenging target class.

GPCRs are a well-known class of receptors. Reference is for example made to the following reviews: Surgand et al., Proteins 62:509-538 (2006); Vassilatis et al., Proc Natl Acad Sci USA 100:4903-4908 (2003) and Pierce et al., Nat Rev Mol Cell Biol 3:639-650 (2002); as well as to for example: George et al., Nat Rev Drug Discov 1:808-820 (2002); Kenakin, Trends Pharmacol Sci 25:186-192 (2002); Rios et al., Pharmacol Ther 92:71-87 (2001); Jacoby et al., ChemMedChem 2006, 1, 760-782; and Schlyer and Horuk, Drug Discovery Today, 11, 11/12. June 2006, 481; and also for example to Rosenkilde, Oncogene (2001), 20, 1582-1593 and Sadee et al., AAPS PharmSci 2001; 3; 1-16; as well as to the further references cited therein.

G-protein-coupled receptors (GPCRs) are the largest class of cell-surface receptors (more than 1000 genes are present in the human genome). They can be activated by a diverse array of stimuli, e.g. hormones, peptides, amino acids, photons of light, and these receptors play a large role in the central nervous system and in the periphery. GPCRs are proteins with 7 transmembrane domains with highly conserved domains.

As half of all known drugs work through G-protein coupled receptors, it is commercially very attractive to select Nanobodies against this protein family. It was estimated that in the year 2000 half of all modern drugs and almost one-quarter of the top 200 best-selling drugs are directed against or modulate GPCR targets (approximately 30 in total). However, due to their architecture of 7 membrane-spanning helices and their strong tendency to aggregate, it's a very challenging target class.

GPCRs can be grouped on the basis of sequence homology into several distinct families. Although all GPCRs have a similar architecture of seven membrane-spanning α-helices, the different families within this receptor class show no sequence homology to one another, thus suggesting that the similarity of their transmembrane domain structure might define common functional requirements. Depending on the size of the extracellular domain three families are discriminated (FIG. 1).

Members of Family 1 (also called family A or rhodopsin-like family; panel a of FIG. 1) only have small extracellular loops and the interaction of the ligands occurs with residues within the transmembrane cleft. This is by far the largest group (>90% of the GPCRs) and contains receptors for odorants, small molecules such as catecholamines and amines, (neuro)peptides and glycoprotein hormones. Rhodopsin, which belongs to this family, is the only GPCR for which the structure has been solved.

Family 2 or family B GPCRs (FIG. 1, panel b) are characterized by a relatively long amino terminal extracellular domain involved in ligand-binding. Little is known about the orientation of the transmembrane domains, but it is probably quite different from that of rhodopsin. Ligands for these GPCRs are hormones, such as glucagon, gonadotropin-releasing hormone and parathyroid hormone.

Family 3 members (FIG. 1, panel c) also have a large extracellular domain, which functions like a "Venus fly trap" since it can open and close with the agonist bound inside. Family members are the metabotropic glutamate, the Ca2+-sensing and the γ-aminobutyric acid (GABA)B receptors.

SUMMARY

Traditionally small molecules are used for development of drugs directed against GPCRs, not only because pharmaceutical companies have historical reasons to work with these, but more importantly because of the structural constraints of Family 1 GPCRs, which have the ligand binding site within the transmembrane cleft (Nat Rev Drug Discov. (2004) The state of GPCR research in 2004. Nature Reviews Drug Discovery GPCR Questionnaire Participants 3(7):575, 577-626). For this reason it proved to be difficult or impossible to generate monoclonal antibodies against this target class. The amino acid sequences of the invention (and in particular Nanobodies of the invention) can solve this particular problem by means of their intrinsic property of binding via extended CDR loops into cavities (as further described herein).

Some non-limiting examples of therapeutically relevant GPCRs are for example the following, which are all targets of known drugs that have either been approved or are in clinical development. The text between brackets indicates the desired action of an amino acid sequence, a NANOBODY® ($V_{HH}$) or a polypeptide of the invention (i.e. as agonist or antagonist):

Class A GPCRs
  Muscarinic M1 receptor (agonist)
  Adrenoceptor (agonist);
  Histamine receptor (agonist);
  5-HT GPCR (agonist);
  Cannabinoid receptor (agonist);
  Class A hormone protein GPCR (agonist);
  Chemokine (agonist);
  Galanin (agonist);
  Melanocortin (agonist);
  Neuropeptide Y receptor (agonist);
  Neurotensin receptor (agonist);
  Opioid (agonist);
  Somatostatin (agonist);
  Vasopressin like receptor (agonist);
  Prostanoid receptor (agonist)
Class B GPCRs
  ACTH releasing factor receptor (modulator);
Class C GPCRs
  GABA B receptor (agonist);
  Metabotropic glutamate receptor (agonist);

Some other non-limiting examples of therapeutically relevant GPCRs are mentioned in Table C. A more extensive list of human GPCRs is given in Table D.

The polypeptides and compositions of the present invention can generally be used to modulate (as defined herein), and in particular inhibit and/or prevent, GPCRs mediated signalling and/or to modulate the biological pathways in which GPCRs are involved, and/or to modulate the biological mechanisms, responses and effects associated with such signalling or these pathways.

As such, the polypeptides and compositions of the present invention can be used for the prevention and treatment (as defined herein) of GPCR-related diseases and disorders. Generally, "GPCR-related diseases and disorders" can be defined as diseases and disorders that can be prevented and/or treated, respectively, by suitably administering to a subject in need thereof (i.e. having the disease or disorder or at least one symptom thereof and/or at risk of attracting or developing the disease or disorder) of either a polypeptide or composition of the invention (and in particular, of a pharmaceutically active amount thereof) and/or of a known active principle active against GPCRs or a biological pathway or mechanism in which GPCRs is involved (and in particular, of a pharmaceutically active amount thereof). Examples of such GPCR-related diseases and disorders will be clear to the skilled person based on the disclosure herein.

Thus, without being limited thereto, the amino acid sequences and polypeptides of the invention can for example be used to prevent and/or to treat all diseases and disorders that are currently being prevented or treated with active principles that can modulate GPCRs-mediated signalling, such as those mentioned in the prior art cited above. It is also envisaged that the polypeptides of the invention can be used to prevent and/or to treat all diseases and disorders for which treatment with such active principles is currently being developed, has been proposed, or will be proposed or developed in future. In addition, it is envisaged that, because of their favourable properties as further described herein, the polypeptides of the present invention may be used for the prevention and treatment of other diseases and disorders than those for which these known active principles are being used or will be proposed or developed; and/or that the polypeptides of the present invention may provide new methods and regimens for treating the diseases and disorders described herein.

Other applications and uses of the amino acid sequences and polypeptides of the invention will become clear to the skilled person from the further disclosure herein.

Generally, it is an object of the invention to provide pharmacologically active agents, as well as compositions comprising the same, that can be used in the diagnosis, prevention and/or treatment of GPCR-related diseases and disorders and of the further diseases and disorders mentioned herein; and to provide methods for the diagnosis, prevention and/or treatment of such diseases and disorders that involve the administration and/or use of such agents and compositions.

In particular, it is an object of the invention to provide such pharmacologically active agents, compositions and/or methods that have certain advantages compared to the agents, compositions and/or methods that are currently used and/or known in the art. These advantages will become clear from the further description below.

More in particular, it is an object of the invention to provide therapeutic proteins that can be used as pharmacologically active agents, as well as compositions comprising the same, for the diagnosis, prevention and/or treatment of GPCR-related diseases and disorders and of the further diseases and disorders mentioned herein; and to provide methods for the diagnosis, prevention and/or treatment of such diseases and disorders that involve the administration and/or the use of such therapeutic proteins and compositions.

Accordingly, it is a specific object of the present invention to provide amino acid sequences that are directed against (as defined herein) GPCRs, in particular against GPCRs from a warm-blooded animal, more in particular against GPCRs from a mammal, and especially against human GPCRs; and to provide proteins and polypeptides comprising or essentially consisting of at least one such amino acid sequence.

In particular, it is a specific object of the present invention to provide such amino acid sequences and such proteins and/or polypeptides that are suitable for prophylactic, therapeutic and/or diagnostic use in a warm-blooded animal, and in particular in a mammal, and more in particular in a human being.

More in particular, it is a specific object of the present invention to provide such amino acid sequences and such proteins and/or polypeptides that can be used for the prevention, treatment, alleviation and/or diagnosis of one or more diseases, disorders or conditions associated with GPCRs and/or mediated by GPCRs (such as the diseases, disorders and conditions mentioned herein) in a warm-blooded animal, in particular in a mammal, and more in particular in a human being.

It is also a specific object of the invention to provide such amino acid sequences and such proteins and/or polypeptides that can be used in the preparation of pharmaceutical or veterinary compositions for the prevention and/or treatment of one or more diseases, disorders or conditions associated with and/or mediated by GPCRs (such as the diseases, disorders and conditions mentioned herein) in a warm-blooded animal, in particular in a mammal, and more in particular in a human being.

In the invention, generally, these objects are achieved by the use of the amino acid sequences, proteins, polypeptides and compositions that are described herein.

In general, the invention provides amino acid sequences that are directed against (as defined herein) and/or can specifically bind (as defined herein) to GPCRs; as well as compounds and constructs, and in particular proteins and polypeptides, that comprise at least one such amino acid sequence.

More in particular, the invention provides amino acid sequences that can bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein; as well as compounds and constructs, and in particular proteins and polypeptides, that comprise at least one such amino acid sequence.

In particular, amino acid sequences and polypeptides of the invention are preferably such that they:
bind to GPCRs with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);
and/or such that they:
bind to GPCRs with a $k_{on}$-rate of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ $s^{-1}$, such as between $10^5$ $M^{-1}$ $s^{-1}$ and $10^7$ $M^{-1}$ $s^{-1}$;
and/or such that they:
bind to GPCRs with a $k_{off}$-rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, a monovalent amino acid sequence of the invention (or a polypeptide that contains only one amino acid sequence of the invention) is preferably such that it will bind to GPCRs with an affinity less than 500 nM, preferably less than 200 nM, more preferably less than 10 nM, such as less than 500 pM.

Some preferred IC50 values for binding of the amino acid sequences or polypeptides of the invention to GPCRs will become clear from the further description and examples herein.

For binding to GPCRs, an amino acid sequence of the invention will usually contain within its amino acid sequence one or more amino acid residues or one or more stretches of amino acid residues (i.e. with each "stretch" comprising two or amino acid residues that are adjacent to each other or in close proximity to each other, i.e. in the primary or tertiary structure of the amino acid sequence) via which the amino acid sequence of the invention can bind to GPCRs, which amino acid residues or stretches of amino acid residues thus form the "site" for binding to GPCRs (also referred to herein as the "antigen binding site").

The amino acid sequences provided by the invention are preferably in essentially isolated form (as defined herein), or form part of a protein or polypeptide of the invention (as defined herein), which may comprise or essentially consist of one or more amino acid sequences of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit (i.e. against one or more other targets than GPCRs), so as to provide a monovalent, multivalent or multispecific polypeptide of the invention, respectively, all as described herein. Preferably, two or more amino acid sequences of the invention may be used as a binding unit against the same GPCR, so as to provide a biparatopic or multiparatopic protein or polypeptide. Such a protein or polypeptide may also be in essentially isolated form (as defined herein). For example a "bivalent" polypeptide of the invention comprises two amino acid sequences which may be the same or different (i.e. regardless of their antigen binding specificity), optionally linked via a suitable linker sequence. Polypeptides that comprise two the same amino acid sequences will be referred herein to mono-specific bivalent polypeptides, whereas polypeptides comprising two different amino acid sequences will be referred to "bispecific" or "biparatopic" polypeptides as further described herein. In particular, a polypeptide of the invention which comprises two amino acid sequences which are directed against different targets (e.g. have a different antigen specificity) will be referred to as a "bispecific" polypeptide of the invention. Thus, for example, a "bispecific" polypeptide of the invention is a polypeptide that comprises at least one amino acid sequence directed against a first antigen (i.e. GPCR), and at least one further amino acid sequence directed against a different antigen (i.e. different from said GPCR), and optionally linked via a suitable linker sequence. In a most preferred embodiment the polypeptide of the invention is a "biparatopic" polypeptide. As used herein the term "biparatopic" means that a polypeptide comprises two amino acid sequences which are directed against different antigenic determinants, epitopes, parts, domains, subunits or confirmations of a same antigen (i.e. have a different specificity with respect to the epitopes of an antigen). Thus, for example a "biparatopic" polypeptide of the invention is a polypeptide that comprises at least one amino acid sequence directed against a first antigenic determinant, epitope, part, domain, subunit or confirmation of a GPCR, and at least one further amino acid sequence directed against a second antigenic determinant, epitope, part, domain, subunit or confirmation of said GPCR different from the first, in which said first and second amino acid sequence may optionally be linked via a linker sequence (as defined herein). Accordingly, in its simplest form, a bispecific or biparatopic polypeptide of the invention is a bivalent polypeptide of the invention comprising two amino acid sequences, optionally linked via a suitable linker sequence.

The amino acid sequences and polypeptides of the invention as such preferably essentially consist of a single amino acid chain that is not linked via disulphide bridges to any other amino acid sequence or chain (but that may or may not contain one or more intramolecular disulphide bridges. For example, it is known that Nanobodies—as described herein—may sometimes contain a disulphide bridge between CDR3 and CDR1 or FR2). However, it should be noted that one or more amino acid sequences of the invention may be linked to each other and/or to other amino acid sequences (e.g. via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat Biotechnol. 2005 September; 23(9):1126-36), which is incorporated herein by reference.

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, in essentially isolated form (as defined herein).

It will also be clear to the skilled person that for pharmaceutical use, the amino acid sequences of the invention (as well as compounds, constructs and polypeptides comprising the same) are preferably directed against human GPCRs; whereas for veterinary purposes, the amino acid sequences and polypeptides of the invention are preferably directed against GPCRs from the species to be treated, or at least cross-reactive with GPCRs from the species to be treated.

Furthermore, an amino acid sequence of the invention may optionally, and in addition to the at least one binding site for binding against GPCRs, contain one or more further binding sites for binding against other antigens, proteins or targets.

The efficacy of the amino acid sequences and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include the expression of the receptors in Xenopus oocytes, after which the coupling of many GPCRs to ion channels allows the activation or inhibition of these GPCRs to be monitored in oocytes via voltage clamping techniques. Heterologous GPCRs can be functionally expressed in the oocyte by injecting exogenous, GPCR-encoding mRNA into the oocyte and then allowing 20 the oocyte's endogenous cellular machinery to translate and insert the receptors into the plasma membrane. (See, e.g., Houamed et al., Science 252:1318-21, 1991; Dahmen et al., J. Neurochem. 58:1176-79, 1992.) Following functional expression of receptors, the ability of ligands to induce transmembrane conductance changes can be observed via a two-electrode voltage clamp system (Dahmen et al., supra), which can detect either a depolarization or hyperpolarization of the membrane potential.

Other techniques for screening GPCRs will be clear to the skilled person, for example from the handbooks, reviews and prior art cited herein. These include for example the radioligand binding assays, as for example used in Lundstrom et al., J Struct Funct Genomics. 2006 Nov. 22; [Epub ahead of print] and as described in Andre' et al., Protein Sci 5:1115 (2006); Hassaine et al., (2006) Prot Purif Expr 45:343; Nicholson et al. J Pharmacol Exp Ther. 2006 May; 317(2):771-7. [Epub 2006 Jan. 25]. and Vilardaga et al., J Biol Chem. 2001 Sep. 7; 276(36):33435-43. Epub 2001 May 31, for example using membrane preparations that can be made as described in Hovius et al., (1998) J Neurochem 70:824. Some HTS techniques for screening GPCRs are mentioned in Table 4 of the review by Jacoby et al., Also, according to the invention, amino acid sequences and polypeptides that are directed against GPCRs from a first species of warm-blooded animal may or may not show cross-reactivity with GPCRs from one or more other species of warm-blooded animal. For example, amino acid sequences and polypeptides directed against human GPCRs may or may not show cross reactivity with GPCRs from one or more other species of primates (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*)) and/or with GPCRs from one or more species of animals that are often used in animal models for diseases (for example mouse, rat, rabbit, pig or dog), and in particular in animal models for diseases and disorders associated with GPCRs (such as the species and animal models mentioned herein). In this respect, it will be clear to the skilled person that such cross-reactivity, when present, may have advantages from a drug development point of view, since it allows the amino acid sequences and polypeptides against human GPCRs to be tested in such disease models.

More generally, amino acid sequences and polypeptides of the invention that are cross-reactive with GPCRs from multiple species of mammal will usually be advantageous for use in veterinary applications, since it will allow the same amino acid sequence or polypeptide to be used across multiple species. Thus, it is also encompassed within the scope of the invention that amino acid sequences and polypeptides directed against GPCRs from one species of animal (such as amino acid sequences and polypeptides against human GPCRs) can be used in the treatment of another species of animal, as long as the use of the amino acid sequences and/or polypeptides provide the desired effects in the species to be treated.

The present invention is in its broadest sense also not particularly limited to or defined by a specific antigenic determinant, epitope, part, domain, subunit or conformation (where applicable) of GPCRs against which the amino acid sequences and polypeptides of the invention are directed. For example, the amino acid sequences and polypeptides may or may not be directed against an "interaction site" (as defined herein). For example, amino acid sequences of the invention may be raised by suitably immunizing a mammal (such as a Camelid) with GPCR that has been expressed in a suitable expression system or that has been isolated from a suitable cell or cell fraction. In particular, amino acid sequences of the invention may be raised against GPCRs (or suitable parts or fragments thereof) that have been refolded (for example using the techniques described in the review by Kiefer, Biochim. Biophys. Acta, 1610 (2003), 57-62), and amino acid sequences, Nanobodies and polypeptides that are directed against and/or that have been raised against a refolded GPCR form a further aspect of the invention.

The amino acid sequences and polypeptides of the invention may generally be directed against any desired GPCR, and may in particular be directed against a GPCR that has at least one extracellular loop or domain. Examples of such GPCRs will be clear to the skilled person based on the prior art cited herein According to a specific aspect of the invention, an amino acid sequence or polypeptide of the invention may be directed against (as defined herein) a GPCR that is expressed on the surface of a cell and/or against at least one extracellular region, domain, loop or other extracellular epitope of a GPCR. For example, such amino acid sequences may be raised by suitably immunizing a mammal (such as a Camelid) with a cell or cell fraction that has a GPCR on its surface. For example, the mammal (and in particular, Camelid) may be suitably immunized with whole cells that express (and preferably overexpress) the desired GPCR, such as with cells of a cell line that (over)expresses the desired GPCR.

In particular, according to this aspect, an amino acid sequence or polypeptide of the invention is directed against (as defined herein) at least one extracellular region, domain, loop or other extracellular epitope of a GPCR; and is preferably further such that said amino acid sequence or polypeptide of the invention is capable of modulating (as defined herein) said GPCR. More in particular, according to this aspect, an amino acid sequence or polypeptide of the invention is directed against (as defined herein) at least one extracellular region, domain, loop or other extracellular epitope of a GPCR; and is preferably further such that said amino acid sequence or polypeptide of the invention is capable of (fully or partially) blocking said GPCR.

According to this aspect of the invention, the amino acid sequence or polypeptide of the invention may be directed against any suitable extracellular part, region, domain, loop or other extracellular epitope of a GPCR, but is preferably directed against one of the extracellular parts of the transmembrane domains or more preferably against one of the extracellular loops that link the transmembrane domains.

The amino acid sequence of such suitable extracellular parts, regions, domains, loops or epitopes may be derived by Kyte-Doolittle analysis of the amino acid sequence of the pertinent GPCR; by aligning GPCRs belonging to the same (sub)families and identifying the various transmembrane domains and extracellular parts, regions, domain or loops; by TMAP-analysis; or by any suitable combination thereof. The invention also relates to amino acid sequences and (as further defined herein) that are directed against and/or have been raised against such extracellular parts, regions, domains, loops or epitopes (and/or that are directed against and/or have been raised against suitable parts or fragments of such extracellular parts, regions, domains, loops or epitopes and/or against synthetic or semi-synthetic peptides that are derived from or based on such extracellular parts, regions, domains, loops or epitopes).

In particular, amino acid sequences and polypeptides of the invention are preferably such that they:
bind to an extracellular part, region, domain, loop or other extracellular epitope of a GPCR (as described herein) or against a peptide derived therefrom with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that they:
bind to an extracellular part, region, domain, loop or other extracellular epitope of a GPCR (as described herein) or against a peptide derived therefrom with a $k_{on}$-rate of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ $s^{-1}$, such as between $10^5$ $M^{-1}$ $s^{-1}$ and $10^7$ $M^{-1}$ $s^{-i}$;

and/or such that they:
bind to an extracellular part, region, domain, loop or other extracellular epitope of a GPCR (as described herein) or against a peptide derived therefrom with a $k_{off}$ rate between $1$ $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, a monovalent amino acid sequence of the invention (or a polypeptide that contains only one amino acid sequence of the invention) is preferably such that it will bind to an extracellular part, region, domain, loop or other extracellular epitope of a GPCR (as described herein) with an affinity less than 500 nM, preferably less than 200 nM, more preferably less than 10 nM, such as less than 500 pM.

Also, according to this aspect, any multivalent or multispecific (as defined herein) polypeptides of the invention may also be suitably directed against two or more different extracellular parts, regions, domains, loops or other extracellular epitopes on the same antigen, for example against two different extracellular loops, against two different extracellular parts of the transmembrane domains or against one extracellular loops and one extracellular loop. More particularly, such multivalent or multispecific polypeptides may for example be suitably directed against two or more different extracellular parts, regions, domains, loops or other extracellular epitopes on the same GPCR; or such a polypeptide may be biparatopic/and or multiparatopic (as defined herein). Such multivalent or multispecific polypeptides of the invention may also have (or be engineered and/or selected for) increased avidity and/or improved selectivity for the desired GPCR, and/or for any other desired property or combination of desired properties that may be obtained by the use of such multivalent or multispecific polypeptides.

Generally, it is expected that amino acid sequences and polypeptides of the invention that are directed against an extracellular loop or domain of a GPCR (or against a small peptide derived therefrom or based thereon), and/or that have been screened against, selected using and/or raised against an extracellular loop or domain of a GPCR (or against a small peptide derived therefrom or based thereon) will also be able to bind (and in particular, to specifically bind, as defined herein) to such an extracellular loop or domain (or peptide derived therefrom) that forms part of a GPCR (or at least one subunit thereof) that is present on the surface of a cell. Thus, such (peptides derived from) an extracellular loop or domain may find particular use in methods for generating amino acid sequences and polypeptides of the invention (as defined herein); and such methods and uses form further aspects of the invention; as do amino acid sequences, Nanobodies and polypeptides of the invention that are directed against or raised against such an extracellular loop, domain or peptide derived therefrom.

For example, such a method may comprise one of the following steps or a suitable combination of both of the following steps:

a) a step of suitably immunizing a Camelid with a suitable antigen that comprises the desired extracellular part, region, domain, loop or other extracellular epitope(s), or with a suitable peptide derived therefrom or based thereon, such that an immune response against the desired extracellular part, region, domain, loop or other extracellular epitope(s) is raised. The antigen may be any suitable antigen that is capable of raising an immune response against the desired extracellular part, region, domain, loop or other extracellular epitope(s); such as, for example and without limitation, whole cells that have the desired extracellular part, region, domain, loop or other extracellular epitope(s) on their surface, cell wall fragments thereof or any other suitable preparation derived from such cells, vesicles that have the desired extracellular part, region, domain, loop or other extracellular epitope(s) on their surface, a subunit or fragment of a subunit of a GPCR that comprises the desired extracellular part, region, domain, loop or other extracellular epitope(s), or a synthetic or semi-synthetic peptide that comprises and/or is based on (the amino acid sequence of) the desired extracellular part, region, domain, loop or other extracellular epitope(s);

and/or b) a step of screening for affinity and/or binding for the desired extracellular part, region, domain, loop or other extracellular epitope(s). This may for example be performed by screening a set, collection or library of cells that express heavy chain antibodies on their surface (e.g. B-cells obtained from a suitably immunized Camelid), by screening of a (naïve or immune) library of VHH sequences or NANOBODY® ($V_{HH}$) sequences, or by screening of a (naïve or immune) library of nucleic acid sequences that encode VHH sequences or NANOBODY® ($V_{HH}$) sequences; which may all be performed in a manner known per se, for which reference is made to the further disclosure and prior art mentioned herein;

and which method may optionally further comprise one or more other suitable steps known per se, such as, for example and without limitation, a step of affinity maturation, a step of expressing the desired amino acid sequence, a step of screening for binding and/or for activity against the desired antigen (in this case, the GPCR), a step of determining the desired amino acid sequence or nucleotide sequence, a step of introducing one or more humanizing substitutions (e.g. as further described herein), a step of formatting in a suitable multivalent and/or multispecific format, a step of screening for the desired biological and/or physiological properties (i.e. using a suitable assay, such as those described herein); and/or any suitable combination of one or more of such steps, in any suitable order.

Such methods and the amino acid sequences obtained via such methods, as well as proteins and polypeptides comprising or essentially consisting of the same, form further aspects of this invention.

The amino acid sequences, Nanobodies and polypeptides of the invention may also bind to the GPCR at the same site as the endogenous agonist (i.e. at an orthosteric site), so as to activate or increase receptor signalling; or alternatively so as to decrease or inhibit receptor signalling.

The amino acid sequences, Nanobodies and polypeptides of the invention may also bind to the GPCR in such a way that they block the constitutive activity of the GPCR.

The amino acid sequences, Nanobodies and polypeptides of the invention may also bind to the GPCR in such a way that they mediate allosteric modulation (e.g. bind to the GPCR at an allosteric site). In this way, the amino acid sequences, Nanobodies and polypeptides of the invention may mediate modulation of the receptor function by binding to different regions in the receptor (e.g. at allosteric sites). Reference is for example made to George et al., Nat Rev Drug Discov 1:808-820 (2002); Kenakin, Trends Pharmacol Sci 25:186-192 (2002) and Rios et al., Pharmacol Ther 92:71-87 (2001)).

The amino acid sequences, Nanobodies and polypeptides of the invention may also bind to the GPCR in such a way that they inhibit or enhance the assembly of GPCR functional homodimers or heterodimers.

The amino acid sequences, Nanobodies and polypeptides of the invention may also bind to the GPCR in such a way that they prolong the duration of the GPCR-mediated signalling.

The amino acid sequences, Nanobodies and polypeptides of the invention may also enhance receptor signalling by increasing receptor-ligand affinity.

Polypeptides of the invention that are directed against a GPCR and its ligand may also provide for enhanced binding of the ligand to the GPCR by cross-linking the ligand to the orthosteric site; and/or stabilize the binding of the ligand to the orthosteric site. Thus, a further aspect of the invention relates to a multispecific polypeptide of the invention (as defined herein) that comprises at least one amino acid sequence of the invention (such as a NANOBODY® ($V_{HH}$)) against a GPCR receptor and at least one binding unit directed against its natural ligand. Such multispecific proteins may further be as described herein.

Also, as will be clear from the further disclosure herein, and depending on the GPCR against which they are directed and their desired (therapeutic) effect, the amino acid sequences, Nanobodies and polypeptides of the invention may act as (full or partial) agonists, (full or partial, and competitive or non-competitive) antagonists or as inverse agonists of the GPCR (and/or of the ligand of the GPCR) and/or of the biological function, pathway, mechanism, effect, signalling or response associated therewith. They may do so in an irreversible but preferably reversible manner.

In one embodiment, the amino acid sequence or polypeptide of the invention is a "monoclonal" amino acid sequence or polypeptide, by which is meant that at least each of the one or more amino acid sequences directed against the GPCR that are present in said protein or polypeptide (and preferably all of the immunoglobulin sequences that are present in said protein or polypeptide) are "monoclonal" as commonly understood by the skilled person. In this respect, it should however be noted that, as further described herein, the present invention explicitly covers multivalent or multispecific proteins that comprise two or more immunoglobulin sequences (and in particular monoclonal immunoglobulin sequences) that are directed against different parts, regions, domains, loops or epitopes of the same GPCR, and in particular against different extracellular parts, regions, domains, loops or epitopes of the same GPCR.

As further described herein, a polypeptide of the invention may contain two or more amino acid sequences of the invention that are directed against a GPCR. Generally, such polypeptides will bind to a GPCR with increased avidity compared to a single amino acid sequence of the invention. Such a polypeptide may for example comprise two amino acid sequences of the invention that are directed against the same antigenic determinant, epitope, part, domain, subunit or conformation (where applicable) of a GPCR (which may or may not be an interaction site); or comprise at least one "first" amino acid sequence of the invention that is directed against a first same antigenic determinant, epitope, part, domain, subunit or conformation (where applicable) of a GPCR (which may or may not be an interaction site); and at least one "second" amino acid sequence of the invention that is directed against a second antigenic determinant, epitope, part, domain, subunit or conformation (where applicable) different from the first (and which again may or may not be an interaction site). Preferably, in such "biparatopic" polypeptides of the invention, at least one amino acid sequence of the invention is directed against an interaction site (as defined herein), although the invention in its broadest sense is not limited thereto.

For example, when a polypeptide of the invention is a biparatopic polypeptide of the invention, it may contain at least one amino acid sequence of the invention (such as a NANOBODY® ($V_{HH}$)) that is directed against a first extracellular part, region, domain, loop or other extracellular epitope of a GPCR and at least one amino acid sequence of the invention (such as a NANOBODY® ($V_{HH}$)) that is directed against a second extracellular part, region, domain, loop or other extracellular epitope of a GPCR different from said first extracellular part, region, domain, loop or other extracellular epitope.

Also, when the target is part of a binding pair (for example, a receptor-ligand binding pair), the amino acid sequences and polypeptides may be such that they compete with the cognate binding partner (e.g. the ligand, receptor or other binding partner, as applicable) for binding to the target, and/or such that they (fully or partially) neutralize binding of the binding partner to the target.

It is also within the scope of the invention that, where applicable, an amino acid sequence of the invention can bind to two or more antigenic determinants, epitopes, parts, domains, subunits or conformations of GPCRs. In such a case, the antigenic determinants, epitopes, parts, domains or subunits of GPCRs to which the amino acid sequences and/or polypeptides of the invention bind may be essentially the same (for example, if GPCRs contains repeated structural motifs or occurs in a multimeric form) or may be different (and in the latter case, the amino acid sequences and polypeptides of the invention may bind to such different antigenic determinants, epitopes, parts, domains, subunits of GPCRs with an affinity and/or specificity which may be the same or different). Also, for example, when GPCRs exists in an activated conformation and in an inactive conformation, the amino acid sequences and polypeptides of the invention may bind to either one of these conformations, or may bind to both these conformations (i.e. with an affinity and/or specificity which may be the same or different). Also, for example, the amino acid sequences and polypeptides of the invention may bind to a conformation of GPCRs in which it is bound to a pertinent ligand, may bind to a conformation of GPCRs in which it is not bound to a pertinent ligand, or may bind to both such conformations (again with an affinity and/or specificity which may be the same or different).

It is also expected that the amino acid sequences and polypeptides of the invention will generally bind to all naturally occurring or synthetic analogs, variants, mutants, alleles, parts and fragments of GPCRs; or at least to those analogs, variants, mutants, alleles, parts and fragments of GPCRs that contain one or more antigenic determinants or epitopes that are essentially the same as the antigenic determinant(s) or epitope(s) to which the amino acid sequences and polypeptides of the invention bind in GPCRs (e.g. in wild-type GPCRs). Again, in such a case, the amino acid sequences and polypeptides of the invention may bind to such analogs, variants, mutants, alleles, parts and fragments with an affinity and/or specificity that are the same as, or that are different from (i.e. higher than or lower than), the affinity and specificity with which the amino acid sequences of the invention bind to (wild-type) GPCRs. It is also included within the scope of the invention that the amino acid sequences and polypeptides of the invention bind to some analogs, variants, mutants, alleles, parts and fragments of GPCRs, but not to others.

When GPCRs exists in a monomeric form and in one or more multimeric forms, it is within the scope of the invention that the amino acid sequences and polypeptides of the invention only bind to GPCRs in monomeric form, only bind to GPCRs in multimeric form, or bind to both the monomeric and the multimeric form. Again, in such a case, the amino acid sequences and polypeptides of the invention may bind to the monomeric form with an affinity and/or specificity that are the same as, or that are different from (i.e. higher than or lower than), the affinity and specificity with which the amino acid sequences of the invention bind to the multimeric form.

Also, when GPCRs can associate with other proteins or polypeptides to form protein complexes (e.g. with multiple subunits), it is within the scope of the invention that the amino acid sequences and polypeptides of the invention bind to GPCRs in its non-associated state, bind to GPCRs in its associated state, or bind to both. In all these cases, the amino acid sequences and polypeptides of the invention may bind to such multimers or associated protein complexes with an affinity and/or specificity that may be the same as or different from (i.e. higher than or lower than) the affinity and/or specificity with which the amino acid sequences and polypeptides of the invention bind to GPCRs in its monomeric and non-associated state.

Also, as will be clear to the skilled person, proteins or polypeptides that contain two or more amino acid sequences directed against GPCRs may bind with higher avidity to GPCRs than the corresponding monomeric amino acid sequence(s). For example, and without limitation, proteins or polypeptides that contain two or more amino acid sequences directed against different epitopes of GPCRs (e.g. biparatopic polypeptides) may (and usually will) bind with higher avidity than each of the different monomers. Proteins or polypeptides that contain two or more amino acid sequences directed against GPCRs may (and usually will) bind also with higher avidity to a multimer of GPCRs. The inventors have prepared such polypeptides in accordance with the invention. The amino acid sequences of monovalent and bivalent polypeptides directed against different representative GPCRs are shown in Tables B-4, J and M as described herein. For example, polypeptides of the invention may be formatted e.g., in a biparatopic way such as to combine two monomeric amino acid sequences against different epitopes as characterized in the experimental part (see Examples 5A, 6 and 7). Of these, particularly preferred polypeptides in accordance with the invention are biparatopic polypeptides directed against GPCRs. Preferred examples hereof are the biparatopic constructs against human CXCR4 as previously described in WO09/138519. Particularly preferred polypeptides are the biparatopic constructs that comprise 238D2 and/or 238D4 (see for example SEQ ID NO:s 261 to 266 in WO 09/138519 or SEQ ID NO:s 528 to 531 herein, and more particularly 238D2-20GS-238D4). As will be clear to the skilled person, polypeptides that are bivalent may (and usually will) bind with higher avidity to their target than a corresponding monovalent binder. However present inventors have demonstrated for the first time that the biparatopic polypeptides of the invention (e.g. polypeptides comprising two amino acid sequences which are directed against different epitopes of the same target as defined herein) completely unexpectedly resulted in a significantly increased affinity. This affinity was much higher to that obtained in the mere bivalent constructs which mono-specifically bind to their target, i.e. to the same epitope. Thus, by constructing biparatopic constructs directed against GPCRs the inventors were able to significantly increase the potency compared to corresponding monovalent and mono-specific bivalent binders. These special technical features will become clear from the experimental data provided herein.

Generally, amino acid sequences and polypeptides of the invention will at least bind to those forms of GPCRs (including monomeric, multimeric and associated forms) that are the most relevant from a biological and/or therapeutic point of view, as will be clear to the skilled person.

It is also within the scope of the invention to use parts, fragments, analogs, mutants, variants, alleles and/or derivatives of the amino acid sequences and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against GPCRs; and more preferably will be capable of specific binding to GPCRs, and even more preferably capable of binding to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

In one specific, but non-limiting aspect of the invention, which will be further described herein, such analogs, mutants, variants, alleles, derivatives have an increased half-life in serum (as further described herein) compared to the amino acid sequence from which they have been derived. For example, an amino acid sequence of the invention may be linked (chemically or otherwise) to one or more groups or moieties that extend the half-life (such as PEG), so as to provide a derivative of an amino acid sequence of the invention with increased half-life.

In one specific, but non-limiting aspect, the amino acid sequence of the invention may be an amino acid sequence that comprises an immunoglobulin fold or may be an amino acid sequence that, under suitable conditions (such as physiological conditions) is capable of forming an immunoglobulin fold (i.e. by folding). Reference is inter alia made to the review by Halaby et al., J. (1999) Protein Eng. 12, 563-71. Preferably, when properly folded so as to form an immunoglobulin fold, such an amino acid sequence is capable of specific binding (as defined herein) to GPCRs; and more preferably capable of binding to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein. Also, parts, fragments, analogs, mutants, variants, alleles and/or derivatives of such amino acid sequences are preferably such that they comprise an immunoglobulin fold or are capable for forming, under suitable conditions, an immunoglobulin fold.

In particular, but without limitation, the amino acid sequences of the invention may be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's, as further described herein).

The amino acid sequences of the invention may in particular be an immunoglobulin sequence or a suitable fragment thereof, and more in particular be an immunoglobulin variable domain sequence or a suitable fragment thereof, such as light chain variable domain sequence (e.g. a $V_L$-sequence) or a suitable fragment thereof; or a heavy chain variable domain sequence (e.g. a $V_H$-sequence) or a suitable fragment thereof. When the amino acid sequence of the invention is a heavy chain variable domain sequence, it may be a heavy chain variable domain sequence that is derived from a conventional four-chain antibody (such as, without limitation, a $V_H$ sequence that is derived from a human antibody) or be a so-called $V_{HH}$-sequence (as defined herein) that is derived from a so-called "heavy chain antibody" (as defined herein).

However, it should be noted that the invention is not limited as to the origin of the amino acid sequence of the invention (or of the nucleotide sequence of the invention used to express it), nor as to the way that the amino acid sequence or nucleotide sequence of the invention is (or has been) generated or obtained. Thus, the amino acid sequences of the invention may be naturally occurring amino acid sequences (from any suitable species) or synthetic or semi-synthetic amino acid sequences. In a specific but non-limiting aspect of the invention, the amino acid sequence is a naturally occurring immunoglobulin sequence (from any suitable species) or a synthetic or semi-synthetic immunoglobulin sequence, including but not limited to "humanized" (as defined herein) immunoglobulin sequences (such as partially or fully humanized mouse or rabbit immunoglobulin sequences, and in particular partially or fully humanized $V_{HH}$ sequences or Nanobodies), "camelized" (as defined herein) immunoglobulin sequences, as well as immunoglobulin sequences that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing. Reference is for example made to the standard handbooks, as well as to the further description and prior art mentioned herein.

Similarly, the nucleotide sequences of the invention may be naturally occurring nucleotide sequences or synthetic or semi-synthetic sequences, and may for example be sequences that are isolated by PCR from a suitable naturally occurring template (e.g. DNA or RNA isolated from a cell), nucleotide sequences that have been isolated from a library (and in particular, an expression library), nucleotide sequences that have been prepared by introducing mutations into a naturally occurring nucleotide sequence (using any suitable technique known per se, such as mismatch PCR), nucleotide sequence that have been prepared by PCR using overlapping primers, or nucleotide sequences that have been prepared using techniques for DNA synthesis known per se.

The amino acid sequence of the invention may in particular be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a NANOBODY® ($V_{HH}$) (as defined herein, and including but not limited to a $V_{HH}$ sequence); other single variable domains, or any suitable fragment of any one thereof. [Note: domain antibody, domain antibodies, dAb and dAbs are trademarks of the GlaxoSmithKline group of companies].

For a general description of (single) domain antibodies, reference is also made to the prior art cited above, as well as to EP 0 368 684. For the term "dAb's", reference is for example made to Ward et al. (Nature 1989 Oct. 12; 341 (6242): 544-6), to Holt et al., Trends Biotechnol., 2003, 21(11):484-490; as well as to for example WO 06/030220, WO 06/003388 and other published patent applications of Domantis Ltd. It should also be noted that, although less preferred in the context of the present invention because they are not of mammalian origin, single domain antibodies or single variable domains can be derived from certain species of shark (for example, the so-called "IgNAR domains", see for example WO 05/18629).

In particular, the amino acid sequence of the invention may be a NANOBODY® ($V_{HH}$) (as defined herein) or a suitable fragment thereof. [Note: Nanobody®, Nanobodies® and Nanoclone® are registered trademarks of Ablynx N.V.] Such Nanobodies directed against GPCRs will also be referred to herein as "Nanobodies of the invention". The terms "amino acid sequence" and "Nanobody" are used interchangeably herein, unless the context indicates otherwise.

For a general description of Nanobodies, reference is made to the further description below, as well as to the prior art cited herein. In this respect, it should however be noted that this description and the prior art mainly described Nanobodies of the so-called "$V_H3$ class" (i.e. Nanobodies with a high degree of sequence homology to human germline sequences of the $V_H3$ class such as DP-47, DP-51 or DP-29), which Nanobodies form a preferred aspect of this invention. It should however be noted that the invention in its broadest sense generally covers any type of NANOBODY® ($V_{HH}$) directed against GPCRs, and for example also covers the Nanobodies belonging to the so-called "$V_H4$ class" (i.e. Nanobodies with a high degree of sequence homology to human germline sequences of the $V_H4$ class such as DP-78), as for example described in the U.S. provisional application 60/792,279 by Ablynx N.V. entitled "DP-78-like Nanobodies" filed on Apr. 14, 2006 (see also WO07/118670).

Generally, Nanobodies (in particular $V_{HH}$ sequences and partially humanized Nanobodies) can in particular be characterized by the presence of one or more "Hallmark residues" (as described herein) in one or more of the framework sequences (again as further described herein).

Thus, generally, a NANOBODY® ($V_{HH}$) can be defined as an amino acid sequence with the (general) structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which one or more of the Hallmark residues are as further defined herein.

In particular, a NANOBODY® ($V_{HH}$) can be an amino acid sequence with the (general) structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which the framework sequences are as further defined herein.

More in particular, a NANOBODY® ($V_{HH}$) can be an amino acid sequence with the (general) structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which:
i) preferably one or more of the amino acid residues at positions 11, 37, 44, 45, 47, 83, 84, 103, 104 and 108 according to the Kabat numbering are chosen from the Hallmark residues mentioned in Table A-3 below;
and in which:
ii) said amino acid sequence has at least 80% amino acid identity with at least one of the amino acid sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded.

In these Nanobodies, the CDR sequences are generally as further defined herein.

Thus, the invention also relates to such Nanobodies that can bind to (as defined herein) and/or are directed against GPCRs, to suitable fragments thereof, as well as to polypeptides that comprise or essentially consist of one or more of such Nanobodies and/or suitable fragments.

SEQ ID NO's 526 to 527, 538 to 541, 413 to 453 and 517 to 525 give the amino acid sequences of a number of $V_{HH}$ sequences that have been raised against five representative GPCRs, and in particular against the Chemokine Receptors CXCR4 and CXCR7, the Cannabinoid Receptor 1 (CB1R, see for example Pacher et al, Pharmacol Rev 58:389-462); the parathyroid hormone receptor (PTHR1, see for example Gensure et al, Biochim Biophys Res Commun 328:666-678); and melanocortin 4 receptor (MC4R), which are given in SEQ ID NO's 526 to 527; SEQ ID NO's 538 to 541; 413 to 430, 517 and 518; SEQ ID NO's 431 to 453; and SEQ ID NO's: 519 to 525, respectively.

In one embodiment, the amino acid sequences and peptides of the invention (which may be as further described herein) are directed against the chemokine receptor CXCR4, preferably human CXCR4 (Table N, SEQ ID NO: 584).

It is expected that amino acid sequences, Nanobodies and polypeptides of the invention directed against CXCR4, as well as compositions comprising the same, may find particular use in the prevention and treatment of diseases involving CXCR4 mediated signaling, such as the various diseases in the group of cancer such as hematopoietic cancers like CLL, AML, ALL, MM, Non-Hodgkin lymphoma, solid tumors such as breast cancer, lung cancer, brain tumors, ovarian cancer, stromal chemoresistance of tumors, leukemia and other cancers, disrupting adhesive stromal interactions that confer tumor cell survival and drug resistance, mobilizing tumour cells from tissue sites and making them better accessible to conventional therapy, inhibiting of migration and dissemination of tumor cells (metastasis), inhibiting or paracrine growth and survival signals, inhibiting pro-angiogenesis effects of SDF-1, inflammation and inflammatory disorders such as bowel diseases (colitis, Crohn' disease, IBD), infectious diseases, psioriasis, autoimmune diseases (such as MS), sarcoidosis, transplant rejection, cystic fibrosis, asthma, chronic obstructive pulmonary disease, rheumatoid arthritis, viral infection, HIV, West Nile Virus encephalitis, common variable immunodeficiency. Furthermore, the amino acid sequences of the invention can be used for stem cell mobilization in various patients in need of stem cells after X-ray radiation such as e.g. cancer patients after radiation treatment to replenish the stem cell pool after radiation in cancer patients, or in patients in need of more stem cells, e.g. in patients with ischemic diseases such as myocardial infarction (MI), stroke and/or diabetes (i.e. patients in need of tissue repair) wherein more stem cell would be re-transfused (after mobilization, screening, selection for lineage in need (e.g. cardiac, vascular lineages) and ex-vivo expansion of patient's own stem cells).

In one embodiment, the amino acid sequences and peptides of the invention (which may be as further described herein) are directed against the chemokine receptor CXCR7, preferably human CXCR7 (Table N, SEQ ID NO: 585).

It is expected that amino acid sequences, Nanobodies and polypeptides of the invention directed against CXCR7, as well as compositions comprising the same, may find particular use in the prevention and treatment of diseases involving CXCR7 mediated metastasis, chemotaxis, cell adhesion, trans endothelial migration, cell proliferation and/or survival.

In one embodiment, the amino acid sequences and peptides of the invention (which may be as further described herein) are directed against a receptor (i.e. a GPCR) from the family of cannabinoid receptor family It is expected that amino acid sequences, Nanobodies and polypeptides of the invention of the invention directed against CB1R (and in particular antagonists), as well as compositions comprising the same, may find particular use in the prevention and treatment of for example cachexia and anorexia; pain and inflammation; mental disorders such as schizophrenia; anxiety and depression; drug abuse disorders and insomnia; Syndrome X; nicotine dependence; obesity; psychosis; atherosclerosis; hypotension; lipid metabolism disorders; metabolic disorders; non-insulin dependent diabetes; as an appetite suppressant. Antagonists of CB1R may also find use as antiarteriosclerotic agents; antipsychotic agents; hypoglycemic agents; and antihyperlipidemic agents.

In one embodiment, the amino acid sequences and peptides of the invention (which may be as further described herein) are directed against a receptor (i.e. a GPCR) from the family of parathyroid hormone receptors (for examples, receptors for parathyroid hormone (PTH) and/or parathyroid hormone-like hormone (PTHLH)).

It is expected that amino acid sequences, Nanobodies and polypeptides of the invention of the invention directed against PTHR1, as well as compositions comprising the same, may find particular use in the prevention and treatment of osteoporosis and disorders of bone metabolism (agonist); hyperparathyroidism (antagonist) and Jansen's chondrodysplasia (inverse agonist). Antagonists of PTHR1 may also find use as agents for the prevention or treatment of hypercalcemia; bone metastases and cachexia.

In one embodiment, the amino acid sequences and polypeptides of the invention (which may be as further described herein) are directed against a receptor from the family of melanocortin receptors, such as MC1R, MC2R, MC3R, MC4R and MC4R. It is expected that amino acid sequences, Nanobodies and polypeptides of the invention of the invention directed against such receptors, and in particular against MC4R, as well as compositions comprising the same, may find particular use in the prevention and treatment of diseases and disorders associated with melanocortin receptors (e.g. with insufficient, undesired or abnormal signalling mediated by melanocortin receptors), such as diseases and disorders that are caused by and/or associated with aberrations in physiological processes such as energy homeostasis (for example, cachexia and/or obesity), immunity, inflammation, sexual function, pigmentation and neurite outgrowth. Reference is inter alia made to the review by Bednarek and Fong, Expert Opin. Ther. Patents (2004) 14(3): 327-336, which also lists a number of synthetic ligands for receptors belonging to the family of melanocortin receptors, and it is expected that the amino acid sequences and polypeptides of the invention may be used for all diseases and disorders that are/can be treated with such ligands and/or for which said ligands are being developed. Reference is also made to the review by Getting, S. J. 2006, Pharmacol Ther 111:1-15.

Accordingly, some particularly preferred Nanobodies of the invention are Nanobodies which can bind (as further defined herein) to and/or are directed against to GPCRs and which:

i) have at least 80% amino acid identity with at least one of the amino acid sequences of SEQ ID NO's: 526 to 527, 538 to 541, 413 to 453 and 517 to 525, in which for the purposes of determining the degree of amino acid identity, the amino acid residues that form the CDR sequences are disregarded. In this respect, reference is also made to Table A-1, which lists the framework 1 sequences (SEQ ID NO's: 542 to 547; 126 to 166 and 454 to 462), framework 2 sequences (SEQ ID NO's: 554 to 559; 208 to 248 and 472 to 480), framework 3 sequences (SEQ ID NO's: 566 to 571; 290 to 330 and 490 to 498) and framework 4 sequences (SEQ ID NO's: 578 to 583; 372 to 412 and 508 to 516) of the Nanobodies of SEQ ID NO's: 526 to 527, 538 to 541, 413 to 453 and 517 to 525 (with respect to the amino acid residues at positions 1 to 4 and 27 to 30 of the framework 1 sequences, reference is also made to the comments made below. Thus, for determining the degree of amino acid identity, these residues are preferably disregarded);

and in which:

ii) preferably one or more of the amino acid residues at positions 11, 37, 44, 45, 47, 83, 84, 103, 104 and 108 according to the Kabat numbering are chosen from the Hallmark residues mentioned in Table A-3 below.

In these Nanobodies, the CDR sequences are generally as further defined herein.

Again, such Nanobodies may be derived in any suitable manner and from any suitable source, and may for example be naturally occurring $V_{HH}$ sequences (i.e. from a suitable species of Camelid) or synthetic or semi-synthetic amino acid sequences, including but not limited to "humanized" (as defined herein) Nanobodies, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein. Also, when a NANOBODY® ($V_{HH}$) comprises a $V_{HH}$ sequence, said NANOBODY® ($V_{HH}$) may be suitably humanized, as further described herein, so as to provide one or more further (partially or fully) humanized Nanobodies of the invention. Similarly, when a NANOBODY® ($V_{HH}$) comprises a synthetic or semi-synthetic sequence (such as a partially humanized sequence), said NANOBODY® ($V_{HH}$) may optionally be further suitably humanized, again as described herein, again so as to provide one or more further (partially or fully) humanized Nanobodies of the invention.

In particular, humanized Nanobodies may be amino acid sequences that are as generally defined for Nanobodies in the previous paragraphs, but in which at least one amino acid residue is present (and in particular, in at least one of the framework residues) that is and/or that corresponds to a humanizing substitution (as defined herein). Some preferred, but non-limiting humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a NANOBODY® ($V_{HH}$) may be partially humanized or fully humanized.

Some particularly preferred humanized Nanobodies of the invention are humanized variants of the Nanobodies of SEQ ID NO's: 526 to 527, 538 to 541, 413 to 453 and/or 517 to 525.

Thus, some other preferred Nanobodies of the invention are Nanobodies which can bind (as further defined herein) to GPCRs and which:
i) are a humanized variant of one of the amino acid sequences of SEQ ID NO's: 526 to 527, 538 to 541, 413 to 453 and/or 517 to 525; and/or
ii) have at least 80% amino acid identity with at least one of the amino acid sequences of SEQ ID NO's: 526 to 527, 538 to 541, 413 to 453 and/or 517 to 525, in which for the purposes of determining the degree of amino acid identity, the amino acid residues that form the CDR sequences are disregarded;
and in which:
i) preferably one or more of the amino acid residues at positions 11, 37, 44, 45, 47, 83, 84, 103, 104 and 108 according to the Kabat numbering are chosen from the Hallmark residues mentioned in Table A-3 below.

According to another specific aspect of the invention, the invention provides a number of stretches of amino acid residues (i.e. small peptides) that are particularly suited for binding to GPCRs. These stretches of amino acid residues may be present in, and/or may be corporated into, an amino acid sequence of the invention, in particular in such a way that they form (part of) the antigen binding site of an amino acid sequence of the invention. As these stretches of amino acid residues were first generated as CDR sequences of heavy chain antibodies or $V_{HH}$ sequences that were raised against GPCRs (or may be based on and/or derived from such CDR sequences, as further described herein), they will also generally be referred to herein as "CDR sequences" (i.e. as CDR1 sequences, CDR2 sequences and CDR3 sequences, respectively). It should however be noted that the invention in its broadest sense is not limited to a specific structural role or function that these stretches of amino acid residues may have in an amino acid sequence of the invention, as long as these stretches of amino acid residues allow the amino acid sequence of the invention to bind to GPCRs. Thus, generally, the invention in its broadest sense comprises any amino acid sequence that is capable of binding to GPCRs and that comprises one or more CDR sequences as described herein, and in particular a suitable combination of two or more such CDR sequences, that are suitably linked to each other via one or more further amino acid sequences, such that the entire amino acid sequence forms a binding domain and/or binding unit that is capable of binding to GPCRs. It should however also be noted that the presence of only one such CDR sequence in an amino acid sequence of the invention may by itself already be sufficient to provide an amino acid sequence of the invention that is capable of binding to GPCRs; reference is for example again made to the so-called "Expedite fragments" described in WO 03/050531.

Thus, in another specific, but non-limiting aspect, the amino acid sequence of the invention may be an amino acid sequence that comprises at least one amino acid sequence that is chosen from the group consisting of the CDR1 sequences, CDR2 sequences and CDR3 sequences that are described herein (or any suitable combination thereof). In particular, an amino acid sequence of the invention may be an amino acid sequence that comprises at least one antigen binding site, wherein said antigen binding site comprises at least one amino acid sequence that is chosen from the group consisting of the CDR1 sequences, CDR2 sequences and CDR3 sequences that are described herein (or any suitable combination thereof).

Generally, in this aspect of the invention, the amino acid sequence of the invention may be any amino acid sequence that comprises at least one stretch of amino acid residues, in which said stretch of amino acid residues has an amino acid sequence that corresponds to the sequence of at least one of the CDR sequences described herein. Such an amino acid sequence may or may not comprise an immunoglobulin fold. For example, and without limitation, such an amino acid sequence may be a suitable fragment of an immunoglobulin sequence that comprises at least one such CDR sequence, but that is not large enough to form a (complete) immunoglobulin fold (reference is for example again made to the "Expedite fragments" described in WO 03/050531). Alternatively, such an amino acid sequence may be a suitable "protein scaffold" that comprises least one stretch of amino acid residues that corresponds to such a CDR sequence (i.e. as part of its antigen binding site). Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al., Nat. Biotech 2005, Vol 23:1257), and binding moieties based on DNA or RNA including but not limited to DNA or RNA aptamers (Ulrich et al., Comb Chem High Throughput Screen 2006 9(8):619-32).

Again, any amino acid sequence of the invention that comprises one or more of these CDR sequences is preferably such that it can specifically bind (as defined herein) to GPCRs, and more in particular such that it can bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), that is as defined herein.

More in particular, the amino acid sequences according to this aspect of the invention may be any amino acid sequence that comprises at least one antigen binding site, wherein said antigen binding site comprises at least two amino acid sequences that are chosen from the group consisting of the CDR1 sequences described herein, the CDR2 sequences described herein and the CDR3 sequences described herein, such that (i) when the first amino acid sequence is chosen from the CDR1 sequences described herein, the second amino acid sequence is chosen from the CDR2 sequences described herein or the CDR3 sequences described herein; (ii) when the first amino acid sequence is chosen from the CDR2 sequences described herein, the second amino acid sequence is chosen from the CDR1 sequences described herein or the CDR3 sequences described herein; or (iii) when the first amino acid sequence is chosen from the CDR3 sequences described herein, the second amino acid sequence is chosen from the CDR1 sequences described herein or the CDR3 sequences described herein.

Even more in particular, the amino acid sequences of the invention may be amino acid sequences that comprise at least one antigen binding site, wherein said antigen binding site comprises at least three amino acid sequences that are chosen from the group consisting of the CDR1 sequences described herein, the CDR2 sequences described herein and the CDR3 sequences described herein, such that the first amino acid sequence is chosen from the CDR1 sequences described herein, the second amino acid sequence is chosen from the CDR2 sequences described herein, and the third amino acid sequence is chosen from the CDR3 sequences described herein. Preferred combinations of CDR1, CDR2 and CDR3 sequences will become clear from the further description herein. As will be clear to the skilled person, such an amino acid sequence is preferably an immunoglobulin sequence (as further described herein), but it may for example also be any other amino acid sequence that comprises a suitable scaffold for presenting said CDR sequences.

Thus, in one specific, but non-limiting aspect, the invention relates to an amino acid sequence directed against GPCRs, that comprises one or more stretches of amino acid residues chosen from the group consisting of:
a) the amino acid sequences of SEQ ID NO's: 548 to 553; 167 to 207 and/or 463 to 471;
b) amino acid sequences that have at least 80% amino acid identity with at least one of the amino acid sequences of SEQ ID NO's: 548 to 553; 167 to 207 and/or 463 to 471;
c) amino acid sequences that have 3, 2, or 1 amino acid difference with at least one of the amino acid sequences of SEQ ID NO's: 548 to 553; 167 to 207 and/or 463 to 471;
d) the amino acid sequences of SEQ ID NO's: 560 to 565; 249 to 289 and/or 481 to 489;
e) amino acid sequences that have at least 80% amino acid identity with at least one of the amino acid sequences of SEQ ID NO's: 560 to 565; 249 to 289 and/or 481 to 489;
f) amino acid sequences that have 3, 2, or 1 amino acid difference with at least one of the amino acid sequences of SEQ ID NO's: 560 to 565; 249 to 289 and/or 481 to 489;
g) the amino acid sequences of SEQ ID NO's: 572 to 577; 331 to 371 and/or 499 to 507;
h) amino acid sequences that have at least 80% amino acid identity with at least one of the amino acid sequences of SEQ ID NO's: 572 to 577; 331 to 371 and/or 499 to 507;
i) amino acid sequences that have 3, 2, or 1 amino acid difference with at least one of the amino acid sequences of SEQ ID NO's: 572 to 577; 331 to 371 and/or 499 to 507;
or any suitable combination thereof.

When an amino acid sequence of the invention contains one or more amino acid sequences according to b) and/or c):
1) any amino acid substitution in such an amino acid sequence according to b) and/or c) is preferably, and compared to the corresponding amino acid sequence according to a), a conservative amino acid substitution, (as defined herein);
and/or
2) the amino acid sequence according to b) and/or c) preferably only contains amino acid substitutions, and no amino acid deletions or insertions, compared to the corresponding amino acid sequence according to a);
and/or
3) the amino acid sequence according to b) and/or c) may be an amino acid sequence that is derived from an amino acid sequence according to a) by means of affinity maturation using one or more techniques of affinity maturation known per se.

Similarly, when an amino acid sequence of the invention contains one or more amino acid sequences according to e) and/or f):
1) any amino acid substitution in such an amino acid sequence according to e) and/or f) is preferably, and compared to the corresponding amino acid sequence according to d), a conservative amino acid substitution, (as defined herein);
and/or
2) the amino acid sequence according to e) and/or f) preferably only contains amino acid substitutions, and no amino acid deletions or insertions, compared to the corresponding amino acid sequence according to d);
and/or
3) the amino acid sequence according to e) and/or f) may be an amino acid sequence that is derived from an amino acid sequence according to d) by means of affinity maturation using one or more techniques of affinity maturation known per se.

Also, similarly, when an amino acid sequence of the invention contains one or more amino acid sequences according to h) and/or i):
1) any amino acid substitution in such an amino acid sequence according to h) and/or i) is preferably, and compared to the corresponding amino acid sequence according to g), a conservative amino acid substitution, (as defined herein);
and/or
2) the amino acid sequence according to h) and/or i) preferably only contains amino acid substitutions, and no amino acid deletions or insertions, compared to the corresponding amino acid sequence according to g);
and/or
3) the amino acid sequence according to h) and/or i) may be an amino acid sequence that is derived from an amino acid sequence according to g) by means of affinity maturation using one or more techniques of affinity maturation known per se.

It should be understood that the last preceding paragraphs also generally apply to any amino acid sequences of the invention that comprise one or more amino acid sequences according to b), c), e), f), h) or i), respectively.

In this specific aspect, the amino acid sequence preferably comprises one or more stretches of amino acid residues chosen from the group consisting of:
i) the amino acid sequences of SEQ ID NO's: 548 to 553; 167 to 207 and/or 463 to 471;
ii) the amino acid sequences of SEQ ID NO's: 560 to 565; 249 to 289 and/or 481 to 489; and
iii) the amino acid sequences of SEQ ID NO's: 572 to 577; 331 to 371 and/or 499 to 507;
or any suitable combination thereof.

Also, preferably, in such an amino acid sequence, at least one of said stretches of amino acid residues forms part of the antigen binding site for binding against GPCRs.

In all of the above amino acid sequences of the invention, the framework sequences may be any suitable framework sequences, and examples of suitable framework sequences will be clear to the skilled person, for example on the basis the standard handbooks and the further disclosure and prior art mentioned herein.

The framework sequences are preferably (a suitable combination of) immunoglobulin framework sequences or framework sequences that have been derived from immunoglobulin framework sequences (for example, by humanization or camelization). For example, the framework sequences may be framework sequences derived from a light chain variable domain (e.g. a $V_L$-sequence) and/or from a heavy chain variable domain (e.g. a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences are preferably such that the amino acid sequence of the invention is a domain antibody (or an amino acid sequence that is suitable for use as a domain antibody); is a single domain antibody (or an amino acid sequence that is suitable for use as a single domain antibody); is a "dAb" (or an amino acid sequence that is suitable for use as a dAb); or is a NANOBODY® ($V_{HH}$) (including but not limited to $V_{HH}$ sequence). Again, suitable framework sequences will be clear to the skilled person, for example on the basis the standard handbooks and the further disclosure and prior art mentioned herein.

In particular, the framework sequences present in the amino acid sequences of the invention may contain one or more of Hallmark residues (as defined herein), such that the amino acid sequence of the invention is a NANOBODY® ($V_{HH}$). Some preferred, but non-limiting examples of (suitable combinations of) such framework sequences will become clear from the further disclosure herein.

Again, as generally described herein for the amino acid sequences of the invention, it is also possible to use suitable fragments (or combinations of fragments) of any of the foregoing, such as fragments that contain one or more CDR sequences, suitably flanked by and/or linked via one or more framework sequences (for example, in the same order as these CDR's and framework sequences may occur in the full-sized immunoglobulin sequence from which the fragment has been derived). Such fragments may also again be such that they comprise or can form an immunoglobulin fold, or alternatively be such that they do not comprise or cannot form an immunoglobulin fold.

In one specific aspect, such a fragment comprises a single CDR sequence as described herein (and in particular a CDR3 sequence), that is flanked on each side by (part of) a framework sequence (and in particular, part of the framework sequence(s) that, in the immunoglobulin sequence from which the fragment is derived, are adjacent to said CDR sequence. For example, a CDR3 sequence may be preceded by (part of) a FR3 sequence and followed by (part of) a FR4 sequence). Such a fragment may also contain a disulphide bridge, and in particular a disulphide bridge that links the two framework regions that precede and follow the CDR sequence, respectively (for the purpose of forming such a disulphide bridge, cysteine residues that naturally occur in said framework regions may be used, or alternatively cysteine residues may be synthetically added to or introduced into said framework regions). For a further description of these "Expedite fragments", reference is again made to WO 03/050531, as well as to as well as to the US provisional application of Ablynx N.V. entitled "Peptides capable of binding to serum proteins" of Ablynx N.V. (inventors: Revets, Hilde Adi Pierrette; Kolkman, Joost Alexander; and Hoogenboom, Hendricus Renerus Jacobus Mattheus) filed on Dec. 5, 2006 (see also WO08/068280).

In another aspect, the invention relates to a compound or construct, and in particular a protein or polypeptide (also referred to herein as a "compound of the invention" or "polypeptide of the invention", respectively) that comprises or essentially consists of one or more amino acid sequences of the invention (or suitable fragments thereof), and optionally further comprises one or more other groups, residues, moieties or binding units. As will become clear to the skilled person from the further disclosure herein, such further groups, residues, moieties, binding units or amino acid sequences may or may not provide further functionality to the amino acid sequence of the invention (and/or to the compound or construct in which it is present) and may or may not modify the properties of the amino acid sequence of the invention.

For example, such further groups, residues, moieties or binding units may be one or more additional amino acid sequences, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies.

Alternatively, such groups, residues, moieties or binding units may for example be chemical groups, residues, moieties, which may or may not by themselves be biologically and/or pharmacologically active. For example, and without limitation, such groups may be linked to the one or more amino acid sequences of the invention so as to provide a "derivative" of an amino acid sequence or polypeptide of the invention, as further described herein.

Also within the scope of the present invention are compounds or constructs, that comprises or essentially consists of one or more derivatives as described herein, and optionally further comprises one or more other groups, residues, moieties or binding units, optionally linked via one or more linkers. Preferably, said one or more other groups, residues, moieties or binding units are amino acid sequences.

In the compounds or constructs described above, the one or more amino acid sequences of the invention and the one or more groups, residues, moieties or binding units may be linked directly to each other and/or via one or more suitable linkers or spacers. For example, when the one or more groups, residues, moieties or binding units are amino acid sequences, the linkers may also be amino acid sequences, so that the resulting compound or construct is a fusion (protein) or fusion (polypeptide).

As will be clear from the further description above and herein, this means that the amino acid sequences of the invention can be used as "building blocks" to form polypeptides of the invention, i.e. by suitably combining them with other groups, residues, moieties or binding units, in order to form compounds or constructs as described herein (such as, without limitations, the biparatopic, bi/multivalent and bi/multispecific polypeptides of the invention described herein) which combine within one molecule one or more desired properties or biological functions. Particularly preferred polypeptides of the invention are biparatopic polypeptides as will be clear from the further description herein.

The compounds or polypeptides of the invention can generally be prepared by a method which comprises at least one step of suitably linking the one or more amino acid sequences of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted amino acid sequences form a further aspect of the invention.

In one specific aspect of the invention, a compound of the invention or a polypeptide of the invention may have an increased half-life, compared to the corresponding amino acid sequence of the invention. Some preferred, but non-limiting examples of such compounds and polypeptides will become clear to the skilled person based on the further disclosure herein, and for example comprise amino acid sequences or polypeptides of the invention that have been chemically modified to increase the half-life thereof (for example, by means of pegylation); amino acid sequences of the invention that comprise at least one additional binding site for binding to a serum protein (such as serum albumin); or polypeptides of the invention that comprise at least one amino acid sequence of the invention that is linked to at least one moiety (and in particular at least one amino acid sequence) that increases the half-life of the amino acid sequence of the invention. Examples of polypeptides of the invention that comprise such half-life extending moieties or amino acid sequences will become clear to the skilled person based on the further disclosure herein; and for example include, without limitation, polypeptides in which the one or more amino acid sequences of the invention are suitable linked to one or more serum proteins or fragments thereof (such as (human) serum albumin or suitable fragments thereof) or to one or more binding units that can bind to serum proteins (such as, for example, domain antibodies, amino acid sequences that are suitable for use as a domain antibody, single domain antibodies, amino acid sequences that are suitable for use as a single domain antibody, "dAb"'s, amino acid sequences that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more amino acid sequences of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006. (see also WO08/068280).

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or polypeptides of the invention have a serum half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another aspect, the invention relates to a nucleic acid that encodes an amino acid sequence of the invention or a polypeptide of the invention (or a suitable fragment thereof). Such a nucleic acid will also be referred to herein as a "nucleic acid of the invention" and may for example be in the form of a genetic construct, as further described herein.

In another aspect, the invention relates to a host or host cell that expresses (or that under suitable circumstances is capable of expressing) an amino acid sequence of the invention and/or a polypeptide of the invention; and/or that contains a nucleic acid of the invention. Some preferred but non-limiting examples of such hosts or host cells will become clear from the further description herein.

The invention further relates to a product or composition containing or comprising at least one amino acid sequence of the invention, at least one polypeptide of the invention (or a suitable fragment thereof) and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention also relates to the use of an amino acid sequence, NANOBODY® ($V_{HH}$) or polypeptide of the invention, or of a composition comprising the same, in (methods or compositions for) modulating a GPCR, either in vitro (e.g. in an in vitro or cellular assay) or in vivo (e.g. in an a single cell or in a multicellular organism, and in particular in a mammal, and more in particular in a human being, such as in a human being that is at risk of or suffers from a GPCR related disease or disorder).

The invention also relates to methods for modulating a GPCR, either in vitro (e.g. in an in vitro or cellular assay) or in vivo (e.g. in an a single cell or multicellular organism, and in particular in a mammal, and more in particular in a human being, such as in a human being that is at risk of or suffers from a GPCR related disease or disorder), which method comprises at least the step of contacting a GPCR with at least one amino acid sequence, NANOBODY® ($V_{HH}$) or polypeptide of the invention, or with a composition comprising the same, in a manner and in an amount suitable to modulate a GPCR, with at least one amino acid sequence, NANOBODY® ($V_{HH}$) or polypeptide of the invention.

The invention also relates to the use of an amino acid sequence, NANOBODY® ($V_{HH}$) or polypeptide of the invention in the preparation of a composition (such as, without limitation, a pharmaceutical composition or preparation as further described herein) for modulating (as defined herein) a GPCR, either in vitro (e.g. in an in vitro or cellular assay) or in vivo (e.g. in an a single cell or multicellular organism, and in particular in a mammal, and more in particular in a human being, such as in a human being that is at risk of or suffers from a GPCR related disease or disorder).

In the context of the present specification, "modulating" may be as generally defined herein, but may for also involve allosteric modulation (see for example George et al., Nat Rev Drug Discov 1:808-820 (2002); Kenakin, Trends Pharmacol Sci 25:186-192 (2002) and Rios et al., Pharmacol Ther 92:71-87 (2001)) and/or reducing or inhibiting the binding of a GPCR to one of its substrates or ligands and/or competing with a natural ligand, substrate for binding to a GPCR. Modulating may also involve activating a GPCR or the mechanism or pathway in which it is involved. Modulating may be reversible or irreversible, but for pharmaceutical and pharmacological purposes will usually be in a reversible manner.

The invention further relates to methods for preparing or generating the amino acid sequences, polypeptides, nucleic acids, host cells, products and compositions described herein. Some preferred but non-limiting examples of such methods will become clear from the further description herein.

Generally, these methods may comprise the steps of:
a) providing a set, collection or library of amino acid sequences; and
b) screening said set, collection or library of amino acid sequences for amino acid sequences that can bind to and/or have affinity for GPCRs; and
c) isolating the amino acid sequence(s) that can bind to and/or have affinity for GPCRs.

In particular, in step b) of such a method, the set, collection or library may be screened for amino acid sequences that can bind to and/or have affinity for GPCRs that are expressed on the surface of a suitable cell; for amino acid sequences that can bind to and/or have affinity for an extracellular part, region, domain, loop or other extracellular epitope of a GPCR (as described herein); and/or for amino acid sequences that can bind to and/or have affinity for a peptide that has been derived from or based on the amino acid sequence of an extracellular part, region, domain, loop or other extracellular epitope of a GPCR. This can be performed using methods and techniques known per se, for example those mentioned herein.

In such a method, the set, collection or library of amino acid sequences may be any suitable set, collection or library of amino acid sequences. For example, the set, collection or library of amino acid sequences may be a set, collection or library of immunoglobulin sequences (as described herein), such as a naïve set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of amino acid sequences may be a set, collection or library of heavy chain variable domains (such as $V_H$ domains or $V_{HH}$ domains) or of light chain variable domains. For example, the set, collection or library of amino acid sequences may be a set, collection or library of domain antibodies or single domain antibodies, or may be a set, collection or library of amino acid sequences that are capable of functioning as a domain antibody or single domain antibody.

In a preferred aspect of this method, the set, collection or library of amino acid sequences may be an immune set, collection or library of immunoglobulin sequences, for example derived from a mammal that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s), or a suitable peptide derived therefrom. Alternatively, as mentioned herein, the set, collection or library of amino acid sequences may be an immune set, collection or library of immunoglobulin sequences, for example derived from a mammal that has been suitably immunized with a refolded GPCR or with a cell, or cell fraction or preparation derived from a cell that has a GPCR on its surface.

In the above methods, the set, collection or library of amino acid sequences may be displayed on a phage, phagemid, ribosome or suitable micro-organism (such as yeast), such as to facilitate screening. Suitable methods, techniques and host organisms for displaying and screening (a set, collection or library of) amino acid sequences will be clear to the person skilled in the art, for example on the basis of the further disclosure herein. Reference is also made to the review by Hoogenboom in Nature Biotechnology, 23, 9, 1105-1116 (2005).

In another aspect, the method for generating amino acid sequences comprises at least the steps of:
a) providing a collection or sample of cells expressing amino acid sequences;
b) screening said collection or sample of cells for cells that express an amino acid sequence that can bind to and/or have affinity for GPCRs; and
c) either (i) isolating said amino acid sequence; or (ii) isolating from said cell a nucleic acid sequence that encodes said amino acid sequence, followed by expressing said amino acid sequence.

In particular, in step b) of such a method, the set, collection or library may be screened for cells that express amino acid sequences that can bind to and/or have affinity for GPCRs that are expressed on the surface of a suitable cell; for cells that express amino acid sequences that can bind to and/or have affinity for an extracellular part, region, domain, loop or other extracellular epitope of a GPCR (as described herein); and/or for cells that express amino acid sequences that can bind to and/or have affinity for a peptide that has been derived from or based on the amino acid sequence of an extracellular part, region, domain, loop or other extracellular epitope of a GPCR. This can be performed using methods and techniques known per se, for example those mentioned herein.

For example, when the desired amino acid sequence is an immunoglobulin sequence, the collection or sample of cells may for example be a collection or sample of B-cells. Also, in this method, the sample of cells may be derived from a mammal that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s), or a suitable peptide derived therefrom. Alternatively, as mentioned herein, the sample of cells may be derived from a mammal that has been suitably immunized with a refolded GPCR or with a cell, or cell fraction or preparation derived from a cell that has a GPCR on its surface.

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820 (2001).

In another aspect, the method for generating an amino acid sequence directed against GPCRs may comprise at least the steps of:
a) providing a set, collection or library of nucleic acid sequences encoding amino acid sequences;
b) screening said set, collection or library of nucleic acid sequences for nucleic acid sequences that encode an amino acid sequence that can bind to and/or has affinity for GPCRs; and
c) isolating said nucleic acid sequence, followed by expressing said amino acid sequence.

In particular, in step b) of such a method, the set, collection or library may be screened for nucleotide sequences that encode amino acid sequences that can bind to and/or have affinity for GPCRs that are expressed on the surface of a suitable cell; for nucleotide sequences that encode amino acid sequences that can bind to and/or have affinity for an extracellular part, region, domain, loop or other extracellular epitope of a GPCR (as described herein); and/or for nucleotide sequences that encode amino acid sequences that can bind to and/or have affinity for a peptide that has been derived from or based on the amino acid sequence of an extracellular part, region, domain, loop or other extracellular epitope of a GPCR. This can be performed using methods and techniques known per se, for example those mentioned herein.

In such a method, the set, collection or library of nucleic acid sequences encoding amino acid sequences may for example be a set, collection or library of nucleic acid sequences encoding a naïve set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

Also, in such a method, the set, collection or library of nucleic acid sequences may encode a set, collection or library of heavy chain variable domains (such as $V_H$ domains or $V_{HH}$ domains) or of light chain variable domains. For example, the set, collection or library of nucleic acid sequences may encode a set, collection or library of domain antibodies or single domain antibodies, or a set, collection or library of amino acid sequences that are capable of functioning as a domain antibody or single domain antibody.

In a preferred aspect of this method, the set, collection or library of amino acid sequences may be an immune set, collection or library of nucleic acid sequences, for example derived from a mammal that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s), or a suitable peptide derived therefrom. Alternatively, as mentioned herein, the set, collection or library of nucleic acid sequences may be an immune set, collection or library derived from a mammal that has been suitably immunized with a refolded GPCR or with a cell, or cell fraction or preparation derived from a cell that has a GPCR on its surface.

The set, collection or library of nucleic acid sequences may for example encode an immune set, collection or library of heavy chain variable domains or of light chain variable domains. In one specific aspect, the set, collection or library of nucleotide sequences may encode a set, collection or library of $V_{HH}$ sequences.

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to the review by Hoogenboom in Nature Biotechnology, 23, 9, 1105-1116 (2005).

The invention also relates to amino acid sequences that are obtained by the above methods, or alternatively by a method that comprises the one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Also, following the steps above, one or more amino acid sequences of the invention may be suitably humanized (or alternatively camelized); and/or the amino acid sequence(s) thus obtained may be linked to each other or to one or more other suitable amino acid sequences (optionally via one or more suitable linkers) so as to provide a polypeptide of the invention. Also, a nucleic acid sequence encoding an amino acid sequence of the invention may be suitably humanized (or alternatively camelized) and suitably expressed; and/or one or more nucleic acid sequences encoding an amino acid sequence of the invention may be linked to each other or to one or more nucleic acid sequences that encode other suitable amino acid sequences (optionally via nucleotide sequences that encode one or more suitable linkers), after which the nucleotide sequence thus obtained may be suitably expressed so as to provide a polypeptide of the invention.

The invention further relates to applications and uses of the amino acid sequences, polypeptides, nucleic acids, host cells, products and compositions described herein, as well as to methods for the prevention and/or treatment for diseases and disorders associated with GPCRs. Some preferred but non-limiting applications and uses will become clear from the further description herein. For example, as mentioned herein, it is expected that amino acid sequences, Nanobodies and polypeptides of the invention that are directed against olfactory GPCRs can find use as artificial flavourings or even perfumes. The amino acid sequences, Nanobodies and polypeptides of the invention may also find use as markers for detecting cells that express the GPCRs against which they are directed, for example in vitro (e.g. using Western blot, immunoprecipitation or immunofluorescence techniques) or in vivo (e.g. using suitable imaging techniques). The amino acid sequences, Nanobodies and polypeptides of the invention may also find use in affinity purification techniques for (cells expressing) the GPCRs against which they are directed.

Other aspects, embodiments, advantages and applications of the invention will also become clear from the further description herein, in which the invention will be described and discussed in more detail with reference to the Nanobodies of the invention and polypeptides of the invention comprising the same, which form some of the preferred aspects of the invention.

As will become clear from the further description herein, Nanobodies generally offer certain advantages (outlined herein) compared to "dAb's" or similar (single) domain antibodies or immunoglobulin sequences, which advantages are also provided by the Nanobodies of the invention. However, it will be clear to the skilled person that the more general aspects of the teaching below can also be applied (either directly or analogously) to other amino acid sequences of the invention.

DETAILED DESCRIPTION OF THE INVENTION

Figure 1:
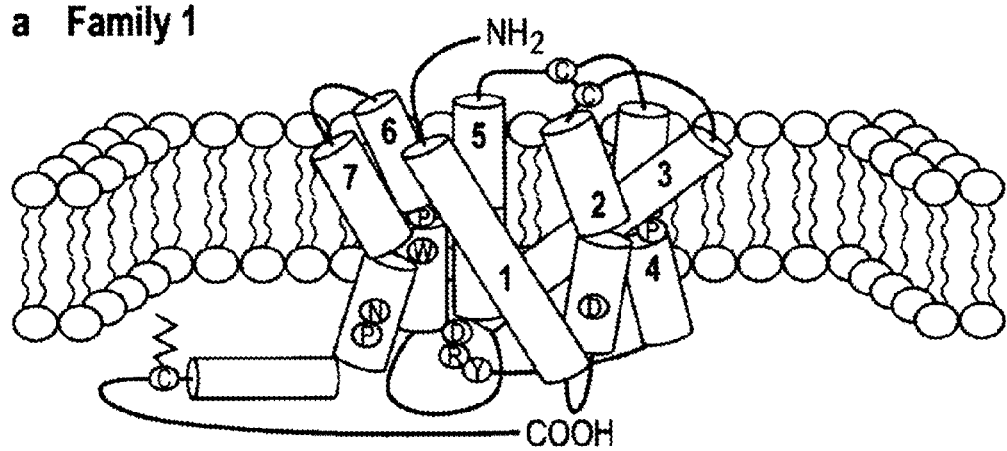
FIG. 1: Schematic representation of the structure of the three different classes of GPCRs.
Figure 1:
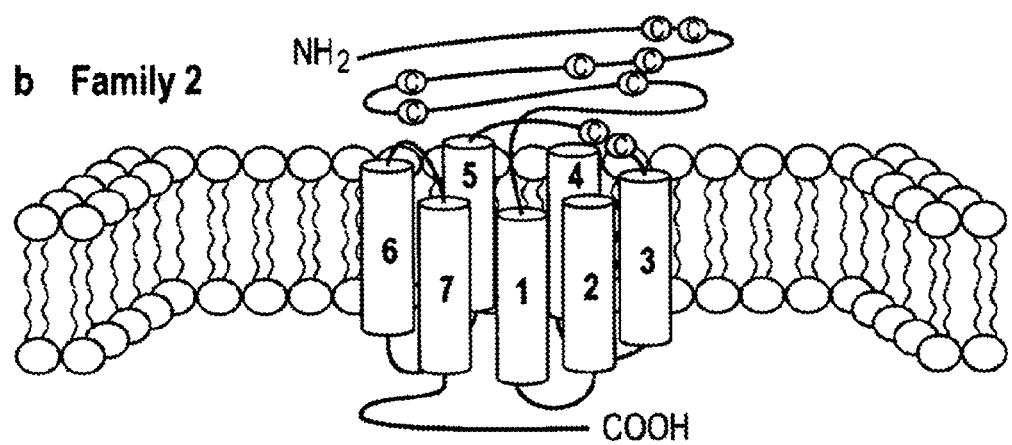
Figure 1:
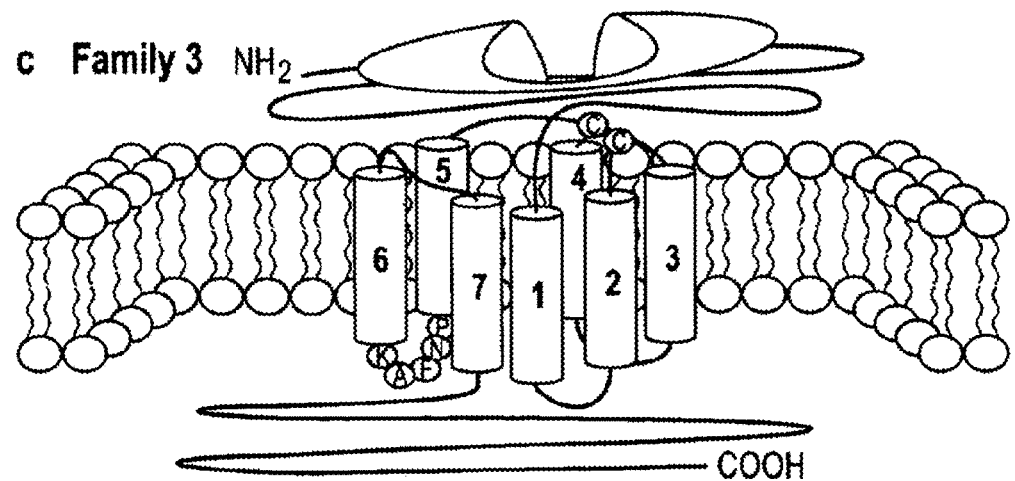

G protein-coupled receptors (GPCRs), also known as seven transmembrane receptors, 7TM receptors, heptahelical receptors, and G protein linked receptors (GPLR), are a protein family of transmembrane receptors that transduce an extracellular signal (ligand binding) into an intracellular signal (G protein activation). GPCRs are integral membrane proteins that possess seven membrane-spanning domains or transmembrane helices. The extracellular parts of the receptor can be glycosylated. These extracellular loops also contain two highly conserved cysteine residues which build disulfide bonds to stabilize the receptor structure.

The GPCRs form the largest and most diverse group of transmembrane proteins involved in signal transduction (Howard et al., Trends Pharmacol. Sci. 22:132-40, 2001). GPCRs are involved in various cellular and biological functions, such as stimulus-response pathways (from intercellular communication to physiological senses), including, for example, embryogenesis, neurotransmitter release, neurosensation (e.g., 15 chemosensory functions such as taste and smell) (Mombaerts, Science 286:707-711, 1999), neuronal axon pathfinding (Mombaerts et al., Cell 87:675, 1996; Mombaerts et al., Cold Spring Harbor Symp. Quant. Biol. 56:135, 1996), leukocyte targeting to sites of inflammation (Tager et al., J. Exp. Med., 192:439-46, 2000), and cell survival, proliferation, and differentiation. (Ryan et al., J. Biol Chem. 273:13613-24, 1998).

The complexity of the GPCR repertoire surpasses that of the immunoglobulin and T cell receptor genes combined, with members of the GPCR superfamily estimated at as many as 2,000, or more than 1.5% of the human genome. Further, members of the GPCR superfamily are the direct or indirect target of more than 50% of the current pharmaceutical drugs used clinically in humans.

The diversity of functions is matched by the wide range of ligands recognized by members of the family, from photons (rhodopsin, the archetypal GPCR) to small molecules (in the case of the histamine receptors) to proteins (for example, chemokine receptors). For an overview of the human GPCR family and ligands of human GPCRs reference is made to FIG. 1 in the US application 2002/0106739.

GPCRs can be grouped into 4 classes based on structural homology and functional similarity: Class A (rhodopsin-like), Class B (secretin-like), Class C (metabotropic/pheromone), and Class D (Fungal pheromone), of which Class A receptors, Class B receptors, and receptors with virtually non-existent carboxyl-terminal tails form the major classes. GPCRs can be classified accordingly based on their interactions with an affinity for rat beta-arrestin-2 in HEK-293 cells and may be predicted based on the amino acid residues in their carboxyl-terminal tail and the length of their carboxyl-terminal tail. A Class B receptor is a GPCR that has one or more sites of phosphorylation (e.g., clusters of phosphorylation sites) properly positioned in its carboxyl-terminal tail such that it does recruit rat beta-arrestin-2 to endosomes in HEK-293 cells under conditions as described in U.S. Pat. No. 5,891,646, Oakley, et al., Journal of Biological Chemistry, Vol 275, No. 22, pp 17201-17210, Jun. 2, 2000, and Oakley et al., Journal of Biological Chemistry, Vol. 276, No. 22, pp 19452-19460, 2001. A Class A receptor is a GPCR that does not have one or more sites of phosphorylation (e.g., clusters of phosphorylation sites) properly positioned in its carboxyl-terminal tail such that it does not recruit rat p-arrestin-2 to endosomes in HEK-293 cells under conditions as described above for Class B receptors. Receptors with virtually non existent carboxyl-terminal tails include, for example, olfactory and taste receptors.

Some examples of the biological and physiological roles of GPCRs include:
- the visual sense: the opsins use a photoisomerization reaction to translate electromagnetic radiation into cellular signals. Rhodopsin, for example, uses the conversion of 11-cis-retinal to all-trans-retinal for this purpose.
- the sense of smell: receptors of the olfactory epithelium bind odorants (olfactory receptors) and pheromones (vomeronasal receptors)
- behavioral and mood regulation: receptors in the mammalian brain bind several different neurotransmitters, including serotonin, dopamine, GABA and glutamate.
- regulation of immune system activity and inflammation: chemokine receptors bind ligands that mediate intercellular communication between cells of the immune system; receptors such as histamine receptors bind inflammatory mediators and engage target cell types in the inflammatory response
- autonomic nervous system transmission: both the sympathetic and parasympathetic nervous systems are regulated by GPCR pathways. These systems are responsible for control of many automatic functions of the body such as blood pressure, heart rate and digestive processes.

Generally, for GPCRs reference is made to the standard handbooks, such as the G Protein Coupled Receptors Handbook, L. Devi (Ed.), Humana Press, 2005, as well as to the available databases, such as GPCRDB (see for example http://www.gper.org/7tm/htmls/entries.html).

Thus, generally, as used herein, the term "G-protein coupled receptor" (or "GPCR") refers to a receptor that, when expressed by a cell, associates with a G-protein (e.g., a protein composed of cc, P and y subunits and which hydrolyzes GTP). Preferably, the GPCR is a "seven transmembrane segment receptor" (or "7 TMS receptor"), which refers to a protein that structurally comprises seven hydrophobic transmembrane spanning regions.

Some non-limiting examples of GPCRs include, but are not limited to:
- GPCRs that are known targets for pharmaceuticals (either small molecules or biologicals) that are currently on the market or in clinical development (for example, those mentioned herein);
- the luteinizing hormone releasing hormone (LHRH) (also known as gonadotropin releasing hormone, GnRH) receptor, the MI muscarinic receptor and the D2-adrenergic receptor;
- opioid receptors, endothelin receptors, angiotensin receptors, neuropeptide Y receptors and serotonin K receptors;
- GPCRs that couple to (i.e., associates with) a Gq/1 I G-protein, such as LHRH (=GnRH), acetylcholine (ml, 3 and 5 subtypes), MI muscarinic, adenosine 1, CC-adrenergic (alA, alB and a I C subtypes), angiotensin (AT I A subtype), bombesin (BB I and B132 subtypes), bradykinin (132 subtype), C5a, cholycystokinin (CCKa and CCKb subtypes), endothelin (Eta and Etb subtypes), glutamate (mGlul, 5 subtypes), 5HT (2A, B and C subtypes), histamine (H I subtype), neurotensin, neurokinin (NK2, 3 subtypes), oxytocin, thyrotropin releasing hormone (TRIJ), thyroid stimulating hormone (TSH), thromoboxane A2 and vasopressin (V I a subtypes);
- GPCRs that couple to a Gs G-protein, such as the following receptors: P2-adrenergic, cardiac P-adrenergic, histamine (H2 subtype), thyrotropin, growth hormone releasing factor, adrenocorticotropic hormone (ACTH), 5HT4, follicle stimulating hormone (FSH), thyroid stimulating hormone (TSH), GLP-1, glucagon, dopamine5 (D5), doparninel (DI), calcitonin, adenosine2p (A2p), vasopressin2, vasoactive intestinal polypeptide and parathyroid hormone;
- GPCRs that couple to a Gi G-protein, such as the following receptors: 5HT (I A, I B, I D and I F subtypes), mGlutamineR (2, 3 subtypes), dopamine4 (D4), dopamine-2 (D2) cannabinoid, adenosine3 (A3), somatostatin (4, 3 subtypes), t-opioid, 6-opioid, K-Opioid, neuropeptide Y (1, 2 subtypes);
- The GPCRs mentioned in US 2002/0106739;
- The GPCRs listed in Table 1 of Lundstrom et al., J. Struct. Funct. Genomics, 2006 Nov. 22; [Epub ahead of print]
- GPCRs that are so-called "orphan" receptors, i.e. a GPCR that is structurally similar to other GPCRs but for which the natural ligand is not yet known;
- The GPCRs mentioned in Table C;
- The GPCRs mentioned in Table D.

Other GPCRs will be clear to the skilled person, for example from the standard handbooks, such as the G Protein Coupled Receptors Handbook, L. Devi (Ed.), Humana Press, 2005; as well as from the standard databases, such as GPCRDB (see for example http://www.gper.org/7tm/htmls/entries.html).

In the present description, examples and claims:
a) Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd.Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10$^{th}$ Ed. Blackwell Publishing, UK (2001); and Janeway et al., "Immunobiology" (6th Ed.), Garland Science Publishing/Churchill Livingstone, N.Y. (2005), as well as to the general background art cited herein;
b) Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). In addition, the term "sequence" as used herein (for example in terms like "immunoglobulin sequence", "antibody sequence", "variable domain sequence", "VHH sequence" or "protein sequence"), should generally be understood to include both the relevant amino acid sequence as well as nucleic acids or nucleotide sequences encoding the same, unless the context requires a more limited interpretation. Also, the term "nucleotide sequence" as used herein also encompasses a nucleic acid molecule with said nucleotide sequence, so that the terms "nucleotide sequence" and "nucleic acid" should be considered equivalent and are used interchangeably herein;

c) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

d) Amino acid residues will be indicated according to the standard three-letter or one-letter amino acid code, as mentioned in Table A-2;

TABLE A-2 one-letter and three-letter amino acid code

| | | | |
|---|---|---|---|
| Nonpolar, uncharged (at pH 6.0-7.0)[3] | Alanine | Ala | A |
| | Valine | Val | V |
| | Leucine | Leu | L |
| | Isoleucine | Ile | I |
| | Phenylalanine | Phe | F |
| | Methionine[1] | Met | M |
| | Tryptophan | Trp | W |
| | Proline | Pro | P |
| Polar, uncharged (at pH 6.0-7.0) | Glycine[2] | Gly | G |
| | Serine | Ser | S |
| | Threonine | Thr | T |
| | Cysteine | Cys | C |
| | Asparagine | Asn | N |
| | Glutamine | Gln | Q |
| | Tyrosine | Tyr | Y |
| Polar, charged (at pH 6.0-7.0) | Lysine | Lys | K |
| | Arginine | Arg | R |
| | Histidine[4] | His | H |
| | Aspartate | Asp | D |
| | Glutamate | Glu | E |

Notes:
[1]Sometimes also considered to be a polar uncharged amino acid.
[2]Sometimes also considered to be a nonpolar uncharged amino acid.
[3]As will be clear to the skilled person, the fact that an amino acid residue is referred to in this Table as being either charged or uncharged at pH 6.0 to 7.0 does not reflect in any way on the charge said amino acid residue may have at a pH lower than 6.0 and/or at a pH higher than 7.0; the amino acid residues mentioned in the Table can be either charged and/or uncharged at such a higher or lower pH, as will be clear to the skilled person.
[4]As is known in the art, the charge of a His residue is greatly dependant upon even small shifts in pH, but a His residue can generally be considered essentially uncharged at a pH of about 6.5.

e) For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position).

Alternatively, the degree of sequence identity between two or more nucleotide sequences may be calculated using a known computer algorithm for sequence alignment such as NCBI Blast v2.0, using standard settings.

Some other techniques, computer algorithms and settings for determining the degree of sequence identity are for example described in WO 04/037999, EP 0 967 284, EP 1 085 089, WO 00/55318, WO 00/78972, WO 98/49185 and GB 2 357 768-A.

Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence;

f) For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein.

Alternatively, the degree of sequence identity between two amino acid sequences may be calculated using a known computer algorithm, such as those mentioned above for determining the degree of sequence identity for nucleotide sequences, again using standard settings.

Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB-A-3 357 768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp.

Particularly preferred conservative substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Nad. Acad Sci. USA 81: 140-144, 1984; Kyte & Doolittle; J Molec. Biol. 157: 105-132, 198 1, and Goldman et al., Ann. Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

g) Amino acid sequences and nucleic acid sequences are said to be "exactly the same" if they have 100% sequence identity (as defined herein) over their entire length;

h) When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences;

i) When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the firstmentioned nucleotide sequence or amino acid sequence, respectively, but more usually this generally means that the firstmentioned nucleotide sequence or amino acid sequence comprises within its sequence a stretch of nucleotides or amino acid residues, respectively, that has the same nucleotide sequence or amino acid sequence, respectively, as the latter sequence, irrespective of how the firstmentioned sequence has actually been generated or obtained (which may for example be by any suitable method described herein). By means of a non-limiting example, when a NANOBODY® ($V_{HH}$) of the invention is said to comprise a CDR sequence, this may mean that said CDR sequence has been incorporated into the NANOBODY® ($V_{HH}$) of the invention, but more usually this generally means that the NANOBODY® ($V_{HH}$) of the invention contains within its sequence a stretch of amino acid residues with the same amino acid sequence as said CDR sequence, irrespective of how said NANOBODY® ($V_{HH}$) of the invention has been generated or obtained. It should also be noted that when the latter amino acid sequence has a specific biological or structural function, it preferably has essentially the same, a similar or an equivalent biological or structural function in the firstmentioned amino acid sequence (in other words, the firstmentioned amino acid sequence is preferably such that the latter sequence is capable of performing essentially the same, a similar or an equivalent biological or structural function). For example, when a NANOBODY® ($V_{HH}$) of the invention is said to comprise a CDR sequence or framework sequence, respectively, the CDR sequence and framework are preferably capable, in said NANOBODY® ($V_{HH}$), of functioning as a CDR sequence or framework sequence, respectively. Also, when a nucleotide sequence is said to comprise another nucleotide sequence, the firstmentioned nucleotide sequence is preferably such that, when it is expressed into an expression product (e.g. a polypeptide), the amino acid sequence encoded by the latter nucleotide sequence forms part of said expression product (in other words, that the latter nucleotide sequence is in the same reading frame as the firstmentioned, larger nucleotide sequence).

j) A nucleic acid sequence or amino acid sequence is considered to be "(in) essentially isolated (form)" —for example, compared to its native biological source and/or the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid sequence or amino acid sequence is considered "essentially isolated" when it has been purified at least 2-fold, in particular at least 10-fold, more in particular at least 100-fold, and up to 1000-fold or more. A nucleic acid sequence or amino acid sequence that is "in essentially isolated form" is preferably essentially homogeneous, as determined using a suitable technique, such as a suitable chromatographical technique, such as polyacrylamide-gel electrophoresis;

k) The term "domain" as used herein generally refers to a globular region of an amino acid sequence (such as an antibody chain, and in particular to a globular region of a heavy chain antibody), or to a polypeptide that essentially consists of such a globular region. Usually, such a domain will comprise peptide loops (for example 3 or 4 peptide loops) stabilized, for example, as a sheet or by disulfide bonds. The term "binding domain" refers to such a domain that is directed against an antigenic determinant (as defined herein);

l) The term "antigenic determinant" refers to the epitope on the antigen recognized by the antigen-binding molecule (such as a NANOBODY® ($V_{HH}$) or a polypeptide of the invention) and more in particular by the antigen-binding site of said molecule. The terms "antigenic determinant" and "epitope" may also be used interchangeably herein.

m) An amino acid sequence (such as a NANOBODY® ($V_{HH}$), an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

n) The term "specificity" refers to the number of different types of antigens or antigenic determinants to which a particular antigen-binding molecule or antigen-binding protein (such as a NANOBODY® ($V_{HH}$) or a polypeptide of the invention) molecule can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$). As will be clear to the skilled person (for example on the basis of the further disclosure herein), affinity can be determined in a manner known per se, depending on the specific antigen of interest. Avidity is the measure of the strength of binding between an antigen-binding molecule (such as a NANOBODY® ($V_{HH}$) or polypeptide of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the amino acid sequences, Nanobodies and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more then $10^{-4}$ moles/liter or $10^{-3}$ moles/liter (e.g., of $10^{-2}$ moles/liter). Optionally, as will also be clear to the skilled person, the (actual or apparent) dissociation constant may be calculated on the basis of the (actual or apparent) association constant ($K_A$), by means of the relationship [$K_D=1/K_A$].

The affinity denotes the strength or stability of a molecular interaction. The affinity is commonly given as by the $K_D$, or dissociation constant, which has units of mol/liter (or M). The affinity can also be expressed as an association constant, $K_A$, which equals $1/K_D$ and has units of (mol/liter)$^{-1}$ (or $M^{-1}$). In the present specification, the stability of the interaction between two molecules (such as an amino acid sequence, NANOBODY® ($V_{HH}$) or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$-value characterizes the strength of a molecular interaction also in a thermodynamic sense as it is related to the free energy (DG) of binding by the well known relation DG=RT.ln($K_D$) (equivalently DG=−RT.ln($K_A$)), where R equals the gas constant, T equals the absolute temperature and ln denotes the natural logarithm. The $K_D$ for biological interactions which are considered meaningful (e.g. specific) are typically in the range of $10^{-10}$M (0.1 nM) to $10^{-5}$M (10000 nM). The stronger an interaction is, the lower is its $K_D$.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units $s^{-1}$ (where s is the SI unit notation of second). The on-rate $k_{on}$ has units $M^{-1}$ $s^{-1}$. The on-rate may vary between $10^2$ $M^{-1}$ $s^{-1}$ to about $10^7$ $M^{-1}$ $s^{-1}$, approaching the diffusion-limited association rate constant for bimolecular interactions. The off-rate is related to the half-life of a given molecular interaction by the relation $t_{1/2}$=ln(2)/$k_{off}$. The off-rate may vary between $10^{-6}$ $s^{-1}$ (near irreversible complex with a $t_{1/2}$ of multiple days) to 1 $s^{-1}$ ($t_{1/2}$=0.69 s).

The affinity of a molecular interaction between two molecules can be measured via different techniques known per se, such as the well known surface plasmon resonance (SPR) biosensor technique (see for example Ober et al., Intern. Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition sites for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol. Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labor-intensive and as consequence, often apparent $K_D$ values are determined to assess the binding strength of two molecules. It should be noted that as long all measurements are made in a consistent way (e.g. keeping the assay conditions unchanged) apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in an ELISA or FACS (Fluorescent activated cell sorting) or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an $IC_{50}$ value is obtained corresponding to the concentration of A at which the signal measured for C in absence of A is halved.

Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{D\ ref})$. Note that if $c_{ref}\ll K_{D\ ref}$ $K_D\approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

o) The half-life of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally involve the steps of suitably administering to a warm-blooded animal (i.e. to a human or to another suitable mammal, such as a mouse, rabbit, rat, pig, dog or a primate, for example monkeys from the genus *Macaca* (such as, and in particular, cynomolgus monkeys (*Macaca fascicularis*) and/or rhesus monkeys (*Macaca mulatta*)) and baboon (*Papio ursinus*)) a suitable dose of the amino acid sequence, compound or polypeptide of the invention; collecting blood samples or other samples from said animal; determining the level or concentration of the amino acid sequence, compound or polypeptide of the invention in said blood sample; and calculating, from (a plot of) the data thus obtained, the time until the level or concentration of the amino acid sequence, compound or polypeptide of the invention has been reduced by 50% compared to the initial level upon dosing. Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982).

As will also be clear to the skilled person (see for example pages 6 and 7 of WO 04/003019 and in the further references cited therein), the half-life can be expressed using parameters such as the t1/2-alpha, t1/2-beta and the area under the curve (AUC). In the present specification, an "increase in half-life" refers to an increase in any one of these parameters, such as any two of these parameters, or essentially all three these parameters. As used herein "increase in half-life" or "increased half-life" in particular refers to an increase in the t1/2-beta, either with or without an increase in the t1/2-alpha and/or the AUC or both.

p) In the context of the present invention, "modulating" or "to modulate" generally means either reducing or inhibiting the activity of, or alternatively increasing the activity of, a target or antigen, as measured using a suitable in vitro, cellular or in vivo assay. In particular, "modulating" or "to modulate" may mean either reducing or inhibiting the activity of, or alternatively increasing a (relevant or intended) biological activity of, a target or antigen, as measured using a suitable in vitro, cellular or in vivo assay (which will usually depend on the target or antigen involved), by at least 1%, preferably at least 5%, such as at least 10% or at least 25%, for example by at least 50%, at least 60%, at least 70%, at least 80%, or 90% or more, compared to activity of the target or antigen in the same assay under the same conditions but without the presence of the construct of the invention.

As will be clear to the skilled person, "modulating" may also involve effecting a change (which may either be an increase or a decrease) in affinity, avidity, specificity and/or selectivity of a target or antigen for one or more of its ligands, binding partners, partners for association into a homomultimeric or heteromultimeric form, or substrates; and/or effecting a change (which may either be an increase or a decrease) in the sensitivity of the target or antigen for one or more conditions in the medium or surroundings in which the target or antigen is present (such as pH, ion strength, the presence of co-factors, etc.), compared to the same conditions but without the presence of the construct of the invention. As will be clear to the skilled person, this may again be determined in any suitable manner and/or using any suitable assay known per se, depending on the target or antigen involved.

"Modulating" may also mean effecting a change (i.e. an activity as an agonist, as an antagonist or as a reverse agonist, respectively, depending on the target or antigen and the desired biological or physiological effect) with respect to one or more biological or physiological mechanisms, effects, responses, functions, pathways or activities in which the target or antigen (or in which its substrate(s), ligand(s) or pathway(s) are involved, such as its signalling pathway or metabolic pathway and their associated biological or physiological effects) is involved. Again, as will be clear to the skilled person, such an action as an agonist or an antagonist may be determined in any suitable manner and/or using any suitable (in vitro and usually cellular or in assay) assay known per se, depending on the target or antigen involved. In particular, an action as an agonist or antagonist may be such that an intended biological or physiological activity is increased or decreased, respectively, by at least 1%, preferably at least 5%, such as at least 10% or at least 25%, for example by at least 50%, at least 60%, at least 70%, at least 80%, or 90% or more, compared to the biological or physiological activity in the same assay under the same conditions but without the presence of the construct of the invention. Modulating may for example also involve allosteric modulation of the target or antigen; and/or reducing or inhibiting the binding of the target or antigen to one of its substrates or ligands and/or competing with a natural ligand, substrate for binding to the target or antigen. Modulating may also involve activating the target or antigen or the mechanism or pathway in which it is involved. Modulating may for example also involve effecting a change in respect of the folding or conformation of the target or antigen, or in respect of the ability of the target or antigen to fold, to change its conformation (for example, upon binding of a ligand), to associate with other (sub)units, or to disassociate. Modulating may for example also involve effecting a change in the ability of the target or antigen to transport other compounds or to serve as a channel for other compounds (such as ions). Modulating may be reversible or irreversible, but for pharmaceutical and pharmacological purposes will usually be in a reversible manner.

q) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerisation (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

r) An amino acid sequence or polypeptide is said to be "specific for" a first target or antigen compared to a second target or antigen when is binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10.000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10.000 times less or even less than that, than the $K_D$ with which said amino acid sequence or polypeptide binds to the second target or polypeptide. Preferably, when an amino acid sequence or polypeptide is "specific for" a first target or antigen compared to a second target or antigen, it is directed against (as defined herein) said first target or antigen, but not directed against said second target or antigen.

s) The terms "cross-block", "cross-blocked" and "cross-blocking" are used interchangeably herein to mean the ability of an amino acid sequence or other binding agents (such as a polypeptide of the invention) to interfere with the binding of other amino acid sequences or binding agents of the invention to a given target. The extend to which an amino acid sequence or other binding agents of the invention is able to interfere with the binding of another to [target], and therefore whether it can be said to cross-block according to the invention, can be determined using competition binding assays. One particularly suitable quantitative assay uses a Biacore machine which can measure the extent of interactions using surface plasmon resonance technology. Another suitable quantitative cross-blocking assay uses an ELISA-based approach to measure competition between amino acid sequence or another binding agents in terms of their binding to the target.

The following generally describes a suitable Biacore assay for determining whether an amino acid sequence or other binding agent cross-blocks or is capable of cross-blocking according to the invention. It will be appreciated that the assay can be used with any of the amino acid sequence or other binding agents described herein. The Biacore machine (for example the Biacore 3000) is operated in line with the manufacturer's recommendations. Thus in one cross-blocking assay, the target protein is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test amino acid sequences (termed A* and B*) to be assessed for their ability to cross-block each other are mixed at a one to one molar ratio of binding sites in a suitable buffer to create the test mixture. When calculating the concentrations on a binding site basis the molecular weight of an amino acid sequence is assumed to be the total molecular weight of the amino acid sequence divided by the number of target binding sites on that amino acid sequence. The concentration of each amino acid sequence in the test mix should be high enough to readily saturate the binding sites for that amino acid sequence on the target molecules captured on the Biacore chip. The amino acid sequences in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound amino acid sequences without damaging the chip-bound target. Typically this is done by treating the chip with 30 mM HCl for 60 seconds. The solution of A* alone is then passed over the target-coated surface and the amount of binding recorded. The chip is again treated to remove all of the bound amino acid sequences without damaging the chip-bound target. The solution of B* alone is then passed over the target-coated surface and the amount of binding recorded. The maximum theoretical binding of the mixture of A* and B* is next calculated, and is the sum of the binding of each amino acid sequence when passed over the target surface alone. If the actual recorded binding of the mixture is less than this theoretical maximum then the two amino acid sequences are cross-blocking each other. Thus, in general, a cross-blocking amino acid sequence or other binding agent according to the invention is one which will bind to the target in the above Biacore cross-blocking assay such that during the assay and in the presence of a second amino acid sequence or other binding agent of the invention the recorded binding is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%) of maximum theoretical binding (as just defined above) of the two amino acid sequences or binding agents in combination. The Biacore assay described above is a primary assay used to determine if amino acid sequences or other binding agents cross-block each other according to the invention. On rare occasions particular amino acid sequences or other binding agents may not bind to target coupled via amine chemistry to a CM5 Biacore chip (this usually occurs when the relevant binding site on target is masked or destroyed by the coupling to the chip). In such cases cross-blocking can be determined using a tagged version of the target, for example a N-terminal His-tagged version (R & D Systems, Minneapolis, Minn., USA; 2005 cat#1406-ST-025). In this particular format, an anti-His amino acid sequence would be coupled to the Biacore chip and then the His-tagged target would be passed over the surface of the chip and captured by the anti-His amino acid sequence. The cross blocking analysis would be carried out essentially as described above, except that after each chip regeneration cycle, new His-tagged target would be loaded back onto the anti-His amino acid sequence coated surface. In addition to the example given using N-terminal His-tagged [target], C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an amino acid sequence or other binding agent directed against a target cross-blocks or is capable of cross-blocking as defined herein. It will be appreciated that the assay can be used with any of the amino acid sequences (or other binding agents such as polypeptides of the invention) described herein. The general principal of the assay is to have an amino acid sequence or binding agent that is directed against the target coated onto the wells of an ELISA plate. An excess amount of a second, potentially cross-blocking, anti-target amino acid sequence is added in solution (i.e. not bound to the ELISA plate). A limited amount of the target is then added to the wells. The coated amino acid sequence and the amino acid sequence in solution compete for binding of the limited number of target molecules. The plate is washed to remove excess target that has not been bound by the coated amino acid sequence and to also remove the second, solution phase amino acid sequence as well as any complexes formed between the second, solution phase amino acid sequence and target. The amount of bound target is then measured using a reagent that is appropriate to detect the target. An amino acid sequence in solution that is able to cross-block the coated amino acid sequence will be able to cause a decrease in the number of target molecules that the coated amino acid sequence can bind relative to the number of target molecules that the coated amino acid sequence can bind in the absence of the second, solution phase, amino acid sequence. In the instance where the first amino acid sequence, e.g. an Ab-X, is chosen to be the immobilized amino acid sequence, it is coated onto the wells of the ELISA plate, after which the plates are blocked with a suitable blocking solution to minimize non-specific binding of reagents that are subsequently added. An excess amount of the second amino acid sequence, i.e. Ab-Y, is then added to the ELISA plate such that the moles of Ab-Y [target] binding sites per well are at least 10 fold higher than the moles of Ab-X [target] binding sites that were used, per well, during the coating of the ELISA plate. [target] is then added such that the moles of [target] added per well are at least 25-fold lower than the moles of Ab-X [target] binding sites that were used for coating each well. Following a suitable incubation period the ELISA plate is washed and a reagent for detecting the target is added to measure the amount of target specifically bound by the coated anti-[target] amino acid sequence (in this case Ab-X). The background signal for the assay is defined as the signal obtained in wells with the coated amino acid sequence (in this case Ab-X), second solution phase amino acid sequence (in this case Ab-Y), [target] buffer only (i.e. no target) and target detection reagents. The positive control signal for the assay is defined as the signal obtained in wells with the coated amino acid sequence (in this case Ab-X), second solution phase amino acid sequence buffer only (i.e. no second solution phase amino acid sequence), target and target detection reagents. The ELISA assay may be run in such a manner so as to have the positive control signal be at least 6 times the background signal. To avoid any artefacts (e.g. significantly different affinities between Ab-X and Ab-Y for [target]) resulting from the choice of which amino acid sequence to use as the coating amino acid sequence and which to use as the second (competitor) amino acid sequence, the cross-blocking assay may to be run in two formats: 1) format 1 is where Ab-X is the amino acid sequence that is coated onto the ELISA plate and Ab-Y is the competitor amino acid sequence that is in solution and 2) format 2 is where Ab-Y is the amino acid sequence that is coated onto the ELISA plate and Ab-X is the competitor amino acid sequence that is in solution. Ab-X and Ab-Y are defined as cross-blocking if, either in format 1 or in format 2, the solution phase anti-target amino acid sequence is able to cause a reduction of between 60% and 100%, specifically between 70% and 100%, and more specifically between 80% and 100%, of the target detection signal {i.e. the amount of target bound by the coated amino acid sequence) as compared to the target detection signal obtained in the absence of the solution phase anti-target amino acid sequence (i.e. the positive control wells).

t) As further described herein, the total number of amino acid residues in a NANOBODY® ($V_{HH}$) can be in the region of 110-120, is preferably 112-115, and is most preferably 113. It should however be noted that parts, fragments, analogs or derivatives (as further described herein) of a NANOBODY® ($V_{HH}$) are not particularly limited as to their length and/or size, as long as such parts, fragments, analogs or derivatives meet the further requirements outlined herein and are also preferably suitable for the purposes described herein;

u) The amino acid residues of a NANOBODY® ($V_{HH}$) are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication); or referred to herein. According to this numbering, FR1 of a NANOBODY® ($V_{HH}$) comprises the amino acid residues at positions 1-30, CDR1 of a NANOBODY® ($V_{HH}$) comprises the amino acid residues at positions 31-35, FR2 of a NANOBODY® ($V_{HH}$) comprises the amino acids at positions 36-49, CDR2 of a NANOBODY® ($V_{HH}$) comprises the amino acid residues at positions 50-65, FR3 of a NANOBODY® ($V_{HH}$) comprises the amino acid residues at positions 66-94, CDR3 of a NANOBODY® ($V_{HH}$) comprises the amino acid residues at positions 95-102, and FR4 of a NANOBODY® ($V_{HH}$) comprises the amino acid residues at positions 103-113. [In this respect, it should be noted that—as is well known in the art for $V_H$ domains and for $V_{HH}$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.]. Alternative methods for numbering the amino acid residues of $V_H$ domains, which methods can also be applied in an analogous manner to $V_{HH}$ domains from Camelids and to Nanobodies, are the method described by Chothia et al. (Nature 342, 877-883 (1989)), the so-called "AbM definition" and the so-called "contact definition". However, in the present description, claims and figures, the numbering according to Kabat as applied to $V_{HH}$ domains by Riechmann and Muyldermans will be followed, unless indicated otherwise; and v) The Figures, Sequence Listing and the Experimental Part/Examples are only given to further illustrate the invention and should not be interpreted or construed as limiting the scope of the invention and/or of the appended claims in any way, unless explicitly indicated otherwise herein.

For a general description of heavy chain antibodies and the variable domains thereof, reference is inter alia made to the prior art cited herein, to the review article by Muyldermans in Reviews in Molecular Biotechnology 74(2001), 277-302; as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference.

In accordance with the terminology used in the art (see the above references), the variable domains present in naturally occurring heavy chain antibodies will also be referred to as "$V_{HH}$ domains", in order to distinguish them from the heavy chain variable domains that are present in conventional 4-chain antibodies (which will be referred to hereinbelow as "$V_H$ domains") and from the light chain variable domains that are present in conventional 4-chain antibodies (which will be referred to hereinbelow as "$V_L$ domains").

As mentioned in the prior art referred to above, $V_{HH}$ domains have a number of unique structural characteristics and functional properties which make isolated $V_{HH}$ domains (as well as Nanobodies based thereon, which share these structural characteristics and functional properties with the naturally occurring $V_{HH}$ domains) and proteins containing the same highly advantageous for use as functional antigen-binding domains or proteins. In particular, and without being limited thereto, $V_{HH}$ domains (which have been "designed" by nature to functionally bind to an antigen without the presence of, and without any interaction with, a light chain variable domain) and Nanobodies can function as a single, relatively small, functional antigen-binding structural unit, domain or protein. This distinguishes the $V_{HH}$ domains from the $V_H$ and $V_L$ domains of conventional 4-chain antibodies, which by themselves are generally not suited for practical application as single antigen-binding proteins or domains, but need to be combined in some form or another to provide a functional antigen-binding unit (as in for example conventional antibody fragments such as Fab fragments; in ScFv's fragments, which consist of a $V_H$ domain covalently linked to a $V_L$ domain).

Because of these unique properties, the use of $V_{HH}$ domains and Nanobodies as single antigen-binding proteins or as antigen-binding domains (i.e. as part of a larger protein or polypeptide) offers a number of significant advantages over the use of conventional $V_H$ and $V_L$ domains, scFv's or conventional antibody fragments (such as Fab- or F(ab')$_2$-fragments):

only a single domain is required to bind an antigen with high affinity and with high selectivity, so that there is no need to have two separate domains present, nor to assure that these two domains are present in the right spatial conformation and configuration (i.e. through the use of especially designed linkers, as with scFv's);

$V_{HH}$ domains and Nanobodies can be expressed from a single gene and require no post-translational folding or modifications;

$V_{HH}$ domains and Nanobodies can easily be engineered into multivalent and multispecific formats (as further discussed herein);

$V_{HH}$ domains and Nanobodies are highly soluble and do not have a tendency to aggregate (as with the mouse-derived "dAb's" described by Ward et al., Nature, Vol. 341, 1989, p. 544);

$V_{HH}$ domains and Nanobodies are highly stable to heat, pH, proteases and other denaturing agents or conditions (see for example Ewert et al, supra);

$V_{HH}$ domains and Nanobodies are easy and relatively cheap to prepare, even on a scale required for production. For example, $V_{HH}$ domains, Nanobodies and proteins/polypeptides containing the same can be produced using microbial fermentation (e.g. as further described below) and do not require the use of mammalian expression systems, as with for example conventional antibody fragments;

$V_{HH}$ domains and Nanobodies are relatively small (approximately 15 kDa, or 10 times smaller than a conventional IgG) compared to conventional 4-chain antibodies and antigen-binding fragments thereof, and therefore show high(er) penetration into tissues (including but not limited to solid tumors and other dense tissues) than such conventional 4-chain antibodies and antigen-binding fragments thereof;

$V_{HH}$ domains and Nanobodies can show so-called cavity-binding properties (inter alia due to their extended CDR3 loop, compared to conventional $V_H$ domains) and can therefore also access targets and epitopes not accessible to conventional 4-chain antibodies and antigen-binding fragments thereof. For example, it has been shown that $V_{HH}$ domains and Nanobodies can inhibit enzymes (see for example WO 97/49805; Transue et al., Proteins 1998 Sep. 1; 32(4): 515-22; Lauwereys et al., EMBO J. 1998 Jul. 1; 17(13): 3512-20).

In a specific and preferred aspect, the invention provides Nanobodies against GPCRs, and in particular Nanobodies against GPCRs from a warm-blooded animal, and more in particular Nanobodies against GPCRs from a mammal, and especially Nanobodies against human GPCRs; as well as proteins and/or polypeptides comprising at least one such NANOBODY® ($V_{HH}$).

In particular, the invention provides Nanobodies against GPCRs, and proteins and/or polypeptides comprising the same, that have improved therapeutic and/or pharmacological properties and/or other advantageous properties (such as, for example, improved ease of preparation and/or reduced costs of goods), compared to conventional antibodies against GPCRs or fragments thereof, compared to constructs that could be based on such conventional antibodies or antibody fragments (such as Fab' fragments, F(ab')$_2$ fragments, ScFv constructs, "diabodies" and other multispecific constructs (see for example the review by Holliger and Hudson, Nat Biotechnol. 2005 September; 23(9):1126-36)), and also compared to the so-called "dAb's" or similar (single) domain antibodies that may be derived from variable domains of conventional antibodies. These improved and advantageous properties will become clear from the further description herein, and for example include, without limitation, one or more of:

increased affinity and/or avidity for GPCRs, either in a monovalent format, in a multivalent format (for example in a bivalent format) and/or in a multispecific format (for example one of the multispecific formats described hereinbelow);

better suitability for formatting in a multivalent format (for example in a bivalent format);

better suitability for formatting in a multispecific format (for example one of the multispecific formats described hereinbelow);

improved suitability or susceptibility for "humanizing" substitutions (as defined herein);

less immunogenicity, either in a monovalent format, in a multivalent format (for example in a bivalent format) and/or in a multispecific format (for example one of the multispecific formats described hereinbelow);

increased stability, either in a monovalent format, in a multivalent format (for example in a bivalent format) and/or in a multispecific format (for example one of the multispecific formats described hereinbelow);

increased specificity towards GPCRs, either in a monovalent format, in a multivalent format (for example in a bivalent format) and/or in a multispecific format (for example one of the multispecific formats described hereinbelow);

decreased or where desired increased cross-reactivity with GPCRs from different species;

and/or one or more other improved properties desirable for pharmaceutical use (including prophylactic use and/or therapeutic use) and/or for diagnostic use (including but not limited to use for imaging purposes), either in a monovalent format, in a multivalent format (for example in a bivalent format) and/or in a multispecific format (for example one of the multispecific formats described hereinbelow).

As generally described herein for the amino acid sequences of the invention, the Nanobodies of the invention are preferably in essentially isolated form (as defined herein), or form part of a protein or polypeptide of the invention (as defined herein), which may comprise or essentially consist of one or more Nanobodies of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit (i.e. against one or more other targets than GPCRs), so as to provide a monovalent, multivalent or multispecific polypeptide of the invention, respectively, all as described herein. In particular, such a protein or polypeptide may comprise or essentially consist of one or more Nanobodies of the invention and optionally one or more (other) Nanobodies (i.e. directed against other targets than GPCRs), all optionally linked via one or more suitable linkers, so as to provide a monovalent, multivalent or multispecific NANOBODY® ($V_{HH}$) construct, respectively, as further described herein.

More particularly, the protein or polypeptide of the invention comprises or essentially consists of two or more Nanobodies wherein at least and "first" NANOBODY® ($V_{HH}$) is directed against a first antigenic determinant, epitope, part, domain, subunit or confirmation of a GPCR; and wherein at least one "second" NANOBODY® ($V_{HH}$) is directed against a second antigenic determinant, epitope, part, domain, subunit or confirmation of said GPCR different from the first, so as to provide biparatopic or multiparatopic NANOBODY® ($V_{HH}$) constructs as further described herein. Such proteins or polypeptides may also be in essentially isolated form (as defined herein).

In a NANOBODY® ($V_{HH}$) of the invention, the binding site for binding against GPCRs is preferably formed by the CDR sequences. Optionally, a NANOBODY® ($V_{HH}$) of the invention may also, and in addition to the at least one binding site for binding against GPCRs, contain one or more further binding sites for binding against other antigens, proteins or targets. For methods and positions for introducing such second binding sites, reference is for example made to Keck and Huston, Biophysical Journal, 71, October 1996, 2002-2011; EP 0 640 130 and WO 06/07260.

As generally described herein for the amino acid sequences of the invention, when a NANOBODY® ($V_{HH}$) of the invention (or a polypeptide of the invention comprising the same) is intended for administration to a subject (for example for therapeutic and/or diagnostic purposes as described herein), it is preferably directed against human GPCRs; whereas for veterinary purposes, it is preferably directed against GPCRs from the species to be treated. Also, as with the amino acid sequences of the invention, a NANOBODY® ($V_{HH}$) of the invention may or may not be cross-reactive (i.e. directed against GPCRs from two or more species of mammal, such as against human GPCRs and GPCRs from at least one of the species of mammal mentioned herein).

Also, again as generally described herein for the amino acid sequences of the invention, the Nanobodies of the invention may generally be directed against any antigenic determinant, epitope, part, domain, subunit or conformation (where applicable) of GPCRs. However, it is generally assumed and preferred that the Nanobodies of the invention (and polypeptides comprising the same) are directed against and/or have been raised against at least one extracellular region, domain, loop or other extracellular epitope of a GPCR (or a suitable peptide derived therefrom).

As already described herein, the amino acid sequence and structure of a NANOBODY® ($V_{HH}$) can be considered—without however being limited thereto—to be comprised of four framework regions or "FR's" (or sometimes also referred to as "FW's"), which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. Some preferred framework sequences and CDR's (and combinations thereof) that are present in the Nanobodies of the invention are as described herein. Other suitable CDR sequences can be obtained by the methods described herein.

According to a non-limiting but preferred aspect of the invention, (the CDR sequences present in) the Nanobodies of the invention are such that:

the Nanobodies can bind to GPCRs with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);

and/or such that:

the Nanobodies can bind to GPCRs with a $k_{on}$-rate of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ $s^{-1}$, such as between $10^5$ $M^{-1}$ $s^{-1}$ and $10^7$ $M^{-1}$ $s^{-1}$;

and/or such that they:

the Nanobodies can bind to GPCRs with a $k_{off}$ rate between $1$ $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Preferably, (the CDR sequences present in) the Nanobodies of the invention are such that: a monovalent NANOBODY® ($V_{HH}$) of the invention (or a polypeptide that contains only one NANOBODY® ($V_{HH}$) of the invention) is preferably such that it will bind to GPCRs with an affinity less than 500 nM, preferably less than 200 nM, more preferably less than 10 nM, such as less than 500 pM.

The affinity of the NANOBODY® ($V_{HH}$) of the invention against GPCRs can be determined in a manner known per se, for example using the general techniques for measuring $K_D$, $K_A$, $k_{off}$ or $k_{on}$ mentioned herein, as well as some of the specific assays described herein.

Some preferred IC50 values for binding of the Nanobodies of the invention (and of polypeptides comprising the same) to GPCRs will become clear from the further description and examples herein.

Some particularly preferred, but non-limiting combinations of CDR sequences, as well as preferred combinations of CDR sequences and framework sequences, are mentioned in Table A-1 below, which lists the CDR sequences and framework sequences that are present in a number of preferred (but non-limiting) Nanobodies of the invention. As will be clear to the skilled person, a combination of CDR1, CDR2 and CDR3 sequences that occur in the same clone (i.e. CDR1, CDR2 and CDR3 sequences that are mentioned on the same line in Table A-1) will usually be preferred (although the invention in its broadest sense is not limited thereto, and also comprises other suitable combinations of the CDR sequences mentioned in Table A-1). Also, a combination of CDR sequences and framework sequences that occur in the same clone (i.e. CDR sequences and framework sequences that are mentioned on the same line in Table A-1) will usually be preferred (although the invention in its broadest sense is not limited thereto, and also comprises other suitable combinations of the CDR sequences and framework sequences mentioned in Table A-1, as well as combinations of such CDR sequences and other suitable framework sequences, e.g. as further described herein).

Also, in the Nanobodies of the invention that comprise the combinations of CDR's mentioned in Table A-1, each CDR can be replaced by a CDR chosen from the group consisting of amino acid sequences that have at least 80%, preferably at least 90%, more preferably at least 95%, even more preferably at least 99% sequence identity (as defined herein) with the mentioned CDR's; in which:

i) any amino acid substitution in such a CDR is preferably, and compared to the corresponding CDR sequence mentioned in Table A-1, a conservative amino acid substitution (as defined herein);
and/or
ii) any such CDR sequence preferably only contains amino acid substitutions, and no amino acid deletions or insertions, compared to the corresponding CDR sequence mentioned in Table A-1;
and/or
iii) any such CDR sequence is a CDR that is derived by means of a technique for affinity maturation known per se, and in particular starting from the corresponding CDR sequence mentioned in Table A-1.

However, as will be clear to the skilled person, the (combinations of) CDR sequences, as well as (the combinations of) CDR sequences and framework sequences mentioned in Table A-1 will generally be preferred.

TABLE A-1

CDR's and framework sequences of Nanobodies against five representative GPCRs (CB1R, PTHR1, MC4R, CXCR4 and CXCR7)

| Clones against CB1R | SEQ FR1 | | SEQ CDR1 | | SEQ FR2 | | SEQ CDR2 | | SEQ FR3 | | SEQ CDR3 | | SEQ FR4 | |
|---|---|---|---|---|---|---|---|---|---|---|---|---|---|---|
| LGPM P5_A6 | 126 | EVQLVESGGGLVQAGGSLRLACAASGSIFS | 167 | FNAMG | 208 | WYRQAPGKQRELLA | 249 | VITRDGITKYADSVKG | 290 | RFTISRDNAKNTMYLQMNSLKPEDTAVYYCHT | 331 | GLPTGRGSHSDY | 372 | WGQGTQVTVSS |
| LGPM P5_A7 | 127 | EVQLVESGGGLVQAGGSLRLSCAASGRTLS | 168 | NYDMG | 209 | WFRQAPGKEREFVA | 250 | TIRWSTSSTYYADSVKG | 291 | RFTISSDNTKNTVDLRMNSLTPEDTAVYYCAA | 332 | RSVYSYEYNY | 373 | WGQGTQVTVSS |
| LGPM P5_B6 | 128 | EVQLVESGGGLVQAGGSLRLSCAASGRTLT | 169 | NYDMG | 210 | WFRQAPGKEREFVA | 251 | TIRWSTSETYYADSVKG | 292 | RFTISKDNTKNTVALQMNSLTPEDTALYYCAA | 333 | RSVYSYEYNY | 374 | WGQGTQVTVSS |
| LGPM P5_B9 | 129 | EVQLVESGGGLVQAGGSLRLSCAASGRTLN | 170 | NHDMG | 211 | WFRQAPGKEREFVA | 252 | TVRWGTSSTYYADSVKG | 293 | RFTISSDNTKNTVALQMNRLTPEDTGVYYCAA | 334 | RSVYSYEYTY | 375 | WGQGTQVTVSS |
| LGPM P5_D12 | 130 | EVQLVESGGGLVQAGGSLRLSCAASRRTFS | 171 | SFVMA | 212 | WFRQAPGKEREFVA | 253 | AIYGTGGELVYYENSVKG | 294 | RFTISRDNAKSTMYLQMNSLKPEDTGVYYCAV | 335 | ELTVRSIDLRRPLEYDY | 376 | WGQGTQVTVSS |
| LGPM P5_F9 | 131 | EVQLVESGGGLVQAGGSLRLSCAASGRTLV | 172 | NYDMG | 213 | WFRQAPGKEREFVA | 254 | TIRWSTSETYYADSVKG | 295 | RFTISSDNTKNTVDLQMNSLTPEDTAVYYCAA | 336 | RSVYSYEYNY | 377 | WGQGTQVTVSS |
| LGPM P5_G11 | 132 | EVQLVKSGGGLVQAGGSLRLSCAASGRTLS | 173 | NYDMG | 214 | WFRQAPGKEREFVA | 255 | TIRWSTGETYYTDSVKG | 296 | RFTISKDNTKNTVDLQMNSLTPEDTAVYYCAS | 337 | RSVYSYEYNY | 378 | WGQGTQVTVSS |
| LGPM P6_B7 | 133 | EVQLVESGGGLVQAGGSLRLSCAASGRTLR | 174 | NYDMG | 215 | WFRQAPGKEREFVA | 256 | TIRWSTSETYYADSVKG | 297 | RFTISSDNAKNTVDLQMNSLTPGDTGVYYCAA | 338 | RSVYSYDYNY | 379 | WGQGTQVTVSS |
| LGPM P6_C7 | 134 | EVQLVESGGGLVQAGGSLRLSCAASGRTLS | 175 | NYDVG | 216 | WFRQAPGKEREFVA | 257 | TIRWSTSSTYYADPVKG | 298 | RFTISSDNIKNTVDLQMNSLTPEDTAVYYCAA | 339 | RSVYSYEYNY | 380 | WGQGTQVTVSS |
| LGPM P6_C9 | 135 | EVQLVESGGGLVQAGGSLRLSCAASGRTLS | 176 | NYDMG | 217 | WFRQAPGKEREFVA | 258 | TIRWSTSETYYADSVKG | 299 | RFTISSSNTKNTVDLQMNSLTPEDTAVYYCAA | 340 | RSVYSYEYNY | 381 | WGQGTQVTVSS |
| LGPM P6_D2 | 136 | EVQLMESGGGLVQAGGSLRLSCAASGRTLT | 177 | NYDMG | 218 | WFRQAPGKEREFVA | 259 | TIRWSTSETYYADSVKG | 300 | RFTISKDNTKNTVALQMNSLTPEDTALYYCAA | 341 | RSVYSYEYNY | 382 | WGQGTQVTVSS |
| LGPM P6_D5 | 137 | EVQLVESGGGLEQAGGSLRLSCAVSRSIFE | 178 | TNTMA | 219 | WFRQAPGKQRELVA | 260 | RISSTGDTNYADSVKG | 301 | RFTISRDNAKNTVYLQMNSLKPEDTAVYYCHV | 342 | AGPYGSKFA | 383 | WGQGTQVTVSS |
| LGPM P6_D12 | 138 | EVQLVESGGGLVQAGGSLRLSCAASGRTLS | 179 | NHDVG | 220 | WFRQAPGKEREFVA | 261 | TMRWSTGSTYYADSVKG | 302 | RFTISSDNTKNTVDLQMNSLTPEDTAVYYCAA | 343 | RSVYSYEYNY | 384 | WGQGTQVTVSS |
| LGPM P6_E11 | 139 | EVQLVESGGGLVQAGGSLRLSCAASGRTLR | 180 | NYDLG | 221 | WFRQAPGKEREFVA | 262 | TIRWSTSETYYADSVKG | 303 | RFTISSDNAKNTVDLQMNSLTPEDTGVYYCAA | 344 | RSVYSYDYNY | 385 | WGQGTQVTVSS |
| LGPM P6_F12 | 140 | EVQLVESGGGLVQAGGSLRLSCAASGRTLT | 181 | NHDMG | 222 | WFRQAPGKEREFVA | 263 | TIRWGTTDTYYADSVKG | 304 | RFTISSDNTKNTVHLQMNSLTPEDTGVYYCAA | 345 | RSVYSYEYTY | 386 | WGQGTQVTVSS |
| LGPM P6_H4 | 141 | EVQLVESGGGLVQAGGSLRLACAASGSIFS | 182 | FNAMG | 223 | WYRQAPGKQRELLA | 264 | VITRDGITKYADSVKG | 305 | RFTISRDNAKNTMYLQMNSLKPEDTAVYYCHT | 346 | GLPTGRGSHSDY | 387 | WGQGTQVTVSS |
| LGPM P6_H9 | 142 | EVQLVESGGGLVQAGGSLRLSCAASGRTLN | 183 | DHDVG | 224 | WFRQAPGKEREFVA | 265 | TIRWSSKSTYYADSVKG | 306 | RFTISSDNTKNTVDLRMNSLTPEDTAVYYCAA | 347 | RSVYSYEYNY | 388 | WGQGTQVTVSS |
| LGPM P6_H12 | 143 | EVQLVESGGGLVQAGGSLRLSCAASGRTLS | 184 | NYDMG | 225 | WFRQAPGKEREFVA | 266 | TIRWSTRETYYTDSVKG | 307 | RFTISSDNTKNTVHLQMNSLTPEDTAVYYCAA | 348 | RSVYSYEYNY | 389 | WGQGTQVTVSS |
| 6F12 | 454 | EVQLVESGGGLVQAGGSLRLSCAASGRTLS | 463 | DHDMG | 472 | WFRQAPGKEREFVA | 481 | TMRWGTSSTYYADSVKG | 490 | RFTISSDNTKNTVYLQMNSLTPEDTAVYYCAA | 499 | RSVYSYEYTY | 508 | WGQGTQVTVSS |

TABLE A-1-continued

CDR's and framework sequences of Nanobodies against five representative GPCRs (CB1R, PTHR1, MC4R, CXCR4 and CXCR7)

| | FR1 | CDR1 | FR2 | CDR2 | FR3 | CDR3 | FR4 |
|---|---|---|---|---|---|---|---|
| 5D12 | 455 EVQLVESGGGLVQAGGSLRLSCTASERTFS | 464 SYNMG | 473 WFRQAPGKERVFVA | 482 VIDWSGGLAYYADSVKG | 491 RFTISRDNAKKTVYLQMNSLKPEDTAVYYCAA | 500 RSVYRGSTKPYEYDY | 509 WGQGTQVTVSS |

| Clones against PTHR1 | SEQFR1 | SEQCDR1 | SEQFR2 | SEQCDR2 | SEQFR3 | SEQCDR3 | SEQFR4 |
|---|---|---|---|---|---|---|---|
| PMPLG22-A2 | 144 EVQLVESGGGLVQAGGSLRLSCSSSGFTST | 185 DYAIG | 226 WFRQAPGKARTGVS | 267 IISRSDGSTWYADSVKG | 308 RFTISSDNAKNTVYLQMNSLKPEDTAVYYCAA | 349 QLRHNFGMGDYDY | 390 WGQGTQVTVSS |
| PMPLG22-A3 | 145 EVQLVESGGGLVQAGGSLRLSCAASGNIFA | 186 NNIMG | 227 WYRQPPGKEREFVA | 268 HVSHDGDSMYAVSVKG | 309 RFAISRKDATNLYLQMNSLKPEDTAIYFCR | 350 LLNIPTQGRMEG | 391 WGQGTQVTVSS |
| PMPLG22-A9 | 146 EVQLVESGGGLVQPGGSLRLSCAASGFTLD | 187 GYAIG | 228 WFRQAPGKEREGVS | 269 CSNKDGSTAYSDSVKG | 310 RFTISRDNAKNTVYLEMNGLKPEDAAIYYCAT | 351 KSGRYCLSHMDY | 392 WGIGTLVTVSS |
| PMPLG22-B7 | 147 EVQLVESGGGLVQTGGSLRLSCAASGMTFR | 188 LYALS | 229 WYRQAPGERREVVA | 270 TITIDGKTNYAEPLKG | 311 RFTISRDNAKNTIYLQMNSLKPEDTAVYYCNA | 352 VFSRGPLTY | 393 WGRGTQVTVSS |
| PMPLG22-B11 | 148 EVQLVESGGGLVQAGGSLRLSCAASRSRSS | 189 FDDMG | 230 WYRQAPGKQREFVA | 271 GITLGGSTIYADSKVG | 312 RFTISMDSARNTGYLQMNSLKPEDTAVYYCNA | 353 ALDGYSGSS | 394 WGQGTQVTVSS |
| PMPLG22-B12 | 149 EVQLVESGGGLVQAGGSLRLSCVASGNIFS | 190 DNLMG | 231 WYRQAPGKQREFVA | 272 HMSDGTTNYEDSVKG | 313 RFTISRENAKNTLYLHMNSLKPEDTAIYYCRL | 354 LTIPTTGRAEGF | 395 WGQGTQVTVSS |
| PMPLG22-C3 | 150 EVQLVESGGGLVQAGGSLRLSCAASRSRSS | 191 FNDMG | 232 WYRQAPGKQREFVA | 273 GIPVGGSTVYADSVKG | 314 RFTISMDSARNRGYLQMNSLKPEDTAVYYCNA | 355 YLDGYSGSS | 396 WGQGTQVTVSS |
| PMPLG23-A3 | 151 EVQLVESGGGLVQAGGSLRLSCAASGLTFS | 192 NYAMG | 233 WFRQAPGKEREWVA | 274 SINWSGGSTYYEDSVEG | 315 RFTISRDNAKNTVNLQMNSLKPEDTAVYYCAA | 356 KRGHYSREYDY | 397 WGQGTQVTVSS |
| PMPLG23-C1 | 152 KVQLVESGGGLVQAGGSLRLSCAASASIIS | 193 SAALG | 234 WYRQAPGKRREFVA | 275 GILSDGRELYVDSVKG | 316 RFTVSRDNAKNTVYLQMNSLKPEDTAVYYCNL | 357 DIDYRDY | 398 WGQGTQVTVSS |
| PMPLG23-E12 | 153 EVQLVESGGGLVQAGGSLRLSCAASASIIS | 194 SAALG | 235 WYRQAPGRRREFVA | 276 GILSDGRELYVDSVKG | 317 RFTISRDNAKNTVYLQMNSLKPEDTAVYYCNL | 358 DIDYRDY | 399 WGQGTQVTVSS |
| PMPLG23-F2 | 154 KVQLVESGGGLVQAGGSLRLSCAASGSIFS | 195 ISLVG | 236 WYRQAPGKQREFVA | 277 HIYSDGSINYGNSVKG | 318 RFTISRDNAKNTVDLQMNNLKPEDTAVYYCRL | 359 LDTARGVGY | 400 WGQGTQVTVSS |
| PMPLG23-H9 | 155 EVQLVESGGGLVQAGGSLRLSCAASASIIS | 196 SAALG | 237 WYRQAPGKRREFVA | 278 GILSDGRELYVDSVKG | 319 RFTVSRDNAKNTVYLQMNSLKPEDTAVYYCNL | 360 DIDYRDY | 401 WGQGTQVTVSS |
| PMPLG26-A2 | 156 EVQLVESGGGLVQAGGALRLSCTASGITFK | 197 RYDMG | 238 WYRQAPGKEREWVT | 279 TITSEGTANSADSVKG | 320 RFTISRDNAKNTVYLQMNSLKSEDTAVYYCNA | 361 QFTLARHLVY | 402 WGQGTQVTVSS |
| PMPLG26-A6 | 157 EVQLVESGGGLVQAGGSLRLSCAASRSRSS | 198 FDDMG | 239 WYRQAPGKQREFVG | 280 GITLGGSTIYADSVKG | 321 RFTISMDSARNTGYLQMNSLKPEDTAVYYCNA | 362 ALDGYSGSS | 403 WGQGTQVTVSS |
| PMPLG26-B6 | 158 EVQLVESGGGLVQAGGSLRLSCAASRSRSS | 199 FDDMG | 240 WYRQAPGKQREFVA | 281 GITLGGSTIYADSVKG | 322 RFTISMDSARNTGYLQMSSLKPEDTAVYYCNA | 363 VLDGYSGSS | 404 WGQGTQVTVSS |
| PMPLG26-C4 | 159 EVQLVESGGGLVQAGGSLRLSCAASGNIF | 200 ANNIMG | 241 WYRQPPGKEREFVA | 282 HVSHDGYSMYAVSVEG | 323 RFTISRENATNLYLQMNSLKPEDTAIYFCR | 364 LLTIPPQGRMEGF | 405 WGQGTQVTVSS |
| PMPLG26-C5 | 160 EVQLVESGGGLVQAGGSLRLSCAASGNIFS | 201 DNIMG | 242 WYRQAPGKQREFVA | 283 HMSRDGTSNYEDSVKG | 324 RFTISRENAKNTLYLQMNSLKPEDTAIYYCRL | 365 LTIPTTGRKEGF | 406 WGQGTQVTVSS |
| PMPLG26-D12 | 161 EVQLVESGGGLVQAGGSLRLSCAASGSISN | 202 DNSMGWYRQAPG | 243 WQRELVAIKFSGGT | 284 TDIAESAKG | 325 RFTISRDNAKNTVYLQMNSLRPEDTAVYYCRL | 366 FLPSLAMGY | 407 WGQGTQVTVSS |
| PMPLG26-E4 | 162 EVQLVESGGGLVQAGGSLRLSCAASGNIF | 203 ANNIMG | 244 WYRQPPGKEREFVA | 285 HVSHDGDSMYAVSVK | 326 GRFTISRKDATNLYLQMNSLKPEDTAIYFCR | 367 LLNIPTQGRMEGF | 408 WGQGTQVTVSS |
| PMPLG26-E6 | 163 EVQLVESGGGLVQAGGSLRLSCAASGNIF | 204 ANNIMG | 245 WYRQPPGKEREFVA | 286 HVSDDGDSMYAVSVK | 327 GRFTISRKNATNLYLQMNSLKPEDTAIYFCR | 368 LLNIPTQGRMEGFELDRQGG | 409 WGQGTQVTVSS |
| PMPLG26-F2 | 164 EVQLVESGGGLVQAGGSLRLSCVASGFSFD | 205 DYAIG | 246 WFRQAPGQDREPLA | 287 CITSGGTRNYNPSVMA | 328 RFRIDRDNSVKTVYLQINTLKPEDTAVYYCST | 369 SAHECREYDT | 410 WGQGTQVTVSS |
| PMPLG26-G11 | 165 EVQLVESGGGLVQAGGSLRLSCAASESISS | 206 FNAMG | 247 WYRQGPGKLRELVA | 288 QITDLHKDYAESAKG | 329 RFTISRDNAKNTVDLQMNSLKPEDTGVYYCAA | 370 FRGIMRPDY | 411 WGQGTQVTVSS |

TABLE A-1-continued

CDR's and framework sequences of Nanobodies against five representative GPCRs (CB1R, PTHR1, MC4R, CXCR4 and CXCR7)

| | SEQ FR1 | SEQ CDR1 | SEQ FR2 | SEQ CDR2 | SEQ FR3 | SEQ CDR3 | SEQ FR4 |
|---|---|---|---|---|---|---|---|
| PMPL G26-H11 | 166 EVQLVESGGG LVQAGKSLSL SCAASDSRFS | 207 GRFNI LNMG | 248 WYRQAPG KQREWVT | 289 TLLSTGSPIYA DSVKG | 330 RFTISRDHAKNTVYL QMHSLKPDDTANYI CFA | 371 RLTPTG TV | 412 WGQGTQV TVSS |

| Clones against MC4R | SEQ FR1 | SEQ CDR1 | SEQ FR2 | SEQ CDR2 | SEQ FR3 | SEQ CDR3 | SEQ FR4 |
|---|---|---|---|---|---|---|---|
| 60-11B | 456 EVQLVESGG GLVQPGGSL RLSCAASGFT LD | 465 DYAVS | 474 WFRRAPG KEREGVS | 483 CISSSSSSDTY YADSVRG | 492 RFSISRDSAKNTV YLQMNSLKPEDTA VYYCAA | 501 DRHCLG SDWDEY DY | 510 WGQGTQ VTVSS |
| 59-8A | 457 EVQLVESGG GLVHAGDSL RLSCAASGFT LD | 466 DYAVS | 475 WFRQAPG KAREGLS | 484 CISAEDGSTYY ADSVKG | 493 RFIISRDNAKNTVY LQMNSLKPEDTAV YYCAA | 502 EDSCLS SDYDAY DG | 511 WGQGTQ VTVSS |
| 58-4H | 458 EVQLVESGG GLAQPGGSL RLSCVASGF SLA | 467 DYAIS | 476 WFRQAPG KVREGVS | 485 CISSSDGSTYY ADSVKG | 494 RFTISRDNAKNAV YLQMSTLKPEDTA VYYCAA | 503 ERSCLS SDYDSY DA | 512 WGQGTQ VTVSS |
| 60-5E | 459 EVQLVESGG GLVQPGGSL RLSCAASGFT LD | 468 DYAIG | 477 WFRQAPG KEREGVS | 486 CISSSDGSTYY ADSVKG | 495 RFTISRDNAKNTV YLQMNSLKPEDTA VYYCAA | 504 DLGYGS NCLEYD F | 513 WGQGTQ VTVSS |
| 60-4A | 460 EVQLVESGG GLVQAGGSL RLSCAASGFT FD | 469 EYAIG | 478 WFRQAPG KEREGVS | 487 CISRSDGSTYY APSVKG | 496 RFTISSDNAKNTV YLQMNSLKPEDTA VYYCAV | 505 DLEYGS NCYEYD S | 514 WGQGTQ VTVSS |
| 58-10H | 461 EVQLVESGG GLVQPGGSM RLSCAASGS SLD | 470 AYGLG | 479 WFRQAPG KEREGVS | 488 CISGSDNSTYY ADSVKG | 497 RFSISRDIAKNTVY LQMNGLKPEDTA VYYCAA | 506 KFLGFR QRSPTW FSRSWS EGSDYQ Y | 515 WGQGTQ VTVSS |
| 60-10E | 462 EVQLVESGG GLVQPGGSL RLSCAASGFT LD | 471 DYAIG | 480 WFRQAPG KEREGVS | 489 CITSSDGSTYY ADSVKG | 498 RFTISRDNAKNTV YLQINSLKPEDTA VYYCAA | 507 DLGVGT QCDEYD Y | 516 WGQGTQ VTVSS |

| Clones against CXCR4 | SEQ FR1 | SEQ CDR1 | SEQ FR2 | SEQ CDR2 | SEQ FR3 | SEQ CDR3 | SEQ FR4 |
|---|---|---|---|---|---|---|---|
| 238D2 | 542 EVQLVESGG GLVQTGGSL RLSCAASGFT FS | 549 SYAMS | 554 WYRQAPG KGLEWVS | 560 GIKSSGDSTRY AGSVKG | 566 RFTISRDNAKNML YLQMYSLKPEDTA VYYCAK | 572 SRVSRT GLYTYD N | 578 RGQGTQV TVSS |
| 238D4 | 543 EVQLMESGG GLVQAGGSL RLSCAASGR TFN | 549 NYAMG | 555 WFRRAPG KEREFVA | 561 AITRSGVRSGV SAIYGDSVKD | 567 RFTISRDNAKNTL YLQMNSLKPEDTA VYTCAA | 573 SAIGSG ALRRFE YDY | 579 SGQGTQV TVSS |

| Clones against CXCR7 | FR1 | CDR1 | FR2 | CDR2 | FR3 | CDR3 | FR4 |
|---|---|---|---|---|---|---|---|
| 14G03 | 544 EVQLVESGG GLVQPGGSL RISCAASGSI YL | 550 INYMG | 556 WYRQAPG KQRELVA | 562 TLTSGGSTNYA GSVKG | 568 RFAISRDNAKNTV YLQMNSLKPEDTA VYYCNI | 574 GGTLYD RRRFES | 580 WGQGTQ VTVSS |
| 01C10 | 545 EVQLVESGG GLVQTGASL RLSCAASGR TFS | 551 NYAMG | 557 WFRQAPG KERERVA | 563 AITPRAFTTYY DASVKG | 569 RFTISRDNAKNTA YLQMVSLKPEDTA VYYCAA | 575 QLVGSG SNLGRQ ESYAY | 581 WGQGTQ VTVSS |
| 08A10 | 546 EVQLVESGG GLVQAGGSL RLSCAASGSI FS | 552 IAAMG | 558 WYRQATG KQRELVA | 564 TITDGGTTTYA DSVKG | 570 RVTISRDRSANTV YLAMNNLKPDDTA VYYCYA | 576 YLRYTS RVPGDN Y | 582 WGQGTQ VTVSS |
| 08A05 | 547 EVQLVESGG GLVQAGDSL RLSCAASGLT FS | 553 NYDMG | 559 WFRQAPG KEREFVG | 565 ASWWSGGAPYY SDSVKG | 571 RFTISRDNAKNTV YLQANSLRPEDTA VYYCAA | 577 KRLRSF ASGGSY DY | 583 WGQGTQ VTVSS |

In another preferred, but non-limiting aspect, the invention relates to a NANOBODY® ($V_{HH}$) in which the CDR sequences (as defined herein) have more than 80%, preferably more than 90%, more preferably more than 95%, such as 99% or more sequence identity (as defined herein) with the CDR sequences of at least one of the amino acid sequences of SEQ ID NO's: 526 to 527; SEQ ID NO's 538 to 541; 413 to 453 and 517 to 525.

Generally, Nanobodies with the above CDR sequences may be as further described herein, and preferably have framework sequences that are also as further described herein. Thus, for example and as mentioned herein, such Nanobodies may be naturally occurring Nanobodies (from any suitable species), naturally occurring $V_{HH}$ sequences (i.e. from a suitable species of Camelid) or synthetic or semi-synthetic amino acid sequences or Nanobodies, including but not limited to partially humanized Nanobodies or $V_{HH}$ sequences, fully humanized Nanobodies or $V_{HH}$ sequences, camelized heavy chain variable domain sequences, as well as Nanobodies that have been obtained by the techniques mentioned herein.

Thus, in one specific, but non-limiting aspect, the invention relates to a humanized NANOBODY® ($V_{HH}$), which consists of 4 framework regions (FR1 to FR4 respectively) and 3 complementarity determining regions (CDR1 to CDR3 respectively), in which CDR1 to CDR3 are as defined herein and in which said humanized NANOBODY® ($V_{HH}$) comprises at least one humanizing substitution (as defined herein), and in particular at least one humanizing substitution in at least one of its framework sequences (as defined herein).

In another preferred, but non-limiting aspect, the invention relates to a NANOBODY® ($V_{HH}$) in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 526 to 527; SEQ ID NO's 538 to 541; 413 to 453 and 517 to 525. This degree of amino acid identity can for example be determined by determining the degree of amino acid identity (in a manner described herein) between said NANOBODY® ($V_{HH}$) and one or more of the sequences of SEQ ID NO's: 526 to 527; SEQ ID NO's 538 to 541; 413 to 453 and 517 to 525, in which the amino acid residues that form the framework regions are disregarded. Such Nanobodies can be as further described herein.

In another preferred, but non-limiting aspect, the invention relates to a NANOBODY® ($V_{HH}$) with an amino acid sequence that is chosen from the group consisting of SEQ ID NO's: 526 to 527; SEQ ID NO's 538 to 541; 413 to 453 and 517 to 525 or from the group consisting of from amino acid sequences that have more than 80%, preferably more than 90%, more preferably more than 95%, such as 99% or more sequence identity (as defined herein) with at least one of the amino acid sequences of SEQ ID NO's: 526 to 527; SEQ ID NO's 538 to 541; 413 to 453 and 517 to 525.

Another preferred, but non-limiting aspect of the invention relates to humanized variants of the Nanobodies of SEQ ID NO's: 526 to 527; SEQ ID NO's 538 to 541; 413 to 453 and 517 to 525, that comprise, compared to the corresponding native $V_{HH}$ sequence, at least one humanizing substitution (as defined herein), and in particular at least one humanizing substitution in at least one of its framework sequences (as defined herein).

The polypeptides of the invention comprise or essentially consist of at least one NANOBODY® ($V_{HH}$) of the invention.

It will be clear to the skilled person that the Nanobodies that are mentioned herein as "preferred" (or "more preferred", "even more preferred", etc.) are also preferred (or more preferred, or even more preferred, etc.) for use in the polypeptides described herein. Thus, polypeptides that comprise or essentially consist of one or more "preferred" Nanobodies of the invention will generally be preferred, and polypeptides that comprise or essentially consist of one or more "more preferred" Nanobodies of the invention will generally be more preferred, etc.

Generally, proteins or polypeptides that comprise or essentially consist of a single NANOBODY® ($V_{HH}$) (such as a single NANOBODY® ($V_{HH}$) of the invention) will be referred to herein as "monovalent" proteins or polypeptides or as "monovalent constructs". Proteins and polypeptides that comprise or essentially consist of two or more Nanobodies (such as at least two Nanobodies of the invention or at least one NANOBODY® ($V_{HH}$) of the invention and at least one other NANOBODY® ($V_{HH}$)) will be referred to herein as "multivalent" proteins or polypeptides or as "multivalent constructs", and these may provide certain advantages compared to the corresponding monovalent Nanobodies of the invention. Some non-limiting examples of such multivalent constructs will become clear from the further description herein.

According to one specific, but non-limiting aspect, a polypeptide of the invention comprises or essentially consists of at least two Nanobodies of the invention, such as two or three Nanobodies of the invention. As further described herein, such multivalent constructs can provide certain advantages compared to a protein or polypeptide comprising or essentially consisting of a single NANOBODY® ($V_{HH}$) of the invention, such as a much improved avidity for GPCRs. Such multivalent constructs will be clear to the skilled person based on the disclosure herein. According to a particular preferred aspect, a polypeptide of the invention comprises or essentially consists of two or more Nanobodies of the invention, which are directed against GPCRs, wherein at least one "first" NANOBODY® ($V_{HH}$) is directed against a first antigenic determinant, epitope, part, domain, subunit or confirmation of a GPCR; and wherein at least one "second" NANOBODY® ($V_{HH}$) is directed against a second antigenic determinant, epitope, part, domain, subunit or confirmation of said GPCR different from the first, so as to provide biparatopic or multiparatopic constructs as described herein. Although it will be clear to the skilled person that such constructs may provide favourable properties over the monovalent constructs, present inventors however demonstrated completely unexpectedly that the affinity of the resulting "biparatopic" polypeptides of the invention was significantly improved compared to the corresponding monovalent and mono-specific bivalent constructs. Examples of such biparatopic polypeptides of the invention will become clear from the further description herein.

According to another specific, but non-limiting aspect, a polypeptide of the invention comprises or essentially consists of at least one NANOBODY® ($V_{HH}$) of the invention and at least one other binding unit (i.e. directed against another epitope, antigen, target, protein or polypeptide), which is preferably also a NANOBODY® ($V_{HH}$). Such proteins or polypeptides are also referred to herein as "multispecific" proteins or polypeptides or as "multispecific constructs", and these may provide certain advantages compared to the corresponding monovalent Nanobodies of the invention (as will become clear from the further discussion herein of some preferred, but-nonlimiting multispecific constructs). Such multispecific constructs will be clear to the skilled person based on the disclosure herein.

According to yet another specific, but non-limiting aspect, a polypeptide of the invention comprises or essentially consists of at least one NANOBODY® ($V_{HH}$) of the invention, optionally one or more further Nanobodies, and at least one other amino acid sequence (such as a protein or polypeptide) that confers at least one desired property to the NANOBODY® ($V_{HH}$) of the invention and/or to the resulting fusion protein. Again, such fusion proteins may provide certain advantages compared to the corresponding monovalent Nanobodies of the invention. Some non-limiting examples of such amino acid sequences and of such fusion constructs will become clear from the further description herein.

It is also possible to combine two or more of the above aspects, for example to provide a trivalent bispecific construct comprising two Nanobodies of the invention and one other NANOBODY® ($V_{HH}$), and optionally one or more other amino acid sequences. Further non-limiting examples of such constructs, as well as some constructs that are particularly preferred within the context of the present invention, will become clear from the further description herein.

In the above constructs, the one or more Nanobodies and/or other amino acid sequences may be directly linked to each other and/or suitably linked to each other via one or more linker sequences. Some suitable but non-limiting examples of such linkers will become clear from the further description herein.

In one specific aspect of the invention, a NANOBODY® ($V_{HH}$) of the invention or a compound, construct or polypeptide of the invention comprising at least one NANOBODY® ($V_{HH}$) of the invention may have an increased half-life, compared to the corresponding amino acid sequence of the invention. Some preferred, but non-limiting examples of such Nanobodies, compounds and polypeptides will become clear to the skilled person based on the further disclosure herein, and for example comprise Nanobodies sequences or polypeptides of the invention that have been chemically modified to increase the half-life thereof (for example, by means of pegylation); amino acid sequences of the invention that comprise at least one additional binding site for binding to a serum protein (such as serum albumin, see for example EP 0 368 684 B1, page 4); or polypeptides of the invention that comprise at least one NANOBODY® ($V_{HH}$) of the invention that is linked to at least one moiety (and in particular at least one amino acid sequence) that increases the half-life of the NANOBODY® ($V_{HH}$) of the invention. Examples of polypeptides of the invention that comprise such half-life extending moieties or amino acid sequences will become clear to the skilled person based on the further disclosure herein; and for example include, without limitation, polypeptides in which the one or more Nanobodies of the invention are suitable linked to one or more serum proteins or fragments thereof (such as serum albumin or suitable fragments thereof) or to one or more binding units that can bind to serum proteins (such as, for example, Nanobodies or (single) domain antibodies that can bind to serum proteins such as serum albumin, serum immunoglobulins such as IgG, or transferrin); polypeptides in which a NANOBODY® ($V_{HH}$) of the invention is linked to an Fc portion (such as a human Fc) or a suitable part or fragment thereof; or polypeptides in which the one or more Nanobodies of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N.V. entitled "Peptides capable of binding to serum proteins" of Ablynx N.V. filed on Dec. 5, 2006 (see also WO08/068280).

Again, as will be clear to the skilled person, such Nanobodies, compounds, constructs or polypeptides may contain one or more additional groups, residues, moieties or binding units, such as one or more further amino acid sequences and in particular one or more additional Nanobodies (i.e. not directed against GPCRs), so as to provide a tri- of multi-specific NANOBODY® ($V_{HH}$) construct.

Generally, the Nanobodies of the invention (or compounds, constructs or polypeptides comprising the same) with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the Nanobodies, compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such Nanobodies, compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another one aspect of the invention, a polypeptide of the invention comprises one or more (such as two or preferably one) Nanobodies of the invention linked (optionally via one or more suitable linker sequences) to one or more (such as two and preferably one) amino acid sequences that allow the resulting polypeptide of the invention to cross the blood brain barrier. In particular, said one or more amino acid sequences that allow the resulting polypeptides of the invention to cross the blood brain barrier may be one or more (such as two and preferably one) Nanobodies, such as the Nanobodies described in WO 02/057445, of which FC44 (SEQ ID NO: 189 of WO 06/040153) and FC5 (SEQ ID NO: 190 of WO 06/040154) are preferred examples.

In particular, polypeptides comprising one or more Nanobodies of the invention are preferably such that they:
bind to GPCRs with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);
and/or such that they:
bind to GPCRs with a $k_{on}$-rate of between $10^2$ $M^{-1}$ $s^{-1}$ to about $10^7$ $M^{-1}$ $s^{-1}$, preferably between $10^3$ $M^{-1}$ $s^{-1}$ and $10^7$ M$^{-1}$ s$^{-1}$, more preferably between $10^4$ M$^{-1}$ s$^{-1}$ and $10^7$ M$^{-1}$ s$^{-1}$, such as between $10^5$ M$^{-1}$ s$^{-1}$ and $10^7$ M$^{-1}$ s$^{-1}$;

and/or such that they:

bind to GPCRs with a $k_{off}$ rate between 1 s$^{-1}$ ($t_{1/2}$=0.69 s) and $10^{-6}$ s$^{-1}$ (providing a near irreversible complex with a $t_{1/2}$ of multiple days), preferably between $10^{-2}$ s$^{-1}$ and $10^{-6}$ s$^{-1}$, more preferably between $10^{-3}$ s$^{-1}$ and $10^{-6}$ s$^{-1}$, such as between $10^4$ s$^{-1}$ and $10^{-6}$ s$^{-1}$.

Preferably, a polypeptide that contains only one amino acid sequence of the invention is preferably such that it will bind to GPCRs with an affinity less than 500 nM, preferably less than 200 nM, more preferably less than 10 nM, such as less than 500 pM. In this respect, it will be clear to the skilled person that a polypeptide that contains two or more Nanobodies of the invention may bind to GPCRs with an increased avidity, compared to a polypeptide that contains only one amino acid sequence of the invention.

Some preferred IC$_{50}$ values for binding of the amino acid sequences or polypeptides of the invention to GPCRs will become clear from the further description and examples herein.

Another aspect of this invention relates to a nucleic acid that encodes an amino acid sequence of the invention (such as a NANOBODY® (V$_{HH}$) of the invention) or a polypeptide of the invention comprising the same. Again, as generally described herein for the nucleic acids of the invention, such a nucleic acid may be in the form of a genetic construct, as defined herein.

In another aspect, the invention relates to host or host cell that expresses or that is capable of expressing an amino acid sequence (such as a NANOBODY® (V$_{HH}$)) of the invention and/or a polypeptide of the invention comprising the same; and/or that contains a nucleic acid of the invention. Some preferred but non-limiting examples of such hosts or host cells will become clear from the further description herein.

Another aspect of the invention relates to a product or composition containing or comprising at least one amino acid sequence of the invention, at least one polypeptide of the invention and/or at least one nucleic acid of the invention, and optionally one or more further components of such compositions known per se, i.e. depending on the intended use of the composition. Such a product or composition may for example be a pharmaceutical composition (as described herein), a veterinary composition or a product or composition for diagnostic use (as also described herein). Some preferred but non-limiting examples of such products or compositions will become clear from the further description herein.

The invention further relates to methods for preparing or generating the amino acid sequences, compounds, constructs, polypeptides, nucleic acids, host cells, products and compositions described herein. Some preferred but non-limiting examples of such methods will become clear from the further description herein.

The invention further relates to applications and uses of the amino acid sequences, compounds, constructs, polypeptides, nucleic acids, host cells, products and compositions described herein, as well as to methods for the prevention and/or treatment for diseases and disorders associated with GPCRs. Some preferred but non-limiting applications and uses will become clear from the further description herein.

Other aspects, embodiments, advantages and applications of the invention will also become clear from the further description hereinbelow.

Generally, it should be noted that the term NANOBODY® (V$_{HH}$) as used herein in its broadest sense is not limited to a specific biological source or to a specific method of preparation. For example, as will be discussed in more detail below, the Nanobodies of the invention can generally be obtained: (1) by isolating the V$_{HH}$ domain of a naturally occurring heavy chain antibody; (2) by expression of a nucleotide sequence encoding a naturally occurring V$_{HH}$ domain; (3) by "humanization" (as described herein) of a naturally occurring V$_{HH}$ domain or by expression of a nucleic acid encoding a such humanized V$_{HH}$ domain; (4) by "camelization" (as described herein) of a naturally occurring V$_H$ domain from any animal species, and in particular a from species of mammal, such as from a human being, or by expression of a nucleic acid encoding such a camelized V$_H$ domain; (5) by "camelisation" of a "domain antibody" or "dAb" as described by Ward et al (supra), or by expression of a nucleic acid encoding such a camelized V$_H$ domain; (6) by using synthetic or semi-synthetic techniques for preparing proteins, polypeptides or other amino acid sequences known per se; (7) by preparing a nucleic acid encoding a NANOBODY® (V$_{HH}$) using techniques for nucleic acid synthesis known per se, followed by expression of the nucleic acid thus obtained; and/or (8) by any combination of one or more of the foregoing. Suitable methods and techniques for performing the foregoing will be clear to the skilled person based on the disclosure herein and for example include the methods and techniques described in more detail herein.

One preferred class of Nanobodies corresponds to the V$_{HH}$ domains of naturally occurring heavy chain antibodies directed against GPCRs. As further described herein, such V$_{HH}$ sequences can generally be generated or obtained by suitably immunizing a species of Camelid with GPCRs (i.e. so as to raise an immune response and/or heavy chain antibodies directed against GPCRs), by obtaining a suitable biological sample from said Camelid (such as a blood sample, serum sample or sample of B-cells), and by generating V$_{HH}$ sequences directed against GPCRs, starting from said sample, using any suitable technique known per se. Such techniques will be clear to the skilled person and/or are further described herein.

Alternatively, such naturally occurring V$_{HH}$ domains against GPCRs, can be obtained from naïve libraries of Camelid V$_{HH}$ sequences, for example by screening such a library using GPCRs, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from naïve V$_{HH}$ libraries may be used, such as V$_{HH}$ libraries obtained from naïve V$_{HH}$ libraries by techniques such as random mutagenesis and/or CDR shuffling, as for example described in WO 00/43507.

Thus, in another aspect, the invention relates to a method for generating Nanobodies, that are directed against GPCRs. In one aspect, said method at least comprises the steps of:

a) providing a set, collection or library of NANOBODY® (V$_{HH}$) sequences; and b) screening said set, collection or library of NANOBODY® (V$_{HH}$) sequences for NANOBODY® (V$_{HH}$) sequences that can bind to and/or have affinity for GPCRs; and c) isolating the amino acid sequence(s) that can bind to and/or have affinity for GPCRs.

In such a method, the set, collection or library of NANOBODY® (V$_{HH}$) sequences may be a naïve set, collection or library of NANOBODY® (V$_{HH}$) sequences; a synthetic or semi-synthetic set, collection or library of NANOBODY® (V$_{HH}$) sequences; and/or a set, collection or library of NANOBODY® (V$_{HH}$) sequences that have been subjected to affinity maturation.

In a preferred aspect of this method, the set, collection or library of NANOBODY® (V$_{HH}$) sequences may be an immune set, collection or library of NANOBODY® (V$_{HH}$) sequences, and in particular an immune set, collection or library of V$_{HH}$ sequences, that have been derived from a species of Camelid that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of NANOBODY® (V$_{HH}$) or V$_{HH}$ sequences may be displayed on a phage, phagemid, ribosome or suitable micro-organism (such as yeast), such as to facilitate screening. Suitable methods, techniques and host organisms for displaying and screening (a set, collection or library of) NANOBODY® (V$_{HH}$) sequences will be clear to the person skilled in the art, for example on the basis of the further disclosure herein. Reference is also made to WO 03/054016 and to the review by Hoogenboom in Nature Biotechnology, 23, 9, 1105-1116 (2005).

In another aspect, the method for generating NANOBODY® (V$_{HH}$) sequences comprises at least the steps of:
a) providing a collection or sample of cells derived from a species of Camelid that express immunoglobulin sequences;
b) screening said collection or sample of cells for (i) cells that express an immunoglobulin sequence that can bind to and/or have affinity for GPCRs; and (ii) cells that express heavy chain antibodies, in which substeps (i) and (ii) can be performed essentially as a single screening step or in any suitable order as two separate screening steps, so as to provide at least one cell that expresses a heavy chain antibody that can bind to and/or has affinity for GPCRs; and
c) either (i) isolating from said cell the V$_{HH}$ sequence present in said heavy chain antibody;
or (ii) isolating from said cell a nucleic acid sequence that encodes the V$_{HH}$ sequence present in said heavy chain antibody, followed by expressing said V$_{HH}$ domain.

In the method according to this aspect, the collection or sample of cells may for example be a collection or sample of B-cells. Also, in this method, the sample of cells may be derived from a Camelid that has been suitably immunized with GPCRs or a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

The above method may be performed in any suitable manner, as will be clear to the skilled person. Reference is for example made to EP 0 542 810, WO 05/19824, WO 04/051268 and WO 04/106377. The screening of step b) is preferably performed using a flow cytometry technique such as FACS. For this, reference is for example made to Lieby et al., Blood, Vol. 97, No. 12, 3820. Particular reference is made to the so-called "Nanoclone™" technique described in International application WO 06/079372 by Ablynx N.V.

In another aspect, the method for generating an amino acid sequence directed against GPCRs may comprise at least the steps of:
a) providing a set, collection or library of nucleic acid sequences encoding heavy chain antibodies or NANOBODY® (V$_{HH}$) sequences;
b) screening said set, collection or library of nucleic acid sequences for nucleic acid sequences that encode a heavy chain antibody or a NANOBODY® (V$_{HH}$) sequence that can bind to and/or has affinity for GPCRs; and
c) isolating said nucleic acid sequence, followed by expressing the V$_{HH}$ sequence present in said heavy chain antibody or by expressing said NANOBODY® (V$_{HH}$) sequence, respectively.

In such a method, the set, collection or library of nucleic acid sequences encoding heavy chain antibodies or NANOBODY® (V$_{HH}$) sequences may for example be a set, collection or library of nucleic acid sequences encoding a naïve set, collection or library of heavy chain antibodies or V$_{HH}$ sequences; a set, collection or library of nucleic acid sequences encoding a synthetic or semi-synthetic set, collection or library of NANOBODY® (V$_{HH}$) sequences; and/or a set, collection or library of nucleic acid sequences encoding a set, collection or library of NANOBODY® (V$_{HH}$) sequences that have been subjected to affinity maturation.

In a preferred aspect of this method, the set, collection or library of amino acid sequences may be an immune set, collection or library of nucleic acid sequences encoding heavy chain antibodies or V$_{HH}$ sequences derived from a Camelid that has been suitably immunized with GPCRs or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of nucleotide sequences may be displayed on a phage, phagemid, ribosome or suitable micro-organism (such as yeast), such as to facilitate screening. Suitable methods, techniques and host organisms for displaying and screening (a set, collection or library of) nucleotide sequences encoding amino acid sequences will be clear to the person skilled in the art, for example on the basis of the further disclosure herein. Reference is also made to WO 03/054016 and to the review by Hoogenboom in Nature Biotechnology, 23, 9, 1105-1116 (2005).

As will be clear to the skilled person, the screening step of the methods described herein can also be performed as a selection step. Accordingly the term "screening" as used in the present description can comprise selection, screening or any suitable combination of selection and/or screening techniques. Also, when a set, collection or library of sequences is used, it may contain any suitable number of sequences, such as 1, 2, 3 or about 5, 10, 50, 100, 500, 1000, 5000, $10^4$, $10^5$, $10^6$, $10^7$, $10^8$ or more sequences.

Also, one or more or all of the sequences in the above set, collection or library of amino acid sequences may be obtained or defined by rational, or semi-empirical approaches such as computer modelling techniques or biostatics or datamining techniques.

Furthermore, such a set, collection or library can comprise one, two or more sequences that are variants from one another (e.g. with designed point mutations or with randomized positions), comprise multiple sequences derived from a diverse set of naturally diversified sequences (e.g. an immune library)), or any other source of diverse sequences (as described for example in Hoogenboom et al, Nat Biotechnol 23:1105, 2005 and Binz et al, Nat Biotechnol 2005, 23:1247). Such set, collection or library of sequences can be displayed on the surface of a phage particle, a ribosome, a bacterium, a yeast cell, a mammalian cell, and linked to the nucleotide sequence encoding the amino acid sequence within these carriers. This makes such set, collection or library amenable to selection procedures to isolate the desired amino acid sequences of the invention. More generally, when a sequence is displayed on a suitable host or host cell, it is also possible (and customary) to first isolate from said host or host cell a nucleotide sequence that encodes the desired sequence, and then to obtain the desired sequence by suitably expressing said nucleotide sequence in a suitable host organism. Again, this can be performed in any suitable manner known per se, as will be clear to the skilled person.

Yet another technique for obtaining $V_{HH}$ sequences or NANOBODY® ($V_{HH}$) sequences directed against GPCRs involves suitably immunizing a transgenic mammal that is capable of expressing heavy chain antibodies (i.e. so as to raise an immune response and/or heavy chain antibodies directed against GPCRs), obtaining a suitable biological sample from said transgenic mammal that contains (nucleic acid sequences encoding) said $V_{HH}$ sequences or NANOBODY® ($V_{HH}$) sequences (such as a blood sample, serum sample or sample of B-cells), and then generating $V_{HH}$ sequences directed against GPCRs, starting from said sample, using any suitable technique known per se (such as any of the methods described herein or a hybridoma technique). For example, for this purpose, the heavy chain antibody-expressing mice and the further methods and techniques described in WO 02/085945, WO 04/049794 and WO 06/008548 and Janssens et al., Proc. Natl. Acad. Sci. USA. 2006 Oct. 10; 103(41):15130-5 can be used. For example, such heavy chain antibody expressing mice can express heavy chain antibodies with any suitable (single) variable domain, such as (single) variable domains from natural sources (e.g. human (single) variable domains, Camelid (single) variable domains or shark (single) variable domains), as well as for example synthetic or semi-synthetic (single) variable domains.

The invention also relates to the $V_{HH}$ sequences or NANOBODY® ($V_{HH}$) sequences that are obtained by the above methods, or alternatively by a method that comprises the one of the above methods and in addition at least the steps of determining the nucleotide sequence or amino acid sequence of said $V_{HH}$ sequence or NANOBODY® ($V_{HH}$) sequence; and of expressing or synthesizing said $V_{HH}$ sequence or NANOBODY® ($V_{HH}$) sequence in a manner known per se, such as by expression in a suitable host cell or host organism or by chemical synthesis.

As mentioned herein, a particularly preferred class of Nanobodies of the invention comprises Nanobodies with an amino acid sequence that corresponds to the amino acid sequence of a naturally occurring $V_{HH}$ domain, but that has been "humanized", i.e. by replacing one or more amino acid residues in the amino acid sequence of said naturally occurring $V_{HH}$ sequence (and in particular in the framework sequences) by one or more of the amino acid residues that occur at the corresponding position(s) in a $V_H$ domain from a conventional 4-chain antibody from a human being (e.g. indicated above). This can be performed in a manner known per se, which will be clear to the skilled person, for example on the basis of the further description herein and the prior art on humanization referred to herein. Again, it should be noted that such humanized Nanobodies of the invention can be obtained in any suitable manner known per se (i.e. as indicated under points (1)-(8) above) and thus are not strictly limited to polypeptides that have been obtained using a polypeptide that comprises a naturally occurring $V_{HH}$ domain as a starting material.

Another particularly preferred class of Nanobodies of the invention comprises Nanobodies with an amino acid sequence that corresponds to the amino acid sequence of a naturally occurring $V_H$ domain, but that has been "camelized", i.e. by replacing one or more amino acid residues in the amino acid sequence of a naturally occurring $V_H$ domain from a conventional 4-chain antibody by one or more of the amino acid residues that occur at the corresponding position(s) in a $V_{HH}$ domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$-$V_L$ interface, and/or at the so-called Camelidae hallmark residues, as defined herein (see for example WO 94/04678 and Davies and Riechmann (1994 and 1996), supra). Preferably, the $V_H$ sequence that is used as a starting material or starting point for generating or designing the camelized NANOBODY® ($V_{HH}$) is preferably a $V_H$ sequence from a mammal, more preferably the $V_H$ sequence of a human being, such as a $V_H3$ sequence. However, it should be noted that such camelized Nanobodies of the invention can be obtained in any suitable manner known per se (i.e. as indicated under points (1)-(8) above) and thus are not strictly limited to polypeptides that have been obtained using a polypeptide that comprises a naturally occurring $V_H$ domain as a starting material.

For example, again as further described herein, both "humanization" and "camelization" can be performed by providing a nucleotide sequence that encodes a naturally occurring $V_{HH}$ domain or $V_H$ domain, respectively, and then changing, in a manner known per se, one or more codons in said nucleotide sequence in such a way that the new nucleotide sequence encodes a "humanized" or "camelized" NANOBODY® ($V_{HH}$) of the invention, respectively. This nucleic acid can then be expressed in a manner known per se, so as to provide the desired NANOBODY® ($V_{HH}$) of the invention. Alternatively, based on the amino acid sequence of a naturally occurring $V_{HH}$ domain or $V_H$ domain, respectively, the amino acid sequence of the desired humanized or camelized NANOBODY® ($V_{HH}$) of the invention, respectively, can be designed and then synthesized de novo using techniques for peptide synthesis known per se. Also, based on the amino acid sequence or nucleotide sequence of a naturally occurring $V_{HH}$ domain or $V_H$ domain, respectively, a nucleotide sequence encoding the desired humanized or camelized NANOBODY® ($V_{HH}$) of the invention, respectively, can be designed and then synthesized de novo using techniques for nucleic acid synthesis known per se, after which the nucleic acid thus obtained can be expressed in a manner known per se, so as to provide the desired NANOBODY® ($V_{HH}$) of the invention.

Other suitable methods and techniques for obtaining the Nanobodies of the invention and/or nucleic acids encoding the same, starting from naturally occurring $V_H$ sequences or preferably $V_{HH}$ sequences, will be clear from the skilled person, and may for example comprise combining one or more parts of one or more naturally occurring $V_H$ sequences (such as one or more FR sequences and/or CDR sequences), one or more parts of one or more naturally occurring $V_{HH}$ sequences (such as one or more FR sequences or CDR sequences), and/or one or more synthetic or semi-synthetic sequences, in a suitable manner, so as to provide a NANOBODY® ($V_{HH}$) of the invention or a nucleotide sequence or nucleic acid encoding the same (which may then be suitably expressed). Nucleotide sequences encoding framework sequences of $V_{HH}$ sequences or Nanobodies will be clear to the skilled person based on the disclosure herein and/or the further prior art cited herein (and/or may alternatively be obtained by PCR starting from the nucleotide sequences obtained using the methods described herein) and may be suitably combined with nucleotide sequences that encode the desired CDR's (for example, by PCR assembly using overlapping primers), so as to provide a nucleic acid encoding a NANOBODY® ($V_{HH}$) of the invention.

As mentioned herein, Nanobodies may in particular be characterized by the presence of one or more "Hallmark residues" (as described herein) in one or more of the framework sequences.

Thus, according to one preferred, but non-limiting aspect of the invention, a NANOBODY® ($V_{HH}$) in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or:
b) an amino acid sequence that is comprised of four framework regions/sequences interrupted by three complementarity determining regions/sequences, in which the amino acid residue at position 45 according to the Kabat numbering is a charged amino acid (as defined herein) or a cysteine residue, and position 44 is preferably an E;
and/or:
c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, in a first preferred, but non-limiting aspect, a NANOBODY® ($V_{HH}$) of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q; and/or in which:
b) the amino acid residue at position 45 according to the Kabat numbering is a charged amino acid or a cysteine and the amino acid residue at position 44 according to the Kabat numbering is preferably E;
and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein, and are preferably as defined according to one of the preferred aspects herein, and are more preferably as defined according to one of the more preferred aspects herein.

In particular, a NANOBODY® ($V_{HH}$) in its broadest sense can be generally defined as a polypeptide comprising:
a) an amino acid sequence that is comprised of four framework regions/sequences interrupted by three complementarity determining regions/sequences, in which the amino acid residue at position 108 according to the Kabat numbering is Q;
and/or:
b) an amino acid sequence that is comprised of four framework regions/sequences interrupted by three complementarity determining regions/sequences, in which the amino acid residue at position 44 according to the Kabat numbering is E and in which the amino acid residue at position 45 according to the Kabat numbering is an R;
and/or:
c) an amino acid sequence that is comprised of four framework regions/sequences interrupted by three complementarity determining regions/sequences, in which the amino acid residue at position 103 according to the Kabat numbering is chosen from the group consisting of P, R and S, and is in particular chosen from the group consisting of R and S.

Thus, according to a preferred, but non-limiting aspect, a NANOBODY® ($V_{HH}$) of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q; and/or in which:
b) the amino acid residue at position 44 according to the Kabat numbering is E and in which the amino acid residue at position 45 according to the Kabat numbering is an R;
and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein, and are preferably as defined according to one of the preferred aspects herein, and are more preferably as defined according to one of the more preferred aspects herein.

In particular, a NANOBODY® ($V_{HH}$) against GPCRs according to the invention may have the structure:
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which
a) the amino acid residue at position 108 according to the Kabat numbering is Q;
and/or in which:
b) the amino acid residue at position 44 according to the Kabat numbering is E and in which the amino acid residue at position 45 according to the Kabat numbering is an R;
and/or in which:
c) the amino acid residue at position 103 according to the Kabat numbering is chosen from the group consisting of P, R and S, and is in particular chosen from the group consisting of R and S;
and in which:
d) CDR1, CDR2 and CDR3 are as defined herein, and are preferably as defined according to one of the preferred aspects herein, and are more preferably as defined according to one of the more preferred aspects herein.

In particular, according to one preferred, but non-limiting aspect of the invention, a NANOBODY® ($V_{HH}$) can generally be defined as a polypeptide comprising an amino acid sequence that is comprised of four framework regions/sequences interrupted by three complementarity determining regions/sequences, in which;

a-1) the amino acid residue at position 44 according to the Kabat numbering is chosen from the group consisting of A, G, E, D, G, Q, R, S, L; and is preferably chosen from the group consisting of G, E or Q; and a-2) the amino acid residue at position 45 according to the Kabat numbering is chosen from the group consisting of L, R or C; and is preferably chosen from the group consisting of L or R; and a-3) the amino acid residue at position 103 according to the Kabat numbering is chosen from the group consisting of W, R or S; and is preferably W or R, and is most preferably W;

a-4) the amino acid residue at position 108 according to the Kabat numbering is Q;

or in which:

b-1) the amino acid residue at position 44 according to the Kabat numbering is chosen from the group consisting of E and Q; and b-2) the amino acid residue at position 45 according to the Kabat numbering is R; and b-3) the amino acid residue at position 103 according to the Kabat numbering is chosen from the group consisting of W, R and S; and is preferably W;

b-4) the amino acid residue at position 108 according to the Kabat numbering is chosen from the group consisting of Q and L; and is preferably Q;

or in which:

c-1) the amino acid residue at position 44 according to the Kabat numbering is chosen from the group consisting of A, G, E, D, Q, R, S and L; and is preferably chosen from the group consisting of G, E and Q; and c-2) the amino acid residue at position 45 according to the Kabat numbering is chosen from the group consisting of L, R and C; and is preferably chosen from the group consisting of L and R; and c-3) the amino acid residue at position 103 according to the Kabat numbering is chosen from the group consisting of P, R and S; and is in particular chosen from the group consisting of R and S; and c-4) the amino acid residue at position 108 according to the Kabat numbering is chosen from the group consisting of Q and L; is preferably Q;

and in which d) CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a NANOBODY® ($V_{HH}$) of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

a-1) the amino acid residue at position 44 according to the Kabat numbering is chosen from the group consisting of A, G, E, D, G, Q, R, S, L; and is preferably chosen from the group consisting of G, E or Q;

and in which:

a-2) the amino acid residue at position 45 according to the Kabat numbering is chosen from the group consisting of L, R or C; and is preferably chosen from the group consisting of L or R;

and in which:

a-3) the amino acid residue at position 103 according to the Kabat numbering is chosen from the group consisting of W, R or S; and is preferably W or R, and is most preferably W;

and in which a-4) the amino acid residue at position 108 according to the Kabat numbering is Q;

and in which:

d) CDR1, CDR2 and CDR3 are as defined herein, and are preferably as defined according to one of the preferred aspects herein, and are more preferably as defined according to one of the more preferred aspects herein.

In another preferred, but non-limiting aspect, a NANOBODY® ($V_{HH}$) of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

b-1) the amino acid residue at position 44 according to the Kabat numbering is chosen from the group consisting of E and Q;

and in which:

b-2) the amino acid residue at position 45 according to the Kabat numbering is R;

and in which:

b-3) the amino acid residue at position 103 according to the Kabat numbering is chosen from the group consisting of W, R and S; and is preferably W;

and in which:

b-4) the amino acid residue at position 108 according to the Kabat numbering is chosen from the group consisting of Q and L; and is preferably Q;

and in which:

d) CDR1, CDR2 and CDR3 are as defined herein, and are preferably as defined according to one of the preferred aspects herein, and are more preferably as defined according to one of the more preferred aspects herein.

In another preferred, but non-limiting aspect, a NANOBODY® ($V_{HH}$) of the invention may have the structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

c-1) the amino acid residue at position 44 according to the Kabat numbering is chosen from the group consisting of A, G, E, D, Q, R, S and L; and is preferably chosen from the group consisting of G, E and Q;

and in which:

c-2) the amino acid residue at position 45 according to the Kabat numbering is chosen from the group consisting of L, R and C; and is preferably chosen from the group consisting of L and R;
and in which:
c-3) the amino acid residue at position 103 according to the Kabat numbering is chosen from the group consisting of P, R and S; and is in particular chosen from the group consisting of R and S;
and in which:
c-4) the amino acid residue at position 108 according to the Kabat numbering is chosen from the group consisting of Q and L; is preferably Q;
and in which:
d) CDR1, CDR2 and CDR3 are as defined herein, and are preferably as defined according to one of the preferred aspects herein, and are more preferably as defined according to one of the more preferred aspects herein.

Two particularly preferred, but non-limiting groups of the Nanobodies of the invention are those according to a) above; according to (a-1) to (a-4) above; according to b) above; according to (b-1) to (b-4) above; according to (c) above; and/or according to (c-1) to (c-4) above, in which either:
i) the amino acid residues at positions 44-47 according to the Kabat numbering form the sequence GLEW (or a GLEW-like sequence as described herein) and the amino acid residue at position 108 is Q;
or in which:
ii) the amino acid residues at positions 43-46 according to the Kabat numbering form the sequence KERE or KQRE (or a KERE-like sequence as described) and the amino acid residue at position 108 is Q or L, and is preferably Q.

Thus, in another preferred, but non-limiting aspect, a NANOBODY® ($V_{HH}$) of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which:
i) the amino acid residues at positions 44-47 according to the Kabat numbering form the sequence GLEW (or a GLEW-like sequence as defined herein) and the amino acid residue at position 108 is Q;
and in which:
ii) CDR1, CDR2 and CDR3 are as defined herein, and are preferably as defined according to one of the preferred aspects herein, and are more preferably as defined according to one of the more preferred aspects herein.

In another preferred, but non-limiting aspect, a NANOBODY® ($V_{HH}$) of the invention may have the structure
FR1-CDR1-FR2-CDR2-FR3-CDR3-FR4
in which FR1 to FR4 refer to framework regions 1 to 4, respectively, and in which CDR1 to CDR3 refer to the complementarity determining regions 1 to 3, respectively, and in which:
i) the amino acid residues at positions 43-46 according to the Kabat numbering form the sequence KERE or KQRE (or a KERE-like sequence) and the amino acid residue at position 108 is Q or L, and is preferably Q;
and in which:
ii) CDR1, CDR2 and CDR3 are as defined herein, and are preferably as defined according to one of the preferred aspects herein, and are more preferably as defined according to one of the more preferred aspects herein.

In the Nanobodies of the invention in which the amino acid residues at positions 43-46 according to the Kabat numbering form the sequence KERE or KQRE, the amino acid residue at position 37 is most preferably F. In the Nanobodies of the invention in which the amino acid residues at positions 44-47 according to the Kabat numbering form the sequence GLEW, the amino acid residue at position 37 is chosen from the group consisting of Y, H, I, L, V or F, and is most preferably V.

Thus, without being limited hereto in any way, on the basis of the amino acid residues present on the positions mentioned above, the Nanobodies of the invention can generally be classified on the basis of the following three groups:
i) The "GLEW-group": Nanobodies with the amino acid sequence GLEW at positions 44-47 according to the Kabat numbering and Q at position 108 according to the Kabat numbering. As further described herein, Nanobodies within this group usually have a V at position 37, and can have a W, P, R or S at position 103, and preferably have a W at position 103. The GLEW group also comprises some GLEW-like sequences such as those mentioned in Table A-3 below More generally, and without limitation, Nanobodies belonging to the GLEW-group can be defined as Nanobodies with a G at position 44 and/or with a W at position 47, in which position 46 is usually E and in which preferably position 45 is not a charged amino acid residue and not cysteine;
ii) The "KERE-group": Nanobodies with the amino acid sequence KERE or KQRE (or another KERE-like sequence) at positions 43-46 according to the Kabat numbering and Q or L at position 108 according to the Kabat numbering. As further described herein, Nanobodies within this group usually have a F at position 37, an L or F at position 47; and can have a W, P, R or S at position 103, and preferably have a W at position 103. More generally, and without limitation, Nanobodies belonging to the KERE-group can be defined as Nanobodies with a K, Q or R at position 44 (usually K) in which position 45 is a charged amino acid residue or cysteine, and position 47 is as further defined herein;
iii) The "103 P, R, S-group": Nanobodies with a P, R or S at position 103. These Nanobodies can have either the amino acid sequence GLEW at positions 44-47 according to the Kabat numbering or the amino acid sequence KERE or KQRE at positions 43-46 according to the Kabat numbering, the latter most preferably in combination with an F at position 37 and an L or an F at position 47 (as defined for the KERE-group); and can have Q or L at position 108 according to the Kabat numbering, and preferably have Q.

Also, where appropriate, Nanobodies may belong to (i.e. have characteristics of) two or more of these classes. For example, one specifically preferred group of Nanobodies has GLEW or a GLEW-like sequence at positions 44-47; P, R or S (and in particular R) at position 103; and Q at position 108 (which may be humanized to L).

More generally, it should be noted that the definitions referred to above describe and apply to Nanobodies in the form of a native (i.e. non-humanized) $V_{HH}$ sequence, and that humanized variants of these Nanobodies may contain other amino acid residues than those indicated above (i.e. one or more humanizing substitutions as defined herein). For example, and without limitation, in some humanized Nanobodies of the GLEW-group or the 103 P, R, S-group, Q at position 108 may be humanized to 108L. As already mentioned herein, other humanizing substitutions (and suitable combinations thereof) will become clear to the skilled person based on the disclosure herein. In addition, or alternatively, other potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) a NANOBODY® ($V_{HH}$) may be partially humanized or fully humanized.

Thus, in another preferred, but non-limiting aspect, a NANOBODY® ($V_{HH}$) of the invention may be a NANOBODY® ($V_{HH}$) belonging to the GLEW-group (as defined herein), and in which CDR1, CDR2 and CDR3 are as defined herein, and are preferably as defined according to one of the preferred aspects herein, and are more preferably as defined according to one of the more preferred aspects herein.

In another preferred, but non-limiting aspect, a NANOBODY® ($V_{HH}$) of the invention may be a NANOBODY® ($V_{HH}$) belonging to the KERE-group (as defined herein), and CDR1, CDR2 and CDR3 are as defined herein, and are preferably as defined according to one of the preferred aspects herein, and are more preferably as defined according to one of the more preferred aspects herein.

Thus, in another preferred, but non-limiting aspect, a NANOBODY® ($V_{HH}$) of the invention may be a NANOBODY® ($V_{HH}$) belonging to the 103 P, R, S-group (as defined herein), and in which CDR1, CDR2 and CDR3 are as defined herein, and are preferably as defined according to one of the preferred aspects herein, and are more preferably as defined according to one of the more preferred aspects herein.

Also, more generally and in addition to the 108Q, 43E/44R and 103 P,R,S residues mentioned above, the Nanobodies of the invention can contain, at one or more positions that in a conventional $V_H$ domain would form (part of) the $V_H/V_L$ interface, one or more amino acid residues that are more highly charged than the amino acid residues that naturally occur at the same position(s) in the corresponding naturally occurring $V_H$ sequence, and in particular one or more charged amino acid residues (as mentioned in Table A-2). Such substitutions include, but are not limited to, the GLEW-like sequences mentioned in Table A-3 below; as well as the substitutions that are described in the International Application WO 00/29004 for so-called "microbodies", e.g. so as to obtain a NANOBODY® ($V_{HH}$) with Q at position 108 in combination with KLEW at positions 44-47. Other possible substitutions at these positions will be clear to the skilled person based upon the disclosure herein.

In one aspect of the Nanobodies of the invention, the amino acid residue at position 83 is chosen from the group consisting of L, M, S, V and W; and is preferably L.

Also, in one aspect of the Nanobodies of the invention, the amino acid residue at position 83 is chosen from the group consisting of R, K, N, E, G, I, T and Q; and is most preferably either K or E (for Nanobodies corresponding to naturally occurring $V_{HH}$ domains) or R (for "humanized" Nanobodies, as described herein). The amino acid residue at position 84 is chosen from the group consisting of P, A, R, S, D T, and V in one aspect, and is most preferably P (for Nanobodies corresponding to naturally occurring $V_{HH}$ domains) or R (for "humanized" Nanobodies, as described herein).

Furthermore, in one aspect of the Nanobodies of the invention, the amino acid residue at position 104 is chosen from the group consisting of G and D; and is most preferably G.

Collectively, the amino acid residues at positions 11, 37, 44, 45, 47, 83, 84, 103, 104 and 108, which in the Nanobodies are as mentioned above, will also be referred to herein as the "Hallmark Residues". The Hallmark Residues and the amino acid residues at the corresponding positions of the most closely related human $V_H$ domain, $V_H3$, are summarized in Table A-3.

Some especially preferred but non-limiting combinations of these Hallmark Residues as occur in naturally occurring $V_{HH}$ domains are mentioned in Table A-4. For comparison, the corresponding amino acid residues of the human $V_H3$ called DP-47 have been indicated in italics.

TABLE A-3

Hallmark Residues in Nanobodies

| Position | Human $V_H3$ | Hallmark Residues |
|---|---|---|
| 11 | L, V; predominantly L | L, M, S, V, W; preferably L |
| 37 | V, I, F; usually V | $F^{(1)}$, Y, H, I, L or V, preferably $F^{(1)}$ or Y |
| 44[8] | G | $G^{(2)}$, $E^{(3)}$, A, D, Q, R, S, L; preferably $G^{(2)}$, $E^{(3)}$ or Q; most preferably $G^{(2)}$ or $E^{(3)}$. |
| 45[8] | L | $L^{(2)}$, $R^{(3)}$, C, I, L, P, Q, V; preferably $L^{(2)}$ or $R^{(3)}$ |
| 47[8] | W, Y | $W^{(2)}$, $L^{(1)}$ or $F^{(1)}$, A, G, I, M, R, S, V or Y; preferably $W^{(2)}$, $L^{(1)}$, $F^{(1)}$ or R |
| 83 | R or K; usually R | R, $K^{(5)}$, N, $E^{(5)}$, G, I, M, Q or T; preferably K or R; most preferably K |
| 84 | A, T, D; predominantly A | $P^{(5)}$, A, L, R, S, T, D, V; preferably P |
| 103 | W | $W^{(4)}$, $P^{(6)}$, $R^{(6)}$, S; preferably W |
| 104 | G | G or D; preferably G |
| 108 | L, M or T; predominantly L | Q, $L^{(7)}$ or R; preferably Q or $L^{(7)}$ |

Notes:
[1] In particular, but not exclusively, in combination with KERE or KQRE at positions 43-46.
[2] Usually as GLEW at positions 44-47.
[3] Usually as KERE or KQRE at positions 43-46, e.g. as KEREL, KEREF, KQREL, KQREF or KEREG at positions 43-47. Alternatively, also sequences such as TERE (for example TEREL), KECE (for example KECEL or KECER), RERE (for example REREG), QERE (for example QEREG), KGRE (for example KGREG), KDRE (for example KDREV) are possible. Some other possible, but less preferred sequences include for example DECKL and NVCEL.
[4] With both GLEW at positions 44-47 and KERE or KQRE at positions 43-46.
[5] Often as KP or EP at positions 83-84 of naturally occurring $V_{HH}$ domains.
[6] In particular, but not exclusively, in combination with GLEW at positions 44-47.
[7] With the proviso that when positions 44-47 are GLEW, position 108 is always Q in (non-humanized) $V_{HH}$ sequences that also contain a W at 103.
[8] The GLEW group also contains GLEW-like sequences at positions 44-47, such as for example GVEW, EPEW, GLER, DQEW, DLEW, GIEW, ELEW, GPEW, EWLP, GPER, GLER and ELEW.

TABLE A-4

Some preferred but non-limiting combinations of Hallmark Residues in naturally occurring Nanobodies. For humanization of these combinations, reference is made to the specification.

| | 11 | 37 | 44 | 45 | 47 | 83 | 84 | 103 | 104 | 108 |
|---|---|---|---|---|---|---|---|---|---|---|
| DP-47 (human) | M | V | G | L | W | R | A | W | G | L |
| "KERE" group | L | F | E | R | L | K | P | W | G | Q |
| | L | F | E | R | F | E | P | W | G | Q |
| | L | F | E | R | F | K | P | W | G | Q |
| | L | Y | Q | R | L | K | P | W | G | Q |

TABLE A-4-continued

Some preferred but non-limiting combinations of Hallmark Residues in naturally occurring Nanobodies. For humanization of these combinations, reference is made to the specification.

|  | 11 | 37 | 44 | 45 | 47 | 83 | 84 | 103 | 104 | 108 |
|---|---|---|---|---|---|---|---|---|---|---|
|  | L | F | L | R | V | K | P | Q | G | Q |
|  | L | F | Q | R | L | K | P | W | G | Q |
|  | L | F | E | R | F | K | P | W | G | Q |
| "GLEW" group | L | V | G | L | W | K | S | W | G | Q |
|  | M | V | G | L | W | K | P | R | G | Q |

In the Nanobodies, each amino acid residue at any other position than the Hallmark Residues can be any amino acid residue that naturally occurs at the corresponding position (according to the Kabat numbering) of a naturally occurring $V_{HH}$ domain.

Such amino acid residues will be clear to the skilled person. Tables A-5 to A-8 mention some non-limiting residues that can be present at each position (according to the Kabat numbering) of the FR1, FR2, FR3 and FR4 of naturally occurring $V_{HH}$ domains. For each position, the amino acid residue that most frequently occurs at each position of a naturally occurring $V_{HH}$ domain (and which is the most preferred amino acid residue for said position in a NANOBODY® ($V_{HH}$)) is indicated in bold; and other preferred amino acid residues for each position have been underlined (note: the number of amino acid residues that are found at positions 26-30 of naturally occurring $V_{HH}$ domains supports the hypothesis underlying the numbering by Chothia (supra) that the residues at these positions already form part of CDR1.)

In Tables A-5-A-8, some of the non-limiting residues that can be present at each position of a human $V_H3$ domain have also been mentioned. Again, for each position, the amino acid residue that most frequently occurs at each position of a naturally occurring human $V_H3$ domain is indicated in bold; and other preferred amino acid residues have been underlined.

For reference only, Tables A-5-A-8 also contain data on the $V_{HH}$ entropy ("$V_{HH}$ Ent.") and $V_{HH}$ variability ("$V_{HH}$ Var.") at each amino acid position for a representative sample of 1118 $V_{HH}$ sequences (data kindly provided by David Lutje Hulsing and Prof. Theo Verrips of Utrecht University). The values for the $V_{HH}$ entropy and the $V_{HH}$ variability provide a measure for the variability and degree of conservation of amino acid residues between the 1118 $V_{HH}$ sequences analyzed: low values (i.e. <1, such as <0.5) indicate that an amino acid residue is highly conserved between the $V_{HH}$ sequences (i.e. little variability). For example, the G at position 8 and the G at position 9 have values for the $V_{HH}$ entropy of 0.1 and 0 respectively, indicating that these residues are highly conserved and have little variability (and in case of position 9 is G in all 1118 sequences analysed), whereas for residues that form part of the CDR's generally values of 1.5 or more are found (data not shown). Note that (1) the amino acid residues listed in the second column of Tables A-5-A-8 are based on a bigger sample than the 1118 $V_{HH}$ sequences that were analysed for determining the $V_{HH}$ entropy and $V_{HH}$ variability referred to in the last two columns; and (2) the data represented below support the hypothesis that the amino acid residues at positions 93 and 94 already form part of the CDR's (although the invention is not limited to any specific hypothesis or explanation, and as mentioned above, herein the numbering according to Kabat is used). For a general explanation of sequence entropy, sequence variability and the methodology for determining the same, see Oliveira et al., PROTEINS: Structure, Function and Genetics, 52: 544-552 (2003).

TABLE A-5

Non-limiting examples of amino acid residues in FR1 (for the footnotes, see the footnotes to Table A-3)

| Pos. | Amino acid residue(s): Human $V_H3$ | Camelid $V_{HH}$'s | $V_{HH}$ Ent. | $V_{HH}$ Var. |
|---|---|---|---|---|
| 1 | E, Q | Q, A, E | — | — |
| 2 | V | V | 0.2 | 1 |
| 3 | Q | Q, K | 0.3 | 2 |
| 4 | L | L | 0.1 | 1 |
| 5 | V, L | Q, E, L, V | 0.8 | 3 |
| 6 | E | E, D, Q, A | 0.8 | 4 |
| 7 | S, T | S, F | 0.3 | 2 |
| 8 | G, R | G | 0.1 | 1 |
| 9 | G | G | 0 | 1 |
| 10 | G, V | G, D, R | 0.3 | 2 |
| 11 | Hallmark residue: L, M, S, V, W; preferably L | | 0.8 | 2 |
| 12 | V, I | V, A | 0.2 | 2 |
| 13 | Q, K, R | Q, E, K, P, R | 0.4 | 4 |
| 14 | P | A, Q, A, G, P, S, T, V | 1 | 5 |
| 15 | G | G | 0 | 1 |
| 16 | G, R | G, A, E, D | 0.4 | 3 |
| 17 | S | S, F | 0.5 | 2 |
| 18 | L | L, V | 0.1 | 1 |
| 19 | R, K | R, K, L, N, S, T | 0.6 | 4 |
| 20 | L | L, F, I, V | 0.5 | 4 |
| 21 | S | S, A, F, T | 0.2 | 3 |
| 22 | C | C | 0 | 1 |
| 23 | A, T | A, D, E, P, S, T, V | 1.3 | 5 |
| 24 | A | A, I, L, S, T, V | 1 | 6 |
| 25 | S | S, A, F, P, T | 0.5 | 5 |
| 26 | G | G, A, D, E, R, S, T, V | 0.7 | 7 |
| 27 | F | S, F, R, L, P, G, N, | 2.3 | 13 |
| 28 | T | N, T, E, D, S, I, R, A, G, R, F, Y | 1.7 | 11 |
| 29 | F, V | F, L, D, S, I, G, V, A | 1.9 | 11 |
| 30 | S, D, G | N, S, E, G, A, D, M, T | 1.8 | 11 |

TABLE A-6

Non-limiting examples of amino acid residues in FR2 (for the footnotes, see the footnotes to Table A-3)

| Pos. | Amino acid residue(s): Human $V_H3$ | Camelid $V_{HH}$'s | $V_{HH}$ Ent. | $V_{HH}$ Var. |
|---|---|---|---|---|
| 36 | W | W | 0.1 | 1 |
| 37 | Hallmark residue: F[(1)], H, I, L, Y or V, preferably F[(1)] or Y | | 1.1 | 6 |
| 38 | R | R | 0.2 | 1 |
| 39 | Q | Q, H, P, R | 0.3 | 2 |
| 40 | A | A, F, G, L, P, T, V | 0.9 | 7 |
| 41 | P, S, T | P, A, L, S | 0.4 | 3 |
| 42 | G | G, E | 0.2 | 2 |
| 43 | K | K, D, E, N, Q, R, T, V | 0.7 | 6 |
| 44 | Hallmark residue: G[(2)], E[(3)], A, D, Q, R, S, L; preferably G[(2)], E[(3)] or Q; most preferably G[(2)] or E[(3)]. | | 1.3 | 5 |
| 45 | Hallmark residue: L[(2)], R[(3)], C, I, L, P, Q, V; preferably L[(2)] or R[(3)] | | 0.6 | 4 |
| 46 | E, V | E, D, K, Q, V | 0.4 | 2 |
| 47 | Hallmark residue: W[(2)], L[(1)] or F[(1)], A, G, I, M, R, S, V or Y; preferably W[(2)], L[(1)], F[(1)] or R | | 1.9 | 9 |
| 48 | V | V, I, L | 0.4 | 3 |
| 49 | S, A, G | A, S, G, T, V | 0.8 | 3 |

TABLE A-7

Non-limiting examples of amino acid residues in FR3
(for the footnotes, see the footnotes to Table A-3)

| Pos. | Human V$_H$3 | Camelid V$_{HH}$'s | V$_{HH}$ Ent. | V$_{HH}$ Var. |
|---|---|---|---|---|
| 66 | R | R | 0.1 | 1 |
| 67 | F | F, L, V | 0.1 | 1 |
| 68 | T | T, A, N, S | 0.5 | 4 |
| 69 | I | I, L, M, V | 0.4 | 4 |
| 70 | S | S, A, F, T | 0.3 | 4 |
| 71 | R | R, G, H, I, L, K, Q, S, T, W | 1.2 | 8 |
| 72 | D, E | D, E, G, N, V | 0.5 | 4 |
| 73 | N, D, G | N, A, D, F, I, K, L, R, S, T, V, Y | 1.2 | 9 |
| 74 | A, S | A, D, G, N, P, S, T, V | 1 | 7 |
| 75 | K | K, A, E, K, L, N, Q, R | 0.9 | 6 |
| 76 | N, S | N, D, K, R, S, T, Y | 0.9 | 6 |
| 77 | S, T, I | T, A, E, I, M, P, S | 0.8 | 5 |
| 78 | L, A | V, L, A, F, G, I, M | 1.2 | 5 |
| 79 | Y, H | Y, A, D, F, H, N, S, T | 1 | 7 |
| 80 | L | L, F, V | 0.1 | 1 |
| 81 | Q | Q, E, I, L, R, T | 0.6 | 5 |
| 82 | M | M, I, L, V | 0.2 | 2 |
| 82a | N, G | N, D, G, H, S, T | 0.8 | 4 |
| 82b | S | S, N, D, G, R, T | 1 | 6 |
| 82c | L | L, P, V | 0.1 | 2 |
| 83 | Hallmark residue: R, K$^{(5)}$, N, E$^{(5)}$, G, I, M, Q or T; preferably K or R; most preferably K | | 0.9 | 7 |
| 84 | Hallmark residue: P$^{(5)}$, A, D, L, R, S, T, V; preferably P | | 0.7 | 6 |
| 85 | E, G | E, D, G, Q | 0.5 | 3 |
| 86 | D | D | 0 | 1 |
| 87 | T, M | T, A, S | 0.2 | 3 |
| 88 | A | A, G, S | 0.3 | 2 |
| 89 | V, L | V, A, D, I, L, M, N, R, T | 1.4 | 6 |
| 90 | Y | Y, F | 0 | 1 |
| 91 | Y, H | Y, D, F, H, L, S, T, V | 0.6 | 4 |
| 92 | C | C | 0 | 1 |
| 93 | A, K, T | A, N, G, H, K, N, R, S, T, V, Y | 1.4 | 10 |
| 94 | K, R, T | A, V, C, F, G, I, K, L, R, S or T | 1.6 | 9 |

TABLE A-8

Non-limiting examples of amino acid residues in FR4
(for the footnotes, see the footnotes to Table A-3)

| Pos. | Human V$_H$3 | Camelid V$_{HH}$'s | V$_{HH}$ Ent. | V$_{HH}$ Var. |
|---|---|---|---|---|
| 103 | Hallmark residue: W$^{(4)}$, P$^{(6)}$, R$^{(6)}$, S; preferably W | | 0.4 | 2 |
| 104 | Hallmark residue: G or D; preferably G | | 0.1 | 1 |
| 105 | Q, R | Q, E, K, P, R | 0.6 | 4 |
| 106 | G | G | 0.1 | 1 |
| 107 | T | T, A, I | 0.3 | 2 |
| 108 | Hallmark residue: Q, L$^{(7)}$ or R; preferably Q or L$^{(7)}$ | | 0.4 | 3 |
| 109 | V | V | 0.1 | 1 |
| 110 | T | T, I, A | 0.2 | 1 |
| 111 | V | V, A, I | 0.3 | 2 |
| 112 | S | S, F | 0.3 | 1 |
| 113 | S | S, A, L, P, T | 0.4 | 3 |

Thus, in another preferred, but not limiting aspect, a NANOBODY® (V$_{HH}$) of the invention can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) one or more of the amino acid residues at positions 11, 37, 44, 45, 47, 83, 84, 103, 104 and 108 according to the Kabat numbering are chosen from the Hallmark residues mentioned in Table A-3;

and in which:

ii) CDR1, CDR2 and CDR3 are as defined herein, and are preferably as defined according to one of the preferred aspects herein, and are more preferably as defined according to one of the more preferred aspects herein.

The above Nanobodies may for example be V$_{HH}$ sequences or may be humanized Nanobodies. When the above NANOBODY® (V$_{HH}$) sequences are V$_{HH}$ sequences, they may be suitably humanized, as further described herein. When the Nanobodies are partially humanized Nanobodies, they may optionally be further suitably humanized, again as described herein.

In particular, a NANOBODY® (V$_{HH}$) of the invention can be an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) (preferably) one or more of the amino acid residues at positions 11, 37, 44, 45, 47, 83, 84, 103, 104 and 108 according to the Kabat numbering are chosen from the Hallmark residues mentioned in Table A-3 (it being understood that V$_{HH}$ sequences will contain one or more Hallmark residues; and that partially humanized Nanobodies will usually, and preferably, [still] contain one or more Hallmark residues [although it is also within the scope of the invention to provide—where suitable in accordance with the invention—partially humanized Nanobodies in which all Hallmark residues, but not one or more of the other amino acid residues, have been humanized]; and that in fully humanized Nanobodies, where suitable in accordance with the invention, all amino acid residues at the positions of the Hallmark residues will be amino acid residues that occur in a human V$_H$3 sequence. As will be clear to the skilled person based on the disclosure herein that such V$_{HH}$ sequences, such partially humanized Nanobodies with at least one Hallmark residue, such partially humanized Nanobodies without Hallmark residues and such fully humanized Nanobodies all form aspects of this invention);

and in which:

ii) said amino acid sequence has at least 80% amino acid identity with at least one of the amino acid sequences of SEQ ID NO's: 1 to 22, in which for the purposes of determining the degree of amino acid identity, the amino acid residues that form the CDR sequences (indicated with X in the sequences of SEQ ID NO's: 1 to 22) are disregarded;

and in which:

iii) CDR1, CDR2 and CDR3 are as defined herein, and are preferably as defined according to one of the preferred aspects herein, and are more preferably as defined according to one of the more preferred aspects herein.

The above Nanobodies may for example be V$_{HH}$ sequences or may be humanized Nanobodies. When the above NANOBODY® (V$_{HH}$) sequences are V$_{HH}$ sequences, they may be suitably humanized, as further described herein. When the Nanobodies are partially humanized Nanobodies, they may optionally be further suitably humanized, again as described herein.

TABLE A-9

| | | Representative amino acid sequences for Nanobodies of the KERE, GLEW and P, R, S 103 group. |
|---|---|---|
| KERE sequence no. 1 | SEQ ID NO: 1 | EVQLVESGGGLVQPGGSLRLSCAASGIPFSXXXXXXWFRQAPGKQRDSVAXXXXXXRFTISRDNAKNTVYLQMNSLKPEDTAVYRCYFXXXXXXWGQGTQVTVSS |
| KERE sequence no. 2 | SEQ ID NO: 2 | QVKLEESGGGLVQAGGSLRLSCVGSGRTFSXXXXXXWFRLAPGKEREFVAXXXXXXRFTISRDTASNRGYLHMNNLTPEDTAVYYCAAXXXXXXWGQGTQVTVSS |
| KERE sequence no. 3 | SEQ ID NO: 3 | AVQLVDSGGGLVQAGDSLKLSCALTGGAFTXXXXXXWFRQTPGREREFVAXXXXXXRFTISRDNAKNMVYLRMNSLIPEDAAVYSCAAXXXXXXWGQGTLVTVSS |
| KERE sequence no. 4 | SEQ ID NO: 4 | QVQLVESGGGLVEAGGSLRLSCTASESPFRXXXXXXWFRQTSGQEREFVAXXXXXXRFTISRDDAKNTVWLHGSTLKPEDTAVYYCAAXXXXXXWGQGTQVTVSS |
| KERE sequence no. 5 | SEQ ID NO: 5 | AVQLVESGGGLVQGGGSLRLACAASERIFDXXXXXXWYRQGPGNERELVAXXXXXXRFTISMDYTKQTVYLHMNSLRPEDTGLYYCKIXXXXXXWGQGTQVTVSS |
| KERE sequence no. 6 | SEQ ID NO: 6 | DVKFVESGGGLVQAGGSLRLSCVASGFNFDXXXXXXWFRQAPGKEREEVAXXXXXXRFTISSEKDKNSVYLQMNSLKPEDTALYICAGXXXXXXWGRGTQVTVSS |
| KERE sequence no. 7 | SEQ ID NO: 7 | QVRLAESGGGLVQSGGSLRLSCVASGSTYTXXXXXXWYRQYPGKQRALVAXXXXXXRFTIARDSTKDTFCLQMNNLKPEDTAVYYCYAXXXXXXWGQGTQVTVSS |
| KERE sequence no. 8 | SEQ ID NO: 8 | EVQLVESGGGLVQAGGSLRLSCAASGFTSDXXXXXXWFRQAPGKPREGVSXXXXXXRFTISTDNAKNTVHLLMNRVNAEDTALYYCAVXXXXXXWGRGTRVTVSS |
| KERE sequence no. 9 | SEQ ID NO: 9 | QVQLVESGGGLVQPGGSLRLSCQASGDISTXXXXXXWYRQVPGKLREFVAXXXXXXRFTISGDNAKRAIYLQMNNLKPDDTAVYYCNRXXXXXXWGQGTQVTVSP |
| KERE sequence no. 10 | SEQ ID NO: 10 | QVPVVESGGGLVQAGDSLRLFCAVPSFTSTXXXXXXWFRQAPGKEREFVAXXXXXXRFTISRNATKNTLTLRMDSLKPEDTAVYYCAAXXXXXXWGQGTQVTVSS |
| KERE sequence no. 11 | SEQ ID NO: 11 | EVQLVESGGGLVQAGDSLRLFCTVSGGTASXXXXXXWFRQAPGEKREFVAXXXXXXRFTIARENAGNMVYLQMNNLKPDDTALYTCAAXXXXXXWGRGTQVTVSS |
| KERE sequence no. 12 | SEQ ID NO: 12 | AVQLVESGGDSVQPGDSQTLSCAASGRTNSXXXXXXWFRQAPGKERVFLAXXXXXXRFTISRDSAKNMMYLQMNNLKPQDTAVYYCAAXXXXXXWGQGTQVTVSS |
| KERE sequence no. 13 | SEQ ID NO: 13 | AVQLVESGGGLVQAGGSLRLSCVVSGLTSSXXXXXXWFRQTPWQERDFVAXXXXXXRFTISRDNYKDTVLLEMNFLKPEDTAIYYCAAXXXXXXWGQGTQVTVSS |
| KERE sequence no. 14 | SEQ ID NO: 14 | AVQLVESGGGLVQAGASLRLSCATSTRTLDXXXXXXWFRQAPGRDREFVAXXXXXXRFTVSRDSAENTVALQMNSLKPEDTAVYYCAAXXXXXXWGQGTRVTVSS |
| KERE sequence no. 15 | SEQ ID NO: 15 | QVQLVESGGGLVQPGGSLRLSCTVSRLTAHXXXXXXWFRQAPGKEREAVSXXXXXXRFTISRDYAGNTAFLQMDSLKPEDTGVYYCATXXXXXXWGQGTQVTVSS |
| KERE sequence no. 16 | SEQ ID NO: 16 | EVQLVESGGELVQAGGSLKLSCTASGRNFVXXXXXXWFRRAPGKEREFVAXXXXXXRFTVSRDNGKNTAYLRMNSLKPEDTADYYCAVXXXXXXLGSGTQVTVSS |
| GLEW sequence no. 1 | SEQ ID NO: 17 | AVQLVESGGGLVQPGGSLRLSCAASGFTFSXXXXXXWVRQAPGKVLEWVSXXXXXXRFTISRDNAKNTLYLQMNSLKPEDTAVYYCVKXXXXXXGSQGTQVTVSS |
| GLEW sequence no. 2 | SEQ ID NO: 18 | EVQLVESGGGLVQPGGSLRLSCVCVSSGCTXXXXXXWVRQAPGKAEEWVSXXXXXXRFKISRDNAKKTLYLQMNSLGPEDTAMYYCQRXXXXXXRGQGTQVTVSS |
| GLEW sequence no. 3 | SEQ ID NO: 19 | EVQLVESGGGLALPGGSLTLSCVFSGTFSXXXXXXWVRHTPGKAEEWVSXXXXXXRFTISRDNAKNTLYLEMNSLPEDTAMYYCGRXXXXXXRSKGIQVTVSS |
| P, R, S 103 sequence no. 1 | SEQ ID NO: 20 | AVQLVESGGGLVQAGGSLRLSCAASGRTFSXXXXXXWFRQAPGKEREFVAXXXXXXRFTISRDNAKNTVYLQMNSLKPEDTAVYYCAAXXXXXXRGQGTQVTVSS |
| P, R, S 103 sequence no. 2 | SEQ ID NO: 21 | DVQLVESGGDLVQPGGSLRLSCAASGFSFDXXXXXXWLRQTPGKGLEWVGXXXXXXRFTISRDNAKNMLYLHLNNLKSEDTAVYYCRRXXXXXXLGQGTQVTVSS |
| P, R, S 103 sequence no. 3 | SEQ ID NO: 22 | EVQLVESGGGLVQPGGSLRLSCVCVSSGCTXXXXXXWVRQAPGKAEEWVSXXXXXXRFKISRDNAKKTLYLQMNSLGPEDTAMYYCQRXXXXXXRGQGTQVTVSS |

The CDR's are indicated with XXXX

In particular, a NANOBODY® (V$_{HH}$) of the invention of the KERE group can be an amino acid sequence with the (general) structure
FR1-CDR1-FR2-CDR2-FR3-CDR3-FR4
in which:
i) the amino acid residue at position 45 according to the Kabat numbering is a charged amino acid (as defined herein) or a cysteine residue, and position 44 is preferably an E;
and in which:
ii) FR1 is an amino acid sequence that has at least 80% amino acid identity with at least one of the following amino acid sequences:

TABLE A-10

Representative FW1 sequences for Nanobodies of the KERE-group.

| | | |
|---|---|---|
| KERE FW1 sequence no. 1 SEQ ID NO: 23 | QVQRVESGGGLVQAGGSLRLSCAASGRTSS |
| KERE FW1 sequence no. 2 SEQ ID NO: 24 | QVQLVESGGGLVQTGDSLSLSCSASGRTFS |
| KERE FW1 sequence no. 3 SEQ ID NO: 25 | QVKLEESGGGLVQAGDSLRLSCAATGRAFG |
| KERE FW1 sequence no. 4 SEQ ID NO: 26 | AVQLVESGGGLVQPGESLGLSCVASGRDFV |
| KERE FW1 sequence no. 5 SEQ ID NO: 27 | EVQLVESGGGLVQAGGSLRLSCEVLGRTAG |
| KERE FW1 sequence no. 6 SEQ ID NO: 28 | QVQLVESGGGWVQPGGSLRLSCAASETILS |
| KERE FW1 sequence no. 7 SEQ ID NO: 29 | QVQLVESGGGTVQPGGSLNLSCVASGNTFN |
| KERE FW1 sequence no. 8 SEQ ID NO: 30 | EVQLVESGGGLAQPGGSLQLSCSAPGFTLD |
| KERE FW1 sequence no. 9 SEQ ID NO: 31 | AQELEESGGGLVQAGGSLRLSCAASGRTFN | and in which:
iii) FR2 is an amino acid sequence that has at least 80% amino acid identity with at least one of the following amino acid sequences:

TABLE A-11

Representative FW2 sequences for Nanobodies of the KERE-group.

| | |
|---|---|
| KERE FW2 sequence no. 1 SEQ ID NO: 41 | WFRQAPGKEREFVA |
| KERE FW2 sequence no. 2 SEQ ID NO: 42 | WFRQTPGREREFVA |
| KERE FW2 sequence no. 3 SEQ ID NO: 43 | WYRQAPGKQREMVA |
| KERE FW2 sequence no. 4 SEQ ID NO: 44 | WYRQGPGKQRELVA |
| KERE FW2 sequence no. 5 SEQ ID NO: 45 | WIRQAPGKEREGVS |
| KERE FW2 sequence no. 6 SEQ ID NO: 46 | WFREAPGKEREGIS |
| KERE FW2 sequence no. 7 SEQ ID NO: 47 | WYRQAPGKERDLVA |
| KERE FW2 sequence no. 8 SEQ ID NO: 48 | WFRQAPGKQREEVS |
| KERE FW2 sequence no. 9 SEQ ID NO: 49 | WFRQPPGKVREFVG | and in which:
iv) FR3 is an amino acid sequence that has at least 80% amino acid identity with at least one of the following amino acid sequences:

TABLE A-12

Representative FW3 sequences for Nanobodies of the KERE-group.

| | | |
|---|---|---|
| KERE FW3 sequence no. 1 | SEQ ID NO: 50 | RFTISRDNAKNTVYLQMNSLKPEDTAVYRCYF |
| KERE FW3 sequence no. 2 | SEQ ID NO: 51 | RFAISRDNNKNTGYLQMNSLEPEDTAVYYCAA |
| KERE FW3 sequence no. 3 | SEQ ID NO: 52 | RFTVARNNAKNTVNLEMNSLKPEDTAVYYCAA |
| KERE FW3 sequence no. 4 | SEQ ID NO: 53 | RFTISRDIAKNTVDLLMNNLEPEDTAVYYCAA |
| KERE FW3 sequence no. 5 | SEQ ID NO: 54 | RLTISRDNAVDTMYLQMNSLKPEDTAVYYCAA |
| KERE FW3 sequence no. 6 | SEQ ID NO: 55 | RFTISRDNAKNTVYLQMDNVKPEDTAIYYCAA |
| KERE FW3 sequence no. 7 | SEQ ID NO: 56 | RFTISKDSGKNTVYLQMTSLKPEDTAVYYCAT |
| KERE FW3 sequence no. 8 | SEQ ID NO: 57 | RFTISRDSAKNMMYLQMNNLKPQDTAVYYCAA |

TABLE A-12-continued

Representative FW3 sequences for Nanobodies of the KERE-group.

KERE FW3 sequence no. 9  SEQ ID NO: 58  RFTISRENDKSTVYLQLNSLKPEDTAVYYCAA
KERE FW3 sequence no. 10 SEQ ID NO: 59  RFTISRDYAGNTAYLQMNSLKPEDTGVYYCAT and in which:

v) FR4 is an amino acid sequence that has at least 80% amino acid identity with at least one of the following amino acid sequences:

TABLE A-13

Representative FW4 sequences for Nanobodies of the KERE-group.

| KERE FW4 sequence no. 1 | SEQ ID NO: 60 | WGQGTQVTVSS |
| KERE FW4 sequence no. 2 | SEQ ID NO: 61 | WGKGTLVTVSS |
| KERE FW4 sequence no. 3 | SEQ ID NO: 62 | RGQGTRVTVSS |
| KERE FW4 sequence no. 4 | SEQ ID NO: 63 | WGLGTQVTISS | and in which:

vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

Also, the above Nanobodies may for example be $V_{HH}$ sequences or may be humanized Nanobodies. When the above NANOBODY® ($V_{HH}$) sequences are $V_{HH}$ sequences, they may be suitably, as further described herein.

When the Nanobodies are partially humanized Nanobodies, they may optionally be further suitably humanized, again as described herein.

With regard to framework 1, it will be clear to the skilled person that, when an amino acid sequence as outlined above is generated by expression of a nucleotide sequence, the first four amino acid sequences (i.e. amino acid residues 1-4 according to the Kabat numbering) may often be determined by the primer(s) that have been used to generate said nucleic acid. Thus, for determining the degree of amino acid identity, the first four amino acid residues are preferably disregarded.

Also, with regard to framework 1, and although amino acid positions 27 to 30 are according to the Kabat numbering considered to be part of the framework regions (and not the CDR's), it has been found by analysis of a database of more than 1000 $V_{HH}$ sequences that the positions 27 to 30 have a variability (expressed in terms of $V_{HH}$ entropy and $V_{HH}$ variability—see Tables A-5 to A-8) that is much greater than the variability on positions 1 to 26. Because of this, for determining the degree of amino acid identity, the amino acid residues at positions 27 to 30 are preferably also disregarded.

In view of this, a NANOBODY® ($V_{HH}$) of the KERE class may be an amino acid sequence that is comprised of four framework regions/sequences interrupted by three complementarity determining regions/sequences, in which:

i) the amino acid residue at position 45 according to the Kabat numbering is a charged amino acid (as defined herein) or a cysteine residue, and position 44 is preferably an E;

and in which:

ii) FR1 is an amino acid sequence that, on positions 5 to 26 of the Kabat numbering, has at least 80% amino acid identity with at least one of the following amino acid sequences:

TABLE A-14

Representative FW1 sequences (amino acid residues 5 to 26) for Nanobodies of the KERE-group.

| KERE FW1 sequence no. 10 | SEQ ID NO: 32 | VESGGGLVQPGGSLRLSCAASG |
| KERE FW1 sequence no. 11 | SEQ ID NO: 33 | VDSGGGLVQAGDSLKLSCALTG |
| KERE FW1 sequence no. 12 | SEQ ID NO: 34 | VDSGGGLVQAGDSLRLSCAASG |
| KERE FW1 sequence no. 13 | SEQ ID NO: 35 | VDSGGGLVEAGGSLRLSCQVSE |
| KERE FW1 sequence no. 14 | SEQ ID NO: 36 | QDSGGGSVQAGGSLKLSCAASG |
| KERE FW1 sequence no. 15 | SEQ ID NO: 37 | VQSGGRLVQAGDSLRLSCAASE |
| KERE FW1 sequence no. 16 | SEQ ID NO: 38 | VESGGTLVQSGDSLKLSCASST |
| KERE FW1 sequence no. 17 | SEQ ID NO: 39 | MESGGDSVQSGGSLTLSCVASG |
| KERE FW1 sequence no. 18 | SEQ ID NO: 40 | QASGGGLVQAGGSLRLSCSASV | and in which:

iii) FR2, FR3 and FR4 are as mentioned herein for FR2, FR3 and FR4 of Nanobodies of the KERE-class;

and in which:

iv) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above NANOBODY® ($V_{HH}$) sequences are $V_{HH}$ sequences, they may be suitably humanized, as further described herein. When the Nanobodies are partially humanized Nanobodies, they may optionally be further suitably humanized, again as described herein.

A NANOBODY® ($V_{HH}$) of the GLEW class may be an amino acid sequence that is comprised of four framework regions/sequences interrupted by three complementarity determining regions/sequences, in which i) preferably, when the NANOBODY® ($V_{HH}$) of the GLEW-class is a non-humanized NANOBODY® ($V_{HH}$), the amino acid residue in position 108 is Q;

ii) FR1 is an amino acid sequence that has at least 80% amino acid identity with at least one of the following amino acid sequences:

TABLE A-15

| Representative FW1 sequences for Nanobodies of the GLEW-group. |
| --- |
| GLEW FW1 sequence no. 1 SEQ ID NO: 64 QVQLVESGGGLVQPGGSLRLSCAASGFTFS |
| GLEW FW1 sequence no. 2 SEQ ID NO: 65 EVHLVESGGGLVRPGGSLRLSCAAFGFIFK |
| GLEW FW1 sequence no. 3 SEQ ID NO: 66 QVKLEESGGGLAQPGGSLRLSCVASGFTFS |
| GLEW FW1 sequence no. 4 SEQ ID NO: 67 EVQLVESGGGLVQPGGSLRLSCVCVSSGCT |
| GLEW FW1 sequence no. 5 SEQ ID NO: 68 EVQLVESGGGLALPGGSLTLSCVFSGSTFS | and in which:

iii) FR2 is an amino acid sequence that has at least 80% amino acid identity with at least one of the following amino acid sequences:

TABLE A-16

| Representative FW2 sequences for Nanobodies of the GLEW-group. |
| --- |
| GLEW FW2 sequence no. 1 SEQ ID NO: 72 WVRQAPGKVLEWVS |
| GLEW FW2 sequence no. 2 SEQ ID NO: 73 WVRRPPGKGLEWVS |
| GLEW FW2 sequence no. 3 SEQ ID NO: 74 WVRQAPGMGLEWVS |
| GLEW FW2 sequence no. 4 SEQ ID NO: 75 WVRQAPGKEPEWVS |
| GLEW FW2 sequence no. 5 SEQ ID NO: 76 WVRQAPGKDQEWVS |
| GLEW FW2 sequence no. 6 SEQ ID NO: 77 WVRQAPGKAEEWVS |
| GLEW FW2 sequence no. 7 SEQ ID NO: 78 WVRQAPGKGLEWVA |
| GLEW FW2 sequence no. 8 SEQ ID NO: 79 WVRQAPGRATEWVS | and in which:

iv) FR3 is an amino acid sequence that has at least 80% amino acid identity with at least one of the following amino acid sequences:

TABLE A-17

| Representative FW3 sequences for Nanobodies of the GLEW-group. |
| --- |
| GLEW FW3 sequence no. 1 SEQ ID NO: 80 RFTISRDNAKNTLYLQMNSLKPEDTAVYYCVK |
| GLEW FW3 sequence no. 2 SEQ ID NO: 81 RFTISRDNARNTLYLQMDSLIPEDTALYYCAR |
| GLEW FW3 sequence no. 3 SEQ ID NO: 82 RFTSSRDNAKSTLYLQMNDLKPEDTALYYCAR |
| GLEW FW3 sequence no. 4 SEQ ID NO: 83 RFIISRDNAKNTLYLQMNSLGPEDTAMYYCQR |
| GLEW FW3 sequence no. 5 SEQ ID NO: 84 RFTASRDNAKNTLYLQMNSLKSEDTARYYCAR |
| GLEW FW3 sequence no. 6 SEQ ID NO: 85 RFTISRDNAKNTLYLQMDDLQSEDTAMYYCGR | and in which:

v) FR4 is an amino acid sequence that has at least 80% amino acid identity with at least one of the following amino acid sequences:

TABLE A-18

Representative FW4 sequences for Nanobodies of the GLEW-group.

| | | |
|---|---|---|
| GLEW FW4 sequence no. 1 | SEQ ID NO: 86 | GSQGTQVTVSS |
| GLEW FW4 sequence no. 2 | SEQ ID NO: 87 | LRGGTQVTVSS |
| GLEW FW4 sequence no. 3 | SEQ ID NO: 88 | RGQGTLVTVSS |
| GLEW FW4 sequence no. 4 | SEQ ID NO: 89 | RSRGIQVTVSS |
| GLEW FW4 sequence no. 5 | SEQ ID NO: 90 | WGKGTQVTVSS |
| GLEW FW4 sequence no. 6 | SEQ ID NO: 91 | WGQGTQVTVSS | and in which:

vi) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a NANOBODY® ($V_{HH}$) of the GLEW class may be an amino acid sequence that is comprised of four framework regions/sequences interrupted by three complementarity determining regions/sequences, in which:

i) preferably, when the NANOBODY® ($V_{HH}$) of the GLEW-class is a non-humanized NANOBODY® ($V_{HH}$), the amino acid residue in position 108 is Q;

and in which:

ii) FR1 is an amino acid sequence that, on positions 5 to 26 of the Kabat numbering, has at least 80% amino acid identity with at least one of the following amino acid sequences:

TABLE A-19

Representative FW1 sequences (amino acid residues 5 to 26) for Nanobodies of the GLEW-group.

| | | |
|---|---|---|
| GLEW FW1 sequence no. 6 | SEQ ID NO: 69 | VESGGGLVQPGGSLRLSCAASG |
| GLEW FW1 sequence no. 7 | SEQ ID NO: 70 | EESGGGLAQPGGSLRLSCVASG |
| GLEW FW1 sequence no. 8 | SEQ ID NO: 71 | VESGGGLALPGGSLTLSCVFSG | and in which:

iii) FR2, FR3 and FR4 are as mentioned herein for FR2, FR3 and FR4 of Nanobodies of the GLEW-class;

and in which:

iv) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above NANOBODY® ($V_{HH}$) sequences are $V_{HH}$ sequences, they may be suitably humanized, as further described herein. When the Nanobodies are partially humanized Nanobodies, they may optionally be further suitably humanized, again as described herein. In the above Nanobodies, one or more of the further Hallmark residues are preferably as described herein (for example, when they are $V_{HH}$ sequences or partially humanized Nanobodies).

A NANOBODY® ($V_{HH}$) of the P, R, S 103 class may be an amino acid sequence that is comprised of four framework regions/sequences interrupted by three complementarity determining regions/sequences, in which i) the amino acid residue at position 103 according to the Kabat numbering is different from W;

and in which:

ii) preferably the amino acid residue at position 103 according to the Kabat numbering is P, R or S, and more preferably R;

and in which:

iii) FR1 is an amino acid sequence that has at least 80% amino acid identity with at least one of the following amino acid sequences:

TABLE A-20

| Representative FW1 sequences for Nanobodies of the P, R, S 103-group. | | |
|---|---|---|
| P, R, S 103 FW1 sequence no. 1 | SEQ ID NO: 92 | AVQLVESGGGLVQAGGSLRLSCAASGRTFS |
| P, R, S 103 FW1 sequence no. 2 | SEQ ID NO: 93 | QVQLQESGGGMVQPGGSLRLSCAASGFDFG |
| P, R, S 103 FW1 sequence no. 3 | SEQ ID NO: 94 | EVHLVESGGGLVRPGGSLRLSCAAFGFIFK |
| P, R, S 103 FW1 sequence no. 4 | SEQ ID NO: 95 | QVQLAESGGGLVQPGGSLKLSCAASRTIVS |
| P, R, S 103 FW1 sequence no. 5 | SEQ ID NO: 96 | QEHLVESGGGLVDIGGSLRLSCAASERIFS |
| P, R, S 103 FW1 sequence no. 6 | SEQ ID NO: 97 | QVKLEESGGGLAQPGGSLRLSCVASGFTFS |
| P, R, S 103 FW1 sequence no. 7 | SEQ ID NO: 98 | EVQLVESGGGLVQPGGSLRLSCVCVSSGCT |
| P, R, S 103 FW1 sequence no. 8 | SEQ ID NO: 99 | EVQLVESGGGLALPGGSLTLSCVFSGSTFS | and in which iv) FR2 is an amino acid sequence that has at least 80% amino acid identity with at least one of the following amino acid sequences:

TABLE A-21

| Representative FW2 sequences for Nanobodies of the P, R, S 103-group. | | |
|---|---|---|
| P, R, S 103 FW2 sequence no. 1 | SEQ ID NO: 102 | WFRQAPGKEREFVA |
| P, R, S 103 FW2 sequence no. 2 | SEQ ID NO: 103 | WVRQAPGKVLEWVS |
| P, R, S 103 FW2 sequence no. 3 | SEQ ID NO: 104 | WVRRPPGKGLEWVS |
| P, R, S 103 FW2 sequence no. 4 | SEQ ID NO: 105 | WIRQAPGKEREGVS |
| P, R, S 103 FW2 sequence no. 5 | SEQ ID NO: 106 | WVRQYPGKEPEWVS |
| P, R, S 103 FW2 sequence no. 6 | SEQ ID NO: 107 | WFRQPPGKEHEFVA |
| P, R, S 103 FW2 sequence no. 7 | SEQ ID NO: 108 | WYRQAPGKRTELVA |
| P, R, S 103 FW2 sequence no. 8 | SEQ ID NO: 109 | WLRQAPGQGLEWVS |
| P, R, S 103 FW2 sequence no. 9 | SEQ ID NO: 110 | WLRQTPGKGLEWVG |
| P, R, S 103 FW2 sequence no. 10 | SEQ ID NO: 111 | WVRQAPGKAEEFVS | and in which:

v) FR3 is an amino acid sequence that has at least 80% amino acid identity with at least one of the following amino acid sequences:

TABLE A-22

| Representative FW3 sequences for Nanobodies of the P, R, S 103-group. | | |
|---|---|---|
| P, R, S 103 FW3 sequence no. 1 | SEQ ID NO: 112 | RFTISRDNAKNTVYLQMNSLKPEDTAVYYCAA |
| P, R, S 103 FW3 sequence no. 2 | SEQ ID NO: 113 | RFTISRDNARNTLYLQMDSLIPEDTALYYCAR |
| P, R, S 103 FW3 sequence no. 3 | SEQ ID NO: 114 | RFTISRDNAKNEMYLQMNNLKTEDTGVYWCGA |
| P, R, S 103 FW3 sequence no. 4 | SEQ ID NO: 115 | RFTISSDSNRNMIYLQMNNLKPEDTAVYYCAA |
| P, R, S 103 FW3 sequence no. 5 | SEQ ID NO: 116 | RFTISRDNAKNMLYLHLNNLKSEDTAVYYCRR |

TABLE A-22-continued

Representative FW3 sequences for Nanobodies of the P, R, S 103-group.

```
P, R, S 103 FW3 sequence no. 6    SEQ ID NO: 117    RFTISRDNAKKTVYLRLNSLNPEDTAVYSCNL P, R, S 103 FW3 sequence no. 7    SEQ ID NO: 118    RFKISRDNAKKTLYLQMNSLGPEDTAMYYCQR P, R, S 103 FW3 sequence no. 8    SEQ ID NO: 119    RFTVSRDNGKNTAYLRMNSLKPEDTADYYCAV
``` and in which:

vi) FR4 is an amino acid sequence that has at least 80% amino acid identity with at least one of the following amino acid sequences:

TABLE A-23

Representative FW4 sequences for Nanobodies of the P, R, S 103-group.

```
P, R, S 103 FW4 sequence no. 1    SEQ ID NO: 120    RGQGTQVTVSS

P, R, S 103 FW4 sequence no. 2    SEQ ID NO: 121    LRGGTQVTVSS

P, R, S 103 FW4 sequence no. 3    SEQ ID NO: 122    GNKGTLVTVSS

P, R, S 103 FW4 sequence no. 4    SEQ ID NO: 123    SSPGTQVTVSS

P, R, S 103 FW4 sequence no. 5    SEQ ID NO: 124    SSQGTLVTVSS

P, R, S 103 FW4 sequence no. 6    SEQ ID NO: 125    RSRGIQVTVSS
``` and in which:

vii) CDR1, CDR2 and CDR3 are as defined herein, and are preferably as defined according to one of the preferred aspects herein, and are more preferably as defined according to one of the more preferred aspects herein.

In the above Nanobodies, one or more of the further Hallmark residues are preferably as described herein (for example, when they are $V_{HH}$ sequences or partially humanized Nanobodies).

With regard to framework 1, it will again be clear to the skilled person that, for determining the degree of amino acid identity, the amino acid residues on positions 1 to 4 and 27 to 30 are preferably disregarded.

In view of this, a NANOBODY® ($V_{HH}$) of the P,R,S 103 class may be an amino acid sequence that is comprised of four framework regions/sequences interrupted by three complementarity determining regions/sequences, in which:

i) the amino acid residue at position 103 according to the Kabat numbering is different from W;

and in which:

ii) preferably the amino acid residue at position 103 according to the Kabat numbering is P, R or S, and more preferably R;

and in which:

iii) FR1 is an amino acid sequence that, on positions 5 to 26 of the Kabat numbering, has at least 80% amino acid identity with at least one of the following amino acid sequences:

and in which:

iv) FR2, FR3 and FR4 are as mentioned herein for FR2, FR3 and FR4 of Nanobodies of the P, R, S 103 class;

and in which:

v) CDR1, CDR2 and CDR3 are as defined herein, and are preferably as defined according to one of the preferred aspects herein, and are more preferably as defined according to one of the more preferred aspects herein.

The above Nanobodies may for example be $V_{HH}$ sequences or may be humanized Nanobodies. When the above NANOBODY® ($V_{HH}$) sequences are $V_{HH}$ sequences, they may be suitably humanized, as further described herein. When the Nanobodies are partially humanized Nanobodies, they may optionally be further suitably humanized, again as described herein.

In the above Nanobodies, one or more of the further Hallmark residues are preferably as described herein (for example, when they are $V_{HH}$ sequences or partially humanized Nanobodies).

In another preferred, but non-limiting aspect, the invention relates to a NANOBODY® ($V_{HH}$) as described above, in which the CDR sequences have at least 70% amino acid identity, preferably at least 80% amino acid identity, more preferably at least 90% amino acid identity, such as 95% amino acid identity or more or even essentially 100% amino acid identity with the CDR sequences of at least one of the amino acid sequences of SEQ ID NO's: 526 to 527, 538 to 541, 413 to 453 and 517 to 525. This degree of amino acid identity can for example be determined by determining the degree of amino acid identity (in a manner described herein) between said NANOBODY® ($V_{HH}$) and one or more of the sequences of SEQ ID NO's: 526 to 527, 538 to 541, 413 to

TABLE A-24

Representative FW1 sequences (amino acid residues 5 to 26) for Nanobodies of the P, R, S 103-group.

```
P, R, S 103 FW1 sequence no. 9     SEQ ID NO: 100    VESGGGLVQAGGSLRLSCAASG

P, R, S 103 FW1 sequence no. 10    SEQ ID NO: 101    AESGGGLVQPGGSLKLSCAASR
```

453 and 517 to 525, in which the amino acid residues that form the framework regions are disregarded. Such Nanobodies can be as further described herein.

As already mentioned herein, another preferred but non-limiting aspect of the invention relates to a NANOBODY® ($V_{HH}$) with an amino acid sequence that is chosen from the group consisting of SEQ ID NO's: 526 to 527, 538 to 541, 413 to 453 and 517 to 525 or from the group consisting of from amino acid sequences that have more than 80%, preferably more than 90%, more preferably more than 95%, such as 99% or more sequence identity (as defined herein) with at least one of the amino acid sequences of SEQ ID NO's: 526 to 527, 538 to 541, 413 to 453 and 517 to 525.

Also, in the above Nanobodies:
i) any amino acid substitution (when it is not a humanizing substitution as defined herein) is preferably, and compared to the corresponding amino acid sequence of SEQ ID NO's: 526 to 527, 538 to 541, 413 to 453 and 517 to 525, a conservative amino acid substitution, (as defined herein);
and/or:
ii) its amino acid sequence preferably contains either only amino acid substitutions, or otherwise preferably no more than 5, preferably no more than 3, and more preferably only 1 or 2 amino acid deletions or insertions, compared to the corresponding amino acid sequence of SEQ ID NO's: 526 to 527, 538 to 541, 413 to 453 and 517 to 525;
and/or
iii) the CDR's may be CDR's that are derived by means of affinity maturation, for example starting from the CDR's of to the corresponding amino acid sequence of SEQ ID NO's: 526 to 527, 538 to 541, 413 to 453 and 517 to 525.

Preferably, the CDR sequences and FR sequences in the Nanobodies of the invention are such that the Nanobodies of the invention (and polypeptides of the invention comprising the same):
bind to GPCRs with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e. with an association constant ($K_A$) of $10^5$ to $10^{12}$ liter/moles or more, and preferably $10^7$ to $10^{12}$ liter/moles or more and more preferably $10^8$ to $10^{12}$ liter/moles);
and/or such that they:
bind to GPCRs with a $k_{on}$-rate of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ such as between $10^5$ $M^{-1}$ $s^{-1}$ and $10^7$ $M^{-1}$ $s^{-1}$;
and/or such that they:
bind to GPCRs with a $k_{off}$ rate between 1 $s^{-1}$ ($t_{1/2}$=0.69 s) and $10^{-6}$ $s^{-1}$ (providing a near irreversible complex with a $t_{1/2}$ of multiple days), preferably between $10^{-2}$ $s^{-1}$ and $10^{-6}$ $s^{-1}$, more preferably between $10^{-3}$ $s^{-1}$ and $10^{-6}$ $s^{-1}$, such as between $10^4$ $s^{-1}$ and $10^{-6}$ $s^{-1}$.

Preferably, CDR sequences and FR sequences present in the Nanobodies of the invention are such that the Nanobodies of the invention will bind to GPCRs with an affinity less than 500 nM, preferably less than 200 nM, more preferably less than 10 nM, such as less than 500 pM.

According to one non-limiting aspect of the invention, a NANOBODY® ($V_{HH}$) may be as defined herein, but with the proviso that it has at least "one amino acid difference" (as defined herein) in at least one of the framework regions compared to the corresponding framework region of a naturally occurring human $V_H$ domain, and in particular compared to the corresponding framework region of DP-47. More specifically, according to one non-limiting aspect of the invention, a NANOBODY® ($V_{HH}$) may be as defined herein, but with the proviso that it has at least "one amino acid difference" (as defined herein) at at least one of the Hallmark residues (including those at positions 108, 103 and/or 45) compared to the corresponding framework region of a naturally occurring human $V_H$ domain, and in particular compared to the corresponding framework region of DP-47. Usually, a NANOBODY® ($V_{HH}$) will have at least one such amino acid difference with a naturally occurring $V_H$ domain in at least one of FR2 and/or FR4, and in particular at at least one of the Hallmark residues in FR2 and/or FR4 (again, including those at positions 108, 103 and/or 45).

Also, a humanized NANOBODY® ($V_{HH}$) of the invention may be as defined herein, but with the proviso that it has at least "one amino acid difference" (as defined herein) in at least one of the framework regions compared to the corresponding framework region of a naturally occurring $V_{HH}$ domain. More specifically, according to one non-limiting aspect of the invention, a humanized NANOBODY® ($V_{HH}$) may be as defined herein, but with the proviso that it has at least "one amino acid difference" (as defined herein) at at least one of the Hallmark residues (including those at positions 108, 103 and/or 45) compared to the corresponding framework region of a naturally occurring $V_{HH}$ domain. Usually, a humanized NANOBODY® ($V_{HH}$) will have at least one such amino acid difference with a naturally occurring $V_{HH}$ domain in at least one of FR2 and/or FR4, and in particular at at least one of the Hallmark residues in FR2 and/or FR4 (again, including those at positions 108, 103 and/or 45).

As will be clear from the disclosure herein, it is also within the scope of the invention to use natural or synthetic analogs, mutants, variants, alleles, homologs and orthologs (herein collectively referred to as "analogs") of the Nanobodies of the invention as defined herein, and in particular analogs of the Nanobodies of SEQ ID NO's 526 to 527, 538 to 541, 413 to 453 and 517 to 525. Thus, according to one aspect of the invention, the term "NANOBODY® ($V_{HH}$) of the invention" in its broadest sense also covers such analogs.

Generally, in such analogs, one or more amino acid residues may have been replaced, deleted and/or added, compared to the Nanobodies of the invention as defined herein. Such substitutions, insertions or deletions may be made in one or more of the framework regions and/or in one or more of the CDR's. When such substitutions, insertions or deletions are made in one or more of the framework regions, they may be made at one or more of the Hallmark residues and/or at one or more of the other positions in the framework residues, although substitutions, insertions or deletions at the Hallmark residues are generally less preferred (unless these are suitable humanizing substitutions as described herein).

By means of non-limiting examples, a substitution may for example be a conservative substitution (as described herein) and/or an amino acid residue may be replaced by another amino acid residue that naturally occurs at the same position in another $V_{HH}$ domain (see Tables A-5 to A-8 for some non-limiting examples of such substitutions), although the invention is generally not limited thereto. Thus, any one or more substitutions, deletions or insertions, or any combination thereof, that either improve the properties of the NANOBODY® ($V_{HH}$) of the invention or that at least do not detract too much from the desired properties or from the balance or combination of desired properties of the NANOBODY® ($V_{HH}$) of the invention (i.e. to the extent that the NANOBODY® ($V_{HH}$) is no longer suited for its intended use) are included within the scope of the invention. A skilled person will generally be able to determine and select suitable substitutions, deletions or insertions, or suitable combinations of thereof, based on the disclosure herein and optionally after a limited degree of routine experimentation, which may for example involve introducing a limited number of possible substitutions and determining their influence on the properties of the Nanobodies thus obtained.

For example, and depending on the host organism used to express the NANOBODY® ($V_{HH}$) or polypeptide of the invention, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups (as described herein), for example to allow site-specific pegylation (again as described herein).

As can be seen from the data on the $V_{HH}$ entropy and $V_{HH}$ variability given in Tables A-5 to A-8 above, some amino acid residues in the framework regions are more conserved than others. Generally, although the invention in its broadest sense is not limited thereto, any substitutions, deletions or insertions are preferably made at positions that are less conserved. Also, generally, amino acid substitutions are preferred over amino acid deletions or insertions.

The analogs are preferably such that they can bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

The analogs are preferably also such that they retain the favourable properties the Nanobodies, as described herein.

Also, according to one preferred aspect, the analogs have a degree of sequence identity of at least 70%, preferably at least 80%, more preferably at least 90%, such as at least 95% or 99% or more; and/or preferably have at most 20, preferably at most 10, even more preferably at most 5, such as 4, 3, 2 or only 1 amino acid difference (as defined herein), with one of the Nanobodies of SEQ ID NOs: 526 to 527, 538 to 541, 413 to 453 and 517 to 525.

Also, the framework sequences and CDR's of the analogs are preferably such that they are in accordance with the preferred aspects defined herein. More generally, as described herein, the analogs will have (a) a Q at position 108; and/or (b) a charged amino acid or a cysteine residue at position 45 and preferably an E at position 44, and more preferably E at position 44 and R at position 45; and/or (c) P, R or S at position 103.

One preferred class of analogs of the Nanobodies of the invention comprise Nanobodies that have been humanized (i.e. compared to the sequence of a naturally occurring NANOBODY® ($V_{HH}$) of the invention). As mentioned in the background art cited herein, such humanization generally involves replacing one or more amino acid residues in the sequence of a naturally occurring $V_{HH}$ with the amino acid residues that occur at the same position in a human $V_H$ domain, such as a human $V_H3$ domain. Examples of possible humanizing substitutions or combinations of humanizing substitutions will be clear to the skilled person, for example from the Tables herein, from the possible humanizing substitutions mentioned in the background art cited herein, and/or from a comparison between the sequence of a NANOBODY® ($V_{HH}$) and the sequence of a naturally occurring human $V_H$ domain.

The humanizing substitutions should be chosen such that the resulting humanized Nanobodies still retain the favourable properties of Nanobodies as defined herein, and more preferably such that they are as described for analogs in the preceding paragraphs. A skilled person will generally be able to determine and select suitable humanizing substitutions or suitable combinations of humanizing substitutions, based on the disclosure herein and optionally after a limited degree of routine experimentation, which may for example involve introducing a limited number of possible humanizing substitutions and determining their influence on the properties of the Nanobodies thus obtained.

Generally, as a result of humanization, the Nanobodies of the invention may become more "human-like", while still retaining the favorable properties of the Nanobodies of the invention as described herein. As a result, such humanized Nanobodies may have several advantages, such as a reduced immunogenicity, compared to the corresponding naturally occurring $V_{HH}$ domains. Again, based on the disclosure herein and optionally after a limited degree of routine experimentation, the skilled person will be able to select humanizing substitutions or suitable combinations of humanizing substitutions which optimize or achieve a desired or suitable balance between the favourable properties provided by the humanizing substitutions on the one hand and the favourable properties of naturally occurring $V_{HH}$ domains on the other hand.

The Nanobodies of the invention may be suitably humanized at any framework residue(s), such as at one or more Hallmark residues (as defined herein) or at one or more other framework residues (i.e. non-Hallmark residues) or any suitable combination thereof. One preferred humanizing substitution for Nanobodies of the "P,R,S-103 group" or the "KERE group" is Q108 into L108. Nanobodies of the "GLEW class" may also be humanized by a Q108 into L108 substitution, provided at least one of the other Hallmark residues contains a camelid (camelizing) substitution (as defined herein). For example, as mentioned above, one particularly preferred class of humanized Nanobodies has GLEW or a GLEW-like sequence at positions 44-47; P, R or S (and in particular R) at position 103, and an L at position 108.

The humanized and other analogs, and nucleic acid sequences encoding the same, can be provided in any manner known per se. For example, the analogs can be obtained by providing a nucleic acid that encodes a naturally occurring $V_{HH}$ domain, changing the codons for the one or more amino acid residues that are to be substituted into the codons for the corresponding desired amino acid residues (e.g. by site-directed mutagenesis or by PCR using suitable mismatch primers), expressing the nucleic acid/nucleotide sequence thus obtained in a suitable host or expression system; and optionally isolating and/or purifying the analog thus obtained to provide said analog in essentially isolated form (e.g. as further described herein). This can generally be performed using methods and techniques known per se, which will be clear to the skilled person, for example from the handbooks and references cited herein, the background art cited herein and/or from the further description herein. Alternatively, a nucleic acid encoding the desired analog can be synthesized in a manner known per se (for example using an automated apparatus for synthesizing nucleic acid sequences with a predefined amino acid sequence) and can then be expressed as described herein. Yet another technique may involve combining one or more naturally occurring and/or synthetic nucleic acid sequences each encoding a part of the desired analog, and then expressing the combined nucleic acid sequence as described herein. Also, the analogs can be provided using chemical synthesis of the pertinent amino acid sequence using techniques for peptide synthesis known per se, such as those mentioned herein.

In this respect, it will be also be clear to the skilled person that the Nanobodies of the invention (including their analogs) can be designed and/or prepared starting from human $V_H$ sequences (i.e. amino acid sequences or the corresponding nucleotide sequences), such as for example from human $V_H3$ sequences such as DP-47, DP-51 or DP-29, i.e. by introducing one or more camelizing substitutions (i.e. changing one or more amino acid residues in the amino acid sequence of said human $V_H$ domain into the amino acid residues that occur at the corresponding position in a $V_{HH}$ domain), so as to provide the sequence of a NANOBODY® ($V_{HH}$) of the invention and/or so as to confer the favourable properties of a NANOBODY® ($V_{HH}$) to the sequence thus obtained. Again, this can generally be performed using the various methods and techniques referred to in the previous paragraph, using an amino acid sequence and/or nucleotide sequence for a human $V_H$ domain as a starting point.

Some preferred, but non-limiting camelizing substitutions can be derived from Tables A-5-A-8. It will also be clear that camelizing substitutions at one or more of the Hallmark residues will generally have a greater influence on the desired properties than substitutions at one or more of the other amino acid positions, although both and any suitable combination thereof are included within the scope of the invention. For example, it is possible to introduce one or more camelizing substitutions that already confer at least some the desired properties, and then to introduce further camelizing substitutions that either further improve said properties and/or confer additional favourable properties. Again, the skilled person will generally be able to determine and select suitable camelizing substitutions or suitable combinations of camelizing substitutions, based on the disclosure herein and optionally after a limited degree of routine experimentation, which may for example involve introducing a limited number of possible camelizing substitutions and determining whether the favourable properties of Nanobodies are obtained or improved (i.e. compared to the original $V_H$ domain). Generally, however, such camelizing substitutions are preferably such that the resulting an amino acid sequence at least contains (a) a Q at position 108; and/or (b) a charged amino acid or a cysteine residue at position 45 and preferably also an E at position 44, and more preferably E at position 44 and R at position 45; and/or (c) P, R or S at position 103; and optionally one or more further camelizing substitutions. More preferably, the camelizing substitutions are such that they result in a NANOBODY® ($V_{HH}$) of the invention and/or in an analog thereof (as defined herein), such as in a humanized analog and/or preferably in an analog that is as defined in the preceding paragraphs.

As will also be clear from the disclosure herein, it is also within the scope of the invention to use parts or fragments, or combinations of two or more parts or fragments, of the Nanobodies of the invention as defined herein, and in particular parts or fragments of the Nanobodies of SEQ ID NO's: 526 to 527, 538 to 541, 413 to 453 and 517 to 525. Thus, according to one aspect of the invention, the term "NANOBODY® ($V_{HH}$) of the invention" in its broadest sense also covers such parts or fragments.

Generally, such parts or fragments of the Nanobodies of the invention (including analogs thereof) have amino acid sequences in which, compared to the amino acid sequence of the corresponding full length NANOBODY® ($V_{HH}$) of the invention (or analog thereof), one or more of the amino acid residues at the N-terminal end, one or more amino acid residues at the C-terminal end, one or more contiguous internal amino acid residues, or any combination thereof, have been deleted and/or removed.

The parts or fragments are preferably such that they can bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

Any part or fragment is preferably such that it comprises at least 10 contiguous amino acid residues, preferably at least 20 contiguous amino acid residues, more preferably at least 30 contiguous amino acid residues, such as at least 40 contiguous amino acid residues, of the amino acid sequence of the corresponding full length NANOBODY® ($V_{HH}$) of the invention.

Also, any part or fragment is such preferably that it comprises at least one of CDR1, CDR2 and/or CDR3 or at least part thereof (and in particular at least CDR3 or at least part thereof). More preferably, any part or fragment is such that it comprises at least one of the CDR's (and preferably at least CDR3 or part thereof) and at least one other CDR (i.e. CDR1 or CDR2) or at least part thereof, preferably connected by suitable framework sequence(s) or at least part thereof. More preferably, any part or fragment is such that it comprises at least one of the CDR's (and preferably at least CDR3 or part thereof) and at least part of the two remaining CDR's, again preferably connected by suitable framework sequence(s) or at least part thereof.

According to another particularly preferred, but non-limiting aspect, such a part or fragment comprises at least CDR3, such as FR3, CDR3 and FR4 of the corresponding full length NANOBODY® ($V_{HH}$) of the invention, i.e. as for example described in the International application WO 03/050531 (Lasters et al.).

As already mentioned above, it is also possible to combine two or more of such parts or fragments (i.e. from the same or different Nanobodies of the invention), i.e. to provide an analog (as defined herein) and/or to provide further parts or fragments (as defined herein) of a NANOBODY® ($V_{HH}$) of the invention. It is for example also possible to combine one or more parts or fragments of a NANOBODY® ($V_{HH}$) of the invention with one or more parts or fragments of a human $V_H$ domain.

According to one preferred aspect, the parts or fragments have a degree of sequence identity of at least 50%, preferably at least 60%, more preferably at least 70%, even more preferably at least 80%, such as at least 90%, 95% or 99% or more with one of the Nanobodies of SEQ ID NOs 526 to 527; SEQ ID NO's 538 to 541; 413 to 453 and 517 to 525.

The parts and fragments, and nucleic acid sequences encoding the same, can be provided and optionally combined in any manner known per se. For example, such parts or fragments can be obtained by inserting a stop codon in a nucleic acid that encodes a full-sized NANOBODY® ($V_{HH}$) of the invention, and then expressing the nucleic acid thus obtained in a manner known per se (e.g. as described herein). Alternatively, nucleic acids encoding such parts or fragments can be obtained by suitably restricting a nucleic acid that encodes a full-sized NANOBODY® ($V_{HH}$) of the invention or by synthesizing such a nucleic acid in a manner known per se. Parts or fragments may also be provided using techniques for peptide synthesis known per se.

The invention in its broadest sense also comprises derivatives of the Nanobodies of the invention. Such derivatives can generally be obtained by modification, and in particular by chemical and/or biological (e.g. enzymatical) modification, of the Nanobodies of the invention and/or of one or more of the amino acid residues that form the Nanobodies of the invention.

Examples of such modifications, as well as examples of amino acid residues within the NANOBODY® ($V_{HH}$) sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the NANOBODY® ($V_{HH}$) of the invention, and in particular of one or more functional groups, residues or moieties that confer one or more desired properties or functionalities to the NANOBODY® ($V_{HH}$) of the invention. Example of such functional groups will be clear to the skilled person.

For example, such modification may comprise the introduction (e.g. by covalent binding or in any other suitable manner) of one or more functional groups that increase the half-life, the solubility and/or the absorption of the NANOBODY® ($V_{HH}$) of the invention, that reduce the immunogenicity and/or the toxicity of the NANOBODY® ($V_{HH}$) of the invention, that eliminate or attenuate any undesirable side effects of the NANOBODY® ($V_{HH}$) of the invention, and/or that confer other advantageous properties to and/or reduce the undesired properties of the Nanobodies and/or polypeptides of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to a NANOBODY® ($V_{HH}$) of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a NANOBODY® ($V_{HH}$) of the invention, a NANOBODY® ($V_{HH}$) of the invention may be modified so as to suitably introduce one or more cysteine residues for attachment of PEG, or an amino acid sequence comprising one or more cysteine residues for attachment of PEG may be fused to the N- and/or C-terminus of a NANOBODY® ($V_{HH}$) of the invention, all using techniques of protein engineering known per se to the skilled person.

Preferably, for the Nanobodies and proteins of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the NANOBODY® ($V_{HH}$) or polypeptide of the invention.

Yet another modification may comprise the introduction of one or more detectable labels or other signal-generating groups or moieties, depending on the intended use of the labelled NANOBODY® ($V_{HH}$). Suitable labels and techniques for attaching, using and detecting them will be clear to the skilled person, and for example include, but are not limited to, fluorescent labels (such as fluorescein, isothiocyanate, rhodamine, phycoerythrin, phycocyanin, allophycocyanin, o-phthaldehyde, and fluorescamine and fluorescent metals such as $^{152}$Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio isotopes (such as $^3$H, $^{125}$I, $^{32}$P, $^{35}$S, $^{14}$C, $^{51}$Cr, $^{36}$Cl, $^{57}$Co, $^{58}$Co, $^{59}$Fe, and $^{75}$Se), metals, metal chelates or metallic cations (for example metallic cations such as $^{99m}$Tc, $^{123}$I, $^{111}$In, $^{131}$I, $^{97}$Ru, $^{67}$Cu, $^{67}$Ga, and $^{68}$Ga or other metals or metallic cations that are particularly suited for use in in vivo, in vitro or in situ diagnosis and imaging, such as ($^{157}$Gd, $^{55}$Mn, $^{162}$Dy, $^{52}$Cr, and $^{56}$Fe), as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person, and for example include moieties that can be detected using NMR or ESR spectroscopy.

Such labelled Nanobodies and polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the NANOBODY® ($V_{HH}$) of the invention to another protein, polypeptide or chemical compound that is bound to the other half of the binding pair, i.e. through formation of the binding pair. For example, a NANOBODY® ($V_{HH}$) of the invention may be conjugated to biotin, and linked to another protein, polypeptide, compound or carrier conjugated to avidin or streptavidin. For example, such a conjugated NANOBODY® ($V_{HH}$) may be used as a reporter, for example in a diagnostic system where a detectable signal-producing agent is conjugated to avidin or streptavidin. Such binding pairs may for example also be used to bind the NANOBODY® ($V_{HH}$) of the invention to a carrier, including carriers suitable for pharmaceutical purposes. One non-limiting example are the liposomal formulations described by Cao and Suresh, Journal of Drug Targetting, 8, 4, 257 (2000). Such binding pairs may also be used to link a therapeutically active agent to the NANOBODY® ($V_{HH}$) of the invention.

For some applications, in particular for those applications in which it is intended to kill a cell that expresses the target against which the Nanobodies of the invention are directed (e.g. in the treatment of cancer), or to reduce or slow the growth and/or proliferation such a cell, the Nanobodies of the invention may also be linked to a toxin or to a toxic residue or moiety. Examples of toxic moieties, compounds or residues which can be linked to a NANOBODY® ($V_{HH}$) of the invention to provide—for example—a cytotoxic compound will be clear to the skilled person and can for example be found in the prior art cited above and/or in the further description herein. One example is the so-called ADEPT™ technology described in WO 03/055527.

Other potential chemical and enzymatical modifications will be clear to the skilled person. Such modifications may also be introduced for research purposes (e.g. to study function-activity relationships). Reference is for example made to Lundblad and Bradshaw, Biotechnol. Appl. Biochem., 26, 143-151 (1997).

Preferably, the derivatives are such that they bind to GPCRs with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) that is as defined herein for the Nanobodies of the invention.

As mentioned above, the invention also relates to proteins or polypeptides that essentially consist of or comprise at least one NANOBODY® ($V_{HH}$) of the invention. By "essentially consist of" is meant that the amino acid sequence of the polypeptide of the invention either is exactly the same as the amino acid sequence of a NANOBODY® ($V_{HH}$) of the invention or corresponds to the amino acid sequence of a NANOBODY® ($V_{HH}$) of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the amino acid sequence of the NANOBODY® ($V_{HH}$).

Said amino acid residues may or may not change, alter or otherwise influence the (biological) properties of the NANOBODY® ($V_{HH}$) and may or may not add further functionality to the NANOBODY® ($V_{HH}$). For example, such amino acid residues:

can comprise an N-terminal Met residue, for example as result of expression in a heterologous host cell or host organism.

may form a signal sequence or leader sequence that directs secretion of the NANOBODY® ($V_{HH}$) from a host cell upon synthesis. Suitable secretory leader peptides will be clear to the skilled person, and may be as further described herein. Usually, such a leader sequence will be linked to the N-terminus of the NANOBODY® ($V_{HH}$), although the invention in its broadest sense is not limited thereto;

may form a sequence or signal that allows the NANOBODY® ($V_{HH}$) to be directed towards and/or to penetrate or enter into specific organs, tissues, cells, or parts or compartments of cells, and/or that allows the NANOBODY® ($V_{HH}$) to penetrate or cross a biological barrier such as a cell membrane, a cell layer such as a layer of epithelial cells, a tumor including solid tumors, or the blood-brain-barrier. Examples of such amino acid sequences will be clear to the skilled person. Some non-limiting examples are the small peptide vectors ("Pep-trans vectors") described in WO 03/026700 and in Temsamani et al., Expert Opin. Biol. Ther., 1, 773 (2001); Temsamani and Vidal, Drug Discov. Today, 9, 1012 (004) and Rousselle, J. Pharmacol. Exp. Ther., 296, 124-131 (2001), and the membrane translocator sequence described by Zhao et al., Apoptosis, 8, 631-637 (2003). C-terminal and N-terminal amino acid sequences for intracellular targeting of antibody fragments are for example described by Cardinale et al., Methods, 34, 171 (2004). Other suitable techniques for intracellular targeting involve the expression and/or use of so-called "intrabodies" comprising a NANOBODY® ($V_{HH}$) of the invention, as mentioned below;

may form a "tag", for example an amino acid sequence or residue that allows or facilitates the purification of the NANOBODY® ($V_{HH}$), for example using affinity techniques directed against said sequence or residue. Thereafter, said sequence or residue may be removed (e.g. by chemical or enzymatical cleavage) to provide the NANOBODY® ($V_{HH}$) sequence (for this purpose, the tag may optionally be linked to the NANOBODY® ($V_{HH}$) sequence via a cleavable linker sequence or contain a cleavable motif). Some preferred, but non-limiting examples of such residues are multiple histidine residues, glutathione residues and a myc-tag (see for example SEQ ID NO:31 of WO 06/12282).

may be one or more amino acid residues that have been functionalized and/or that can serve as a site for attachment of functional groups. Suitable amino acid residues and functional groups will be clear to the skilled person and include, but are not limited to, the amino acid residues and functional groups mentioned herein for the derivatives of the Nanobodies of the invention.

According to another aspect, a polypeptide of the invention comprises a NANOBODY® ($V_{HH}$) of the invention, which is fused at its amino terminal end, at its carboxy terminal end, or both at its amino terminal end and at its carboxy terminal end to at least one further amino acid sequence, i.e. so as to provide a fusion protein comprising said NANOBODY® ($V_{HH}$) of the invention and the one or more further amino acid sequences. Such a fusion will also be referred to herein as a "NANOBODY® ($V_{HH}$) fusion".

The one or more further amino acid sequence may be any suitable and/or desired amino acid sequences. The further amino acid sequences may or may not change, alter or otherwise influence the (biological) properties of the NANOBODY® ($V_{HH}$), and may or may not add further functionality to the NANOBODY® ($V_{HH}$) or the polypeptide of the invention. Preferably, the further amino acid sequence is such that it confers one or more desired properties or functionalities to the NANOBODY® ($V_{HH}$) or the polypeptide of the invention.

For example, the further amino acid sequence may also provide a second binding site, which binding site may be directed against any desired protein, polypeptide, antigen, antigenic determinant or epitope (including but not limited to the same protein, polypeptide, antigen, antigenic determinant or epitope against which the NANOBODY® ($V_{HH}$) of the invention is directed, or a different protein, polypeptide, antigen, antigenic determinant or epitope).

Example of such amino acid sequences will be clear to the skilled person, and may generally comprise all amino acid sequences that are used in peptide fusions based on conventional antibodies and fragments thereof (including but not limited to ScFv's and single domain antibodies). Reference is for example made to the review by Holliger and Hudson, Nature Biotechnology, 23, 9, 1126-1136 (2005), For example, such an amino acid sequence may be an amino acid sequence that increases the half-life, the solubility, or the absorption, reduces the immunogenicity or the toxicity, eliminates or attenuates undesirable side effects, and/or confers other advantageous properties to and/or reduces the undesired properties of the polypeptides of the invention, compared to the NANOBODY® ($V_{HH}$) of the invention per se. Some non-limiting examples of such amino acid sequences are serum proteins, such as human serum albumin (see for example WO 00/27435) or haptenic molecules (for example haptens that are recognized by circulating antibodies, see for example WO 98/22141).

In particular, it has been described in the art that linking fragments of immunoglobulins (such as $V_H$ domains) to serum albumin or to fragments thereof can be used to increase the half-life. Reference is for made to WO 00/27435 and WO 01/077137). According to the invention, the NANOBODY® ($V_{HH}$) of the invention is preferably either directly linked to serum albumin (or to a suitable fragment thereof) or via a suitable linker, and in particular via a suitable peptide linked so that the polypeptide of the invention can be expressed as a genetic fusion (protein). According to one specific aspect, the NANOBODY® ($V_{HH}$) of the invention may be linked to a fragment of serum albumin that at least comprises the domain III of serum albumin or part thereof. Reference is for example made to the U.S. provisional application 60/788,256 of Ablynx N.V. entitled "Albumin derived amino acid sequence, use thereof for increasing the half-life of therapeutic proteins and of other therapeutic proteins and entities, and constructs comprising the same" filed on Mar. 31, 2006 (see also WO07/112940).

Alternatively, the further amino acid sequence may provide a second binding site or binding unit that is directed against a serum protein (such as, for example, human serum albumin or another serum protein such as IgG), so as to provide increased half-life in serum. Such amino acid sequences for example include the Nanobodies described below, as well as the small peptides and binding proteins described in WO 91/01743, WO 01/45746 and WO 02/076489 and the dAb's described in WO 03/002609 and WO 04/003019. Reference is also made to Harmsen et al., Vaccine, 23 (41); 4926-42, 2005, as well as to EP 0 368 684, as well as to the following U.S. provisional applications 60/843,349 (see also WO08/028977), 60/850,774 (see also WO08/043821), 60/850,775 (see also WO08/043822) by Ablynx N.V. mentioned herein US provisional application of Ablynx N.V. entitled "Peptides capable of binding to serum proteins" filed on Dec. 5, 2006 (see also WO08/068280).

Such amino acid sequences may in particular be directed against serum albumin (and more in particular human serum albumin) and/or against IgG (and more in particular human IgG). For example, such amino acid sequences may be amino acid sequences that are directed against (human) serum albumin and amino acid sequences that can bind to amino acid residues on (human) serum albumin that are not involved in binding of serum albumin to FcRn (see for example WO 06/0122787) and/or amino acid sequences that are capable of binding to amino acid residues on serum albumin that do not form part of domain III of serum albumin (see again for example WO 06/0122787); amino acid sequences that have or can provide an increased half-life (see for example the U.S. provisional application 60/843,349 by Ablynx N.V. entitled "Serum albumin binding proteins with long half-lives" filed on Sep. 8, 2006; see also WO08/028977); amino acid sequences against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*), reference is again made to the U.S. provisional application 60/843,349 and WO08/028977); amino acid sequences that can bind to serum albumin in a pH independent manner (see for example the U.S. provisional application 60/850,774 by Ablynx N.V. entitled "Amino acid sequences that bind to serum proteins in a manner that is essentially independent of the pH, compounds comprising the same, and uses thereof", filed on Oct. 11, 2006; see also WO08/043821) and/or amino acid sequences that are conditional binders (see for example the U.S. provisional application 60/850,775 by Ablynx N.V. entitled "Amino acid sequences that bind to a desired molecule in a conditional manner", filed on Oct. 11, 2006; see also WO08/043822).

According to another aspect, the one or more further amino acid sequences may comprise one or more parts, fragments or domains of conventional 4-chain antibodies (and in particular human antibodies) and/or of heavy chain antibodies. For example, although usually less preferred, a NANOBODY® ($V_{HH}$) of the invention may be linked to a conventional (preferably human) $V_H$ or $V_L$ domain or to a natural or synthetic analog of a $V_H$ or $V_L$ domain, again optionally via a linker sequence (including but not limited to other (single) domain antibodies, such as the dAb's described by Ward et al.).

The at least one NANOBODY® ($V_{HH}$) may also be linked to one or more (preferably human) $C_H1$, $C_H2$ and/or $C_H3$ domains, optionally via a linker sequence. For instance, a NANOBODY® ($V_{HH}$) linked to a suitable $C_H1$ domain could for example be used—together with suitable light chains—to generate antibody fragments/structures analogous to conventional Fab fragments or F(ab')$_2$ fragments, but in which one or (in case of an F(ab')$_2$ fragment) one or both of the conventional $V_H$ domains have been replaced by a NANOBODY® ($V_{HH}$) of the invention. Also, two Nanobodies could be linked to a $C_H3$ domain (optionally via a linker) to provide a construct with increased half-life in vivo.

According to one specific aspect of a polypeptide of the invention, one or more Nanobodies of the invention may be linked (optionally via a suitable linker or hinge region) to one or more constant domains (for example, 2 or 3 constant domains that can be used as part of/to form an Fc portion), to an Fc portion and/or to one or more antibody parts, fragments or domains that confer one or more effector functions to the polypeptide of the invention and/or may confer the ability to bind to one or more Fc receptors. For example, for this purpose, and without being limited thereto, the one or more further amino acid sequences may comprise one or more $C_H2$ and/or $C_H3$ domains of an antibody, such as from a heavy chain antibody (as described herein) and more preferably from a conventional human 4-chain antibody; and/or may form (part of) and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid $V_{HH}$ domain or a humanized derivative thereof (i.e. a NANOBODY® ($V_{HH}$)), in which the Camelidae $C_H2$ and/or $C_H3$ domain have been replaced by human $C_H2$ and $C_H3$ domains, so as to provide an immunoglobulin that consists of 2 heavy chains each comprising a NANOBODY® ($V_{HH}$) and human $C_H2$ and $C_H3$ domains (but no $C_H1$ domain), which immunoglobulin has the effector function provided by the $C_H2$ and $C_H3$ domains and which immunoglobulin can function without the presence of any light chains. Other amino acid sequences that can be suitably linked to the Nanobodies of the invention so as to provide an effector function will be clear to the skilled person, and may be chosen on the basis of the desired effector function(s). Reference is for example made to WO 04/058820, WO 99/42077, WO 02/056910 and WO 05/017148, as well as the review by Holliger and Hudson, supra; and WO09/068628. Coupling of a NANOBODY® ($V_{HH}$) of the invention to an Fc portion may also lead to an increased half-life, compared to the corresponding NANO-BODY® ($V_{HH}$) of the invention. For some applications, the use of an Fc portion and/or of constant domains (i.e. $C_H2$ and/or $C_H3$ domains) that confer increased half-life without any biologically significant effector function may also be suitable or even preferred. Other suitable constructs comprising one or more Nanobodies and one or more constant domains with increased half-life in vivo will be clear to the skilled person, and may for example comprise two Nanobodies linked to a $C_H3$ domain, optionally via a linker sequence. Generally, any fusion protein or derivatives with increased half-life will preferably have a molecular weight of more than 50 kDa, the cut-off value for renal absorption.

In another one specific, but non-limiting, aspect, in order to form a polypeptide of the invention, one or more amino acid sequences of the invention may be linked (optionally via a suitable linker or hinge region) to naturally occurring, synthetic or semisynthetic constant domains (or analogs, variants, mutants, parts or fragments thereof) that have a reduced (or essentially no) tendency to self-associate into dimers (i.e. compared to constant domains that naturally occur in conventional 4-chain antibodies). Such monomeric (i.e. not self-associating) Fc chain variants, or fragments thereof, will be clear to the skilled person. For example, Helm et al., J Biol Chem 1996 271 7494, describe monomeric Fcε chain variants that can be used in the polypeptide chains of the invention.

Also, such monomeric Fc chain variants are preferably such that they are still capable of binding to the complement or the relevant Fc receptor(s) (depending on the Fc portion from which they are derived), and/or such that they still have some or all of the effector functions of the Fc portion from which they are derived (or at a reduced level still suitable for the intended use). Alternatively, in such a polypeptide chain of the invention, the monomeric Fc chain may be used to confer increased half-life upon the polypeptide chain, in which case the monomeric Fc chain may also have no or essentially no effector functions.

Bivalent/multivalent, bispecific/multispecific or biparatopic/multiparatopic polypeptides of the invention may also be linked to Fc portions, in order to provide polypeptide constructs of the type that is described in WO09/068630.

The further amino acid sequence may also form a sequence or signal that allows the NANOBODY® ($V_{HH}$) or polypeptide of the invention to be directed towards and/or to penetrate or enter into specific organs, tissues, cells, or parts or compartments of cells, and/or that allows the NANOBODY® ($V_{HH}$) or polypeptide of the invention to penetrate or cross a biological barrier such as a cell membrane, a cell layer such as a layer of epithelial cells, a tumor including solid tumors, or the blood-brain-barrier. Suitable examples of such amino acid sequences will be clear to the skilled person, and for example include, but are not limited to, the "Peptrans" vectors mentioned above, the sequences described by Cardinale et al. and the amino acid sequences and antibody fragments known per se that can be used to express or produce the Nanobodies and polypeptides of the invention as so-called "intrabodies", for example as described in WO 94/02610, WO 95/22618, U.S. Pat. No. 7,004,940, WO 03/014960, WO 99/07414; WO 05/01690; EP 1 512 696; and in Cattaneo, A. & Biocca, S. (1997) Intracellular Antibodies: Development and Applications. Landes and Springer-Verlag; and in Kontermann, Methods 34, (2004), 163-170, and the further references described therein.

For some applications, in particular for those applications in which it is intended to kill a cell that expresses the target against which the Nanobodies of the invention are directed (e.g. in the treatment of cancer), or to reduce or slow the growth and/or proliferation of such a cell, the Nanobodies of the invention may also be linked to a (cyto)toxic protein or polypeptide. Examples of such toxic proteins and polypeptides which can be linked to a NANOBODY® ($V_{HH}$) of the invention to provide—for example—a cytotoxic polypeptide of the invention will be clear to the skilled person and can for example be found in the prior art cited above and/or in the further description herein. One example is the so-called ADEPT™ technology described in WO 03/055527.

According to one preferred, but non-limiting aspect, said one or more further amino acid sequences comprise at least one further NANOBODY® ($V_{HH}$), so as to provide a polypeptide of the invention that comprises at least two, such as three, four, five or more Nanobodies, in which said Nanobodies may optionally be linked via one or more linker sequences (as defined herein). Polypeptides of the invention that comprise two or more Nanobodies, of which at least one is a NANOBODY® ($V_{HH}$) of the invention, will also be referred to herein as "multivalent" polypeptides of the invention, and the Nanobodies present in such polypeptides will also be referred to herein as being in a "multivalent format". For example a "bivalent" polypeptide of the invention comprises two Nanobodies, optionally linked via a linker sequence, whereas a "trivalent" polypeptide of the invention comprises three Nanobodies, optionally linked via two linker sequences; etc.; in which at least one of the Nanobodies present in the polypeptide, and up to all of the Nanobodies present in the polypeptide, is/are a NANOBODY® ($V_{HH}$) of the invention.

In a multivalent polypeptide of the invention, the two or more Nanobodies may be the same or different, and may be directed against the same antigen or antigenic determinant (for example against the same part(s) or epitope(s) or against different parts or epitopes) or may alternatively be directed against different antigens or antigenic determinants; or any suitable combination thereof. For example, a bivalent polypeptide of the invention may comprise (a) two identical Nanobodies; (b) a first NANOBODY® ($V_{HH}$) directed against a first antigenic determinant of a protein or antigen and a second NANOBODY® ($V_{HH}$) directed against the same antigenic determinant of said protein or antigen which is different from the first NANOBODY® ($V_{HH}$); (c) a first NANOBODY® ($V_{HH}$) directed against a first antigenic determinant of a protein or antigen and a second NANOBODY® ($V_{HH}$) directed against another antigenic determinant of said protein or antigen (i.e. biparatopic NANOBODY® ($V_{HH}$) constructs); or (d) a first NANOBODY® ($V_{HH}$) directed against a first protein or antigen and a second NANOBODY® ($V_{HH}$) directed against a second protein or antigen (i.e. different from said first antigen). Similarly, a trivalent polypeptide of the invention may, for example and without being limited thereto. comprise (a) three identical Nanobodies; (b) two identical NANOBODY® ($V_{HH}$) against a first antigenic determinant of an antigen and a third NANOBODY® ($V_{HH}$) directed against a different antigenic determinant of the same antigen; (c) two identical NANOBODY® ($V_{HH}$) against a first antigenic determinant of an antigen and a third NANOBODY® ($V_{HH}$) directed against a second antigen different from said first antigen; (d) a first NANOBODY® ($V_{HH}$) directed against a first antigenic determinant of a first antigen, a second NANOBODY® ($V_{HH}$) directed against a second antigenic determinant of said first antigen and a third NANOBODY® ($V_{HH}$) directed against a second antigen different from said first antigen; or (e) a first NANOBODY® ($V_{HH}$) directed against a first antigen, a second NANOBODY® ($V_{HH}$) directed against a second antigen different from said first antigen, and a third NANOBODY® ($V_{HH}$) directed against a third antigen different from said first and second antigen. Particularly preferred polypeptides in accordance with the invention are biparatopic polypeptides directed against GPCRs. Such polypeptides may comprise two or more Nanobodies which are directed against GPCRs, wherein at least one "first" NANOBODY® ($V_{HH}$) is directed against a first antigenic determinant, epitope, part, domain, subunit or confirmation of a GPCR (e.g. CXCR4); and wherein at least one "second" NANOBODY® ($V_{HH}$) is directed against a second antigenic determinant, epitope, part, domain, subunit or confirmation of said GPCR different from the first, in which said Nanobodies may be suitably linked, for example via a suitable linker as further described herein. Such biparatopic NANOBODY® ($V_{HH}$) constructs were prepared by the inventors and are provided herein. For example, WO 09/138519 describes a number of amino acid sequences and in particular VHHs and constructs thereof that are directed against human CXCR4 (see for example the amino acid sequences mentioned such as SEQ ID NO: 238 and SEQ ID NO: 239 in Table B-1.1 of WO 09/138519). WO 09/138519 also describes multivalent, multispecific and/or biparatopic constructs (as defined in WO 09/138519) that are directed against human CXCR4. Reference is for example made to the constructs referred to in Example 4 of WO 09/138519 such as SEQ ID NO: 264 in Table B-5 of WO 09/138519).

One particularly preferred example of an amino acid sequence against human CXCR4 from WO 09/138519 is the sequence designated 238D2 (see SEQ ID NO: 238 in WO 09/138519 and SEQ ID NO: 526 herein). One other particularly preferred example of an amino acid sequence against the human CXCR4 from WO 09/138519 is the sequence designated 238D4 (see SEQ ID NO: 239 in WO 09/138519 and SEQ ID NO: 527 herein). WO 09/138519 further gives some non-limiting examples of multivalent, multispecific and/or biparatopic constructs that comprise 238D2 and/or 238D4 (see for example SEQ ID NO's: 261 to 266 in WO 09/138519 and in particular the biparatopic construct 238D2-20GS-238D4.

Completely unexpectedly, present inventors have constructed biparatopic Nanobodies, obtained by linkage of 238D2 to 238D4 which resulted in a significantly increased affinity for CXCR4 (27 and 17-fold increase over its respective monovalent constructs, see Example 6 described herein).

WO2011/161266 describes a number of sequence-optimized/improved variants of the amino acid sequences 238D2 and 238D4, as well as biparatopic constructs that comprise such improved variants as building blocks. Also further exemplified herein are biparatopic polypeptides of the invention directed against another respresentative GPCR, such as CXCR7; wherein the inventors repeatedly demonstrate that a biparatopic polypeptide of the invention is more effective in biological assays, e.g. β-arrestin assay, than mono-specific bivalent polypeptides (Example 7 described herein). Reference is for example made to WO2012/130874. Thus, present inventors have demonstrated for the first time that the construction of biparatopic constructs directed against GPCRs completely unexpectedly resulted in a significant increase in potency compared to its corresponding monovalent and mono-specific bivalent binders. Particularly preferred biparatopic polypeptides in accordance with the invention are those shown in Examples 5A, 6 and 7 described herein.

Polypeptides of the invention that contain at least two Nanobodies, in which at least one NANOBODY® ($V_{HH}$) is directed against a first antigen (i.e. against GPCRs) and at least one NANOBODY® ($V_{HH}$) is directed against a second antigen (i.e. different from GPCRs), will also be referred to as "multispecific" polypeptides of the invention, and the Nanobodies present in such polypeptides will also be referred to herein as being in a "multispecific format". Thus, for example, a "bispecific" polypeptide of the invention is a polypeptide that comprises at least one NANOBODY® ($V_{HH}$) directed against a first antigen (i.e. GPCRs) and at least one further NANOBODY® ($V_{HH}$) directed against a second antigen (i.e. different from GPCRs), whereas a "trispecific" polypeptide of the invention is a polypeptide that comprises at least one NANOBODY® ($V_{HH}$) directed against a first antigen (i.e. GPCRs), at least one further NANOBODY® ($V_{HH}$) directed against a second antigen (i.e. different from GPCRs) and at least one further NANOBODY® ($V_{HH}$) directed against a third antigen (i.e. different from both GPCRs, and the second antigen); etc.

Accordingly, in its simplest form, a bispecific polypeptide of the invention is a bivalent polypeptide of the invention (as defined herein), comprising a first NANOBODY® ($V_{HH}$) directed against GPCRs, and a second NANOBODY® ($V_{HH}$) directed against a linked via a linker sequence (as defined herein); whereas a trispecific polypeptide of the invention in its simplest form is a trivalent polypeptide of the invention (as defined herein), comprising a first NANOBODY® ($V_{HH}$) directed against GPCRs, a second NANOBODY® ($V_{HH}$) directed against a second antigen and a third NANOBODY® ($V_{HH}$) directed against a third antigen, in which said first, second and third NANOBODY® ($V_{HH}$) may optionally be linked via one or more, and in particular one and more, in particular two, linker sequences.

Polypeptides of the invention that contain at least two Nanobodies which are directed against GPCRs, wherein at least one "first" Nanbody is directed against a first antigenic determinant, epitope, part, domain, subunit or confirmation of a GPCR (e.g. CXCR4); and wherein at least one "second" NANOBODY® ($V_{HH}$) is directed against a second antigenic determinant, epitope, part, domain, subunit or confirmation of said GPCR (e.g. CXCR4) different from the first, will also be referred to as "multiparatopic" polypeptides of the invention, and the Nanobodies present in such polypeptides will also be referred to herein as being in a "multiparatopic format". Thus, for example, a "biparatopic" polypeptide of the invention is a polypeptide that comprises at least one NANOBODY® ($V_{HH}$) directed against a first antigenic determinant, epitope, part, domain, subunit or confirmation of an antigen (i.e. GPCRs) and at least one further NANOBODY® ($V_{HH}$) directed against a second antigenic determinant, epitope, part, domain, subunit or confirmation of said antigen (i.e. same GPCRs) different from the first, whereas a "triparatopic" polypeptide of the invention is a polypeptide that comprises at least one NANOBODY® ($V_{HH}$) directed against a first antigenic determinant, epitope, part, domain, subunit or confirmation of an antigen (i.e. GPCRs), at least one further NANOBODY® ($V_{HH}$) directed against a second antigenic determinant, epitope, part, domain, subunit or confirmation of said antigen (i.e. same GPCRs) different from the first, and at least one further NANOBODY® ($V_{HH}$) directed against a third antigenic determinant, epitope, part, domain, subunit or confirmation of an antigen (i.e. same GPCRs) but different from said first and said second antigenic determinant, epitope, part, domain, subunit or confirmation of said antigen; etc.

Accordingly, in its simplest form, a biparatopic polypeptide of the invention is a bivalent polypeptide of the invention (as defined herein), comprising a first NANOBODY® ($V_{HH}$) directed against a first antigenic determinant, epitope, part, domain, subunit or confirmation of a GPCR, and a second NANOBODY® ($V_{HH}$) directed against a second antigenic determinant, epitope, part, domain, subunit or confirmation of said GPCR different from the first, in which said first and said second NANOBODY® ($V_{HH}$) may optionally be linked via a linker sequence (as defined herein); whereas a triparatopic polypeptide of the invention in its simplest form is a trivalent polypeptide of the invention (as defined herein), comprising a first NANOBODY® ($V_{HH}$) directed against a first antigenic determinant, epitope, part, domain, subunit or confirmation of a GPCR, a second NANOBODY® ($V_{HH}$) directed against a second antigenic determinant, epitope, part, domain, subunit or confirmation of said GPCR different from the first, and a third NANOBODY® ($V_{HH}$) directed against a third antigenic determinant, epitope, part, domain, subunit or confirmation of the same GPCR but different from said first and said second antigenic determinant, epitope, part, domain, subunit or confirmation, in which said first, second and third NANOBODY® ($V_{HH}$) may optionally be linked via one or more, and in particular one and more, in particular two, linker sequences.

However, as will be clear from the description hereinabove, the invention is not limited thereto, in the sense that a multispecific polypeptide of the invention may comprise at least one NANOBODY® ($V_{HH}$) against GPCRs, and any number of Nanobodies directed against one or more antigens different from GPCRs.

Furthermore, although it is encompassed within the scope of the invention that the specific order or arrangement of the various Nanobodies in the polypeptides of the invention may have some influence on the properties of the final polypeptide of the invention (including but not limited to the affinity, specificity or avidity for GPCRs, or against the one or more other antigens), said order or arrangement is usually not critical and may be suitably chosen by the skilled person, optionally after some limited routine experiments based on the disclosure herein. Thus, when reference is made to a specific multivalent or multispecific polypeptide of the invention, it should be noted that this encompasses any order or arrangements of the relevant Nanobodies, unless explicitly indicated otherwise.

Finally, it is also within the scope of the invention that the polypeptides of the invention contain two or more Nanobodies and one or more further amino acid sequences (as mentioned herein).

For multivalent and multispecific polypeptides containing one or more $V_{HH}$ domains and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103 and WO 99/23221. Some other examples of some specific multispecific and/or multivalent polypeptide of the invention can be found in the applications by Ablynx N.V. referred to herein.

One preferred, but non-limiting example of a multispecific polypeptide of the invention comprises at least one NANOBODY® ($V_{HH}$) of the invention and at least one NANOBODY® ($V_{HH}$) that provides for an increased half-life. Such Nanobodies may for example be Nanobodies that are directed against a serum protein, and in particular a human serum protein, such as human serum albumin, thyroxine-binding protein, (human) transferrin, fibrinogen, an immunoglobulin such as IgG, IgE or IgM, or against one of the serum proteins listed in WO 04/003019. Of these, Nanobodies that can bind to serum albumin (and in particular human serum albumin) or to IgG (and in particular human IgG, see for example NANOBODY® ($V_{HH}$) VH-1 described in the review by Muyldermans, supra) are particularly preferred (although for example, for experiments in mice or primates, Nanobodies against or cross-reactive with mouse serum albumin (MSA) or serum albumin from said primate, respectively, can be used. However, for pharmaceutical use, Nanobodies against human serum albumin or human IgG will usually be preferred). Nanobodies that provide for increased half-life and that can be used in the polypeptides of the invention include the Nanobodies directed against serum albumin that are described in WO 04/041865, in WO 06/122787 and in the further patent applications by Ablynx N.V., such as those mentioned above.

For example, the some preferred Nanobodies that provide for increased half-life for use in the present invention include Nanobodies that can bind to amino acid residues on (human) serum albumin that are not involved in binding of serum albumin to FcRn (see for example WO 06/0122787); Nanobodies that are capable of binding to amino acid residues on serum albumin that do not form part of domain III of serum albumin (see for example WO 06/0122787); Nanobodies that have or can provide an increased half-life (see for example the U.S. provisional application 60/843, 349 by Ablynx N.V mentioned herein; see also WO08/ 028977); Nanobodies against human serum albumin that are cross-reactive with serum albumin from at least one species of mammal, and in particular with at least one species of primate (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*)) (see for example the U.S. provisional application 60/843,349 by Ablynx N.V; see also WO08/028977); Nanobodies that can bind to serum albumin in a pH independent manner (see for example the U.S. provisional application 60/850,774 by Ablynx N.V. mentioned herein) and/or Nanobodies that are conditional binders (see for example the U.S. provisional application 60/850,775 by Ablynx N.V.; see also WO08/043822).

Some particularly preferred Nanobodies that provide for increased half-life and that can be used in the polypeptides of the invention include the Nanobodies ALB-1 to ALB-10 disclosed in WO 06/122787 (see Tables II and III) of which ALB-8 (SEQ ID NO: 62 in WO 06/122787) is particularly preferred.

According to a specific, but non-limiting aspect of the invention, the polypeptides of the invention contain, besides the one or more Nanobodies of the invention, at least one NANOBODY® ($V_{HH}$) against human serum albumin.

Generally, any polypeptides of the invention with increased half-life that contain one or more Nanobodies of the invention, and any derivatives of Nanobodies of the invention or of such polypeptides that have an increased half-life, preferably have a half-life that is at least 1.5 times, preferably at least 2 times, such as at least 5 times, for example at least 10 times or more than 20 times, greater than the half-life of the corresponding NANOBODY® ($V_{HH}$) of the invention per se. For example, such a derivative or polypeptides with increased half-life may have a half-life that is increased with more than 1 hours, preferably more than 2 hours, more preferably more than 6 hours, such as more than 12 hours, or even more than 24, 48 or 72 hours, compared to the corresponding NANOBODY® ($V_{HH}$) of the invention per se.

In a preferred, but non-limiting aspect of the invention, such derivatives or polypeptides may exhibit a serum half-life in human of at least about 12 hours, preferably at least 24 hours, more preferably at least 48 hours, even more preferably at least 72 hours or more. For example, such derivatives or polypeptides may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

According to one aspect of the invention the polypeptides are capable of binding to one or more molecules which can increase the half-life of the polypeptide in vivo.

The polypeptides of the invention are stabilised in vivo and their half-life increased by binding to molecules which resist degradation and/or clearance or sequestration. Typically, such molecules are naturally occurring proteins which themselves have a long half-life in vivo.

Another preferred, but non-limiting example of a multi-specific polypeptide of the invention comprises at least one NANOBODY® ($V_{HH}$) of the invention and at least one NANOBODY® ($V_{HH}$) that directs the polypeptide of the invention towards, and/or that allows the polypeptide of the invention to penetrate or to enter into specific organs, tissues, cells, or parts or compartments of cells, and/or that allows the NANOBODY® ($V_{HH}$) to penetrate or cross a biological barrier such as a cell membrane, a cell layer such as a layer of epithelial cells, a tumor including solid tumors, or the blood-brain-barrier. Examples of such Nanobodies include Nanobodies that are directed towards specific cell-surface proteins, markers or epitopes of the desired organ, tissue or cell (for example cell-surface markers associated with tumor cells), and the single-domain brain targeting antibody fragments described in WO 02/057445 and WO 06/040153, of which FC44 (SEQ ID NO: 189 of WO 06/040153) and FC5 (SEQ ID NO: 190 of WO 06/040154) are preferred examples.

In the polypeptides of the invention, the one or more Nanobodies and the one or more polypeptides may be directly linked to each other (as for example described in WO 99/23221) and/or may be linked to each other via one or more suitable spacers or linkers, or any combination thereof.

Suitable spacers or linkers for use in multivalent and multispecific polypeptides will be clear to the skilled person, and may generally be any linker or spacer used in the art to link amino acid sequences. Preferably, said linker or spacer is suitable for use in constructing proteins or polypeptides that are intended for pharmaceutical use.

Some particularly preferred spacers include the spacers and linkers that are used in the art to link antibody fragments or antibody domains. These include the linkers mentioned in the general background art cited above, as well as for example linkers that are used in the art to construct diabodies or ScFv fragments (in this respect, however, its should be noted that, whereas in diabodies and in ScFv fragments, the linker sequence used should have a length, a degree of flexibility and other properties that allow the pertinent $V_H$ and $V_L$ domains to come together to form the complete antigen-binding site, there is no particular limitation on the length or the flexibility of the linker used in the polypeptide of the invention, since each NANOBODY® ($V_{HH}$) by itself forms a complete antigen-binding site).

For example, a linker may be a suitable amino acid sequence, and in particular amino acid sequences of between 1 and 50, preferably between 1 and 30, such as between 1 and 10 amino acid residues. Some preferred examples of such amino acid sequences include GLY-SER linkers, for example of the type $(GLY_xSER_y)_z$, such as (for example $(GLY_4SER)_3$ or $(GLY_3SER_2)_3$, as described in WO 99/42077 and the GS30, GS15, GS9 and GS7 linkers described in the applications by Ablynx mentioned herein (see for example WO 06/040153 and WO 06/122825), as well as hinge-like regions, such as the hinge regions of naturally occurring heavy chain antibodies or similar sequences (such as described in WO 94/04678).

Some other particularly preferred linkers are poly-alanine (such as AAA), as well as the linkers GS30 (SEQ ID NO: 85 in WO 06/122825) and GS9 (SEQ ID NO: 84 in WO 06/122825).

Other suitable linkers generally comprise organic compounds or polymers, in particular those suitable for use in proteins for pharmaceutical use. For instance, poly(ethyleneglycol) moieties have been used to link antibody domains, see for example WO 04/081026.

It is encompassed within the scope of the invention that the length, the degree of flexibility and/or other properties of the linker(s) used (although not critical, as it usually is for linkers used in ScFv fragments) may have some influence on the properties of the final polypeptide of the invention, including but not limited to the affinity, specificity or avidity for GPCRs, or for one or more of the other antigens. Based on the disclosure herein, the skilled person will be able to determine the optimal linker(s) for use in a specific polypeptide of the invention, optionally after some limited routine experiments.

For example, in multivalent polypeptides of the invention that comprise Nanobodies directed against a multimeric antigen (such as a multimeric receptor or other protein), the length and flexibility of the linker are preferably such that it allows each NANOBODY® ($V_{HH}$) of the invention present in the polypeptide to bind to the antigenic determinant on each of the subunits of the multimer. Similarly, in a multi-specific polypeptide of the invention that comprises Nanobodies directed against two or more different antigenic determinants on the same antigen (for example against different epitopes of an antigen and/or against different subunits of a multimeric receptor, channel or protein), the length and flexibility of the linker are preferably such that it allows each NANOBODY® ($V_{HH}$) to bind to its intended antigenic determinant. Again, based on the disclosure herein, the skilled person will be able to determine the optimal linker(s) for use in a specific polypeptide of the invention, optionally after some limited routine experiments.

It is also within the scope of the invention that the linker(s) used confer one or more other favourable properties or functionality to the polypeptides of the invention, and/or provide one or more sites for the formation of derivatives and/or for the attachment of functional groups (e.g. as described herein for the derivatives of the Nanobodies of the invention). For example, linkers containing one or more charged amino acid residues (see Table A-2 above) can provide improved hydrophilic properties, whereas linkers that form or contain small epitopes or tags can be used for the purposes of detection, identification and/or purification. Again, based on the disclosure herein, the skilled person will be able to determine the optimal linkers for use in a specific polypeptide of the invention, optionally after some limited routine experiments.

Finally, when two or more linkers are used in the polypeptides of the invention, these linkers may be the same or different. Again, based on the disclosure herein, the skilled person will be able to determine the optimal linkers for use in a specific polypeptide of the invention, optionally after some limited routine experiments.

Usually, for easy of expression and production, a polypeptide of the invention will be a linear polypeptide. However, the invention in its broadest sense is not limited thereto. For example, when a polypeptide of the invention comprises three of more Nanobodies, it is possible to link them by use of a linker with three or more "arms", which each "arm" being linked to a NANOBODY® ($V_{HH}$), so as to provide a "star-shaped" construct. It is also possible, although usually less preferred, to use circular constructs.

The invention also comprises derivatives of the polypeptides of the invention, which may be essentially analogous to the derivatives of the Nanobodies of the invention, i.e. as described herein.

The invention also comprises proteins or polypeptides that "essentially consist" of a polypeptide of the invention (in which the wording "essentially consist of" has essentially the same meaning as indicated hereinabove).

According to one aspect of the invention, the polypeptide of the invention is in essentially isolated from, as defined herein.

The amino acid sequences, Nanobodies, polypeptides and nucleic acids of the invention can be prepared in a manner known per se, as will be clear to the skilled person from the further description herein. For example, the Nanobodies and polypeptides of the invention can be prepared in any manner known per se for the preparation of antibodies and in particular for the preparation of antibody fragments (including but not limited to (single) domain antibodies and ScFv fragments). Some preferred, but non-limiting methods for preparing the amino acid sequences, Nanobodies, polypeptides and nucleic acids include the methods and techniques described herein.

As will be clear to the skilled person, one particularly useful method for preparing an amino acid sequence, NANOBODY® ($V_{HH}$) and/or a polypeptide of the invention generally comprises the steps of:

i) the expression, in a suitable host cell or host organism (also referred to herein as a "host of the invention") or in another suitable expression system of a nucleic acid that encodes said amino acid sequence, NANOBODY® ($V_{HH}$) or polypeptide of the invention (also referred to herein as a "nucleic acid of the invention"), optionally followed by:

ii) isolating and/or purifying the amino acid sequence, NANOBODY® ($V_{HH}$) or polypeptide of the invention thus obtained.

In particular, such a method may comprise the steps of:

i) cultivating and/or maintaining a host of the invention under conditions that are such that said host of the invention expresses and/or produces at least one amino acid sequence, NANOBODY® ($V_{HH}$) and/or polypeptide of the invention; optionally followed by:

ii) isolating and/or purifying the amino acid sequence, NANOBODY® ($V_{HH}$) or polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the amino acid sequences for the polypeptides of the invention given herein, and/or can be isolated from a suitable natural source. To provide analogs, nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a NANOBODY® ($V_{HH}$) and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring form of GPCRs as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art. Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises
i) at least one nucleic acid of the invention; operably connected to
ii) one or more regulatory elements, such as a promoter and optionally a suitable terminator;
and optionally also
iii) one or more further elements of genetic constructs known per se;
in which the terms "regulatory element", "promoter", "terminator" and "operably connected" have their usual meaning in the art (as further described herein); and in which said "further elements" present in the genetic constructs may for example be 3'- or 5'-UTR sequences, leader sequences, selection markers, expression markers/reporter genes, and/or elements that may facilitate or increase (the efficiency of) transformation or integration. These and other suitable elements for such genetic constructs will be clear to the skilled person, and may for instance depend upon the type of construct used, the intended host cell or host organism; the manner in which the nucleotide sequences of the invention of interest are to be expressed (e.g. via constitutive, transient or inducible expression); and/or the transformation technique to be used. For example, regulatory sequences, promoters and terminators known per se for the expression and production of antibodies and antibody fragments (including but not limited to (single) domain antibodies and ScFv fragments) may be used in an essentially analogous manner.

Preferably, in the genetic constructs of the invention, said at least one nucleic acid of the invention and said regulatory elements, and optionally said one or more further elements, are "operably linked" to each other, by which is generally meant that they are in a functional relationship with each other. For instance, a promoter is considered "operably linked" to a coding sequence if said promoter is able to initiate or otherwise control/regulate the transcription and/or the expression of a coding sequence (in which said coding sequence should be understood as being "under the control of" said promoter). Generally, when two nucleotide sequences are operably linked, they will be in the same orientation and usually also in the same reading frame. They will usually also be essentially contiguous, although this may also not be required.

Preferably, the regulatory and further elements of the genetic constructs of the invention are such that they are capable of providing their intended biological function in the intended host cell or host organism.

For instance, a promoter, enhancer or terminator should be "operable" in the intended host cell or host organism, by which is meant that (for example) said promoter should be capable of initiating or otherwise controlling/regulating the transcription and/or the expression of a nucleotide sequence—e.g. a coding sequence—to which it is operably linked (as defined herein).

Some particularly preferred promoters include, but are not limited to, promoters known per se for the expression in the host cells mentioned herein; and in particular promoters for the expression in the bacterial cells, such as those mentioned herein and/or those used in the Examples.

A selection marker should be such that it allows—i.e. under appropriate selection conditions—host cells and/or host organisms that have been (successfully) transformed with the nucleotide sequence of the invention to be distinguished from host cells/organisms that have not been (successfully) transformed. Some preferred, but non-limiting examples of such markers are genes that provide resistance against antibiotics (such as kanamycin or ampicillin), genes that provide for temperature resistance, or genes that allow the host cell or host organism to be maintained in the absence of certain factors, compounds and/or (food) components in the medium that are essential for survival of the non-transformed cells or organisms.

A leader sequence should be such that—in the intended host cell or host organism—it allows for the desired post-translational modifications and/or such that it directs the transcribed mRNA to a desired part or organelle of a cell. A leader sequence may also allow for secretion of the expression product from said cell. As such, the leader sequence may be any pro-, pre-, or prepro-sequence operable in the host cell or host organism. Leader sequences may not be required for expression in a bacterial cell. For example, leader sequences known per se for the expression and production of antibodies and antibody fragments (including but not limited to single domain antibodies and ScFv fragments) may be used in an essentially analogous manner.

An expression marker or reporter gene should be such that—in the host cell or host organism—it allows for detection of the expression of (a gene or nucleotide sequence present on) the genetic construct. An expression marker may optionally also allow for the localisation of the expressed product, e.g. in a specific part or organelle of a cell and/or in (a) specific cell(s), tissue(s), organ(s) or part(s) of a multicellular organism. Such reporter genes may also be expressed as a protein fusion with the amino acid sequence of the invention. Some preferred, but non-limiting examples include fluorescent proteins such as GFP.

Some preferred, but non-limiting examples of suitable promoters, terminator and further elements include those that can be used for the expression in the host cells mentioned herein; and in particular those that are suitable for expression in bacterial cells, such as those mentioned herein and/or those used in the Examples below. For some (further) non-limiting examples of the promoters, selection markers, leader sequences, expression markers and further elements that may be present/used in the genetic constructs of the invention—such as terminators, transcriptional and/or translational enhancers and/or integration factors—reference is made to the general handbooks such as Sambrook et al. and Ausubel et al. mentioned above, as well as to the examples that are given in WO 95/07463, WO 96/23810, WO 95/07463, WO 95/21191, WO 97/11094, WO 97/42320, WO 98/06737, WO 98/21355, U.S. Pat. No. 7,207,410, U.S. Pat. No. 5,693,492 and EP 1 085 089. Other examples will be clear to the skilled person. Reference is also made to the general background art cited above and the further references cited herein.

The genetic constructs of the invention may generally be provided by suitably linking the nucleotide sequence(s) of the invention to the one or more further elements described above, for example using the techniques described in the general handbooks such as Sambrook et al. and Ausubel et al., mentioned above.

Often, the genetic constructs of the invention will be obtained by inserting a nucleotide sequence of the invention in a suitable (expression) vector known per se. Some preferred, but non-limiting examples of suitable expression vectors are those used in the Examples below, as well as those mentioned herein.

The nucleic acids of the invention and/or the genetic constructs of the invention may be used to transform a host cell or host organism, i.e. for expression and/or production of the amino acid sequence, NANOBODY® ($V_{HH}$) or polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example:

- a bacterial strain, including but not limited to gram-negative strains such as strains of *Escherichia coli*; of *Proteus*, for example of *Proteus mirabilis*; of *Pseudomonas*, for example of *Pseudomonas fluorescens*; and gram-positive strains such as strains of *Bacillus*, for example of *Bacillus subtilis* or of *Bacillus brevis*; of *Streptomyces*, for example of *Streptomyces lividans*; of *Staphylococcus*, for example of *Staphylococcus carnosus*; and of *Lactococcus*, for example of *Lactococcus lactis;*
- a fungal cell, including but not limited to cells from species of *Trichoderma*, for example from *Trichoderma reesei*; of *Neurospora*, for example from *Neurospora crassa*; of *Sordaria*, for example from *Sordaria macrospora*; of *Aspergillus*, for example from *Aspergillus niger* or from *Aspergillus sojae*; or from other filamentous fungi;
- a yeast cell, including but not limited to cells from species of *Saccharomyces*, for example of *Saccharomyces cerevisiae*; of *Schizosaccharomyces*, for example of *Schizosaccharomyces pombe*; of *Pichia*, for example of *Pichia pastoris* or of *Pichia methanolica*; of *Hansenula*, for example of *Hansenula polymorpha*; of *Kluyveromyces*, for example of *Kluyveromyces lactis*; of *Arxula*, for example of *Arxula adeninivorans*; of *Yarrowia*, for example of *Yarrowia lipolytica;*
- an amphibian cell or cell line, such as Xenopus oocytes;
- an insect-derived cell or cell line, such as cells/cell lines derived from lepidoptera, including but not limited to *Spodoptera* SF9 and Sf21 cells or cells/cell lines derived from *Drosophila*, such as Schneider and Kc cells;
- a plant or plant cell, for example in tobacco plants; and/or
- a mammalian cell or cell line, for example a cell or cell line derived from a human, a cell or a cell line from mammals including but not limited to CHO-cells, BHK-cells (for example BHK-21 cells) and human cells or cell lines such as HeLa, COS (for example COS-7) and PER.C6 cells;

as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077; Frenken et al., (1998), supra; Riechmann and Muyldermans, (1999), supra; van der Linden, (2000), supra; Thomassen et al., (2002), supra; Joosten et al., (2003), supra; Joosten et al., (2005), supra; and the further references cited herein.

The amino acid sequences, Nanobodies and polypeptides of the invention can also be introduced and expressed in one or more cells, tissues or organs of a multicellular organism, for example for prophylactic and/or therapeutic purposes (e.g. as a gene therapy). For this purpose, the nucleotide sequences of the invention may be introduced into the cells or tissues in any suitable way, for example as such (e.g. using liposomes) or after they have been inserted into a suitable gene therapy vector (for example derived from retroviruses such as adenovirus, or parvoviruses such as adeno-associated virus). As will also be clear to the skilled person, such gene therapy may be performed in vivo and/or in situ in the body of a patient by administering a nucleic acid of the invention or a suitable gene therapy vector encoding the same to the patient or to specific cells or a specific tissue or organ of the patient; or suitable cells (often taken from the body of the patient to be treated, such as explanted lymphocytes, bone marrow aspirates or tissue biopsies) may be treated in vitro with a nucleotide sequence of the invention and then be suitably (re-)introduced into the body of the patient. All this can be performed using gene therapy vectors, techniques and delivery systems which are well known to the skilled person, and for example described in Culver, K. W., "Gene Therapy", 1994, p. xii, Mary Ann Liebert, Inc., Publishers, New York, N.Y); Giordano, Nature F Medicine 2 (1996), 534-539; Schaper, Circ. Res. 79 (1996), 911-919; Anderson, Science 256 (1992),808-813; Verma, Nature 389 (1994),239; Isner, Lancet 348 (1996), 370-374; Muhlhauser, Circ. Res. 77 (1995),1077-1086; Onodera, Blood 91; (1998),30-36; Verma, Gene Ther. 5 (1998),692-699; Nabel, Ann. N.Y. Acad. Sci.: 811 (1997), 289-292; Verzeletti, Hum. Gene Ther. 9 (1998), 2243-51; Wang, Nature Medicine 2 (1996),714-716; WO 94/29469; WO 97/00957, U.S. Pat. No. 5,580,859; U.S. Pat. No. 5,589,5466; or Schaper, Current Opinion in Biotechnology 7 (1996), 635-640. For example, in situ expression of ScFv fragments (Afanasieva et al., Gene Ther., 10, 1850-1859 (2003)) and of diabodies (Blanco et al., J. Immunol, 171, 1070-1077 (2003)) has been described in the art.

For expression of the Nanobodies in a cell, they may also be expressed as so-called "intrabodies", as for example described in WO 94/02610, WO 95/22618 and U.S. Pat. No. 7,004,940; WO 03/014960; in Cattaneo, A. & Biocca, S. (1997) Intracellular Antibodies: Development and Applications. Landes and Springer-Verlag; and in Kontermann, Methods 34, (2004), 163-170.

The amino acid sequences, Nanobodies and polypeptides of the invention can for example also be produced in the milk of transgenic mammals, for example in the milk of rabbits, cows, goats or sheep (see for example U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or tubers (for example in tobacco, maize, soybean or alfalfa) or in for example pupae of the silkworm *Bombix mori.*

Furthermore, the amino acid sequences, Nanobodies and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the *E. coli* Zubay system.

As mentioned above, one of the advantages of the use of Nanobodies is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of Nanobodies or NANOBODY® ($V_{HH}$)-containing protein therapeutics include strains of *E. coli, Pichia pastoris, S. cerevisiae* that are suitable for large scale expression/production/fermentation, and in particular for large scale pharmaceutical (i.e. GMP grade) expression/production/fermentation. Suitable examples of such strains will be clear to the skilled person. Such strains and production/expression systems are also made available by companies such as Biovitrum (Uppsala, Sweden).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a NANOBODY® ($V_{HH}$)-containing recombinant protein for which glycosylation is desired or required would necessitate the use of mammalian expression hosts that have the ability to glycosylate the expressed protein. In this respect, it will be clear to the skilled person that the glycosylation pattern obtained (i.e. the kind, number and position of residues attached) will depend on the cell or cell line that is used for the expression. Preferably, either a human cell or cell line is used (i.e. leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired amino acid sequence, NANOBODY® ($V_{HH}$) or polypeptide to be obtained.

Thus, according to one non-limiting aspect of the invention, the amino acid sequence, NANOBODY® ($V_{HH}$) or polypeptide of the invention is glycosylated. According to another non-limiting aspect of the invention, the amino acid sequence, NANOBODY® ($V_{HH}$) or polypeptide of the invention is non-glycosylated.

According to one preferred, but non-limiting aspect of the invention, the amino acid sequence, NANOBODY® ($V_{HH}$) or polypeptide of the invention is produced in a bacterial cell, in particular a bacterial cell suitable for large scale pharmaceutical production, such as cells of the strains mentioned above.

According to another preferred, but non-limiting aspect of the invention, the amino acid sequence, NANOBODY® ($V_{HH}$) or polypeptide of the invention is produced in a yeast cell, in particular a yeast cell suitable for large scale pharmaceutical production, such as cells of the species mentioned above.

According to yet another preferred, but non-limiting aspect of the invention, the amino acid sequence, NANOBODY® ($V_{HH}$) or polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

When expression in a host cell is used to produce the amino acid sequences, Nanobodies and the polypeptides of the invention, the amino acid sequences, Nanobodies and polypeptides of the invention can be produced either intracellullarly (e.g. in the cytosol, in the periplasma or in inclusion bodies) and then isolated from the host cells and optionally further purified; or can be produced extracellularly (e.g. in the medium in which the host cells are cultured) and then isolated from the culture medium and optionally further purified. When eukaryotic host cells are used, extracellular production is usually preferred since this considerably facilitates the further isolation and downstream processing of the Nanobodies and proteins obtained. Bacterial cells such as the strains of *E. coli* mentioned above normally do not secrete proteins extracellularly, except for a few classes of proteins such as toxins and hemolysin, and secretory production in *E. coli* refers to the translocation of proteins across the inner membrane to the periplasmic space. Periplasmic production provides several advantages over cytosolic production. For example, the N-terminal amino acid sequence of the secreted product can be identical to the natural gene product after cleavage of the secretion signal sequence by a specific signal peptidase. Also, there appears to be much less protease activity in the periplasm than in the cytoplasm. In addition, protein purification is simpler due to fewer contaminating proteins in the periplasm. Another advantage is that correct disulfide bonds may form because the periplasm provides a more oxidative environment than the cytoplasm. Proteins overexpressed in *E. coli* are often found in insoluble aggregates, so-called inclusion bodies. These inclusion bodies may be located in the cytosol or in the periplasm; the recovery of biologically active proteins from these inclusion bodies requires a denaturation/refolding process. Many recombinant proteins, including therapeutic proteins, are recovered from inclusion bodies. Alternatively, as will be clear to the skilled person, recombinant strains of bacteria that have been genetically modified so as to secrete a desired protein, and in particular an amino acid sequence, NANOBODY® ($V_{HH}$) or a polypeptide of the invention, can be used.

Thus, according to one non-limiting aspect of the invention, the amino acid sequence, NANOBODY® ($V_{HH}$) or polypeptide of the invention is an amino acid sequence, NANOBODY® ($V_{HH}$) or polypeptide that has been produced intracellularly and that has been isolated from the host cell, and in particular from a bacterial cell or from an inclusion body in a bacterial cell. According to another non-limiting aspect of the invention, the amino acid sequence, NANOBODY® ($V_{HH}$) or polypeptide of the invention is an amino acid sequence, NANOBODY® ($V_{HH}$) or polypeptide that has been produced extracellularly, and that has been isolated from the medium in which the host cell is cultivated.

Some preferred, but non-limiting promoters for use with these host cells include, for expression in *E. coli*: lac promoter (and derivatives thereof such as the lacUV5 promoter); arabinose promoter; left-(PL) and rightward (PR) promoter of phage lambda; promoter of the trp operon; hybrid lac/trp promoters (tac and trc); T7-promoter (more specifically that of T7-phage gene 10) and other T-phage promoters; promoter of the Tn10 tetracycline resistance gene; engineered variants of the above promoters that include one or more copies of an extraneous regulatory operator sequence;

for expression in *S. cerevisiae*: constitutive: ADH1 (alcohol dehydrogenase 1), ENO (enolase), CYC1 (cytochrome c iso-1), GAPDH (glyceraldehydes-3-phosphate dehydrogenase), PGK1 (phosphoglycerate kinase), PYK1 (pyruvate kinase); regulated: GAL1, 10,7 (galactose metabolic enzymes), ADH2 (alcohol dehydrogenase 2), PHOS (acid phosphatase), CUP1 (copper metallothionein); heterologous: CaMV (cauliflower mosaic virus 35S promoter);

for expression in *Pichia pastoris*: the AOX1 promoter (alcohol oxidase I);

for expression in mammalian cells: human cytomegalovirus (hCMV) immediate early enhancer/promoter; human cytomegalovirus (hCMV) immediate early promoter variant that contains two tetracycline operator sequences such that the promoter can be regulated by the Tet repressor; Herpes Simplex Virus thymidine kinase (TK) promoter; Rous Sarcoma Virus long terminal repeat (RSV LTR) enhancer/promoter; elongation factor 1α (hEF-1α) promoter from human, chimpanzee, mouse or rat; the SV40 early promoter; HIV-1 long terminal repeat promoter; β-actin promoter;

Some preferred, but non-limiting vectors for use with these host cells include:

vectors for expression in mammalian cells: pMAMneo (Clontech), pcDNA3 (Invitrogen), pMClneo (Stratagene), pSG5 (Stratagene), EBO-pSV2-neo (ATCC 37593), pBPV-1 (8-2) (ATCC 37110), pdBPV-MMT-neo (342-12) (ATCC 37224), pRSVgpt (ATCC37199), pRSVneo (ATCC37198), pSV2-dhfr (ATCC 37146), pUCTag (ATCC 37460) and 1ZD35 (ATCC 37565), as well as viral-based expression systems, such as those based on adenovirus;

vectors for expression in bacterial cells: pET vectors (Novagen) and pQE vectors (Qiagen);

vectors for expression in yeast or other fungal cells: pYES2 (Invitrogen) and *Pichia* expression vectors (Invitrogen);

vectors for expression in insect cells: pBlueBacII (Invitrogen) and other baculovirus vectors vectors for expression in plants or plant cells: for example vectors based on cauliflower mosaic virus or tobacco mosaic virus, suitable strains of *Agrobacterium*, or Ti-plasmid based vectors.

Some preferred, but non-limiting secretory sequences for use with these host cells include:

for use in bacterial cells such as *E. coli*: PelB, Bla, OmpA, OmpC, OmpF, OmpT, StII, PhoA, PhoE, MalE, Lpp, LamB, and the like; TAT signal peptide, hemolysin C-terminal secretion signal;

for use in yeast: α-mating factor prepro-sequence, phosphatase (phol), invertase (Suc), etc.;

for use in mammalian cells: indigenous signal in case the target protein is of eukaryotic origin; murine Ig κ-chain V-J2-C signal peptide; etc.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g. using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g. under suitable conditions), an amino acid sequence, NANOBODY® ($V_{HH}$) or polypeptide of the invention (and in case of a host organism: in at least one cell, part, tissue or organ thereof). The invention also includes further generations, progeny and/or offspring of the host cell or host organism of the invention, that may for instance be obtained by cell division or by sexual or asexual reproduction.

To produce/obtain expression of the amino acid sequences of the invention, the transformed host cell or transformed host organism may generally be kept, maintained and/or cultured under conditions such that the (desired) amino acid sequence, NANOBODY® ($V_{HH}$) or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

It will also be clear to the skilled person that the amino acid sequence, NANOBODY® ($V_{HH}$) or polypeptide of the invention may (first) be generated in an immature form (as mentioned above), which may then be subjected to post-translational modification, depending on the host cell/host organism used. Also, the amino acid sequence, NANOBODY® ($V_{HH}$) or polypeptide of the invention may be glycosylated, again depending on the host cell/host organism used.

The amino acid sequence, NANOBODY® ($V_{HH}$) or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the amino acid sequence, NANOBODY® ($V_{HH}$) or polypeptide of the invention) and/or preparative immunological techniques (i.e. using antibodies against the amino acid sequence to be isolated).

Generally, for pharmaceutical use, the polypeptides of the invention may be formulated as a pharmaceutical preparation or compositions comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. Such suitable administration forms—which may be solid, semi-solid or liquid, depending on the manner of administration—as well as methods and carriers for use in the preparation thereof, will be clear to the skilled person, and are further described herein.

Thus, in a further aspect, the invention relates to a pharmaceutical composition that contains at least one amino acid of the invention, at least one NANOBODY® ($V_{HH}$) of the invention or at least one polypeptide of the invention and at least one suitable carrier, diluent or excipient (i.e. suitable for pharmaceutical use), and optionally one or more further active substances.

Generally, the amino acid sequences, Nanobodies and polypeptides of the invention can be formulated and administered in any suitable manner known per se, for which reference is for example made to the general background art cited above (and in particular to WO 04/041862, WO 04/041863, WO 04/041865 and WO 04/041867) as well as to the standard handbooks, such as Remington's Pharmaceutical Sciences, 18" Ed., Mack Publishing Company, USA (1990) or Remington, the Science and Practice of Pharmacy, 21st Edition, Lippincott Williams and Wilkins (2005).

For example, the amino acid sequences, Nanobodies and polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e. transdermal or intradermal) administration.

Preparations for parenteral administration may for example be sterile solutions, suspensions, dispersions or emulsions that are suitable for infusion or injection. Suitable carriers or diluents for such preparations for example include, without limitation, sterile water and aqueous buffers and solutions such as physiological phosphate-buffered saline, Ringer's solutions, dextrose solution, and Hank's solution; water oils; glycerol; ethanol; glycols such as propylene glycol or as well as mineral oils, animal oils and vegetable oils, for example peanut oil, soybean oil, as well as suitable mixtures thereof. Usually, aqueous solutions or suspensions will be preferred.

The amino acid sequences, Nanobodies and polypeptides of the invention can also be administered using gene therapy methods of delivery. See, e.g., U.S. Pat. No. 5,399,346, which is incorporated by reference in its entirety. Using a gene therapy method of delivery, primary cells transfected with the gene encoding an amino acid sequence, NANOBODY® ($V_{HH}$) or polypeptide of the invention can additionally be transfected with tissue specific promoters to target specific organs, tissue, grafts, tumors, or cells and can additionally be transfected with signal and stabilization sequences for subcellularly localized expression.

Thus, the amino acid sequences, Nanobodies and polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the amino acid sequences, Nanobodies and polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the amino acid sequence, NANOBODY® ($V_{HH}$) or polypeptide of the invention. Their percentage in the compositions and preparations may, of course, be varied and may conveniently be between about 2 to about 60% of the weight of a given unit dosage form. The amount of the amino acid sequence, NANOBODY® ($V_{HH}$) or polypeptide of the invention in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the amino acid sequences, Nanobodies and polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the amino acid sequences, Nanobodies and polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The amino acid sequences, Nanobodies and polypeptides of the invention may also be administered intravenously or intraperitoneally by infusion or injection. Solutions of the amino acid sequences, Nanobodies and polypeptides of the invention or their salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the amino acid sequences, Nanobodies and polypeptides of the invention in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the amino acid sequences, Nanobodies and polypeptides of the invention may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, hydroxyalkyls or glycols or water-alcohol/glycol blends, in which the amino acid sequences, Nanobodies and polypeptides of the invention can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the amino acid sequences, Nanobodies and polypeptides of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the amino acid sequences, Nanobodies and polypeptides of the invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the amino acid sequences, Nanobodies and polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the amino acid sequences, Nanobodies and polypeptides of the invention required for use in treatment will vary not only with the particular amino acid sequence, NANOBODY® ($V_{HH}$) or polypeptide selected but also with the route of administration, the nature of the condition being treated and the age and condition of the patient and will be ultimately at the discretion of the attendant physician or clinician. Also the dosage of the amino acid sequences, Nanobodies and polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one GPCR-related diseases and disorders, said method comprising administering, to a subject in need thereof, a pharmaceutically active amount of an amino acid sequence of the invention, of a NANOBODY® ($V_{HH}$) of the invention, of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease or disorder that is associated with GPCRs, with its biological or pharmacological activity, and/or with the biological pathways or signalling in which GPCRs is involved, said method comprising administering, to a subject in need thereof, a pharmaceutically active amount of an amino acid sequence of the invention, of a NANOBODY® ($V_{HH}$) of the invention, of a polypeptide of the invention, and/or of a pharmaceutical composition comprising the same. In particular, the invention relates to a method for the prevention and/or treatment of at least one disease or disorder that can be treated by modulating GPCRs, its biological or pharmacological activity, and/or the biological pathways or signalling in which GPCRs is involved, said method comprising administering, to a subject in need thereof, a pharmaceutically active amount of an amino acid sequence of the invention, of a NANOBODY® ($V_{HH}$) of the invention, of a polypeptide of the invention, and/or of a pharmaceutical composition comprising the same. In particular, said pharmaceutically effective amount may be an amount that is sufficient to modulate GPCRs, its biological or pharmacological activity, and/or the biological pathways or signalling in which GPCRs is involved; and/or an amount that provides a level of the amino acid sequence of the invention, of a NANOBODY® ($V_{HH}$) of the invention, of a polypeptide of the invention in the circulation that is sufficient to modulate GPCRs, its biological or pharmacological activity, and/or the biological pathways or signalling in which GPCRs is involved.

The invention furthermore relates to a method for the prevention and/or treatment of at least one disease or disorder that can be prevented and/or treated by administering an amino acid sequence of the invention, a NANOBODY® ($V_{HH}$) of the invention or a polypeptide of the invention to a patient, said method comprising administering, to a subject in need thereof, a pharmaceutically active amount of an amino acid sequence of the invention, of a NANOBODY® ($V_{HH}$) of the invention, of a polypeptide of the invention, and/or of a pharmaceutical composition comprising the same.

More in particular, the invention relates to a method for the prevention and/or treatment of at least one disease or disorder chosen from the group consisting of the diseases and disorders listed herein, said method comprising administering, to a subject in need thereof, a pharmaceutically active amount of an amino acid sequence of the invention, of a NANOBODY® ($V_{HH}$) of the invention, of a polypeptide of the invention, and/or of a pharmaceutical composition comprising the same.

In another aspect, the invention relates to a method for immunotherapy, and in particular for passive immunotherapy, which method comprises administering, to a subject suffering from or at risk of the diseases and disorders mentioned herein, a pharmaceutically active amount of an amino acid sequence of the invention, of a NANOBODY® ($V_{HH}$) of the invention, of a polypeptide of the invention, and/or of a pharmaceutical composition comprising the same.

In the above methods, the amino acid sequences, Nanobodies and/or polypeptides of the invention and/or the compositions comprising the same can be administered in any suitable manner, depending on the specific pharmaceutical formulation or composition to be used. Thus, the amino acid sequences, Nanobodies and/or polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The amino acid sequences, Nanobodies and/or polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific amino acid sequence, NANOBODY® ($V_{HH}$) or polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more amino acid sequences, Nanobodies and/or polypeptides of the invention, or of one or more compositions comprising the same, in one or more pharmaceutically effective amounts or doses. The specific amount(s) or doses to administer can be determined by the clinician, again based on the factors cited above.

Generally, for the prevention and/or treatment of the diseases and disorders mentioned herein and depending on the specific disease or disorder to be treated, the potency of the specific amino acid sequence, NANOBODY® ($V_{HH}$) and polypeptide of the invention to be used, the specific route of administration and the specific pharmaceutical formulation or composition used, the amino acid sequences, Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single amino acid sequence, NANOBODY® ($V_{HH}$) or polypeptide of the invention will be used. It is however within the scope of the invention to use two or more amino acid sequences, Nanobodies and/or polypeptides of the invention in combination.

The Nanobodies, amino acid sequences and polypeptides of the invention may also be used in combination with one or more further pharmaceutically active compounds or principles, i.e. as a combined treatment regimen, which may or may not lead to a synergistic effect. Again, the clinician will be able to select such further compounds or principles, as well as a suitable combined treatment regimen, based on the factors cited above and his expert judgement.

In particular, the amino acid sequences, Nanobodies and polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

When two or more substances or principles are to be used as part of a combined treatment regimen, they can be administered via the same route of administration or via different routes of administration, at essentially the same time or at different times (e.g. essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of an amino acid sequence, NANOBODY® ($V_{HH}$) or polypeptide of the invention in the preparation of a pharmaceutical composition for prevention and/or treatment of at least one GPCR-related diseases and disorders; and/or for use in one or more of the methods of treatment mentioned herein.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention also relates to the use of an amino acid sequence, NANOBODY® ($V_{HH}$) or polypeptide of the invention in the preparation of a pharmaceutical composition for the prevention and/or treatment of at least one disease or disorder that can be prevented and/or treated by administering an amino acid sequence, NANOBODY® ($V_{HH}$) or polypeptide of the invention to a patient.

More in particular, the invention relates to the use of an amino acid sequence, NANOBODY® ($V_{HH}$) or polypeptide of the invention in the preparation of a pharmaceutical composition for the prevention and/or treatment of GPCR-related diseases and disorders, and in particular for the prevention and treatment of one or more of the diseases and disorders listed herein.

Again, in such a pharmaceutical composition, the one or more amino acid sequences, Nanobodies or polypeptides of the invention may also be suitably combined with one or more other active principles, such as those mentioned herein.

Finally, although the use of the Nanobodies of the invention (as defined herein) and of the polypeptides of the invention is much preferred, it will be clear that on the basis of the description herein, the skilled person will also be able to design and/or generate, in an analogous manner, other amino acid sequences and in particular (single) domain antibodies against GPCRs, as well as polypeptides comprising such (single) domain antibodies.

For example, it will also be clear to the skilled person that it may be possible to "graft" one or more of the CDR's mentioned above for the Nanobodies of the invention onto such (single) domain antibodies or other protein scaffolds, including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0 605 522, EP 0 460 167, U.S. Pat. No. 7,054,297, Nicaise et al., Protein Science (2004), 13:1882-1891; Ewert et al., Methods, 2004 October; 34(2): 184-199; Kettleborough et al., Protein Eng. 1991 October; 4(7): 773-783; O'Brien and Jones, Methods Mol. Biol. 2003: 207: 81-100; Skerra, J. Mol. Recognit. 2000: 13: 167-187, and Saerens et al., J. Mol. Biol. 2005 Sep. 23; 352(3):597-607, and the further references cited therein. For example, techniques known per se for grafting mouse or rat CDR's onto human frameworks and scaffolds can be used in an analogous manner to provide chimeric proteins comprising one or more of the CDR's of the Nanobodies of the invention and one or more human framework regions or sequences.

It should also be noted that, when the Nanobodies of the inventions contain one or more other CDR sequences than the preferred CDR sequences mentioned above, these CDR sequences can be obtained in any manner known per se, for example from Nanobodies (preferred), $V_H$ domains from conventional antibodies (and in particular from human antibodies), heavy chain antibodies, conventional 4-chain antibodies (such as conventional human 4-chain antibodies) or other immunoglobulin sequences directed against GPCRs. Such immunoglobulin sequences directed against GPCRs can be generated in any manner known per se, as will be clear to the skilled person, i.e. by immunization with GPCRs or by screening a suitable library of immunoglobulin sequences with GPCRs, or any suitable combination thereof. Optionally, this may be followed by techniques such as random or site-directed mutagenesis and/or other techniques for affinity maturation known per se. Suitable techniques for generating such immunoglobulin sequences will be clear to the skilled person, and for example include the screening techniques reviewed by Hoogenboom, Nature Biotechnology, 23, 9, 1105-1116 (2005) Other techniques for generating immunoglobulins against a specified target include for example the Nanoclone technology (as for example described in the published US patent application 2006-0211088), so-called SLAM technology (as for example described in the European patent application 0 542 810), the use of transgenic mice expressing human immunoglobulins or the well-known hybridoma techniques (see for example Larrick et al, Biotechnology, Vol. 7, 1989, p. 934). All these techniques can be used to generate immunoglobulins against GPCRs, and the CDR's of such immunoglobulins can be used in the Nanobodies of the invention, i.e. as outlined above. For example, the sequence of such a CDR can be determined, synthesized and/or isolated, and inserted into the sequence of a NANOBODY® ($V_{HH}$) of the invention (e.g. so as to replace the corresponding native CDR), all using techniques known per se such as those described herein, or Nanobodies of the invention containing such CDR's (or nucleic acids encoding the same) can be synthesized de novo, again using the techniques mentioned herein.

Further uses of the amino acid sequences, Nanobodies, polypeptides, nucleic acids, genetic constructs and hosts and host cells of the invention will be clear to the skilled person based on the disclosure herein. For example, and without limitation, the amino acid sequences of the invention can be linked to a suitable carrier or solid support so as to provide a medium than can be used in a manner known per se to purify GPCRs from compositions and preparations comprising the same. Derivatives of the amino acid sequences of the invention that comprise a suitable detectable label can also be used as markers to determine (qualitatively or quantitatively) the presence of GPCRs in a composition or preparation or as a marker to selectively detect the presence of GPCRs on the surface of a cell or tissue (for example, in combination with suitable cell sorting techniques).

Figure 2:
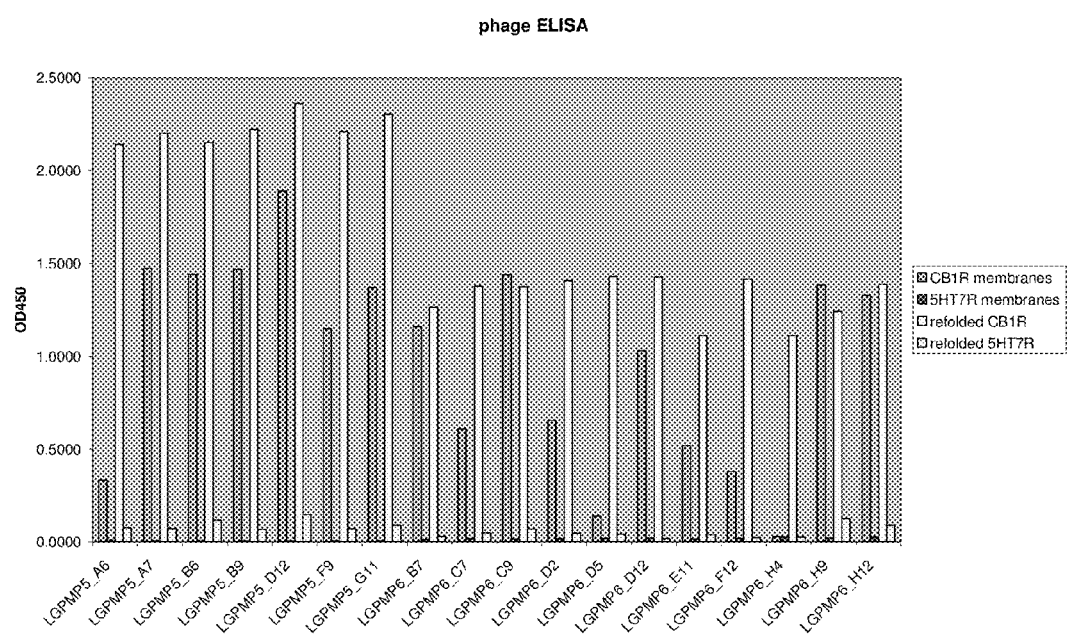
FIG. 2: GPCR binding specificity determined in a phage ELISA binding assay (as described in Example 3).

The invention will now be further described by means of the following non-limiting examples and in FIG. 1 (which schematically shows the structure of the three different classes of GPCRs) and FIG. 2 (which is a graph showing the screening results obtained in Example 3):

Example 1

Immunization and Library Construction

Mouse CB1R Membranes were purchased from Bioxtal (Mundolshein, France).

N-terminal biotinylated MC4R peptide was purchased from NeoMPS S.A. (Strasbourg, France). Sequence: biotinyl-KTSLHLWNRSSYRLHS (SP061354; lot. Nr. CK01160). The peptide sequence is located in the extracellular part of MC4R.

Two llamas (086 and 087) were immunized with 6 boosts of refolded GPCRs (PTHR, CB1R) according to standard protocols. The proteins were refolded using a standard protocol, based on the techniques described by Kiefer (Biochim. Biophys. Acta, 1610 (2003), 57-62). Blood was collected from these animals after 7 and 10 days after boost 6

Two llamas (100 and 101) were immunized with 6 boosts of KLH-NT peptide (derived from MC4R) according to Ablynx protocols. Blood was collected from these animals after 7 and 10 days after boost 6

Phage display libraries were prepared according to a standard protocol. Peripheral blood mononuclear cells were prepared from blood samples using Ficoll-Hypaque according to the manufacturer's instructions. Total RNA was extracted from these cells and used as starting material for RT-PCR to amplify NANOBODY® ($V_{HH}$) encoding gene fragments. These fragments were cloned into phagemid vector pAX50. Phage suspensions were prepared according to standard methods and stored after filter sterilization at 4° C. prior to selections.

Example 2

GPCR NANOBODY® ($V_{HH}$) Selections

Phage libraries were used for two rounds of selections on either refolded CB1R or on refolded PTHR. A second round on CB1R membranes was also performed for the CB1R NANOBODY® ($V_{HH}$) selection. All antigens were solid-phase immobilized on Nunc Maxisorp ELISA plates at 10 microg/well, 2 microg/well, 0.4 microg/well and 0 microg/well (background control) for the first round of selection. For the second round of selection either 2 microg/well, 0.4 microg/well refolded GPCR was used or 5 microg/well and 1 microg/well CB1R membranes were used in the MaxiSorp plates. Interacting phages were retrieved from both first and second round of selections using triethylamine elution.

Individual clones were isolated and were grown on 10 ml or 50 ml scale, and induced by adding IPTG for NANOBODY® ($V_{HH}$) expression. Periplasmic extracts (volume: 1 to 5 ml) were prepared according to standard methods.

Two phage libraries were used for selections for two rounds on biotinylated MC4R peptide. The peptide was captured by neutravidin which was solid-phase immobilized on Nunc Maxisorp ELISA plates at 500 ng/well. The peptide was coated in the first round of selection at a concentration ranging from 100 to 0.01 µM. For the second round of selection the peptide was used at a concentration ranging from 5 to 0.05 µM. Interacting phages were retrieved from both first and second round of selections using triethylamine elution. Individual clones were isolated and were grown 1 ml deep well plates, and induced by adding IPTG for NANOBODY® ($V_{HH}$) expression. Periplasmic extracts were prepared according to standard methods.

Phage libraries 100 and 101 were used for selections for two rounds on biotinylated MC4R peptide. The peptide was captured by neutravidin which was solid-phase immobilized on Nunc Maxisorp ELISA plates at 500 ng/well. The peptide was coated in the first round of selection at a concentration ranging from 100 to 0.01 µM. For the second round of selection the peptide was used at a concentration ranging from 5 to 0.05 µM. Interacting phages were retrieved from both first and second round of selections using triethylamine elution.

Individual clones were isolated and were grown 1 ml deep well plates, and induced by adding IPTG for NANO-BODY® ($V_{HH}$) expression. Periplasmic extracts were prepared according to standard methods.

Example 3

Screening

For the determination of the binding specificity to the GPCRs, the clones were tested in a phage ELISA binding assay setup. 500 ng/well refolded GPCR or GPCR membrane was solid-phase immobilized on Maxisorp microtiter plates (Nunc), and free binding sites were blocked using 4% Marvel Milk in PBS. 10 ul of phage suspension of the different clones in 100 µl 2% Marvel PBS was incubated with the immobilized antigen. After 1 h incubation, non-bound phage was removed by washing with PBS-Tween, followed by PBS. Next mouse-anti-M13-HRP antibody was incubated with the interacting phages. After 1 h incubation, non-bound phage was removed by washing with PBS-Tween, followed by PBS. Anti-M13 antibody presence was detected using TMB substrate (Pierce). Binding specificity was determined based on OD values compared to a control GPCR. The results are schematically shown in FIG. 2.

The amino acid sequences were tested for activity against CB1R, PTHR1 and MC4R, respectively, using a standard radioligand assay (see for example Andre' et al., Protein Sci 5:1115 (2006); Hassaine et al., (2006) Prot Purif Expr 45:343; Nicholson et al. J Pharmacol Exp Ther. 2006 May; 317(2):771-7. [Epub 2006 Jan. 25]. and Vilardaga et al., J Biol Chem. 2001 Sep. 7; 276(36):33435-43. Epub 2001 May 31), for example using membrane preparations that can be made as described in Hovius et al., (1998) J Neurochem 70:824).

Example 4

Binding Data

Binding of 4 clones directed against CB1R and of 4 clones against PTHR was measured on Biacore. The results are given in Tables B-2 and B-3.

TABLE B-2

| Binding of clones against CB1R | | | |
|---|---|---|---|
| vHH6B7 | vHH6H4 | vHH5G11 | vHH5D12 |
| CB1R 12 nM | 36 nM | 12 nM | non calculable |

TABLE B-3

| binding of clones on PTHR | | | | |
|---|---|---|---|---|
| | vHH22A3 | vHH26F2 | vHH23A3 | vHH26A6 | PTH (1-34) (ligand) |
| PTHR + CaCl2 | 9 nM | 70 nM | NT | NT | 0.2-16 nM |
| PTHR − CaCl2 | 17 nM | / | 22 nM | 17 nM | 4-23 nM |
| PTHR Fos12 | NT | 360 nM | NT | NT | 260 uM |

Table B-4 gives the amino acid sequences of a number of Nanobodies against some representative GPCRs.

SEQ ID NO's 413 to 430, 517 and 518: Nanobodies against CB1R
SEQ ID NO's 431 to 453: Nanobodies against PTHR1
SEQ ID NO's 519 to 525: Nanobodies against MCR4

Example 5

Highly Diverse Pool of Generated Nanobodies Underscores the Construction of Biparatopic Binders The CDR sequences of the different Nanobodies identified for each of the GPCR targets (CB1R, PTHR1 and MCR4) as described herein were compared to each other to indicate the diversity of binding properties present within the set of generated Nanobodies. The data for each of the GPCR targets are presented in Tables E, F and G respectively, and show a clear overview of the percentage of sequence identity (data presented below diagonal) and the number of different residues (data present above diagonal) amongst the generated Nanobodies previously provided in Table B-4 of US20100062004.

The data recited in Tables E to F respectively, illustrate that a high sequence diversity is present within the previously identified pool of Nanobodies (Table B-4).

Molecules with very different CDR sequences will bind to divergent epitopes. Hence, it is self-explanatory that the high sequence diversity observed for the CDRs generated against all 3 GPCR targets, i.e. CB1R, PTHR1 and MCR4 is correlated with a diversity of binding properties, and accordingly supports the production of biparatopic binders against these GPCR targets.

Example 5A

Biparatopic CB1R, PTHR1 and MCR4 Nanobodies

The monovalent CB1R, PTHR1 and MCR4 Nanobodies which displayed a high CDR sequence diversity as demonstrated by Tables E, F and G respectively are now further selected to engineer biparatopic binders. Different sets of CB1R, PTHR1 and MCR4 biparatopic Nanobodies are prepared by recombinantly linking the diverse monovalent binders using amino linkers with repetitive GGGGS sequences of various sizes. The potency of these constructs can be assessed by using the PathHunter® eXpress β-Arrestin GPCR assay which provides a direct measure of β-Arrestin binding to the GPCR of interest.

Example 6

Biparatopic CXCR4 Nanobodies

Another example of a therapeutic relevant GPCR is CXCR4, which was previously identified as such in Table C and Table D of US20100062004. This representative GPCR has now been further investigated by the present inventors. Different pools of highly similar clones able to inhibit specific [$^{125}$I]-CXCL12 binding were identified in a CXCR4 competition binding assay. Nanobodies representing these different pools were purified and further pharmacologically analyzed as detailed in the Example section of WO09/138519. In particular two representative monovalent Nanobodies 238D2 and 238D4 and different mono- and heterobivalent constructs thereof have been analyzed in depth:

6.1 Sequence Identity and Epitope Mapping

Similar to Example 5, the CDR sequences of the two monovalent Nanobodies 238D2 and 238D4 were compared to each other to investigate their binding diversity.

Table H indicates a CDR sequence similarity of only 37% between the two CXCR4 Nanobodies 238D2 and 238D4 and are thus assumed to bind different epitopes within CXCR4 as explained in Example 5.

Figure 3:
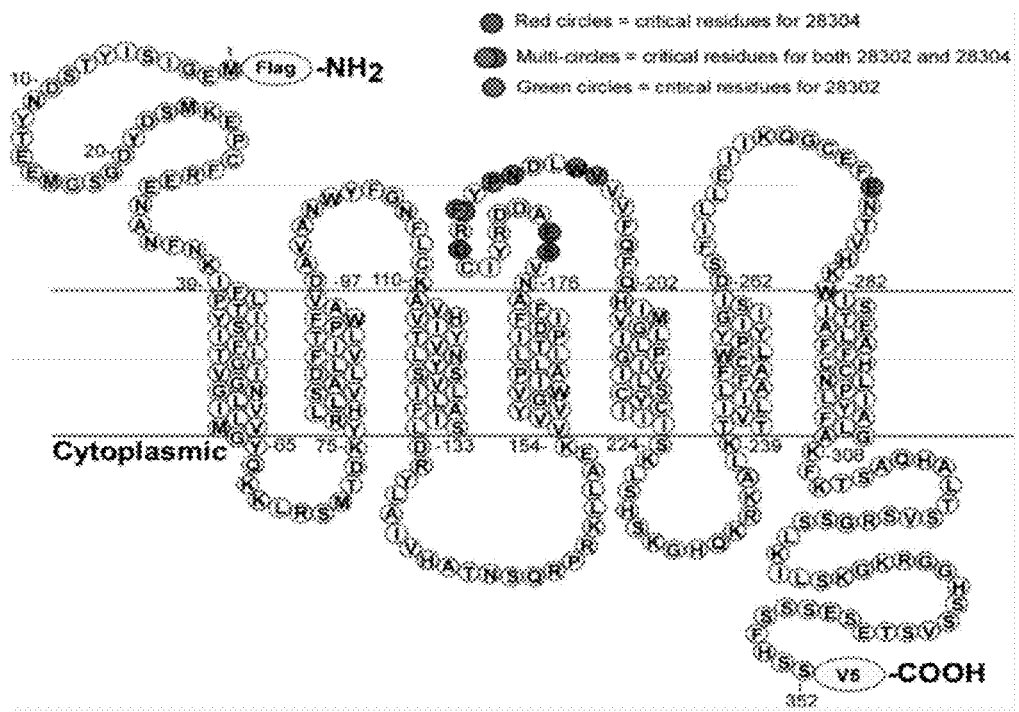
FIG. 3: Snake plot representation of human CXCR4 with highlighted amino acid residues involved in the binding of 238D2 (green filled circles) and 238D4 (red filled circles)

Moreover this hypothesis was further corroborated using the shotgun mutagenesis technology platform from Integral Moleuclar, which mapped the epitopes of the anti-CXCR4 Nanobodies at single amino acid resolution. This analysis (depicted in FIG. 3) clearly indicates that the two Nanobodies bind distinct but partially overlapping sites in the extracellular loops.

6.2 Potency of Mono-Specific Bivalent CXCR4 Nanobodies Versus Biparatopic CXCR4 Nanobodies Additionally, the inventors engineered a series of monospecific bivalent and biparatopic CXCR4 constructs. Recombinantly linking of 238D2 to 238D2 and 238D4 to 238D4 (i.e. mono-specific bivalent constructs) using amino acid linkers with repetitive GGGGS sequences of different sizes resulted in a 14 and 4.4-fold increase in affinity to CXCR4, respectively (Table I). Overall, short peptide linkers were used favoring binding to CXCR4 monomers.

Astonishingly, a more significant increase in affinity was observed when 238D2 was linked to 238D4 (i.e. biparatopic constructs). In case of the obtained biparatopic NANOBODY® ($V_{HH}$) 238D2-20GS-238D4, the affinity to CXCR4 was increased by 27 and 17-fold over the respective monovalent counterparts 238D2 and 238D4. Alteration in the linker size between 15 amino acids and 20 amino acids does not show any influence in respect to the receptor affinity (compare L3 and L8).

6.3 Comparison Effectivity 12G5 vs Monovalent 238D2, 238D4 and Bivalent Nanobodies In membrane binding experiments mAb 12G5, which is a known neutralizing CXCR4 antibody, seems only to displace 50% of radiolabeled 125I-CXCL12 (CXCR4 ligand). We were therefore interested to test whether 12G5 effectively inhibits CXCR4 function.

Inositol Phosphate Measurement

In an effort to functionally characterize the Nanobodies 238D2 and 238D4, the inventors measured their ability to activate G-protein signaling or to inhibit the CXCL12-induced G-protein signaling in HEK293T cells transiently co-transfected with cDNAs encoding CXCR4 and Gαqi5. This assay is based upon the use of the chimeric Gαqi5-protein that contains of a Gαq backbone with the 5 C-terminal amino acids replaced by those from Gαi. The chimeric G-protein is activated by CXCR4 like a Gαi subunit but transduces signals like Gαq proteins (Coward, P., et al., Chimeric G Proteins Allow a High-Throughput Signaling Assay of G1-Coupled Receptors, Analytical Biochemistry (1999) 270: 242-248). Thus, the activation of Gαqi5 can be quantified by the measurement of accumulated inositol phosphates.

12G5 has been tested as a full curve (n=2) and single point (10 nM) on hCXCR4/Gαqi5; cells were stimulated with 30 nM CXCL12.

Methods: On day 1, HEK293T cells were plated out at a density of 2 million cells/dish. On day 2, these cells were transfected with 2.5 µg CXCR4 DNA and 2.5 µg Gαqi5, using the PEI method. Cells were plated out the next day in poly-L-lysine coated 24 well plates (500 µl/well) and labeled after 4-6 hours with 2 µCi/ml 3H-inositol in inositol-free medium. On day 4, cells were pre-stimulated with either nanobodies, 12G5 or 1 µM AMD3100 in Rosenkilde buffer for 2 hours at 37° C. After this pre-stimulation, both 30 nM CXCL12 (or buffer for basal signaling) and 10 mM LiCl were added to each well (final concentrations), followed by a final 2 hour incubation at 37° C. After this final incubation, the reaction was stopped by aspiration of stimulation medium and addition of 10 mM formic acid (FIG. 4).

Figure 4:
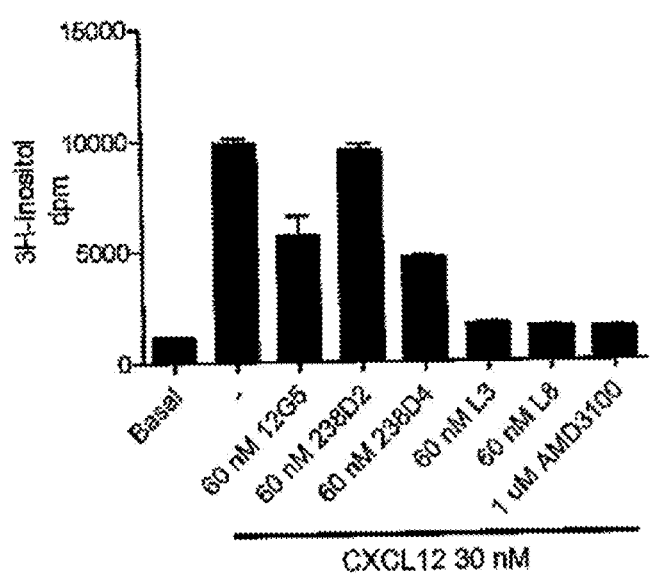
FIG. 4: Bivalent nanobodies inhibit CXCR4-mediated signalings. CXCL12-induced inositol phosphate accumulation in cells transfected with CXCR4 and the chimeric G$\alpha$qi5, protein is inhibited by monovalent and bivalent nanobodies.

As seen in FIG. 4, the biparatopic 238D2-238D4 Nanobodies (L3 and L8 constructs) clearly show a significantly increased inhibitory potency compared to their monovalent counterparts and the monoclonal antibody 12G5.

Moreover, the biparatopic constructs effectively inhibited CXCR4 function at a concentration of 60 nM, which is approximately 16-fold lower than the concentration needed for the clinically validated small molecule compound plerixafor or AMD3100 (1 µM).

Example 7

Biparatopic CXCR7 Nanobodies

CXCR-7 is a member of the G-protein coupled receptor family, which binds to the chemokines CXCL12/SDF-1 and CXCL11. Ligand binding to CXCR7 activates MAP kinases through Beta-arrestins.

After immunizations of llamas, selections of phage displaying human CXCR7 binding Nanobodies were performed. CXCR7 specific Nanobodies were identified by phage ELISA and FACS analysis. Nanobodies 08A05, 08A10, 07C03, 01C10 and 14G03 were characterized in more detail.

7.1 Epitope Mapping

The minimal epitope of Mab 11G8 (human CXCR7 specific monoclonal antibody, R&D systems) is known to be F14SDISWP20 located at the CXCR7 N-terminus (see e.g., WO2008/048519). In order to map the epitope of the Nanobodies, cells were incubated simultaneously with 20 nM Mab 11G8 APC (R&D) and with diluted test molecules for 2 h at 4° C. The level of competition with Mab 11G8 APC ranges from about 20% to 100%, suggesting that the respective NANOBODY® ($V_{HH}$) epitopes match to a high degree (high % of competition) with the Mab 11G8 epitope or to a low degree (low % of competition) or induce allosteric changes affecting the Mab 11G8 binding. The results suggest that NANOBODY® ($V_{HH}$) 01C10 hits an epitope distinct from the epitope(s) hit by the other selected Nanobodies.

Nanobodies 08A05, 08A10, 07C03, 01C10 and 14G03, Mab 8F11 (Biolegend), Mab 11G8 (R&D) and Mab 9C4 (MBL) were further tested for competition with Alexa647-labelled 14G03 in FACS analysis. Nanobodies 08A05, 08A10, 07C03, Mab 8F11, Mab 11G8 and Mab 9C4 compete with 14G03 binding to CXCR7, while 01C10 does not, suggesting again that 01C10 hits an epitope distinct from the epitope(s) hit by the other selected Nanobodies.

In a third approach, Nanobodies were tested for their binding to a set of 10 point mutants of CXCR7 (S9A, F14Y, I17L, S18N, W19A, S23G, D25A, V32A, M33Q, N36T), which yielded information on the individual NANOBODY® ($V_{HH}$) epitopes. For Nanobodies 08A05, 08A10, 07C03 and 14G03, the epitope included residue M33, while that of 01C10 did not. The binding of 01C10 was affected by the W19A mutation, while this mutation did not affect the binding of 08A05, 08A10, 07C03 and 14G03. Once more, these data indicate that 01C10 hits a distinct epitope.

Based on the foregoing results, the Nanobodies 14G03, 08A05, 08A10 and 07C03 were grouped together (Group 2), while NANOBODY® (V$_{HH}$) 01C10 was classified into another group (Group 1).

7.2 Potency of Biparatopic Constructs Versus Bivalent and Trivalent CXCR7 Nanobodies The PathHunter eXpress β-arrestin assay (DiscoverX) was used to assess the potency of the CXCR7 NANOBODY® (V$_{HH}$) constructs in inhibiting β-arrestin recruitment.

The anti-CXCR7 constructs have an ALB8 building block, which binds serum albumin (HSA). ALB8 is intended for half life extension (see for example WO08/028977 described herein). The β-arrestin assay was run in the presence of HSA. Longer linkers preceding the ALB8 building block were evaluated to minimize sterical interference of HSA binding to the NANOBODY® (V$_{HH}$) (Table K).

The biparatopic constructs 038, 085 and 052 have an IC50 value in the low nM range in the presence of HSA.

In contrast, the mono-specific bivalent constructs 055 and 093 show no or weak antagonism. If only one CXCR7 building block is used in the construct, the concentration for reaching IC50 is dramatically higher than with the biparatopic constructs.

In conclusion, biparatopic constructs inhibit β-arrestin recruitment better than corresponding mono-specific bivalent constructs.

7.3 Inhibition of β-Arrestin Recruitment of Trivalent CXCR7 Nanobodies

The PathHunter eXpress β-arrestin assay (DiscoverX) was also used to assess the antagonistic effect of trivalent CXCR7 Nanobodies on recruitment of β-arrestin (see point 7.2 above). A panel of Nanobodies (clones) was screened at a 100 nM concentration in the assay. Results are ranked in Table L on the basis of efficiency of inhibition. The most efficient molecules constitute combinations of Group 1 (01C10) and Group 2 building blocks=biparatopic constructs, i.e. clones 038, 052, 021, 023 and 049.

Although Nanobodies of Group 2 either monovalently or bivalently demonstrate superior binding and competition characteristics than the corresponding Nanobodies of Group 1, Nanobodies of Group 1 combined with Nanobodies of Group 2 gave wholly unexpectedly the best results in the β-arrestin recruitment assay (see Table L).

TABLE B-4

Nanobodies against some representative GPCRs.
SEQ ID NO's 413 to 430, 517 and 518: Nanobodies against CB1R
SEQ ID NO's 431 to 453: Nanobodies against PTHR1
SEQ ID NO's 519 to 525: Nanobodies against MCR4

LGPMP5_A6 SEQ ID NO 413
EVQLVESGGGLVQAGGSLRLACAASGSIFSFNAMGWYRQAPGKQRELL
AVITRDGITKYADSVKGRFTISRDNAKNTMYLQMNSLKPEDTAVYYCHTG
LPTGRGSHSDYWGQGTQVTVSS

LGPMP5_A7 SEQ ID NO 414
EVQLVESGGGLVQAGGSLRLSCAASGRTLSNYDMGWFRQAPGKEREFV
ATIRWSTSSTYYADSVKGRFTISSDNTKNTVDLRMNSLTPEDTAVYYCAA
RSVYSYEYNYWGQGTQVTVSS

LGPMP5_B6 SEQ ID NO 415
EVQLVESGGGLVQAGGSLRLSCAASGRTLTNYDMGWFRQAPGKEREFV
ATIRWSTSETYYADSVKGRFTISKDNTKNTVALQMNSLTPEDTALYYCAA
RSVYSYEYNYWGQGTQVTVSS

TABLE B-4-continued

Nanobodies against some representative GPCRs.
SEQ ID NO's 413 to 430, 517 and 518: Nanobodies against CB1R
SEQ ID NO's 431 to 453: Nanobodies against PTHR1
SEQ ID NO's 519 to 525: Nanobodies against MCR4

LGPMP5_B9 SEQ ID NO 416
EVQLVESGGGLVQAGGSLRLSCAASGRTLNNHDMGWFRQAPGKEREFV
ATVRWGTSSTYYADSVKGRFTISSDNTKNTVALQMNRLTPEDTGVYYCAA
RSVYSYEYTYWGQGTQVTVSS

LGPMP5_D12 SEQ ID NO 417
EVQLVESGGGLVQAGGSLRLSCAASRRTFSSFVMAWFRQAPGKEREFV
AAIYGTGGELVYYENSVKGRFTISRDNAKSTMYLQMNSLKPEDTGVYYCA
VELTVRSIDLRRPLEYDYWGQGTQVTVSS

LGPMP5_F9 SEQ ID NO 418
EVQLVESGGGLVQAGGSLRLSCAASGRTLVNYDMGWFRQAPGKEREFV
ATIRWSTSETYYADSVKGRFTISSDNTKNTVDLQMNSLTPEDTAVYYCAA
RSVYSYEYNYWGQGTQVTVSS

LGPMP5_G11 SEQ ID NO 419
EVQLVKSGGGLVQAGGSLRLSCAASGRTLSNYDMGWFRQAPGKEREFV
ATIRWSTGETYYTDSVKGRFTISKDNTKNTVDLQMNSLTPEDTAVYYCAS
RSVYSYEYNYWGQGTQVTVSS

LGPMP6_B7 SEQ ID NO 420
EVQLVESGGGLVQAGGSLRLSCAASGRTLRNYDMGWFRQAPGKEREFV
ATIRWSTSETYYADSVKGRFTISSDNAKNTVDLQMNSLTPGDTGVYYCAA
RSVYSYDYNYWGQGTQVTVSS

LGPMP6_C7 SEQ ID NO 421
EVQLVESGGGLVQAGGSLRLSCAASGRTLSNYDVGWFRQAPGKEREFV
ATIRWSTSSTYYADPVKGRFTISSDNIKNTVDLQMNSLTPEDTAVYYCAA
RSVYSYEYNYWGQGTQVTVSS

LGPMP6_C9 SEQ ID NO 422
EVQLVESGGGLVQAGGSLRLSCAASGRTLSNYDMGWFRQAPGKEREFV
ATIRWSTSETYYADSVKGRFTISSSNTKNTVDLQMNSLTPEDTAVYYCAA
RSVYSYEYNYWGQGTQVTVSS

LGPMP6_D2 SEQ ID NO 423
EVQLMESGGGLVQAGGSLRLSCAASGRTLTNYDMGWFRQAPGKEREFV
ATIRWSTSETYYADSVKGRFTISKDNTKNTVALQMNSLTPEDTALYYCAA
RSVYSYEYNYWGQGTQVTVSS

LGPMP6_D5 SEQ ID NO 424
EVQLVESGGGLEQAGGSLRLSCAVSRSIFETNTMAWFRQAPGKQRELVA
RISSTGDTNYADSVKGRFTISRDNAKNTVYLQMNSLKPEDTAVYYCHVAG
PYGSKFAWGQGTQVTVSS

LGPMP6_D12 SEQ ID NO 425
EVQLVESGGGLVQAGGSLRLSCAASGRTLSNHDVGWFRQAPGKEREFV
ATMRWSTGSTYYADSVKGRFTISSDNTKNTVDLQMNSLTPEDTAVYYCAA
RSVYSYEYNYWGQGTQVTVSS

LGPMP6_E11 SEQ ID NO 426
EVQLVESGGGLVQAGGSLRLSCAASGRTLRNYDLGWFRQAPGKEREFV
ATIRWSTSETYYADSVKGRFTISSDNAKNTVDLQMNSLTPEDTGVYYCAA
RSVYSYDYNYWGQGTQVTVSS

LGPMP6_F12 SEQ ID NO 427
EVQLVESGGGLVQAGGSLRLSCAASGRTLTNHDMGWFRQAPGKEREFV
ATIRWGTTDTYYADSVKGRFTISSDNTKNTVHLQMNSLTPEDTGVYYCAA
RSVYSYEYTYWGQGTQVTVSS

LGPMP6_H4 SEQ ID NO 428
EVQLVESGGGLVQAGGSLRLACAASGSIFSFNAMGWYRQAPGKQRELL
AVITRDGITKYADSVKGRFTISRDNAKNTMYLQMNSLKPEDTAVYYCHTG
LPTGRGSHSDYWGQGTQVTVSS

LGPMP6_H9 SEQ ID NO 429
EVQLVESGGGLVQAGGSLRLSCAASGRTLNDHDVGWFRQAPGKEREFV
ATIRWSSKSTYYADSVKGRFTISSDNTKNTVDLRMNSLTPEDTAVYYCAA
RSVYSYEYNYWGQGTQVTVSS

TABLE B-4-continued

Nanobodies against some representative GPCRs.
SEQ ID NO's 413 to 430, 517 and 518: Nanobodies against CB1R
SEQ ID NO's 431 to 453: Nanobodies against PTHR1
SEQ ID NO's 519 to 525: Nanobodies against MCR4

LGPMP6_H12 SEQ ID NO 430
EVQLVESGGGLVQAGGSLRLSCAASGRTLSNYDMGWFRQAPGKEREFV
ATIRWSTRETYYTDSVKGRFTISSDNTKNTVHLQMNSLTPEDTAVYYCAA
RSVYSYEYNYWGQGTQVTVSS

PMPLG22-A2 SEQ ID NO 431
EVQLVESGGGLVQAGGSLRLSCSSSGFTSTDYAIGWFRQAPGKARTGVSI
ISRSDGSTWYADSVKGRFTISSDNAKNTVYLQMNSLKPEDTAVYYCAAQL
RHNFGMGDYDYWGQGTQVTVSS

PMPLG22-A3 SEQ ID NO 432
EVQLVESGGGLVQAGGSLRLSCAASGNIFANNIMGWYRQPPGKEREFVA
HVSHDGDSMYAVSVKGRFAISRKDATNLYLQMNSLKPEDTAIYFCRLLNI
PTQGRMEGFWGQGTQVTVSS

PMPLG22-A9 SEQ ID NO 433
EVQLVESGGGLVQPGGSLRLSCAASGFTLDGYAIGWFRQAPGKEREGVS
CSNKDGSTAYSDSVKGRFTISRDNAKNTVYLEMNGLKPEDAAIYYCATKS
GRYCLSHMDYWGIGTLVTVSS

PMPLG22-B7 SEQ ID NO 434
EVQLVESGGGLVQTGGSLRLSCAASGMTFRLYALSWYRQAPGERREVV
ATITIDGKTNYAEPLKGRFTISRDNAKNTIYLQMNSLKPEDTAVYYCNAV
FSRGPLTYWGRGTQVTVSS

PMPLG22-B11 SEQ ID NO 435
EVQLVESGGGLVQAGGSLRLSCAASRSRSSFDDMGWYRQAPGKQREFV
AGITLGGSTIYADSVKGRFTISMDSARNTGYLQMNSLKPEDTAVYYCNAA
LDGYSGSSWGQGTQVTVSS

PMPLG22-B12 SEQ ID NO 436
EVQLVESGGGLVQAGGSLRLSCVASGNIFSDNLMGWYRQAPGKQREFV
AHMSHDGTTNYEDSVKGRFTISRENAKNTLYLHMNSLKPEDTAIYYCRLL
TIPTTGRAEGFWGQGTQVTVSS

PMPLG22-C3 SEQ ID NO 437
EVQLVESGGGLVQAGGSLRLSCAASRSRSSFNDMGWYRQAPGKQREFV
AGIPVGGSTVYADSVKGRFTISMDSARNRGYLQMNSLKPEDTAVYYCNAY
LDGYSGSSWGQGTQVTVSS

PMPLG23-A3 SEQ ID NO 438
EVQLVESGGGLVQAGGSLRLSCAASGLTFSNYAMGWFRQAPGKEREW
VASINWSGGSTYYEDSVEGRFTISRDNAKNTVNLQMNSLKPEDTAVYYCA
AKRGHYSREYDYWGQGTQVTVSS

PMPLG23-C1 SEQ ID NO 439
KVQLVESGGGLVQAGGSLRLSCAASASIISS AALGWYRQAPGKRREFVA
GILSDGRELYVDSVKGRFTVSRDNAKNTVYLQMNSLKPEDTAVYYCNLDI
DYRDYWGQGTQVTVSS

PMPLG23-E12 SEQ ID NO 440
EVQLVESGGGLVQAGGSLRLSCAASASIISSAALGWYRQAPGRRREFVA
GILSDGRELYVDSVKGRFTVSRDNAKNTVYLQMNSLKPEDTAVYYCNLDI
DYRDYWGQGTQVTVSS

PMPLG23-F2 SEQ ID NO 441
KVQLVESGGGLVQAGGSLRLSCAASGSIFSISLVGWYRQAPGKQREFVA
HIYSDGSINYGNSVKGRFTISRDNAKNTVDLQMNNLKPEDTAVYYCRLLD
TARGVGYWGQGTQVTVSS

PMPLG23-H9 SEQ ID NO 442
EVQLVESGGGLVQAGGSLRLSCAASASIISSAALGWYRQAPGKRREFVA
GILSDGRELYVDSVKGRFTVSRDNAKNTVYLQMNSLKPEDTAVYYCNLDI
DYRDYWGQGTQVTVSS

PMPLG26-A2 SEQ ID NO 443
EVQLVESGGGLVQAGGALRLSCTASGITFKRYDMGWYRQAPGKEREW
VTTITSEGTANSADSVKGRFTISRDNAKNTVYLQMNSLKSEDTAVYYCNA
QFTLARHLVYWGQGTQVTVSS

PMPLG26-A6 SEQ ID NO 444
EVQLVESGGGLVQAGGSLRLSCAASRSRSSFDDMGWYRQAPGKQREFV
GGITLGGSTIYADSVKGRFTISMDSARNTGYLQMNSLKPEDTAVYYCNAA
LDGYSGSSWGQGTQVTVSS

PMPLG26-B6 SEQ ID NO 445
EVQLVESGGGLVQAGGSLRLSCAASRSRSSFDDMGWYRQAPGKQREFV
AGITLGGSTIYADSVKGRFTISMDSARNTGYLQMNSSLKPEDTAVYYCNAV
LDGYSGSSWGQGTQVTVSS

PMPLG26-C4 SEQ ID NO 446
EVQLVESGGGLVQAGGSLRLSCAASGNIFANNIMGWYRQPPGKEREFVA
HVSHDGYSMYAVSVEGRFTISRENATNLYLQMNSLKPEDTAIYFCRLLTI
PPQGRMEGFWGQGTQVTVSS

PMPLG26-C5 SEQ ID NO 447
EVQLVESGGGLVQAGGSLRLSCAASGNIFSDNIMGWYRQAPGKQREFV
AHMSRDGTSNYEDSVKGRFTISRENAKNTLYLQMNSLKPEDTAIYYCRLL
TIPTTGRKEGFWGQGTQVTVSS

PMPLG26-D12 SEQ ID NO 448
EVQLVESGGGLVQAGGSLRLSCAASGSISNDNSMGWYRQAPGWQRELV
AIKFSGGTTDIAESAKGRFTISRDNAKNTVYLQMNSLRPEDTAVYYCRLF
LPSLAMGYWGQGTQVTVSS

PMPLG26-E4 SEQ ID NO 449
EVQLVESGGGLVQAGGSLRLSCAASGNIFANNIMGWYRQPPGKEREFVA
HVSHDGDSMYAVSVKGRFTISRKDATNLYLQMNSLKPEDTAIYFCRLLNI
PTQGRMEGFWGQGTQVTVSS

PMPLG26-E6 SEQ ID NO 450
EVQLVESGGGLVQAGGSLRLSCAASGNIFANNIMGWYRQPPGKEREFVA
HVSDDGDSMYAVSVKGRFTISRKNATNLYLQMNSLKPEDTAIYFCRLLNI
PTQGRMEGFWGQGTQVTVSS

PMPLG26-F2 SEQ ID NO 451
EVQLVESGGGLVQAGGSLRLSCVASGFSFDDDYAIGWFRQAPGQDREPLA
CITSGGTRNYNPSVMARFRIDRDNSVKTVYLQINTLKPEDTAVYYCSTEL
DRQGGSAHECREYDTWGQGTQVTVSS

PMPLG26-G11 SEQ ID NO 452
EVQLVESGGGLVQAGGSLRLSCAASESISSFNAMGWYRQGPGKLRELVA
QITDLHKDYAESAKGRFTISRDNAKNTVDLQMNSLKPEDTGVYYCAAFRG
IMRPDYWGQGTQVTVSS

PMPLG26-H11 SEQ ID NO 453
EVQLVESGGGLVQAGKSLSLSCAASDSRFSGRFNILNMGWYRQAPGKQ
REWVTTLLSTGSPIYADSVKGRFTISRDHAKNTVYLQMHSLKPDDTANYI
CFARLTPTGTVWGQGTQVTVSS

6F12 SEQ ID NO 517
EVQLVESGGGLVQAGGSLRLSCAASGRTLSDHDMGWFRQAPGKEREFV
ATMRWGTSSTYYADSVKGRFTISSDNTKNTVYLQMNSLTPEDTAVYYCAA
RSVYSYEYTYWGQGTQVTVSS

5D12 SEQ ID NO 518
EVQLVESGGGLVQAGGSLRLSCTASERTFSSYNMGWFRQAPGKERVFV
AVIDWSGGLAYYADSVKGRFTISRDNAKKTVYLQMNSLKPEDTAVYYCAA
RSVYRGSTKPYEYDYWGQGTQVTVSS 60-11B SEQ ID NO 519
EVQLVESGGGLVQPGGSLRLSCAASGFTLDDYAVSWFRRAPGKEREGVS
CISSSSSSDTYYADSVRGRFSISRDSAKNTVYLQMNSLKPEDTAVYYCAA
DRHCLGSDWDEYDWGQGTQVTVSS 59-8A SEQ ID NO 520
EVQLVESGGGLVHAGDSLRLSCAASGFTLDDYAVSWFRQAPGKAREGL
SCISAEDGSTYYADSVKGRFIISRDNAKNTVYLQMNSLKPEDTAVYYCAA
EDSCLSSDYDAYDGWGQGTQVTVSS

TABLE B-4-continued

Nanobodies against some representative GPCRs.
SEQ ID NO's 413 to 430, 517 and 518: Nanobodies against CB1R
SEQ ID NO's 431 to 453: Nanobodies against PTHR1
SEQ ID NO's 519 to 525: Nanobodies against MCR4

58-4H SEQ ID NO 521
EVQLVESGGGLAQPGGSLRLSCVASGFSLADYAISWFRQAPGKVREGVS
CISSSDGSTYYADSVKGRFTISRDNAKNAVYLQMSTLKPEDTAVYYCAAE
RSCLSSDYDSYDAWGQGTQVTVSS 60-5E SEQ ID NO 522
EVQLVESGGGLVQPGGSLRLSCAASGFTLDDYAIGWFRQAPGKEREGVS
CISSSDGSTYYADSVKGRFTISRDNAKNTVYLQMNSLKPEDTAVYYCAAD
LGYGSNCLEYDFWGQGTQVTVSS 60-4A SEQ ID NO 523
EVQLVESGGGLVQAGGSLRLSCAASGFTFDEYAIGWFRQAPGKEREGVS
CISRSDGSTYYAPSVKGRFTISSDNAKNTVYLQMNSLKPEDTAVYYCAVD
LEYGSNCYEYDSWGQGTQVTVSS 58-10H SEQ ID NO 524
EVQLVESGGGLVQPGGSMRLSCAASGSSLDAYGLGWFRQAPGKEREGV
SCISGSDNSTYYADSVKGRFSISRDIAKNTVYLQMNGLKPEDTAVYYCAA
KFLGFRQRSPTWFSRSWSEGSDYQYWGQGTQVTVSS 60-10E SEQ ID NO 525
EVQLVESGGGLVQPGGSLRLSCAASGFTLDDYAIGWFRQAPGKEREGVS
CITSSDGSTYYADSVKGRFTISRDNAKNTVYLQINSLKPEDTAVYYCAAD
LGVGTQCDEYDYWGQGTQVTVSS

TABLE C non-limiting list of some therapeutically relevant GPCRs (and desired action of an amino acid sequence, a Nanobody or a polypeptide of the invention).

Class A GPCRs

Acetylcholine receptor (agonist),
Muscarinic receptor (agonist),
Muscarinic M1 receptor (agonist),
Muscarinic M2 receptor (agonist),
Muscarinic M3 receptor (agonist),
Muscarinic M4 receptor (agonist),
Muscarinic M5 receptor (agonist)
Muscarinic receptor (partial agonist)
Adrenoceptor (agonist),
Alpha adrenoceptor (agonist),
Alpha 1 adrenoceptor (agonist),
Alpha 1A adrenoceptor (agonist),
Alpha 1B adrenoceptor (agonist),
Alpha 1D adrenoceptor (agonist)
Alpha 2 adrenoceptor (agonist),
Alpha 2A adrenoceptor (agonist),
Alpha 2B adrenoceptor (agonist),
Alpha 2C adrenoceptor (agonist),
Alpha 2 adrenoceptor (partial agonist)
Alpha 3 adrenoceptor (agonist),
Beta adrenoceptor (agonist),
Beta 1 adrenoceptor (agonist),
Beta 2 adrenoceptor (agonist),
Beta 3 adrenoceptor (agonist),
Dopamine receptor (agonist),
Dopamine D5 receptor (agonist)
Dopamine D1 receptor (agonist),
Dopamine D2 receptor (agonist),
Dopamine D3 receptor (agonist),
Dopamine D4 receptor (agonist),
Histamine receptor (agonist),
Histamine H1 receptor (agonist),
Histamine H2 receptor (agonist),
Histamine H3 receptor (agonist),
Histamine H4 receptor (agonist),
5-HT GPCR (agonist),
5-HT 1 (agonist),

TABLE C-continued non-limiting list of some therapeutically relevant GPCRs (and desired action of an amino acid sequence, a Nanobody or a polypeptide of the invention).

5-HT 2 (agonist),
5-HT 4 (agonist),
5-HT 5a (agonist),
5-HT 5b (agonist)
5-HT 6 (agonist),
5-HT 7 (agonist),
Trace amine-associated receptor (agonist),
Trace amine-associated receptor-1 (agonist),
Trace amine-associated receptor-2 (agonist)
Trace amine-associated receptor-3 (agonist)
Trace amine-associated receptor-4 (agonist)
Trace amine-associated receptor-5 (agonist)
Trace amine-associated receptor-6 (agonist)
Trace amine-associated receptor-7 (agonist)
Trace amine-associated receptor-8 (agonist)
Trace amine-associated receptor-9 (agonist)
Apelin receptor (agonist),
Cannabinoid receptor (agonist),
Cannabinoid CB1 receptor (agonist),
Cannabinoid CB2 receptor (agonist),
Lysosphingolipid receptor (agonist),
Sphingosine-1-phosphate receptor-1 (agonist),
Lysophosphatidate-1 receptor (agonist)
Sphingosine-1-phosphate receptor-3 (agonist),
Lysophosphatidate-2 receptor (agonist)
Sphingosine-1-phosphate receptor-2 (agonist)
Sphingosine-1-phosphate receptor-4 (agonist),
Lysophosphatidate-3 receptor (agonist)
Sphingosine-1-phosphate receptor-5 (agonist)
Class A hormone protein GPCR (agonist),
FSH (agonist),
Luteinizing hormone receptor (agonist),
TSH (agonist),
Leukotriene (agonist),
Leukotriene BLT receptor (agonist),
Cysteinyl leukotriene receptor (agonist),
Melatonin (agonist),
Melatonin MT1 (agonist),
Melatonin MT2 (agonist),
Melatonin MT3 (agonist)
Class A nucleotide like GPCR (agonist),
Adenosine receptor (agonist),
P2Y receptor (agonist),
Class A orphan GPCR (agonist),
Ghrelin (agonist),
Class A peptide GPCR (agonist),
Angiotensin receptor (agonist),
Angiotensin I receptor (agonist),
Angiotensin II receptor (agonist),
Bombesin receptor (agonist),
Bombesin BB1 receptor (agonist)
Bombesin BB2 receptor (agonist)
Bombesin bb3 receptor (agonist),
Gastrin releasing peptide ligand,
Neuromedin B ligand
Neuromedin C ligand
Bradykinin receptor (agonist),
Bradykinin B1 receptor (agonist),
Bradykinin B2 receptor (agonist),
C3a receptor (agonist),
C5a (agonist),
CCK receptor (agonist),
CCK 1 receptor (agonist),
CCK 2 receptor (agonist),
Gastrin (agonist),
Chemokine (agonist),
CC chemokine receptor (agonist),
CCR1 chemokine (agonist),
CCR2 chemokine (agonist),
CCR3 chemokine (agonist),
CCR4 chemokine (agonist),
CCR5 chemokine (agonist),
CCR6 chemokine (agonist),
CCR7 chemokine (agonist)
CCR8 chemokine (agonist),
CCR9 chemokine (agonist)

TABLE C-continued non-limiting list of some therapeutically relevant GPCRs (and desired action of an amino acid sequence, a Nanobody or a polypeptide of the invention).

CCR10 chemokine (agonist),
CCR11 chemokine (agonist)
CX3C chemokine receptor (agonist),
CX3CR1 chemokine (agonist),
XCR1 chemokine (agonist)
CXC chemokine receptor (agonist),
CXCR1 chemokine (agonist)
CXCR3 chemokine (agonist),
CXCR4 chemokine (agonist),
CXCR5 chemokine (agonist)
Adrenomedullin receptor (agonist),
Endothelin (agonist),
Endothelin ET-A (agonist),
Endothelin ET-B (agonist),
Galanin (agonist),
Galanin GAL1 (agonist),
Galanin GAL2 (agonist),
Galanin GAL3 (agonist)
IL-9 (agonist),
KiSS-1 receptor (agonist),
Melanin concentrating hormone (agonist),
MCH receptor-1 (agonist)
MCH receptor-2 (agonist)
Melanocortin (agonist),
Melanocortin MC1 (agonist),
ACTH receptor (agonist),
Melanocortin MC3 (agonist),
Melanocortin MC4 (agonist),
Melanocortin MC5 (agonist),
NK (agonist),
NK1 (agonist),
NK2 (agonist)
NK3 (agonist), Drugs: 1
Neuropeptide Y receptor (agonist),
Neuropeptide Y1 receptor (agonist)
Neuropeptide Y2 receptor (agonist),
Neuropeptide Y4 receptor (agonist),
Neuropeptide Y5 receptor (agonist),
Neuropeptide Y6 receptor (agonist)
Neurotensin receptor (agonist),
Neurotensin NTS1 (agonist),
Neurotensin NTS2 (agonist)
Orexin & neuropeptide FF receptor (agonist),
Orexin (agonist),
Opioid (agonist),
Delta Opioid (agonist),
Kappa Opioid (agonist),
Mu Opioid (agonist),
ORL1 receptor (agonist),
Opioid (partial agonist)
Sigma Opioid (agonist),
Orexin & neuropeptide FF receptor (agonist),
Neuropeptide FF receptor (agonist),
Neuropeptide FF1 receptor (agonist)
Neuropeptide FF2 receptor (agonist),
Orexin (agonist),
Orexin-1 (agonist)
Orexin-2 (agonist)
Protease-activated receptor (agonist),
Protease-activated receptor-1 (agonist),
Protease-activated receptor-2 (agonist),
Protease-activated receptor-3 (agonist)
Protease-activated receptor-4 (agonist)
Prokineticin receptor (agonist),
Prokineticin receptor-1 (agonist),
Prokineticin receptor-2 (agonist),
Somatostatin (agonist),
Somatostatin 1 (agonist),
Somatostatin 2 (agonist),
Somatostatin 3 (agonist),
Somatostatin 4 (agonist),
Somatostatin 5 (agonist),
Urotensin II (agonist),
Vasopressin like receptor (agonist),
Oxytocin (agonist),
Vasopressin (agonist), TABLE C-continued non-limiting list of some therapeutically relevant GPCRs (and desired action of an amino acid sequence, a Nanobody or a polypeptide of the invention).

Vasopressin V1 (agonist),
Vasopressin V2 (agonist),
Prostanoid receptor (agonist),
DP prostanoid (agonist),
PGD2 (agonist),
EP1 prostanoid (agonist),
PGE2 (agonist),
EP2 prostanoid (agonist),
PGE2 (agonist),
EP3 prostanoid (agonist),
PGE2 (agonist),
EP4 prostanoid (agonist),
PGE2 (agonist),
FP prostanoid (agonist),
PGF2 alpha (agonist),
IP prostanoid (agonist),
Prostacyclin (agonist),
Prostanoid receptor (partial agonist)
TP prostanoid (agonist),
Thromboxane A2 (agonist)
Succinate receptor 1 (agonist)
TRH (agonist),
TRH1 (agonist)
TRH2 (agonist)
Vomeronasal type-1 receptor (agonist)
Vomeronasal type-1 receptor-1 (agonist)
Vomeronasal type-1 receptor-2 (agonist)
Vomeronasal type-1 receptor-3 (agonist)
Vomeronasal type-1 receptor-4 (agonist)
Vomeronasal type-1 receptor-5 (agonist)
Apelin receptor (modulator),
Cannabinoid receptor (modulator),
Chemokine receptor-like 1 (modulator),
Lysosphingolipid receptor (modulator),
Class A hormone protein GPCR (modulator),
Leukotriene receptor (modulator),
Melatonin receptor (modulator),
Class A nucleotide like GPCR (modulator),
Class A orphan GPCR (modulator),
PAF receptor (modulator),
Class A peptide GPCR (modulator),
Prostanoid receptor (modulator),
Succinate receptor 1 (modulator)
TRH receptor (modulator),
Vomeronasal type-1 receptor (modulator),
Class B GPCRs G-protein coupled receptor-3 (modulator),
G-protein coupled receptor-3 (agonist)
G-protein coupled receptor-3 (antagonist),
G-protein coupled receptor-6 (modulator),
G-protein coupled receptor-6 (agonist)
G-protein coupled receptor-6 (antagonist),
G-protein coupled receptor-12 (modulator),
G-protein coupled receptor-12 (agonist)
G-protein coupled receptor-12 (antagonist),
G-protein coupled receptor-14 (modulator)
G-protein coupled receptor-14 (agonist)
G-protein coupled receptor-14 (antagonist)
Class B GPCR (agonist),
CRF-1 receptor (agonist)
CRF-2 receptor (agonist),
Calcitonin receptor (modulator),
Calcitonin (agonist),
Calcitonin (antagonist),
ACTH releasing factor receptor (modulator),
CRF-1 receptor (modulator),
CRF-1 receptor (agonist)
CRF-1 receptor (antagonist),
CRF-2 receptor (modulator),
CRF-2 receptor (agonist),
CRF-2 receptor (antagonist),
ACTH releasing factor (agonist),
CRF-1 receptor (agonist)
CRF-2 receptor (agonist),
ACTH releasing factor (antagonist),

TABLE C-continued non-limiting list of some therapeutically relevant GPCRs (and desired action of an amino acid sequence, a Nanobody or a polypeptide of the invention).

CRF-1 receptor (antagonist),
CRF-2 receptor (antagonist),
Glucagon-like peptide receptor (modulator),
Glucagon-like peptide 1 receptor (modulator),
Glucagon-like peptide 2 receptor (modulator),
Glucagon-like peptide (agonist),
Glucagon-like peptide (antagonist),
Glucagon receptor (modulator),
Glucagon (agonist),
Glucagon (antagonist),
GHRH receptor (modulator),
GHRH (agonist),
Growth hormone releasing factor (antagonist),
PACAP type I receptor (modulator),
PACAP type I receptor (agonist),
PACAP type I receptor (antagonist)
PTH receptor (modulator),
PTH-1 receptor (modulator)
PTH-2 receptor (modulator)
PTH (agonist),
PTH (antagonist),
Secretin receptor (modulator),
Secretin (agonist),
Secretin (antagonist)
VIP receptor (modulator),
VIP-1 receptor (modulator),
VIP-2 receptor (modulator),
VIP (agonist),
VIP (antagonist),
Class C GPCRs Class C GPCR (modulator),
Class C GPCR (agonist),
GABA B receptor (agonist),
Metabotropic glutamate receptor (agonist),
Metabotropic glutamate receptor 1 (agonist),
Metabotropic glutamate receptor 2 (agonist),
Metabotropic glutamate receptor 3 (agonist),
Metabotropic glutamate receptor 4 (agonist),
Metabotropic glutamate receptor 5 (agonist),
Metabotropic glutamate receptor 6 (agonist)
Metabotropic glutamate receptor 7 (agonist)
Metabotropic glutamate receptor 8 (agonist)

TABLE D non-limiting list human GPCRs

| | | | | |
|---|---|---|---|---|
| 5HT1A_HUMAN | (P08908) | HTR1A | Serotonin type 1 | *Homo sapiens* (Human) |
| 5HT1B_HUMAN | (P28222) | HTR1B | Serotonin type 1 | *Homo sapiens* (Human) |
| 5HT1D_HUMAN | (P28221) | HTR1D | Serotonin type 1 | *Homo sapiens* (Human) |
| 5HT1E_HUMAN | (P28566) | HTR1E | Serotonin type 1 | *Homo sapiens* (Human) |
| 5HT1F_HUMAN | (P30939) | HTR1F | Serotonin type 1 | *Homo sapiens* (Human) |
| 5HT2A_HUMAN | (P28223) | HTR2A | Serotonin type 2 | *Homo sapiens* (Human) |
| 5HT2B_HUMAN | (P41595) | HTR2B | Serotonin type 2 | *Homo sapiens* (Human) |
| 5HT2C_HUMAN | (P28335) | HTR2C | Serotonin type 2 | *Homo sapiens* (Human) |
| 5HT4R_HUMAN | (Q13639) | HTR4 | Serotonin type 4 | *Homo sapiens* (Human) |
| 5HT5A_HUMAN | (P47898) | HTR5A | Serotonin type 5 | *Homo sapiens* (Human) |
| 5HT6R_HUMAN | (P50406) | HTR6 | Serotonin type 6 | *Homo sapiens* (Human) |
| 5HT7R_HUMAN | (P34969) | HTR7 | Serotonin type 7 | *Homo sapiens* (Human) |
| AA1R_HUMAN | (P30542) | ADORA1 | Adenosine type 1 | *Homo sapiens* (Human) |
| AA2AR_HUMAN | (P29274) | ADORA2A | Adenosine type 2 | *Homo sapiens* (Human) |
| AA2BR_HUMAN | (P29275) | ADORA2B | Adenosine type 2 | *Homo sapiens* (Human) |
| AA3R_HUMAN | (P33765) | ADORA3 | Adenosine type 3 | *Homo sapiens* (Human) |
| ACM1_HUMAN | (P11229) | CHRM1 | Musc. acetylcholine Vertebrate type 1 | *Homo sapiens* (Human) |
| ACM2_HUMAN | (P08172) | CHRM2 | Musc. acetylcholine Vertebrate type 2 | *Homo sapiens* (Human) |
| ACM3_HUMAN | (P20309) | CHRM3 | Musc. acetylcholine Vertebrate type 3 | *Homo sapiens* (Human) |
| ACM4_HUMAN | (P08173) | CHRM4 | Musc. acetylcholine Vertebrate type 4 | *Homo sapiens* (Human) |
| ACM5_HUMAN | (P08912) | CHRM5 | Musc. acetylcholine Vertebrate type 5 | *Homo sapiens* (Human) |
| ACTHR_HUMAN | (Q01718) | MC2R | Adrenocorticotropic hormone | *Homo sapiens* (Human) |
| ADA1A_HUMAN | (P35348) | ADRA1A | Alpha Adrenoceptors type 1 | *Homo sapiens* (Human) |
| ADA1B_HUMAN | (P35368) | ADRA1B | Alpha Adrenoceptors type 1 | *Homo sapiens* (Human) |
| ADA1D_HUMAN | (P25100) | ADRA1D | Alpha Adrenoceptors type 1 | *Homo sapiens* (Human) |
| ADA2A_HUMAN | (P08913) | ADRA2A | Alpha Adrenoceptors type 2 | *Homo sapiens* (Human) |
| ADA2B_HUMAN | (P18089) | ADRA2B | Alpha Adrenoceptors type 2 | *Homo sapiens* (Human) |
| ADA2C_HUMAN | (P18825) | ADRA2C | Alpha Adrenoceptors type 2 | *Homo sapiens* (Human) |
| ADMR_HUMAN | (O15218) | ADMR | Adrenomedullin (G10D) | *Homo sapiens* (Human) |
| ADRB1_HUMAN | (P08588) | ADRB1 | Beta Adrenoceptors type 1 | *Homo sapiens* (Human) |
| ADRB2_HUMAN | (P07550) | ADRB2 | Beta Adrenoceptors type 2 | *Homo sapiens* (Human) |
| ADRB3_HUMAN | (P13945) | ADRB3 | Beta Adrenoceptors type 3 | *Homo sapiens* (Human) |
| AGTR1_HUMAN | (P30556) | AGTR1 | Angiotensin type 1 | *Homo sapiens* (Human) |
| AGTR2_HUMAN | (P50052) | AGTR2 | Angiotensin type 2 | *Homo sapiens* (Human) |
| APJ_HUMAN | (P35414) | AGTRL1 | APJ like | *Homo sapiens* (Human) |
| BAI1_HUMAN | (O14514) | BAI1 | Brain-specific angiogenesis inhibitor (BAI) | *Homo sapiens* (Human) |
| BAI2_HUMAN | (O60241) | BAI2 | Brain-specific angiogenesis inhibitor (BAI) | *Homo sapiens* (Human) |
| BAI3_HUMAN | (O60242) | BAI3 | Brain-specific angiogenesis inhibitor (BAI) | *Homo sapiens* (Human) |
| BKRB1_HUMAN | (P46663) | BDKRB1 | Bradykinin | *Homo sapiens* (Human) |
| BKRB2_HUMAN | (P30411) | BDKRB2 | Bradykinin | *Homo sapiens* (Human) |
| BRS3_HUMAN | (P32247) | BRS3 | Bombesin | *Homo sapiens* (Human) |
| C3AR_HUMAN | (Q16581) | C3AR1 | C5a anaphylatoxin | *Homo sapiens* (Human) |
| C5ARL_HUMAN | (Q9P296) | GPR77 | C5a anaphylatoxin | *Homo sapiens* (Human) |
| C5AR_HUMAN | (P21730) | C5AR1 | C5a anaphylatoxin | *Homo sapiens* (Human) |
| CALCR_HUMAN | (P30988) | CALCR | Calcitonin | *Homo sapiens* (Human) |
| CALRL_HUMAN | (Q16602) | CALCRL | Calcitonin | *Homo sapiens* (Human) |
| CASR_HUMAN | (P41180) | CASR | Extracellular calcium-sensing | *Homo sapiens* (Human) |

TABLE D-continued non-limiting list human GPCRs

| | | | | |
|---|---|---|---|---|
| CCBP2_HUMAN | (O00590) | CCBP2 | C-C Chemokine type X | *Homo sapiens* (Human) |
| CCKAR_HUMAN | (P32238) | CCKAR | CCK type A | *Homo sapiens* (Human) |
| CCR10_HUMAN | (P46092) | CCR10 | C-C Chemokine type 10 | *Homo sapiens* (Human) |
| CCR1_HUMAN | (P32246) | CCR1 | C-C Chemokine type 1 | *Homo sapiens* (Human) |
| CCR2_HUMAN | (P41597) | CCR2 | C-C Chemokine type 2 | *Homo sapiens* (Human) |
| CCR3_HUMAN | (P51677) | CCR3 | C-C Chemokine type 3 | *Homo sapiens* (Human) |
| CCR4_HUMAN | (P51679) | CCR4 | C-C Chemokine type 4 | *Homo sapiens* (Human) |
| CCR5_HUMAN | (P51681) | CCR5 | C-C Chemokine type 5 | *Homo sapiens* (Human) |
| CCR6_HUMAN | (P51684) | CCR6 | C-C Chemokine type 6 | *Homo sapiens* (Human) |
| CCR7_HUMAN | (P32248) | CCR7 | C-C Chemokine type 7 | *Homo sapiens* (Human) |
| CCR8_HUMAN | (P51685) | CCR8 | C-C Chemokine type 8 | *Homo sapiens* (Human) |
| CCR9_HUMAN | (P51686) | CCR9 | C-C Chemokine type 9 | *Homo sapiens* (Human) |
| CCRL1_HUMAN | (Q9NPB9) | CCRL1 | C-C Chemokine type 11 | *Homo sapiens* (Human) |
| CD97_HUMAN | (P48960) | CD97 | EMR1 | *Homo sapiens* (Human) |
| CELR1_HUMAN | (Q9NYQ6) | CELSR1 | Cadherin EGF LAG (CELSR) | *Homo sapiens* (Human) |
| CELR2_HUMAN | (Q9HCU4) | CELSR2 | Cadherin EGF LAG (CELSR) | *Homo sapiens* (Human) |
| CELR3_HUMAN | (Q9NYQ7) | CELSR3 | Cadherin EGF LAG (CELSR) | *Homo sapiens* (Human) |
| CLTR1_HUMAN | (Q9Y271) | CYSLTR1 | Cysteinyl leukotriene | *Homo sapiens* (Human) |
| CLTR2_HUMAN | (Q9NS75) | CYSLTR2 | Cysteinyl leukotriene | *Homo sapiens* (Human) |
| CML1_HUMAN | (Q99788) | CMKLR1 | Chemokine receptor-like 1 | *Homo sapiens* (Human) |
| CML2_HUMAN | (Q99527) | GPR30 | Chemokine receptor-like 2 | *Homo sapiens* (Human) |
| CNR1_HUMAN | (P21554) | CNR1 | Cannabinoid | *Homo sapiens* (Human) |
| CNR2_HUMAN | (P34972) | CNR2 | Cannabinoid | *Homo sapiens* (Human) |
| CRFR1_HUMAN | (P34998) | CRHR1 | Corticotropin releasing factor | *Homo sapiens* (Human) |
| CRFR2_HUMAN | (Q13324) | CRHR2 | Corticotropin releasing factor | *Homo sapiens* (Human) |
| CX3C1_HUMAN | (P49238) | CX3CR1 | C—X3—C Chemokine | *Homo sapiens* (Human) |
| CXCR1_HUMAN | (P25024) | IL8RA | Interleukin-8 type A | *Homo sapiens* (Human) |
| CXCR3_HUMAN | (P49682) | CXCR3 | C—X—C Chemokine type 3 | *Homo sapiens* (Human) |
| CXCR4_HUMAN | (P61073) | CXCR4 | C—X—C Chemokine type 4 | *Homo sapiens* (Human) |
| CXCR5_HUMAN | (P32302) | BLR1 | C—X—C Chemokine type 5 | *Homo sapiens* (Human) |
| CXCR6_HUMAN | (O00574) | CXCR6 | C—X—C Chemokine type 6 (Bonzo) | *Homo sapiens* (Human) |
| DRD1_HUMAN | (P21728) | DRD1 | Dopamine Vertebrate type 1 | *Homo sapiens* (Human) |
| DRD2_HUMAN | (P14416) | DRD2 | Dopamine Vertebrate type 2 | *Homo sapiens* (Human) |
| DRD3_HUMAN | (P35462) | DRD3 | Dopamine Vertebrate type 3 | *Homo sapiens* (Human) |
| DRD4_HUMAN | (P21917) | DRD4 | Dopamine Vertebrate type 4 | *Homo sapiens* (Human) |
| DRD5_HUMAN | (P21918) | DRD5 | Dopamine Vertebrate type 1 | *Homo sapiens* (Human) |
| DUFFY_HUMAN | (Q16570) | DARC | Duffy antigen | *Homo sapiens* (Human) |
| EBI2_HUMAN | (P32249) | EBI2 | EBV-induced | *Homo sapiens* (Human) |
| EDG1_HUMAN | (P21453) | EDG1 | Sphingosine 1-phosphate Edg-1 | *Homo sapiens* (Human) |
| EDG2_HUMAN | (Q92633) | EDG2 | Lysophosphatidic acid Edg-2 | *Homo sapiens* (Human) |
| EDG3_HUMAN | (Q99500) | EDG3 | Sphingosine 1-phosphate Edg-3 | *Homo sapiens* (Human) |
| EDG4_HUMAN | (Q9HBW0) | EDG4 | Lysophosphatidic acid Edg-4 | *Homo sapiens* (Human) |
| EDG5_HUMAN | (O95136) | EDG5 | Sphingosine 1-phosphate Edg-5 | *Homo sapiens* (Human) |
| EDG6_HUMAN | (O95977) | EDG6 | Sphingosine 1-phosphate Edg-6 | *Homo sapiens* (Human) |
| EDG7_HUMAN | (Q9UBY5) | EDG7 | Lysophosphatidic acid Edg-7 | *Homo sapiens* (Human) |
| EDG8_HUMAN | (Q9H228) | EDG8 | Sphingosine 1-phosphate Edg-8 | *Homo sapiens* (Human) |
| EDNRA_HUMAN | (P25101) | EDNRA | Endothelin | *Homo sapiens* (Human) |
| EDNRB_HUMAN | (P24530) | EDNRB | Endothelin | *Homo sapiens* (Human) |
| ELTD1_HUMAN | (Q9HBW9) | ELTD1 | ETL receptors | *Homo sapiens* (Human) |
| EMR1_HUMAN | (Q14246) | EMR1 | EMR1 | *Homo sapiens* (Human) |
| EMR2_HUMAN | (Q9UHX3) | EMR2 | EMR1 | *Homo sapiens* (Human) |
| EMR3_HUMAN | (Q9BY15) | EMR3 | EMR1 | *Homo sapiens* (Human) |
| EMR4_HUMAN | (Q86SQ3) | EMR4 | fragments | *Homo sapiens* (Human) |
| ETBR2_HUMAN | (O60883) | GPR37L1 | GPR37/endothelin B-like | *Homo sapiens* (Human) |
| FFAR1_HUMAN | (O14842) | FFAR1 | Free fatty acid receptor (GP40, GP41, GP43) | *Homo sapiens* (Human) |
| FFAR2_HUMAN | (O15552) | FFAR2 | Free fatty acid receptor (GP40, GP41, GP43) | *Homo sapiens* (Human) |
| FFAR3_HUMAN | (O14843) | FFAR3 | Free fatty acid receptor (GP40, GP41, GP43) | *Homo sapiens* (Human) |
| FPR1_HUMAN | (P21462) | FPR1 | Fmet-leu-phe | *Homo sapiens* (Human) |
| FPRL1_HUMAN | (P25090) | FPRL1 | Fmet-leu-phe | *Homo sapiens* (Human) |
| FPRL2_HUMAN | (P25089) | FPRL2 | Fmet-leu-phe | *Homo sapiens* (Human) |
| FSHR_HUMAN | (P23945) | FSHR | Follicle stimulating hormone | *Homo sapiens* (Human) |
| FZD10_HUMAN | (Q9ULW2) | FZD10 | frizzled Group A (Fz 1&2&4&5&7-9) | *Homo sapiens* (Human) |
| FZD1_HUMAN | (Q9UP38) | FZD1 | frizzled Group A (Fz 1&2&4&5&7-9) | *Homo sapiens* (Human) |
| FZD2_HUMAN | (Q14332) | FZD2 | frizzled Group A (Fz 1&2&4&5&7-9) | *Homo sapiens* (Human) |
| FZD3_HUMAN | (Q9NPG1) | FZD3 | frizzled Group B (Fz 3 & 6) | *Homo sapiens* (Human) |
| FZD4_HUMAN | (Q9ULV1) | FZD4 | frizzled Group A (Fz 1&2&4&5&7-9) | *Homo sapiens* (Human) |
| FZD5_HUMAN | (Q13467) | FZD5 | frizzled Group A (Fz 1&2&4&5&7-9) | *Homo sapiens* (Human) |
| FZD6_HUMAN | (O60353) | FZD6 | frizzled Group B (Fz 3 & 6) | *Homo sapiens* (Human) |
| FZD7_HUMAN | (O75084) | FZD7 | frizzled Group A (Fz 1&2&4&5&7-9) | *Homo sapiens* (Human) |
| FZD8_HUMAN | (Q9H461) | FZD8 | frizzled Group A (Fz 1&2&4&5&7-9) | *Homo sapiens* (Human) |
| FZD9_HUMAN | (O00144) | FZD9 | frizzled Group A (Fz 1&2&4&5&7-9) | *Homo sapiens* (Human) |
| G109A_HUMAN | (Q8TDS4) | GPR109A | Putative/unclassified Class A GPCRs | *Homo sapiens* (Human) |
| G109B_HUMAN | (P49019) | GPR109B | Putative/unclassified Class A GPCRs | *Homo sapiens* (Human) |
| GABR1_HUMAN | (Q9UBS5) | GABBR1 | GABA-B subtype 1 | *Homo sapiens* (Human) |
| GABR2_HUMAN | (O75899) | GABBR2 | GABA-B subtype 2 | *Homo sapiens* (Human) |
| GALR1_HUMAN | (P47211) | GALR1 | Galanin | *Homo sapiens* (Human) |
| GALR2_HUMAN | (O43603) | GALR2 | Galanin | *Homo sapiens* (Human) |
| GALR3_HUMAN | (O60755) | GALR3 | Galanin | *Homo sapiens* (Human) |

TABLE D-continued non-limiting list human GPCRs

| | | | | |
|---|---|---|---|---|
| GASR_HUMAN | (P32239) | CCKBR | CCK type B | *Homo sapiens* (Human) |
| GHRHR_HUMAN | (Q02643) | GHRHR | Growth hormone-releasing hormone | *Homo sapiens* (Human) |
| GHSR_HUMAN | (Q92847) | GHSR | Growth hormone secretagogue | *Homo sapiens* (Human) |
| GIPR_HUMAN | (P48546) | GIPR | Gastric inhibitory peptide | *Homo sapiens* (Human) |
| GLP1R_HUMAN | (P43220) | GLP1R | Glucagon | *Homo sapiens* (Human) |
| GLP2R_HUMAN | (O95838) | GLP2R | Glucagon | *Homo sapiens* (Human) |
| GLR_HUMAN | (P47871) | GCGR | Glucagon | *Homo sapiens* (Human) |
| GNRHR_HUMAN | (P30968) | GNRHR | Gonadotropin-releasing hormone type I | *Homo sapiens* (Human) |
| GNRR2_HUMAN | (Q96P88) | GNRHR2 | Gonadotropin-releasing hormone type II | *Homo sapiens* (Human) |
| GP101_HUMAN | (Q96P66) | GPR101 | Putative/unclassified Class A GPCRs | *Homo sapiens* (Human) |
| GP107_HUMAN | (Q5VW38) | GPR107 | Putative/unclassified other | *Homo sapiens* (Human) |
| GP110_HUMAN | (Q5T601) | GPR110 | Putative/unclassified Class B GPCRs | *Homo sapiens* (Human) |
| GP111_HUMAN | (Q8IZF7) | GPR111 | Putative/unclassified Class B GPCRs | *Homo sapiens* (Human) |
| GP112_HUMAN | (Q8IZF6) | GPR112 | Putative/unclassified Class B GPCRs | *Homo sapiens* (Human) |
| GP113_HUMAN | (Q8IZF5) | GPR113 | Putative/unclassified Class B GPCRs | *Homo sapiens* (Human) |
| GP114_HUMAN | (Q8IZF4) | GPR114 | Putative/unclassified Class B GPCRs | *Homo sapiens* (Human) |
| GP115_HUMAN | (Q8IZF3) | GPR115 | Putative/unclassified Class B GPCRs | *Homo sapiens* (Human) |
| GP116_HUMAN | (Q8IZF2) | GPR116 | Putative/unclassified Class B GPCRs | *Homo sapiens* (Human) |
| GP119_HUMAN | (Q8TDV5) | GPR119 | Putative/unclassified Class A GPCRs | *Homo sapiens* (Human) |
| GP120_HUMAN | (Q5NUL3) | GPR120 | Putative/unclassified Class A GPCRs | *Homo sapiens* (Human) |
| GP123_HUMAN | (Q86SQ6) | GPR123 | Putative/unclassified Class B GPCRs | *Homo sapiens* (Human) |
| GP124_HUMAN | (Q96PE1) | GPR124 | Putative/unclassified Class B GPCRs | *Homo sapiens* (Human) |
| GP125_HUMAN | (Q8IWK6) | GPR125 | Putative/unclassified Class B GPCRs | *Homo sapiens* (Human) |
| GP126_HUMAN | (Q86SQ4) | GPR126 | Putative/unclassified Class B GPCRs | *Homo sapiens* (Human) |
| GP128_HUMAN | (Q96K78) | GPR128 | Putative/unclassified Class B GPCRs | *Homo sapiens* (Human) |
| GP132_HUMAN | (Q9UNW8) | GPR132 | Putative/unclassified Class A GPCRs | *Homo sapiens* (Human) |
| GP133_HUMAN | (Q6QNK2) | GPR133 | Putative/unclassified Class B GPCRs | *Homo sapiens* (Human) |
| GP135_HUMAN | (Q8IZ08) | GPR135 | Putative/unclassified Class A GPCRs | *Homo sapiens* (Human) |
| GP139_HUMAN | (Q6DWJ6) | GPR139 | Putative/unclassified Class A GPCRs | *Homo sapiens* (Human) |
| GP141_HUMAN | (Q7Z602) | GPR141 | Putative/unclassified Class A GPCRs | *Homo sapiens* (Human) |
| GP142_HUMAN | (Q7Z601) | GPR142 | Putative/unclassified Class A GPCRs | *Homo sapiens* (Human) |
| GP143_HUMAN | (P51810) | GPR143 | Ocular albinism proteins | *Homo sapiens* (Human) |
| GP144_HUMAN | (Q7Z7M1) | GPR144 | Putative/unclassified Class B GPCRs | *Homo sapiens* (Human) |
| GP146_HUMAN | (Q96CH1) | GPR146 | Putative/unclassified Class A GPCRs | *Homo sapiens* (Human) |
| GP148_HUMAN | (Q8TDV2) | GPR148 | Putative/unclassified Class A GPCRs | *Homo sapiens* (Human) |
| GP149_HUMAN | (Q86SP6) | GPR149 | Putative/unclassified Class A GPCRs | *Homo sapiens* (Human) |
| GP150_HUMAN | (Q8NGU9) | GPR150 | Putative/unclassified Class A GPCRs | *Homo sapiens* (Human) |
| GP151_HUMAN | (Q8TDV0) | GPR151 | Putative/unclassified Class A GPCRs | *Homo sapiens* (Human) |
| GP152_HUMAN | (Q8TDT2) | GPR152 | Putative/unclassified Class A GPCRs | *Homo sapiens* (Human) |
| GP153_HUMAN | (Q6NV75) | GPR153 | Putative/unclassified Class A GPCRs | *Homo sapiens* (Human) |
| GP154_HUMAN | (Q6W5P4) | GPR154 | Putative/unclassified Class A GPCRs | *Homo sapiens* (Human) |
| GP155_HUMAN | (Q7Z3F1) | GPR155 | Putative/unclassified other | *Homo sapiens* (Human) |
| GP156_HUMAN | (Q8NFN8) | GPR156 | GABA-B like | *Homo sapiens* (Human) |
| GP157_HUMAN | (Q5UAW9) | GPR157 | Putative/unclassified Class B GPCRs | *Homo sapiens* (Human) |
| GP158_HUMAN | (Q5T848) | GPR158 | Putative/unclassified Class C GPCRs | *Homo sapiens* (Human) |
| GP160_HUMAN | (Q9UJ42) | GPR160 | Putative/unclassified Class A GPCRs | *Homo sapiens* (Human) |
| GP161_HUMAN | (Q8N6U8) | GPR161 | Putative/unclassified Class A GPCRs | *Homo sapiens* (Human) |
| GP162_HUMAN | (Q16538) | GPR162 | Putative/unclassified Class A GPCRs | *Homo sapiens* (Human) |
| GP171_HUMAN | (O14626) | GPR171 | Putative/unclassified Class A GPCRs | *Homo sapiens* (Human) |
| GP173_HUMAN | (Q9NS66) | GPR173 | SREB | *Homo sapiens* (Human) |
| GP174_HUMAN | (Q9BXC1) | GPR174 | Purinoceptor P2RY5,8,9,10 GPR35,92,174 | *Homo sapiens* (Human) |
| GP175_HUMAN | (Q86W33) | GPR175 | Putative/unclassified other | *Homo sapiens* (Human) |
| GP176_HUMAN | (Q14439) | GPR176 | Putative/unclassified Class A GPCRs | *Homo sapiens* (Human) |
| GP179_HUMAN | (Q6PRD1) | GPR179 | Putative/unclassified Class C GPCRs | *Homo sapiens* (Human) |
| GPBAR_HUMAN | (Q8TDU6) | GPBAR1 | G-protein coupled bile acid receptor | *Homo sapiens* (Human) |
| GPC5B_HUMAN | (Q9NZH0) | GPRC5B | Orphan GPRC5 | *Homo sapiens* (Human) |
| GPC5C_HUMAN | (Q9NQ84) | GPRC5C | Orphan GPRC5 | *Homo sapiens* (Human) |
| GPC5D_HUMAN | (Q9NZD1) | GPRC5D | Orphan GPRC5 | *Homo sapiens* (Human) |
| GPC6A_HUMAN | (Q5T6X5) | GPRC6A | Orphan GPCR6 | *Homo sapiens* (Human) |
| GPR12_HUMAN | (P47775) | GPR12 | GPR | *Homo sapiens* (Human) |
| GPR15_HUMAN | (P49685) | GPR15 | GPR | *Homo sapiens* (Human) |
| GPR17_HUMAN | (Q13304) | GPR17 | GPR | *Homo sapiens* (Human) |
| GPR18_HUMAN | (Q14330) | GPR18 | Putative/unclassified Class A GPCRs | *Homo sapiens* (Human) |
| GPR19_HUMAN | (Q15760) | GPR19 | GPR | *Homo sapiens* (Human) |
| GPR1_HUMAN | (P46091) | GPR1 | GPR | *Homo sapiens* (Human) |
| GPR20_HUMAN | (Q99678) | GPR20 | GPR | *Homo sapiens* (Human) |
| GPR21_HUMAN | (Q99679) | GPR21 | GPR | *Homo sapiens* (Human) |
| GPR22_HUMAN | (Q99680) | GPR22 | GPR | *Homo sapiens* (Human) |
| GPR25_HUMAN | (O00155) | GPR25 | GPR | *Homo sapiens* (Human) |
| GPR26_HUMAN | (Q8NDV2) | GPR26 | Putative/unclassified Class A GPCRs | *Homo sapiens* (Human) |
| GPR27_HUMAN | (Q9NS67) | GPR27 | SREB | *Homo sapiens* (Human) |
| GPR31_HUMAN | (O00270) | GPR31 | GPR | *Homo sapiens* (Human) |
| GPR32_HUMAN | (O75388) | GPR32 | Chemokine receptor-like 1 | *Homo sapiens* (Human) |
| GPR33_HUMAN | (Q49SQ1) | GPR33 | Chemokine receptor-like 1 | *Homo sapiens* (Human) |
| GPR34_HUMAN | (Q9UPC5) | GPR34 | Putative/unclassified Class A GPCRs | *Homo sapiens* (Human) |
| GPR35_HUMAN | (Q9HC97) | GPR35 | Purinoceptor P2RY5,8,9,10 GPR35,92,174 | *Homo sapiens* (Human) |
| GPR37_HUMAN | (O15354) | GPR37 | GPR37/endothelin B-like | *Homo sapiens* (Human) |
| GPR39_HUMAN | (O43194) | GPR39 | Putative/unclassified Class A GPCRs | *Homo sapiens* (Human) |

TABLE D-continued non-limiting list human GPCRs

| | | | | |
|---|---|---|---|---|
| GPR3_HUMAN | (P46089) | GPR3 | GPR | *Homo sapiens* (Human) |
| GPR42_HUMAN | (O15529) | GPR42 | Free fatty acid receptor (GP40, GP41, GP43) | *Homo sapiens* (Human) |
| GPR44_HUMAN | (Q9Y5Y4) | GPR44 | Chemokine receptor-like 1 | *Homo sapiens* (Human) |
| GPR45_HUMAN | (Q9Y5Y3) | GPR45 | GPR45 like | *Homo sapiens* (Human) |
| GPR4_HUMAN | (P46093) | GPR4 | GPR | *Homo sapiens* (Human) |
| GPR52_HUMAN | (Q9Y2T5) | GPR52 | GPR | *Homo sapiens* (Human) |
| GPR55_HUMAN | (Q9Y2T6) | GPR55 | Putative/unclassified Class A GPCRs | *Homo sapiens* (Human) |
| GPR56_HUMAN | (Q9Y653) | GPR56 | Putative/unclassified Class B GPCRs | *Homo sapiens* (Human) |
| GPR61_HUMAN | (Q9BZJ8) | GPR61 | Putative/unclassified Class A GPCRs | *Homo sapiens* (Human) |
| GPR62_HUMAN | (Q9BZJ7) | GPR62 | Putative/unclassified Class A GPCRs | *Homo sapiens* (Human) |
| GPR63_HUMAN | (Q9BZJ6) | GPR63 | GPR45 like | *Homo sapiens* (Human) |
| GPR64_HUMAN | (Q8IZP9) | GPR64 | Putative/unclassified Class B GPCRs | *Homo sapiens* (Human) |
| GPR6_HUMAN | (P46095) | GPR6 | GPR | *Homo sapiens* (Human) |
| GPR75_HUMAN | (O95800) | GPR75 | Putative/unclassified Class A GPCRs | *Homo sapiens* (Human) |
| GPR78_HUMAN | (Q96P69) | GPR78 | Putative/unclassified Class A GPCRs | *Homo sapiens* (Human) |
| GPR81_HUMAN | (Q9BXC0) | GPR81 | Putative/unclassified Class A GPCRs | *Homo sapiens* (Human) |
| GPR82_HUMAN | (Q96P67) | GPR82 | Putative/unclassified Class A GPCRs | *Homo sapiens* (Human) |
| GPR83_HUMAN | (Q9NYM4) | GPR83 | Neuropeptide Y other | *Homo sapiens* (Human) |
| GPR84_HUMAN | (Q9NQS5) | GPR84 | Putative/unclassified Class A GPCRs | *Homo sapiens* (Human) |
| GPR85_HUMAN | (P60893) | GPR85 | SREB | *Homo sapiens* (Human) |
| GPR87_HUMAN | (Q9BY21) | GPR87 | Purinoceptor P2RY12-14 GPR87 (UDP-Glucose) | *Homo sapiens* (Human) |
| GPR88_HUMAN | (Q9GZN0) | GPR88 | Putative/unclassified Class A GPCRs | *Homo sapiens* (Human) |
| GPR92_HUMAN | (Q9H1C0) | GPR92 | Purinoceptor P2RY5,8,9,10 GPR35,92,174 | *Homo sapiens* (Human) |
| GPR97_HUMAN | (Q86Y34) | GPR97 | Putative/unclassified Class B GPCRs | *Homo sapiens* (Human) |
| GRPR_HUMAN | (P30550) | GRPR | Bombesin | *Homo sapiens* (Human) |
| HRH1_HUMAN | (P35367) | HRH1 | Histamine type 1 | *Homo sapiens* (Human) |
| HRH2_HUMAN | (P25021) | HRH2 | Histamine type 2 | *Homo sapiens* (Human) |
| HRH3_HUMAN | (Q9Y5N1) | HRH3 | Histamine type 3 | *Homo sapiens* (Human) |
| HRH4_HUMAN | (Q9H3N8) | HRH4 | Histamine type 4 | *Homo sapiens* (Human) |
| KISSR_HUMAN | (Q969F8) | KISS1R | Kiss receptor (GPR54) | *Homo sapiens* (Human) |
| LGR4_HUMAN | (Q9BXB1) | LGR4 | LGR like (hormone receptors) | *Homo sapiens* (Human) |
| LGR5_HUMAN | (O75473) | LGR5 | LGR like (hormone receptors) | *Homo sapiens* (Human) |
| LGR6_HUMAN | (Q9HBX8) | LGR6 | LGR like (hormone receptors) | *Homo sapiens* (Human) |
| LGR8_HUMAN | (Q8WXD0) | LGR8 | LGR like (hormone receptors) | *Homo sapiens* (Human) |
| LPHN1_HUMAN | (O94910) | LPHN1 | Latrophilin type 1 | *Homo sapiens* (Human) |
| LPHN2_HUMAN | (O95490) | LPHN2 | Latrophilin type 2 | *Homo sapiens* (Human) |
| LPHN3_HUMAN | (Q9HAR2) | LPHN3 | Latrophilin type 3 | *Homo sapiens* (Human) |
| LSHR_HUMAN | (P22888) | LHCGR | Lutropin-choriogonadotropic hormone | *Homo sapiens* (Human) |
| LT4R1_HUMAN | (Q15722) | LTB4R | Leukotriene B4 receptor BLT1 | *Homo sapiens* (Human) |
| LT4R2_HUMAN | (Q9NPC1) | LTB4R2 | Leukotriene B4 receptor BLT2 | *Homo sapiens* (Human) |
| MAS1L_HUMAN | (P35410) | MAS1L | Mas proto-oncogene & Mas-related (MRGs) | *Homo sapiens* (Human) |
| MASS1_HUMAN | (Q8WXG9) | MASS1 | Very large G-protein coupled receptor | *Homo sapiens* (Human) |
| MAS_HUMAN | (P04201) | MAS1 | Mas proto-oncogene & Mas-related (MRGs) | *Homo sapiens* (Human) |
| MC3R_HUMAN | (P41968) | MC3R | Melanocortin hormone | *Homo sapiens* (Human) |
| MC4R_HUMAN | (P32245) | MC4R | Melanocortin hormone | *Homo sapiens* (Human) |
| MC5R_HUMAN | (P33032) | MC5R | Melanocortin hormone | *Homo sapiens* (Human) |
| MCHR1_HUMAN | (Q99705) | MCHR1 | Melanin-concentrating hormone receptors | *Homo sapiens* (Human) |
| MCHR2_HUMAN | (Q969V1) | MCHR2 | Melanin-concentrating hormone receptors | *Homo sapiens* (Human) |
| MGR1_HUMAN | (Q13255) | GRM1 | Metabotropic glutamate group I | *Homo sapiens* (Human) |
| MGR2_HUMAN | (Q14416) | GRM2 | Metabotropic glutamate group II | *Homo sapiens* (Human) |
| MGR3_HUMAN | (Q14832) | GRM3 | Metabotropic glutamate group II | *Homo sapiens* (Human) |
| MGR4_HUMAN | (Q14833) | GRM4 | Metabotropic glutamate group III | *Homo sapiens* (Human) |
| MGR5_HUMAN | (P41594) | GRM5 | Metabotropic glutamate group I | *Homo sapiens* (Human) |
| MGR6_HUMAN | (O15303) | GRM6 | Metabotropic glutamate group III | *Homo sapiens* (Human) |
| MGR7_HUMAN | (Q14831) | GRM7 | Metabotropic glutamate group III | *Homo sapiens* (Human) |
| MGR8_HUMAN | (O00222) | GRM8 | Metabotropic glutamate group III | *Homo sapiens* (Human) |
| MRGRD_HUMAN | (Q8TDS7) | MRGPRD | Mas proto-oncogene & Mas-related (MRGs) | *Homo sapiens* (Human) |
| MRGRE_HUMAN | (Q86SM8) | MRGPRE | fragments | *Homo sapiens* (Human) |
| MRGRF_HUMAN | (Q96AM1) | MRGPRF | Putative/unclassified Class A GPCRs | *Homo sapiens* (Human) |
| MRGRG_HUMAN | (Q86SM5) | MRGPRG | fragments | *Homo sapiens* (Human) |
| MRGX1_HUMAN | (Q96LB2) | MRGPRX1 | Mas proto-oncogene & Mas-related (MRGs) | *Homo sapiens* (Human) |
| MRGX2_HUMAN | (Q96LB1) | MRGPRX2 | Mas proto-oncogene & Mas-related (MRGs) | *Homo sapiens* (Human) |
| MRGX3_HUMAN | (Q96LB0) | MRGPRX3 | Mas proto-oncogene & Mas-related (MRGs) | *Homo sapiens* (Human) |
| MRGX4_HUMAN | (Q96LA9) | MRGPRX4 | Mas proto-oncogene & Mas-related (MRGs) | *Homo sapiens* (Human) |
| MSHR_HUMAN | (Q01726) | MC1R | Melanocyte stimulating hormone | *Homo sapiens* (Human) |
| MTLR_HUMAN | (O43193) | MLNR | Growth hormone secretagogue like | *Homo sapiens* (Human) |
| MTR1A_HUMAN | (P48039) | MTNR1A | Melatonin | *Homo sapiens* (Human) |
| MTR1B_HUMAN | (P49286) | MTNR1B | Melatonin | *Homo sapiens* (Human) |
| MTR1L_HUMAN | (Q13585) | GPR50 | Melatonin | *Homo sapiens* (Human) |
| NK1R_HUMAN | (P25103) | TACR1 | Substance P (NK1) | *Homo sapiens* (Human) |
| NK2R_HUMAN | (P21452) | TACR2 | Substance K (NK2) | *Homo sapiens* (Human) |
| NK3R_HUMAN | (P29371) | TACR3 | Neuromedin K (NK3) | *Homo sapiens* (Human) |
| NMBR_HUMAN | (P28336) | NMBR | Bombesin | *Homo sapiens* (Human) |
| NMUR1_HUMAN | (Q9HB89) | NMUR1 | Neuromedin U | *Homo sapiens* (Human) |
| NMUR2_HUMAN | (Q9GZQ4) | NMUR2 | Neuromedin U | *Homo sapiens* (Human) |
| NPBW1_HUMAN | (P48145) | NPBWR1 | GPR | *Homo sapiens* (Human) |
| NPBW2_HUMAN | (P48146) | NPBWR2 | GPR | *Homo sapiens* (Human) |
| NPFF1_HUMAN | (Q9GZQ6) | NPFFR1 | Neuropeptide FF | *Homo sapiens* (Human) |

TABLE D-continued non-limiting list human GPCRs

| | | | | |
|---|---|---|---|---|
| NPFF2_HUMAN | (Q9Y5X5) | NPFFR2 | Neuropeptide FF | *Homo sapiens* (Human) |
| NPY1R_HUMAN | (P25929) | NPY1R | Neuropeptide Y type 1 | *Homo sapiens* (Human) |
| NPY2R_HUMAN | (P49146) | NPY2R | Neuropeptide Y type 2 | *Homo sapiens* (Human) |
| NPY4R_HUMAN | (P50391) | PPYR1 | Neuropeptide Y type 4 | *Homo sapiens* (Human) |
| NPY5R_HUMAN | (Q15761) | NPY5R | Neuropeptide Y type 5 | *Homo sapiens* (Human) |
| NTR1_HUMAN | (P30989) | NTSR1 | Neurotensin | *Homo sapiens* (Human) |
| NTR2_HUMAN | (O95665) | NTSR2 | Neurotensin | *Homo sapiens* (Human) |
| O00325_HUMAN | (O00325) | PTGER3 | Prostaglandin E2 subtype EP3 | *Homo sapiens* (Human) |
| O00421_HUMAN | (O00421) | ccr6 | C-C Chemokine other | *Homo sapiens* (Human) |
| O10A1_HUMAN | (O95223) | OR10A1 | fragments | *Homo sapiens* (Human) |
| O10A3_HUMAN | (P58181) | OR10A3 | Olfactory II fam 10/MOR263-269 | *Homo sapiens* (Human) |
| O10A4_HUMAN | (Q9H209) | OR10A4 | Olfactory II fam 10/MOR263-269 | *Homo sapiens* (Human) |
| O10A5_HUMAN | (Q9H207) | OR10A5 | Olfactory II fam 10/MOR263-269 | *Homo sapiens* (Human) |
| O10A6_HUMAN | (Q8NH74) | OR10A6 | Olfactory II fam 10/MOR263-269 | *Homo sapiens* (Human) |
| O10A7_HUMAN | (Q8NGE5) | OR10A7 | Olfactory II fam 10/MOR263-269 | *Homo sapiens* (Human) |
| O10AD_HUMAN | (Q8NGE0) | OR10AD1 | Olfactory II fam 10/MOR263-269 | *Homo sapiens* (Human) |
| O10AG_HUMAN | (Q8NH19) | OR10AG1 | Olfactory II fam 10/MOR263-269 | *Homo sapiens* (Human) |
| O10C1_HUMAN | (Q96KK4) | OR10C1 | Olfactory II fam 10/MOR263-269 | *Homo sapiens* (Human) |
| O10D4_HUMAN | (Q8NGN7) | OR10D4 | Olfactory II fam 10/MOR263-269 | *Homo sapiens* (Human) |
| O10G2_HUMAN | (Q8NGC3) | OR10G2 | Olfactory II fam 10/MOR263-269 | *Homo sapiens* (Human) |
| O10G3_HUMAN | (Q8NGC4) | OR10G3 | Olfactory II fam 10/MOR263-269 | *Homo sapiens* (Human) |
| O10G4_HUMAN | (Q8NGN3) | OR10G4 | Olfactory II fam 10/MOR263-269 | *Homo sapiens* (Human) |
| O10G6_HUMAN | (Q8NH81) | OR10G6 | Olfactory II fam 10/MOR263-269 | *Homo sapiens* (Human) |
| O10G7_HUMAN | (Q8NGN6) | OR10G7 | Olfactory II fam 10/MOR263-269 | *Homo sapiens* (Human) |
| O10G8_HUMAN | (Q8NGN5) | OR10G8 | Olfactory II fam 10/MOR263-269 | *Homo sapiens* (Human) |
| O10G9_HUMAN | (Q8NGN4) | OR10G9 | Olfactory II fam 10/MOR263-269 | *Homo sapiens* (Human) |
| O10H1_HUMAN | (Q9Y4A9) | OR10H1 | Olfactory II fam 10/MOR263-269 | *Homo sapiens* (Human) |
| O10H2_HUMAN | (O60403) | OR10H2 | Olfactory II fam 10/MOR263-269 | *Homo sapiens* (Human) |
| O10H3_HUMAN | (O60404) | OR10H3 | Olfactory II fam 10/MOR263-269 | *Homo sapiens* (Human) |
| O10H4_HUMAN | (Q8NGA5) | OR10H4 | Olfactory II fam 10/MOR263-269 | *Homo sapiens* (Human) |
| O10H5_HUMAN | (Q8NGA6) | OR10H5 | Olfactory II fam 10/MOR263-269 | *Homo sapiens* (Human) |
| O10J1_HUMAN | (P30954) | OR10J1 | Olfactory II fam 10/MOR263-269 | *Homo sapiens* (Human) |
| O10J3_HUMAN | (Q5JRS4) | OR10J3 | Olfactory II fam 10/MOR263-269 | *Homo sapiens* (Human) |
| O10J5_HUMAN | (Q8NHC4) | OR10J5 | Olfactory II fam 10/MOR263-269 | *Homo sapiens* (Human) |
| O10J6_HUMAN | (Q8NGY7) | OR10J6 | Olfactory II fam 10/MOR263-269 | *Homo sapiens* (Human) |
| O10K1_HUMAN | (Q8NGX5) | OR10K1 | Olfactory II fam 10/MOR263-269 | *Homo sapiens* (Human) |
| O10K2_HUMAN | (Q6IF99) | OR10K2 | Olfactory II fam 10/MOR263-269 | *Homo sapiens* (Human) |
| O10P1_HUMAN | (Q8NGE3) | OR10P1 | Olfactory II fam 10/MOR263-269 | *Homo sapiens* (Human) |
| O10Q1_HUMAN | (Q8NGQ4) | OR10Q1 | Olfactory II fam 10/MOR263-269 | *Homo sapiens* (Human) |
| O10R2_HUMAN | (Q8NGX6) | OR10R2 | Olfactory II fam 10/MOR263-269 | *Homo sapiens* (Human) |
| O10S1_HUMAN | (Q8NGN2) | OR10S1 | Olfactory II fam 10/MOR263-269 | *Homo sapiens* (Human) |
| O10T2_HUMAN | (Q8NGX3) | OR10T2 | Olfactory II fam 10/MOR263-269 | *Homo sapiens* (Human) |
| O10V1_HUMAN | (Q8NGI7) | OR10V1 | Olfactory II fam 10/MOR263-269 | *Homo sapiens* (Human) |
| O10W1_HUMAN | (Q8NGF6) | OR10W1 | Olfactory II fam 10/MOR263-269 | *Homo sapiens* (Human) |
| O10X1_HUMAN | (Q8NGY0) | OR10X1 | Olfactory II fam 10/MOR263-269 | *Homo sapiens* (Human) |
| O10Z1_HUMAN | (Q8NGY1) | OR10Z1 | Olfactory II fam 10/MOR263-269 | *Homo sapiens* (Human) |
| O11A1_HUMAN | (Q9GZK7) | OR11A1 | Olfactory II fam 11/MOR106,121-122 | *Homo sapiens* (Human) |
| O11G2_HUMAN | (Q8NGC1) | OR11G2 | Olfactory II fam 11/MOR106,121-122 | *Homo sapiens* (Human) |
| O11H1_HUMAN | (Q8NG94) | OR11H1 | Olfactory II fam 11/MOR106,121-122 | *Homo sapiens* (Human) |
| O11H4_HUMAN | (Q8NGC9) | OR11H4 | Olfactory II fam 11/MOR106,121-122 | *Homo sapiens* (Human) |
| O11H6_HUMAN | (Q8NGC7) | OR11H6 | Olfactory II fam 11/MOR106,121-122 | *Homo sapiens* (Human) |
| O11L1_HUMAN | (Q8NGX0) | OR11L1 | Olfactory II fam 11/MOR106,121-122 | *Homo sapiens* (Human) |
| O12D2_HUMAN | (P58182) | OR12D2 | Olfactory II fam 12/MOR250 | *Homo sapiens* (Human) |
| O12D3_HUMAN | (Q9UGF7) | OR12D3 | Olfactory II fam 12/MOR250 | *Homo sapiens* (Human) |
| O13A1_HUMAN | (Q8NGR1) | OR13A1 | Olfactory II fam 13/MOR253 | *Homo sapiens* (Human) |
| O13C2_HUMAN | (Q8NGS9) | OR13C2 | Olfactory II fam 13/MOR253 | *Homo sapiens* (Human) |
| O13C3_HUMAN | (Q8NGS6) | OR13C3 | Olfactory II fam 13/MOR253 | *Homo sapiens* (Human) |
| O13C4_HUMAN | (Q8NGS5) | OR13C4 | Olfactory II fam 13/MOR253 | *Homo sapiens* (Human) |
| O13C5_HUMAN | (Q8NGS8) | OR13C5 | Olfactory II fam 13/MOR253 | *Homo sapiens* (Human) |
| O13C8_HUMAN | (Q8NGS7) | OR13C8 | Olfactory II fam 13/MOR253 | *Homo sapiens* (Human) |
| O13C9_HUMAN | (Q8NGT0) | OR13C9 | Olfactory II fam 13/MOR253 | *Homo sapiens* (Human) |
| O13D1_HUMAN | (Q8NGV5) | OR13D1 | Olfactory II fam 13/MOR253 | *Homo sapiens* (Human) |
| O13F1_HUMAN | (Q8NGS4) | OR13F1 | Olfactory II fam 13/MOR253 | *Homo sapiens* (Human) |
| O13G1_HUMAN | (Q8NGZ3) | OR13G1 | Olfactory II fam 13/MOR253 | *Homo sapiens* (Human) |
| O13H1_HUMAN | (Q8NG92) | OR13H1 | Olfactory II fam 13/MOR253 | *Homo sapiens* (Human) |
| O13J1_HUMAN | (Q8NGT2) | OR13J1 | Olfactory II fam 13/MOR253 | *Homo sapiens* (Human) |
| O14694_HUMAN | (O14694) | CCR5 | fragments | *Homo sapiens* (Human) |
| O2A12_HUMAN | (Q8NGT7) | OR2A12 | Olfactory II fam 2/MOR256-262,270-285 | *Homo sapiens* (Human) |
| O2A14_HUMAN | (Q96R47) | OR2A14 | Olfactory II fam 2/MOR256-262,270-285 | *Homo sapiens* (Human) |
| O2A42_HUMAN | (Q8NGT9) | OR2A42 | Olfactory II fam 2/MOR256-262,270-285 | *Homo sapiens* (Human) |
| O2AE1_HUMAN | (Q8NHA4) | OR2AE1 | Olfactory II fam 2/MOR256-262,270-285 | *Homo sapiens* (Human) |
| O2AG1_HUMAN | (Q9H205) | OR2AG1 | Olfactory II fam 2/MOR256-262,270-285 | *Homo sapiens* (Human) |
| O2AJ1_HUMAN | (Q8NGZ0) | OR2AJ1 | Olfactory II fam 2/MOR256-262,270-285 | *Homo sapiens* (Human) |
| O2AK2_HUMAN | (Q8NG84) | OR2AK2 | Olfactory II fam 2/MOR256-262,270-285 | *Homo sapiens* (Human) |
| O2AP1_HUMAN | (Q8NGE2) | OR2AP1 | Olfactory II fam 6/MOR103-105,107-119 | *Homo sapiens* (Human) |
| O2T10_HUMAN | (Q8NGZ9) | OR2T10 | Olfactory II fam 2/MOR256-262,270-285 | *Homo sapiens* (Human) |
| O2T11_HUMAN | (Q8NH01) | OR2T11 | Olfactory II fam 2/MOR256-262,270-285 | *Homo sapiens* (Human) |
| O2T12_HUMAN | (Q8NG77) | OR2T12 | Olfactory II fam 2/MOR256-262,270-285 | *Homo sapiens* (Human) |

TABLE D-continued non-limiting list human GPCRs

| | | | | |
|---|---|---|---|---|
| O2T27_HUMAN | (Q8NH04) | OR2T27 | Olfactory II fam 2/MOR256-262,270-285 | *Homo sapiens* (Human) |
| O2T29_HUMAN | (Q8NH02) | OR2T29 | Olfactory II fam 2/MOR256-262,270-285 | *Homo sapiens* (Human) |
| O2T33_HUMAN | (Q8NG76) | OR2T33 | Olfactory II fam 2/MOR256-262,270-285 | *Homo sapiens* (Human) |
| O2T34_HUMAN | (Q8NGX1) | OR2T34 | Olfactory II fam 2/MOR256-262,270-285 | *Homo sapiens* (Human) |
| O2T35_HUMAN | (Q8NGX2) | OR2T35 | Olfactory II fam 2/MOR256-262,270-285 | *Homo sapiens* (Human) |
| O43192_HUMAN | (O43192) | | Vasopressin type 2 | *Homo sapiens* (Human) |
| O43200_HUMAN | (O43200) | TSHR | fragments | *Homo sapiens* (Human) |
| O43624_HUMAN | (O43624) | OLFR 42A | fragments | *Homo sapiens* (Human) |
| O43625_HUMAN | (O43625) | OLFR 42A | fragments | *Homo sapiens* (Human) |
| O43626_HUMAN | (O43626) | OLFR 42B | fragments | *Homo sapiens* (Human) |
| O43627_HUMAN | (O43627) | OR2H5P | fragments | *Homo sapiens* (Human) |
| O43789_HUMAN | (O43789) | | fragments | *Homo sapiens* (Human) |
| O43871_HUMAN | (O43871) | OR16-36 | fragments | *Homo sapiens* (Human) |
| O43872_HUMAN | (O43872) | OR16-37 | fragments | *Homo sapiens* (Human) |
| O43873_HUMAN | (O43873) | OR16-88 | fragments | *Homo sapiens* (Human) |
| O43874_HUMAN | (O43874) | OR16-89 | fragments | *Homo sapiens* (Human) |
| O43875_HUMAN | (O43875) | OR16-90 | fragments | *Homo sapiens* (Human) |
| O43876_HUMAN | (O43876) | OR17-130 | fragments | *Homo sapiens* (Human) |
| O43878_HUMAN | (O43878) | OR17-137 | fragments | *Homo sapiens* (Human) |
| O43879_HUMAN | (O43879) | OR17-15 | fragments | *Homo sapiens* (Human) |
| O43880_HUMAN | (O43880) | OR17-16 | fragments | *Homo sapiens* (Human) |
| O43886_HUMAN | (O43886) | OR7-139 | fragments | *Homo sapiens* (Human) |
| O43887_HUMAN | (O43887) | OR7-140 | fragments | *Homo sapiens* (Human) |
| O43898_HUMAN | (O43898) | | GPR45 like | *Homo sapiens* (Human) |
| O4A15_HUMAN | (Q8NGL6) | OR4A15 | Olfactory II fam 4/MOR225-248 | *Homo sapiens* (Human) |
| O4A16_HUMAN | (Q8NH70) | OR4A16 | Olfactory II fam 4/MOR225-248 | *Homo sapiens* (Human) |
| O4A47_HUMAN | (Q6IF82) | OR4A47 | Olfactory II fam 4/MOR225-248 | *Homo sapiens* (Human) |
| O4F15_HUMAN | (Q8NGB8) | OR4F15 | Olfactory II fam 4/MOR225-248 | *Homo sapiens* (Human) |
| O4F17_HUMAN | (Q8NGA8) | OR4F17 | Olfactory II fam 4/MOR225-248 | *Homo sapiens* (Human) |
| O4F29_HUMAN | (Q6IEY1) | OR4F29 | Olfactory II fam 4/MOR225-248 | *Homo sapiens* (Human) |
| O51A2_HUMAN | (Q8NGJ7) | OR51A2 | Olfactory I fam 51-52/MOR1-42 | *Homo sapiens* (Human) |
| O51A4_HUMAN | (Q8NGJ6) | OR51A4 | Olfactory I fam 51-52/MOR1-42 | *Homo sapiens* (Human) |
| O51A7_HUMAN | (Q8NH64) | OR51A7 | Olfactory I fam 51-52/MOR1-42 | *Homo sapiens* (Human) |
| O51B2_HUMAN | (Q9Y5P1) | OR51B2 | Olfactory I fam 51-52/MOR1-42 | *Homo sapiens* (Human) |
| O51B4_HUMAN | (Q9Y5P0) | OR51B4 | Olfactory I fam 51-52/MOR1-42 | *Homo sapiens* (Human) |
| O51B5_HUMAN | (Q9H339) | OR51B5 | Olfactory I fam 51-52/MOR1-42 | *Homo sapiens* (Human) |
| O51B6_HUMAN | (Q9H340) | OR51B6 | Olfactory I fam 51-52/MOR1-42 | *Homo sapiens* (Human) |
| O51D1_HUMAN | (Q8NGF3) | OR51D1 | Olfactory I fam 51-52/MOR1-42 | *Homo sapiens* (Human) |
| O51E1_HUMAN | (Q8TCB6) | OR51E1 | Olfactory I fam 51-52/MOR1-42 | *Homo sapiens* (Human) |
| O51E2_HUMAN | (Q9H255) | OR51E2 | Olfactory I fam 51-52/MOR1-42 | *Homo sapiens* (Human) |
| O51F1_HUMAN | (Q8NH61) | OR51F2 | Olfactory I fam 51-52/MOR1-42 | *Homo sapiens* (Human) |
| O51G1_HUMAN | (Q8NGK1) | OR51G1 | Olfactory I fam 51-52/MOR1-42 | *Homo sapiens* (Human) |
| O51G2_HUMAN | (Q8NGK0) | OR51G2 | Olfactory I fam 51-52/MOR1-42 | *Homo sapiens* (Human) |
| O51H1_HUMAN | (Q8NH63) | OR51H1 | Olfactory I fam 51-52/MOR1-42 | *Homo sapiens* (Human) |
| O51I1_HUMAN | (Q9H343) | OR51I1 | Olfactory I fam 51-52/MOR1-42 | *Homo sapiens* (Human) |
| O51I2_HUMAN | (Q9H344) | OR51I2 | Olfactory I fam 51-52/MOR1-42 | *Homo sapiens* (Human) |
| O51L1_HUMAN | (Q8NGJ5) | OR51L1 | Olfactory I fam 51-52/MOR1-42 | *Homo sapiens* (Human) |
| O51M1_HUMAN | (Q9H341) | OR51M1 | Olfactory I fam 51-52/MOR1-42 | *Homo sapiens* (Human) |
| O51Q1_HUMAN | (Q8NH59) | OR51Q1 | Olfactory I fam 51-52/MOR1-42 | *Homo sapiens* (Human) |
| O51S1_HUMAN | (Q8NGJ8) | OR51S1 | Olfactory I fam 51-52/MOR1-42 | *Homo sapiens* (Human) |
| O51T1_HUMAN | (Q8NGJ9) | OR51T1 | Olfactory I fam 51-52/MOR1-42 | *Homo sapiens* (Human) |
| O51V1_HUMAN | (Q9H2C8) | OR51V1 | Olfactory I fam 51-52/MOR1-42 | *Homo sapiens* (Human) |
| O52A1_HUMAN | (Q9UKL2) | OR52A1 | Olfactory I fam 51-52/MOR1-42 | *Homo sapiens* (Human) |
| O52A5_HUMAN | (Q9H2C5) | OR52A5 | Olfactory I fam 51-52/MOR1-42 | *Homo sapiens* (Human) |
| O52B2_HUMAN | (Q96RD2) | OR52B2 | Olfactory I fam 51-52/MOR1-42 | *Homo sapiens* (Human) |
| O52B4_HUMAN | (Q8NGK2) | OR52B4 | Olfactory I fam 51-52/MOR1-42 | *Homo sapiens* (Human) |
| O52B6_HUMAN | (Q8NGF0) | OR52B6 | Olfactory I fam 51-52/MOR1-42 | *Homo sapiens* (Human) |
| O52D1_HUMAN | (Q9H346) | OR52D1 | Olfactory I fam 51-52/MOR1-42 | *Homo sapiens* (Human) |
| O52E1_HUMAN | (Q8NGJ3) | OR52E1 | Olfactory I fam 51-52/MOR1-42 | *Homo sapiens* (Human) |
| O52E2_HUMAN | (Q8NGJ4) | OR52E2 | Olfactory I fam 51-52/MOR1-42 | *Homo sapiens* (Human) |
| O52E4_HUMAN | (Q8NGH9) | OR52E4 | Olfactory I fam 51-52/MOR1-42 | *Homo sapiens* (Human) |
| O52E5_HUMAN | (Q8NH55) | OR52E5 | Olfactory I fam 51-52/MOR1-42 | *Homo sapiens* (Human) |
| O52E6_HUMAN | (Q96RD3) | OR52E6 | Olfactory I fam 51-52/MOR1-42 | *Homo sapiens* (Human) |
| O52E8_HUMAN | (Q6IFG1) | OR52E8 | Olfactory I fam 51-52/MOR1-42 | *Homo sapiens* (Human) |
| O52H1_HUMAN | (Q8NGJ2) | OR52H1 | Olfactory I fam 51-52/MOR1-42 | *Homo sapiens* (Human) |
| O52I1_HUMAN | (Q8NGK6) | OR52I1 | Olfactory I fam 51-52/MOR1-42 | *Homo sapiens* (Human) |
| O52I2_HUMAN | (Q8NH67) | OR52I2 | Olfactory I fam 51-52/MOR1-42 | *Homo sapiens* (Human) |
| O52J3_HUMAN | (Q8NH60) | OR52J3 | Olfactory I fam 51-52/MOR1-42 | *Homo sapiens* (Human) |
| O52K1_HUMAN | (Q8NGK4) | OR52K1 | Olfactory I fam 51-52/MOR1-42 | *Homo sapiens* (Human) |
| O52K2_HUMAN | (Q8NGK3) | OR52K2 | Olfactory I fam 51-52/MOR1-42 | *Homo sapiens* (Human) |
| O52L1_HUMAN | (Q8NGH7) | OR52L1 | Olfactory I fam 51-52/MOR1-42 | *Homo sapiens* (Human) |
| O52L2_HUMAN | (Q8NGH6) | OR52L2 | Olfactory I fam 51-52/MOR1-42 | *Homo sapiens* (Human) |
| O52M1_HUMAN | (Q8NGK5) | OR52M1 | Olfactory I fam 51-52/MOR1-42 | *Homo sapiens* (Human) |
| O52N1_HUMAN | (Q8NH53) | OR52N1 | Olfactory I fam 51-52/MOR1-42 | *Homo sapiens* (Human) |
| O52N2_HUMAN | (Q8NGI0) | OR52N2 | Olfactory I fam 51-52/MOR1-42 | *Homo sapiens* (Human) |
| O52N4_HUMAN | (Q8NGI2) | OR52N4 | Olfactory I fam 51-52/MOR1-42 | *Homo sapiens* (Human) |
| O52N5_HUMAN | (Q8NH56) | OR52N5 | Olfactory I fam 51-52/MOR1-42 | *Homo sapiens* (Human) |
| O52P1_HUMAN | (Q8NH57) | OR52P1 | Olfactory I fam 51-52/MOR1-42 | *Homo sapiens* (Human) |

TABLE D-continued

| | | | non-limiting list human GPCRs | |
|---|---|---|---|---|
| O52R1_HUMAN | (Q8NGF1) | OR52R1 | Olfactory I fam 51-52/MOR1-42 | *Homo sapiens* (Human) |
| O52W1_HUMAN | (Q6IF63) | OR52W1 | Olfactory I fam 51-52/MOR1-42 | *Homo sapiens* (Human) |
| O56A1_HUMAN | (Q8NGH5) | OR56A1 | Olfactory I fam 51-52/MOR1-42 | *Homo sapiens* (Human) |
| O56A3_HUMAN | (Q8NH54) | OR56A3 | Olfactory I fam 51-52/MOR1-42 | *Homo sapiens* (Human) |
| O56A4_HUMAN | (Q8NGH8) | OR56A4 | Olfactory I fam 51-52/MOR1-42 | *Homo sapiens* (Human) |
| O56B1_HUMAN | (Q8NGI3) | OR56B1 | Olfactory I fam 51-52/MOR1-42 | *Homo sapiens* (Human) |
| O56B2_HUMAN | (Q8NGI1) | OR56B2P | Olfactory I fam 51-52/MOR1-42 | *Homo sapiens* (Human) |
| O56B4_HUMAN | (Q8NH76) | OR56B4 | Olfactory I fam 51-52/MOR1-42 | *Homo sapiens* (Human) |
| O5AC2_HUMAN | (Q9NZP5) | OR5AC2 | Olfactory II fam 5/MOR172-224,249,254 | *Homo sapiens* (Human) |
| O5AK2_HUMAN | (Q8NH90) | OR5AK2 | Olfactory II fam 5/MOR172-224,249,254 | *Homo sapiens* (Human) |
| O5AK3_HUMAN | (Q8NH89) | OR5AK3 | Olfactory II fam 5/MOR172-224,249,254 | *Homo sapiens* (Human) |
| O5AN1_HUMAN | (Q8NGI8) | OR5AN1 | Olfactory II fam 5/MOR172-224,249,254 | *Homo sapiens* (Human) |
| O5AP2_HUMAN | (Q8NGF4) | OR5AP2 | Olfactory II fam 5/MOR172-224,249,254 | *Homo sapiens* (Human) |
| O5AR1_HUMAN | (Q8NGP9) | OR5AR1 | Olfactory II fam 5/MOR172-224,249,254 | *Homo sapiens* (Human) |
| O5AS1_HUMAN | (Q8N127) | OR5AS1 | Olfactory II fam 5/MOR172-224,249,254 | *Homo sapiens* (Human) |
| O5AT1_HUMAN | (Q8NHC5) | OR5AT1 | Olfactory II fam 5/MOR172-224,249,254 | *Homo sapiens* (Human) |
| O5AU1_HUMAN | (Q8NGC0) | OR5AU1 | Olfactory II fam 5/MOR172-224,249,254 | *Homo sapiens* (Human) |
| O5AV1_HUMAN | (Q8NHC6) | OR5AV1P | Olfactory II fam 5/MOR172-224,249,254 | *Homo sapiens* (Human) |
| O5AY1_HUMAN | (Q8NGZ2) | OR5AY1 | Olfactory II fam 5/MOR172-224,249,254 | *Homo sapiens* (Human) |
| O5BF1_HUMAN | (Q8NHC7) | OR5BF1 | Olfactory II fam 5/MOR172-224,249,254 | *Homo sapiens* (Human) |
| O60411_HUMAN | (O60411) | | fragments | *Homo sapiens* (Human) |
| O75228_HUMAN | (O75228) | TBXA2R | Thromboxane | *Homo sapiens* (Human) |
| O75307_HUMAN | (O75307) | CCRL2 | C-C Chemokine other | *Homo sapiens* (Human) |
| O75824_HUMAN | (O75824) | CCKBR | fragments | *Homo sapiens* (Human) |
| O95220_HUMAN | (O95220) | OR5D3 | fragments | *Homo sapiens* (Human) |
| O95499_HUMAN | (O95499) | olfr89 | Olfactory II fam 2/MOR256-262,270-285 | *Homo sapiens* (Human) |
| O95950_HUMAN | (O95950) | | fragments | *Homo sapiens* (Human) |
| OPN3_HUMAN | (Q9H1Y3) | OPN3 | Rhodopsin Other | *Homo sapiens* (Human) |
| OPN4_HUMAN | (Q9UHM6) | OPN4 | Rhodopsin Other | *Homo sapiens* (Human) |
| OPN5_HUMAN | (Q6U736) | OPN5 | Rhodopsin Other | *Homo sapiens* (Human) |
| OPRD_HUMAN | (P41143) | OPRD1 | Opioid type D | *Homo sapiens* (Human) |
| OPRK_HUMAN | (P41145) | OPRK1 | Opioid type K | *Homo sapiens* (Human) |
| OPRM_HUMAN | (P35372) | OPRM1 | Opioid type M | *Homo sapiens* (Human) |
| OPRX_HUMAN | (P41146) | OPRL1 | Opioid type X | *Homo sapiens* (Human) |
| OPSB_HUMAN | (P03999) | OPN1SW | Rhodopsin Vertebrate type 3 | *Homo sapiens* (Human) |
| OPSD_HUMAN | (P08100) | RHO | Rhodopsin Vertebrate type 1 | *Homo sapiens* (Human) |
| OPSG_HUMAN | (P04001) | OPN1MW | Rhodopsin Vertebrate type 2 | *Homo sapiens* (Human) |
| OPSR_HUMAN | (P04000) | OPN1LW | Rhodopsin Vertebrate type 2 | *Homo sapiens* (Human) |
| OPSX_HUMAN | (O14718) | RRH | Rhodopsin Other | *Homo sapiens* (Human) |
| OR1A1_HUMAN | (Q9P1Q5) | OR1A1 | Olfactory II fam 1/MOR125-138,156 | *Homo sapiens* (Human) |
| OR1A2_HUMAN | (Q9Y585) | OR1A2 | Olfactory II fam 1/MOR125-138,156 | *Homo sapiens* (Human) |
| OR1B1_HUMAN | (Q8NGR6) | OR1B1 | Olfactory II fam 1/MOR125-138,156 | *Homo sapiens* (Human) |
| OR1C1_HUMAN | (Q15619) | OR1C1 | Olfactory II fam 1/MOR125-138,156 | *Homo sapiens* (Human) |
| OR1D2_HUMAN | (P34982) | OR1D2 | Olfactory II fam 1/MOR125-138,156 | *Homo sapiens* (Human) |
| OR1D4_HUMAN | (P47884) | OR1D4 | Olfactory II fam 1/MOR125-138,156 | *Homo sapiens* (Human) |
| OR1D5_HUMAN | (P58170) | OR1D5 | Olfactory II fam 1/MOR125-138,156 | *Homo sapiens* (Human) |
| OR1E1_HUMAN | (P30953) | OR1E1 | Olfactory II fam 1/MOR125-138,156 | *Homo sapiens* (Human) |
| OR1E2_HUMAN | (P47887) | OR1E2 | Olfactory II fam 1/MOR125-138,156 | *Homo sapiens* (Human) |
| OR1F1_HUMAN | (O43749) | OR1F1 | Olfactory II fam 1/MOR125-138,156 | *Homo sapiens* (Human) |
| OR1F2_HUMAN | (Q96R84) | OR1F2 | Olfactory II fam 1/MOR125-138,156 | *Homo sapiens* (Human) |
| OR1FC_HUMAN | (Q8NHA8) | OR1F12P | Olfactory II fam 1/MOR125-138,156 | *Homo sapiens* (Human) |
| OR1G1_HUMAN | (P47890) | OR1G1 | Olfactory II fam 1/MOR125-138,156 | *Homo sapiens* (Human) |
| OR1I1_HUMAN | (O60431) | OR1I1 | Olfactory II fam 1/MOR125-138,156 | *Homo sapiens* (Human) |
| OR1J1_HUMAN | (Q8NGS3) | OR1J1 | Olfactory II fam 1/MOR125-138,156 | *Homo sapiens* (Human) |
| OR1J2_HUMAN | (Q8NGS2) | OR1J2 | Olfactory II fam 1/MOR125-138,156 | *Homo sapiens* (Human) |
| OR1J4_HUMAN | (Q8NGS1) | OR1J4 | Olfactory II fam 1/MOR125-138,156 | *Homo sapiens* (Human) |
| OR1K1_HUMAN | (Q8NGR3) | OR1K1 | Olfactory II fam 1/MOR125-138,156 | *Homo sapiens* (Human) |
| OR1L1_HUMAN | (Q8NH94) | OR1L1 | Olfactory II fam 1/MOR125-138,156 | *Homo sapiens* (Human) |
| OR1L3_HUMAN | (Q8NH93) | OR1L3 | Olfactory II fam 1/MOR125-138,156 | *Homo sapiens* (Human) |
| OR1L4_HUMAN | (Q8NGR5) | OR1L4 | Olfactory II fam 1/MOR125-138,156 | *Homo sapiens* (Human) |
| OR1L6_HUMAN | (Q8NGR2) | OR1L6 | Olfactory II fam 1/MOR125-138,156 | *Homo sapiens* (Human) |
| OR1L8_HUMAN | (Q8NGR8) | OR1L8 | Olfactory II fam 1/MOR125-138,156 | *Homo sapiens* (Human) |
| OR1M1_HUMAN | (Q8NGA1) | OR1M1 | Olfactory II fam 1/MOR125-138,156 | *Homo sapiens* (Human) |
| OR1N1_HUMAN | (Q8NGS0) | OR1N1 | Olfactory II fam 1/MOR125-138,156 | *Homo sapiens* (Human) |
| OR1N2_HUMAN | (Q8NGR9) | OR1N2 | Olfactory II fam 1/MOR125-138,156 | *Homo sapiens* (Human) |
| OR1Q1_HUMAN | (Q15612) | OR1Q1 | Olfactory II fam 1/MOR125-138,156 | *Homo sapiens* (Human) |
| OR1S1_HUMAN | (Q8NH92) | OR1S1 | Olfactory II fam 1/MOR125-138,156 | *Homo sapiens* (Human) |
| OR1S2_HUMAN | (Q8NGQ3) | OR1S2 | Olfactory II fam 1/MOR125-138,156 | *Homo sapiens* (Human) |
| OR2A2_HUMAN | (Q6IF42) | OR2A2 | Olfactory II fam 2/MOR256-262,270-285 | *Homo sapiens* (Human) |
| OR2A4_HUMAN | (O95047) | OR2A4 | Olfactory II fam 2/MOR256-262,270-285 | *Homo sapiens* (Human) |
| OR2A5_HUMAN | (Q96R48) | OR2A5 | Olfactory II fam 2/MOR256-262,270-285 | *Homo sapiens* (Human) |
| OR2A7_HUMAN | (Q96R45) | OR2A7 | Olfactory II fam 2/MOR256-262,270-285 | *Homo sapiens* (Human) |
| OR2B2_HUMAN | (Q9GZK3) | OR2B2 | Olfactory II fam 2/MOR256-262,270-285 | *Homo sapiens* (Human) |
| OR2B3_HUMAN | (O76000) | OR2B3 | Olfactory II fam 2/MOR256-262,270-285 | *Homo sapiens* (Human) |
| OR2B6_HUMAN | (P58173) | OR2B6 | Olfactory II fam 2/MOR256-262,270-285 | *Homo sapiens* (Human) |
| OR2B8_HUMAN | (P59922) | OR2B8 | Olfactory II fam 2/MOR256-262,270-285 | *Homo sapiens* (Human) |
| OR2BB_HUMAN | (Q5JQS5) | OR2B11 | Olfactory II fam 2/MOR256-262,270-285 | *Homo sapiens* (Human) |
| OR2C1_HUMAN | (O95371) | OR2C1 | Olfactory II fam 2/MOR256-262,270-285 | *Homo sapiens* (Human) |

TABLE D-continued non-limiting list human GPCRs

| | | | | |
|---|---|---|---|---|
| OR2C3_HUMAN | (Q8N628) | OR2C3 | Olfactory II fam 2/MOR256-262,270-285 | *Homo sapiens* (Human) |
| OR2D2_HUMAN | (Q9H210) | OR2D2 | Olfactory II fam 2/MOR256-262,270-285 | *Homo sapiens* (Human) |
| OR2D3_HUMAN | (Q8NGH3) | OR2D3 | Olfactory II fam 2/MOR256-262,270-285 | *Homo sapiens* (Human) |
| OR2F1_HUMAN | (Q13607) | OR2F1 | Olfactory II fam 2/MOR256-262,270-285 | *Homo sapiens* (Human) |
| OR2F2_HUMAN | (O95006) | OR2F2 | Olfactory II fam 2/MOR256-262,270-285 | *Homo sapiens* (Human) |
| OR2G2_HUMAN | (Q8NGZ5) | OR2G2 | Olfactory II fam 2/MOR256-262,270-285 | *Homo sapiens* (Human) |
| OR2G3_HUMAN | (Q8NGZ4) | OR2G3 | Olfactory II fam 2/MOR256-262,270-285 | *Homo sapiens* (Human) |
| OR2G6_HUMAN | (Q5TZ20) | OR2G6 | Olfactory II fam 2/MOR256-262,270-285 | *Homo sapiens* (Human) |
| OR2H1_HUMAN | (Q9GZK4) | OR2H1 | Olfactory II fam 2/MOR256-262,270-285 | *Homo sapiens* (Human) |
| OR2H2_HUMAN | (O95918) | OR2H2 | Olfactory II fam 2/MOR256-262,270-285 | *Homo sapiens* (Human) |
| OR2I1_HUMAN | (Q8NGU4) | OR2I1P | Olfactory II fam 2/MOR256-262,270-285 | *Homo sapiens* (Human) |
| OR2J1_HUMAN | (Q9GZK6) | OR2J1 | Olfactory II fam 2/MOR256-262,270-285 | *Homo sapiens* (Human) |
| OR2J2_HUMAN | (O76002) | OR2J2 | Olfactory II fam 2/MOR256-262,270-285 | *Homo sapiens* (Human) |
| OR2J3_HUMAN | (O76001) | OR2J3 | Olfactory II fam 2/MOR256-262,270-285 | *Homo sapiens* (Human) |
| OR2K1_HUMAN | (Q8NGT1) | OR2K2 | Olfactory II fam 13/MOR253 | *Homo sapiens* (Human) |
| OR2L2_HUMAN | (Q8NH16) | OR2L2 | Olfactory II fam 2/MOR256-262,270-285 | *Homo sapiens* (Human) |
| OR2L3_HUMAN | (Q8NG85) | OR2L3 | Olfactory II fam 2/MOR256-262,270-285 | *Homo sapiens* (Human) |
| OR2L5_HUMAN | (Q8NG80) | OR2L5 | Olfactory II fam 2/MOR256-262,270-285 | *Homo sapiens* (Human) |
| OR2L8_HUMAN | (Q8NGY9) | OR2L8 | Olfactory II fam 2/MOR256-262,270-285 | *Homo sapiens* (Human) |
| OR2LD_HUMAN | (Q8N349) | OR2L13 | Olfactory II fam 2/MOR256-262,270-285 | *Homo sapiens* (Human) |
| OR2M2_HUMAN | (Q96R28) | OR2M2 | Olfactory II fam 2/MOR256-262,270-285 | *Homo sapiens* (Human) |
| OR2M3_HUMAN | (Q8NG83) | OR2M3 | Olfactory II fam 2/MOR256-262,270-285 | *Homo sapiens* (Human) |
| OR2M4_HUMAN | (Q96R27) | OR2M4 | Olfactory II fam 2/MOR256-262,270-285 | *Homo sapiens* (Human) |
| OR2M7_HUMAN | (Q8NG81) | OR2M7 | Olfactory II fam 2/MOR256-262,270-285 | *Homo sapiens* (Human) |
| OR2S1_HUMAN | (Q9NQN1) | OR2S2 | Olfactory II fam 13/MOR253 | *Homo sapiens* (Human) |
| OR2T1_HUMAN | (O43869) | OR2T1 | Olfactory II fam 2/MOR256-262,270-285 | *Homo sapiens* (Human) |
| OR2T2_HUMAN | (Q6IF00) | OR2T2 | Olfactory II fam 2/MOR256-262,270-285 | *Homo sapiens* (Human) |
| OR2T3_HUMAN | (Q8NH03) | OR2T3 | Olfactory II fam 2/MOR256-262,270-285 | *Homo sapiens* (Human) |
| OR2T4_HUMAN | (Q8NH00) | OR2T4 | Olfactory II fam 2/MOR256-262,270-285 | *Homo sapiens* (Human) |
| OR2T5_HUMAN | (Q6IEZ7) | OR2T5 | Olfactory II fam 2/MOR256-262,270-285 | *Homo sapiens* (Human) |
| OR2T6_HUMAN | (Q8NHC8) | OR2T6 | Olfactory II fam 2/MOR256-262,270-285 | *Homo sapiens* (Human) |
| OR2V2_HUMAN | (Q96R30) | OR2V2 | Olfactory II fam 2/MOR256-262,270-285 | *Homo sapiens* (Human) |
| OR2W1_HUMAN | (Q9Y3N9) | OR2W1 | Olfactory II fam 2/MOR256-262,270-285 | *Homo sapiens* (Human) |
| OR2W3_HUMAN | (Q7Z3T1) | OR2W3 | Olfactory II fam 2/MOR256-262,270-285 | *Homo sapiens* (Human) |
| OR2Y1_HUMAN | (Q8NGV0) | OR2Y1 | Olfactory II fam 2/MOR256-262,270-285 | *Homo sapiens* (Human) |
| OR2Z1_HUMAN | (Q8NG97) | OR2Z1 | Olfactory II fam 2/MOR256-262,270-285 | *Homo sapiens* (Human) |
| OR3A1_HUMAN | (P47881) | OR3A1 | Olfactory II fam 3/MOR255 | *Homo sapiens* (Human) |
| OR3A2_HUMAN | (P47893) | OR3A2 | Olfactory II fam 3/MOR255 | *Homo sapiens* (Human) |
| OR3A3_HUMAN | (P47888) | OR3A3 | Olfactory II fam 3/MOR255 | *Homo sapiens* (Human) |
| OR3A4_HUMAN | (P47883) | OR3A4 | Olfactory II fam 3/MOR255 | *Homo sapiens* (Human) |
| OR4A4_HUMAN | (Q8NGN8) | OR4A4 | Olfactory II fam 4/MOR225-248 | *Homo sapiens* (Human) |
| OR4A5_HUMAN | (Q8NH83) | OR4A5 | Olfactory II fam 4/MOR225-248 | *Homo sapiens* (Human) |
| OR4B1_HUMAN | (Q8NGF8) | OR4B1 | Olfactory II fam 4/MOR225-248 | *Homo sapiens* (Human) |
| OR4C3_HUMAN | (Q8NH37) | OR4C3 | Olfactory II fam 4/MOR225-248 | *Homo sapiens* (Human) |
| OR4C5_HUMAN | (Q8NGB2) | OR4C5 | Olfactory II fam 4/MOR225-248 | *Homo sapiens* (Human) |
| OR4C6_HUMAN | (Q8NH72) | OR4C6 | Olfactory II fam 4/MOR225-248 | *Homo sapiens* (Human) |
| OR4CB_HUMAN | (Q6IEV9) | OR4C11 | Olfactory II fam 4/MOR225-248 | *Homo sapiens* (Human) |
| OR4CC_HUMAN | (Q96R67) | OR4C12 | Olfactory II fam 4/MOR225-248 | *Homo sapiens* (Human) |
| OR4CD_HUMAN | (Q8NGP0) | OR4C13 | Olfactory II fam 4/MOR225-248 | *Homo sapiens* (Human) |
| OR4CF_HUMAN | (Q8NGM1) | OR4C15 | Olfactory II fam 4/MOR225-248 | *Homo sapiens* (Human) |
| OR4CG_HUMAN | (Q8NGL9) | OR4C16 | Olfactory II fam 4/MOR225-248 | *Homo sapiens* (Human) |
| OR4D1_HUMAN | (Q15615) | OR4D1 | Olfactory II fam 4/MOR225-248 | *Homo sapiens* (Human) |
| OR4D2_HUMAN | (P58180) | OR4D2 | Olfactory II fam 4/MOR225-248 | *Homo sapiens* (Human) |
| OR4D5_HUMAN | (Q8NGN0) | OR4D5 | Olfactory II fam 4/MOR225-248 | *Homo sapiens* (Human) |
| OR4D6_HUMAN | (Q8NGJ1) | OR4D6 | Olfactory II fam 4/MOR225-248 | *Homo sapiens* (Human) |
| OR4D9_HUMAN | (Q8NGE8) | OR4D9 | Olfactory II fam 4/MOR225-248 | *Homo sapiens* (Human) |
| OR4DA_HUMAN | (Q8NGI6) | OR4D10 | Olfactory II fam 4/MOR225-248 | *Homo sapiens* (Human) |
| OR4DB_HUMAN | (Q8NGI4) | OR4D11 | Olfactory II fam 4/MOR225-248 | *Homo sapiens* (Human) |
| OR4E2_HUMAN | (Q8NGC2) | OR4E2 | Olfactory II fam 4/MOR225-248 | *Homo sapiens* (Human) |
| OR4F3_HUMAN | (O95013) | OR4F3 | Olfactory II fam 4/MOR225-248 | *Homo sapiens* (Human) |
| OR4F4_HUMAN | (Q96R69) | OR4F4 | Olfactory II fam 4/MOR225-248 | *Homo sapiens* (Human) |
| OR4F5_HUMAN | (Q8NH21) | OR4F5 | Olfactory II fam 4/MOR225-248 | *Homo sapiens* (Human) |
| OR4F6_HUMAN | (Q8NGB9) | OR4F6 | Olfactory II fam 4/MOR225-248 | *Homo sapiens* (Human) |
| OR4K1_HUMAN | (Q8NGD4) | OR4K1 | Olfactory II fam 4/MOR225-248 | *Homo sapiens* (Human) |
| OR4K2_HUMAN | (Q8NGD2) | OR4K2 | Olfactory II fam 4/MOR225-248 | *Homo sapiens* (Human) |
| OR4K3_HUMAN | (Q96R72) | OR4K3 | Olfactory II fam 4/MOR225-248 | *Homo sapiens* (Human) |
| OR4K5_HUMAN | (Q8NGD3) | OR4K5 | Olfactory II fam 4/MOR225-248 | *Homo sapiens* (Human) |
| OR4KD_HUMAN | (Q8NH42) | OR4K13 | Olfactory II fam 4/MOR225-248 | *Homo sapiens* (Human) |
| OR4KE_HUMAN | (Q8NGD5) | OR4K14 | Olfactory II fam 4/MOR225-248 | *Homo sapiens* (Human) |
| OR4KF_HUMAN | (Q8NH41) | OR4K15 | Olfactory II fam 4/MOR225-248 | *Homo sapiens* (Human) |
| OR4KH_HUMAN | (Q8NGC6) | OR4K17 | Olfactory II fam 4/MOR225-248 | *Homo sapiens* (Human) |
| OR4L1_HUMAN | (Q8NH43) | OR4L1 | Olfactory II fam 4/MOR225-248 | *Homo sapiens* (Human) |
| OR4M1_HUMAN | (Q8NGD0) | OR4M1 | Olfactory II fam 4/MOR225-248 | *Homo sapiens* (Human) |
| OR4M2_HUMAN | (Q8NGB6) | OR4M2 | Olfactory II fam 4/MOR225-248 | *Homo sapiens* (Human) |
| OR4N2_HUMAN | (Q8NGD1) | OR4N2 | Olfactory II fam 4/MOR225-248 | *Homo sapiens* (Human) |
| OR4N4_HUMAN | (Q8N0Y3) | OR4N4 | Olfactory II fam 4/MOR225-248 | *Homo sapiens* (Human) |
| OR4N5_HUMAN | (Q8IXE1) | OR4N5 | Olfactory II fam 4/MOR225-248 | *Homo sapiens* (Human) |
| OR4P4_HUMAN | (Q8NGL7) | OR4P4 | Olfactory II fam 4/MOR225-248 | *Homo sapiens* (Human) |

TABLE D-continued non-limiting list human GPCRs

| | | | | |
|---|---|---|---|---|
| OR4Q3_HUMAN | (Q8NH05) | OR4Q3 | Olfactory II fam 4/MOR225-248 | *Homo sapiens* (Human) |
| OR4S1_HUMAN | (Q8NGB4) | OR4S1 | Olfactory II fam 4/MOR225-248 | *Homo sapiens* (Human) |
| OR4S2_HUMAN | (Q8NH73) | OR4S2 | Olfactory II fam 4/MOR225-248 | *Homo sapiens* (Human) |
| OR4X1_HUMAN | (Q8NH49) | OR4X1 | Olfactory II fam 4/MOR225-248 | *Homo sapiens* (Human) |
| OR4X2_HUMAN | (Q8NGF9) | OR4X2 | Olfactory II fam 4/MOR225-248 | *Homo sapiens* (Human) |
| OR5A1_HUMAN | (Q8NGJ0) | OR5A1 | Olfactory II fam 5/MOR172-224,249,254 | *Homo sapiens* (Human) |
| OR5A2_HUMAN | (Q8NGI9) | OR5A2 | Olfactory II fam 5/MOR172-224,249,254 | *Homo sapiens* (Human) |
| OR5B2_HUMAN | (Q96R09) | OR5B2 | Olfactory II fam 5/MOR172-224,249,254 | *Homo sapiens* (Human) |
| OR5B3_HUMAN | (Q8NH48) | OR5B3 | Olfactory II fam 5/MOR172-224,249,254 | *Homo sapiens* (Human) |
| OR5BC_HUMAN | (Q96R08) | OR5B12 | Olfactory II fam 5/MOR172-224,249,254 | *Homo sapiens* (Human) |
| OR5BH_HUMAN | (Q8NGF7) | OR5B17 | Olfactory II fam 5/MOR172-224,249,254 | *Homo sapiens* (Human) |
| OR5C1_HUMAN | (Q8NGR4) | OR5C1 | Olfactory II fam 5/MOR172-224,249,254 | *Homo sapiens* (Human) |
| OR5DD_HUMAN | (Q8NGL4) | OR5D13 | Olfactory II fam 5/MOR172-224,249,254 | *Homo sapiens* (Human) |
| OR5DE_HUMAN | (Q8NGL3) | OR5D14 | Olfactory II fam 5/MOR172-224,249,254 | *Homo sapiens* (Human) |
| OR5DG_HUMAN | (Q8NGK9) | OR5D16 | Olfactory II fam 5/MOR172-224,249,254 | *Homo sapiens* (Human) |
| OR5DI_HUMAN | (Q8NGL1) | OR5D18 | Olfactory II fam 5/MOR172-224,249,254 | *Homo sapiens* (Human) |
| OR5F1_HUMAN | (O95221) | OR5F1 | Olfactory II fam 5/MOR172-224,249,254 | *Homo sapiens* (Human) |
| OR5H2_HUMAN | (Q8NGV7) | OR5H2 | Olfactory II fam 5/MOR172-224,249,254 | *Homo sapiens* (Human) |
| OR5H6_HUMAN | (Q8NGV6) | OR5H6 | Olfactory II fam 5/MOR172-224,249,254 | *Homo sapiens* (Human) |
| OR5I1_HUMAN | (Q13606) | OR5I1 | Olfactory II fam 5/MOR172-224,249,254 | *Homo sapiens* (Human) |
| OR5J2_HUMAN | (Q8NH18) | OR5J2 | Olfactory II fam 5/MOR172-224,249,254 | *Homo sapiens* (Human) |
| OR5K1_HUMAN | (Q8NHB7) | OR5K1 | Olfactory II fam 5/MOR172-224,249,254 | *Homo sapiens* (Human) |
| OR5K2_HUMAN | (Q8NHB8) | OR5K2 | Olfactory II fam 5/MOR172-224,249,254 | *Homo sapiens* (Human) |
| OR5L1_HUMAN | (Q8NGL2) | OR5L1 | Olfactory II fam 5/MOR172-224,249,254 | *Homo sapiens* (Human) |
| OR5L2_HUMAN | (Q8NGL0) | OR5L2 | Olfactory II fam 5/MOR172-224,249,254 | *Homo sapiens* (Human) |
| OR5M1_HUMAN | (Q8NGP8) | OR5M1 | Olfactory II fam 5/MOR172-224,249,254 | *Homo sapiens* (Human) |
| OR5M3_HUMAN | (Q8NGP4) | OR5M3 | Olfactory II fam 5/MOR172-224,249,254 | *Homo sapiens* (Human) |
| OR5M8_HUMAN | (Q8NGP6) | OR5M8 | Olfactory II fam 5/MOR172-224,249,254 | *Homo sapiens* (Human) |
| OR5M9_HUMAN | (Q8NGP3) | OR5M9 | Olfactory II fam 5/MOR172-224,249,254 | *Homo sapiens* (Human) |
| OR5MA_HUMAN | (Q6IEU7) | OR5M10 | Olfactory II fam 5/MOR172-224,249,254 | *Homo sapiens* (Human) |
| OR5MB_HUMAN | (Q96RB7) | OR5M11 | Olfactory II fam 5/MOR172-224,249,254 | *Homo sapiens* (Human) |
| OR5P2_HUMAN | (Q8WZ92) | OR5P2 | Olfactory II fam 5/MOR172-224,249,254 | *Homo sapiens* (Human) |
| OR5P3_HUMAN | (Q8WZ94) | OR5P3 | Olfactory II fam 5/MOR172-224,249,254 | *Homo sapiens* (Human) |
| OR5R1_HUMAN | (Q8NH85) | OR5R1 | Olfactory II fam 8/MOR161-171 | *Homo sapiens* (Human) |
| OR5T1_HUMAN | (Q8NG75) | OR5T1 | Olfactory II fam 5/MOR172-224,249,254 | *Homo sapiens* (Human) |
| OR5T2_HUMAN | (Q8NGG2) | OR5T2 | Olfactory II fam 5/MOR172-224,249,254 | *Homo sapiens* (Human) |
| OR5T3_HUMAN | (Q8NGG3) | OR5T3 | Olfactory II fam 5/MOR172-224,249,254 | *Homo sapiens* (Human) |
| OR5U1_HUMAN | (Q9UGF5) | OR5U1 | Olfactory II fam 5/MOR172-224,249,254 | *Homo sapiens* (Human) |
| OR5V1_HUMAN | (Q9UGF6) | OR5V1 | Olfactory II fam 5/MOR172-224,249,254 | *Homo sapiens* (Human) |
| OR5W2_HUMAN | (Q8NH69) | OR5W2 | Olfactory II fam 5/MOR172-224,249,254 | *Homo sapiens* (Human) |
| OR6A2_HUMAN | (O95222) | OR6A2 | Olfactory II fam 6/MOR103-105,107-119 | *Homo sapiens* (Human) |
| OR6B1_HUMAN | (O95007) | OR6B1 | Olfactory II fam 6/MOR103-105,107-119 | *Homo sapiens* (Human) |
| OR6B2_HUMAN | (Q6IFH4) | OR6B2 | Olfactory II fam 6/MOR103-105,107-119 | *Homo sapiens* (Human) |
| OR6B3_HUMAN | (Q8NGW1) | OR6B3 | Olfactory II fam 6/MOR103-105,107-119 | *Homo sapiens* (Human) |
| OR6C1_HUMAN | (Q96RD1) | OR6C1 | Olfactory II fam 6/MOR103-105,107-119 | *Homo sapiens* (Human) |
| OR6C2_HUMAN | (Q9NZP2) | OR6C2 | Olfactory II fam 6/MOR103-105,107-119 | *Homo sapiens* (Human) |
| OR6C3_HUMAN | (Q9NZP0) | OR6C3 | Olfactory II fam 6/MOR103-105,107-119 | *Homo sapiens* (Human) |
| OR6C4_HUMAN | (Q8NGE1) | OR6C4 | Olfactory II fam 6/MOR103-105,107-119 | *Homo sapiens* (Human) |
| OR6F1_HUMAN | (Q8NGZ6) | OR6F1 | Olfactory II fam 6/MOR103-105,107-119 | *Homo sapiens* (Human) |
| OR6J1_HUMAN | (Q8NGC5) | OR6J1 | Olfactory II fam 6/MOR103-105,107-119 | *Homo sapiens* (Human) |
| OR6K2_HUMAN | (Q8NGY2) | OR6K2 | Olfactory II fam 6/MOR103-105,107-119 | *Homo sapiens* (Human) |
| OR6K3_HUMAN | (Q8NGY3) | OR6K3 | Olfactory II fam 6/MOR103-105,107-119 | *Homo sapiens* (Human) |
| OR6K6_HUMAN | (Q8NGW6) | OR6K6 | Olfactory II fam 6/MOR103-105,107-119 | *Homo sapiens* (Human) |
| OR6M1_HUMAN | (Q8NGM8) | OR6M1 | Olfactory II fam 6/MOR103-105,107-119 | *Homo sapiens* (Human) |
| OR6N1_HUMAN | (Q8NGY5) | OR6N1 | Olfactory II fam 6/MOR103-105,107-119 | *Homo sapiens* (Human) |
| OR6N2_HUMAN | (Q8NGY6) | OR6N2 | Olfactory II fam 6/MOR103-105,107-119 | *Homo sapiens* (Human) |
| OR6P1_HUMAN | (Q8NGX9) | OR6P1 | Olfactory II fam 6/MOR103-105,107-119 | *Homo sapiens* (Human) |
| OR6Q1_HUMAN | (Q8NGQ2) | OR6Q1 | Olfactory II fam 6/MOR103-105,107-119 | *Homo sapiens* (Human) |
| OR6S1_HUMAN | (Q8NH40) | OR6S1 | Olfactory II fam 6/MOR103-105,107-119 | *Homo sapiens* (Human) |
| OR6T1_HUMAN | (Q8NGN1) | OR6T1 | Olfactory II fam 6/MOR103-105,107-119 | *Homo sapiens* (Human) |
| OR6V1_HUMAN | (Q8N148) | OR6V1 | Olfactory II fam 6/MOR103-105,107-119 | *Homo sapiens* (Human) |
| OR6X1_HUMAN | (Q8NH79) | OR6X1 | Olfactory II fam 6/MOR103-105,107-119 | *Homo sapiens* (Human) |
| OR6Y1_HUMAN | (Q8NGX8) | OR6Y1 | Olfactory II fam 6/MOR103-105,107-119 | *Homo sapiens* (Human) |
| OR7A2_HUMAN | (Q8NGA2) | OR7A2 | Olfactory II fam 7/MOR139-155 | *Homo sapiens* (Human) |
| OR7A5_HUMAN | (Q15622) | OR7A5 | Olfactory II fam 7/MOR139-155 | *Homo sapiens* (Human) |
| OR7AA_HUMAN | (O76100) | OR7A10 | Olfactory II fam 7/MOR139-155 | *Homo sapiens* (Human) |
| OR7AH_HUMAN | (O14581) | OR7A17 | Olfactory II fam 7/MOR139-155 | *Homo sapiens* (Human) |
| OR7C1_HUMAN | (O76099) | OR7C1 | Olfactory II fam 7/MOR139-155 | *Homo sapiens* (Human) |
| OR7C2_HUMAN | (O60412) | OR7C2 | Olfactory II fam 7/MOR139-155 | *Homo sapiens* (Human) |
| OR7D2_HUMAN | (Q96RA2) | OR7D2 | Olfactory II fam 7/MOR139-155 | *Homo sapiens* (Human) |
| OR7D4_HUMAN | (Q8NG98) | OR7D4 | Olfactory II fam 7/MOR139-155 | *Homo sapiens* (Human) |
| OR7G1_HUMAN | (Q8NGA0) | OR7G1 | Olfactory II fam 7/MOR139-155 | *Homo sapiens* (Human) |
| OR7G2_HUMAN | (Q8NG99) | OR7G2 | Olfactory II fam 7/MOR139-155 | *Homo sapiens* (Human) |
| OR7G3_HUMAN | (Q8NG95) | OR7G3 | Olfactory II fam 7/MOR139-155 | *Homo sapiens* (Human) |
| OR8A1_HUMAN | (Q8NGG7) | OR8A1 | Olfactory II fam 8/MOR161-171 | *Homo sapiens* (Human) |
| OR8B2_HUMAN | (Q96RD0) | OR8B2 | Olfactory II fam 8/MOR161-171 | *Homo sapiens* (Human) |
| OR8B3_HUMAN | (Q8NGG8) | OR8B3 | Olfactory II fam 8/MOR161-171 | *Homo sapiens* (Human) |
| OR8B4_HUMAN | (Q96RC9) | OR8B4 | Olfactory II fam 8/MOR161-171 | *Homo sapiens* (Human) |

TABLE D-continued non-limiting list human GPCRs

| | | | | |
|---|---|---|---|---|
| OR8B8_HUMAN | (Q15620) | OR8B8 | Olfactory II fam 8/MOR161-171 | *Homo sapiens* (Human) |
| OR8BC_HUMAN | (Q8NGG6) | OR8B12 | Olfactory II fam 8/MOR161-171 | *Homo sapiens* (Human) |
| OR8D1_HUMAN | (Q8WZ84) | OR8D1 | Olfactory II fam 8/MOR161-171 | *Homo sapiens* (Human) |
| OR8D2_HUMAN | (Q9GZM6) | OR8D2 | Olfactory II fam 8/MOR161-171 | *Homo sapiens* (Human) |
| OR8D4_HUMAN | (Q8NGM9) | OR8D4 | Olfactory II fam 8/MOR161-171 | *Homo sapiens* (Human) |
| OR8G1_HUMAN | (Q15617) | OR8G1 | Olfactory II fam 8/MOR161-171 | *Homo sapiens* (Human) |
| OR8G2_HUMAN | (Q15614) | OR8G2 | Olfactory II fam 8/MOR161-171 | *Homo sapiens* (Human) |
| OR8G5_HUMAN | (Q8NG78) | OR8G5 | Olfactory II fam 8/MOR161-171 | *Homo sapiens* (Human) |
| OR8H1_HUMAN | (Q8NGG4) | OR8H1 | Olfactory II fam 8/MOR161-171 | *Homo sapiens* (Human) |
| OR8H2_HUMAN | (Q8N162) | OR8H2 | Olfactory II fam 8/MOR161-171 | *Homo sapiens* (Human) |
| OR8H3_HUMAN | (Q8N146) | OR8H3 | Olfactory II fam 8/MOR161-171 | *Homo sapiens* (Human) |
| OR8I2_HUMAN | (Q8N0Y5) | OR8I2 | Olfactory II fam 8/MOR161-171 | *Homo sapiens* (Human) |
| OR8J1_HUMAN | (Q8NGP2) | OR8J1 | Olfactory II fam 8/MOR161-171 | *Homo sapiens* (Human) |
| OR8J3_HUMAN | (Q8NGG0) | OR8J3 | Olfactory II fam 8/MOR161-171 | *Homo sapiens* (Human) |
| OR8K1_HUMAN | (Q8NGG5) | OR8K1 | Olfactory II fam 5/MOR172-224,249,254 | *Homo sapiens* (Human) |
| OR8K3_HUMAN | (Q8NH51) | OR8K3 | Olfactory II fam 8/MOR161-171 | *Homo sapiens* (Human) |
| OR8K5_HUMAN | (Q8NH50) | OR8K5 | Olfactory II fam 8/MOR161-171 | *Homo sapiens* (Human) |
| OR8S1_HUMAN | (Q8NH09) | OR8S1 | Olfactory unclassified class II | *Homo sapiens* (Human) |
| OR8U1_HUMAN | (Q8NH10) | OR8U1 | Olfactory II fam 8/MOR161-171 | *Homo sapiens* (Human) |
| OR9A2_HUMAN | (Q8NGT5) | OR9A2 | Olfactory II fam 9/MOR120 | *Homo sapiens* (Human) |
| OR9A4_HUMAN | (Q8NGU2) | OR9A4 | Olfactory II fam 9/MOR120 | *Homo sapiens* (Human) |
| OR9G1_HUMAN | (Q8NH87) | OR9G1 | Olfactory II fam 9/MOR120 | *Homo sapiens* (Human) |
| OR9G4_HUMAN | (Q8NGQ1) | OR9G4 | Olfactory II fam 9/MOR120 | *Homo sapiens* (Human) |
| OR9G5_HUMAN | (Q8NGQ0) | OR9G5 | Olfactory II fam 9/MOR120 | *Homo sapiens* (Human) |
| OR9I1_HUMAN | (Q8NGQ6) | OR9I1 | Olfactory II fam 9/MOR120 | *Homo sapiens* (Human) |
| OR9K2_HUMAN | (Q8NGE7) | OR9K2 | Olfactory II fam 9/MOR120 | *Homo sapiens* (Human) |
| OR9Q1_HUMAN | (Q8NGQ5) | OR9Q1 | Olfactory II fam 9/MOR120 | *Homo sapiens* (Human) |
| OR9Q2_HUMAN | (Q8NGE9) | OR9Q2 | Olfactory II fam 9/MOR120 | *Homo sapiens* (Human) |
| OX1R_HUMAN | (O43613) | HCRTR1 | Orexin | *Homo sapiens* (Human) |
| OX2R_HUMAN | (O43614) | HCRTR2 | Orexin | *Homo sapiens* (Human) |
| OXER1_HUMAN | (Q8TDS5) | OXER1 | Putative/unclassified Class A GPCRs | *Homo sapiens* (Human) |
| OXGR1_HUMAN | (Q96P68) | OXGR1 | Putative/unclassified Class A GPCRs | *Homo sapiens* (Human) |
| OXYR_HUMAN | (P30559) | OXTR | Oxytocin/mesotocin | *Homo sapiens* (Human) |
| P2RY1_HUMAN | (P47900) | P2RY1 | Purinoceptor P2RY1-4,6,11 GPR91 | *Homo sapiens* (Human) |
| P2RY2_HUMAN | (P41231) | P2RY2 | Purinoceptor P2RY1-4,6,11 GPR91 | *Homo sapiens* (Human) |
| P2RY4_HUMAN | (P51582) | P2RY4 | Purinoceptor P2RY1-4,6,11 GPR91 | *Homo sapiens* (Human) |
| P2RY5_HUMAN | (P43657) | P2RY5 | Purinoceptor P2RY5,8,9,10 GPR35,92,174 | *Homo sapiens* (Human) |
| P2RY6_HUMAN | (Q15077) | P2RY6 | Purinoceptor P2RY1-4,6,11 GPR91 | *Homo sapiens* (Human) |
| P2RY8_HUMAN | (Q86VZ1) | P2RY8 | Purinoceptor P2RY5,8,9,10 GPR35,92,174 | *Homo sapiens* (Human) |
| P2RY9_HUMAN | (Q99677) | GPR23 | Purinoceptor P2RY5,8,9,10 GPR35,92,174 | *Homo sapiens* (Human) |
| P2Y10_HUMAN | (O00398) | P2RY10 | Purinoceptor P2RY5,8,9,10 GPR35,92,174 | *Homo sapiens* (Human) |
| P2Y11_HUMAN | (Q96G91) | P2RY11 | Purinoceptor P2RY1-4,6,11 GPR91 | *Homo sapiens* (Human) |
| P2Y12_HUMAN | (Q9H244) | P2RY12 | Purinoceptor P2RY12-14 GPR87 (UDP-Glucose) | *Homo sapiens* (Human) |
| P2Y13_HUMAN | (Q9BPV8) | P2RY13 | Purinoceptor P2RY12-14 GPR87 (UDP-Glucose) | *Homo sapiens* (Human) |
| P2Y14_HUMAN | (Q15391) | P2RY14 | Purinoceptor P2RY12-14 GPR87 (UDP-Glucose) | *Homo sapiens* (Human) |
| P78470_HUMAN | (P78470) | | fragments | *Homo sapiens* (Human) |
| P78471_HUMAN | (P78471) | | fragments | *Homo sapiens* (Human) |
| PACR_HUMAN | (P41586) | ADCYAP1R1 | PACAP | *Homo sapiens* (Human) |
| PAR1_HUMAN | (P25116) | F2R | Thrombin | *Homo sapiens* (Human) |
| PAR2_HUMAN | (P55085) | F2RL1 | Proteinase-activated | *Homo sapiens* (Human) |
| PAR3_HUMAN | (O00254) | F2RL2 | Proteinase-activated | *Homo sapiens* (Human) |
| PAR4_HUMAN | (Q96RI0) | F2RL3 | Proteinase-activated | *Homo sapiens* (Human) |
| PD2R_HUMAN | (Q13258) | PTGDR | Prostaglandin E2/D2 subtype EP2 | *Homo sapiens* (Human) |
| PE2R1_HUMAN | (P34995) | PTGER1 | Prostaglandin E2 subtype EP1 | *Homo sapiens* (Human) |
| PE2R2_HUMAN | (P43116) | PTGER2 | Prostaglandin E2/D2 subtype EP2 | *Homo sapiens* (Human) |
| PE2R3_HUMAN | (P43115) | PTGER3 | Prostaglandin E2 subtype EP3 | *Homo sapiens* (Human) |
| PE2R4_HUMAN | (P35408) | PTGER4 | Prostaglandin E2 subtype EP4 | *Homo sapiens* (Human) |
| PF2R_HUMAN | (P43088) | PTGFR | Prostaglandin F2-alpha | *Homo sapiens* (Human) |
| PI2R_HUMAN | (P43119) | PTGIR | Prostacyclin | *Homo sapiens* (Human) |
| PKR1_HUMAN | (Q8TCW9) | PROKR1 | Prokineticin receptors | *Homo sapiens* (Human) |
| PKR2_HUMAN | (Q8NFJ6) | PROKR2 | Prokineticin receptors | *Homo sapiens* (Human) |
| PRLHR_HUMAN | (P49683) | PRLHR | Prolactin-releasing peptide (GPR10) | *Homo sapiens* (Human) |
| PSYR_HUMAN | (Q8IYL9) | GPR65 | Putative/unclassified Class A GPCRs | *Homo sapiens* (Human) |
| PTAFR_HUMAN | (P25105) | PTAFR | Platelet activating factor | *Homo sapiens* (Human) |
| PTHR1_HUMAN | (Q03431) | PTHR1 | Parathyroid hormone | *Homo sapiens* (Human) |
| PTHR2_HUMAN | (P49190) | PTHR2 | Parathyroid hormone | *Homo sapiens* (Human) |
| Q13027_HUMAN | (Q13027) | | fragments | *Homo sapiens* (Human) |
| Q13167_HUMAN | (Q13167) | DRD3 | Dopamine Vertebrate type 3 | *Homo sapiens* (Human) |
| Q14968_HUMAN | (Q14968) | | Putative/unclassified Class A GPCRs | *Homo sapiens* (Human) |
| Q15613_HUMAN | (Q15613) | tpcr110 | fragments | *Homo sapiens* (Human) |
| Q15616_HUMAN | (Q15616) | OR5E1P | fragments | *Homo sapiens* (Human) |
| Q15618_HUMAN | (Q15618) | OR7E18P | fragments | *Homo sapiens* (Human) |
| Q16144_HUMAN | (Q16144) | | CCK type B | *Homo sapiens* (Human) |
| Q16292_HUMAN | (Q16292) | | thrombin receptor fragments | *Homo sapiens* (Human) |
| Q16303_HUMAN | (Q16303) | | dopamine D4 receptor fragments | *Homo sapiens* (Human) |
| Q16503_HUMAN | (Q16503) | | fragments | *Homo sapiens* (Human) |
| Q2F3K1_HUMAN | (Q2F3K1) | CASR | fragments | *Homo sapiens* (Human) |
| Q2HIZ3_HUMAN | (Q2HIZ3) | OR10H3 | Olfactory II fam 10/MOR263-269 | *Homo sapiens* (Human) |

TABLE D-continued non-limiting list human GPCRs

| | | | | |
|---|---|---|---|---|
| Q2I7G5_HUMAN | (Q2I7G5) | EMR1 | EMR1 | *Homo sapiens* (Human) |
| Q2I8G2_HUMAN | (Q2I8G2) | ADRA2A | Alpha Adrenoceptors type 2 | *Homo sapiens* (Human) |
| Q2KHP3_HUMAN | (Q2KHP3) | PTGFR | Prostaglandin F2-alpha | *Homo sapiens* (Human) |
| Q2L7J7_HUMAN | (Q2L7J7) | ADORA2B | fragments | *Homo sapiens* (Human) |
| Q2M1L3_HUMAN | (Q2M1L3) | GPR133 | Putative/unclassified Class B GPCRs | *Homo sapiens* (Human) |
| Q2M1M6_HUMAN | (Q2M1M6) | OR10J1 | fragments | *Homo sapiens* (Human) |
| Q2M1M8_HUMAN | (Q2M1M8) | OR10J1 | Olfactory II fam 10/MOR263-269 | *Homo sapiens* (Human) |
| Q2M1T0_HUMAN | (Q2M1T0) | CASR | Extracellular calcium-sensing | *Homo sapiens* (Human) |
| Q2M1U3_HUMAN | (Q2M1U3) | PTHR1 | Parathyroid hormone | *Homo sapiens* (Human) |
| Q2M1V1_HUMAN | (Q2M1V1) | TAAR5 | Trace amine | *Homo sapiens* (Human) |
| Q2M1V7_HUMAN | (Q2M1V7) | MRGPRE | Mas proto-oncogene & Mas-related (MRGs) | *Homo sapiens* (Human) |
| Q2M1W5_HUMAN | (Q2M1W5) | TAAR1 | Trace amine | *Homo sapiens* (Human) |
| Q2M1Y3_HUMAN | (Q2M1Y3) | OR2H2 | Olfactory II fam 2/MOR256-262,270-285 | *Homo sapiens* (Human) |
| Q2M215_HUMAN | (Q2M215) | RXFP1 | LGR like (hormone receptors) | *Homo sapiens* (Human) |
| Q2M229_HUMAN | (Q2M229) | GLP1R | Glucagon | *Homo sapiens* (Human) |
| Q2M249_HUMAN | (Q2M249) | RHO | Rhodopsin Vertebrate type 1 | *Homo sapiens* (Human) |
| Q2M2D2_HUMAN | (Q2M2D2) | HTR5A | Serotonin type 5 | *Homo sapiens* (Human) |
| Q2M2E2_HUMAN | (Q2M2E2) | GPR26 | Putative/unclassified Class A GPCRs | *Homo sapiens* (Human) |
| Q2M339_HUMAN | (Q2M339) | TRHR | Thyrotropin-releasing hormone | *Homo sapiens* (Human) |
| Q2M369_HUMAN | (Q2M369) | GPR148 | Putative/unclassified Class A GPCRs | *Homo sapiens* (Human) |
| Q2M3C0_HUMAN | (Q2M3C0) | PROKR2 | Prokineticin receptors | *Homo sapiens* (Human) |
| Q2M3E2_HUMAN | (Q2M3E2) | VN1R4 | Vomeronasal receptors V1RL | *Homo sapiens* (Human) |
| Q2M3F7_HUMAN | (Q2M3F7) | GPR174 | Purinoceptor P2RY5,8,9,10 GPR35,92,174 | *Homo sapiens* (Human) |
| Q2M3L0_HUMAN | (Q2M3L0) | OR2S2 | Olfactory II fam 13/MOR253 | *Homo sapiens* (Human) |
| Q2M3M4_HUMAN | (Q2M3M4) | OR13A1 | Olfactory II fam 13/MOR253 | *Homo sapiens* (Human) |
| Q2M3M5_HUMAN | (Q2M3M5) | GCGR | Glucagon | *Homo sapiens* (Human) |
| Q2M3T5_HUMAN | (Q2M3T5) | OR2L2 | Olfactory II fam 2/MOR256-262,270-285 | *Homo sapiens* (Human) |
| Q2MZ38_HUMAN | (Q2MZ38) | GNRHR2 | fragments | *Homo sapiens* (Human) |
| Q2NKN6_HUMAN | (Q2NKN6) | BAI3 | Brain-specific angiogenesis inhibitor (BAI) | *Homo sapiens* (Human) |
| Q2NL85_HUMAN | (Q2NL85) | GPRC5C | Orphan GPRC5 | *Homo sapiens* (Human) |
| Q2PNZ0_HUMAN | (Q2PNZ0) | GPR115 | Putative/unclassified Class B GPCRs | *Homo sapiens* (Human) |
| Q2PNZ1_HUMAN | (Q2PNZ1) | GPR111 | Putative/unclassified Class B GPCRs | *Homo sapiens* (Human) |
| Q2TBC9_HUMAN | (Q2TBC9) | MAS1 | Mas proto-oncogene & Mas-related (MRGs) | *Homo sapiens* (Human) |
| Q2VPE4_HUMAN | (Q2VPE4) | | fragments | *Homo sapiens* (Human) |
| Q2YD84_HUMAN | (Q2YD84) | | C—X—C Chemokine type 5 | *Homo sapiens* (Human) |
| Q2YD89_HUMAN | (Q2YD89) | | Prostacyclin | *Homo sapiens* (Human) |
| Q2YDB9_HUMAN | (Q2YDB9) | | C-C Chemokine type 3 | *Homo sapiens* (Human) |
| Q2YEF8_HUMAN | (Q2YEF8) | | Interleukin-8 type A | *Homo sapiens* (Human) |
| Q2YEG4_HUMAN | (Q2YEG4) | | Interleukin-8 type A | *Homo sapiens* (Human) |
| Q2YEG5_HUMAN | (Q2YEG5) | | Interleukin-8 type A | *Homo sapiens* (Human) |
| Q2YEG7_HUMAN | (Q2YEG7) | | Interleukin-8 type A | *Homo sapiens* (Human) |
| Q2YEG8_HUMAN | (Q2YEG8) | | Interleukin-8 type A | *Homo sapiens* (Human) |
| Q32MN8_HUMAN | (Q32MN8) | GALR2 | Galanin | *Homo sapiens* (Human) |
| Q32VQ0_HUMAN | (Q32VQ0) | GPCRLTM7 | Olfactory II fam 4/MOR225-248 | *Homo sapiens* (Human) |
| Q38L21_HUMAN | (Q38L21) | CCR5 | C-C Chemokine type 5 | *Homo sapiens* (Human) |
| Q3C1V7_HUMAN | (Q3C1V7) | | fragments | *Homo sapiens* (Human) |
| Q3KNQ8_HUMAN | (Q3KNQ8) | CCR8 | C-C Chemokine type 8 | *Homo sapiens* (Human) |
| Q3KNR3_HUMAN | (Q3KNR3) | CCR8 | C-C Chemokine type 8 | *Homo sapiens* (Human) |
| Q3KNS9_HUMAN | (Q3KNS9) | GPR22 | GPR | *Homo sapiens* (Human) |
| Q3KNV3_HUMAN | (Q3KNV3) | GPRC5D | Orphan GPRC5 | *Homo sapiens* (Human) |
| Q3KP37_HUMAN | (Q3KP37) | CMKLR1 | Chemokine receptor-like 1 | *Homo sapiens* (Human) |
| Q3KPF5_HUMAN | (Q3KPF5) | P2RY5 | Purinoceptor P2RY5,8,9,10 GPR35,92,174 | *Homo sapiens* (Human) |
| Q3KRG8_HUMAN | (Q3KRG8) | CEACAM1 | fragments | *Homo sapiens* (Human) |
| Q3KU23_HUMAN | (Q3KU23) | | LGR like (hormone receptors) | *Homo sapiens* (Human) |
| Q3KU24_HUMAN | (Q3KU24) | | LGR like (hormone receptors) | *Homo sapiens* (Human) |
| Q3KU25_HUMAN | (Q3KU25) | | LGR like (hormone receptors) | *Homo sapiens* (Human) |
| Q3L3Q6_HUMAN | (Q3L3Q6) | CCR5 | C-C Chemokine type 5 | *Homo sapiens* (Human) |
| Q3MI45_HUMAN | (Q3MI45) | MC2R | fragments | *Homo sapiens* (Human) |
| Q3MIJ6_HUMAN | (Q3MIJ6) | MC4R | Melanocortin hormone | *Homo sapiens* (Human) |
| Q3MIL4_HUMAN | (Q3MIL4) | GPR15 | GPR | *Homo sapiens* (Human) |
| Q3MIS8_HUMAN | (Q3MIS8) | OR5P2 | Olfactory II fam 5/MOR172-224,249,254 | *Homo sapiens* (Human) |
| Q3MIV9_HUMAN | (Q3MIV9) | GRM8 | Metabotropic glutamate group III | *Homo sapiens* (Human) |
| Q3MJ87_HUMAN | (Q3MJ87) | PTGER4 | Prostaglandin E2 subtype EP4 | *Homo sapiens* (Human) |
| Q3MJB1_HUMAN | (Q3MJB1) | RXFP4 | Somatostatin- and angiogenin-like peptide | *Homo sapiens* (Human) |
| Q3MJC7_HUMAN | (Q3MJC7) | OR6A2 | Olfactory II fam 6/MOR103-105,107-119 | *Homo sapiens* (Human) |
| Q3MJD3_HUMAN | (Q3MJD3) | AVPR2 | Vasopressin type 2 | *Homo sapiens* (Human) |
| Q3S2J4_HUMAN | (Q3S2J4) | AVPR1 | Vasopressin type 1 | *Homo sapiens* (Human) |
| Q3SAH0_HUMAN | (Q3SAH0) | GPR34 | Putative/unclassified Class A GPCRs | *Homo sapiens* (Human) |
| Q3SAH2_HUMAN | (Q3SAH2) | GPR34 | Putative/unclassified Class A GPCRs | *Homo sapiens* (Human) |
| Q3ZAR0_HUMAN | (Q3ZAR0) | GPR50 | Melatonin | *Homo sapiens* (Human) |
| Q495D1_HUMAN | (Q495D1) | OR5F1 | Olfactory II fam 5/MOR172-224,249,254 | *Homo sapiens* (Human) |
| Q495H1_HUMAN | (Q495H1) | GPR120 | Putative/unclassified Class A GPCRs | *Homo sapiens* (Human) |
| Q495H7_HUMAN | (Q495H7) | GPR119 | Putative/unclassified Class A GPCRs | *Homo sapiens* (Human) |
| Q499G4_HUMAN | (Q499G4) | OPRK1 | Opioid type K | *Homo sapiens* (Human) |
| Q499H0_HUMAN | (Q499H0) | GPR64 | Putative/unclassified Class B GPCRs | *Homo sapiens* (Human) |
| Q4G0I6_HUMAN | (Q4G0I6) | HRH4 | Histamine type 4 | *Homo sapiens* (Human) |
| Q4G0K7_HUMAN | (Q4G0K7) | GPR116 | fragments | *Homo sapiens* (Human) |
| Q4G0Q6_HUMAN | (Q4G0Q6) | MGC72080 | fragments | *Homo sapiens* (Human) |

TABLE D-continued non-limiting list human GPCRs

| | | | | |
|---|---|---|---|---|
| Q4KKW2_HUMAN | (Q4KKW2) | PPYR1 | Neuropeptide Y type 4 | *Homo sapiens* (Human) |
| Q4KN04_HUMAN | (Q4KN04) | TAS2R8 | Taste receptors T2R | *Homo sapiens* (Human) |
| Q4KN27_HUMAN | (Q4KN27) | MC3R | Melanocortin hormone | *Homo sapiens* (Human) |
| Q4KN29_HUMAN | (Q4KN29) | TAS2R8 | Taste receptors T2R | *Homo sapiens* (Human) |
| Q4QRI5_HUMAN | (Q4QRI5) | TACR2 | Substance K (NK2) | *Homo sapiens* (Human) |
| Q4QRI9_HUMAN | (Q4QRI9) | HTR1F | fragments | *Homo sapiens* (Human) |
| Q4QRJ0_HUMAN | (Q4QRJ0) | DRD1 | Dopamine Vertebrate type 1 | *Homo sapiens* (Human) |
| Q4QRJ1_HUMAN | (Q4QRJ1) | CRHR1 | Corticotropin releasing factor | *Homo sapiens* (Human) |
| Q4QRJ3_HUMAN | (Q4QRJ3) | FSHR | Follicle stimulating hormone | *Homo sapiens* (Human) |
| Q4QRJ4_HUMAN | (Q4QRJ4) | CRHR2 | Corticotropin releasing factor | *Homo sapiens* (Human) |
| Q4V749_HUMAN | (Q4V749) | CCR10 | C-C Chemokine type 10 | *Homo sapiens* (Human) |
| Q4V9L2_HUMAN | (Q4V9L2) | MRGPRX1 | Mas proto-oncogene & Mas-related (MRGs) | *Homo sapiens* (Human) |
| Q4VAM0_HUMAN | (Q4VAM0) | LGR5 | LGR like (hormone receptors) | *Homo sapiens* (Human) |
| Q4VAM2_HUMAN | (Q4VAM2) | LGR5 | LGR like (hormone receptors) | *Homo sapiens* (Human) |
| Q4VAT1_HUMAN | (Q4VAT1) | GLP2R | fragments | *Homo sapiens* (Human) |
| Q4VAT2_HUMAN | (Q4VAT2) | GLP2R | fragments | *Homo sapiens* (Human) |
| Q4VAT3_HUMAN | (Q4VAT3) | GLP2R | Glucagon | *Homo sapiens* (Human) |
| Q4VAT4_HUMAN | (Q4VAT4) | GLP2R | fragments | *Homo sapiens* (Human) |
| Q4VAV7_HUMAN | (Q4VAV7) | | Neuropeptide Y type 4 | *Homo sapiens* (Human) |
| Q4VAY7_HUMAN | (Q4VAY7) | HTR1B | Serotonin type 1 | *Homo sapiens* (Human) |
| Q4VB06_HUMAN | (Q4VB06) | OR3A1 | Olfactory II fam 3/MOR255 | *Homo sapiens* (Human) |
| Q4VBB0_HUMAN | (Q4VBB0) | CCRL2 | C-C Chemokine other | *Homo sapiens* (Human) |
| Q4VBB4_HUMAN | (Q4VBB4) | GPR68 | GPR | *Homo sapiens* (Human) |
| Q4VBK6_HUMAN | (Q4VBK6) | CHRM2 | Musc. acetylcholine Vertebrate type 2 | *Homo sapiens* (Human) |
| Q4VBK7_HUMAN | (Q4VBK7) | CHRM4 | fragments | *Homo sapiens* (Human) |
| Q4VBK8_HUMAN | (Q4VBK8) | CNR2 | fragments | *Homo sapiens* (Human) |
| Q4VBL0_HUMAN | (Q4VBL0) | NMBR | Bombesin | *Homo sapiens* (Human) |
| Q4VBL2_HUMAN | (Q4VBL2) | CCR2 | C-C Chemokine type 2 | *Homo sapiens* (Human) |
| Q4VBL3_HUMAN | (Q4VBL3) | GPR31 | fragments | *Homo sapiens* (Human) |
| Q4VBL6_HUMAN | (Q4VBL6) | GPR52 | GPR | *Homo sapiens* (Human) |
| Q4VBL7_HUMAN | (Q4VBL7) | GALR1 | Galanin | *Homo sapiens* (Human) |
| Q4VBL8_HUMAN | (Q4VBL8) | TACR1 | fragments | *Homo sapiens* (Human) |
| Q4VBL9_HUMAN | (Q4VBL9) | TACR3 | fragments | *Homo sapiens* (Human) |
| Q4VBM3_HUMAN | (Q4VBM3) | CCR9 | fragments | *Homo sapiens* (Human) |
| Q4VBM7_HUMAN | (Q4VBM7) | ADRA1A | Alpha Adrenoceptors type 1 | *Homo sapiens* (Human) |
| Q4VBN0_HUMAN | (Q4VBN0) | GPR61 | fragments | *Homo sapiens* (Human) |
| Q4VBN1_HUMAN | (Q4VBN1) | GPR81 | fragments | *Homo sapiens* (Human) |
| Q4VBN3_HUMAN | (Q4VBN3) | GPR119 | Putative/unclassified Class A GPCRs | *Homo sapiens* (Human) |
| Q4VBN4_HUMAN | (Q4VBN4) | CCRL1 | fragments | *Homo sapiens* (Human) |
| Q4VBN5_HUMAN | (Q4VBN5) | GPR35 | fragments | *Homo sapiens* (Human) |
| Q4VBN6_HUMAN | (Q4VBN6) | F2RL2 | fragments | *Homo sapiens* (Human) |
| Q4VBN7_HUMAN | (Q4VBN7) | P2RY10 | Purinoceptor P2RY5,8,9,10 GPR35,92,174 | *Homo sapiens* (Human) |
| Q4VBP0_HUMAN | (Q4VBP0) | SSTR2 | Somatostatin type 2 | *Homo sapiens* (Human) |
| Q4VBP1_HUMAN | (Q4VBP1) | GIPR | fragments | *Homo sapiens* (Human) |
| Q4VWM1_HUMAN | (Q4VWM1) | OPRM1 | Opioid type M | *Homo sapiens* (Human) |
| Q4VWM2_HUMAN | (Q4VWM2) | OPRM1 | Opioid type M | *Homo sapiens* (Human) |
| Q4VWM3_HUMAN | (Q4VWM3) | OPRM1 | Opioid type M | *Homo sapiens* (Human) |
| Q4VWM4_HUMAN | (Q4VWM4) | OPRM1 | Opioid type M | *Homo sapiens* (Human) |
| Q4VWM6_HUMAN | (Q4VWM6) | OPRM1 | Opioid type M | *Homo sapiens* (Human) |
| Q4VWX6_HUMAN | (Q4VWX6) | OPRM | Opioid type M | *Homo sapiens* (Human) |
| Q4W594_HUMAN | (Q4W594) | ADRA2C | Alpha Adrenoceptors type 2 | *Homo sapiens* (Human) |
| Q4W5G7_HUMAN | (Q4W5G7) | NPY2R | Neuropeptide Y type 2 | *Homo sapiens* (Human) |
| Q4ZFV2_HUMAN | (Q4ZFV2) | GPR35 | Purinoceptor P2RY5,8,9,10 GPR35,92,174 | *Homo sapiens* (Human) |
| Q4ZIL0_HUMAN | (Q4ZIL0) | | fragments | *Homo sapiens* (Human) |
| Q502U7_HUMAN | (Q502U7) | GPR32 | Chemokine receptor-like 1 | *Homo sapiens* (Human) |
| Q502U9_HUMAN | (Q502U9) | GPR23 | Purinoceptor P2RY5,8,9,10 GPR35,92,174 | *Homo sapiens* (Human) |
| Q502V0_HUMAN | (Q502V0) | XCR1 | XC Chemokine | *Homo sapiens* (Human) |
| Q502V1_HUMAN | (Q502V1) | MC5R | Melanocortin hormone | *Homo sapiens* (Human) |
| Q502V2_HUMAN | (Q502V2) | RXFP3 | Somatostatin- and angiogenin-like peptide | *Homo sapiens* (Human) |
| Q502V7_HUMAN | (Q502V7) | TAS2R9 | Taste receptors T2R | *Homo sapiens* (Human) |
| Q502V9_HUMAN | (Q502V9) | MAS1L | Mas proto-oncogene & Mas-related (MRGs) | *Homo sapiens* (Human) |
| Q504X6_HUMAN | (Q504X6) | MC2R | Adrenocorticotropic hormone | *Homo sapiens* (Human) |
| Q506J9_HUMAN | (Q506J9) | | Cannabinoid | *Homo sapiens* (Human) |
| Q50KD4_HUMAN | (Q50KD4) | Hosa(Biaka)-T2R55 | fragments | *Homo sapiens* (Human) |
| Q50KD6_HUMAN | (Q50KD6) | Hosa(Adygei)-T2R55 | fragments | *Homo sapiens* (Human) |
| Q50KT0_HUMAN | (Q50KT0) | Hosa(Biaka)-T2R9 | fragments | *Homo sapiens* (Human) |
| Q50KT1_HUMAN | (Q50KT1) | Hosa(Japanese)-T2R9 | fragments | *Homo sapiens* (Human) |
| Q50KU1_HUMAN | (Q50KU1) | Hosa(Biaka)-T2R8 | fragments | *Homo sapiens* (Human) |
| Q50KU2_HUMAN | (Q50KU2) | Hosa(Japanese)-T2R8 | fragments | *Homo sapiens* (Human) |
| Q50KV5_HUMAN | (Q50KV5) | Hosa(Biaka)-T2R7 | fragments | *Homo sapiens* (Human) |
| Q50KV7_HUMAN | (Q50KV7) | Hosa(Adygei)-T2R7 | fragments | *Homo sapiens* (Human) |
| Q52LG8_HUMAN | (Q52LG8) | PTGER2 | Prostaglandin E2/D2 subtype EP2 | *Homo sapiens* (Human) |
| Q52M04_HUMAN | (Q52M04) | GIPR | Gastric inhibitory peptide | *Homo sapiens* (Human) |
| Q52M68_HUMAN | (Q52M68) | F2RL2 | Proteinase-activated | *Homo sapiens* (Human) |
| Q52R92_HUMAN | (Q52R92) | | fragments | *Homo sapiens* (Human) |
| Q52R93_HUMAN | (Q52R93) | | fragments | *Homo sapiens* (Human) |
| Q52R94_HUMAN | (Q52R94) | | fragments | *Homo sapiens* (Human) |
| Q53EM0_HUMAN | (Q53EM0) | | fragments | *Homo sapiens* (Human) |

TABLE D-continued

| non-limiting list human GPCRs | | | | |
|---|---|---|---|---|
| Q53EZ5_HUMAN | (Q53EZ5) | | fragments | *Homo sapiens* (Human) |
| Q53F99_HUMAN | (Q53F99) | | fragments | *Homo sapiens* (Human) |
| Q53FA0_HUMAN | (Q53FA0) | | fragments | *Homo sapiens* (Human) |
| Q53FA1_HUMAN | (Q53FA1) | | fragments | *Homo sapiens* (Human) |
| Q53GA6_HUMAN | (Q53GA6) | | fragments | *Homo sapiens* (Human) |
| Q53GM2_HUMAN | (Q53GM2) | | fragments | *Homo sapiens* (Human) |
| Q53GP0_HUMAN | (Q53GP0) | | fragments | *Homo sapiens* (Human) |
| Q53PC4_HUMAN | (Q53PC4) | IL8RB | Interleukin-8 type B | *Homo sapiens* (Human) |
| Q53QQ5_HUMAN | (Q53QQ5) | NTSR2 | fragments | *Homo sapiens* (Human) |
| Q53QT9_HUMAN | (Q53QT9) | GPR73 | Prokineticin receptors | *Homo sapiens* (Human) |
| Q53R18_HUMAN | (Q53R18) | IL8RA | Interleukin-8 type A | *Homo sapiens* (Human) |
| Q53R22_HUMAN | (Q53R22) | FZD5 | frizzled Group A (Fz 1&2&4&5&7-9) | *Homo sapiens* (Human) |
| Q53RU7_HUMAN | (Q53RU7) | GPR39 | fragments | *Homo sapiens* (Human) |
| Q53RV4_HUMAN | (Q53RV4) | tmp_locus_35 | RDC1 | *Homo sapiens* (Human) |
| Q53S49_HUMAN | (Q53S49) | LHCGR | fragments | *Homo sapiens* (Human) |
| Q53S59_HUMAN | (Q53S59) | FZD7 | frizzled Group A (Fz 1&2&4&5&7-9) | *Homo sapiens* (Human) |
| Q53S69_HUMAN | (Q53S69) | CXCR4 | C—X—C Chemokine type 4 | *Homo sapiens* (Human) |
| Q53SF6_HUMAN | (Q53SF6) | PTHR2 | fragments | *Homo sapiens* (Human) |
| Q53T00_HUMAN | (Q53T00) | SCTR | Secretin | *Homo sapiens* (Human) |
| Q53T35_HUMAN | (Q53T35) | PTHR2 | fragments | *Homo sapiens* (Human) |
| Q53TA5_HUMAN | (Q53TA5) | GPR113 | Putative/unclassified Class B GPCRs | *Homo sapiens* (Human) |
| Q53TI1_HUMAN | (Q53TI1) | HTR2B | Serotonin type 2 | *Homo sapiens* (Human) |
| Q53TQ2_HUMAN | (Q53TQ2) | TACR1 | fragments | *Homo sapiens* (Human) |
| Q53TR1_HUMAN | (Q53TR1) | TACR1 | fragments | *Homo sapiens* (Human) |
| Q53TS5_HUMAN | (Q53TS5) | CALCRL | fragments | *Homo sapiens* (Human) |
| Q53XJ8_HUMAN | (Q53XJ8) | F2RL1 | Proteinase-activated | *Homo sapiens* (Human) |
| Q53XV0_HUMAN | (Q53XV0) | | Thrombin | *Homo sapiens* (Human) |
| Q53XV5_HUMAN | (Q53XV5) | | Leukotriene B4 receptor BLT1 | *Homo sapiens* (Human) |
| Q53XZ3_HUMAN | (Q53XZ3) | | Musc. acetylcholine Vertebrate type 1 | *Homo sapiens* (Human) |
| Q53Y09_HUMAN | (Q53Y09) | | Vasoactive intestinal polypeptide | *Homo sapiens* (Human) |
| Q53YA1_HUMAN | (Q53YA1) | CCBP2 | C-C Chemokine type X | *Homo sapiens* (Human) |
| Q53YJ4_HUMAN | (Q53YJ4) | GALR3 | Galanin | *Homo sapiens* (Human) |
| Q53YY0_HUMAN | (Q53YY0) | AGTR1 | Angiotensin type 1 | *Homo sapiens* (Human) |
| Q53ZR7_HUMAN | (Q53ZR7) | SSTR3 | Somatostatin type 3 | *Homo sapiens* (Human) |
| Q541E0_HUMAN | (Q541E0) | | Somatostatin type 5 | *Homo sapiens* (Human) |
| Q546Q1_HUMAN | (Q546Q1) | HTR4 | Serotonin type 4 | *Homo sapiens* (Human) |
| Q548M6_HUMAN | (Q548M6) | HRH3 | Histamine type 3 | *Homo sapiens* (Human) |
| Q548Y0_HUMAN | (Q548Y0) | HCRTR2 | Orexin | *Homo sapiens* (Human) |
| Q549E0_HUMAN | (Q549E0) | CCR9 | C-C Chemokine type 9 | *Homo sapiens* (Human) |
| Q57Z87_HUMAN | (Q57Z87) | NTSR2 | fragments | *Homo sapiens* (Human) |
| Q59EH9_HUMAN | (Q59EH9) | | fragments | *Homo sapiens* (Human) |
| Q59ER8_HUMAN | (Q59ER8) | | fragments | *Homo sapiens* (Human) |
| Q59ES7_HUMAN | (Q59ES7) | | fragments | *Homo sapiens* (Human) |
| Q59FC0_HUMAN | (Q59FC0) | | fragments | *Homo sapiens* (Human) |
| Q59FW2_HUMAN | (Q59FW2) | | fragments | *Homo sapiens* (Human) |
| Q59G39_HUMAN | (Q59G39) | | fragments | *Homo sapiens* (Human) |
| Q59G72_HUMAN | (Q59G72) | | fragments | *Homo sapiens* (Human) |
| Q59G95_HUMAN | (Q59G95) | | fragments | *Homo sapiens* (Human) |
| Q59GA2_HUMAN | (Q59GA2) | | fragments | *Homo sapiens* (Human) |
| Q59GB1_HUMAN | (Q59GB1) | | fragments | *Homo sapiens* (Human) |
| Q59GE5_HUMAN | (Q59GE5) | glutamate receptor homolog | fragments | *Homo sapiens* (Human) |
| Q59GI0_HUMAN | (Q59GI0) | | fragments | *Homo sapiens* (Human) |
| Q59GL3_HUMAN | (Q59GL3) | | fragments | *Homo sapiens* (Human) |
| Q59GP3_HUMAN | (Q59GP3) | | fragments | *Homo sapiens* (Human) |
| Q59H16_HUMAN | (Q59H16) | | fragments | *Homo sapiens* (Human) |
| Q59HC2_HUMAN | (Q59HC2) | | fragments | *Homo sapiens* (Human) |
| Q59HG8_HUMAN | (Q59HG8) | | fragments | *Homo sapiens* (Human) |
| Q5CZ57_HUMAN | (Q5CZ57) | EP3-I | Prostaglandin E2 subtype EP3 | *Homo sapiens* (Human) |
| Q5CZ59_HUMAN | (Q5CZ59) | EP3e | Prostaglandin E2 subtype EP3 | *Homo sapiens* (Human) |
| Q5CZ60_HUMAN | (Q5CZ60) | EP3f | Prostaglandin E2 subtype EP3 | *Homo sapiens* (Human) |
| Q5CZ61_HUMAN | (Q5CZ61) | EP3-VI | Prostaglandin E2 subtype EP3 | *Homo sapiens* (Human) |
| Q5CZ62_HUMAN | (Q5CZ62) | EP3-V | Prostaglandin E2 subtype EP3 | *Homo sapiens* (Human) |
| Q5CZ63_HUMAN | (Q5CZ63) | EP3-IV | Prostaglandin E2 subtype EP3 | *Homo sapiens* (Human) |
| Q5CZ64_HUMAN | (Q5CZ64) | EP3-III | Prostaglandin E2 subtype EP3 | *Homo sapiens* (Human) |
| Q5EGP2_HUMAN | (Q5EGP2) | GPR112 | Putative/unclassified Class B GPCRs | *Homo sapiens* (Human) |
| Q5EKM8_HUMAN | (Q5EKM8) | CCR5 | C-C Chemokine type 5 | *Homo sapiens* (Human) |
| Q5EKM9_HUMAN | (Q5EKM9) | CCR5 | C-C Chemokine type 5 | *Homo sapiens* (Human) |
| Q5EKN0_HUMAN | (Q5EKN0) | CCR5 | C-C Chemokine type 5 | *Homo sapiens* (Human) |
| Q5HYM4_HUMAN | (Q5HYM4) | DKFZp686H1993 | fragments | *Homo sapiens* (Human) |
| Q5HYQ4_HUMAN | (Q5HYQ4) | GPR173 | SREB | *Homo sapiens* (Human) |
| Q5IFH6_HUMAN | (Q5IFH6) | GPR24 | Melanin-concentrating hormone receptors | *Homo sapiens* (Human) |
| Q5IFI4_HUMAN | (Q5IFI4) | GPR24 | Melanin-concentrating hormone receptors | *Homo sapiens* (Human) |
| Q5ISU3_HUMAN | (Q5ISU3) | PPYR1 | Neuropeptide Y type 4 | *Homo sapiens* (Human) |
| Q5JNZ1_HUMAN | (Q5JNZ1) | DAQB-117O11.7-001 | fragments | *Homo sapiens* (Human) |
| Q5JPQ2_HUMAN | (Q5JPQ2) | GPR64 | Putative/unclassified Class B GPCRs | *Homo sapiens* (Human) |
| Q5JPQ3_HUMAN | (Q5JPQ3) | GPR64 | Putative/unclassified Class B GPCRs | *Homo sapiens* (Human) |
| Q5JPQ4_HUMAN | (Q5JPQ4) | GPR64 | Putative/unclassified Class B GPCRs | *Homo sapiens* (Human) |
| Q5JPQ5_HUMAN | (Q5JPQ5) | GPR64 | Putative/unclassified Class B GPCRs | *Homo sapiens* (Human) |

TABLE D-continued

| | | | non-limiting list human GPCRs | |
|---|---|---|---|---|
| Q5JPQ6_HUMAN | (Q5JPQ6) | GPR64 | Putative/unclassified Class B GPCRs | *Homo sapiens* (Human) |
| Q5JQT0_HUMAN | (Q5JQT0) | RP11-978I15.6 | Olfactory II fam 5/MOR172-224,249,254 | *Homo sapiens* (Human) |
| Q5JRH7_HUMAN | (Q5JRH7) | CNR2 | Cannabinoid | *Homo sapiens* (Human) |
| Q5JSM8_HUMAN | (Q5JSM8) | GPR101 | Putative/unclassified Class A GPCRs | *Homo sapiens* (Human) |
| Q5JU89_HUMAN | (Q5JU89) | GPR112 | fragments | *Homo sapiens* (Human) |
| Q5JUH7_HUMAN | (Q5JUH7) | EBI2 | EBV-induced | *Homo sapiens* (Human) |
| Q5JUH9_HUMAN | (Q5JUH9) | GPR18 | fragments | *Homo sapiens* (Human) |
| Q5JVI7_HUMAN | (Q5JVI7) | PTGFR | Prostaglandin F2-alpha | *Homo sapiens* (Human) |
| Q5JVK3_HUMAN | (Q5JVK3) | GPR112 | fragments | *Homo sapiens* (Human) |
| Q5JVL5_HUMAN | (Q5JVL5) | CNR1 | Cannabinoid | *Homo sapiens* (Human) |
| Q5KSY4_HUMAN | (Q5KSY4) | CCR5 | fragments | *Homo sapiens* (Human) |
| Q5KU14_HUMAN | (Q5KU14) | KPG_013 | Putative/unclassified Class A GPCRs | *Homo sapiens* (Human) |
| Q5KU17_HUMAN | (Q5KU17) | KPG_011 | Cysteinyl leukotriene | *Homo sapiens* (Human) |
| Q5KU18_HUMAN | (Q5KU18) | KPG_010 | Purinoceptor P2RY5,8,9,10 GPR35,92,174 | *Homo sapiens* (Human) |
| Q5KU19_HUMAN | (Q5KU19) | KPG_009 | Putative/unclassified Class B GPCRs | *Homo sapiens* (Human) |
| Q5KU20_HUMAN | (Q5KU20) | KPG_008 | Putative/unclassified Class B GPCRs | *Homo sapiens* (Human) |
| Q5KU21_HUMAN | (Q5KU21) | KPG_007 | Purinoceptor P2RY5,8,9,10 GPR35,92,174 | *Homo sapiens* (Human) |
| Q5KU22_HUMAN | (Q5KU22) | KPG_006 | Putative/unclassified Class B GPCRs | *Homo sapiens* (Human) |
| Q5KU27_HUMAN | (Q5KU27) | KPG_005 | Putative/unclassified Class A GPCRs | *Homo sapiens* (Human) |
| Q5KU28_HUMAN | (Q5KU28) | KPG_004 | Leukotriene B4 receptor BLT2 | *Homo sapiens* (Human) |
| Q5KU34_HUMAN | (Q5KU34) | KPG_003 | ETL receptors | *Homo sapiens* (Human) |
| Q5KU35_HUMAN | (Q5KU35) | KPG_002 | Purinoceptor P2RY12-14 GPR87 (UDP-Glucose) | *Homo sapiens* (Human) |
| Q5QIN9_HUMAN | (Q5QIN9) | CCR5 | C-C Chemokine type 5 | *Homo sapiens* (Human) |
| Q5QIP0_HUMAN | (Q5QIP0) | CCR5 | C-C Chemokine type 5 | *Homo sapiens* (Human) |
| Q5QIP1_HUMAN | (Q5QIP1) | CCR5 | C-C Chemokine type 5 | *Homo sapiens* (Human) |
| Q5RJ87_HUMAN | (Q5RJ87) | DAQB-36F16.7-002 | fragments | *Homo sapiens* (Human) |
| Q5S4P5_HUMAN | (Q5S4P5) | POGR | Olfactory I fam 51-52/MOR1-42 | *Homo sapiens* (Human) |
| Q5SQD8_HUMAN | (Q5SQD8) | EDG3 | Sphingosine 1-phosphate Edg-3 | *Homo sapiens* (Human) |
| Q5SQI9_HUMAN | (Q5SQI9) | XXbac-BCX92J3.1-001 | Olfactory II fam 5/MOR172-224,249,254 | *Homo sapiens* (Human) |
| Q5ST16_HUMAN | (Q5ST16) | DAQB-304F3.2-001 | Olfactory II fam 11/MOR106,121-122 | *Homo sapiens* (Human) |
| Q5ST27_HUMAN | (Q5ST27) | XXbac-BCX147D4.2-001 | Olfactory II fam 5/MOR172-224,249,254 | *Homo sapiens* (Human) |
| Q5ST39_HUMAN | (Q5ST39) | OR2J2 | Olfactory II fam 2/MOR256-262,270-285 | *Homo sapiens* (Human) |
| Q5STL4_HUMAN | (Q5STL4) | GABBR1 | fragments | *Homo sapiens* (Human) |
| Q5STL7_HUMAN | (Q5STL7) | GABBR1 | fragments | *Homo sapiens* (Human) |
| Q5SUJ6_HUMAN | (Q5SUJ6) | XXbac-BPG171B11.5-001 | Olfactory II fam 2/MOR256-262,270-285 | *Homo sapiens* (Human) |
| Q5SUJ7_HUMAN | (Q5SUJ7) | XXbac-BPG171B11.3-001 | Olfactory II fam 2/MOR256-262,270-285 | *Homo sapiens* (Human) |
| Q5SUJ8_HUMAN | (Q5SUJ8) | GABBR1 | GABA-B subtype 1 | *Homo sapiens* (Human) |
| Q5SUJ9_HUMAN | (Q5SUJ9) | GABBR1 | GABA-B subtype 1 | *Homo sapiens* (Human) |
| Q5SUK1_HUMAN | (Q5SUK1) | OR2H2 | Olfactory II fam 2/MOR256-262,270-285 | *Homo sapiens* (Human) |
| Q5SUL3_HUMAN | (Q5SUL3) | GABBR1 | GABA-B subtype 1 | *Homo sapiens* (Human) |
| Q5SUN5_HUMAN | (Q5SUN5) | MAS1L | Mas proto-oncogene & Mas-related (MRGs) | *Homo sapiens* (Human) |
| Q5SUN6_HUMAN | (Q5SUN6) | DAQB-12N14.4-001 | Olfactory II fam 2/MOR256-262,270-285 | *Homo sapiens* (Human) |
| Q5SUN7_HUMAN | (Q5SUN7) | XXbac-BPG13B8.1-001 | Olfactory II fam 10/MOR263-269 | *Homo sapiens* (Human) |
| Q5SUN9_HUMAN | (Q5SUN9) | XXbac-BPG13B8.6-001 | Olfactory II fam 12/MOR250 | *Homo sapiens* (Human) |
| Q5SWW2_HUMAN | (Q5SWW2) | ELTD1 | fragments | *Homo sapiens* (Human) |
| Q5SWW3_HUMAN | (Q5SWW3) | ELTD1 | ETL receptors | *Homo sapiens* (Human) |
| Q5SXP7_HUMAN | (Q5SXP7) | RP11-294K24.1-001 | GPR37/endothelin B-like | *Homo sapiens* (Human) |
| Q5SY22_HUMAN | (Q5SY22) | TAS1R1 | fragments | *Homo sapiens* (Human) |
| Q5SY23_HUMAN | (Q5SY23) | TAS1R1 | fragments | *Homo sapiens* (Human) |
| Q5SY24_HUMAN | (Q5SY24) | TAS1R1 | fragments | *Homo sapiens* (Human) |
| Q5T234_HUMAN | (Q5T234) | GPR123 | Putative/unclassified Class B GPCRs | *Homo sapiens* (Human) |
| Q5T261_HUMAN | (Q5T261) | EDG2 | fragments | *Homo sapiens* (Human) |
| Q5T2X9_HUMAN | (Q5T2X9) | PPYR1 | fragments | *Homo sapiens* (Human) |
| Q5T2Y7_HUMAN | (Q5T2Y7) | CELSR2 | Cadherin EGF LAG (CELSR) | *Homo sapiens* (Human) |
| Q5T5Y4_HUMAN | (Q5T5Y4) | ADRB1 | Beta Adrenoceptors type 1 | *Homo sapiens* (Human) |
| Q5T6D8_HUMAN | (Q5T6D8) | GPR147 | fragments | *Homo sapiens* (Human) |
| Q5T6K0_HUMAN | (Q5T6K0) | BAI2 | Brain-specific angiogenesis inhibitor (BAI) | *Homo sapiens* (Human) |
| Q5T7Z3_HUMAN | (Q5T7Z3) | RP11-64P14.4-001 | Olfactory II fam 1/MOR125-138,156 | *Homo sapiens* (Human) |
| Q5T8C0_HUMAN | (Q5T8C0) | HTR2A | Serotonin type 2 | *Homo sapiens* (Human) |
| Q5T8P3_HUMAN | (Q5T8P3) | GPR12 | GPR | *Homo sapiens* (Human) |
| Q5T9D2_HUMAN | (Q5T9D2) | LPHN2 | fragments | *Homo sapiens* (Human) |
| Q5TBX0_HUMAN | (Q5TBX0) | OPRM1 | Opioid type M | *Homo sapiens* (Human) |
| Q5TF06_HUMAN | (Q5TF06) | RP3-365O12.1-001 | Putative/unclassified Class B GPCRs | *Homo sapiens* (Human) |
| Q5TGK2_HUMAN | (Q5TGK2) | GPR161 | Putative/unclassified Class A GPCRs | *Homo sapiens* (Human) |
| Q5TGN7_HUMAN | (Q5TGN7) | GPR126 | Putative/unclassified Class B GPCRs | *Homo sapiens* (Human) |
| Q5TGZ1_HUMAN | (Q5TGZ1) | HTR6 | Serotonin type 6 | *Homo sapiens* (Human) |
| Q5TH86_HUMAN | (Q5TH86) | PTGER3 | Prostaglandin E2 subtype EP3 | *Homo sapiens* (Human) |
| Q5TH88_HUMAN | (Q5TH88) | PTGER3 | Prostaglandin E2 subtype EP3 | *Homo sapiens* (Human) |
| Q5U003_HUMAN | (Q5U003) | | C-C Chemokine type 1 | *Homo sapiens* (Human) |
| Q5U0H0_HUMAN | (Q5U0H0) | | Chemokine receptor-like 1 | *Homo sapiens* (Human) |
| Q5U5U4_HUMAN | (Q5U5U4) | PTGER1 | Prostaglandin E2 subtype EP1 | *Homo sapiens* (Human) |
| Q5VSV1_HUMAN | (Q5VSV1) | RP11-180D21.2-001 | Olfactory II fam 10/MOR263-269 | *Homo sapiens* (Human) |
| Q5VT13_HUMAN | (Q5VT13) | GPR82 | Putative/unclassified Class A GPCRs | *Homo sapiens* (Human) |
| Q5VT14_HUMAN | (Q5VT14) | GPR34 | Putative/unclassified Class A GPCRs | *Homo sapiens* (Human) |
| Q5VT23_HUMAN | (Q5VT23) | RP11-34P13.6-001 | Olfactory II fam 4/MOR225-248 | *Homo sapiens* (Human) |
| Q5VTM0_HUMAN | (Q5VTM0) | SLC31A2 | Orexin | *Homo sapiens* (Human) |
| Q5VTV7_HUMAN | (Q5VTV7) | GPR145 | Melanin-concentrating hormone receptors | *Homo sapiens* (Human) |
| Q5VUF8_HUMAN | (Q5VUF8) | HTR2C | Serotonin type 2 | *Homo sapiens* (Human) |

TABLE D-continued

| | | | non-limiting list human GPCRs | |
|---|---|---|---|---|
| Q5VUF9_HUMAN | (Q5VUF9) | HTR2C | fragments | Homo sapiens (Human) |
| Q5VUK8_HUMAN | (Q5VUK8) | NMBR | Bombesin | Homo sapiens (Human) |
| Q5VX01_HUMAN | (Q5VX01) | HTR7 | Serotonin type 7 | Homo sapiens (Human) |
| Q5VX02_HUMAN | (Q5VX02) | HTR7 | Serotonin type 7 | Homo sapiens (Human) |
| Q5VX03_HUMAN | (Q5VX03) | HTR7 | Serotonin type 7 | Homo sapiens (Human) |
| Q5VX04_HUMAN | (Q5VX04) | HTR7 | Serotonin type 7 | Homo sapiens (Human) |
| Q5VX75_HUMAN | (Q5VX75) | LPHN2 | Latrophilin type 2 | Homo sapiens (Human) |
| Q5VX77_HUMAN | (Q5VX77) | LPHN2 | Latrophilin type 2 | Homo sapiens (Human) |
| Q5VX78_HUMAN | (Q5VX78) | LPHN2 | Latrophilin type 2 | Homo sapiens (Human) |
| Q5VX79_HUMAN | (Q5VX79) | LPHN2 | Latrophilin type 2 | Homo sapiens (Human) |
| Q5VX80_HUMAN | (Q5VX80) | LPHN2 | Latrophilin type 2 | Homo sapiens (Human) |
| Q5VX81_HUMAN | (Q5VX81) | LPHN2 | Latrophilin type 2 | Homo sapiens (Human) |
| Q5VX82_HUMAN | (Q5VX82) | LPHN2 | Latrophilin type 2 | Homo sapiens (Human) |
| Q5VX83_HUMAN | (Q5VX83) | LPHN2 | Latrophilin type 2 | Homo sapiens (Human) |
| Q5VXR2_HUMAN | (Q5VXR2) | ADRA1D | Alpha Adrenoceptors type 1 | Homo sapiens (Human) |
| Q5VXY3_HUMAN | (Q5VXY3) | CHRM3 | fragments | Homo sapiens (Human) |
| Q5VY37_HUMAN | (Q5VY37) | BAI3 | Brain-specific angiogenesis inhibitor (BAI) | Homo sapiens (Human) |
| Q5VZX0_HUMAN | (Q5VZX0) | EDG2 | Lysophosphatidic acid Edg-2 | Homo sapiens (Human) |
| Q5W0G9_HUMAN | (Q5W0G9) | EDNRB | Endothelin | Homo sapiens (Human) |
| Q5W0N7_HUMAN | (Q5W0N7) | RP11-432E15.1 | LGR like (hormone receptors) | Homo sapiens (Human) |
| Q5Y190_HUMAN | (Q5Y190) | RESDA1 | Cadherin EGF LAG (CELSR) | Homo sapiens (Human) |
| Q5ZGL8_HUMAN | (Q5ZGL8) | HCTR-6 | fragments | Homo sapiens (Human) |
| Q5ZGX3_HUMAN | (Q5ZGX3) | 5HT1A | Serotonin type 1 | Homo sapiens (Human) |
| Q63ZY2_HUMAN | (Q63ZY2) | GPR30 | Chemokine receptor-like 2 | Homo sapiens (Human) |
| Q645Y1_HUMAN | (Q645Y1) | TAS2R7 | Taste receptors T2R | Homo sapiens (Human) |
| Q659U6_HUMAN | (Q659U6) | HCTR-5 | fragments | Homo sapiens (Human) |
| Q66K38_HUMAN | (Q66K38) | MC1R | Melanocyte stimulating hormone | Homo sapiens (Human) |
| Q66X57_HUMAN | (Q66X57) | | Olfactory I fam 51-52/MOR1-42 | Homo sapiens (Human) |
| Q684M0_HUMAN | (Q684M0) | HTR4 | Serotonin type 4 | Homo sapiens (Human) |
| Q68CR4_HUMAN | (Q68CR4) | DKFZp781I1948 | Rhodopsin Vertebrate type 2 | Homo sapiens (Human) |
| Q68DM8_HUMAN | (Q68DM8) | DKFZp686O088 | Bradykinin | Homo sapiens (Human) |
| Q6B0G7_HUMAN | (Q6B0G7) | CNR2 | Cannabinoid | Homo sapiens (Human) |
| Q6DHZ4_HUMAN | (Q6DHZ4) | GPR126 | Putative/unclassified Class B GPCRs | Homo sapiens (Human) |
| Q6DJW7_HUMAN | (Q6DJW7) | OR6W1P | fragments | Homo sapiens (Human) |
| Q6DKN4_HUMAN | (Q6DKN4) | P2RY13 | fragments | Homo sapiens (Human) |
| Q6F3F5_HUMAN | (Q6F3F5) | DREG | Putative/unclassified Class B GPCRs | Homo sapiens (Human) |
| Q6F3F6_HUMAN | (Q6F3F6) | GPR126 | Putative/unclassified Class B GPCRs | Homo sapiens (Human) |
| Q6F3F7_HUMAN | (Q6F3F7) | DREG | Putative/unclassified Class B GPCRs | Homo sapiens (Human) |
| Q6F3F8_HUMAN | (Q6F3F8) | DREG | Putative/unclassified Class B GPCRs | Homo sapiens (Human) |
| Q6FGM5_HUMAN | (Q6FGM5) | OPRL1 | Opioid type X | Homo sapiens (Human) |
| Q6FH06_HUMAN | (Q6FH06) | PPYR1 | fragments | Homo sapiens (Human) |
| Q6FH34_HUMAN | (Q6FH34) | DRD1 | fragments | Homo sapiens (Human) |
| Q6FHI8_HUMAN | (Q6FHI8) | GPR35 | Purinoceptor P2RY5,8,9,10 GPR35,92,174 | Homo sapiens (Human) |
| Q6FHK3_HUMAN | (Q6FHK3) | ADORA1 | fragments | Homo sapiens (Human) |
| Q6FHL1_HUMAN | (Q6FHL1) | GPR30 | Chemokine receptor-like 2 | Homo sapiens (Human) |
| Q6FHU6_HUMAN | (Q6FHU6) | GPR30 | fragments | Homo sapiens (Human) |
| Q6GMT1_HUMAN | (Q6GMT1) | OPN3 | fragments | Homo sapiens (Human) |
| Q6GMT4_HUMAN | (Q6GMT4) | ADRB2 | Beta Adrenoceptors type 2 | Homo sapiens (Human) |
| Q6GPG7_HUMAN | (Q6GPG7) | EDG2 | Lysophosphatidic acid Edg-2 | Homo sapiens (Human) |
| Q6GTR7_HUMAN | (Q6GTR7) | NPY5R | Neuropeptide Y type 5 | Homo sapiens (Human) |
| Q6I939_HUMAN | (Q6I939) | OR17-219 | fragments | Homo sapiens (Human) |
| Q6I940_HUMAN | (Q6I940) | OR17-207 | fragments | Homo sapiens (Human) |
| Q6I941_HUMAN | (Q6I941) | OR17-82 | fragments | Homo sapiens (Human) |
| Q6IBH2_HUMAN | (Q6IBH2) | GPR19 | GPR | Homo sapiens (Human) |
| Q6IET8_HUMAN | (Q6IET8) | RP1-154J13.4-001 | Olfactory II fam 13/MOR253 | Homo sapiens (Human) |
| Q6IET9_HUMAN | (Q6IET9) | OR12D2 | Olfactory II fam 12/MOR250 | Homo sapiens (Human) |
| Q6IEU0_HUMAN | (Q6IEU0) | OR2W1 | Olfactory II fam 2/MOR256-262,270-285 | Homo sapiens (Human) |
| Q6IEU2_HUMAN | (Q6IEU2) | | Olfactory II fam 5/MOR172-224,249,254 | Homo sapiens (Human) |
| Q6IEV0_HUMAN | (Q6IEV0) | | Olfactory II fam 9/MOR120 | Homo sapiens (Human) |
| Q6IEV1_HUMAN | (Q6IEV1) | | Olfactory II fam 9/MOR120 | Homo sapiens (Human) |
| Q6IEV3_HUMAN | (Q6IEV3) | | Olfactory II fam 10/MOR263-269 | Homo sapiens (Human) |
| Q6IEW6_HUMAN | (Q6IEW6) | | Olfactory II fam 8/MOR161-171 | Homo sapiens (Human) |
| Q6IEW7_HUMAN | (Q6IEW7) | | Olfactory II fam 8/MOR161-171 | Homo sapiens (Human) |
| Q6IEX0_HUMAN | (Q6IEX0) | | Olfactory II fam 11/MOR106,121-122 | Homo sapiens (Human) |
| Q6IEX5_HUMAN | (Q6IEX5) | | Olfactory II fam 4/MOR225-248 | Homo sapiens (Human) |
| Q6IEY2_HUMAN | (Q6IEY2) | | Olfactory II fam 4/MOR225-248 | Homo sapiens (Human) |
| Q6IEY3_HUMAN | (Q6IEY3) | | Olfactory II fam 4/MOR225-248 | Homo sapiens (Human) |
| Q6IEZ1_HUMAN | (Q6IEZ1) | | Olfactory II fam 2/MOR256-262,270-285 | Homo sapiens (Human) |
| Q6IEZ2_HUMAN | (Q6IEZ2) | | Olfactory II fam 5/MOR172-224,249,254 | Homo sapiens (Human) |
| Q6IEZ4_HUMAN | (Q6IEZ4) | | Olfactory II fam 4/MOR225-248 | Homo sapiens (Human) |
| Q6IEZ6_HUMAN | (Q6IEZ6) | OR5BF1 | Olfactory II fam 5/MOR172-224,249,254 | Homo sapiens (Human) |
| Q6IF01_HUMAN | (Q6IF01) | | Olfactory II fam 6/MOR103-105,107-119 | Homo sapiens (Human) |
| Q6IF09_HUMAN | (Q6IF09) | | Olfactory II fam 11/MOR106,121-122 | Homo sapiens (Human) |
| Q6IF12_HUMAN | (Q6IF12) | | Olfactory II fam 4/MOR225-248 | Homo sapiens (Human) |
| Q6IF17_HUMAN | (Q6IF17) | | Olfactory II fam 1/MOR125-138,156 | Homo sapiens (Human) |
| Q6IF20_HUMAN | (Q6IF20) | RP11-112J3.12-001 | Olfactory II fam 13/MOR253 | Homo sapiens (Human) |
| Q6IF23_HUMAN | (Q6IF23) | OR12D3 | Olfactory II fam 12/MOR250 | Homo sapiens (Human) |
| Q6IF24_HUMAN | (Q6IF24) | OR2J2 | Olfactory II fam 2/MOR256-262,270-285 | Homo sapiens (Human) |

TABLE D-continued non-limiting list human GPCRs

| | | | | |
|---|---|---|---|---|
| Q6IF25_HUMAN | (Q6IF25) | DAQB-117O11.4-001 | Olfactory II fam 2/MOR256-262,270-285 | *Homo sapiens* (Human) |
| Q6IF31_HUMAN | (Q6IF31) | OR52A1 | Olfactory I fam 51-52/MOR1-42 | *Homo sapiens* (Human) |
| Q6IF34_HUMAN | (Q6IF34) | | Olfactory II fam 2/MOR256-262,270-285 | *Homo sapiens* (Human) |
| Q6IF35_HUMAN | (Q6IF35) | | Olfactory II fam 6/MOR103-105,107-119 | *Homo sapiens* (Human) |
| Q6IF36_HUMAN | (Q6IF36) | | Olfactory II fam 8/MOR161-171 | *Homo sapiens* (Human) |
| Q6IF40_HUMAN | (Q6IF40) | | Olfactory II fam 2/MOR256-262,270-285 | *Homo sapiens* (Human) |
| Q6IF41_HUMAN | (Q6IF41) | | Olfactory II fam 2/MOR256-262,270-285 | *Homo sapiens* (Human) |
| Q6IF43_HUMAN | (Q6IF43) | | Olfactory II fam 2/MOR256-262,270-285 | *Homo sapiens* (Human) |
| Q6IF44_HUMAN | (Q6IF44) | | Olfactory II fam 2/MOR256-262,270-285 | *Homo sapiens* (Human) |
| Q6IF46_HUMAN | (Q6IF46) | | Olfactory II fam 5/MOR172-224,249,254 | *Homo sapiens* (Human) |
| Q6IF50_HUMAN | (Q6IF50) | RP11-317C20.1-001 | Olfactory II fam 13/MOR253 | *Homo sapiens* (Human) |
| Q6IF51_HUMAN | (Q6IF51) | RP11-317C20.4-001 | Olfactory II fam 13/MOR253 | *Homo sapiens* (Human) |
| Q6IF52_HUMAN | (Q6IF52) | | Olfactory II fam 13/MOR253 | *Homo sapiens* (Human) |
| Q6IF53_HUMAN | (Q6IF53) | RP11-317C20.6-001 | Olfactory II fam 13/MOR253 | *Homo sapiens* (Human) |
| Q6IF54_HUMAN | (Q6IF54) | RP11-413C10.2-001 | Olfactory II fam 13/MOR253 | *Homo sapiens* (Human) |
| Q6IF55_HUMAN | (Q6IF55) | | Olfactory II fam 2/MOR256-262,270-285 | *Homo sapiens* (Human) |
| Q6IF56_HUMAN | (Q6IF56) | | Olfactory II fam 4/MOR225-248 | *Homo sapiens* (Human) |
| Q6IF57_HUMAN | (Q6IF57) | | Olfactory II fam 4/MOR225-248 | *Homo sapiens* (Human) |
| Q6IF58_HUMAN | (Q6IF58) | | Olfactory II fam 10/MOR263-269 | *Homo sapiens* (Human) |
| Q6IF59_HUMAN | (Q6IF59) | | Olfactory II fam 10/MOR263-269 | *Homo sapiens* (Human) |
| Q6IF60_HUMAN | (Q6IF60) | | Olfactory II fam 5/MOR172-224,249,254 | *Homo sapiens* (Human) |
| Q6IF61_HUMAN | (Q6IF61) | | Olfactory II fam 5/MOR172-224,249,254 | *Homo sapiens* (Human) |
| Q6IF62_HUMAN | (Q6IF62) | | Olfactory II fam 9/MOR120 | *Homo sapiens* (Human) |
| Q6IF65_HUMAN | (Q6IF65) | | Olfactory II fam 5/MOR172-224,249,254 | *Homo sapiens* (Human) |
| Q6IF66_HUMAN | (Q6IF66) | | Olfactory II fam 5/MOR172-224,249,254 | *Homo sapiens* (Human) |
| Q6IF67_HUMAN | (Q6IF67) | | Olfactory II fam 5/MOR172-224,249,254 | *Homo sapiens* (Human) |
| Q6IF68_HUMAN | (Q6IF68) | | Olfactory II fam 5/MOR172-224,249,254 | *Homo sapiens* (Human) |
| Q6IF69_HUMAN | (Q6IF69) | | Olfactory II fam 5/MOR172-224,249,254 | *Homo sapiens* (Human) |
| Q6IF70_HUMAN | (Q6IF70) | | Olfactory II fam 6/MOR103-105,107-119 | *Homo sapiens* (Human) |
| Q6IF71_HUMAN | (Q6IF71) | | Olfactory II fam 9/MOR120 | *Homo sapiens* (Human) |
| Q6IF72_HUMAN | (Q6IF72) | | Olfactory II fam 4/MOR225-248 | *Homo sapiens* (Human) |
| Q6IF73_HUMAN | (Q6IF73) | | Olfactory II fam 4/MOR225-248 | *Homo sapiens* (Human) |
| Q6IF74_HUMAN | (Q6IF74) | | Olfactory II fam 4/MOR225-248 | *Homo sapiens* (Human) |
| Q6IF77_HUMAN | (Q6IF77) | | Olfactory I fam 51-52/MOR1-42 | *Homo sapiens* (Human) |
| Q6IF78_HUMAN | (Q6IF78) | | Olfactory I fam 51-52/MOR1-42 | *Homo sapiens* (Human) |
| Q6IF79_HUMAN | (Q6IF79) | | Olfactory I fam 51-52/MOR1-42 | *Homo sapiens* (Human) |
| Q6IF85_HUMAN | (Q6IF85) | | Olfactory II fam 5/MOR172-224,249,254 | *Homo sapiens* (Human) |
| Q6IF86_HUMAN | (Q6IF86) | | Olfactory II fam 13/MOR253 | *Homo sapiens* (Human) |
| Q6IF87_HUMAN | (Q6IF87) | | Olfactory II fam 5/MOR172-224,249,254 | *Homo sapiens* (Human) |
| Q6IF88_HUMAN | (Q6IF88) | | Olfactory II fam 5/MOR172-224,249,254 | *Homo sapiens* (Human) |
| Q6IF89_HUMAN | (Q6IF89) | OR2B6 | Olfactory II fam 2/MOR256-262,270-285 | *Homo sapiens* (Human) |
| Q6IF91_HUMAN | (Q6IF91) | | Olfactory I fam 51-52/MOR1-42 | *Homo sapiens* (Human) |
| Q6IF93_HUMAN | (Q6IF93) | | Olfactory I fam 51-52/MOR1-42 | *Homo sapiens* (Human) |
| Q6IF94_HUMAN | (Q6IF94) | | Olfactory I fam 51-52/MOR1-42 | *Homo sapiens* (Human) |
| Q6IF95_HUMAN | (Q6IF95) | | Olfactory II fam 4/MOR225-248 | *Homo sapiens* (Human) |
| Q6IF96_HUMAN | (Q6IF96) | | Olfactory II fam 5/MOR172-224,249,254 | *Homo sapiens* (Human) |
| Q6IFA1_HUMAN | (Q6IFA1) | | Olfactory II fam 2/MOR256-262,270-285 | *Homo sapiens* (Human) |
| Q6IFA2_HUMAN | (Q6IFA2) | | Olfactory II fam 4/MOR225-248 | *Homo sapiens* (Human) |
| Q6IFA3_HUMAN | (Q6IFA3) | | Olfactory II fam 4/MOR225-248 | *Homo sapiens* (Human) |
| Q6IFA4_HUMAN | (Q6IFA4) | | Olfactory II fam 4/MOR225-248 | *Homo sapiens* (Human) |
| Q6IFA5_HUMAN | (Q6IFA5) | | Olfactory II fam 4/MOR225-248 | *Homo sapiens* (Human) |
| Q6IFA7_HUMAN | (Q6IFA7) | | Olfactory II fam 4/MOR225-248 | *Homo sapiens* (Human) |
| Q6IFA8_HUMAN | (Q6IFA8) | | Olfactory II fam 10/MOR263-269 | *Homo sapiens* (Human) |
| Q6IFA9_HUMAN | (Q6IFA9) | | Olfactory II fam 1/MOR125-138,156 | *Homo sapiens* (Human) |
| Q6IFB0_HUMAN | (Q6IFB0) | | Olfactory II fam 1/MOR125-138,156 | *Homo sapiens* (Human) |
| Q6IFB4_HUMAN | (Q6IFB4) | | Olfactory II fam 4/MOR225-248 | *Homo sapiens* (Human) |
| Q6IFB5_HUMAN | (Q6IFB5) | | Olfactory II fam 8/MOR161-171 | *Homo sapiens* (Human) |
| Q6IFB6_HUMAN | (Q6IFB6) | | Olfactory II fam 8/MOR161-171 | *Homo sapiens* (Human) |
| Q6IFB7_HUMAN | (Q6IFB7) | | Olfactory II fam 8/MOR161-171 | *Homo sapiens* (Human) |
| Q6IFB8_HUMAN | (Q6IFB8) | | Olfactory II fam 5/MOR172-224,249,254 | *Homo sapiens* (Human) |
| Q6IFB9_HUMAN | (Q6IFB9) | | Olfactory II fam 5/MOR172-224,249,254 | *Homo sapiens* (Human) |
| Q6IFC0_HUMAN | (Q6IFC0) | | Olfactory II fam 8/MOR161-171 | *Homo sapiens* (Human) |
| Q6IFC1_HUMAN | (Q6IFC1) | | Olfactory II fam 8/MOR161-171 | *Homo sapiens* (Human) |
| Q6IFC2_HUMAN | (Q6IFC2) | | Olfactory II fam 8/MOR161-171 | *Homo sapiens* (Human) |
| Q6IFC3_HUMAN | (Q6IFC3) | | Olfactory II fam 8/MOR161-171 | *Homo sapiens* (Human) |
| Q6IFC4_HUMAN | (Q6IFC4) | | Olfactory II fam 8/MOR161-171 | *Homo sapiens* (Human) |
| Q6IFC5_HUMAN | (Q6IFC5) | | Olfactory II fam 8/MOR161-171 | *Homo sapiens* (Human) |
| Q6IFC7_HUMAN | (Q6IFC7) | | Olfactory II fam 5/MOR172-224,249,254 | *Homo sapiens* (Human) |
| Q6IFC8_HUMAN | (Q6IFC8) | | Olfactory II fam 5/MOR172-224,249,254 | *Homo sapiens* (Human) |
| Q6IFC9_HUMAN | (Q6IFC9) | | Olfactory II fam 5/MOR172-224,249,254 | *Homo sapiens* (Human) |
| Q6IFD0_HUMAN | (Q6IFD0) | | Olfactory II fam 5/MOR172-224,249,254 | *Homo sapiens* (Human) |
| Q6IFD1_HUMAN | (Q6IFD1) | | fragments | *Homo sapiens* (Human) |
| Q6IFD3_HUMAN | (Q6IFD3) | | Olfactory II fam 5/MOR172-224,249,254 | *Homo sapiens* (Human) |
| Q6IFD4_HUMAN | (Q6IFD4) | | Olfactory II fam 5/MOR172-224,249,254 | *Homo sapiens* (Human) |
| Q6IFD5_HUMAN | (Q6IFD5) | | Olfactory II fam 10/MOR263-269 | *Homo sapiens* (Human) |
| Q6IFD6_HUMAN | (Q6IFD6) | | Olfactory II fam 9/MOR120 | *Homo sapiens* (Human) |
| Q6IFD7_HUMAN | (Q6IFD7) | | Olfactory I fam 51-52/MOR1-42 | *Homo sapiens* (Human) |
| Q6IFD9_HUMAN | (Q6IFD9) | | Olfactory II fam 10/MOR263-269 | *Homo sapiens* (Human) |

TABLE D-continued non-limiting list human GPCRs

| | | | | |
|---|---|---|---|---|
| Q6IFE0_HUMAN | (Q6IFE0) | | Olfactory II fam 5/MOR172-224,249,254 | *Homo sapiens* (Human) |
| Q6IFE1_HUMAN | (Q6IFE1) | | Olfactory II fam 5/MOR172-224,249,254 | *Homo sapiens* (Human) |
| Q6IFE4_HUMAN | (Q6IFE4) | | Olfactory I fam 51-52/MOR1-42 | *Homo sapiens* (Human) |
| Q6IFE5_HUMAN | (Q6IFE5) | | Olfactory I fam 51-52/MOR1-42 | *Homo sapiens* (Human) |
| Q6IFE7_HUMAN | (Q6IFE7) | | Olfactory II fam 6/MOR103-105,107-119 | *Homo sapiens* (Human) |
| Q6IFE8_HUMAN | (Q6IFE8) | | Olfactory II fam 10/MOR263-269 | *Homo sapiens* (Human) |
| Q6IFE9_HUMAN | (Q6IFE9) | | Olfactory II fam 8/MOR161-171 | *Homo sapiens* (Human) |
| Q6IFF2_HUMAN | (Q6IFF2) | | Olfactory II fam 5/MOR172-224,249,254 | *Homo sapiens* (Human) |
| Q6IFF4_HUMAN | (Q6IFF4) | | Olfactory II fam 5/MOR172-224,249,254 | *Homo sapiens* (Human) |
| Q6IFF6_HUMAN | (Q6IFF6) | | Olfactory I fam 51-52/MOR1-42 | *Homo sapiens* (Human) |
| Q6IFF7_HUMAN | (Q6IFF7) | | Olfactory I fam 51-52/MOR1-42 | *Homo sapiens* (Human) |
| Q6IFF8_HUMAN | (Q6IFF8) | | Olfactory I fam 51-52/MOR1-42 | *Homo sapiens* (Human) |
| Q6IFF9_HUMAN | (Q6IFF9) | | Olfactory I fam 51-52/MOR1-42 | *Homo sapiens* (Human) |
| Q6IFG0_HUMAN | (Q6IFG0) | | Olfactory I fam 51-52/MOR1-42 | *Homo sapiens* (Human) |
| Q6IFG2_HUMAN | (Q6IFG2) | | Olfactory I fam 51-52/MOR1-42 | *Homo sapiens* (Human) |
| Q6IFG3_HUMAN | (Q6IFG3) | | Olfactory II fam 1/MOR125-138,156 | *Homo sapiens* (Human) |
| Q6IFG4_HUMAN | (Q6IFG4) | | Olfactory II fam 10/MOR263-269 | *Homo sapiens* (Human) |
| Q6IFG5_HUMAN | (Q6IFG5) | | Olfactory II fam 1/MOR125-138,156 | *Homo sapiens* (Human) |
| Q6IFG6_HUMAN | (Q6IFG6) | | Olfactory II fam 10/MOR263-269 | *Homo sapiens* (Human) |
| Q6IFG7_HUMAN | (Q6IFG7) | | Olfactory II fam 2/MOR256-262,270-285 | *Homo sapiens* (Human) |
| Q6IFG8_HUMAN | (Q6IFG8) | | Olfactory II fam 2/MOR256-262,270-285 | *Homo sapiens* (Human) |
| Q6IFG9_HUMAN | (Q6IFG9) | | Olfactory II fam 10/MOR263-269 | *Homo sapiens* (Human) |
| Q6IFH0_HUMAN | (Q6IFH0) | | Olfactory II fam 9/MOR120 | *Homo sapiens* (Human) |
| Q6IFH1_HUMAN | (Q6IFH1) | | Olfactory II fam 6/MOR103-105,107-119 | *Homo sapiens* (Human) |
| Q6IFH2_HUMAN | (Q6IFH2) | OR10J5 | Olfactory II fam 10/MOR263-269 | *Homo sapiens* (Human) |
| Q6IFH6_HUMAN | (Q6IFH6) | | Olfactory I fam 51-52/MOR1-42 | *Homo sapiens* (Human) |
| Q6IFH7_HUMAN | (Q6IFH7) | | Olfactory I fam 51-52/MOR1-42 | *Homo sapiens* (Human) |
| Q6IFH8_HUMAN | (Q6IFH8) | | Olfactory I fam 51-52/MOR1-42 | *Homo sapiens* (Human) |
| Q6IFH9_HUMAN | (Q6IFH9) | | Olfactory I fam 51-52/MOR1-42 | *Homo sapiens* (Human) |
| Q6IFI0_HUMAN | (Q6IFI0) | | Olfactory I fam 51-52/MOR1-42 | *Homo sapiens* (Human) |
| Q6IFI1_HUMAN | (Q6IFI1) | | Olfactory I fam 51-52/MOR1-42 | *Homo sapiens* (Human) |
| Q6IFI2_HUMAN | (Q6IFI2) | | Olfactory I fam 51-52/MOR1-42 | *Homo sapiens* (Human) |
| Q6IFI3_HUMAN | (Q6IFI3) | | Olfactory I fam 51-52/MOR1-42 | *Homo sapiens* (Human) |
| Q6IFI4_HUMAN | (Q6IFI4) | | Olfactory II fam 9/MOR120 | *Homo sapiens* (Human) |
| Q6IFI5_HUMAN | (Q6IFI5) | | Olfactory II fam 13/MOR253 | *Homo sapiens* (Human) |
| Q6IFI7_HUMAN | (Q6IFI7) | | Olfactory I fam 51-52/MOR1-42 | *Homo sapiens* (Human) |
| Q6IFI8_HUMAN | (Q6IFI8) | | Olfactory II fam 2/MOR256-262,270-285 | *Homo sapiens* (Human) |
| Q6IFI9_HUMAN | (Q6IFI9) | | Olfactory II fam 1/MOR125-138,156 | *Homo sapiens* (Human) |
| Q6IFJ0_HUMAN | (Q6IFJ0) | | Olfactory II fam 10/MOR263-269 | *Homo sapiens* (Human) |
| Q6IFJ2_HUMAN | (Q6IFJ2) | | Olfactory II fam 10/MOR263-269 | *Homo sapiens* (Human) |
| Q6IFJ3_HUMAN | (Q6IFJ3) | | Olfactory II fam 1/MOR125-138,156 | *Homo sapiens* (Human) |
| Q6IFJ4_HUMAN | (Q6IFJ4) | | Olfactory II fam 7/MOR139-155 | *Homo sapiens* (Human) |
| Q6IFJ5_HUMAN | (Q6IFJ5) | | Olfactory II fam 7/MOR139-155 | *Homo sapiens* (Human) |
| Q6IFJ6_HUMAN | (Q6IFJ6) | | Olfactory II fam 7/MOR139-155 | *Homo sapiens* (Human) |
| Q6IFJ7_HUMAN | (Q6IFJ7) | | Olfactory II fam 7/MOR139-155 | *Homo sapiens* (Human) |
| Q6IFJ8_HUMAN | (Q6IFJ8) | | Olfactory I fam 51-52/MOR1-42 | *Homo sapiens* (Human) |
| Q6IFJ9_HUMAN | (Q6IFJ9) | | Olfactory II fam 6/MOR103-105,107-119 | *Homo sapiens* (Human) |
| Q6IFK1_HUMAN | (Q6IFK1) | | Olfactory II fam 6/MOR103-105,107-119 | *Homo sapiens* (Human) |
| Q6IFK4_HUMAN | (Q6IFK4) | | Olfactory I fam 51-52/MOR1-42 | *Homo sapiens* (Human) |
| Q6IFK5_HUMAN | (Q6IFK5) | | Olfactory I fam 51-52/MOR1-42 | *Homo sapiens* (Human) |
| Q6IFK7_HUMAN | (Q6IFK7) | | Olfactory I fam 51-52/MOR1-42 | *Homo sapiens* (Human) |
| Q6IFK8_HUMAN | (Q6IFK8) | | Olfactory I fam 51-52/MOR1-42 | *Homo sapiens* (Human) |
| Q6IFK9_HUMAN | (Q6IFK9) | | Olfactory I fam 51-52/MOR1-42 | *Homo sapiens* (Human) |
| Q6IFL0_HUMAN | (Q6IFL0) | | Olfactory I fam 51-52/MOR1-42 | *Homo sapiens* (Human) |
| Q6IFL1_HUMAN | (Q6IFL1) | RP11-413C10.1-001 | Olfactory II fam 13/MOR253 | *Homo sapiens* (Human) |
| Q6IFL2_HUMAN | (Q6IFL2) | RP11-413C10.9-001 | Olfactory II fam 13/MOR253 | *Homo sapiens* (Human) |
| Q6IFL7_HUMAN | (Q6IFL7) | | Olfactory II fam 1/MOR125-138,156 | *Homo sapiens* (Human) |
| Q6IFL8_HUMAN | (Q6IFL8) | OR1D2 | Olfactory II fam 1/MOR125-138,156 | *Homo sapiens* (Human) |
| Q6IFL9_HUMAN | (Q6IFL9) | | Olfactory II fam 1/MOR125-138,156 | *Homo sapiens* (Human) |
| Q6IFM2_HUMAN | (Q6IFM2) | | Olfactory II fam 1/MOR125-138,156 | *Homo sapiens* (Human) |
| Q6IFM3_HUMAN | (Q6IFM3) | OR3A2 | Olfactory II fam 3/MOR255 | *Homo sapiens* (Human) |
| Q6IFM4_HUMAN | (Q6IFM4) | OR3A1 | Olfactory II fam 3/MOR255 | *Homo sapiens* (Human) |
| Q6IFM5_HUMAN | (Q6IFM5) | | Olfactory II fam 1/MOR125-138,156 | *Homo sapiens* (Human) |
| Q6IFM6_HUMAN | (Q6IFM6) | OR3A3 | Olfactory II fam 3/MOR255 | *Homo sapiens* (Human) |
| Q6IFM7_HUMAN | (Q6IFM7) | | Olfactory II fam 1/MOR125-138,156 | *Homo sapiens* (Human) |
| Q6IFM8_HUMAN | (Q6IFM8) | | Olfactory II fam 1/MOR125-138,156 | *Homo sapiens* (Human) |
| Q6IFM9_HUMAN | (Q6IFM9) | | Olfactory II fam 5/MOR172-224,249,254 | *Homo sapiens* (Human) |
| Q6IFN0_HUMAN | (Q6IFN0) | | Olfactory II fam 1/MOR125-138,156 | *Homo sapiens* (Human) |
| Q6IFN2_HUMAN | (Q6IFN2) | | Olfactory II fam 1/MOR125-138,156 | *Homo sapiens* (Human) |
| Q6IFN5_HUMAN | (Q6IFN5) | | Olfactory II fam 7/MOR139-155 | *Homo sapiens* (Human) |
| Q6IFN7_HUMAN | (Q6IFN7) | | Olfactory II fam 2/MOR256-262,270-285 | *Homo sapiens* (Human) |
| Q6IFP1_HUMAN | (Q6IFP1) | OR7A5 | Olfactory II fam 7/MOR139-155 | *Homo sapiens* (Human) |
| Q6IFP2_HUMAN | (Q6IFP2) | | Olfactory II fam 7/MOR139-155 | *Homo sapiens* (Human) |
| Q6IFP3_HUMAN | (Q6IFP3) | | Olfactory II fam 4/MOR225-248 | *Homo sapiens* (Human) |
| Q6IFP4_HUMAN | (Q6IFP4) | | Olfactory II fam 2/MOR256-262,270-285 | *Homo sapiens* (Human) |
| Q6IFP6_HUMAN | (Q6IFP6) | | Olfactory II fam 6/MOR103-105,107-119 | *Homo sapiens* (Human) |
| Q6IFP7_HUMAN | (Q6IFP7) | OR2F1 | Olfactory II fam 2/MOR256-262,270-285 | *Homo sapiens* (Human) |
| Q6IFP9_HUMAN | (Q6IFP9) | | Olfactory II fam 7/MOR139-155 | *Homo sapiens* (Human) |

TABLE D-continued non-limiting list human GPCRs

| | | | | |
|---|---|---|---|---|
| Q6IFQ0_HUMAN | (Q6IFQ0) | | Olfactory II fam 10/MOR263-269 | *Homo sapiens* (Human) |
| Q6IFQ1_HUMAN | (Q6IFQ1) | OR10H2 | Olfactory II fam 10/MOR263-269 | *Homo sapiens* (Human) |
| Q6IFQ2_HUMAN | (Q6IFQ2) | | Olfactory II fam 10/MOR263-269 | *Homo sapiens* (Human) |
| Q6IFQ5_HUMAN | (Q6IFQ5) | DAQB-304F3.1-001 | Olfactory II fam 10/MOR263-269 | *Homo sapiens* (Human) |
| Q6IFQ6_HUMAN | (Q6IFQ6) | OR7A17 | Olfactory II fam 7/MOR139-155 | *Homo sapiens* (Human) |
| Q6IFQ7_HUMAN | (Q6IFQ7) | | Olfactory II fam 8/MOR161-171 | *Homo sapiens* (Human) |
| Q6IFQ8_HUMAN | (Q6IFQ8) | | Olfactory II fam 8/MOR161-171 | *Homo sapiens* (Human) |
| Q6IFR0_HUMAN | (Q6IFR0) | | Olfactory II fam 8/MOR161-171 | *Homo sapiens* (Human) |
| Q6IFR1_HUMAN | (Q6IFR1) | | Olfactory II fam 10/MOR263-269 | *Homo sapiens* (Human) |
| Q6IFR2_HUMAN | (Q6IFR2) | OR6N2 | Olfactory II fam 6/MOR103-105,107-119 | *Homo sapiens* (Human) |
| Q6IFR3_HUMAN | (Q6IFR3) | | Olfactory II fam 6/MOR103-105,107-119 | *Homo sapiens* (Human) |
| Q6IFR4_HUMAN | (Q6IFR4) | | Olfactory II fam 6/MOR103-105,107-119 | *Homo sapiens* (Human) |
| Q6IFR5_HUMAN | (Q6IFR5) | | Olfactory II fam 6/MOR103-105,107-119 | *Homo sapiens* (Human) |
| Q6IFR6_HUMAN | (Q6IFR6) | OR6K2 | Olfactory II fam 6/MOR103-105,107-119 | *Homo sapiens* (Human) |
| Q6IFR7_HUMAN | (Q6IFR7) | | Olfactory II fam 10/MOR263-269 | *Homo sapiens* (Human) |
| Q6IFS1_HUMAN | (Q6IFS1) | | Olfactory II fam 10/MOR263-269 | *Homo sapiens* (Human) |
| Q6IFS2_HUMAN | (Q6IFS2) | OR10K1 | Olfactory II fam 10/MOR263-269 | *Homo sapiens* (Human) |
| Q6IN95_HUMAN | (Q6IN95) | IL8RA | Interleukin-8 type A | *Homo sapiens* (Human) |
| Q6IPX0_HUMAN | (Q6IPX0) | CCRL2 | C-C Chemokine other | *Homo sapiens* (Human) |
| Q6ISR6_HUMAN | (Q6ISR6) | OR6W1P | fragments | *Homo sapiens* (Human) |
| Q6ISR8_HUMAN | (Q6ISR8) | GHSR | Growth hormone secretagogue | *Homo sapiens* (Human) |
| Q6J164_HUMAN | (Q6J164) | GRM5 | Metabotropic glutamate group I | *Homo sapiens* (Human) |
| Q6KH09_HUMAN | (Q6KH09) | OR5D4 | fragments | *Homo sapiens* (Human) |
| Q6L5J4_HUMAN | (Q6L5J4) | | Fmet-leu-phe | *Homo sapiens* (Human) |
| Q6LAJ3_HUMAN | (Q6LAJ3) | | gamrh Adrenomedullin (G10D) | *Homo sapiens* (Human) |
| Q6LD06_HUMAN | (Q6LD06) | ADRA1C | fragments | *Homo sapiens* (Human) |
| Q6LDH7_HUMAN | (Q6LDH7) | DRD2 | fragments | *Homo sapiens* (Human) |
| Q6LEE7_HUMAN | (Q6LEE7) | CMKLR1 | fragments | *Homo sapiens* (Human) |
| Q6N055_HUMAN | (Q6N055) | DKFZp686O11112 | fragments | *Homo sapiens* (Human) |
| Q6N0A5_HUMAN | (Q6N0A5) | DKFZp686I13174 | frizzled Group B (Fz 3 & 6) | *Homo sapiens* (Human) |
| Q6NSL8_HUMAN | (Q6NSL8) | FZD10 | frizzled Group A (Fz 1&2&4&5&7-9) | *Homo sapiens* (Human) |
| Q6NSP5_HUMAN | (Q6NSP5) | GPR23 | Purinoceptor P2RY5,8,9,10 GPR35,92,174 | *Homo sapiens* (Human) |
| Q6NSY0_HUMAN | (Q6NSY0) | CNR2 | Cannabinoid | *Homo sapiens* (Human) |
| Q6NTA9_HUMAN | (Q6NTA9) | OR1A1 | Olfactory II fam 1/MOR125-138,156 | *Homo sapiens* (Human) |
| Q6NTB3_HUMAN | (Q6NTB3) | OR2C1 | Olfactory II fam 2/MOR256-262,270-285 | *Homo sapiens* (Human) |
| Q6NTB5_HUMAN | (Q6NTB5) | OR5V1 | fragments | *Homo sapiens* (Human) |
| Q6NTC7_HUMAN | (Q6NTC7) | NPBWR1 | GPR | *Homo sapiens* (Human) |
| Q6NTD7_HUMAN | (Q6NTD7) | OR51B4 | Olfactory I fam 51-52/MOR1-42 | *Homo sapiens* (Human) |
| Q6NTI7_HUMAN | (Q6NTI7) | GPR143 | Ocular albinism proteins | *Homo sapiens* (Human) |
| Q6NUM3_HUMAN | (Q6NUM3) | CHRM5 | Muse. acetylcholine Vertebrate type 5 | *Homo sapiens* (Human) |
| Q6NUP5_HUMAN | (Q6NUP5) | AGTR1 | Angiotensin type 1 | *Homo sapiens* (Human) |
| Q6NWM4_HUMAN | (Q6NWM4) | GPR4 | GPR | *Homo sapiens* (Human) |
| Q6NWM5_HUMAN | (Q6NWM5) | GPR21 | GPR | *Homo sapiens* (Human) |
| Q6NWQ5_HUMAN | (Q6NWQ5) | NPBWR2 | GPR | *Homo sapiens* (Human) |
| Q6NWQ6_HUMAN | (Q6NWQ6) | NPBWR2 | GPR | *Homo sapiens* (Human) |
| Q6NWQ8_HUMAN | (Q6NWQ8) | GPR77 | C5a anaphylatoxin | *Homo sapiens* (Human) |
| Q6NWQ9_HUMAN | (Q6NWQ9) | GPR77 | C5a anaphylatoxin | *Homo sapiens* (Human) |
| Q6NWR0_HUMAN | (Q6NWR0) | GPR77 | C5a anaphylatoxin | *Homo sapiens* (Human) |
| Q6NWR3_HUMAN | (Q6NWR3) | GPR83 | Neuropeptide Y other | *Homo sapiens* (Human) |
| Q6NWR4_HUMAN | (Q6NWR4) | GPR83 | Neuropeptide Y other | *Homo sapiens* (Human) |
| Q6NWR5_HUMAN | (Q6NWR5) | GPR68 | fragments | *Homo sapiens* (Human) |
| Q6NWR6_HUMAN | (Q6NWR6) | GPR68 | fragments | *Homo sapiens* (Human) |
| Q6NWR7_HUMAN | (Q6NWR7) | GPR63 | GPR45 like | *Homo sapiens* (Human) |
| Q6NWR8_HUMAN | (Q6NWR8) | GPR63 | GPR45 like | *Homo sapiens* (Human) |
| Q6NWR9_HUMAN | (Q6NWR9) | GPR63 | GPR45 like | *Homo sapiens* (Human) |
| Q6NWS6_HUMAN | (Q6NWS6) | GPR12 | fragments | *Homo sapiens* (Human) |
| Q6NWS7_HUMAN | (Q6NWS7) | GPR12 | fragments | *Homo sapiens* (Human) |
| Q6NWS8_HUMAN | (Q6NWS8) | GPR12 | fragments | *Homo sapiens* (Human) |
| Q6NXU6_HUMAN | (Q6NXU6) | GPR45 | GPR45 like | *Homo sapiens* (Human) |
| Q6P2M6_HUMAN | (Q6P2M6) | VIPR1 | Vasoactive intestinal polypeptide | *Homo sapiens* (Human) |
| Q6P4D8_HUMAN | (Q6P4D8) | | fragments | *Homo sapiens* (Human) |
| Q6P523_HUMAN | (Q6P523) | HTR2B | Serotonin type 2 | *Homo sapiens* (Human) |
| Q6P5R4_HUMAN | (Q6P5R4) | MGC72080 | fragments | *Homo sapiens* (Human) |
| Q6P5W7_HUMAN | (Q6P5W7) | OPN3 | fragments | *Homo sapiens* (Human) |
| Q6P7P0_HUMAN | (Q6P7P0) | C10orf97 | fragments | *Homo sapiens* (Human) |
| Q6P9E5_HUMAN | (Q6P9E5) | HRH1 | Histamine type 1 | *Homo sapiens* (Human) |
| Q6PK25_HUMAN | (Q6PK25) | LOC441453 | fragments | *Homo sapiens* (Human) |
| Q6RKA2_HUMAN | (Q6RKA2) | ADCYAP1R1 | fragments | *Homo sapiens* (Human) |
| Q6RKA3_HUMAN | (Q6RKA3) | ADCYAP1R1 | fragments | *Homo sapiens* (Human) |
| Q6RYQ6_HUMAN | (Q6RYQ6) | PTGFR | Prostaglandin F2-alpha | *Homo sapiens* (Human) |
| Q6S991_HUMAN | (Q6S991) | ADCYAP1R1 | fragments | *Homo sapiens* (Human) |
| Q6S992_HUMAN | (Q6S992) | ADCYAP1R1 | fragments | *Homo sapiens* (Human) |
| Q6SL56_HUMAN | (Q6SL56) | CHRM2 | fragments | *Homo sapiens* (Human) |
| Q6TTN3_HUMAN | (Q6TTN3) | PTGER3 | Prostaglandin E2 subtype EP3 | *Homo sapiens* (Human) |
| Q6UPP1_HUMAN | (Q6UPP1) | OPRM1 | Opioid type M | *Homo sapiens* (Human) |
| Q6UQ80_HUMAN | (Q6UQ80) | OPRM1 | Opioid type M | *Homo sapiens* (Human) |
| Q6UR92_HUMAN | (Q6UR92) | MC1R | Melanocyte stimulating hormone | *Homo sapiens* (Human) |
| Q6UR93_HUMAN | (Q6UR93) | MC1R | Melanocyte stimulating hormone | *Homo sapiens* (Human) |

TABLE D-continued

| | | | non-limiting list human GPCRs | |
|---|---|---|---|---|
| Q6UR94_HUMAN | (Q6UR94) | MC1R | Melanocyte stimulating hormone | *Homo sapiens* (Human) |
| Q6UR95_HUMAN | (Q6UR95) | MC1R | Melanocyte stimulating hormone | *Homo sapiens* (Human) |
| Q6UR96_HUMAN | (Q6UR96) | MC1R | Melanocyte stimulating hormone | *Homo sapiens* (Human) |
| Q6UR97_HUMAN | (Q6UR97) | MC1R | Melanocyte stimulating hormone | *Homo sapiens* (Human) |
| Q6UR98_HUMAN | (Q6UR98) | MC1R | Melanocyte stimulating hormone | *Homo sapiens* (Human) |
| Q6UR99_HUMAN | (Q6UR99) | MC1R | Melanocyte stimulating hormone | *Homo sapiens* (Human) |
| Q6URA0_HUMAN | (Q6URA0) | MC1R | Melanocyte stimulating hormone | *Homo sapiens* (Human) |
| Q6UVH2_HUMAN | (Q6UVH2) | ATGR2 | fragments | *Homo sapiens* (Human) |
| Q6UXT6_HUMAN | (Q6UXT6) | UNQ9373 | Olfactory II fam 5/MOR172-224,249,254 | *Homo sapiens* (Human) |
| Q6XGY1_HUMAN | (Q6XGY1) | | fragments | *Homo sapiens* (Human) |
| Q6ZMH0_HUMAN | (Q6ZMH0) | | Putative/unclassified Class B GPCRs | *Homo sapiens* (Human) |
| Q6ZMH4_HUMAN | (Q6ZMH4) | | Putative/unclassified Class B GPCRs | *Homo sapiens* (Human) |
| Q6ZMI9_HUMAN | (Q6ZMI9) | ETL | receptors | *Homo sapiens* (Human) |
| Q6ZMN0_HUMAN | (Q6ZMN0) | EMR1 | | *Homo sapiens* (Human) |
| Q6ZMN6_HUMAN | (Q6ZMN6) | | Olfactory II fam 13/MOR253 | *Homo sapiens* (Human) |
| Q6ZMP1_HUMAN | (Q6ZMP1) | | Putative/unclassified Class B GPCRs | *Homo sapiens* (Human) |
| Q6ZMP9_HUMAN | (Q6ZMP9) | | Purinoceptor P2RY5,8,9,10 GPR35,92,174 | *Homo sapiens* (Human) |
| Q6ZMQ2_HUMAN | (Q6ZMQ2) | | Metabotropic glutamate group III | *Homo sapiens* (Human) |
| Q6ZN22_HUMAN | (Q6ZN22) | | Vasoactive intestinal polypeptide | *Homo sapiens* (Human) |
| Q6ZPB0_HUMAN | (Q6ZPB0) | | fragments | *Homo sapiens* (Human) |
| Q6ZS44_HUMAN | (Q6ZS44) | | fragments | *Homo sapiens* (Human) |
| Q6ZTE9_HUMAN | (Q6ZTE9) | | fragments | *Homo sapiens* (Human) |
| Q6ZW62_HUMAN | (Q6ZW62) | | fragments | *Homo sapiens* (Human) |
| Q711G2_HUMAN | (Q711G2) | P2Y2-like | Putative/unclassified Class A GPCRs | *Homo sapiens* (Human) |
| Q712M9_HUMAN | (Q712M9) | htr4 | Serotonin type 4 | *Homo sapiens* (Human) |
| Q71U75_HUMAN | (Q71U75) | | Taste receptors T2R | *Homo sapiens* (Human) |
| Q71V90_HUMAN | (Q71V90) | OPRM1 | fragments | *Homo sapiens* (Human) |
| Q75LH0_HUMAN | (Q75LH0) | HTR5A | fragments | *Homo sapiens* (Human) |
| Q76E76_HUMAN | (Q76E76) | DRD4 | fragments | *Homo sapiens* (Human) |
| Q76L88_HUMAN | (Q76L88) | GPCR | Putative/unclassified Class A GPCRs | *Homo sapiens* (Human) |
| Q7KYP5_HUMAN | (Q7KYP5) | | fragments | *Homo sapiens* (Human) |
| Q7KYZ9_HUMAN | (Q7KYZ9) | alpha 1c-adrenoceptor subtype | fragments | *Homo sapiens* (Human) |
| Q7KZS6_HUMAN | (Q7KZS6) | | Melanocyte stimulating hormone | *Homo sapiens* (Human) |
| Q7L853_HUMAN | (Q7L853) | EDG1 | fragments | *Homo sapiens* (Human) |
| Q7M4L8_HUMAN | (Q7M4L8) | | Melanocyte stimulating hormone | *Homo sapiens* (Human) |
| Q7Z3W3_HUMAN | (Q7Z3W3) | DKFZp686N1782 | Proteinase-activated | *Homo sapiens* (Human) |
| Q7Z580_HUMAN | (Q7Z580) | HTR2B | fragments | *Homo sapiens* (Human) |
| Q7Z581_HUMAN | (Q7Z581) | GPR50 | fragments | *Homo sapiens* (Human) |
| Q7Z582_HUMAN | (Q7Z582) | GPR50 | fragments | *Homo sapiens* (Human) |
| Q7Z5R9_HUMAN | (Q7Z5R9) | | Histamine type 2 | *Homo sapiens* (Human) |
| Q7Z7I1_HUMAN | (Q7Z7I1) | CCBP2 | C-C Chemokine type X | *Homo sapiens* (Human) |
| Q7Z7Q5_HUMAN | (Q7Z7Q5) | DRD4 | fragments | *Homo sapiens* (Human) |
| Q86SE3_HUMAN | (Q86SE3) | | fragments | *Homo sapiens* (Human) |
| Q86SF1_HUMAN | (Q86SF1) | | fragments | *Homo sapiens* (Human) |
| Q86SF3_HUMAN | (Q86SF3) | | fragments | *Homo sapiens* (Human) |
| Q86SF4_HUMAN | (Q86SF4) | | fragments | *Homo sapiens* (Human) |
| Q86SG0_HUMAN | (Q86SG0) | | fragments | *Homo sapiens* (Human) |
| Q86SG8_HUMAN | (Q86SG8) | | fragments | *Homo sapiens* (Human) |
| Q86SG9_HUMAN | (Q86SG9) | | fragments | *Homo sapiens* (Human) |
| Q86SH1_HUMAN | (Q86SH1) | | fragments | *Homo sapiens* (Human) |
| Q86SH3_HUMAN | (Q86SH3) | | fragments | *Homo sapiens* (Human) |
| Q86SI3_HUMAN | (Q86SI3) | | fragments | *Homo sapiens* (Human) |
| Q86SI5_HUMAN | (Q86SI5) | | fragments | *Homo sapiens* (Human) |
| Q86SI8_HUMAN | (Q86SI8) | | fragments | *Homo sapiens* (Human) |
| Q86SJ4_HUMAN | (Q86SJ4) | | fragments | *Homo sapiens* (Human) |
| Q86SM2_HUMAN | (Q86SM2) | | fragments | *Homo sapiens* (Human) |
| Q86SP4_HUMAN | (Q86SP4) | | fragments | *Homo sapiens* (Human) |
| Q86UG6_HUMAN | (Q86UG6) | | fragments | *Homo sapiens* (Human) |
| Q86UG7_HUMAN | (Q86UG7) | | fragments | *Homo sapiens* (Human) |
| Q86UG8_HUMAN | (Q86UG8) | | fragments | *Homo sapiens* (Human) |
| Q86UG9_HUMAN | (Q86UG9) | | fragments | *Homo sapiens* (Human) |
| Q86UH0_HUMAN | (Q86UH0) | | fragments | *Homo sapiens* (Human) |
| Q86UK4_HUMAN | (Q86UK4) | PTC | Taste receptors T2R | *Homo sapiens* (Human) |
| Q86UN1_HUMAN | (Q86UN1) | HTR5A | fragments | *Homo sapiens* (Human) |
| Q86UN7_HUMAN | (Q86UN7) | CASR | fragments | *Homo sapiens* (Human) |
| Q86UZ8_HUMAN | (Q86UZ8) | FZD2 | fragments | *Homo sapiens* (Human) |
| Q86V80_HUMAN | (Q86V80) | | Opioid type M | *Homo sapiens* (Human) |
| Q86XI5_HUMAN | (Q86XI5) | GLP2R | fragments | *Homo sapiens* (Human) |
| Q86YF2_HUMAN | (Q86YF2) | | fragments | *Homo sapiens* (Human) |
| Q86YG3_HUMAN | (Q86YG3) | | fragments | *Homo sapiens* (Human) |
| Q86YG9_HUMAN | (Q86YG9) | | fragments | *Homo sapiens* (Human) |
| Q86YW1_HUMAN | (Q86YW1) | MC1R | Melanocyte stimulating hormone | *Homo sapiens* (Human) |
| Q8IU63_HUMAN | (Q8IU63) | 6M1-16 | fragments | *Homo sapiens* (Human) |
| Q8IV06_HUMAN | (Q8IV06) | GPR171 | Putative/unclassified Class A GPCRs | *Homo sapiens* (Human) |
| Q8IV17_HUMAN | (Q8IV17) | SCTR | Secretin | *Homo sapiens* (Human) |
| Q8IV19_HUMAN | (Q8IV19) | CYSLTR1 | Cysteinyl leukotriene | *Homo sapiens* (Human) |
| Q8IV68_HUMAN | (Q8IV68) | LOC442421 | fragments | *Homo sapiens* (Human) |
| Q8IVW0_HUMAN | (Q8IVW0) | CHRM5 | Musc. acetylcholine Vertebrate type 5 | *Homo sapiens* (Human) |

TABLE D-continued

| | | | non-limiting list human GPCRs | |
|---|---|---|---|---|
| Q8IW08_HUMAN | (Q8IW08) | GABBR1 | GABA-B subtype 1 | *Homo sapiens* (Human) |
| Q8IWP3_HUMAN | (Q8IWP3) | | Opioid type K | *Homo sapiens* (Human) |
| Q8IWW3_HUMAN | (Q8IWW3) | OPRM | Opioid type M | *Homo sapiens* (Human) |
| Q8IWW4_HUMAN | (Q8IWW4) | OPRM | Opioid type M | *Homo sapiens* (Human) |
| Q8IXA4_HUMAN | (Q8IXA4) | GPR126 | Putative/unclassified Class B GPCRs | *Homo sapiens* (Human) |
| Q8IXB0_HUMAN | (Q8IXB0) | | Opioid type X | *Homo sapiens* (Human) |
| Q8IXD9_HUMAN | (Q8IXD9) | | fragments | *Homo sapiens* (Human) |
| Q8IXE0_HUMAN | (Q8IXE0) | OR11H13P | | *Homo sapiens* (Human) |
| Q8IXE2_HUMAN | (Q8IXE2) | | Putative/unclassified Class A GPCRs | *Homo sapiens* (Human) |
| Q8IXE4_HUMAN | (Q8IXE4) | | Putative/unclassified Class B GPCRs | *Homo sapiens* (Human) |
| Q8IXE5_HUMAN | (Q8IXE5) | | Putative/unclassified Class A GPCRs | *Homo sapiens* (Human) |
| Q8IXE7_HUMAN | (Q8IXE7) | | fragments | *Homo sapiens* (Human) |
| Q8IXH9_HUMAN | (Q8IXH9) | HTR4B | Serotonin type 4 | *Homo sapiens* (Human) |
| Q8N0W0_HUMAN | (Q8N0W0) | | fragments | *Homo sapiens* (Human) |
| Q8N0W1_HUMAN | (Q8N0W1) | | fragments | *Homo sapiens* (Human) |
| Q8N0X1_HUMAN | (Q8N0X1) | | fragments | *Homo sapiens* (Human) |
| Q8N0Y1_HUMAN | (Q8N0Y1) | | Olfactory II fam 8/MOR161-171 | *Homo sapiens* (Human) |
| Q8N0Z0_HUMAN | (Q8N0Z0) | | fragments | *Homo sapiens* (Human) |
| Q8N164_HUMAN | (Q8N164) | | fragments | *Homo sapiens* (Human) |
| Q8N2R3_HUMAN | (Q8N2R3) | | fragments | *Homo sapiens* (Human) |
| Q8N537_HUMAN | (Q8N537) | LGR4 | LGR like (hormone receptors) | *Homo sapiens* (Human) |
| Q8N5S7_HUMAN | (Q8N5S7) | GPR | | *Homo sapiens* (Human) |
| Q8N6T6_HUMAN | (Q8N6T6) | IL8RA | Interleukin-8 type A | *Homo sapiens* (Human) |
| Q8N7J6_HUMAN | (Q8N7J6) | | Putative/unclassified Class A GPCRs | *Homo sapiens* (Human) |
| Q8NCH4_HUMAN | (Q8NCH4) | | fragments | *Homo sapiens* (Human) |
| Q8NEI9_HUMAN | (Q8NEI9) | OR7E91P | fragments | *Homo sapiens* (Human) |
| Q8NEN2_HUMAN | (Q8NEN2) | GPR85 | SREB | *Homo sapiens* (Human) |
| Q8NG71_HUMAN | (Q8NG71) | | Corticotropin releasing factor | *Homo sapiens* (Human) |
| Q8NG73_HUMAN | (Q8NG73) | | fragments | *Homo sapiens* (Human) |
| Q8NG79_HUMAN | (Q8NG79) | | Olfactory unclassified class II | *Homo sapiens* (Human) |
| Q8NG87_HUMAN | (Q8NG87) | | fragments | *Homo sapiens* (Human) |
| Q8NG89_HUMAN | (Q8NG89) | OR7E86P | fragments | *Homo sapiens* (Human) |
| Q8NG90_HUMAN | (Q8NG90) | | fragments | *Homo sapiens* (Human) |
| Q8NG91_HUMAN | (Q8NG91) | | fragments | *Homo sapiens* (Human) |
| Q8NGA3_HUMAN | (Q8NGA3) | | fragments | *Homo sapiens* (Human) |
| Q8NGA4_HUMAN | (Q8NGA4) | | Chemokine receptor-like 1 | *Homo sapiens* (Human) |
| Q8NGA9_HUMAN | (Q8NGA9) | | Putative/unclassified Class B GPCRs | *Homo sapiens* (Human) |
| Q8NGB0_HUMAN | (Q8NGB0) | GPR142 | Putative/unclassified Class A GPCRs | *Homo sapiens* (Human) |
| Q8NGB5_HUMAN | (Q8NGB5) | | fragments | *Homo sapiens* (Human) |
| Q8NGC8_HUMAN | (Q8NGC8) | | fragments | *Homo sapiens* (Human) |
| Q8NGD6_HUMAN | (Q8NGD6) | | Olfactory II fam 4/MOR225-248 | *Homo sapiens* (Human) |
| Q8NGD7_HUMAN | (Q8NGD7) | | fragments | *Homo sapiens* (Human) |
| Q8NGD8_HUMAN | (Q8NGD8) | | fragments | *Homo sapiens* (Human) |
| Q8NGE6_HUMAN | (Q8NGE6) | | fragments | *Homo sapiens* (Human) |
| Q8NGF2_HUMAN | (Q8NGF2) | | Olfactory I fam 51-52/MOR1-42 | *Homo sapiens* (Human) |
| Q8NGG1_HUMAN | (Q8NGG1) | | fragments | *Homo sapiens* (Human) |
| Q8NGG9_HUMAN | (Q8NGG9) | | Olfactory II fam 8/MOR161-171 | *Homo sapiens* (Human) |
| Q8NGH0_HUMAN | (Q8NGH0) | | Olfactory II fam 8/MOR161-171 | *Homo sapiens* (Human) |
| Q8NGH1_HUMAN | (Q8NGH1) | | Olfactory II fam 8/MOR161-171 | *Homo sapiens* (Human) |
| Q8NGH2_HUMAN | (Q8NGH2) | | Olfactory II fam 8/MOR161-171 | *Homo sapiens* (Human) |
| Q8NGH4_HUMAN | (Q8NGH4) | | Olfactory II fam 2/MOR256-262,270-285 | *Homo sapiens* (Human) |
| Q8NGI5_HUMAN | (Q8NGI5) | | fragments | *Homo sapiens* (Human) |
| Q8NGK8_HUMAN | (Q8NGK8) | | fragments | *Homo sapiens* (Human) |
| Q8NGL5_HUMAN | (Q8NGL5) | | Olfactory II fam 5/MOR172-224,249,254 | *Homo sapiens* (Human) |
| Q8NGM0_HUMAN | (Q8NGM0) | | Olfactory II fam 4/MOR225-248 | *Homo sapiens* (Human) |
| Q8NGM3_HUMAN | (Q8NGM3) | OR5E1P | fragments | *Homo sapiens* (Human) |
| Q8NGM4_HUMAN | (Q8NGM4) | | Olfactory II fam 10/MOR263-269 | *Homo sapiens* (Human) |
| Q8NGM5_HUMAN | (Q8NGM5) | | Dopamine Vertebrate type 4 | *Homo sapiens* (Human) |
| Q8NGM6_HUMAN | (Q8NGM6) | | fragments | *Homo sapiens* (Human) |
| Q8NGM7_HUMAN | (Q8NGM7) | | Olfactory I fam 51-52/MOR1-42 | *Homo sapiens* (Human) |
| Q8NGN9_HUMAN | (Q8NGN9) | | Olfactory II fam 4/MOR225-248 | *Homo sapiens* (Human) |
| Q8NGP1_HUMAN | (Q8NGP1) | | fragments | *Homo sapiens* (Human) |
| Q8NGP5_HUMAN | (Q8NGP5) | | fragments | *Homo sapiens* (Human) |
| Q8NGP7_HUMAN | (Q8NGP7) | | fragments | *Homo sapiens* (Human) |
| Q8NGQ7_HUMAN | (Q8NGQ7) | | fragments | *Homo sapiens* (Human) |
| Q8NGQ8_HUMAN | (Q8NGQ8) | | Substance K (NK2) | *Homo sapiens* (Human) |
| Q8NGT3_HUMAN | (Q8NGT3) | | fragments | *Homo sapiens* (Human) |
| Q8NGT4_HUMAN | (Q8NGT4) | | fragments | *Homo sapiens* (Human) |
| Q8NGU0_HUMAN | (Q8NGU0) | | Olfactory II fam 2/MOR256-262,270-285 | *Homo sapiens* (Human) |
| Q8NGU1_HUMAN | (Q8NGU1) | | fragments | *Homo sapiens* (Human) |
| Q8NGU3_HUMAN | (Q8NGU3) | | Putative/unclassified Class A GPCRs | *Homo sapiens* (Human) |
| Q8NGU6_HUMAN | (Q8NGU6) | OR2J4P | fragments | *Homo sapiens* (Human) |
| Q8NGU7_HUMAN | (Q8NGU7) | | fragments | *Homo sapiens* (Human) |
| Q8NGV4_HUMAN | (Q8NGV4) | | Olfactory II fam 13/MOR253 | *Homo sapiens* (Human) |
| Q8NGV8_HUMAN | (Q8NGV8) | | fragments | *Homo sapiens* (Human) |
| Q8NGV9_HUMAN | (Q8NGV9) | | calcium-sensing like other | *Homo sapiens* (Human) |
| Q8NGW2_HUMAN | (Q8NGW2) | DRD5P1 | fragments | *Homo sapiens* (Human) |
| Q8NGW3_HUMAN | (Q8NGW3) | | fragments | *Homo sapiens* (Human) |

TABLE D-continued non-limiting list human GPCRs

| | | | | |
|---|---|---|---|---|
| Q8NGW5_HUMAN | (Q8NGW5) | | fragments | *Homo sapiens* (Human) |
| Q8NGW8_HUMAN | (Q8NGW8) | | Brain-specific angiogenesis inhibitor (BAI) | *Homo sapiens* (Human) |
| Q8NGX4_HUMAN | (Q8NGX4) | OR10K2 | fragments | *Homo sapiens* (Human) |
| Q8NGX7_HUMAN | (Q8NGX7) | OR10R3P | fragments | *Homo sapiens* (Human) |
| Q8NGY4_HUMAN | (Q8NGY4) | | Olfactory II fam 6/MOR103-105,107-119 | *Homo sapiens* (Human) |
| Q8NGY8_HUMAN | (Q8NGY8) | | fragments | *Homo sapiens* (Human) |
| Q8NH06_HUMAN | (Q8NH06) | | fragments | *Homo sapiens* (Human) |
| Q8NH07_HUMAN | (Q8NH07) | | Olfactory II fam 11/MOR106,121-122 | *Homo sapiens* (Human) |
| Q8NH08_HUMAN | (Q8NH08) | | Olfactory unclassified class II | *Homo sapiens* (Human) |
| Q8NH11_HUMAN | (Q8NH11) | | Olfactory II fam 8/MOR161-171 | *Homo sapiens* (Human) |
| Q8NH13_HUMAN | (Q8NH13) | | Brain-specific angiogenesis inhibitor (BAI) | *Homo sapiens* (Human) |
| Q8NH14_HUMAN | (Q8NH14) | | Olfactory unclassified class II | *Homo sapiens* (Human) |
| Q8NH17_HUMAN | (Q8NH17) | | fragments | *Homo sapiens* (Human) |
| Q8NH20_HUMAN | (Q8NH20) | | fragments | *Homo sapiens* (Human) |
| Q8NH22_HUMAN | (Q8NH22) | DRD5P2 | fragments | *Homo sapiens* (Human) |
| Q8NH23_HUMAN | (Q8NH23) | | fragments | *Homo sapiens* (Human) |
| Q8NH24_HUMAN | (Q8NH24) | | fragments | *Homo sapiens* (Human) |
| Q8NH25_HUMAN | (Q8NH25) | | fragments | *Homo sapiens* (Human) |
| Q8NH27_HUMAN | (Q8NH27) | | fragments | *Homo sapiens* (Human) |
| Q8NH28_HUMAN | (Q8NH28) | | C—X—C Chemokine type 4 | *Homo sapiens* (Human) |
| Q8NH29_HUMAN | (Q8NH29) | | fragments | *Homo sapiens* (Human) |
| Q8NH32_HUMAN | (Q8NH32) | | fragments | *Homo sapiens* (Human) |
| Q8NH33_HUMAN | (Q8NH33) | | fragments | *Homo sapiens* (Human) |
| Q8NH36_HUMAN | (Q8NH36) | | Olfactory II fam 10/MOR263-269 | *Homo sapiens* (Human) |
| Q8NH38_HUMAN | (Q8NH38) | | fragments | *Homo sapiens* (Human) |
| Q8NH44_HUMAN | (Q8NH44) | | Olfactory unclassified class II | *Homo sapiens* (Human) |
| Q8NH45_HUMAN | (Q8NH45) | | fragments | *Homo sapiens* (Human) |
| Q8NH46_HUMAN | (Q8NH46) | | fragments | *Homo sapiens* (Human) |
| Q8NH47_HUMAN | (Q8NH47) | | fragments | *Homo sapiens* (Human) |
| Q8NH52_HUMAN | (Q8NH52) | | fragments | *Homo sapiens* (Human) |
| Q8NH58_HUMAN | (Q8NH58) | | fragments | *Homo sapiens* (Human) |
| Q8NH62_HUMAN | (Q8NH62) | | fragments | *Homo sapiens* (Human) |
| Q8NH65_HUMAN | (Q8NH65) | | fragments | *Homo sapiens* (Human) |
| Q8NH66_HUMAN | (Q8NH66) | | Olfactory I fam 51-52/MOR1-42 | *Homo sapiens* (Human) |
| Q8NH68_HUMAN | (Q8NH68) | | Olfactory I fam 51-52/MOR1-42 | *Homo sapiens* (Human) |
| Q8NH71_HUMAN | (Q8NH71) | | fragments | *Homo sapiens* (Human) |
| Q8NH75_HUMAN | (Q8NH75) | | fragments | *Homo sapiens* (Human) |
| Q8NH77_HUMAN | (Q8NH77) | | Olfactory I fam 51-52/MOR1-42 | *Homo sapiens* (Human) |
| Q8NH78_HUMAN | (Q8NH78) | OR52W1 | Olfactory I fam 51-52/MOR1-42 | *Homo sapiens* (Human) |
| Q8NH80_HUMAN | (Q8NH80) | | Olfactory II fam 10/MOR263-269 | *Homo sapiens* (Human) |
| Q8NH82_HUMAN | (Q8NH82) | | fragments | *Homo sapiens* (Human) |
| Q8NH84_HUMAN | (Q8NH84) | | Olfactory II fam 4/MOR225-248 | *Homo sapiens* (Human) |
| Q8NH86_HUMAN | (Q8NH86) | | Olfactory II fam 5/MOR172-224,249,254 | *Homo sapiens* (Human) |
| Q8NH88_HUMAN | (Q8NH88) | | fragments | *Homo sapiens* (Human) |
| Q8NH91_HUMAN | (Q8NH91) | | Olfactory II fam 5/MOR172-224,249,254 | *Homo sapiens* (Human) |
| Q8NH95_HUMAN | (Q8NH95) | | Olfactory II fam 13/MOR253 | *Homo sapiens* (Human) |
| Q8NH96_HUMAN | (Q8NH96) | | fragments | *Homo sapiens* (Human) |
| Q8NH97_HUMAN | (Q8NH97) | | fragments | *Homo sapiens* (Human) |
| Q8NH98_HUMAN | (Q8NH98) | | fragments | *Homo sapiens* (Human) |
| Q8NH99_HUMAN | (Q8NH99) | | Olfactory II fam 7/MOR139-155 | *Homo sapiens* (Human) |
| Q8NHA0_HUMAN | (Q8NHA0) | | Olfactory II fam 7/MOR139-155 | *Homo sapiens* (Human) |
| Q8NHA1_HUMAN | (Q8NHA1) | | Olfactory II fam 7/MOR139-155 | *Homo sapiens* (Human) |
| Q8NHA2_HUMAN | (Q8NHA2) | | Olfactory II fam 2/MOR256-262,270-285 | *Homo sapiens* (Human) |
| Q8NHA5_HUMAN | (Q8NHA5) | | GABA-B subtype 1 | *Homo sapiens* (Human) |
| Q8NHA6_HUMAN | (Q8NHA6) | | Olfactory II fam 2/MOR256-262,270-285 | *Homo sapiens* (Human) |
| Q8NHA7_HUMAN | (Q8NHA7) | | Olfactory II fam 12/MOR250 | *Homo sapiens* (Human) |
| Q8NHA9_HUMAN | (Q8NHA9) | | Metabotropic glutamate group III | *Homo sapiens* (Human) |
| Q8NHB0_HUMAN | (Q8NHB0) | | fragments | *Homo sapiens* (Human) |
| Q8NHB1_HUMAN | (Q8NHB1) | OR2V1 | fragments | *Homo sapiens* (Human) |
| Q8NHB3_HUMAN | (Q8NHB3) | | fragments | *Homo sapiens* (Human) |
| Q8NHB4_HUMAN | (Q8NHB4) | | Parathyroid hormone | *Homo sapiens* (Human) |
| Q8NHB5_HUMAN | (Q8NHB5) | | Olfactory II fam 7/MOR139-155 | *Homo sapiens* (Human) |
| Q8NHB6_HUMAN | (Q8NHB6) | OR5H14 | fragments | *Homo sapiens* (Human) |
| Q8NHB9_HUMAN | (Q8NHB9) | OR7E85P | fragments | *Homo sapiens* (Human) |
| Q8NHC0_HUMAN | (Q8NHC0) | | fragments | *Homo sapiens* (Human) |
| Q8NHC1_HUMAN | (Q8NHC1) | | Olfactory II fam 7/MOR139-155 | *Homo sapiens* (Human) |
| Q8NHC2_HUMAN | (Q8NHC2) | | fragments | *Homo sapiens* (Human) |
| Q8NHC3_HUMAN | (Q8NHC3) | | fragments | *Homo sapiens* (Human) |
| Q8NHD6_HUMAN | (Q8NHD6) | | fragments | *Homo sapiens* (Human) |
| Q8NI49_HUMAN | (Q8NI49) | HRH3 | fragments | *Homo sapiens* (Human) |
| Q8NI50_HUMAN | (Q8NI50) | HRH3 | fragments | *Homo sapiens* (Human) |
| Q8TAM0_HUMAN | (Q8TAM0) | GPR62 | Putative/unclassified Class A GPCRs | *Homo sapiens* (Human) |
| Q8TAN2_HUMAN | (Q8TAN2) | FZD9 | frizzled Group A (Fz 1&2&4&5&7-9) | *Homo sapiens* (Human) |
| Q8TBK4_HUMAN | (Q8TBK4) | AGTR1 | Angiotensin type 1 | *Homo sapiens* (Human) |
| Q8TD34_HUMAN | (Q8TD34) | OPRL1 | Opioid type X | *Homo sapiens* (Human) |
| Q8TDP5_HUMAN | (Q8TDP5) | CCR3 | fragments | *Homo sapiens* (Human) |
| Q8TDP6_HUMAN | (Q8TDP6) | CCR3 | fragments | *Homo sapiens* (Human) |
| Q8TDP8_HUMAN | (Q8TDP8) | CCR3 | fragments | *Homo sapiens* (Human) |

TABLE D-continued non-limiting list human GPCRs

| | | | | |
|---|---|---|---|---|
| Q8TDS9_HUMAN | (Q8TDS9) | GPCR | Putative/unclassified other | *Homo sapiens* (Human) |
| Q8TDT0_HUMAN | (Q8TDT0) | GPCR | Putative/unclassified other | *Homo sapiens* (Human) |
| Q8TDT1_HUMAN | (Q8TDT1) | GPCR | fragments | *Homo sapiens* (Human) |
| Q8TDT4_HUMAN | (Q8TDT4) | GPCR | Putative/unclassified Class B GPCRs | *Homo sapiens* (Human) |
| Q8TDT7_HUMAN | (Q8TDT7) | GPCR | Putative/unclassified other | *Homo sapiens* (Human) |
| Q8TDT8_HUMAN | (Q8TDT8) | GPCR | frizzled Group A (Fz 1&2&4&5&7-9) | *Homo sapiens* (Human) |
| Q8TDT9_HUMAN | (Q8TDT9) | GPCR | frizzled Group B (Fz 3 & 6) | *Homo sapiens* (Human) |
| Q8TDU0_HUMAN | (Q8TDU0) | GPCR | Putative/unclassified other | *Homo sapiens* (Human) |
| Q8TDU1_HUMAN | (Q8TDU1) | GPCR | calcium-sensing like other | *Homo sapiens* (Human) |
| Q8TDU5_HUMAN | (Q8TDU5) | GPCR | fragments | *Homo sapiens* (Human) |
| Q8TDV1_HUMAN | (Q8TDV1) | GPCR | fragments | *Homo sapiens* (Human) |
| Q8TDV3_HUMAN | (Q8TDV3) | GPCR | fragments | *Homo sapiens* (Human) |
| Q8TEV7_HUMAN | (Q8TEV7) | MTNR1B | fragments | *Homo sapiens* (Human) |
| Q8WUR8_HUMAN | (Q8WUR8) | | fragments | *Homo sapiens* (Human) |
| Q8WW42_HUMAN | (Q8WW42) | | fragments | *Homo sapiens* (Human) |
| Q8WXR5_HUMAN | (Q8WXR5) | CRHR1 | fragments | *Homo sapiens* (Human) |
| Q8WXR6_HUMAN | (Q8WXR6) | CRHR1 | fragments | *Homo sapiens* (Human) |
| Q8WXR7_HUMAN | (Q8WXR7) | CRHR1 | fragments | *Homo sapiens* (Human) |
| Q8WXR9_HUMAN | (Q8WXR9) | FZD6 | frizzled Group B (Fz 3 & 6) | *Homo sapiens* (Human) |
| Q8WXV1_HUMAN | (Q8WXV1) | | fragments | *Homo sapiens* (Human) |
| Q8WXV2_HUMAN | (Q8WXV2) | | fragments | *Homo sapiens* (Human) |
| Q8WXZ9_HUMAN | (Q8WXZ9) | HRH3 | Histamine type 3 | *Homo sapiens* (Human) |
| Q8WY00_HUMAN | (Q8WY00) | HRH3 | fragments | *Homo sapiens* (Human) |
| Q8WY01_HUMAN | (Q8WY01) | HRH3 | Histamine type 3 | *Homo sapiens* (Human) |
| Q8WZ72_HUMAN | (Q8WZ72) | MTNR1A | fragments | *Homo sapiens* (Human) |
| Q8WZ85_HUMAN | (Q8WZ85) | PJCG2 | fragments | *Homo sapiens* (Human) |
| Q8WZ86_HUMAN | (Q8WZ86) | JCG4 | fragments | *Homo sapiens* (Human) |
| Q8WZ87_HUMAN | (Q8WZ87) | PJCG1 | fragments | *Homo sapiens* (Human) |
| Q8WZA6_HUMAN | (Q8WZA6) | OR17-210 | fragments | *Homo sapiens* (Human) |
| Q92492_HUMAN | (Q92492) | CCKBR | CCK type B | *Homo sapiens* (Human) |
| Q93003_HUMAN | (Q93003) | hA2aR | fragments | *Homo sapiens* (Human) |
| Q96CD9_HUMAN | (Q96CD9) | OR7E91P | fragments | *Homo sapiens* (Human) |
| Q96EC3_HUMAN | (Q96EC3) | ADRB2 | fragments | *Homo sapiens* (Human) |
| Q96HT6_HUMAN | (Q96HT6) | | fragments | *Homo sapiens* (Human) |
| Q96KE0_HUMAN | (Q96KE0) | | fragments | *Homo sapiens* (Human) |
| Q96KP5_HUMAN | (Q96KP5) | CCR11 | C-C Chemokine other | *Homo sapiens* (Human) |
| Q96LC6_HUMAN | (Q96LC6) | CCKBR | CCK type B | *Homo sapiens* (Human) |
| Q96LD9_HUMAN | (Q96LD9) | | Histamine type 4 | *Homo sapiens* (Human) |
| Q96N54_HUMAN | (Q96N54) | OR7E5P | fragments | *Homo sapiens* (Human) |
| Q96R43_HUMAN | (Q96R43) | | fragments | *Homo sapiens* (Human) |
| Q96R54_HUMAN | (Q96R54) | | fragments | *Homo sapiens* (Human) |
| Q96RE8_HUMAN | (Q96RE8) | ADRA1A | Alpha Adrenoceptors type 1 | *Homo sapiens* (Human) |
| Q96RG8_HUMAN | (Q96RG8) | CHRM4 | Musc. acetylcholine Vertebrate type 4 | *Homo sapiens* (Human) |
| Q96RG9_HUMAN | (Q96RG9) | CHRM3 | fragments | *Homo sapiens* (Human) |
| Q96RH0_HUMAN | (Q96RH0) | CHRM2 | Musc. acetylcholine Vertebrate type 2 | *Homo sapiens* (Human) |
| Q96RH1_HUMAN | (Q96RH1) | CHRM1 | Musc. acetylcholine Vertebrate type 1 | *Homo sapiens* (Human) |
| Q96T96_HUMAN | (Q96T96) | CCR3 | fragments | *Homo sapiens* (Human) |
| Q99412_HUMAN | (Q99412) | 5-HT7 | fragments | *Homo sapiens* (Human) |
| Q99463_HUMAN | (Q99463) | NPY6R | Neuropeptide Y type 6/7 | *Homo sapiens* (Human) |
| Q99586_HUMAN | (Q99586) | dopamine D4 receptor | fragments | *Homo sapiens* (Human) |
| Q99587_HUMAN | (Q99587) | dopamine D4 receptor | fragments | *Homo sapiens* (Human) |
| Q99642_HUMAN | (Q99642) | | fragments | *Homo sapiens* (Human) |
| Q99997_HUMAN | (Q99997) | | fragments | *Homo sapiens* (Human) |
| Q9BSP0_HUMAN | (Q9BSP0) | | fragments | *Homo sapiens* (Human) |
| Q9BXA0_HUMAN | (Q9BXA0) | | C—X—C Chemokine type 4 | *Homo sapiens* (Human) |
| Q9BXX6_HUMAN | (Q9BXX6) | DRD3 | fragments | *Homo sapiens* (Human) |
| Q9BY61_HUMAN | (Q9BY61) | | fragments | *Homo sapiens* (Human) |
| Q9BYT4_HUMAN | (Q9BYT4) | | fragments | *Homo sapiens* (Human) |
| Q9BYX5_HUMAN | (Q9BYX5) | CCR8 | C-C Chemokine type 8 | *Homo sapiens* (Human) |
| Q9BYY6_HUMAN | (Q9BYY6) | CNR1 | fragments | *Homo sapiens* (Human) |
| Q9BYZ0_HUMAN | (Q9BYZ0) | ADRB2 | fragments | *Homo sapiens* (Human) |
| Q9BZC5_HUMAN | (Q9BZC5) | FKSG35 | fragments | *Homo sapiens* (Human) |
| Q9H011_HUMAN | (Q9H011) | GIR | fragments | *Homo sapiens* (Human) |
| Q9H208_HUMAN | (Q9H208) | | fragments | *Homo sapiens* (Human) |
| Q9H2C6_HUMAN | (Q9H2C6) | | Olfactory I fam 51-52/MOR1-42 | *Homo sapiens* (Human) |
| Q9H2C7_HUMAN | (Q9H2C7) | | Olfactory I fam 51-52/MOR1-42 | *Homo sapiens* (Human) |
| Q9H2L2_HUMAN | (Q9H2L2) | | Putative/unclassified Class A GPCRs | *Homo sapiens* (Human) |
| Q9H342_HUMAN | (Q9H342) | | Olfactory I fam 51-52/MOR1-42 | *Homo sapiens* (Human) |
| Q9H345_HUMAN | (Q9H345) | | Olfactory I fam 51-52/MOR1-42 | *Homo sapiens* (Human) |
| Q9H573_HUMAN | (Q9H573) | OPRM1 | Opioid type M | *Homo sapiens* (Human) |
| Q9H7M4_HUMAN | (Q9H7M4) | FLJ00046 | fragments | *Homo sapiens* (Human) |
| Q9H7Q2_HUMAN | (Q9H7Q2) | FLJ00015 | fragments | *Homo sapiens* (Human) |
| Q9HB44_HUMAN | (Q9HB44) | | fragments | *Homo sapiens* (Human) |
| Q9HB45_HUMAN | (Q9HB45) | | Growth hormone-releasing hormone | *Homo sapiens* (Human) |
| Q9HBV6_HUMAN | (Q9HBV6) | HCRTR1 | Orexin | *Homo sapiens* (Human) |
| Q9HD50_HUMAN | (Q9HD50) | | fragments | *Homo sapiens* (Human) |
| Q9NRB8_HUMAN | (Q9NRB8) | | Lysophosphatidic acid Edg-7 | *Homo sapiens* (Human) |
| Q9NSC9_HUMAN | (Q9NSC9) | OR51A1P | fragments | *Homo sapiens* (Human) |

TABLE D-continued non-limiting list human GPCRs

| | | | | |
|---|---|---|---|---|
| Q9NSM3_HUMAN | (Q9NSM3) | DKFZp434B1272 | fragments | *Homo sapiens* (Human) |
| Q9NYK7_HUMAN | (Q9NYK7) | | CCK type B | *Homo sapiens* (Human) |
| Q9NYN8_HUMAN | (Q9NYN8) | CHEDG1 | Sphingosine 1-phosphate Edg-1 | *Homo sapiens* (Human) |
| Q9NZP3_HUMAN | (Q9NZP3) | HSA12 | fragments | *Homo sapiens* (Human) |
| Q9NZP4_HUMAN | (Q9NZP4) | HSA10 | fragments | *Homo sapiens* (Human) |
| Q9P1R1_HUMAN | (Q9P1R1) | OR7E35P | fragments | *Homo sapiens* (Human) |
| Q9P1T4_HUMAN | (Q9P1T4) | CCR5 | fragments | *Homo sapiens* (Human) |
| Q9P1T5_HUMAN | (Q9P1T5) | CCR5 | fragments | *Homo sapiens* (Human) |
| Q9P1V4_HUMAN | (Q9P1V4) | | fragments | *Homo sapiens* (Human) |
| Q9P2Q4_HUMAN | (Q9P2Q4) | HTR1F | fragments | *Homo sapiens* (Human) |
| Q9P2Q9_HUMAN | (Q9P2Q9) | HTR2A | fragments | *Homo sapiens* (Human) |
| Q9UBJ7_HUMAN | (Q9UBJ7) | CCR5 | fragments | *Homo sapiens* (Human) |
| Q9UBT9_HUMAN | (Q9UBT9) | CCR5 | fragments | *Homo sapiens* (Human) |
| Q9UCW0_HUMAN | (Q9UCW0) | | fragments | *Homo sapiens* (Human) |
| Q9UD23_HUMAN | (Q9UD23) | | Endothelin | *Homo sapiens* (Human) |
| Q9UD67_HUMAN | (Q9UD67) | | fragments | *Homo sapiens* (Human) |
| Q9UDD7_HUMAN | (Q9UDD7) | | fragments | *Homo sapiens* (Human) |
| Q9UDD8_HUMAN | (Q9UDD8) | | fragments | *Homo sapiens* (Human) |
| Q9UDD9_HUMAN | (Q9UDD9) | | fragments | *Homo sapiens* (Human) |
| Q9UDE6_HUMAN | (Q9UDE6) | | Substance K (NK2) | *Homo sapiens* (Human) |
| Q9UEB1_HUMAN | (Q9UEB1) | | fragments | *Homo sapiens* (Human) |
| Q9UJ48_HUMAN | (Q9UJ48) | LPHH1 | fragments | *Homo sapiens* (Human) |
| Q9UJ49_HUMAN | (Q9UJ49) | LPHH1 | fragments | *Homo sapiens* (Human) |
| Q9UJ50_HUMAN | (Q9UJ50) | LPHH1 | fragments | *Homo sapiens* (Human) |
| Q9UJ51_HUMAN | (Q9UJ51) | LPHH1 | fragments | *Homo sapiens* (Human) |
| Q9UJ52_HUMAN | (Q9UJ52) | LPHH1 | fragments | *Homo sapiens* (Human) |
| Q9UL14_HUMAN | (Q9UL14) | OR17-1 | fragments | *Homo sapiens* (Human) |
| Q9UM77_HUMAN | (Q9UM77) | OR1E3P | fragments | *Homo sapiens* (Human) |
| Q9UN23_HUMAN | (Q9UN23) | CCR5 | fragments | *Homo sapiens* (Human) |
| Q9UN24_HUMAN | (Q9UN24) | CCR5 | fragments | *Homo sapiens* (Human) |
| Q9UN25_HUMAN | (Q9UN25) | CCR5 | fragments | *Homo sapiens* (Human) |
| Q9UN26_HUMAN | (Q9UN26) | CCR5 | fragments | *Homo sapiens* (Human) |
| Q9UN27_HUMAN | (Q9UN27) | CCR5 | fragments | *Homo sapiens* (Human) |
| Q9UN28_HUMAN | (Q9UN28) | CCR5 | fragments | *Homo sapiens* (Human) |
| Q9UPG0_HUMAN | (Q9UPG0) | CRAM-B | C-C Chemokine other | *Homo sapiens* (Human) |
| Q9UPJ0_HUMAN | (Q9UPJ0) | | fragments | *Homo sapiens* (Human) |
| Q9UPJ1_HUMAN | (Q9UPJ1) | | fragments | *Homo sapiens* (Human) |
| Q9UQQ6_HUMAN | (Q9UQQ6) | CCR9 | C-C Chemokine type 9 | *Homo sapiens* (Human) |
| Q9UQS0_HUMAN | (Q9UQS0) | | fragments | *Homo sapiens* (Human) |
| QRFPR_HUMAN | (Q96P65) | GPR103 | Orexigenic neuropeptide QRFP | *Homo sapiens* (Human) |
| RAI3_HUMAN | (Q8NFJ5) | GPRC5A | Orphan GPRC5 | *Homo sapiens* (Human) |
| RDC1_HUMAN | (P25106) | CMKOR1 | RDC1 | *Homo sapiens* (Human) |
| RGR_HUMAN | (P47804) | RGR | Rhodopsin Other | *Homo sapiens* (Human) |
| RL3R1_HUMAN | (Q9NSD7) | RXFP3 | Somatostatin- and angiogenin-like peptide | *Homo sapiens* (Human) |
| RL3R2_HUMAN | (Q8TDU9) | RXFP4 | Somatostatin- and angiogenin-like peptide | *Homo sapiens* (Human) |
| RXFP1_HUMAN | (Q9HBX9) | RXFP1 | LGR like (hormone receptors) | *Homo sapiens* (Human) |
| SCTR_HUMAN | (P47872) | SCTR | Secretin | *Homo sapiens* (Human) |
| SMO_HUMAN | (Q99835) | SMO | Smoothened | *Homo sapiens* (Human) |
| SNSR2_HUMAN | (Q8TDE0) | SNSR2 | Mas proto-oncogene & Mas-related (MRGs) | *Homo sapiens* (Human) |
| SNSR3_HUMAN | (Q8TDD9) | SNSR3 | Mas proto-oncogene & Mas-related (MRGs) | *Homo sapiens* (Human) |
| SNSR5_HUMAN | (Q8TDD7) | SNSR5 | Mas proto-oncogene & Mas-related (MRGs) | *Homo sapiens* (Human) |
| SPR1_HUMAN | (Q15743) | GPR68 | GPR | *Homo sapiens* (Human) |
| SSR1_HUMAN | (P30872) | SSTR1 | Somatostatin type 1 | *Homo sapiens* (Human) |
| SSR2_HUMAN | (P30874) | SSTR2 | Somatostatin type 2 | *Homo sapiens* (Human) |
| SSR3_HUMAN | (P32745) | SSTR3 | Somatostatin type 3 | *Homo sapiens* (Human) |
| SSR4_HUMAN | (P31391) | SSTR4 | Somatostatin type 4 | *Homo sapiens* (Human) |
| SSR5_HUMAN | (P35346) | SSTR5 | Somatostatin type 5 | *Homo sapiens* (Human) |
| SUCR1_HUMAN | (Q9BXA5) | SUCNR1 | Purinoceptor P2RY1-4,6,11 GPR91 | *Homo sapiens* (Human) |
| T2R10_HUMAN | (Q9NYW0) | TAS2R10 | Taste receptors T2R | *Homo sapiens* (Human) |
| T2R12_HUMAN | (P59531) | TAS2R12 | Taste receptors T2R | *Homo sapiens* (Human) |
| T2R13_HUMAN | (Q9NYV9) | TAS2R13 | Taste receptors T2R | *Homo sapiens* (Human) |
| T2R14_HUMAN | (Q9NYV8) | TAS2R14 | Taste receptors T2R | *Homo sapiens* (Human) |
| T2R16_HUMAN | (Q9NYV7) | TAS2R16 | Taste receptors T2R | *Homo sapiens* (Human) |
| T2R38_HUMAN | (P59533) | TAS2R38 | Taste receptors T2R | *Homo sapiens* (Human) |
| T2R39_HUMAN | (P59534) | TAS2R39 | Taste receptors T2R | *Homo sapiens* (Human) |
| T2R40_HUMAN | (P59535) | TAS2R40 | Taste receptors T2R | *Homo sapiens* (Human) |
| T2R41_HUMAN | (P59536) | TAS2R41 | Taste receptors T2R | *Homo sapiens* (Human) |
| T2R43_HUMAN | (P59537) | TAS2R43 | Taste receptors T2R | *Homo sapiens* (Human) |
| T2R44_HUMAN | (P59538) | TAS2R44 | Taste receptors T2R | *Homo sapiens* (Human) |
| T2R45_HUMAN | (P59539) | TAS2R45 | Taste receptors T2R | *Homo sapiens* (Human) |
| T2R46_HUMAN | (P59540) | TAS2R46 | Taste receptors T2R | *Homo sapiens* (Human) |
| T2R47_HUMAN | (P59541) | TAS2R47 | Taste receptors T2R | *Homo sapiens* (Human) |
| T2R48_HUMAN | (P59542) | TAS2R48 | Taste receptors T2R | *Homo sapiens* (Human) |
| T2R49_HUMAN | (P59543) | TAS2R49 | Taste receptors T2R | *Homo sapiens* (Human) |
| T2R50_HUMAN | (P59544) | TAS2R50 | Taste receptors T2R | *Homo sapiens* (Human) |
| T2R55_HUMAN | (Q7RTR8) | TAS2R55 | Taste receptors T2R | *Homo sapiens* (Human) |
| T2R60_HUMAN | (P59551) | TAS2R60 | Taste receptors T2R | *Homo sapiens* (Human) |
| TA2R1_HUMAN | (Q9NYW7) | TAS2R1 | Taste receptors T2R | *Homo sapiens* (Human) |

TABLE D-continued non-limiting list human GPCRs

| | | | | |
|---|---|---|---|---|
| TA2R3_HUMAN | (Q9NYW6) | TAS2R3 | Taste receptors T2R | Homo sapiens (Human) |
| TA2R4_HUMAN | (Q9NYW5) | TAS2R4 | Taste receptors T2R | Homo sapiens (Human) |
| TA2R5_HUMAN | (Q9NYW4) | TAS2R5 | Taste receptors T2R | Homo sapiens (Human) |
| TA2R7_HUMAN | (Q9NYW3) | TAS2R7 | Taste receptors T2R | Homo sapiens (Human) |
| TA2R8_HUMAN | (Q9NYW2) | TAS2R8 | Taste receptors T2R | Homo sapiens (Human) |
| TA2R9_HUMAN | (Q9NYW1) | TAS2R9 | Taste receptors T2R | Homo sapiens (Human) |
| TA2R_HUMAN | (P21731) | TBXA2R | Thromboxane | Homo sapiens (Human) |
| TAAR1_HUMAN | (Q96RJ0) | TAAR1 | Trace amine | Homo sapiens (Human) |
| TAAR2_HUMAN | (Q9P1P5) | TAAR2 | Trace amine | Homo sapiens (Human) |
| TAAR3_HUMAN | (Q9P1P4) | TAAR3 | Trace amine | Homo sapiens (Human) |
| TAAR5_HUMAN | (O14804) | TAAR5 | Trace amine | Homo sapiens (Human) |
| TAAR6_HUMAN | (Q96RI8) | TAAR6 | Trace amine | Homo sapiens (Human) |
| TAAR8_HUMAN | (Q969N4) | TAAR8 | Trace amine | Homo sapiens (Human) |
| TAAR9_HUMAN | (Q96RI9) | TAAR9 | Trace amine | Homo sapiens (Human) |
| TRFR_HUMAN | (P34981) | TRHR | Thyrotropin-releasing hormone | Homo sapiens (Human) |
| TS1R1_HUMAN | (Q7RTX1) | TAS1R1 | Taste receptors (T1R) | Homo sapiens (Human) |
| TS1R2_HUMAN | (Q8TE23) | TAS1R2 | Taste receptors (T1R) | Homo sapiens (Human) |
| TS1R3_HUMAN | (Q7RTX0) | TAS1R3 | Taste receptors (T1R) | Homo sapiens (Human) |
| TSHR_HUMAN | (P16473) | TSHR | Thyrotropin | Homo sapiens (Human) |
| UR2R_HUMAN | (Q9UKP6) | UTS2R | Urotensin II | Homo sapiens (Human) |
| V1AR_HUMAN | (P37288) | AVPR1A | Vasopressin type 1 | Homo sapiens (Human) |
| V1BR_HUMAN | (P47901) | AVPR1B | Vasopressin type 1 | Homo sapiens (Human) |
| V2R_HUMAN | (P30518) | AVPR2 | Vasopressin type 2 | Homo sapiens (Human) |
| VIPR1_HUMAN | (P32241) | VIPR1 | Vasoactive intestinal polypeptide | Homo sapiens (Human) |
| VIPR2_HUMAN | (P41587) | VIPR2 | Vasoactive intestinal polypeptide | Homo sapiens (Human) |
| VN1R1_HUMAN | (Q9GZP7) | VN1R1 | Vomeronasal receptors V1RL | Homo sapiens (Human) |
| VN1R2_HUMAN | (Q8NFZ6) | VN1R2 | Vomeronasal receptors V1RL | Homo sapiens (Human) |
| VN1R3_HUMAN | (Q9BXE9) | VN1R3 | Vomeronasal receptors V1RL | Homo sapiens (Human) |
| VN1R4_HUMAN | (Q7Z5H5) | VN1R4 | Vomeronasal receptors V1RL | Homo sapiens (Human) |
| VN1R5_HUMAN | (Q7Z5H4) | VN1R5 | Vomeronasal receptors others | Homo sapiens (Human) |
| XCR1_HUMAN | (P46094) | XCR1 | XC Chemokine | Homo sapiens (Human) |

TABLE E

CDR sequence comparison of CB1R binders

| Cluster number | sequence length | Nanobody name | ID | 422-LGPMP6_C9 2 | 414-LGPMP5_A7 3 | 421-LGPMP6_C7 4 | 430-LGPMP6_H12 5 | 419-LGPMP5_G11 6 |
|---|---|---|---|---|---|---|---|---|
| 4 | 119 aa | 421-LGPMP6_C7 | 4 | 93.38 | 96.67 | | 3 | 3 |
| | | 430-LGPMP6_H12 | 5 | 96.67 | 93.33 | 90.00 | | 1 |
| | | 419-LGPMP5_G11 | 6 | 96.67 | 93.33 | 90.00 | 96.67 | |
| | | 425-LGPMP6_D12 | 7 | 83.33 | 86.67 | 90.00 | 83.33 | 86.67 |
| | | 429-LGPMP6_H9 | 8 | 76.67 | 80.00 | 83.33 | 76.67 | 76.67 |
| | | 517-GF12 | 9 | 80.00 | 83.33 | 80.00 | 76.67 | 76.67 |
| | | 415-LGPMP5_B6 | 10 | 96.67 | 93.33 | 90.00 | 93.33 | 93.33 |
| | | 423-LGPMP6_D2 | 11 | 96.67 | 93.33 | 90.00 | 93.33 | 93.33 |
| | | 416-LGPMP5_B9 | 12 | 80.00 | 83.33 | 80.00 | 76.67 | 76.67 |
| | | 420-LGPMP6_B7 | 13 | 93.33 | 90.00 | 86.67 | 90.00 | 90.00 |
| | | 426-LGPMP6_E11 | 14 | 90.00 | 86.67 | 86.67 | 86.67 | 86.67 |
| | | 427-LGPMP6_F12 | 15 | 80.00 | 80.00 | 76.67 | 80.00 | 80.00 |
| 2 | 124 aa | 518-5D12 | 16 | 51.43 | 51.43 | 48.57 | 51.43 | 54.29 |
| 1 | 127 aa | 417-LGPMP5_D12 | 17 | 30.00 | 27.50 | 25.00 | 30.00 | 32.50 |
| 3 | 120 aa | 413-LGPMP5_A6 | 18 | 25.71 | 25.71 | 22.86 | 25.71 | 25.71 |
| | | 428-LGPMP6_H4 | 19 | 25.71 | 25.71 | 22.86 | 25.71 | 25.71 |
| 5 | 117 aa | 424-LGPMP6_D5 | 20 | 14.71 | 14.71 | 11.76 | 14.71 | 14.71 |
| | | | | | | % identity | | |

| Cluster number | sequence length | Nanobody name | ID | 425-LGPMP6_D12 7 | 429-LGPMP6_H9 8 | 517-GF12 9 | 415-LGPMP5_B6 10 | 423-LGPMP6_D2 11 |
|---|---|---|---|---|---|---|---|---|
| 4 | 119 aa | 421-LGPMP6_C7 | 4 | 3 | 5 | 6 | 3 | 3 |
| | | 430-LGPMP6_H12 | 5 | 5 | 7 | 7 | 2 | 2 |
| | | 419-LGPMP5_G11 | 6 | 4 | 7 | 7 | 2 | 2 |
| | | 425-LGPMP6_D12 | 7 | | 5 | 5 | 6 | 6 |
| | | 429-LGPMP6_H9 | 8 | 83.33 | | 7 | 7 | 7 |
| | | 517-GF12 | 9 | 83.33 | 76.67 | | 7 | 7 |
| | | 415-LGPMP5_B6 | 10 | 80.00 | 76.67 | 76.67 | | |
| | | 423-LGPMP6_D2 | 11 | 80.00 | 76.67 | 76.67 | 100.00 | |
| | | 416-LGPMP5_B9 | 12 | 80.00 | 76.67 | 90.00 | 80.00 | 80.00 |
| | | 420-LGPMP6_B7 | 13 | 76.67 | 73.33 | 73.33 | 93.33 | 93.33 |

TABLE E-continued

CDR sequence comparison of CB1R binders

| Cluster number | sequence length | Nanobody name | ID | | | | | |
|---|---|---|---|---|---|---|---|---|
| | | 426-LGPMP6_E11 | 14 | 76.67 | 73.33 | 70.00 | 90.00 | 90.00 |
| | | 427-LGPMP6_F12 | 15 | 76.67 | 73.33 | 83.33 | 83.33 | 83.33 |
| 2 | 124 aa | 518-5D12 | 16 | 45.71 | 42.86 | 42.86 | 48.57 | 48.57 |
| 1 | 127 aa | 417-LGPMP5_D12 | 17 | 25.00 | 22.50 | 25.00 | 27.50 | 27.50 |
| 3 | 120 aa | 413-LGPMP5_A6 | 18 | 20.00 | 20.00 | 22.86 | 22.86 | 22.86 |
| | | 428-LGPMP6_H4 | 19 | 20.00 | 20.00 | 22.86 | 22.86 | 22.86 |
| 5 | 117 aa | 424-LGPMP6_D5 | 20 | 8.82 | 14.71 | 8.82 | 14.71 | 14.71 |
| | | | | | | % identity | | |

| Cluster number | sequence length | Nanobody name | ID | 416-LGPMP5_B9 12 | 420-LGPMP6_B7 13 | 426-LGPMP6_E11 14 | 427-LGPMP6_F12 15 | 518-5D12 16 |
|---|---|---|---|---|---|---|---|---|
| 4 | 119 aa | 421-LGPMP6_C7 | 4 | 6 | 4 | 4 | 7 | 18 |
| | | 430-LGPMP6_H12 | 5 | 7 | 3 | 4 | 6 | 17 |
| | | 419-LGPMP5_G11 | 6 | 7 | 3 | 4 | 6 | 16 |
| | | 425-LGPMP6_D12 | 7 | 6 | 7 | 7 | 7 | 19 |
| | | 429-LGPMP6_H9 | 8 | 7 | 8 | 8 | 8 | 20 |
| | | 517-GF12 | 9 | 3 | 8 | 9 | 5 | 20 |
| | | 415-LGPMP5_B6 | 10 | 6 | 2 | 3 | 5 | 18 |
| | | 423-LGPMP6_D2 | 11 | 5 | 2 | 3 | 5 | 18 |
| | | 416-LGPMP5_B9 | 12 | | 7 | 8 | 4 | 21 |
| | | 420-LGPMP6_B7 | 13 | 76.67 | | 1 | 7 | 19 |
| | | 426-LGPMP6_E11 | 14 | 73.33 | 96.67 | | 8 | 20 |
| | | 427-LGPMP6_F12 | 15 | 86.67 | 76.67 | 73.33 | | 20 |
| 2 | 124 aa | 518-5D12 | 16 | 40.00 | 45.71 | 42.86 | 42.86 | |
| 1 | 127 aa | 417-LGPMP5_D12 | 17 | 22.50 | 25.00 | 22.50 | 25.00 | 42.50 |
| 3 | 120 aa | 413-LGPMP5_A6 | 18 | 20.00 | 22.86 | 20.00 | 22.86 | 22.50 |
| | | 428-LGPMP6_H4 | 19 | 20.00 | 22.86 | 20.00 | 22.86 | 22.50 |
| 5 | 117 aa | 424-LGPMP6_D5 | 20 | 8.82 | 14.71 | 11.76 | 14.71 | 16.22 |
| | | | | | | % identity | | |

| Cluster number | sequence length | Nanobody name | ID | 417-LGPMP_D12 17 | 413-LGPMP5_A6 18 | 428-LGPMP6_H4 19 | 424-LGPMP6-D5 20 | |
|---|---|---|---|---|---|---|---|---|
| 4 | 119 aa | 421-LGPMP6_C7 | 4 | 30 | 27 | 27 | 30 | differences (# residues) |
| | | 430-LGPMP6_H12 | 5 | 28 | 26 | 26 | 29 | |
| | | 419-LGPMP5_G11 | 6 | 27 | 26 | 26 | 29 | |
| | | 425-LGPMP6_D12 | 7 | 30 | 28 | 28 | 31 | |
| | | 429-LGPMP6_H9 | 8 | 31 | 28 | 28 | 29 | |
| | | 517-GF12 | 9 | 30 | 27 | 27 | 31 | |
| | | 415-LGPMP5_B6 | 10 | 29 | 27 | 27 | 29 | |
| | | 423-LGPMP6_D2 | 11 | 29 | 27 | 27 | 29 | |
| | | 416-LGPMP5_B9 | 12 | 31 | 28 | 28 | 31 | |
| | | 420-LGPMP6_B7 | 13 | 30 | 27 | 27 | 29 | |
| | | 426-LGPMP6_E11 | 14 | 31 | 28 | 28 | 30 | |
| | | 427-LGPMP6_F12 | 15 | 30 | 27 | 27 | 29 | |
| 2 | 124 aa | 518-5D12 | 16 | 23 | 31 | 31 | 31 | |
| 1 | 127 aa | 417-LGPMP5_D12 | 17 | | 31 | 31 | 33 | |
| 3 | 120 aa | 413-LGPMP5_A6 | 18 | 22.50 | | 0 | 28 | |
| | | 428-LGPMP6_H4 | 19 | 22.50 | 100.00 | | 28 | |
| 5 | 117 aa | 424-LGPMP6_D5 | 20 | 15.38 | 22.22 | 22.22 | | |
| | | | | | | % identity | | |

TABLE F

CDR sequence comparison of PTHR1 binders

| Cluster number | sequence length | Nanobody name | ID | 436-PMPLG22-B12 5 | 447-PMPLG26-C5 6 | 440-PMPLG23-E12 7 | 442-PMPLG23-H9 8 | 439-PMPLG23-C1 9 |
|---|---|---|---|---|---|---|---|---|
| 7 | 199 aa | 449-PMPLG26-E4 | 2 | 10 | 9 | 26 | 26 | 26 |
| | | 450-PMPLG26-E6 | 3 | 11 | 9 | 26 | 26 | 26 |
| | | 446-PMPLG26-C4 | 4 | 10 | 9 | 26 | 26 | 26 |
| 4 | 120 aa | 436-PMPLG22-B12 | 5 | | 4 | 25 | 25 | 25 |
| | | 447-PMPLG26-C5 | 6 | 87.10 | | 25 | 25 | 25 |
| 14 | 115 aa | 440-PMPLG23-E12 | 7 | 19.35 | 19.35 | | 0 | 0 |
| | | 442-PMPLG23-H9 | 8 | 19.35 | 19.35 | 100.00 | | 0 |
| | | 439-PMPLG23-G1 | 9 | 19.35 | 19.35 | 100.00 | 100.00 | |

TABLE F-continued

CDR sequence comparison of PTHR1 binders

| 11 | 117 aa | 441-PMPLG23-F2 | 10 | 41.94 | 38.71 | 35.71 | 35.71 | 35.71 |
|----|--------|----------------|----|-------|-------|-------|-------|-------|
| 10 | 117 aa | 435-PMPLG22-B11 | 11 | 21.21 | 18.18 | 22.58 | 22.58 | 22.58 |
|    |        | 444-PMPLG26-A6 | 12 | 21.21 | 18.18 | 22.58 | 22.58 | 22.58 |
|    |        | 445-PMPLG26-B6 | 13 | 21.21 | 18.18 | 22.58 | 22.58 | 22.58 |
|    |        | 437-PMPLG22-C3 | 14 | 24.24 | 21.21 | 22.58 | 22.58 | 22.58 |
| 12 | 117 aa | 448-PMPLG26-D12 | 15 | 36.36 | 30.30 | 22.58 | 22.58 | 22.58 |
| 13 | 116 aa | 452-PMPLG26-G11 | 16 | 18.18 | 18.18 | 22.58 | 22.58 | 22.58 |
| 8  | 118 aa | 443-PMPLG26-A2 | 17 | 28.12 | 28.12 | 18.75 | 18.75 | 18.75 |
| 9  | 117 aa | 434-PMPLG22-B7 | 18 | 17.14 | 14.29 | 18.18 | 18.18 | 18.18 |
| 2  | 122 aa | 431-PMPLG22-A2 | 19 | 24.24 | 21.21 | 24.24 | 24.24 | 24.24 |
| 5  | 120 aa | 438-PMPLG23-A3 | 20 | 24.24 | 21.21 | 24.24 | 24.24 | 24.24 |
| 3  | 120 aa | 433-PMPLG22-A9 | 21 | 18.18 | 15.15 | 15.62 | 15.62 | 15.62 |
| 6  | 120 aa | 453-PMPLG26-H11 | 22 | 18.92 | 18.92 | 13.89 | 13.89 | 13.89 |
| 1  | 125 aa | 451-PMPLG26-F2 | 23 | 25    | 25    | 16.67 | 16.67 | 16.67 |
|    |        |                |    |       |       | % identity | | |

| Cluster number | sequence length | Nanobody name | ID | 441-PMPLG23-F2 10 | 435-PMPLG22-B11 11 | 444-PMPLG26-A6 12 | 445-PMPLG26-B6 13 | 437-PMPLG22-C3 14 |
|---|---|---|---|---|---|---|---|---|
| 7 | 199 aa | 449-PMPLG26-E4 | 2 | 22 | 28 | 28 | 28 | 27 |
|   |        | 450-PMPLG26-E6 | 3 | 22 | 28 | 28 | 28 | 27 |
|   |        | 446-PMPLG26-C4 | 4 | 22 | 28 | 28 | 28 | 27 |
| 4 | 120 aa | 436-PMPLG22-B12 | 5 | 18 | 26 | 26 | 26 | 25 |
|   |        | 447-PMPLG26-C5 | 6 | 19 | 27 | 27 | 27 | 26 |
| 14 | 115 aa | 440-PMPLG23-E12 | 7 | 18 | 24 | 24 | 24 | 24 |
|   |        | 442-PMPLG23-H9 | 8 | 18 | 24 | 24 | 24 | 24 |
|   |        | 439-PMPLG23-G1 | 9 | 18 | 24 | 24 | 24 | 24 |
| 11 | 117 aa | 441-PMPLG23-F2 | 10 |    | 25 | 25 | 25 | 25 |
| 10 | 117 aa | 435-PMPLG22-B11 | 11 | 19.35 |   | 0 | 1 | 5 |
|   |        | 444-PMPLG26-A6 | 12 | 19.35 | 100.00 |   | 1 | 5 |
|   |        | 445-PMPLG26-B6 | 13 | 19.35 | 96.43 | 96.43 |   | 5 |
|   |        | 437-PMPLG22-C3 | 14 | 19.35 | 82.14 | 82.14 | 82.14 |   |
| 12 | 117 aa | 448-PMPLG26-D12 | 15 | 29.03 | 31.03 | 31.03 | 31.03 | 34.48 |
| 13 | 116 aa | 452-PMPLG26-G11 | 16 | 19.35 | 20.69 | 26.69 | 20.69 | 24.14 |
| 8 | 118 aa | 443-PMPLG26-A2 | 17 | 31.25 | 19.35 | 19.35 | 19.35 | 16.13 |
| 9 | 117 aa | 434-PMPLG22-B7 | 18 | 21.21 | 13.33 | 13.33 | 16.67 | 10.00 |
| 2 | 122 aa | 431-PMPLG22-A2 | 19 | 24.24 | 21.21 | 21.21 | 21.21 | 21.21 |
| 5 | 120 aa | 438-PMPLG23-A3 | 20 | 39.30 | 25.00 | 25.00 | 25.00 | 25.00 |
| 3 | 120 aa | 433-PMPLG22-A9 | 21 | 18.18 | 12.12 | 12.12 | 12.12 | 12.12 |
| 6 | 120 aa | 453-PMPLG26-H11 | 22 | 19.44 | 32.35 | 32.35 | 32.35 | 26.47 |
| 1 | 125 aa | 451-PMPLG26-F2 | 23 | 22.22 | 16.22 | 16.22 | 16.22 | 13.51 |
|   |        |                |    |       |       | % identity | | |

| Cluster number | sequence length | Nanobody name | ID | 448-PMPLG26-D12 15 | 452-PMPLG26-G11 16 | 443-PMPLG26-A2 17 | 434-PMPLG22-B7 18 | 431-PMPLG22-A2 19 |
|---|---|---|---|---|---|---|---|---|
| 7 | 199 aa | 449-PMPLG26-E4 | 2 | 25 | 28 | 26 | 31 | 27 |
|   |        | 450-PMPLG26-E6 | 3 | 25 | 28 | 26 | 31 | 27 |
|   |        | 446-PMPLG26-C4 | 4 | 25 | 28 | 25 | 31 | 27 |
| 4 | 120 aa | 436-PMPLG22-B12 | 5 | 21 | 27 | 23 | 29 | 25 |
|   |        | 447-PMPLG26-C5 | 6 | 23 | 27 | 23 | 30 | 26 |
| 14 | 115 aa | 440-PMPLG23-E12 | 7 | 24 | 24 | 26 | 27 | 25 |
|   |        | 442-PMPLG23-H9 | 8 | 24 | 24 | 26 | 27 | 25 |
|   |        | 439-PMPLG23-G1 | 9 | 24 | 24 | 26 | 27 | 25 |
| 11 | 117 aa | 441-PMPLG23-F2 | 10 | 22 | 25 | 22 | 26 | 25 |
| 10 | 117 aa | 435-PMPLG22-B11 | 11 | 20 | 23 | 25 | 26 | 26 |
|   |        | 444-PMPLG26-A6 | 12 | 20 | 23 | 25 | 26 | 26 |
|   |        | 445-PMPLG26-B6 | 13 | 20 | 23 | 25 | 25 | 26 |
|   |        | 437-PMPLG22-C3 | 14 | 19 | 22 | 26 | 27 | 26 |
| 12 | 117 aa | 448-PMPLG26-D12 | 15 |    | 19 | 23 | 26 | 23 |
| 13 | 116 aa | 452-PMPLG26-G11 | 16 | 32.14 |   | 28 | 27 | 26 |
| 8 | 118 aa | 443-PMPLG26-A2 | 17 | 25.81 | 9.68 |   | 22 | 24 |
| 9 | 117 aa | 434-PMPLG22-B7 | 18 | 16.13 | 12.90 | 33.33 |   | 26 |
| 2 | 122 aa | 431-PMPLG22-A2 | 19 | 30.30 | 21.21 | 27.27 | 25.71 |   |
| 5 | 120 aa | 438-PMPLG23-A3 | 20 | 31.25 | 21.88 | 35.48 | 23.53 | 42.42 |
| 3 | 120 aa | 433-PMPLG22-A9 | 21 | 18.75 | 15.62 | 18.18 | 20 | 42.42 |
| 6 | 120 aa | 453-PMPLG26-H11 | 22 | 17.65 | 11.76 | 20.59 | 11.76 | 13.51 |
| 1 | 125 aa | 451-PMPLG26-F2 | 23 | 27.03 | 10.81 | 30.55 | 17.95 | 37.84 |
|   |        |                |    |       |       | % identity | | |

TABLE F-continued

CDR sequence comparison of PTHR1 binders

| Cluster number | sequence length | Nanobody name | ID | 438-PMPLG23-A3 20 | 433-PMPLG22-A9 21 | 453-PMPLG26-H11 22 | 451-PMPLG26-F2 23 | |
|---|---|---|---|---|---|---|---|---|
| 7 | 199 aa | 449-PMPLG26-E4 | 2 | 26 | 27 | 32 | 30 | differences |
|  |  | 450-PMPLG26-E6 | 3 | 26 | 27 | 32 | 30 | (# |
|  |  | 446-PMPLG26-C4 | 4 | 26 | 27 | 31 | 30 | residues) |
| 4 | 120 aa | 436-PMPLG22-B12 | 5 | 25 | 27 | 30 | 27 | |
|  |  | 447-PMPLG26-C5 | 6 | 26 | 28 | 30 | 27 | |
| 14 | 115 aa | 440-PMPLG23-E12 | 7 | 25 | 27 | 31 | 30 | |
|  |  | 442-PMPLG23-H9 | 8 | 25 | 27 | 31 | 30 | |
|  |  | 439-PMPLG23-G1 | 9 | 25 | 27 | 31 | 30 | |
| 11 | 117 aa | 441-PMPLG23-F2 | 10 | 23 | 27 | 29 | 28 | |
| 10 | 117 aa | 435-PMPLG22-B11 | 11 | 24 | 29 | 23 | 31 | |
|  |  | 444-PMPLG26-A6 | 12 | 24 | 29 | 23 | 31 | |
|  |  | 445-PMPLG26-B6 | 13 | 24 | 29 | 23 | 31 | |
|  |  | 437-PMPLG22-C3 | 14 | 24 | 29 | 25 | 32 | |
| 12 | 117 aa | 448-PMPLG26-D12 | 15 | 22 | 26 | 28 | 27 | |
| 13 | 116 aa | 452-PMPLG26-G11 | 16 | 25 | 27 | 30 | 33 | |
| 8 | 118 aa | 443-PMPLG26-A2 | 17 | 20 | 27 | 27 | 25 | |
| 9 | 117 aa | 434-PMPLG22-B7 | 18 | 26 | 28 | 30 | 32 | |
| 2 | 122 aa | 431-PMPLG22-A2 | 19 | 19 | 19 | 32 | 23 | |
| 5 | 120 aa | 438-PMPLG23-A3 | 20 |  | 19 | 28 | 23 | |
| 3 | 120 aa | 433-PMPLG22-A9 | 21 | 42.42 |  | 33 | 26 | |
| 6 | 120 aa | 453-PMPLG26-H11 | 22 | 20 | 10.81 |  | 36 | |
| 1 | 125 aa | 451-PMPLG26-F2 | 23 | 37.84 | 29.73 | 12.2 |  | |
|  |  |  |  |  |  | % identity |  | |

TABLE G

CDR sequence comparison of MCR4 binders

| Cluster number | sequence length | Nanobody name | ID | 520-59-8A 1 | 521-58-4H 2 | 519-60-11B 3 | 522-60-5E 4 | 525-60-10E 5 | 523-60-4A 6 | 524-58-10H 7 | |
|---|---|---|---|---|---|---|---|---|---|---|---|
| 3 | 123 aa | 520-59-8A | 1 |  | 8 | 12 | 15 | 16 | 17 | 31 | differences |
| 4 | 123 aa | 521-58-4H | 2 | 76.47 |  | 12 | 14 | 15 | 17 | 30 | (# |
| 2 | 124 aa | 519-60-11B | 3 | 65.71 | 65.71 |  | 13 | 13 | 16 | 32 | residues) |
| 5 | 122 aa | 522-60-5E | 4 | 55.88 | 58.82 | 62.86 |  | 6 | 6 | 30 | |
|  |  | 525-60-10E | 5 | 52.94 | 55.88 | 62.86 | 81.82 |  | 10 | 31 | |
|  |  | 523-60-4A | 6 | 50.00 | 50.00 | 54.29 | 81.82 | 69.70 |  | 31 | |
| 1 | 134 aa | 524-58-10H | 7 | 31.11 | 33.33 | 30.43 | 33.33 | 31.11 | 31.11 |  | |
|  |  |  |  |  |  |  |  | % identity |  |  | |

TABLE H

CDR sequence similarity between 238D2 and 238D4

|  | % identity | Residue differences |
|---|---|---|
| CDR sequence 238D2 versus 238D4 | 37.5 | 25 |

TABLE I

Receptor affinity ($K_i$), relative potency and maximal displacement of [$^{125}$I]-CXCL12 by bivalent Nanobodies in comparison to their monovalent counterparts. The experiments were performed on membranes from HEK293T cells transiently expressing CXCR4. Data were shown as means ± S.E.M. The number of experiments is given as n.

| Clone name | Construct name | Displacem. (%) | $K_i$ (nM) | Rel. potency | N |
|---|---|---|---|---|---|
| L9 | 238D2-10GS-238D2 | 95 ± 5 | 0.69 | 14[a] | 3 |
| L13 | 238D4-20GS-238D4 | 96 ± 5 | 1.00 | 4.4[b] | 4 |
| L3 | 238D2-15GS-238D4 | 92 ± 6 | 0.35 | 28[a]/17[b] | 3 |
| L8 | 238D2-20GS-238D4 | 103 ± 4 | 0.36 | 27[a]/17[b] | 3 |
|  | 238D2 + 238D4(1:1) | 92 ± 11 | 10.0 | 1.0[a]/0.6[b] | 3 |

[a]Potency relative to those of monovalent 238D2.
[b]Potency relative to those of monovalent 238D4.

TABLE J

Preferred CXCR4 polypeptide or compound sequences.

| Construct name (clone) | Amino acid sequence | SEQ ID NO: |
|---|---|---|
| 238D2 | EVQLVESGGGLVQTGGSLRLSCAASGFTFSSYAMSWVRQAPGKGLEWVSGIKSSGDSTRYAGSVKGRFTISRDNAKNMLYLQMYSLKPEDTAVYYCAKSRVSRTGLYTYDNRGQGTQVTVSS | 526 |
| 238D4 | EVQLMESGGGLVQAGGSLRLSCAASGRTFNNYAMGWFRRAPGKEREFVAAITRSGVRSGVSAIYGDSVKDRFTISRDNAKNTLYLQMNSLKPEDTAVYTCAASAIGSGALRRFEYDYSGQGTQVTVSS | 527 |
| 238D2-10GS-238D2 (L9) | EVQLVESGGGLVQTGGSLRLSCAASGFTFSSYAMSWVRQAPGKGLEWVSGIKSSGDSTRYAGSVKGRFTISRDNAKNMLYLQMYSLKPEDTAVYYCAKSRVSRTGLYTYDNRGQGTQVTVSSGGGGSGGGGSEVQLVESGGGLVQTGGSLRLSCAASGFTFSSYAMSWVRQAPGKGLEWVSGIKSSGDSTRYAGSVKGRFTISRDNAKNMLYLQMYSLKPEDTAVYYCAKSRVSRTGLYTYDNRGQGTQVTVSS | 528 |
| 238D4-20GS-238D4 (L13) | EVQLMESGGGLVQAGGSLRLSCAASGRTFNNYAMGWFRRAPGKEREFVAAITRSGVRSGVSAIYGDSVKDRFTISRDNAKNTLYLQMNSLKPEDTAVYTCAASAIGSGALRRFEYDYSGQGTQVTVSSGGGGSGGGGSGGGGSGGGGSEVQLMESGGGLVQAGGSLRLSCAASGRTFNNYAMGWFRRAPGKEREFVAAITRSGVRSGVSAIYGDSVKDRFTISRDNAKNTLYLQMNSLKPEDTAVYTCAASAIGSGALRRFEYDYSGQGTQVTVSS | 529 |
| 238D2-15GS-238D4 (L3) | EVQLVESGGGLVQTGGSLRLSCAASGFTFSSYAMSWVRQAPGKGLEWVSGIKSSGDSTRYAGSVKGRFTISRDNAKNMLYLQMYSLKPEDTAVYYCAKSRVSRTGLYTYDNRGQGTQVTVSSGGGGSGGGGSGGGGSEVQLMESGGGLVQAGGSLRLSCAASGRTFNNYAMGWFRRAPGKEREFVAAITRSGVRSGVSAIYGDSVKDRFTISRDNAKNTLYLQMNSLKPEDTAVYTCAASAIGSGALRRFEYDYSGQGTQVTVSS | 530 |
| 238D2-20GS-238D4 (L8) | EVQLVESGGGLVQTGGSLRLSCAASGFTFSSYAMSWVRQAPGKGLEWVSGIKSSGDSTRYAGSVKGRFTISRDNAKNMLYLQMYSLKPEDTAVYYCAKSRVSRTGLYTYDNRGQGTQVTVSSGGGGSGGGGSGGGGSGGGGSEVQLMESGGGLVQAGGSLRLSCAASGRTFNNYAMGWFRRAPGKEREFVAAITRSGVRSGVSAIYGDSVKDRFTISRDNAKNTLYLQMNSLKPEDTAVYTCAASAIGSGALRRFEYDYSGQGTQVTVSS | 531 |

TABLE K

Optimization of bivalent and trivalent Nanobodies

| Clones | construct | β-arrestin recruitment [IC50] |
|---|---|---|
| 038 | 14G03-35GS-01C10-9GS-ALB8 | 19.38 |
| 085 | 14G03-35GS-01C10-35GS-ALB8 | 22.31 |
| 052 | 01C10-35GS-14G03-9GS-ALB8 | 86.8 |
| 055 | 01C10-35GS-01C10-9GS-ALB8 | no antagonism |
| 093 | 01C10-35GS-01C10-35GS-ALB8 | no antagonism |
| 072 | 14G03-9GS-ALB8 | inefficient antagonism |
| 082 | 14G03-30GS-ALB8 | inefficient antagonism |
|  | 01C10 | No data |
| Mab 8F11 |  | 34.8 |

TABLE L

Inhibition of β-arrestin recruitment of CXCR7 Nanobodies

| Clones | construct | % inhibition of β-arrestin recruitment |
|---|---|---|
| 038 | 14G03-35GS-01C10-9GS-ALB8 | 94.1 |
| 052 | 01C10-35GS-14G03-9GS-ALB8 | 93.7 |
| 021 | 08A10-35GS-01C10-9GS-ALB8 | 89.5 |
| 023 | 08A05-35GS-01C10-9GS-ALB8 | 92.8 |
| 049 | 01C10-35GS-08A05-9GS-ALB8 | 89.3 |
| 025 | 07C03-35GS-07C03-9GS-ALB8 | 54.5 |
| 035 | 14G03-35GS-14G03-9GS-ALB8 | 24.9 |
| 055 | 01C10-35GS-01C10-9GS-ALB8 | −8.5 |

TABLE M

Preferred CXCR7 polypeptide or compound sequences.

| Construct name (clone) | Amino acid sequence | SEQ ID NO: |
|---|---|---|
| 14G03-35GS-01C10-9GS-ALB8 (038) | EVQLVESGGGLVQPGGSLRISCAASGSIYLINYMGWYRQAPGKQRELVATLTSGGSTNYAGSVKGRFAISRDNAKNTVYLQMNSLKPEDTAVYYCNIGGTLYDRRRFESWGQGTLVTVSSGGGSGGGGSGGGGSGGGGSGGGGSGGGGSGGGGSEVQLVESGGGLVQTGASLRLSCAASGRTFSNYAMGWFRQAPGKERERVAAITPRAFTTYYADSVKGRFTISRDNAKNTAYLQMVSLKPEDTAVYYCAAQLVGSGSNLGRQESYAYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS | 532 |
| 14G03-35GS-01C10-35GS-ALB8 (85) | EVQLVESGGGLVQPGGSLRISCAASGSIYLINYMGWYRQAPGKQRELVATLTSGGSTNYAGSVKGRFAISRDNAKNTVYLQMNSLKPEDTAVYYCNIGGTLYDRRRFESWGQGTLVTVSSGGGSGGGGSGGGGSGGGGSGGGGSGGGGSGGGGSEVQLVESGGGLVQTGASLRLSCAASGRTFSNYAMGWFRQAPGKERERVAAITPRAFTTYYADSVKGRFTISRDNAKNTAYLQMVSLKPEDTAVYYCAAQLVGSGSNLGRQESYAYWGQGTLVTVSSGGGGSGGGSGGGGSGGGGSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS | 533 |
| 01C10-35GS-14G03-9GS-ALB8 (52) | EVQLVESGGGLVQTGASLRLSCAASGRTFSNYAMGWFRQAPGKERERVAAITPRAFTTYYADSVKGRFTISRDNAKNTAYLQMVSLKPEDTAVYYCAAQLVGSGSNLGRQESYAYWGQGTLVTVSSGGGSGGGGSGGGGSGGGGSGGGGSGGGGSGGGSEVQLVESGGGLVQPGGSLRISCAASGSIYLINYMGWYRQAPGKQRELVATLTSGGSTNYAGSVKGRFAISRDNAKNTVYLQMNSLKPEDTAVYYCNIGGTLYDRRRFESWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS | 534 |
| 08A10-35GS-01C10-9GS-ALB8 (21) | EVQLVESGGGLVQAGGSLRLSCAASGSIFSIAAMGWYRQATGKQRELVATITDGGTTTYADSVKGRVTISRDRSANTVYLAMNNLKPDDTAVYYCYAYLRYTSRVPGDNYWGQGTLVTVSSGGGGSGGGGSGGGGSGGGGSGGGGSGGGGSGGGGSEVQLVESGGGLVQTGASLRLSCAASGRTFSNYAMGWFRQAPGKERERVAAITPRAFTTYYADSVKGRFTISRDNAKNTAYLQMVSLKPEDTAVYYCAAQLVGSGSNLGRQESYAYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS | 535 |
| 08A05-35GS-01C10-9GS-ALB8 (23) | EVQLVESGGGLVQAGDSLRLSCAASGLTFSNYDMGWFRQAPGKEREFVGASWWSGGAPYYSDVKGRFTISRDNAKNTVYLQANSLRPEDTAVYYCAAKRLRSFASGGSYDYWGQGTLVTVSSGGGGSGGGGSGGGGSGGGGSGGGGSGGGGSGGGGSEVQLVESGGGLVQTGASLRLSCAASGRTFSNYAMGWFRQAPGKERERVAAITPRAFTTYYADSVKGRFTISRDNAKNTAYLQMVSLKPEDTAVYYCAAQLVGSGSNLGRQESYAYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS | 536 |
| 01C10-35GS-08A05-9GS-ALB8 (49) | EVQLVESGGGLVQTGASLRLSCAASGRTFSNYAMGWFRQAPGKERERVAAITPRAFTTYYADSVKGRFTISRDNAKNTAYLQMVSLKPEDTAVYYCAAQLVGSGSNLGRQESYAYWGQGTLVTVSSGGGGSGGGGSGGGGSGGGGSGGGGSGGGGSGGGSEVQLVESGGGLVQAGDSLRLSCAASGLTFSNYDMGWFRQAPGKEREFVGASWWSGGAPYYSDVKGRFTISRDNAKNTVYLQANSLRPEDTAVYYCAAKRLRSFASGGSYDYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS | 537 |
| 14G03 | EVQLVESGGGLVQPGGSLRISCAASGSIYLINYMGWYRQAPGKQRELVATLTSGGSTNYAGSVKGRFAISRDNAKNTVYLQMNSLKPEDTAVYYCNIGGTLYDRRRFESWGQGTQVTVSS | 538 |

TABLE M-continued

Preferred CXCR7 polypeptide or compound sequences.

| Construct name (clone) | Amino acid sequence | SEQ ID NO: |
|---|---|---|
| 01C10 | EVQLVESGGGLVQTGASLRLSCAASGRTFSNYAMGWFRQ APGKERERVAAITPRAFTTYYADSVKGRFTISRDNAKNTAY LQMVSLKPEDTAVYYCAAQLVGSGSNLGRQESYAYWGQG TQVTVSS | 539 |
| 08A10 | EVQLVESGGGLVQAGGSLRLSCAASGSIFSIAAMGWYRQA TGKQRELVATITDGGTTTYADSVKGRVTISRDRSANTVYL AMNNLKPDDTAVYYCYAYLRYTSRVPGDNYWGQGTQVT VSS | 540 |
| 08A05 | EVQLVESGGGLVQAGDSLRLSCAASGLTFSNYDMGWFRQ APGKEREFVGASWWSGGAPYYSDSVKGRFTISRDNAKNTV YLQANSLRPEDTAVYYCAAKRLRSFASGGSYDYWGQGTQ VTVSS | 541 |

TABLE N

CXCR4 and CXCR7 human sequence.

| Name | Amino acid sequence | SEQ ID NO: |
|---|---|---|
| Human CXCR4 or hCXCR4 | MEGISSIPLPLLQIYTSDNYTEEMGSGDYDSMKEPCFRE ENANFNKIFLPTIYSIIFLTGIVGNGLVILVMGYQKKLRS MTDKYRLHLSVADLLFVITLPFWAVDAVANWYFGNFL CKAVHVIYTVNLYSSVLILAFISLDRYLAIVHATNSQRP RKLLAEKVVYVGVWIPALLLTIPDFIFANVSEADDRYIC DRFYPNDLWVVVFQFQHIMVGLILPGIVILSCYCIIISKL SHSKGHQKRKALKTTVILILAFFACWLPYYIGISIDSFIL LEIIKQGCEFENTVHKWISITEALAFFHCCLNPILYAFLG AKFKTSAQHALTSVSRGSSLKILSKGKRGGHSSVSTESE SSSFHSS | 584 |
| Human CXCR7 or hCXCR7 | MDLHLFDYSEPGNFSDISWPCNSSDCIVVDTVMCPNMP NKSVLLYTLSFIYIFIFVIGMIANSVVVWVNIQAKTTGY DTHCYILNLAIADLWVVLTIPVWVVSLVQHNQWPMGE LTCKVTHLIFSINLFGSIFFLTCMSVDRYLSITYFTNTPSS RKKMVRRVVCILVWLLAFCVSLPDTYYLKTVTSASNN ETYCRSFYPEHSIKEWLIGMELVSVVLGFAVPFSIIAVFY FLLARAISASSDQEKHSSRKIIFSYVVVFLVCWLPYHVA VLLDIFSILHYIPFTCRLEHALFTALHVTQCLSLVHCCV NPVLYSFINRNYRYELMKAFIFKYSAKTGLTKLIDASRV SETEYSALEQSTK | 585 |

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the purpose and information indicated in the specification.

We claim:

1. A polypeptide comprising two or more VHH sequences which specifically bind to a C—X—C chemokine receptor 7 (CXCR7), wherein a) at least one first VHH sequence specifically binds a first epitope of CXCR7; and b) at least one second VHH sequence specifically binds a second epitope of CXCR7, wherein the first epitope is different from the second epitope of CXCR7, and wherein the VHH sequences each comprise an amino acid sequence with the general structure FR1-CDR1-FR2-CDR2-FR3-CDR3-FR4 in which FR1-FR4 refer to framework regions 1 to 4, respectively, and in which CDR1 to CDR3 refer to the complementary determining regions 1 to 3 respectively, and wherein c) the first VHH sequence comprises a CDR1 comprising the amino acid sequence of SEQ ID NO: 550, a CDR2 comprising the amino acid sequence of SEQ ID NO: 562, and a CDR3 comprising the amino acid sequence of SEQ ID NO: 574;

and d) the second VHH sequence comprises a CDR1 comprising the amino acid sequence of SEQ ID NO: 551, a CDR2 comprising the amino acid sequence of SEQ ID NO: 563, and a CDR3 comprising the amino acid sequence of SEQ ID NO: 575.

2. The polypeptide according to claim 1, wherein said polypeptide further comprises an amino acid sequence which binds serum albumin.

3. A pharmaceutical composition comprising a polypeptide according to claim 1.

4. A compound or construct comprising a polypeptide according to claim 1.

* * * * *